US008685689B2

(12) United States Patent
Morgan et al.

(10) Patent No.: US 8,685,689 B2
(45) **Date of Patent: *Apr. 1, 2014**

(54) RESTRICTION ENDONUCLEASES, DNA ENCODING THESE ENDONUCLEASES AND METHODS FOR INDENTIFYING NEW ENDONUCLEASES WITH THE SAME OR VARIED SPECIFICITY

(75) Inventors: Richard D. Morgan, Middleton, MA (US); Richard J. Roberts, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,100

(22) Filed: Jun. 6, 2012

(65) Prior Publication Data

US 2012/0254213 A1 Oct. 4, 2012

Related U.S. Application Data

(62) Division of application No. 11/997,614, filed as application No. PCT/US2006/030419 on Aug. 3, 2006, now Pat. No. 8,227,231.

(60) Provisional application No. 60/705,504, filed on Aug. 4, 2005.

(51) Int. Cl.
*C12N 9/22* (2006.01)

(52) U.S. Cl.
USPC ............................ 435/199; 435/193; 435/183

(58) Field of Classification Search
None
See application file for complete search history.

(56) References Cited

U.S. PATENT DOCUMENTS

2004/0137576 A1 7/2004 Roberts et al.

FOREIGN PATENT DOCUMENTS

| | | |
|---|---|---|
| EP | 1516927 | 3/2005 |
| WO | 9964632 | 12/1999 |
| WO | 0121638 | 3/2001 |

OTHER PUBLICATIONS

Altschul, Nucleic Acids Research, 25(17):3389-3402 (1997).
Pearson, William R. Methods in Molecular Biology, 132:185-219 (2000).
Polisson, et al. Nucleic Acids Research, 18(19):5911 (1990).
Rebase webpage, AciI.
Roberts, et al. Nucleic Acids Research, 33:D230-D232 (2005).
Yang, et al. Nucleic Acids Research, 33(6):1892-1901 (2005).
Ngo, et al. The Protein Folding Problem and Tertiary Structure Prediction, 14, 433 amd 492-495 (1994).

*Primary Examiner* — Richard Hutson
(74) *Attorney, Agent, or Firm* — New England Biolabs, Inc; Harriet M. Strimpel

(57) ABSTRACT

Specified restriction endonucleases have been characterized for the first time by their amino acid and DNA sequences. These sequences and those with at least 90% identity thereto have been used as probes in sequence similarity analyses to identify sequence matches in a sequence database that corresponds to novel restriction endonucleases or isoschizomers. The sequence similarity analyses includes selecting a positive sequence match from any sequence producing an expectation value of less than or equal to e−02.

5 Claims, 75 Drawing Sheets

Figure 1-1

| Restriction Enzyme | Recognition Sequence and Cleavage Site |
|---|---|
| AciI | 5'...C^CGC...3'<br>3'...GGC_G...5' |
| AclI | 5'...AA^CGTT...3'<br>3'...TTGC_AA...5' |
| AflII | 5'...C^TTAAG...3'<br>3'...GAATT_C...5' |
| AflIII | 5'...A^CRYGT...3'<br>3'...TGYRC_A...5' |
| ApaI | 5'...GGGCC^C...3'<br>3'...C_CCGGG...5' |
| ApoI | 5'...R^AATTY...3'<br>3'...YTTAA_R...5' |
| AscI | 5'...GG^CGCGCC...3'<br>3'...CCGCGC_GG...5' |
| AseI | 5'...AT^TAAT...3'<br>3'...TAAT_TA...5' |
| AspCNI | 5'...GCCGC...3'<br>Cleavage Site is Variable* |
| AvrII | 5'...C^CTAGG...3'<br>3'...GGATC_C...5' |
| BbvI | 5'...GCAGC(N)$_8$^...3'<br>3'...CGTCG(N)$_{12}$_...5' |
| BbvCIA | 5'...CC^TCAGC...3'<br>3'...GGAGT_CG...5' |
| BbvCIB | 5'...CC^TCAGC...3'<br>3'...GGAGT_CG...5' |
| BccI | 5'...CCATC(N)$_4$^...3'<br>3'...GGTAG(N)$_5$_...5' |
| BceAI | 5'...ACGGC(N)$_{12}$^...3'<br>3'...TGCCG(N)$_{14}$_...5' |

Figure 1-2

| Enzyme | Recognition Site |
|---|---|
| BclI | 5'...T▾GATCA...3'<br>3'...ACTAG▴T...5' |
| BfaIA | 5'...C▾TAG...3'<br>3'...GAT▴C...5' |
| BfaIB | 5'...C▾TAG...3'<br>3'...GAT▴C...5' |
| BfuAI | 5'...ACCTGC(N)₄▾...3'<br>3'...TGGACG(N)₈▴...5' |
| BlpI | 5'...GC▾TNAGC...3'<br>3'...CGANT▴CG...5' |
| BmrI | 5'...ACTGGG(N)₅▾...3'<br>3'...TGACCC(N)₄▴...5' |
| BsaJI | 5'...C▾CNNGG...3'<br>3'...GGNNC▴C...5' |
| BscGI | 5'...CCCGT...3'<br>3'...GGGCA...5' |
| BseYIA | 5'...C▾CCAGC...3'<br>3'...GGGTC▴G...5' |
| BseYIB | 5'...C▾CCAGC...3'<br>3'...GGGTC▴G...5' |
| BsgI | 5'...GTGCAG(N)₁₆▾...3'<br>3'...CACGTC(N)₁₄▴...5' |
| BspCNI | 5'...CTCAG(N)₁₀▾...3'  and  5'...CTCAG(N)₉▾...3'<br>3'...GAGTC(N)₉▴...5'         3'...GAGTC(N)₇▴...5' |
| BspHI | 5'...T▾CATGA...3'<br>3'...AGTAC▴T...5' |
| BspMI | 5'...ACCTGC(N)₄▾...3'<br>3'...TGGACG(N)₈▴...5' |
| BsrBI | 5'...CCG▾CTC...3'<br>3'...GGC▴GAG...5' |
| R1.BsrDI | 5'...GCAATGNN▾...3'<br>3'...CGTTAC▴NN...5' |

Figure 1-3

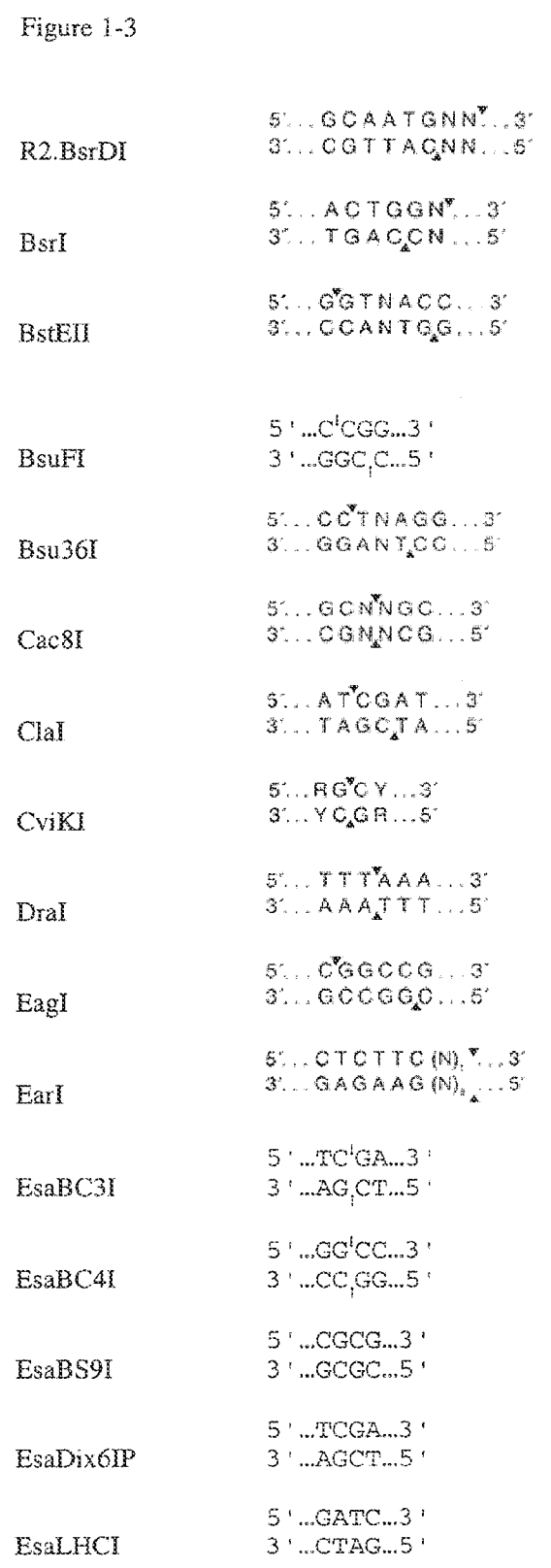

| | |
|---|---|
| R2.BsrDI | 5'...GCAATGNN▼...3'<br>3'...CGTTAC NN...5' |
| BsrI | 5'...ACTGGN▼...3'<br>3'...TGACCN...5' |
| BstEII | 5'...G▼GTNACC...3'<br>3'...CCANTGG...5' |
| BsuFI | 5'...C⁺CGG...3'<br>3'...GGC C...5' |
| Bsu36I | 5'...CC▼TNAGG...3'<br>3'...GGANTCC...5' |
| Cac8I | 5'...GCN▼NGC...3'<br>3'...CGN NCG...5' |
| ClaI | 5'...AT▼CGAT...3'<br>3'...TAGC TA...5' |
| CviKI | 5'...RG▼CY...3'<br>3'...YC GR...5' |
| DraI | 5'...TTT▼AAA...3'<br>3'...AAA TTT...5' |
| EagI | 5'...C▼GGCCG...3'<br>3'...GCCGG C...5' |
| EarI | 5'...CTCTTC(N)₁▼...3'<br>3'...GAGAAG(N)₄...5' |
| EsaBC3I | 5'...TC⁺GA...3'<br>3'...AG CT...5' |
| EsaBC4I | 5'...GG⁺CC...3'<br>3'...CC GG...5' |
| EsaBS9I | 5'...CGCG...3'<br>3'...GCGC...5' |
| EsaDix6IP | 5'...TCGA...3'<br>3'...AGCT...5' |
| EsaLHCI | 5'...GATC...3'<br>3'...CTAG...5' |

Figure 1-4

| | |
|---|---|
| EsaS1IP | 5'...GGCC...3'<br>3'...CCGG...5' |
| FseI | 5'...GGCCGG˅CC...3'<br>3'...CC˄GGCCGG...5' |
| FspI | 5'...TGC˅GCA...3'<br>3'...ACG˄CGT...5' |
| HhaI | 5'...GCG˅C...3'<br>3'...C˄GCG...5' |
| HinP1I | 5'...G˅CGC...3'<br>3'...CGC˄G...5' |
| MfeI | 5'...C˅AATTG...3'<br>3'...GTTAA˄C...5' |
| MluI | 5'...A˅CGCGT...3'<br>3'...TGCGC˄A...5' |
| MmeII | 5'...GATC...3'<br>3'...CTAG...5' |
| MscI | 5'...TGG˅CCA...3'<br>3'...ACC˄GGT...5' |
| NdeI | 5'...CA˅TATG...3'<br>3'...GTAT˄AC...5' |
| NgoMX | Recognition Sequence Unknown |
| NotI | 5'...GC˅GGCCGC...3'<br>3'...CGCCGG˄CG...5' |
| PacI | 5'...TTAAT˅TAA...3'<br>3'...AAT˄TAATT...5' |
| PflMI | 5'...CCANNNN˅NTGG...3'<br>3'...GGTN˄NNNNACC...5' |
| PmeI | 5'...GTTT˅AAAC...3'<br>3'...CAAA˄TTTG...5' |
| PshAI | 5'...GACNN˅NNGTC...3'<br>3'...CTGNN˄NNCAG...5' |

Figure 1-5

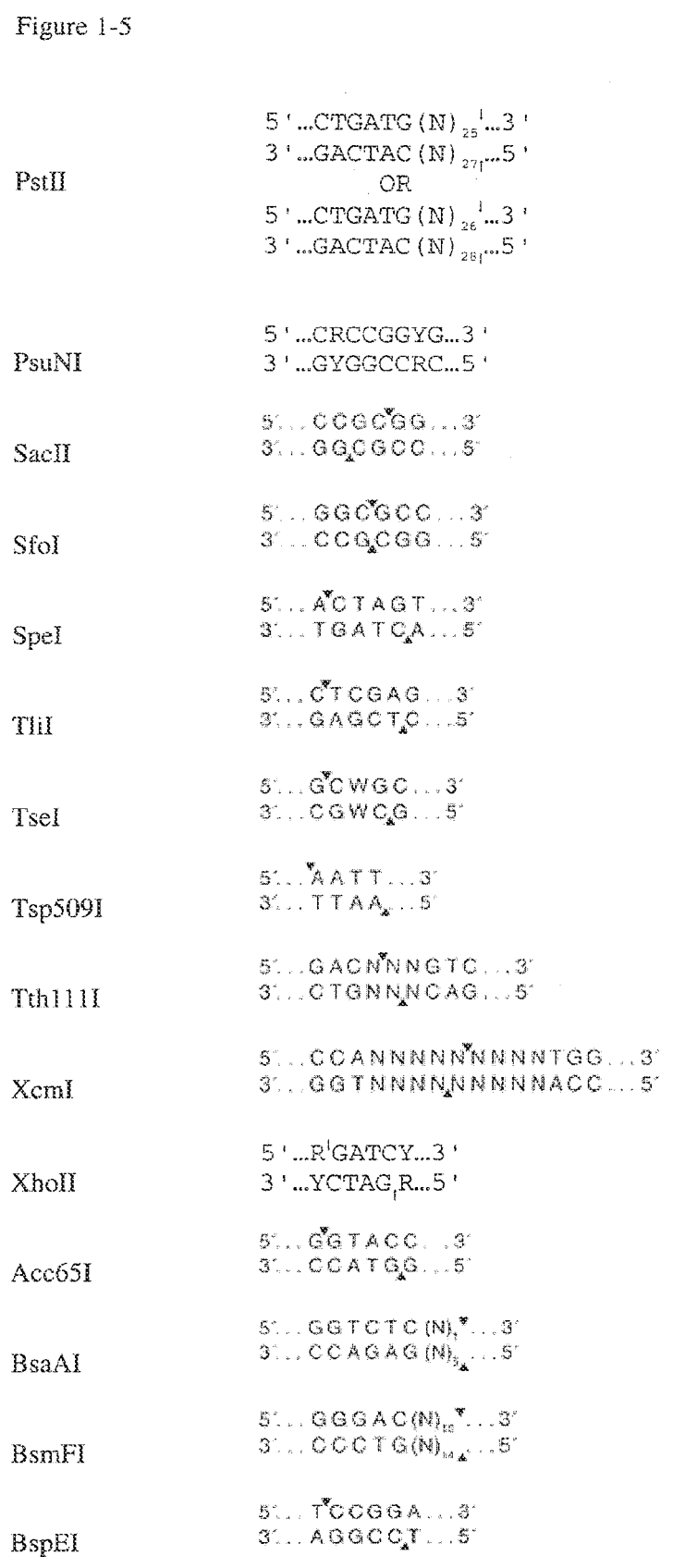

PstII
```
5'...CTGATG(N)₂₅ |...3'
3'...GACTAC(N)₂₇↑...5'
        OR
5'...CTGATG(N)₂₆ |...3'
3'...GACTAC(N)₂₆↑...5'
```

PsuNI
```
5'...CRCCGGYG...3'
3'...GYGGCCRC...5'
```

SacII
```
5'...CCGC▼GG...3'
3'...GG▲CGCC...5'
```

SfoI
```
5'...GGC▼GCC...3'
3'...CCG▲CGG...5'
```

SpeI
```
5'...A▼CTAGT...3'
3'...TGATC▲A...5'
```

TliI
```
5'...C▼TCGAG...3'
3'...GAGCT▲C...5'
```

TseI
```
5'...G▼CWGC...3'
3'...CGWC▲G...5'
```

Tsp509I
```
5'...▼AATT...3'
3'...TTAA▲...5'
```

Tth111I
```
5'...GACN▼NNGTC...3'
3'...CTGNN▲NCAG...5'
```

XcmI
```
5'...CCANNNN▼NNNNTGG...3'
3'...GGTNNNN▲NNNNACC...5'
```

XhoII
```
5'...R|GATCY...3'
3'...YCTAG|R...5'
```

Acc65I
```
5'...G▼GTACC...3'
3'...CCATG▲G...5'
```

BsaAI
```
5'...GGTCTC(N)₁▼...3'
3'...CCAGAG(N)₅▲...5'
```

BsmFI
```
5'...GGGAC(N)₁₀▼...3'
3'...CCCTG(N)₁₄▲...5'
```

BspEI
```
5'...T▼CCGGA...3'
3'...AGGCC▲T...5'
```

Figure 1-6

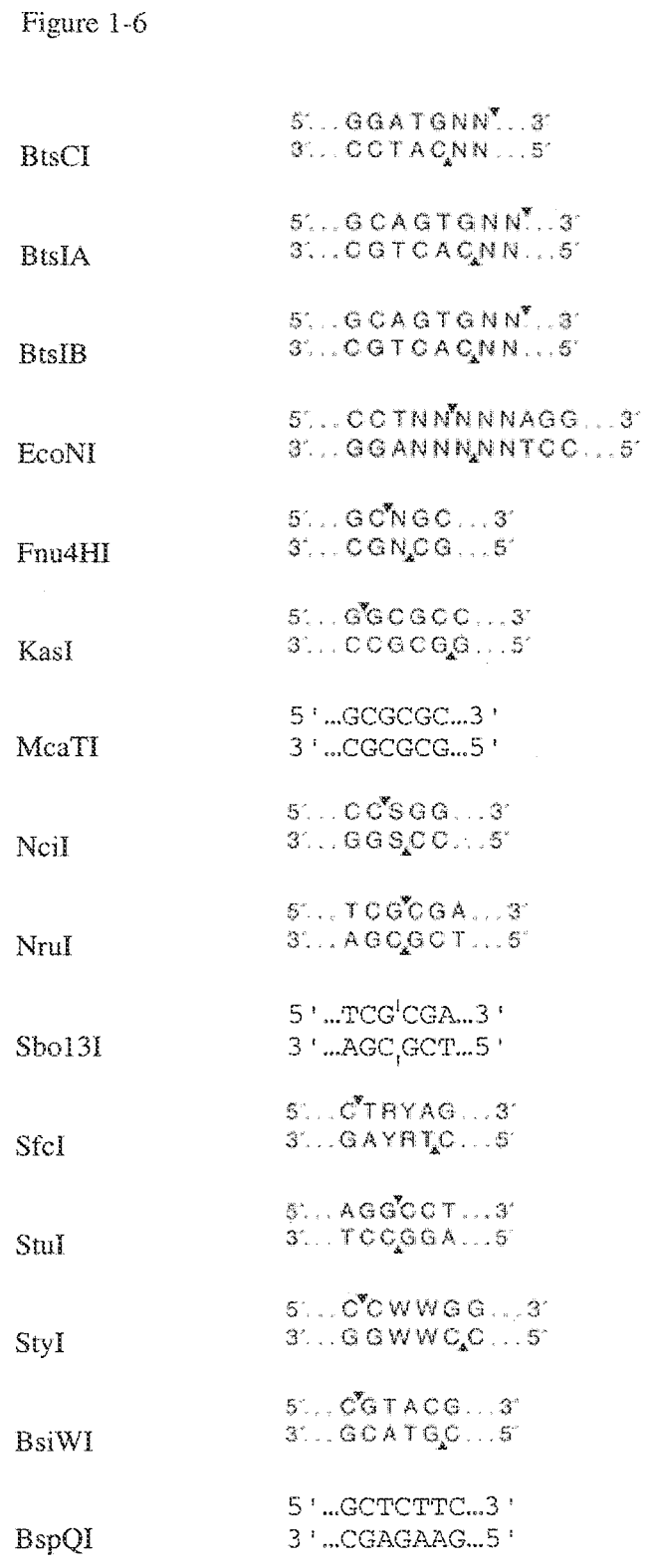

| | |
|---|---|
| BtsCI | 5'...GGATGNN▼...3'<br>3'...CCTAC NN...5' |
| BtsIA | 5'...GCAGTGNN▼...3'<br>3'...CGTCAC NN...5' |
| BtsIB | 5'...GCAGTGNN▼...3'<br>3'...CGTCAC NN...5' |
| EcoNI | 5'...CCTNN▼NNNAGG...3'<br>3'...GGANNN NNTCC...5' |
| Fnu4HI | 5'...GC▼NGC...3'<br>3'...CGN CG...5' |
| KasI | 5'...G▼GCGCC...3'<br>3'...CCGCG G...5' |
| McaTI | 5'...GCGCGC...3'<br>3'...CGCGCG...5' |
| NciI | 5'...CC▼SGG...3'<br>3'...GGS CC...5' |
| NruI | 5'...TCG▼CGA...3'<br>3'...AGC GCT...5' |
| Sbo13I | 5'...TCG|CGA...3'<br>3'...AGC|GCT...5' |
| SfcI | 5'...C▼TRYAG...3'<br>3'...GAYRT C...5' |
| StuI | 5'...AGG▼CCT...3'<br>3'...TCC GGA...5' |
| StyI | 5'...C▼CWWGG...3'<br>3'...GGWWC C...5' |
| BsiWI | 5'...C▼GTACG...3'<br>3'...GCATG C...5' |
| BspQI | 5'...GCTCTTC...3'<br>3'...CGAGAAG...5' |

Figure 2-1

AciI DNA sequence (SEQ ID NO:1)

ATGTTCATGAATGAACACATAAAGGGATCTAATTCGCATGGTAATAGCAATGAGTTG
GAATTGGTTTATGCGTTTGATGGCAAGAAAGTTAAGGATTTAAACACTAATTTAAAA
AATTTTGTACAATTCATTGCAAACGATAACAATATAAAAATTAATAATGATACAAAA
TTATTTGCGAAGTATGTTTCTAATAACAAATTAAAACAAGATTTTATTGTATCGTTT
AATGAAAGAGATTTTTACATTAGTTTAAAAATGGGTTCAGGAAATAGTGTTCATCAA
GAACCGATTGAAGATTTTATTAAATACTTGAATACGAATTATGAAGTAACTGAGAAA
ATTTGTAATGATTTAAGGTTTTTTATTTGGCAGATGGTACGTTAGATGGAAAAGGA
AAATTTGAGAATAGATTTGACGCTAGATATTTTAAAAAGAATTATCCTGAAAAACGA
AGAGAGTTATTACAATTTTTCGAAAAAAATAAGGTAGAACTAATTAAGCATTTTATG
TTTGTTGGTAAACATAATAGTAGAGTTGATTATCTTTATCATGGAACGACTTCGAAT
GGGGCGTGGATGTCAACAAAACAAATAATTGATTACAATATTCAAAACCAAATAGAT
ACTAACAAAGGTAATTCTCCTACTTTAAGCGTCGGAAGAATGTCAATTCAAGCATGG
AATGTTGCAAAGTCTGGAAGCGAGTCAGCAGAAAAGAAACGAGGAGAAATCCAGGTA
AAATACGGAAAACTTAAAGAAGATTTTAAGGAGGTATTAAAATTAAATTCCTCGAAC
AAAGGAACTTTGTTTGGAGATCATGAGGAATTTGATATTTCTGGAACTTTAAATAAA
AATAAAAATCATTTTTATTGGAAGATGATAGCAAGAGATTTGAATTTAAATCAAGAA
GAACTGAATAATTTATATGTTGTTCGTGTTTCTTCAAAAGTTATGTCATCTCTCAGT
AAGAAAAAGGTTCTTCCAAAATCGGATGCTTATATAATTAGAGCTGATCTCTCTAAA
TCTTTTTTACTATCTAAAGAATACAAACTATCTGAAGATGATTTGGTAGGTATAATA
TATAAAAAAGTAGGACGTAGTGGCATTTCAGTAAAAAGAGCTGATTCGAAGAAATAT
ACTATTGTAAAACTTACAGTTGCTTCATTTGAAAAGTGCTTTGAAATCGAGCCAGAG
ATAAAAAAAAATAATTGCTGGACTTTTGTTATATAGTAAAGAGAAGGATATGTATAAA
AATCTTGAAATTTTAAATAAGATTGGTATATCTGAACTTGAATTGATAAATTATACA
AATCGATTTATTGTAGATAAAGTTATTTCGTGCAATGATCCCAAAAATGTCGATATA
ATCAGGAGTACGATGCAAGAACGGACTCGAACACTAATTGAAAAAAATTTAGAAATC
AAAAAAGCACTATTTATGGGTGAAGGCTGGTATGAAGAACCCTATTGCATCAATTAT
ATTTTTAAAGATGGGAAATTATCAAATGATGTATTTTCTGAGTATATTATTACTACA
GGTTCAGGCCGTTCAAAGGGCAATTATACAATTGCGTTGAAGCCTAAGTAA

AciI amino acid sequence (SEQ ID NO:2)

MFMNEHIKGSNSHGNSNELELVYAFDGKKVKDLNTNLKNFVQFIANDNNIKINNDTK
LFAKYVSNNKLKQDFIVSFNERDFYISLKMGSGNSVHQEPIEDFIKYLNTNYEVTEK
ICNDLRFFIWADGTLDGKGKFENRFDARYFKKNYPEKRRELLQFFEKNKVELIKHFM
FVGKHNSRVDYLYHGTTSNGAWMSTKQIIDYNIQNQIDTNKGNSPTLSVGRMSIQAW
NVAKSGSESAEKKRGEIQVKYGKLKEDFKEVLKLNSSNKGTLFGDHEEFDISGTLNK
NKNHFYWKMIARDLNLNQEELNNLYVVRVSSKVMSSLSKKKVLPKSDAYIIRADLSK
SFLLSKEYKLSEDDLVGIIYKKVGRSGISVKRADSKKYTIVKLTVASFEKCFEIEPE
IKKIIAGLLLYSKEKDMYKNLEILNKIGISELELINYTNRFIVDKVISCNDPKNVDI
IRSTMQERTRTLIEKNLEIKKALFMGEGWYEEPYCINYIFKDGKLSNDVFSEYIITT
GSGRSKGNYTIALKPK

AciI DNA sequence (SEQ ID NO:3)

TTGGGAAAACTTAAAAAAATTTTAGCGGGTACTGCTGGTCGAAATACTGGTCATGCA
TATGAAGAATATCTAGCAGATAATATTAATTCATTAAATGTTCCATTAAATATATCA
ATACAACCACTACCGATAGTAGGTTCTTATCAAAATGTCTTTTCTTCAAATAATGAA
GCTTTCACATTAATCACTTATTTGGCTAAAGCATATAATATTTCTCAAATTACTAGA
ATTTATGCTGTTGCAACAGGGGGATTAGCAACATCCGCTAACAGTCAGGGTGTCCAT
TTTAATGGACAAATAATTAAAAAATGTAAAAGTGATATTTTAATTGAAATCGAAGAC

Figure 2-2

CAATCTAATCAAATTCATCGTATTGGGATATCTGTAAAACAATGTAACAATCAGAGA
CCTCTTAATGCTCAAGTTTTTTGTTCCACAGCTTCAGGGTTTTCTAACCTATTAAGA
CAACATAACATTCCAGTTTCTATTTTAGCTGAAAATGAATTACGTAAATTCTGTGGT
CATCCTGGAAGCTCTCCAATAGATCACAATATTCATTTGACCCGTGTAATTGATCAT
AGAAGATACTTTTGGGAAGAACTAGATATTAATGCATCACAGGAGTGGCAAAATATT
TTTGATAATTACAACGCTGAAATAGCTAGAATTTTATTGCAAAAAGCATATAGTAAC
GAACCTTATCCACCTGAGTTTTTATTACATAAAACAAAGAGAACCTCAGGAAATCAG
GAAATTGCTATTTTTGAAATTGCTGATTTAATAGTAAAAAGTTTTCAGTATCAATGC
TTTACAACATCACTCTATAGAGTAAAAAAAGGAACTTTTAAAGAAGCTAAAACTATG
GGAGATACACACGAGGCTCCTAGTTTTGGAATATTTCAAATGCAACGCTTAGGAAAT
ACTCAAAATGCACATCAATTGCAATTTAATTTAAAAGCCGGCTATTTTTATCATATT
TAA

AclI amino acid sequence (SEQ ID NO:4)

MGKLKKILAGTAGRNTGHAYEEYLADNINSLNVPLNISIQPLPIVGSYQNVFSSNNE
AFTLITYLAKAYNISQITRIYAVATGGLATSANSQGVHFNGQIIKKCKSDILIEIED
QSNQIHRIGISVKQCNNQRPLNAQVFCSTASGFSNLLRQHNIPVSILAENELRKFCG
HPGSSPIDHNIHLTRVIDHRRYFWEELDINASQEWQNIFDNYNAEIARILLQKAYSN
EPYPPEFLLHKTKRTSGNQEIAIFEIADLIVKSFQYQCFTTSLYRVKKGTFKEAKTM
GDTHEAPSFGIFQMQRLGNTQNAHQLQFNLKAGYFYHI

AflII DNA sequence (SEQ ID NO:5)

ATGACATTTCAAATAACTCCAGAAAATACCCAAAATAAATCTGCTTTGTTGGAATAT
TTTAGAGAATTAGGAAATGAAAAACTTTCTGAAATTAGAAGAGAAGTCGGTAATAAA
AATTATCAAAAAATAACTCCTCATATCAATAAAGCAATCAATAAAACTAAGAATGAT
TTTTTACATACAATTATTGAAACTGCAAATCAAAATAATTGGAATGATCAAGATAAA
CTTTCCTCACTTCTTTTCACTACTTATTGCGCTCATGTAGTAATGCTTGATTTACGT
CATGAAGTGTGGCCTTATGAATATATGGCATTTTCTCGACGAATTGGTGAGCTTTGG
GAAAATTTTGTAAGATTACCATTTTTGTACCCGCCAAAAGCAGCAGAATTAACCTCT
TTTGTACCACCACTTTTTTCTGAAGTCAGAAAAAATCTAAAAAAAGATATTGAAGAA
TATATTGATACTTTGTTCATTTCTCAAGAACAAAAATATGAACTTATCAATTATTAT
GAAAAAGTATGGGTGCTAGTAGATTCTGGTGAAATAAGTCTTGAGTTAGATTTTCAT
GCTATTATTAGAGGTAAAAGATTCAATATAGATTTTAAAAGTGGATTTGGCTCAAAT
GAGAAAGGAAATACCAACCGACTGCTTATGGTAGCAACTATTTATTGTAATTTAGAA
GATGAATATAGTAATATTCTGCTCGTTCGCGCTAAAGAAGATTTGAATAACAATTAC
TTTAGAACTTTAAAAAAGTCTCATGTTTGGAATGCATATTGTGGTGATGAAGCTTAT
GAAAAAATTGGTGATTTTACAAATTTTGATATGCGAACCTGGATAAATTCAAGTATT
GATTGGCAAAATGATTTATTAAGTACAACAGTAAGTGATTTTGAGAAATTTAATTTA
ATGGGATATTTACAATGGTAA

AflII amino acid sequence (SEQ ID NO:6)

MTFQITPENTQNKSALLEYFRELGNEKLSEIRREVGNKNYQKITPHINKAINKTKND
FLHTIIETANQNNWNDQDKLSSLLFTTYCAHVVMLDLRHEVWPYEYMAFSRRIGELW
ENFVRLPFLYPPKAAELTSFVPPLFSEVRKNLKKDIEEYIDTLFISQEQKYELINYY
EKVWVLVDSGEISLELDFHAIIRGKRFNIDFKSGFGSNEKGNTNRLLMVATIYCNLE
DEYSNILLVRAKEDLNNNYFRTLKKSHVWNAYCGDEAYEKIGDFTNFDMRTWINSSI
DWQNDLLSTTVSDFEKFNLMGYLQW

Figure 2-3

AflIII DNA sequence (SEQ ID NO:7)

ATGATAAATGAAGATGATTTACTGAATATAGCTATAGTAAATATTAGAAAAGTTTCA
AAATTTAAACCTTATAAAAGCTATTCTGGTGTCAATAACAAAGAGGAATTTCAGCAA
TTAATAGCTAATGATCCTGCTTTTGGCTCTTTAGGTTTGGACGACGAAAGATACATT
ATTGCCAGAGTGGGAGGAAATCTTGTAACCTCCTTACATCGCAAACTTGGTGATATG
TATGAGAATTTATTTGCCTATTTATTAAAAGAGAGTTTTGGATTAAATGAGAATGAA
CTACACTTTAGTGTCAATGTTAAAATTGGTAAACGTGACCAGGTTCGATCCACTGAT
GGATTAATCAGAAAAGATAAGTTCAATCAAAATATTCCCTCAGATTGGATTAAATAT
GAAGGAATAGGATTTGAAGTCCGTTCATGCTATCAAATTGGTGATTCTAAAAGAATT
CAGGCTGATTATGATATGTCCTTGGCTTTGAAGTCTTACGAAATTCTGCCTGTAATG
TTAATTTTCTGCAATACATCTTTAAAAAGCCCTGTACTTAGATTATCAAAGAGTTGG
GAACTCTATGAAGGAAGAAACAGTTTTGATTTAGTTCATACTATTACTGGTTTCGAC
CTTTATAATTTCCTTCAGATAAATTCAGAGTTGTTGAAAAAAGAGATAGATAATATT
TTCTCATATTTTCTCTAA

AflIII amino acid sequence (SEQ ID NO:8)

MINEDDLLNIAIVNIRKVSKFKPYKSYSGVNNKEEFQQLIANDPAFGSLGLDDERYI
IARVGGNLVTSLHRKLGDMYENLFAYLLKESFGLNENELHFSVNVKIGKRDQVRSTD
GLIRKDKFNQNIPSDWIKYEGIGFEVRSCYQIGDSKRIQADYDMSLALKSYEILPVM
LIFCNTSLKSPVLRLSKSWELYEGRNSFDLVHTITGFDLYNFLQINSELLKKEIDNI
FSYFL

ApaI DNA sequence (SEQ ID NO:9)

ATGGCCCGCAACGTGTTAGTTGAACGTGCGGTGGACGCTGCGCTTGAACGGCTGGAC
GCCTTCATTGAAGGCGAGAAGCTGGCAAAGTTGCCCGATGCTGCGACCCGAGCATTA
CTGGACGACCAGCTTGGCCACGGATCTAACAGCGTTCGATTAGCATCGCTGTTCTTT
GTCTTCTATGCGTCAGTTGATCTGGCATGGGATTGCAATTCAATCCCGACCGGAATT
CGCGGCACCTACGGCGACAAGCGGTTGGCGACGCAACTTGGGCTTCGTAGCATCACG
CTTCACAATGCCATTACGGCCTTCGGAGAAAACCTTGGCTGGAAAGGAAACGTTACT
AATTCGCGCCTTCAGAACGACGTGCGATTCGACGGATTTGGCCGAACTCTTACTGGC
CTGAACGTCGAACAGCGGACGCTATGCGCTGACTATATGGCCGCACGGTTTGCCGAA
AGCCGGAAAGTCATTGCACCGTTACCACCAGTCGCCGATGACGTGTTGACCTACGCC
CGTGCGCGGAAGCTGTTCTATTCACTGATCGCCCTTCCATCCGAAGGTAACGTTCAG
CAATTCCTTATCGCCGCACTGTTGTTCGTTCATCGCCAGCGATACGGTTATGACATT
CGAACCCATCACGTTCATGCTTCAGACCGCTTCGATACGACAGCGGGCGATATTGAG
GAACTGCTGAACGGCGACCTTGTGCGCGCCTACGAAGTGACAGTTCGACCCGATTGG
AAGAACCGCATGGGCGACTTCCGAAAAAAGATGGATGGTGCGAGCCTTCGCAAATAC
ACCATCATTGCGTCGAACGTGAACAGCGACGACGATCTTGCCGAACCCGCCGACATG
ATCCGCTTCCTTACGCCCTATGGCCGCGACATTGCGATCGTGGATATTCACGATTTC
ATCAACGTGTTCGCAATGGAATTGATCGTCGACGAACTGTGTCGGGCTGTCACGCAA
ACCTACAACTATCTTACAACGCCAAGCTTGTGCGGACGTGCTGATATTATCGATAAG
TTCAACGCTACCGTCGAAGGTTGGTTGGATGAAGTAACCTAA

ApaI amino acid sequence (SEQ ID NO:10)

MARNVLVERAVDAALERLDAFIEGEKLAKLPDAATRALLDDQLGHGSNSVRLASLFF
VFYASVDLAWDCNSIPTGIRGTYGDKRLATQLGLRSITLHNAITAFGENLGWKGNVT
NSRLQNDVRFDGFGRTLTGLNVEQRTLCADYMAARFAESRKVIAPLPPVADDVLTYA
RARKLFYSLIALPSEGNVQQFLIAALLFVHRQRYGYDIRTHHVHASDRFDTTAGDIE

Figure 2-4

ELLNGDLVRAYEVTVRPDWKNRMGDFRKKMDGASLRKYTIIASNVNSDDDLAEPADM
IRFLTPYGRDIAIVDIHDFINVFAMELIVDELCRAVTQTYNYLTTPSLCGRADIIDK
FNATVEGWLDEVT

ApoI DNA sequence (SEQ ID NO:11)

ATGGCGCAGAAGGCACGACTTCGGCAGAACCGCTACGGGACTGTCATCAATACGACC
TCGTCTAAGCAGGAGCTGCAGCTCGGTGACGCGCTTGTCGATGCCACCGAGCGCCTT
ACGGCGAAGTTCGGTATCGCCTTCACGCACGAGAAGAAGGTGATGCTCGCTGATATC
GTCACCTCCCTCCGCCGCAGCTTCCCGACGGTGTCGTTCGATGACCCGCTCCCGAAC
ACTTACATGAGCCCCGACGGCGGCATCCTCTCAATCATGGCGGCGGACGGCGAGCGC
ACATTCCCTGTACTGATCACGGAGGTGAAGAACCAGGGGACCAACGACCTGCGGGCT
CAGGAGGGGCTGAAGAAGCAAGCGATGGGTAATGCCATCGAGCGCCTCGGGAAGAAC
GTGATCGGATTCCGCGCAATGATGCTGGAGGACGGAATCATCCCGTTCGTGTGCTTT
GGCTACGGCTGGGATTTCCACGAGGGTAGTTCGATTCTCGACAGGGTGAAGACCATC
GCTATGTTCGGCGAGCTGAATCAGGTGAACGTCATCCCTGAAGGGGAGGAGGGGCTC
TTCAATCGAGGCAGCTTCTTCTTCCGGATGGAGCCTTGGTCCTTGGAAGAGATGTCG
GATGTGATGTTTGACGTCGGGAGCCGTGCGATTCACTACTACTTCGCTAAGTTCGGC
GATTCTGCGTTCAAAATGATTGGTTCCTAA

ApoI amino acid sequence (SEQ ID NO:12)

MAQKARLRQNRYGTVINTTSSKQELQLGDALVDATERLTAKFGIAFTHEKKVMLADI
VTSLRRSFPTVSFDDPLPNTYMSPDGGILSIMAADGERTFPVLITEVKNQGTNDLRA
QEGLKKQAMGNAIERLGKNVIGFRAMMLEDGIIPFVCFGYGWDFHEGSSILDRVKTI
AMFGELNQVNVIPEGEEGLFNRGSFFFRMEPWSLEEMSDVMFDVGSRAIHYYFAKFG
DSAFKMIGS

AscI DNA sequence (SEQ ID NO:13)

GTGATTGAATTTCCCGAGTATCGAGACAGCTCGGCCGCGCCAAAGATTTCAGACCTT
GAAAGGCTGATGGATCGCTCCTTGACCAACTCGCAGTACGTGGATGGGGCGAACGCA
GCTCGCTTGCTAGGCACATTTATCCGGTCATTTCGTAGCGTCATTGGTAGCGCCGAG
GAGTCGGCCACTCGAGCCAATTTAGTTGAGGCGCACGACGAGGCGAAACTCTTCGGG
TTGATGCTATCCGCGGGATTCGACCTAATTTGTAATGCAGAATATGTCCACGGGCGA
TTGGTCAACAATAAGTGGATCTACTGCCACCGAGGGGGTGAGCCGGCTGTCGCCTAT
TACTCTTTCCTGAAACAGTGTCCTCGGTGCTGCCTTGACCGAGGCTTGGAGGGGCGG
CTGAGTGGCGCACAGCACAAGCCGACGAGCCATCACATCGGTGAGATAACCACCGTC
GCGATCGCCCTTCTTCTCCAGTTGGTGGCTGCCGCTAACGAGAATCCGTTCGAAATC
GCCACGATCACAAAACAGTCGCATGACGTTGATGCCATTGGCTTCCGTGACGATCTT
TTGGTCCTTTTCGAGATTAAAGCTTCCCCAATGGTCTCCTTTCCTCTGGTGACTGAA
CTGGAAGAACCAATGCTGCAGGAGGGCCCCGACGGCCCAGTAGAGTACCGGCAACAC
TCATTGGTGGATTTAACGCTGCAAGGCCGAGAATTCGCTGTAGCTATCCCGCACGCA
GAGACGGCAATCCCTCTCGGTGAACCGAGAGGGGGAGTCTTGGCCCTATGAACCGCTG
ATCGACTACTTCTCAGTACCCGCCAATGCCGCTAGTTATCTGCAGGCGTGGATCGAG
CTGTACGCGGCTTACAGAACCCCCAAGACGCAAAGAGCGGGCCGGACTGCTGCGCTC
GCGTATCTCGTGAACGGCTGGGGTGACGAGATCGACTCCAATAAGACTAAGCCTGGG
CTTGGGCGGACTGATGACGTAAAAAAAGGCACTTATCAGTTGTTGAAGTTCGGTTCC
TACTATAGGGACGACGCCGCAAGTGTGCCTGTAAGGGGTGCTCTGGTCGCCAACCTT
GATCCGCTCTTTCTGCGCCCTGGTTACATCGATGGACTGTCTGACGTGCGCTGGGGC
CACGGGCGCGATTTCACGCTTGAGGAGGGTGAATACAGGATCGCGGAAGGATCGCTG
CGGCATCTGTACGATGCGATACTTGCGTTCAACGACCCGCTGTTAAACGACCCGCTC

Figure 2-5

CTTCAAGAGATATTCGATCTTGGTGCCGTGGAGAGGAAACTGGCCAATGGCGACCTG
GAAGCACTCTTGGACAAATGGATTGCGCGACCCGAGATAGTGCTTGACCCTAGTTGA

AscI amino acid sequence (SEQ ID NO:14)

VIEFPEYRDSSAAPKISDLERLMDRSLTNSQYVDGANAARLLGTFIRSFRSVIGSAE
ESATRANLVEAHDEAKLFGLMLSAGFDLICNAEYVHGRLVNNKWIYCHRGGEPAVAY
YSFLKQCPRCCLDRGLEGRLSGAQHKPTSHHIGEITTVAIALLLQLVAAANENPFEI
ATITKQSHDVDAIGFRDDLLVLFEIKASPMVSFPLVTELEEPMLQEGPDGPVEYRQH
SLVDLTLQGREFAVAIPHAETAIPLGEREGESWPYEPLIDYFSVPANAASYLQAWIE
LYAAYRTPKTQRAGRTAALAYLVNGWGDEIDSNKTKPGLGRTDDVKKGTYQLLKFGS
YYRDDAASVPVRGALVANLDPLFLRPGYIDGLSDVRWGHGRDFTLEEGEYRIAEGSL
RHLYDAILAFNDPLLNDPLLQEIFDLGAVERKLANGDLEALLDKWIARPEIVLDPS

AseI DNA sequence (SEQ ID NO:15)

ATGTTGAGAGGACTAACTGTGGAACTTTTAGAATTAAAAAATAGAATAACCACCTCA
TTTAGCGGTACCGAGGATGATTTAAGAGAAGTTCTAGACTTGATAGAGCAAGATCAG
CCTGTGTTTCCGTTTAATGAGTATGAGCATCTCATTTGTAATCTTATCGAAAAGGGT
GGTCTTAATTATAATCAATATATTGAAATTAGATCGGAATATATCAGTCAAAACCCG
AACTTATGGATTTTTGAAATATCAGCCCCTAGAGGATTTGGTGAGAAATTTGCCCAA
ACATATGTGAAAGGTAAGTGTTCAAAACTAAAAACCCCATCCAAAAAATTAGACCCA
AATTATGCTGGAGAATATGATCTTTGGCTCGACGGAATTACTATTGAGGTAAAAGCA
TCTAGAGCAGTAGATAGTAATAGTGAAGAACCTCTTTATGTGAAAGCATTAGCAAGA
GATACAAACAGGCAATTCATTATGAATTTTCAGCAACTGAAACCGCAATACTGTGAT
GTATTTATATGGGTTGCCGTCTTTCGGGATGAAATTGTGTTATGGATAATGAGTTCA
GATGAGGTTGAAAAAAATCCTTTTTATTCAAAAGGGCAACATAGAGGCAACAAAGGA
AACGAAGGGCAGTTGCATATAAAACATGACAAAATCCACTTATTCTCAAAGTATGAG
CTTAAGGATGATGATTTGGAGGGGGCAATACGGAAAGCAGCAAAAGGATAA

AseI amino acid sequence (SEQ ID NO:16)

MLRGLTVELLELKNRITTSFSGTEDDLREVLDLIEQDQPVFPFNEYEHLICNLIEKG
GLNYNQYIEIRSEYISQNPNLWIFEISAPRGFGEKFAQTYVKGKCSKLKTPSKKLDP
NYAGEYDLWLDGITIEVKASRAVDSNSEEPLYVKALARDTNRQFIMNFQQLKPQYCD
VFIWVAVFRDEIVLWIMSSDEVEKNPFYSKGQHRGNKGNEGQLHIKHDKIHLFSKYE
LKDDDLEGAIRKAAKG

AspCNI DNA sequence (SEQ ID NO:17)

ATGTTTACAAATCTAGACAAGCATCATGGTGGTAATTTTCGTGATGTATTAGAATAC
AATTTAGTTACTGCTAAAAAAGTAAGAATTGCATCTGGTTATGTATCTTTACATACA
ATACAAGCATATCGTACACAATTGGAAGACATAGCTTGTAGGTATGGAAATGTTCAA
CTAATGTTGGGAATGGCTTTTTATGAAGGTCTTTCAGTTAAGCAATTAGATGCTTGT
TTAGATTTACATAATAGCCTGTCACTACACCCTAACTCTGGTGTGTATGTCGCGCAT
GGACGACGATATCATGGAAAAATATACGATTTTAATGAAGGTGTTGATAATAAAATT
TTTGTAGGATCCTCTAACTTCTCCCCTAGTGGTCTAGCAGGTAATATTGAATGTACT
GTTGAAGTTATAGATCGAAGTCAAAAAGCTCAAGTTAATAACTTTCTTGATACCCTG
TTTGATAAGCATTCTGAAAAAATAAATAATGTTGTAATTAATACAGGCACAAAAAGA
GTTGTGAGCCTTAGTATTGATGAAAAGTATCGCAAACTTCTTAGACATTCACGAACT
ATAAATACAGCTTTGAATAAGGTTGAGATAGATCTCGAACGTATAGCAGAAAAGCCA
AGTTCAAATTTAAACGTGTATTTTGGTAAAGGTAGAGAAAATAAACAAACTGGAAAG

Figure 2-6

ATCATTCCTCGTCCGTGGTATGAAATAGAGATCATTTCTAGTAACGATATCAATAGT
TTACCTGATTATCCAAAAGGTGACTTCTATGCATATACGGATGATGGCTTAATTATT
CCTATGAGAACTCAAGGGGACTATTTAAAAATTTAAGATCAAAAGATAGCCTGCAA
ATTTTTGGTATGTGGCTGAAGGGAAAACTAGAAAAAGCGGGAGTGTTAAAAAAATAT
ACGCCTGTTACGATTGACACTTTAAGGGAGTATGGTAATAGCAAGCTAACACTTTAT
AAAATAAGTGAAAATGAGTATTTTATGGATTTTTAG

AspCNI amino acid sequence (SEQ ID NO:18)

MFTNLDKHHGGNFRDVLEYNLVTAKKVRIASGYVSLHTIQAYRTQLEDIACRYGNVQ
LMLGMAFYEGLSVKQLDACLDLHNSLSLHPNSGVYVAHGRRYHGKIYDFNEGVDNKI
FVGSSNFSPSGLAGNIECTVEVIDRSQKAQVNNFLDTLFDKHSEKINNVVINTGTKR
VVSLSIDEKYRKLLRHSRTINTALNKVEIDLERIAEKPSSNLNVYFGKGRENKQTGK
IIPRPWYEIEIISSNDINSLPDYPKGDFYAYTDDGLIIPMRTQGDYFKNLRSKDSLQ
IFGMWLKGKLEKAGVLKKYTPVTIDTLREYGNSKLTLYKISENEYFMDF

AvrII DNA sequence (SEQ ID NO:19)

ATGGAAGAAGACCTTGATTTATCTGAAAATATCGAAGCTGCATCTGCGGAGCTTACG
ACTCTTTATCAGGTAGCTGCTGATGCTATGAAAGATTATATTGAAATCTATCTTGCG
CTGAGTAAACAGTCTGATGGGTTTTCAAATATTAACAATCTTGACTTAACTTCTCGT
AACAGGCGTTTGGTAGTTATACATGGACTTTCGTTAGAGTTAGATCCAGATACTTCG
ACTCCAGAGGAAATTAAACGTGAAGCTGAACGAATGCTAGCGATAGCTCTTGATACA
GAGTCAGCAATTACGGCAGGAGTATATGAAAAAATGCGTCTCTTCGCAAGCTCTTTA
GTAGATCAGCTATTTGAACAAACGGATGAACTTAATTCATTATCATCGGAATATTTG
TCAGCAAATCCAGGATTTTTGCCGTTTTTCCAGCAGTTGGCGGGGCTTAGAAGTAAA
TCAGAGTTAAAGAGAGAAGTAGGAAATGCCTCTGACAATAGTATTTCTAAAGCGGTT
GCAGAGAGAATATTAGAGCGCATTATACGTAACTTGAGAATTCGCACTTTTTCCAAA
GAGAAACTATTACAAGCTGTTGAGCCTACTTTAGAAGGAATAGTCAGGGATCTCGTA
GGAAAAGTGTTATTGGAAAATATAGTTGCTGATGCTTTATCTGATTTACAAGTTCCT
TTCATGCGTGAATCAGAGTATCAAAGCCTTAAAGGAGTGATTTATGATTTCCGCGCT
GATTTTGTGATACCAGACGCACAAAATCCAATTGCTTTTATCGAGGTGCGAAAAAGC
TCTACACGACATGCGTCACTCTATGCCAAGGATAAGATGTTTTCAGCGATTAATTGG
AAAGGAAAAAATAAAAGGCTTTTGGGTATTTTGGTTGTGGAAGGACCTTGGACAAGA
GAAACTCTTCGCGTCATGGCAAATGTGTTTGATTACGTTACACCTTTAACTCGTGTT
TCCCAAGTTGCAGAAGCTATCAGAGCATATCTAGATGGGGATAAAACGAGACTGAAG
TGGTTAGTTAATTTCAGTATTGAAGAAGCAGACCACGACAACATAACCTAA

AvrII amino acid sequence (SEQ ID NO:20)

MEEDLDLSENIEAASAELTTLYQVAADAMKDYIEIYLALSKQSDGFSNINNLDLTSR
NRRLVVIHGLSLELDPDTSTPEEIKREAERMLAIALDTESAITAGVYEKMRLFASSL
VDQLFEQTDELNSLSSEYLSANPGFLPFFQQLAGLRSKSELKREVGNASDNSISKAV
AERILERIIRNLRIRTFSKEKLLQAVEPTLEGIVRDLVGKVLLENIVADALSDLQVP
FMRESEYQSLKGVIYDFRADFVIPDAQNPIAFIEVRKSSTRHASLYAKDKMFSAINW
KGKNKRLLGILVVEGPWTRETLRVMANVFDYVTPLTRVSQVAEAIRAYLDGDKTRLK
WLVNFSIEEADHDNIT

BbvI DNA sequence (SEQ ID NO:21)

ATGACAGAAAGAAAAGTCTGGTTTATTACAAGACCGGAGCGTGATCCAAAGTTTCAC
AGGGAARCCCTTCTGGCTCTGCAGAAAGCAACAAACGGCTTCACAGTAAAGTGGTCC

Figure 2-7

GKAAACCGCACAGCACATCTCGCATATGAGCAGGCGCTGGCCGATGCTGAGGTAAAG
CGTCCAAACATCAGTAATGATGGCTCTGGTGGACGAACATGGGCCGCAATGCTGAAG
ACATTTGCCTACTGCTATACAAACGAAGAGGGCTACCTTGTACCGACCAAAGTCGGA
GAAGCACTGTTAAAAAGGCACAAAGTATTCGACAACGTTAAAAAACAGATTCTCACT
CTTCAGATTCCGAATGCCTATTTTCTGGAGGCCGGATTCCGGCCAAAATTTGATGAA
TCTTTCCGTATTCGTCCAGCCCGGTTCCTGATCCGCCTAGTAAATCAAGAGGAGCTG
GCCTACCACGTCACGAAAGAAGAAATTACTTTCTTTGCGCTAACAGCATCAAAGGAC
AGCCAGTTGTCAGAGATTACAGCAAAAATCAAAGCATTTCGCGTTGCTTCTTCTGCT
GAAAGACTAGAAATGAAAGCAGACATCGCTGCTCAATATGACCATCGTGAGCGAACA
GATAAAGGGGCGCGCGATTTTGAGACTGCTCACTCTGATGTTGCCCATACCTTTATG
CTAATCTGCGACGCCACAGGAATGGTTGAGTACATTCGCGGTCAATCCCTGAGGGTA
AATCCAGAAGAAAATCAGAAGCTTAGCCAGGAGTTGGAGGAGCTGGAGGCACGGTAT
CCCTTCAACAACCGATACAAAATTTCCCTAGAACGGATGGCAGAAAACAATGGTCTT
GATGTCGAAAGCTACAAGGCGAGCCGTAATAGCGGAAAAGGACAAGCGACAAATGCA
GCAAAGAGACTGAGAAAAATAAACGAAATCATGAACGCGTATCCCAATCCCGCTGCT
TTGCCGCAGGAAGAACTGGAGAGAATCCTCGCAGAAGAGGTCGGTCCGCGTGAAGCT
CAAAAGTATGCATTCGAATTAAAAGAAAGTCAGGTAGCCTTCAGCGGACTGAATACA
GAGTTCGTAGAGAGTTATCTGTATGAAGAAGACAATCTCCGATTCGAAGACAAAACA
GGGGAAGTGCTCAAAGCGATCGGTTTTGACGTTGAAATGCGGCCCAAACCTGCATCC
ATGGAGCGAACAGAAATTGAGATCATGGTGAAGTATGGCGATAGGCAGTGCGGTATT
ATTGATGCCAAGAACTACCGGCAAAAGTTTGCTCTTTCTGCCTCACTGACATCGCAT
ATGGCATCCGAGTATATACCGAACTATCAGGGATACAAGGGGCTTAATGTACAGTTT
TTTGGATATGTAACCGCTGCTGACTTTTCTGGCGAAAAAAATCTTGAAAAAATCAGC
AATAAAGTACAGGAACACACTTCTAGCAGAGACATAAAAGGACTAATGCTCAGCGCT
AAAGTATTGCTTGGATTTCTTGATTACTGCTTAGAGAACGATATTCCCGAAAACGAA
CGTGTGAATCTGTTTATACGCGCTGTCCAAAACCGGGGCTACAAAACGCTGGGAGAG
ATGCTGAAAGAAGCTAAATACTAA

BbvI amino acid sequence (SEQ ID NO:22)

MTERKVWFITRPERDPKFHREXLLALQKATNGFTVKWSXNRTAHLAYEQALADAEVK
RPNISNDGSGGRTWAAMLKTFAYCYTNEEGYLVPTKVGEALLKRHKVFDNVKKQILT
LQIPNAYFLEAGFRPKFDESFRIRPARFLIRLVNQEELAYHVTKEEITFFALTASKD
SQLSEITAKIKAFRVASSAERLEMKADIAAQYDHRERTDKGARDFETAHSDVAHTFM
LICDATGMVEYIRGQSLRVNPEENQKLSQELEELEARYPFNNRYKISLERMAENNGL
DVESYKASRNSGKGQATNAAKRLRKINEIMNAYPNPAALPQEELERILAEEVGPREA
QKYAFELKESQVAFSGLNTEFVESYLYEEDNLRFEDKTGEVLKAIGFDVEMRPKPAS
MERTEIEIMVKYGDRQCGIIDAKNYRQKFALSASLTSHMASEYIPNYQGYKGLNVQF
FGYVTAADFSGEKNLEKISNKVQEHTSSRDIKGLMLSAKVLLGFLDYCLENDIPENE
RVNLFIRAVQNRGYKTLGEMLKEAKY

BbvCIA DNA sequence (SEQ ID NO:23)

ATGGGGGTAGTAATGATTAACGAGGACTTTTTTATTTATGAGCAATTGTCTCACAAG
AAAAATTTAGAGCAAAAGGGGAAAAATGCATTTGATGAAGAGACGGAGGAACTTGTA
AGGCAAGCCAAAAGTGGCTATCATGCCTTTATTGAAGGAATAAATTATGACGAAGTA
ACAAAACTGGATCTCAATAGTTCTGTAGCTGCATTAGAAGATTACATCTCCATTGCG
AAAGAAATAGAGAAAAAACATAAAATGTTTAACTGGCGAAGTGACTATGCTGGAAGC
ATTATTCCAGAATTTTTGTATAGAATTGTGCATGTAGCAACTGTGAAAGCTGGGTTA
AAACCTATTTTCTCTACGAGAAATACAATTATTGAGATCAGTGGAGCGGCACATAGG
GAAGGATTACAAATACGACGTAAAAACGAAGATTTTGCGTTGGGTTTTCATGAGGTA
GACGTTAAAATTGCAAGTGAGAGTCATAGAGTTATTAGTTTAGCCGTCGCATGTGAA

Figure 2-8

GTTAAAACAAATATCGATAAAAACAAACTTAATGGGTTAGACTTTTCGGCTGAGCGG
ATGAAACGCACATATCCAGGTTCTGCTTATTTTTAATAACCGAGACCCTAGATTTT
TCCCCAGATGAGAATCATTCATCTGGTCTCATCGATGAAATTTATGTTCTTCGAAAA
CAAGTGCGCACCAAAAACCGAGTTCAGAAGGCACCGCTATGCCCTAGTGTTTTTGCA
GAGTTGTTGGAAGACATTCTTGAAATATCATACCGTGCATCTAATGTAAAAGGACAT
GTTTATGATCGTTTGGAGGGAGGGAAGTTAATACGTGTTTAA

BbvCIA amino acid sequence (SEQ ID NO:24)

MGVVMINEDFFIYEQLSHKKNLEQKGKNAFDEETEELVRQAKSGYHAFIEGINYDEV
TKLDLNSSVAALEDYISIAKEIEKKHKMFNWRSDYAGSIIPEFLYRIVHVATVKAGL
KPIFSTRNTIIEISGAAHREGLQIRRKNEDFALGFHEVDVKIASESHRVISLAVACE
VKTNIDKNKLNGLDFSAERMKRTYPGSAYFLITETLDFSPDENHSSGLIDEIYVLRK
QVRTKNRVQKAPLCPSVFAELLEDILEISYRASNVKGHVYDRLEGGKLIRV

BbvCIB DNA sequence (SEQ ID NO:145)

TTTAACCAATTTAATCCGTTAGTATATACACACGGTGGAAAACTTGAACGGAAGTCT
AAGAAGGATAAAACAGCAAGTAAGGTGTTCGAAGAATTTGGTGTGATGGAGGCTTAT
AATTGTTGGAAGGAAGCTTCCCTATGTATTCAACAAAGAGACAAGGATAGCGTTCTT
AAACTTGTAGCAGCTCTCAATACGTATAAAGACGCAGTAGAACCAATTTTTGACTCA
AGACTGAATAGTGCCCAAGAAGTTCTCCAACCGTCGATTTTAGAAGAATTTTTTGAA
TATCTGTTTAGCAGGATTGACTCTATTGTTGGAGTGAATATTCCAATTCGACATCCA
GCGAAGGGTTATTTAAGTCTCAGCTTTAATCCACATAATATAGAAACGCTCATCCAA
TCGCCGGAGTACACTGTAAGGGCGAAGGATCATGATTTTATTATTGGTGGGTCAGCG
AAATTAACCATTCAAGGACATGGCGGGGAAGGAGAAACAACCAACATTGTGGTTCCT
GCTGTAGCGATTGAATGCAAGCGGTACCTTGAACGAAACATGCTAGATGAATGTGCT
GGTACTGCTGAGCGCTTAAAAAGAGCAACACCATATTGTTTATACTTCGTAGTTGCG
GAGTACTTAAAACTAGATGATGGAGCACCGGAATTAACCGAGATTGATGAGATTTAC
ATACTTCGGCACCAGCGGAACTCAGAGCGGAATAAGCCAGGATTTAAGCCTAACCCC
ATAGATGGTGAACTGATTTGGGATTTGTACCAAGAAGTTATGAATCATCTTGGGAAG
ATTTGGTGGGATCCAAACTCAGCTTTACAACGCGGTAAAGTGTTTAATCGACCATAA

BbvCIB amino acid sequence (SEQ ID NO:146)

MFNQFNPLVYTHGGKLERKSKKDKTASKVFEEFGVMEAYNCWKEASLCIQQRDKDSV
LKLVAALNTYKDAVEPIFDSRLNSAQEVLQPSILEEFFEYLFSRIDSIVGVNIPIRH
PAKGYLSLSFNPHNIETLIQSPEYTVRAKDHDFIIGGSAKLTIQGHGGEGETTNIVV
PAVAIECKRYLERNMLDECAGTAERLKRATPYCLYFVVAEYLKLDDGAPELTEIDEI
YILRHQRNSERNKPGFKPNPIDGELIWDLYQEVMNHLGKIWWDPNSALQRGKVFNRP

BccI DNA sequence (SEQ ID NO:25)

ATGCCTAGAAAACCTGAATATAAGCCGTTGCTTTACACGACTACGATACGAAATCCT
GAGCGTTTTAAAGATTTCATGCACATACTTAAACGATTCAATGGCCGGATACTTAAT
AATAAAACAGTCGAGTTGTTCGAGAGAGAACTGTTTAAGGTTGGCTTGTATCGACCA
ATGAAGCGCCCGGAAACAGTTCAGGATAAGTGGAAATCAACAAAGAACGGGGAATTA
GCCAGCAAACCATTAACAGATGAAGAAACGAAAGATGTGTATCAGCAGAATGATCCC
CAAGTCAACAAAAGTATAAAGGGACATAAAGAAGCAGGGTTTCCTAAAGGGTGGCCG
AGTCGATTTGACACACAATTCAAATTGATGAAAGTTCTGGGCTTTGTATATTATGAA
TGGGGAAAGCCTATAAACTTCTCTCAAACAGGTAACTATCTTGCAGATACTGTATCC
ATTGAAATAGATTCAGGAGCAATATCTCGCGAGATTGTAAATCCACAGAATGAGCAA

Figure 2-9

ATTGCATTTATGCAAGCTTTTGCCAAGCAACAAAGATGCAATCCGTTTATTTGTGAA
TTAAATGATAATATTCCACTGATATTATTGCTTGAAGTTATAAAGAAGTTAAACTCT
GATCCAGATTATAATGGTTCGGGAATCTCATATAAGGAGATACCTTTAGTTATCTTT
TGGAAAGATAATGATGCGGAATCTTTGTATCAGCGTATTAAACTTCTGCGAAAGGAA
CATAGGTACAATCCTTCAAATGAAGTGATAGAGGATATATGTGTAAACGAAATACTT
GGGGGATTCAAGAAATTTGATCTTGACTCTATTGTGTCCGAATATCCCGATGAATTT
GTCCGCAAAATGAGAATGACAGGACTTATATCATTTAGAGGGGGTGGTCGATTTATC
GACATTAACCATAATGAAGATGATAAGATAAATTATATACTGGCTAATTATGCCACA
TATCGCAAGTACACTTCAAAAGAAGAATATTTTGACTATATGTCAGACATTGATGAT
GCATTGTTTGCATTAAAAGCTGTCGAAATCCCCAAAAATGTCGCAGCTGATAAATTA
GCTAAACTCGTGGGTGATTACTCATGGGATTCTATTAAAAAAGAACTTACCCATTTG
GCGAAAAAAACATCATCAAGCCACAATATTTTAAGGTTTATTGCAGCTCCGGCAAGA
TTAGAGTTCCTGACCGCCCTTGCTATTAAGTCAAAACTGCCTGCTGTTGAGGTAATT
CCCAATTATCCATGTGACGATGAAGGTCTGCCAACCTCTACGGCTGGTGGGATATT
GGAGATATTGAGTGTTTCGAGGCTTCTAACAGTATATTGGTGGAAGTCACAATGTCT
GAAGGGCGTCAGCAGACAATGATGGAAGTATGGCCTATTGCGAGACATTTAAAGGAG
CTTAGAGAAAAATATGAATGTGAAAATTTCCAATGTGTGTTTCTGGCACCAAGTATA
TTTGTTGATTCTGAGAATCAGATAGACTGGGTTAAGGATAAAAAGCAGCTTGTTATT
CGTCCATACAAGATTGTAGATTTTATTAACTATCTGGATACAGCAGCATCTTTATAT
CAGATTGTATAA

BccI amino acid sequence (SEQ ID NO:26)

MPRKPEYKPLLYTTTIRNPERFKDFMHILKRFNGRILNNKTVELFERELFKVGLYRP
MKRPETVQDKWKSTKNGELASKPLTDEETKDVYQQNDPQVNKSIKGHKEAGFPKGWP
SRFDTQFKLMKVLGFVYYEWGKPINFSQTGNYLADTVSIEIDSGAISREIVNPQNEQ
IAFMQAFAKQQRCNPFICELNDNIPLILLLEVIKKLNSDPDYNGSGISYKEIPLVIF
WKDNDAESLYQRIKLLRKEHRYNPSNEVIEDICVNEILGGFKKFDLDSIVSEYPDEF
VRKMRMTGLISFRGGGRFIDINHNEDDKINYILANYATYRKYTSKEEYFDYMSDIDD
ALFALKAVEIPKNVAADKLAKLVGDYSWDSIKKELTHLAKKTSSSHNILRFIAAPAR
LEFLTALAIKSKLPAVEVIPNYPCDDEGLPTSTAGGDIGDIECFEASNSILVEVTMS
EGRQQTMMEVWPIARHLKELREKYECENFQCVFLAPSIFVDSENQIDWVKDKKQLVI
RPYKIVDFINYLDTAASLYQIV

BceAI DNA sequence (SEQ ID NO:27)

ATGGTACAAAAAAATAGAAGTAAAGAGGTATGGCTTGTTCCAAAAAGAGGAAGTTTT
CACCAAACGATTTGTTTAATAGAATCCCTTATAAATAGGAATTATGATCAAACACGT
TGGAATGAGCAAAAACAAAATAATATTGGAAATGATTTAAGAAAACGTGGGGCAGTA
AGGGAAAAAAGATCCCCTTCAAATCAATCTATTCGTACTTTACTTGCTTCAATTCCA
CAGTATTTAGGGTTTTTATACATAGATAGCAATACAACGCCTAATACTGTAAAAATC
ACAGATGCTGGTAGATACCTATATAATTTTCATAAAGATAGCATTGAGAATATCGGA
ACCTTAGGGGAAGGTAAAAAAAGTGGAGGTTTAATTGAAACTTCATCGGTATTTCTT
GAACAATTTGAAAAACTTCAAATCACTAATCCGGTAATATTAAAAGATTGTGAAAAT
ATTTTAGTCTTTCCATTTAGAGTTATTTTAAAGTTATTAATTGAATTAAATTATCTT
GATCGAGAGGAATTGGCGTATTTTGTATTTTCGATTAGGGATGAAAGTGAAATTCCA
CTTACAATAGAGAAAATAAAAAAGTACAGGAAACAAGATTTAATGGAACGAGATACT
GAAATTAAACTTTTTAAGGAAACACATATAGGTAATATTACTCTTGTAAAGGCATCT
TCAGCATCTTATTTTGAAAACCTGTGTTATAGTACGGGGATTATTGAGAGATTTAAA
ATTCAGATACCGAACCCTGGAAGCTCTGATTCCAATAAATTACCTGCAATTAAAATT
AAAGATGAACAAGAAGTTTATGTTAAAGAGGTTTTAAGTAGTAAATATGAAAATTCA
CAAGTATATAATTTTGGTAATAATTTAAAGTTATGGGTGGATTACATTGGAAATCCT

Figure 2-10

AATAGAAAGATACCACCAAGGGATATTGAGATTGAAAATAAAGGAAATAGCAATTTA
ATAATAATTATTGAACAAAATGGGGTAATGATAAAAGGTGATTTAATAAAAAGTGGT
TACTCATTAGTTTCTCCAATGTTCATAAATGAGAATTATGACATTATTTTTATAAGC
CCGGTGGATGGAACTGTTTTGGAAAGGGCTACAATCAAGCCGGATTATTTAAGTGGA
AAATATGAATTTAATATTAACTCAAACCTTAGTATTACTAATAATGAAAATATAGAT
GAAATAGGACAAATCATCAATGAACACTCTGCGGCAAAAACATTTGATAAGAATTAT
TTGTCTTATCTAGGAATTATAGGAGACATTATAGGAGCTGATTTAACCAATAATAAA
AACCTTAGGGGAGCTTATTATGAATATTTATTTTATAAATTATTGGAGCAGCTACGA
AAAGAAAAAATAATAGATGATGTGTATTGGAATGGTAAAGTAGGGGAATTTGGTCTT
CCAAGACCAGCGCCTGGGGGGAAGACAGGAACCCCAGATTTTATTTTTATTATTAAT
GATGAATTCTTTATATTAGAATTACCAACAATTAAGGCTAATTCTGCACAATTTAGT
GCTGAAGGTTCTTCATTACCAGACCACATTAATTTATTTGCGGAAGAACCTTCTGAG
GCAATTGTCTATGGAATTTATACTGCACCCACTATTCATGATCGGAATACATCTGCC
ATGAAAGCGATTCTTGATCCACTAGAAATTAATTTAAAATGTATTGAAGATAGAGAA
TTAGTAGATTTGTTATTATCTAAAGATAGAAATCTCATTTACAGTGAATTAACAAGT
GGTAAATAA

BceAI amino acid sequence (SEQ ID NO:28)

MVQKNRSKEVWLVPKRGSFHQTICLIESLINRNYDQTRWNEQKQNNIGNDLRKRGAV
REKRSPSNQSIRTLLASIPQYLGFLYIDSNTTPNTVKITDAGRYLYNFHKDSIENIG
TLGEGKKSGGLIETSSVFLEQFEKLQITNPVILKDCENILVFPFRVILKLLIELNYL
DREELAYFVFSIRDESEIPLTIEKIKKYRKQDLMERDTEIKLFKETHIGNITLVKAS
SASYFENLCYSTGIIERFKIQIPNPGSSDSNKLPAIKIKDEQEVYVKEVLSSKYENS
QVYNFGNNLKLWVDYIGNPNRKIPPRDIEIENKGNSNLIIIIEQNGVMIKGDLIKSG
YSLVSPMFINENYDIIFISPVDGTVLERATIKPDYLSGKYEFNINSNLSITNNENID
EIGQIINEHSAAKTFDKNYLSYLGIIGDIIGADLTNNKNLRGAYYEYLFYKLLEQLR
KEKIIDDVYWNGKVGEFGLPRPAPGGKTGTPDFIFIINDEFFILELPTIKANSAQFS
AEGSSLPDHINLFAEEPSEAIVYGIYTAPTIHDRNTSAMKAILDPLEINLKCIEDRE
LVDLLLSKDRNLIYSELTSGK

BclI DNA sequence (SEQ ID NO:29)

ATGCAACCAAATCCTAAATTTATAAATAAAAGCTCTGCATTTTGGGCTTATGCAAAA
CTGTTGTCTGAACAGTTAGGATATTCTAAAGATGGAGTAGTCATTAGTTATTCAGAG
GCACAGGCAAGAGCAAAACTTAAAAAACTAGGTATAAATGTAAAAGAGGGTATTTTT
AAAGATGTATTGAGGTACCTGAAATACAGAGCAGAATTACTAAATAAACATAAGGAC
TATCTAATGGATGTAGAAGAAGCAAGGAAATATTTCCAAGTAGCACTTAAGCAACAT
CAGCAGAATAATTATACTTGCAAACTTCCGCTTAACAAACAGAAAAATGAAAAGAAA
GATTATGCTTACTTTACATGCATTATTAATATTATTGCAGAAACGGAGCTAAGGTAT
TTTGCAAACAATAATGGTTTAGTTTATGGAAAAGACATTTATTTTGATGATAATCCT
ATGAATCTATCATATATATTAAATTTCAATAGAGAATTGGAAGGTATAATGTCCCGG
CGTTTTGATGGTGCTTTTCCAAGTACAGTAAATCCGATTCTAATTTGGGAAATTAAA
GAGTATTATTACACAACCACTTTTGGAAGTCGAATTGCCGATGGGGTTTATGAAACT
CAGTTAGATGGCTACGAAATAAAAACAATCAGGGAAGAAACAAACAAGAATATTCAA
CATATATACTTTATTGATGACTATAATACTTGGTGGAACATGGGTAAGTCTTATCTT
TGTCGGATCATTGATATGTTACATATGGGATTAGTGGACGAGGTAATTATGGGGAAA
GAGGTTTTCGAAAGATGGCCTCAGATTTTAAGAGCAGTACTTAATCAATACTATAAA
TAA

Figure 2-11

BclI amino acid sequence (SEQ ID NO:30)

MQPNPKFINKSSAFWAYAKLLSEQLGYSKDGVVISYSEAQARAKLKKLGINVKEGIF
KDVLRYLKYRAELLNKHKDYLMDVEEARKYFQVALKQHQQNNYTCKLPLNKQKNEKK
DYAYFTCIINIIAETELRYFANNNGLVYGKDIYFDDNPMNLSYILNFNRELEGIMSR
RFDGAFPSTVNPILIWEIKEYYYTTTFGSRIADGVYETQLDGYEIKTIREETNKNIQ
HIYFIDDYNTWWNMGKSYLCRIIDMLHMGLVDEVIMGKEVFERWPQILRAVLNQYYK

BfaIA DNA sequence (SEQ ID NO:31)

ATGGCAAAGTCAAAGATAAAATTTAATGATGTGTCTTCTGCTAATGGTACTCAGAAA
ATACAGCTTCCAAAATACTCTTCTCAAGTTATTAACCTTGCAAATGGTTATTCAAAG
GCAACCAGACCGGCAAACGTTGGACAGGTATCTGAAGATATAAAAACTTTCAGAGAT
GATGAGACTCTTATAGGATATACAAACCAAGATTGGATAAACTGGCATAAAAATAAA
TATCCAGAGGGCATACAAAAGGCTACTGATGCAACATGGGTTATGTTCCAAAAGATG
GTACAAAGTCTCAATACTGTAACTAAAGAAGATATTCAAAAGTGGGAAGAGGATTTT
GTATTTTCGAAAACCTATGATGGATTAATGGTCCAAAATGCCATCGTTAAGAAAATA
GCAGAAGAGATAAACACTCAAAACTATCGGTTAGCTTCACCCGAGGAAGAACGACAA
GGTATTGATGGCTACATAAATAATCATCCAGTCCAAATTAAGTCAGATACATATGAT
AGAACGGGAAGACTTCATAACGAAGAAATGCAATGTGTTGTAATATCATACCAAAAA
AGCAATAAGACTATAATATTTGACTACAATCCAGAAGATTTTCAATAA

BfaIA amino acid sequence (SEQ ID NO:32)

MAKSKIKFNDVSSANGTQKIQLPKYSSQVINLANGYSKATRPANVGQVSEDIKTFRD
DETLIGYTNQDWINWHKNKYPEGIQKATDATWVMFQKMVQSLNTVTKEDIQKWEEDF
VFSKTYDGLMVQNAIVKKIAEEINTQNYRLASPEEERQGIDGYINNHPVQIKSDTYD
RTGRLHNEEMQCVVISYQKSNKTIIFDYNPEDFQ

BfaIB DNA sequence (SEQ ID NO:147)

ATGAAGAAATTCAAGATTTCAAATGATGAGGTTACGGAGTTGTCAAATGCTCCTCAA
TATCAATTTCCAAAGTATGTGACTCAGGTTATTAACTTGGTAAATAGTAACGCTGGC
GGTACTCGCCCTAAGGTAGTTGGTCAGATGTCAGAACTGGTTAAAGAGTTTGATGGT
AGGACCATTGACGAGTGGATTGAGTGGTACACGGAGAGATACCCTGATGCAATTAAT
GATGCTACTGAAAAGATCTGGGCCATGTATGAGACCATGAAGGGTGCTTTCAATGCT
ATCACCAAAGAGATGGTCGAGAATTGGGTGAAAGATCTTGTCTATGGTAAAACCTTC
TGTGGTTTGAAATTTCAGACAGCTATTATTTCAGCGATAGCCAATCAGTTAGACAAG
TCTTGGAGAGAGGCTGATCCTGAAGAAGAAGCTCAAGGTATTGATGGCTTTATTGGT
GACAAGCCACTTCAGATTAAGTCTGCTACATATAAATTAGAAGCACGCCTTTCTGAA
ACCATCAATGCACCAATAGTGTACTACGACAAGAAGAAGGATGGCATAAGTATTGAG
TATAACCCAACTGACTTTTAA

BfaIB amino acid sequence (SEQ ID NO:148)

MKKFKISNDEVTELSNAPQYQFPKYVTQVINLVNSNAGGTRPKVVGQMSELVKEFDG
RTIDEWIEWYTERYPDAINDATEKIWAMYETMKGAFNAITKEMVENWVKDLVYGKTF
CGLKFQTAIISAIANQLDKSWREADPEEEAQGIDGFIGDKPLQIKSATYKLEARLSE
TINAPIVYYDKKKDGISIEYNPTDF

Figure 2-12

BfuAI DNA sequence (SEQ ID NO:33)

ATGAGCCATGATCTGCTGGCTTCAATATCAAGTGCTTCAATTGCTAACATTTTAACA
GATCAATCAACATTATTTACTTCAGAAACAATAAATAACCTCTCTATTTATGCTAGT
AGAGAAGGGAAAACTTCATGGCCTTTTGCGGATGGAGTAATTGTAATTGAAGAAGAG
GCAACCGTAAAATATAAGATGGCAGTTGAATTTAAAAGAGTTAATGAAGGAATTCAC
GGAATTTTAACTGCATTAGGCCAATCACAAGCGTATTTAAAAAAAGGTTATAATGGA
ACAATCATAATAATTCCAGAAGTGTATAATACTCATGAAGCACCTGGTGAGTATTTA
AAAAGTGTTCTTGATTTAGTTGGTGAAGATTTACCAATAATGATTTTTACTTATAAA
ATAAATGGAGAAAATGATTTAGAAGTTAACTGTATCCGCAATATTGATCTTTCTACG
ACGGCTATCGATTCTGACGATACTACCAATCAAACTAATACAATTAGTACACAGTGG
GCACACTTACGAGAGGGAAGCACAGAGCCAGATACTTTTTATAGATATTTACAAATG
GCAAAAAGAATAGATTTAACAGAGTTAAATGAACCTACAATTGAATTCCCTATTGAA
CTCTTAAACGCATTGCCGAATGATGTAGATCCTCTGAAATACTTATCAAATGCACCT
GGGGATACTTATCATGATTTTGTTTGGAGGCACTTTTGGTTTACATATATCATTAAC
GAAAGAACATTGCCTTTATTTACTTTAGAAGGGGACTTATACAAGGTATGTGATGCT
AGTTCTTCTTTATTAAAAAATGATGGTTTACCTAAGTATTTTTTGGTGGGTAAAAGT
AACTCTCCAAAAAATAAAATTATAGGAAAATTAAATGCTGGTACCATTAACGAGGAA
CAAGCTTGGGTAGAATATGCCCAGAAAATAAAAGACAGAGCACATAGCTTTAGAGAA
GATATAGATTCTTCACTCTATCATATAGGTATGATTGATGAAGATGGAAAGCCTACA
AGTATAGGTTACAAATTTGTAGATGCTTGTGAAAGAAATAGAAATGATAGTATAAAT
GGTACTCCGCTAGCTATTTTTGAAACAGCAATAATCCAGCACGGGGAATTAGGTGCA
TTTATTCATTACATAAGCTTAGCCTCACAAAAGATTTTTAAAGACACTCCATTAAAG
TATAGTGTGATAGAAGGAAATGAATTTAAGTCATTTAATTCGAATAATTATTTAAAA
GAAGTAGAAGAAATATTAGCTAATGATATAAAAGTTATTAGAAAAGTTTCTTTACGT
GGAGGAGTGGGGAGAAAACCTTTCCAAGCAGAATTAGCAGTTTTAGGTTTTTTAGGT
TTCTTTAAAAAAGGTAGAAATAGATTTAAACCTGTTGTTGGATTAGATATCGATTGG
GAGAAAGTATATACAGCTTTAAACCGAGAAATTTAA

BfuAI amino acid sequence (SEQ ID NO:34)

MSHDLLASISSASIANILTDQSTLFTSETINNLSIYASREGKTSWPFADGVIVIEEE
ATVKYKMAVEFKRVNEGIHGILTALGQSQAYLKKGYNGTIIIIPEVYNTHEAPGEYL
KSVLDLVGEDLPIMIFTYKINGENDLEVNCIRNIDLSTTAIDSDDTTNQTNTISTQW
AHLREGSTEPDTFYRYLQMAKRIDLTELNEPTIEFPIELLNALPNDVDPLKYLSNAP
GDTYHDFVWRHFWFTYIINERTLPLFTLEGDLYKVCDASSSLLKNDGLPKYFLVGKS
NSPKNKIIGKLNAGTINEEQAWVEYAQKIKDRAHSFREDIDSSLYHIGMIDEDGKPT
SIGYKFVDACERNRNDSINGTPLAIFETAIIQHGELGAFIHYISLASQKIFKDTPLK
YSVIEGNEFKSFNSNNYLKEVEEILANDIKVIRKVSLRGGVGRKPFQAELAVLGFLG
FFKKGRNRFKPVVGLDIDWEKVYTALNREI

BlpI DNA sequence (SEQ ID NO:35)

ATGTTCGTTCATGGAGATAATTTAACGCAAAAAGAAAATCATCGTACAAAATATACA
GATGGTTTGTCTAAACAATATTTAACAGAAATAAGAGAAAAATATAATGAATGGAAA
AAAGCCAACGAAGAATTGATAGGTCCTTTTGCTGAGGCAACGCCTGAAGATGAAGCA
ATAGTGAAAAAAAGAGTAGAATTGCTGAATGATTATAAAGATTTTGTAGACCAACAA
CACTATGCGGAAAAAATTTGATTCACGTTCGAACCTACATTCCTCAATTTTAGAAGAA
TTTGTCTACTACCTGTTTAAGGATATAGCAAAAAGTTTTAATGATGAAGCCATTGTA
GGTAAATCACATGCTTTTAAAGATTTGTTTATAAATCCTAGTAGTTATAAAGATATG
GTAACTCAACCAAATGTAAAGGTAGAAATTAAGGACCATGATTTTATTATTGGTGTA
GGAATTGAAGCAAAAAATGATTGTCAAAGGTTCAACTGAAATTGAAAATCATACTTTA

Figure 2-13

GAAGTAGCGGCGGTTGCGATTGAATGTAAAACATATTTAGATAAAACAATGCTAGAG
GGTTCATCAGTTGCCGCAGAACAATTGAAAAGTAGGAATCCTAACGCAAAATATATT
GTAGTATCAGAATGGTTAAAGCTATCTGAACAAGTAAACCTTCAGAAATATAAAGTT
GACCAAATTTATGTTTTGAGAAAACAAAAAAATACTGATAGAGAATTTAGATATGCT
GACACGTACGTGAAAAATGCTATTCATGAAGATGTAGTTTTACATTTATTCCATACA
ATAAGATTACACTTAACTACTGAATGGGATGGGTCTATTAGCCATGGTATTGATAGA
GGTTACCTACTATAG

BlpI amino acid sequence (SEQ ID NO:36)

MFVHGDNLTQKENHRTKYTDGLSKQYLTEIREKYNEWKKANEELIGPFAEATPEDEA
IVKKRVELLNDYKDFVDQQHYAEKFDSRSNLHSSILEEFVYYLFKDIAKSFNDEAIV
GKSHAFKDLFINPSSYKDMVTQPNVKVEIKDHDFIIGVGIEAKMIVKGSTEIENHTL
EVAAVAIECKTYLDKTMLEGSSVAAEQLKSRNPNAKYIVVSEWLKLSEQVNLQKYKV
DQIYVLRKQKNTDREFRYADTYVKNAIHEDVVLHLFHTIRLHLTTEWDGSISHGIDR
GYLL

BmrI DNA sequence (SEQ ID NO:37)

TTGAACTATTTCTCTTTGCATCCTAACGTATACGCAACTGGTAGACCAAAAGGATTA
ATAAATATGTTAGAATCCGTGTGGATATCAAACCAAAAACCCGGTGACGGGACTATG
TATTTAATTTCTGGATTTGCAAATTATAATGGTGGAATAAGATTCTACGAAACATTT
ACAGAACATATTAACCATGGTGGTAAAGTTATCGCCATTTTAGGAGGCAGCACCTCC
CAAAGATTGTCAAGTAAACAAGTTGTAGCAGAATTGGTATCTCGAGGTGTAGATGTA
TACATCATTAATAGAAAACGACTTCTTCATGCTAAACTATATGGTTCCAGCAGTAAT
TCTGGAGAATCTTTAGTAGTTTCTTCTGGTAACTTTACTGGTCCAGGCATGTCTCAA
AATGTTGAAGCCTCATTATTGTTAGATAATAATACAACCTCATCGATGGGATTTTCT
TGGAATGGTATGGTCAATTCAATGCTTGATCAGAAATGGCAAATTCATAATTTGAGC
AATTCCAACCCTACATCACCTAGTTGGAATTTATTGTATGACGAACGCACAACAAAT
CTAACTTTAGATGATACTCAGAAAGTGACCTTAATTCTTACCTTAGGTCATGCGGAT
ACCGCAAGAATTCAGGCTGCACCAAAAAGTAAGGCTGGAGAGGGATCTCAATACTTT
TGGTTAAGTAAAGATAGTTATGACTTTTTTCCACCTTTAACAATCCGAAATAAACGT
GGGACTAAAGCAACTTATTCTTGCCTTATAAACATGAACTATTTAGACATAAAATAT
ATTGATAGCGAATGTAGAGTCACTTTTGAAGCAGAAAACAATTTCGATTTTAGGTTA
GGAACAGGAAAACTTAGATACACAAATGTAGCAGCAAGTGATGACATAGCTGCAATT
ACTCGTGTAGGTGATTCAGATTATGAATTAAGAATAATTAAAAAAGGAAGTTCTAAT
TATGATGCACTTGATTCAGCTGCAGTAAATTTTATAGGTAATAGAGGAAAAAGATAC
GGATACATACCTAATGATGAGTTTGGGAGAATCATAGGAGCTAAGTTTTGA

BmrI amino acid sequence (SEQ ID NO:38)

MNYFSLHPNVYATGRPKGLINMLESVWISNQKPGDGTMYLISGFANYNGGITFYETF
TEHINHGGKVIAILGGSTSQRLSSKQVVAELVSRGVDVYIINRKRLLHAKLYGSSSN
SGESLVVSSGNFTGPGMSQNVESSLLLYNNTTSSMGFSWNGMVNSMLDQKWQIHNLS
NSNPTSPSWNLLYDERTTNTLDDTQKVTFILTLCHADTARIQAAPKIKAGEGSQYFW
LSKDSYDFFPPLTIRNKRGTKATYSCLINMNYLDIKYIDSECRVTFEAENNFDFRLG
TGKLIYTNVAASDDIAAITRVGDSDYELRIIKKGSSNYDALDSAAVNFIGNRGKRYG
YIPNDEFGRIIGAKF

Figure 2-14

BsaJI DNA sequence (SEQ ID NO:39)

ATGACTTTTGATAAAATTGCAGTCAAACAGATCTTGTTAAGGCTTCTAAAAGGTGAA
GATTATAGAGGAGAAGTACTTAACATTATTAATGCTGACTTTTTAGACTTTGCTTTG
CAGTTTTTTAAAGATGTCGCTTTAGCAAAACTTCAAAATGAAGAGTTAACCGATGAT
TGGTATAAAAAATATTTTATTCAAAATCCATCTCTCACAAAAGAAAAGGTTGCTATT
TACTCAGGTTTAAACATGAAGACAATAAGTAATACCTATAAAACTACAGCAAAGAAT
GTAGTTGTTGATGCCTCATTAGAGCATTACGATGCATTTGTAAAAACGATCCAAGAA
TTAATAGAAATTGATGATTCTTTAGAACTAATGTTAACTATTAAGTATAACAAGGTT
AGTGTTGAACTTACTCTTAGTGAGTCTTTAATAGTAATGAATGTATTAGCAGTTAAA
AGGGCAGCTATTAGAGGAGGAGCATGGAGTACAGCGGGAAAACGAGTTGAAAAACTT
TTAATGCTAACATTGTGTAAGCTATTTAGGGTACCGGATAAACATTATAAAAGTATT
TATGTAGCGCAATTAAAAGATGAGAACGATTTTAGTAGAGAAATTGATTTTTATTTG
ATTGACCAAAACAACAATGAATTAAAATGCGAGGTCAAATTAATGGGAAAAGGAAAT
CCAGAAAGTGCTGATGCGGTAATCGCTCGTGACAGTAAGATTTTTGTAGCAGATACA
TTATCAGAAACAAATAAGAAACAATTAGATTTTTTAAAAGTTGAGTGGGTTGAGCTT
AGAAGCGAAAAAGGCTATGAAAAATTTAAAACTATTCTTTCTAACAGAGGAATTCCA
TATGAAGATATAGAAGAAATCACTCCAGAATATCTAGAAAAAGTCATTGATGAGTCT
TTAGGAATTTAA

BsaJI amino acid sequence (SEQ ID NO:40)

MTFDKIAVKQILLRLLKGEDYRGEVLNIINADFLDFALQFFKDVALAKLQNEELTDD
WYKKYFIQNPSLTKEKVAIYSGLNMKTISNTYKTTAKNVVVDASLEHYDAFVKTIQE
LIEIDDSLELMLTIKYNKVSVELTLSESLIVMNVLAVKRAAIRGGAWSTAGKRVEKL
LMLTLCKLFRVPDKHYKSIVAQLKDENDFSREIDFYLIDQNNNELKCEVKLMGKGNP
ESADAVIARDSKIFVADTLSETNKKQLDFLKVEWVELRSEKGYEKFKTILSNRGIPY
EDIEEITPEYLEKVIDESLGI

BscGI DNA sequence (SEQ ID NO:41)

ATGAGGTACAATCCAGCAGAGCAATTTAGATGTACTATTATTAGAGGAAAAGCGAAA
AATGCTCTTGATAACCTATTGCCAGCTTATGCCAAGATCATTTCTGATATTTGCCCA
TGTAGTAAGAAAGAGTTCCCTTCGGCATTCAATCAAAGGCTTAACGAGGTTCTTGGT
GAGAGCACGAAAAAAACTTTAGATAATCACAGAACAGAAATTGCTGGTAAATTATTT
GGAATGTTTTATGAGGATGACAATGGGATAGTTTTTCTTCTGAGAGAACTGAAAAG
TATTTAAAGGACTCAGACCAGCCAGCTTTCTTCAAAGATTTGTGTTTTAAGTTCCAG
TTTCCCAATGGTATGGATAAGATAGATAACGTATTAGAAAAAATGCGATTTAAAATA
TCAATTAGGCAGTTTCCTTATATTCTTCAGCTTTTATTGTTAGCTAGTGAAAAAGGA
ATTAAATTAACAAAGGATGAAGTAGGGTATTATGTTTTAAATTCTCTTCACGTTTTA
CAAGGGCAAATACATCCGACTATTGTATTGGAACAAATCATTGCTGATCGAAGGGCA
GGAAATATAAAGAAAGTAATGGTTCCTGGTAAAGCCTCTTCTTATTCTGTACAGCAT
ATAAACGAGCAATTAAACTATTTAGAATTGGCTAACTTGATTAGGATTGATGATAAA
GTTATTTCCATTAATTTTAAGGAATCTGAAACAATTGAATTGATGGCATCTTTTTGG
AATAAAAAGCCTGAGTTCGATGCATATAAATACAATTTGGAAGATAGAGAACAAAGA
AAAAGATTTTATAAGGATTGGCAATTATATTATTCTAATTTAAATAAAGTGAAAGAG
TTCCAAACGACAGTTGAATCCCTTAACATCTCACTTGATACTTCTACTCCTTCTACC
CATATTGATAAAACTGCTATTGGGGATGAAGGAGAGAATTTTGTTTTAGAATATGAG
AAGAAAAGAGTTAGTAAGTTCGACCCAAGATTGGTACAAAAGGTAGTACCTTTAGGT
AAAACCAGAGGATTAGGGTATGATATTCAATCTGTGATTGCTGAGCCTGGAGAAAAT
GCTGAGTTCGTTAAGTATATTGAGGTTAAAACAACTAAGCGAGTTACTGTCCCAGAT
GTCAATGATCCAACTTGGATTGATACCATTAATTTAACTAGAAATGAGTGGATTGCA

Figure 2-15

GCTGCACAACATAGAGAGTTCTATTCTGTATACAGGGTTTATCTAACTCCAGAAAGG
GTTACTGTATTTGTAATAAATGATCCATTTACTAAAAATAAAGACAACATAATTAAA
TGCAAACCTTTAACATATAGGTTAGATTTTTCACACGTAGCAATTGATAATGTTTTG
CAATAG

BscGI amino acid sequence (SEQ ID NO:42)

MRYNPAEQFRCTIIRGKAKNALDNLLPAYAKIISDICPCSKKEFPSAFNQRLNEVLG
ESTKKTLDNHRTEIAGKLFGMFYEDDNGIVFSSERTEKYLKDSDQPAFFKDLCFKFQ
FPNGMDKIDNVLEKMRFKISIRQFPYILQLLLLASEKGIKLTKDEVGYYVLNSLHVL
QGQIHPTIVLEQIIADRRAGNIKKVMVPGKASSYSVQHINEQLNYLELANLIRIDDK
VISINFKESETIELMASFWNKKPEFDAYKYNLEDREQRKRFYKDWQLYYSNLNKVKE
FQTTVESLNISLDTSTPSTHIDKTAIGDEGENFVLEYEKKRVSKFDPRLVQKVVPLG
KTRGLGYDIQSVIAEPGENAEFVKYIEVKTTKRVTVPDVNDPTWIDTINLTRNEWIA
AAQHREFYSVYRVYLTPERVTVFVINDPFTKNKDNIIKCKPLTYRLDFSHVAIDNVL
Q

BseYIA DNA sequence (SEQ ID NO:43)

ATGAAATTGGGTGAAATAAATCTAAAAAAGTTTTTGGAGGAAAAAAAAGGAATAGTT
TACGGCGAACTCGTTCAAGATGCTAAACTACGCTGGTATACGAGAGAATATGAATAT
GCGATATTGAAAGATAATAAAATGGAGATATGGCCGAAGGGTAAAGTAGCAAATAAA
ATCGTTCTACCAACCAAAATAATTTTGGATTCAGAATTGGTTACCTTCTTTGGATTA
TATAGTGGTGACGGCGCAAAAGGCACGGAAATTATAAATAAACCCGGGAGAATTACA
ACTTCTATCTCTTTTTCTCAAAAGGAACCTCATTTAATTAAATTTGCTATAAATCAA
TTCAGGAAAATTTTTGGGGATAATATTTGGTTTGATTTTTCTTTAGGTGAGGACAGT
GCTTATTTCATGGATGAGGATGGGCATAATAGAATTAAATCTGTTCTAAATGATGAT
GTACCATTGGTAATGGAGTCTCTTAATGAATTAAATGTTAATTTAAGTGCGGCAGAT
ATAATATATTTAAATGAGCAAAGGAATGTTTCAATTACTAACGAAGAAGCCTTGGCA
TTTCATTATCAATATAATAATGAAATGCAAAAATATTTAATAGATGTAAAAATGAAT
GATTTAAATGATGTTGGAATTACACTTGGTCCTAATGACCGAGTAAATGCATCTTTA
CGTCGGCCATTCAAAAAAGGCGCAAGAACAATGGGGGAAGTAGCAGATCTGATGAA
CTCTATGTTAAAGGGGTTTCTTTATTTGGGGAGCTATTTTTAAAAATTCTCCATAGT
ATAGAGGAATCTATTTTGAATGATACACAAGAATCAACAGACACTTTAATAAAATGG
GATGGTAAACCATCTACGATAGGGGAAGTTATTGACCTAAAAAATCACTTTTTGGAA
AGTCCTTATGCAGAAATTAATGGTTCTAAGCCAATATTAGAAGAGGAAGCACTCTAC
CTAATTGGAAAATATCCAAGAGGTTCGTTGGTGAAATTAAATAAACGGTTGCGTCAA
ACTCCATTATGGCTGTATGCTGCGGGGCTTTATTTAGCAGAGGGATCTACTGCAAAA
GAAAAAATGTTTCAGATGTATACAAGTAGAGCTAGAGGGCTATCACTAAGCTTTACT
TCTTCTGAACCGTATAGCCTAGAAATTATAATTAAAGCGTTAGAGCTATTATTTTTC
GACGAGCAAATTTTAAGTAGCTGGAAAGTAAAAGTTGGATCCCAGTATTTTCCTGAA
CTAGTCACCACAGGGTTAAAACTTGGTGTCCCTATGTTAAGGGGGGGGCTAAGTGGT
GACGGGAAGTTGAGAACTATGGAAATTTCACTTAGTATTAAGAGATGGGCATTGGAG
ATTGTACCCTTTTTCAGCAAATATGAGGATAGGTTTAGCCATGTTGAACCTACAGGC
GCAGGGGTAGCAAGAATAGATTTTTCAGGATCATCAAAACTATGTAAATGGTATTTT
GGGTTAATAATTTATTCGGCATTTAAGAATACTACTAAAGATCCAAAAGGGGAATTT
TAA

BseYIA amino acid sequence (SEQ ID NO:44)

MKLGEINLKKFLEEKKGIVYGELVQDAKLRWYTREYEYAILKDNKMEIWPKGKVANK
IVLPTKIILDSELVTFFGLYSGDGAKGTEIINKPGRITTSISFSQKEPHLIKFAINQ

Figure 2-16

FRKIFGDNIWFDFSLGEDSAYFMDEDGHNRIKSVLNDDVPLVMESLNELNVNLSAAD
IIYLNEQRNVSITNEEALAFHYQYNNEMQKYLIDVKMNDLNDVGITLGPNDRVNASL
RRPFKKGARTMGGSSRSDELYVKGVSLFGELFLKILHSIEESILNDTQESTDTLIKW
DGKPSTIGEVIDLKNHFLESPYAEINGSKPILEEEALYLIGKYPRGSLVKLNKRLRQ
TPLWLYAAGLYLAEGSTAKEKMFQMYTSRARGLSLSFTSSEPYSLEIIIKALELLFF
DEQILSSWKVKVGSQYFPELVTTGLKLGVPMLRGGLSGDGKLRTMEISLSIKRWALE
IVPFFSKYEDRFSHVEPTGAGVARIDFSGSSKLCKWYFGLIIYSAFKNTTKDPKGEF

BseYIB DNA sequence (SEQ ID NO:87)

ATGGTTATTAATCATTTATTATTGCCTAATTTAAATATTAATAATGAAAAAGCAGTC
CCGGAAGTATATAAACGTATTTTGGAAGGGTATTTAGATTATTTAAATACAGCCCTC
GAATACGAATCAATTGCTATGTCTGAGGTAGTTGCTGGAGTTATAAGTGAATTAATT
TTATATAATGAAATTAAGCATGACTGGTTTTTAATTATAAAAGACTTACTAGAATAT
GATGAATTACCGATATCTTATTCTAAGAATTATGGTGAAAAATTATATGGATTTAAT
TCACAGTGGTTACAACATACTGTTCATGCCACTTATAATCATAGTTTTATTATGAAT
TTGTTAAATAAGAGCCAATTTGATTACTCAAGTATTATATTAGATTTAGTTCAACCT
GATGGATATATTTATAACAAGAAGGTTAGTGCAACCAATCCCCGAACCCGCATGAAA
AGTGAGCTATTAATGTCTTTAACTATGGGGTTATCGTTAATTGATTCTAGTCGAATT
CCTGAACAGTGTATCGTTAAGATAAAGACATTTGATAAAACAGAATTTGTAACAGCA
GAGTATTTTAAGTTGTTCTGTTTAAAGCTTTTGAAAATAGATAACTTAGAAACGTAT
TGCAACTACAATGATATATTATTAGAAAGATGTTTTACCGGTACTGGATATGCTGAT
TTTAATGTTCAAGATAAAGTCGATGATTACATGGGAACATTAAAACGAACTGCTAGA
GATAAATCTGTTGCATCACCCTTAATAACGGTTTACGCAGGAGAAATTGCTGAAGTA
TTAGGTTCTTCTACGTTAGATTTGTATAATTCTAACAAGGAAAAGTATATTCAACAT
TTATCTTTGAACCCGCTAGACATTACCGCTTATAAAATGAGAGATCTTAATGCAGAT
TTTGGGGAAAGTATTACCCCTTTTGAAATTTTTTCCACTATAATTCTGAATAATTAA

BseYIB amino acid sequence (SEQ ID NO:88)

MVINHLLLPNLNINNEKAVPEVYKRILEGYLDYLNTALEYESIAMSEVVAGVISELI
LYNEIKHDWFLIIKDLLEYDELPISYSKNYGEKLYGFNSQWLQHTVHATYNHSFIMN
LLNKSQFDYSSIILDLVQPDGYIYNKKVSATNPRTRMKSELLMSLTMGLSLIDSSRI
PEQCIVKIKTFDKTEFVTAEYFKLFCLKLLKIDNLETYCNYNDILLERCFTGTGYAD
FNVQDKVDDYMGTLKRTARDKSVASPLITVYAGEIAEVLGSSTLDLYNSNKEKYIQH
LSLNPLDITAYKMRDLNADFGESITPFEIFSTIILNN

BsgI DNA sequence (SEQ ID NO:45)

ATGAATAGAGTAGAATCTAAAAAAAAATTAGAACAATTAGTTCAACAGTTCGAGAAG
TATGAAAGTACATATAGCGCTTCGGATTATAAAGAGGCAACTTTAAGATCTAGTTTT
TTAGATCCCTTTTTTGAACTTTTTGGATGGGAAATGCGCCCTGAAAGAATAACTAAT
CCAGCAGACTTAGAAGTGATTATAGAAGAAAGTTTAGAAACGGAAAAATCTACTAAG
TATATAGATTATGTTTTTAAAATTAATAGAACGACTCAGTTTTTGGTAGAAGCTAAA
AAGCCAGCTGAAAGTCTTTCTAAAAAAGATCATATTTTTCAGGCTAAAAGTTATGCA
TTTACTACGGAGATTCCATTTGTCATTTTAACAAATTTTAAAGAGTTCAGATTTTAT
GACGTTTCAACTGAACCTTTACACAATCAACCGGATACAGATAAAGTGGAAGAATAT
TGTTTTGATTATAAAGAATATGTTCAAAACTTTGATAAGTTATGGGAATTATTCAGC
AGAGAAGCACTTGCTAACAGAAGTTTAGCCAAGTTTTATGCTAAAAGAAGAAATATA
GTAGATAGTCCAGATTTAATTTTTAAACTTAATTATCAAATTGATAAAGGTGCATCA
TTACTGGATATATCTTTCTTAAAAAAATTTGAAAATATGGAGAAAATCATTAGCTGAA
AATATCTTTAATAATAATTCACTTAATGTTAACGTAATTAATGAAGTAGTTCAGAGA

Figure 2-17

ATATTAGATAGACTGATATTTATCCGTATCATTGAAGACAGAAATATTGAATCTAAA
GAGTTTTTAAAAGAAATTGTAGAAATGCACGAACAAGATAATTCGATTTCAGTGAAA
AATGAACTAGATAAACTATGTATTGAATTAAATAAGAAATTTAATGGGTTAGTTTTC
CATGACCACACATTTGTTAACGAAGCGTTGATAGATAACGAAATTTTAATAGTTATT
ATTGACAATTTATATTATCCAAAGTCTCCTTATAACTTTAGATTAATTAAGCCAGAA
ATTTTAGGACGAATATTCGAGCAATTTTTGGGTGAAAAAATTGAAATAATCGATGGA
AAAATAACGTTAGGATTAAAAGATATTAATAAAAAATCAGGAGGTGTTTATTATACA
CCTTCATATATAGTTGAAAAAATAGTAGAAAATACATTATCCAAAAAATTACATAAT
GATATTACTATTGAAAATTTAGAACAGATAAAAATAGCTGACATAGCTTGTGGTTCA
GGAAGCTTTTTAATTTCATCATATAAATATTTAATTGATAAATTTCAATATATTTAT
TCCAAATGTTCGGAAGCGGATGTTCAAACATTAATTAGTAATAACTTAGTATTTATA
GACAATGGTAAATTAATGTTAACAATGGAACATAAAAAGGGGATACTTCAGCAAAAT
ATTTTTGGGGTAGATATAGATTCACAAGCAATTCAGGTAGCGAAATTAAGTCTTTAT
ATAACCATGTTAGAAGAAGGATACAGAGAAGGTACATTAAGACCTATATTACCAGAC
TTAAATGATAATATTAAACATGGTAACTCAATAATAGATAATGAAATTTTATTTGAA
GATGATATAAATTACGATATTGATGCAACATTACCATTCGATTGGGAATATGCTTTT
CCTGATATTATAGATAACGGAGGTTTTGATGTAATATTAGGCAATCCACCCTATATA
AGAATTCAAATTTTTGAAGAGTTATATGGAAAAGATGTAGTTAATTATTTGAAAAAA
AAATACGTTTCTGCCGAAAAATTTAACTTTGATATATATGTCGTGTTTATAGAAAAA
GCATTGTCACTCTTGAATGACCAGGGGATATTGGGATATATTGTGATGAACAAATTT
TTTACTACACAATATGGAGAAAAAATTGCGCGAGTTAATAACTTCACAAAAATTATTA
TATGAAATCATTGATTTTGGAATTAATGAAATATTTAATAATGCTACTACTTATACT
TGTATATTAATTTTAGACAAAACTAATCCAGATGAAATAATTATTGAAAGAGTGATT
GATTTAAATACTTGGAAAGCTGGAGAATCTTCAGATCGGAAAGTGGTAGATCATACC
GAATTCACTAGTACTCCTTGGTATTTATCAAGCAATACTGATGAAGAAATTTACAAA
TTCTTTGAAGAAAATATGGTTTTACTTGAAACCATTAGTGATAGGGTTTTTGTTGGT
GTTCAGACAGACTGTGATCCAGTATATATTTTAGAAGAAGTTTATGAAGAAGAAAAT
TATTTATATTGTAAGTCAGAATATACTACTGAAGTACACAAGTTTGAAAAAGATCAT
TTAAAACCATTTTTAAAAGGTTCTCTAGATATAAAGAAATATACTTTTTCAAATGTT
AATAAGTGGTTACTTTTCCCTTATACCAATTCGGAAAATACTTCTGATTTAATTCCC
GAAACAACTTACAAACAGTATTTCCCAGAAACATGGAAATACTTAGAGTCTTGTAAA
GAAAGATTAGCAAAAAGAAAAAGTATTGAAAGAGAATTGGATATTAATCCGAATTAT
AATGAGTGGTATAAATATATTTACAAAAAGAATCACACGAGGATGGACCAATTAAAA
ATAGTATTTCCTGCGATATCGAAGGGTAGTAGCTTTTGTTATGATTCGGATGGAGAG
TACTATTTTGTAGGAAGTGGTGCTGGAGGCGGTGGTGGAGGCGCAATAGTCTTGCCA
GATCAATCTGATTATAATTATTTATCCTTACTTGGAATTCTAAATTCAGAAGTAGTT
TCATATCAAATTGTAAGAAGAGGTTCAAAACATAAAGGTTCTTATTATGGTGTAGAT
AAAAAGAGAATAGAAAATCTATATGTGCCATTGATTAATGAGGATAATAAAAATTTA
TTTAGTAATATTTCAAAAATGGTAGCTCAAATTCTTGATGCGTTTCAAAAAATGCAT
CAAGCAGGGACAACGGATGTTGGTAAAGAACAACTTCAACAAAGAATAAAAATGCTT
AATGCTAGAATAAATGAGCTGGTATATAGACTGTATAATTTACCAGTAGAATATAAA
GAATATATTAAAAATGCCTTAGAAAATTAA

BsgI amino acid sequence (SEQ ID NO:46)

MNRVESKKKLEQLVQQFEKYESTYSASDYKEATLRSSFLDPFFELFGWEMRPERITN
PADLEVIIEESLETEKSTKYIDYVFKINRTTQFLVEAKKPAESLSKKDHIFQAKSYA
FTTEIPFVILTNFKEFRFYDVSTEPLHNQPDTDKVEEYCFDYKEYVQNFDKLWELFS
REAVANRSLAKFYAKRRNIVDSPDLIFKLNYQIDKGASLLDISFLKNLKIWRKSLAE
NIFNNNSLNVNVINEVVQRILDRLIFIRIIEDRNIESKEFLKEIVEMHEQDNSISVK
NELDKLCIELNKKFNGLVFHDHTFVNEALIDNEILIVIIDNLYYPKSPYNFRLIKPE
ILGRIFEQFLGEKIEIIDGKITLGLKDINKKSGGVYYTPSYIVEKIVENTLSKKLHN

Figure 2-18

DITIENLEQIKIADIACGSGSFLISSYKYLIDKFQYIYSKCSEADVQTLISNNLVFI
DNGKLMLTMEHKKGILQQNIFGVDIDSQAIQVAKLSLYITMLEEGYREGTLRPILPD
LNDNIKHGNSIIDNEILFEDDINYDIDATLPFDWEYAFPDIIDNGGFDVILGNPPYI
RIQIFEELYGKDVVNYLKKKYVSAEKFNFDIYVVFIEKALSLLNDQGILGYIVMNKF
FTTQYGEKLRELITSQKLLYEIIDFGINEIFNNATTYTCILILDKTNPDEIIIERVI
DLNTWKAGESSDRKVVDHTEFTSTPWYLSSNTDEEIYKFFEENMVLLETISDRVFVG
VQTDCDPVYILEEVYEEENYLYCKSEYTTEVHKFEKDHLKPFLKGSLDIKKYTFSNV
NKWLLFPYTNSENTSDLIPETTYKQYFPETWKYLESCKERLAKRKSIERELDINPNY
NEWYKYIYKKNHTRMDQLKIVFPAISKGSSFCYDSDGEYYFVGSGAGGGGGGAIVLP
DQSDYNYLSLLGILNSEVVSYQIVRRGSKHKGSYYGVDKKRIENLYVPLINEDNKNL
FSNISKMVAQILDAFQKMHQAGTTDVGKEQLQQRIKMLNARINELVYRLYNLPVEYK
EYIKNALEN

BspCNI DNA sequence (SEQ ID NO:47)

ATGAAAAAAGTGGGAGCAACGCGTGATAATGAACGTAGTTGGGCTATTGATCTAATA
TCAAGGATTAATTCAGGTGCCATTGTTTGTAAAGAAGATAGTATGATACAACATGCA
GGAGGAGAGATGGGGCTATCAACAGGTAGCGGCTCTCTTTTCCCTGATGTTCTTTTA
TTTGGAGATAAGGGCAAAACAAGGGTCTTACAAGGTTGGGAATTAAAATACCCTGAT
ACACCAATAGATGATAGAGAATTATTTATAAATGCTGTAAAAAAGGCAGAGCTTCTA
GGAGTAAACAGTTTCTTATTATGGAATGTATCGGTTGCTCATCTATACGTTAAAAAT
GAAGAAAGTGGAAAATATGAACTATTAAAGAAATGGGATGACCTAAAACATATTACT
AAACGTTCTGAAGTTGCTTATAGTATGGCTGAAATAAATCAAGTGTTAGAAAGTATC
TTGAAGGATTTAGAATACTACTTTCGAAATGGTACATTACGTACCGAAAAAAATACTT
AACTCAATTGTTAATGAGCAAATGCTCTCGTTGGCGTTCAATAATATTGAAGATTGT
GCACTTTCATTAAAAAATGCTTCTGCAAAAGATAGTGATTTTAATGATGAAATAATA
CTTTGGTGGGAAACAGAAGGCTTGAGCTATGGAAAGAAAGCTGATAGGTGGATTGAG
TTATCAAGATTAGCTATCATTTCGCTTATGAATAAATTGATATTTGCAAATATTCTA
AAGAAGTATAATTCTCATGCACAGATTATAGATCAGGTTAACGATTCACTTACAGTA
GAAGAGTGCCTAGATATCCTTAATGAAATATCTGAGAAGTGTGACTTTTATAATATT
TTTGAAGAAAAACCAGGGGAAAGATATATTGATGTAGCTACGTTAAAAGTACTAACA
AACTTTAATGATTATATTATGAATTTAGATTTCAATAGTTATAGTGATAGGTTACTT
GAAGAATTATTAAATATTGTAGTGACAAGAAGTAAGCGGAAAGTTGCTGGTCAATTC
TCAACACCAAAAGAATTAGCTATGATTTTGACCTCTTTAACGATGACGGATAAATCA
TCAAGAATTTCTGATCCGTGTTGTGGAACAGGAACAATTGTAAAAGCAGCTTATGAT
CTTAAATTGGTTTCGGGTATTGATAGCAGCGATGCTATAGATCAAATTTGGGCAGGC
GATAAATTTAGATATCCACTACAGTTTGCTATGCTTGCATTATCATCCCCAGAAAAT
TTAGGTAAGCAGATAAATATATACAAAGATGATGTATTTAACCTAAACGCAAGCCAT
AAGGTAGAACTCCATAGTCCAATCAGTAAGGAAACTTATGAAGTTGATCTGGGAGAG
TTTGATACTGTGGTTTCGAACTTACCTTTTGTTCAACAAGAGACCCTAGCTGAATTA
AATCCAGAAGCTATTAGATTTATTGAAGAATTAAATGAAGCATTCAACGGTAGAAGT
GACTTATATGCATACATAGCATTAAAAATAGATGAAATACTTCCAGAAAAAGGGACA
GCTGGTTTAATAGTATCTAATTCTTGGCTTGGAACAGAATTTGGAGAAAGATTCTTT
GATGAGCTAAAGAAAAGATATCATATTAAATATATATTAACATCTGGAAAAGGTCGA
TGGTTCCAAAATGCTGATGTAGTAACAAACATCATTGTGTTAGAAAAAGGAAATACT
TCCCCTGACAAAAAAGTTAATTTCATAACTCTAAAAAAGACTCTTCAAGAAATTGTC
GTTGAGGGAGAGAAGGAGCAACAATTTGAGAATGTTGCAACAATGGTTGCAAAAATT
CGGAGGGATATGCCTTCAGAATTATATGAGAGTAACAGTTATTCTTATGGTGAAATT
GAGGGCTTGAATAAACTTGGTGTAATTAAAAATGCTCTTTTTGCAGATTGTAGTTGG
CTTTTTGATTTTGAGGATAATTTAGTCCCATTAACGGAGTTTTTCAATGTTAAACGT
GGAGAACGTCGGGGGTGGAATCCTCTATTCTATCCGAAGAATCACAACATTGAACCT
GATTATATAGTACCTGTAATGAAAAAACTGGATACATCCTCTTATATAATGAATCTT

Figure 2-19

AGCGCTTCAATAGAAGGTTTTAGTTGTAGTAGAACCATTGAAGAGCTTGAAGCACTA
AATCACAGTGGAACATTAGAGTGGATAAAGAGTTTTGAAACAGTTAAAAATGGTAGA
GGTGTGTTACTAACAGAAGATTTGCCTAGAAAGAATGTACATTGGTATGAAATGCCA
CTAAAGAAGACCTTTGACATCGGTTTGTTAATTAATCCTGATGAGAGGTTGTTTTTC
TCAAAAGCACCTCAACCAGTATTTTTTGACCAAAGATTAACAGGTCTTGTTAGGAAG
AATCCTCAAGATGACTTAGATATATTGACAGCATTATTAAACAGCATTGTTGGAGTA
TACTACATTGAGGCAATTGGTTTCGGAAGAGGTCTAGGTGCATTAGACTTAAATAAA
AATAAAGTTGAAGATAAATTTAAAATGTTGAATCCTTCTTTAATTAGTGAACAAGAT
AAATTAATAATTTTGGAACTGTATAGAGAACTAGAAAAACGTCAGGTTTTGCCATTA
CTTCAAGAAGTTCAACAAAGAGACCGATATGATTTTGATATGGCTGTGTTAAAAGCT
TTTGGTTTAGAAAAGCATTATGATAGTATAAAAAATTCTCTTATGCAGTTATTTGCA
ATACGTAAATCTGTGAGATAA

BspCNI amino acid sequence (SEQ ID NO:48)

MKKVGATRDNERSWAIDLISRINSGAIVCKEDSMIQHAGGEMGLSTGSGSLFPDVLL
FGDKGKTRVLQGWELKYPDTPIDDRELFINAVKKAELLGVNSFLLWNVSVAHLYVKN
EESGKYELLKKWDDLKHITKRSEVAYSMAEINQVLESILKDLEYYFRNGTLRTEKIL
NSIVNEQMLSLAFNNIEDCALSLKNASAKDSDFNDEIILWWETEGLSYGKKADRWIE
LSRLAIISLMNKLIFANILKKYNSHAQIIDQVNDSLTVEECLDILNEISEKCDFYNI
FEEKPGERYIDVATLKVLTNFNDYIMNLDFNSYSDRLLEELLNIVVTRSKRKVAGQF
STPKELAMILTSLTMTDKSSRISDPCCGTGTIVKAAYDLKLVSGIDSSDAIDQIWAG
DKFRYPLQFAMLALSSPENLGKQINIYKDDVFNLNASHKVELHSPISKETYEVDLGE
FDTVVSNLPFVQQETLAELNPEAIRFIEELNEAFNGRSDLYAYIALKIDEILPEKGT
AGLIVSNSWLGTEFGERFFDELKKRYHIKYILTSGKGRWFQNADVVTNIIVLEKGNT
SPDKKVNFITLKKTLQEIVVEGEKEQQFENVATMVAKIRRDMPSELYESNSYSYGEI
EGLNKLGVIKNALFADCSWLFDFEDNLVPLTEFFNVKRGERRGWNPLFYPKNHNIEP
DYIVPVMKKLDTSSYIMNLSASIEGFSCSRTIEELEALNHSGTLEWIKSFETVKNGR
GVLLTEDLPRKNVHWYEMPLKKTFDIGLLINPDERLFFSKAPQPVFFDQRLTGLVRK
NPQDDLDILTALLNSIVGVYYIEAIGFGRGLGALDLNKNKVEDKFKMLNPSLISEQD
KLIILELYRELEKRQVLPLLQEVQQRDRYDFDMAVLKAFGLEKHYDSIKNSLMQLFA
IRKSVR

BspHI DNA sequence (SEQ ID NO:49)

GTGTCGAAATTATCCGATGTTTTTAAATATATATCTTTCTATAGAAGTGCTGGTCAT
CAAATAGGGCGAAAGGTTGGGGATATGTTAGAAGTGCTAACATATGGAGCTTTACAT
TACGATCAAAATCTGAAAAAAAGATTACATATTGAACCTAACTTATACGGCTTTTCT
GATGCAGGGCATAAAGTTGAGTTTTTAATTACAAAAGATGTAAATGAGAATTTACTT
AAGGGAGGGAGTGTTACTAATCTAGAAAATTATATAGGTTTTATTGAATGTAAAAAG
GTAGGAGTCGAGCAAACAGTCTCAACTTCATTTAAAAATAAATTTAAAGATTATGAA
AATAAACAGACTAAGAAATATGATTTAAAATTAGATAGTATTTTTAATATCGGTTTT
TCAAGTCATGGTATGAATAGACACAAGTTATCTGTATCTTTTGCAAATTGTGATAAT
AATTTATTCATTAATGTAAAAAATGAAATCAATAATGAAATCATTTTTAATGAACAA
GTCAAAGATCATTATAGACTTATAGTTGCACAATGTAGTGATAATAGTATAGATATA
ATAGGAAATAGTCGAAGTTTAAGAGAATTCAATTTACCATTAAATAACTGTCGTATA
TTAGAAATATCTAATTTTAATTTACAGGAGAATAGAATATCTTTAGTTCTTAATAAT
TGTTTAGCTGGTCCGCAAACACCAGAAAAAGCAAAACAGGCTTCATTTGTTGCTTTA
GATGTTCGTAAGAAGAGATTTGGATCATTTGATAAGGTTGATGATCCAAGCTTTAAA
AGTATTTTAGTGTTAACTGAATTTGCACACTGGGAAAGAAAAAGCAGAAATATGATT
AGTGCTTGTATTGATATCAATCTTGTAGTACCAGATAGTATATTAATCGAGGCTTTC
GAAGTATTTAATCAATATTTTGAAAGAAATGGCGCAACGGTATCAAATTTATATGAT

Figure 2-20

CTAATAACAAAAGATAACTTTGAAAAGAATAAAGAGATACAAGATCTTATTATGAGT
ATATTAACAGAATATGATGGTAAAATTTTCCAACAACTTAAGTCAGATGGTACTCAT
ATTGAAGAACTTGTATCTCTAAATTACTTAAATAATAGTTTATCTATTATTTCTGAA
AGATAA

BspHI amino acid sequence (SEQ ID NO:50)

VSKLSDVFKYISFYRSAGHQIGRKVGDMLEVLTYGALHYDQNLKKRLHIEPNLYGFS
DAGHKVEFLITKDVNENLLKGGSVTNLENYIGFIECKKVGVEQTVSTSFKNKFKDYE
NKQTKKYDLKLDSIFNIGFSSHGMNRHKLSVSFANCDNNLFINVKNEINNEIIFNEQ
VKDHYRLIVAQCSDNSIDIIGNSRSLREFNLPLNNCRILEISNFNLQENRISLVLNN
CLAGPQTPEKAKQASFVALDVRKKRFGSFDKVDDPSFKSILVLTEFAHWERKSRNMI
SACIDINLVVPDSILIEAFEVFNQYFERNGATVSNLYDLITKDNFEKNKEIQDLIMS
ILTEYDGKIFQQLKSDGTHIEELVSLNYLNNSLSIISER

BspMI DNA sequence (SEQ ID NO:51)

GCGATACCACAATGAGTCATGATTTATATGCTGCTTGGGCAGCTACAGAAATTACTA
ATATTTTGCAAACAAATCCCCGTTTTTAGTGAGTGACGGTATATCTAGAAATTTTA
CTGTTTATGCTAGTAAAGAAGGAAGAACCAAGTGGCCTATTGCTGATGGTGTTATTC
TTGTTGAAGAAAATGGCCGAGTGGTTTATGAGATAGCAATAGAGTTCAAACGACGAA
ACGAGGGAGTGCACGGTGTACTTACTGCCCTTGGCCAGGCTCATGCCTATTTACATA
AAGGATATCGAGGATCGATAATTGTTATTCCAGAAGCCTACGATACCCATAATAATC
CATCAGGGCATTTAAAAGAAATAATTGAATATACTAGCGATCAAGTCCCTATTGGAG
TATTCAGTTATAAAGATCCTGATGTCACTAAGACTTCTCCGTTTAATGGTAAAATTA
CATGTATTAGACATTTGAATTTGAATACTGGGCTAGGTTCTGTTGTTAGGTCCTCTA
GCCCTCAAAATTTTGTTAAAACTCAATGGGCTCATTTGAGGGAGGGTAGTAGTGATC
CTGATGCATTTTTTCGATACTTACAAACATCTAAGCAGCTAGCAATTGATAGCTTAA
TTGAGCCATCAGTAAATTTCCCCCCGAGTCTAGTTCAGGCTATTCAAGATATACAAC
CAGGTGCAAACCCACTAAAATACTTGTCTAATTCAATAGGCAATGATCTACATGATA
TAGTATGGAGAAATTTTTGGTTTAATTACATTCTTACCGACGAGGCCATACCTATTT
GGAATAATTCTGAAGGTAACTATGTAATTAATGATTCATCTACAAAAATAGTTAAAC
CAGACGAGAGCGGGAACAAGATGTTTTTTGCTGGTCGTTCAGATTCAATAAAAAATC
GATTAGTGAACGATCTGAATATGGGAAATATCTCAGAGTCTGAAGCATGGAAAAAAT
ACGCTCTAAAGATTCGTGAAAGAGCACATAGCTATAGGGAGGATATAGACTCTGGTT
TAGATCATATTGGATTACTTGAAAGTGATGGTAAACCTTCAGAGCTTGGATACCGCT
TTGTTGATGCATGTGAAAGAACTAGAAATAGTAATTCAGGCAGTCCTAAGGCTCTTT
TAGGAGCTGCAATTCTTAAAAATGGAAATTTAGGGGCGTTTTTGCATTATATATACC
GTCTTTCAGAAGAAAAATTTAATGCAGACCCCTTGGCCTTTACAAAACAAAACAATT
CATCAGGACGCTTACAATTTCTGCATAAGGAATATTTGCAATGGTTAGAGAATGAAT
TGGCTACTAATCTAAAAGTTATGAGGAAAGTTAGTATTAGGGGAGGAGCAAGTAGAC
AGCCTTTCCAAGGTGAACTTGCTATTCTGAGGAATTATGAATTTGTAGGAAACTTTC
GGGTAGGTACAGGATTAAAAATAAACTGGCCCAAAATCCAAAATGCTTATGAAGTAG
AGATATAA

Figure 2-21

BspMI amino acid sequence (SEQ ID NO:52)

GDTTMSHDLYAAWAATEITNILQTNPRFLVSDGISRNFTVYASKEGRTKWPIADGVI
LVEENGRVVYEIAIEFKRRNEGVHGVLTALGQAHAYLHKGYRGSIIVIPEAYDTHNN
PSGHLKEIIEYTSDQVPIGVFSYKDPDVTKTSPFNGKITCIRHLNLNTGLGSVVRSS
SPQNFVKTQWAHLREGSSDPDAFFRYLQTSKQLAIDSLIEPSVNFPPSLVQAIQDIQ
PGANPLKYLSNSIGNDLHDIVWRNFWFNYILTDEAIPIWNNSEGNYVINDSSTKIVK
PDESGNKMFFAGRSDSIKNRLVNDLNMGNISESEAWKKYALKIRERAHSYREDIDSG
LDHIGLLESDGKPSELGYRFVDACERTRNSNSGSPKALLGAAILKNGNLGAFLHYIY
RLSEEKFNADPLAFTKQNNSSGRLQFLHKEYLQWLENELATNLKVMRKVSIRGGASR
QPFQGELAILRNYEFVGNFRVGTGLKINWPKIQNAYEVEI

BsrBI DNA sequence (SEQ ID NO:53)

ATGAGTGATAAGGTTAATTTTTCTTCTAACAATATTGACCAAAACTATAGTATTGAG
ATATCCGAATTTGAGTTTGGAACTGGAAGAATTGCCGATATAATCAGGGCACTCAAA
GATTATTATGGCGTTGAATCTTTGGAAAATTTAACACATAGTCAAAAGCTTGATGGT
CTGTGTAAAGCTCTTCAGTTTACTCCATCTCAACTGGATCGTTTAATAGCTCAAAAT
TCTCCTGTACTTCGTACCATTAAGGGCCATGCATTTGAGAGAGTTTTTGATGAAATT
CTTAAAATGAATGGATATGAGGTAACTGAAGTCGGAGGAGACAGTGGAGTTGATAGA
ATTGTAAATAATAAAACCCTTCAGCTAAAAACTCCTAATAAGGCTGGAACAAAGGAA
AATGTCGTAGAATACAAAACACATAAAACTCATGGTGCTAAATCTGAGAGGGAGTCT
TTAGATTACTACTATAGTAAAGAAGACTTTGCTGATTATTTAGTTGGTCTTGTTTCA
TATGAGCCTTTTAACATTCTCTTTATACCTCGGGAGGAATTGCCGACAATTTCCAAA
GATTCATCAAAGATTAAGAGTCCATTTAAGGTAGAATGGGACTCAAACCCAGGTTTA
AACTCCTTTAAATCTATTGGTATAGACAATATTGTTATATCAGAAAAAATTTATAAA
CCTGCACATGGGAATGAACTTTTACCTTTATCATCAAGGAAACTCCAACTAAAAAGC
GAGATAATAATTGATGTGATTTTAAATGAAAGTAATTTCCGTATATGGGATATGAAT
ATGAGAGGATTTGCTAGAGAAATGGCTTTTGTCGAGTATCTATCATCTTTTGGGATT
AGAGTATTTAACCCTGCAAATTGCAGAAAAGAAAGGGCAGATAAGGCTGACATAGCA
TTAAAATCTGCCCAAAATGGCAACTTTTCTTTTCTACAAATTAAAGGTATTACATTA
GATTTAGATAATTTCCGGGGGAGAGAATCAATTGTTGATGTTGAGACACAGCTTTCA
CGTGCACGGGTAAATGATCATCCAACACAAAGTAGGCTCTATCTTGAAACTGATTTT
GATTATTTAATTGTCTGTATAGACCCATGTTATTCAAAACTTTACTCTAAAGAAATT
GGCAAGCCTAATTGTTTTGACTGGGAGTTTTATGCTATCCCTAACAATGTTTTAGAA
CGTCATCCAAAATACACTCGTCGAATAAAATCACATCAAAAGATAAAATATGTTGAA
TTACAGAGATATAGAATAGATGATACTTGGATTAATTTGTGGGAAAAAGGAGCTAAC
TAA

BsrBI amino acid sequence (SEQ ID NO:54)

MSDKVNFSSNNIDQNYSIEISEFEFGTGRIADIIRALKDYYGVESLENLTHSQKLDG
LCKALQFTPSQLDRLIAQNSPVLRTIKGHAFERVFDEILKMNGYEVTEVGGDSGVDR
IVNNKTLQLKTPNKAGTKENVVEYKTHKTHGAKSERESLDYYYSKEDFADYLVGLVS
YEPFNILFIPREELPTISKDSSKIKSPFKVEWDSNPGLNSFKSIGIDNIVISEKIYK
PAHGNELLPLSSRKLQLKSEIIIDVILNESNFRIWDMNMRGFAREMAFVEYLSSFGI
RVFNPANCRKERADKADIALKSAQNGNFSFLQIKGITLDLDNFRGRESIVDVETQLS
RGRVNDHPTQSRLYLETDFDYLIVCIDPCYSKLYSKEIGKPNCFDWEFYAIPNNVLE
RHPKYTRRIKSHQKIKYVELQRYRIDDTWINLWEKGAN

Figure 2-22

R1.BsrDI DNA sequence (SEQ ID NO:55)

ATGACAGAATATGACTTACATTTATATGCTGATAGTTTCCATGAAGGACATTGGTGT
TGTGAAAACTTAGCAAAAATTGCACAATCAGATGGAGGAAAACACCAAATTGATTAT
CTTCAAGGGTTTATACCTAGACATTCTTTAATATTCAGCGATTTAATAATTAATATT
ACTGTATTCGGTTCTTACAAATCATGGAAACATTTACCTAAACAAATTAAAGACCTT
TTATTCTGGGGGAAACCTGATTTTATAGCATATGACCCAAAAAATGATAAAATCTTG
TTTGCAGTTGAAGAAACGGGAGCAGTTCCAACAGGTAATCAGGCTTTACAAAGATGC
GAAAGAATCTACGGAAGCGCAAGAAAACAAATACCTTTCTGGTATTTATTAAGTGAG
TTCGGTCAACATAAGGATGGTGGAACCCGTCGTGATTCCATTTGGCCTACTATAATG
GGATTAAAGTTAACACAGTTAGTAAAAACACCTTCGATTATATTACACTATTCAGAT
ATCAATAATCCCGAAGATTATAATTCTGGTAATGGTCTAAAATTTTTGTTTAAATCT
CTACTACAAATTATTATCAATTACTGCACTCTTAAAAATCCTTTAAAAGGTATGTTG
GAATTACTGTCTATTCAATACGAAAATATGTTAGAATTCATTAAATCCCAATGGAAA
GAGCAGATTGACTTCTTACCAGGAGAAGAAATTTTAAATACAAAAACAAAAGAACTA
GCTCGCATGTACGCATCTTTAGCAATAGGACAAACAGTGAAGATTCCAGAAGAATTG
TTTAATTGGCCAAGAACAGACAAAGTTAATTTCAAGAGTCCACAGGGATTAATTAAG
TATGATGAGTTATGTTATCAATTAGAAAAAGCTGTAGGAAGCAAAAAAGCTTATTGT
TTATCTAATAATGCTGGAGCTAAACCACAAAAATTAGAATCTTTAAAAGAATGGATA
AATAGTCAAAAGAAATTATTTGATAAAGCTCCAAAACTAACACCTCCAGCAGAATTT
AATATGAAGTTAGATGCTTTTCCTGTTACATCAAACAATAATTATTATGTTACTACT
TCTAAAAATATTTTATATCTATTCGATTATTGGAAAGACTTACGCATTGCTATAGAA
ACCGCTTTTCCTAGATTAAAAGGTAAGTTGCCAACTGATATTGATGAGAAACCTGCT
CTAATCTATATCTGTAATAGCGTTAAGCCAGGTCGATTATTTGGAGATCCTTTTACT
GGTCAACTTTCTGCATTTTCTACTATTTTTGGAAAAAAAAATATTGACATGCCACGA
ATAGTGGTAGCTTATTATCCACATCAAATTTATAGTCAAGCTCTTCCAAAGAATAAC
AAATCTAATAAAGGAATAACTTTAAAAAAGGAGTTAACCGATTTCTTAATTTTTCAT
GGGGGAGTAGTTGTTAAATTAAATGAAGGGAAGGCATATTAA

R1.BsrDI amino acid sequence (SEQ ID NO:56)

MTEYDLHLYADSFHEGHWCCENLAKIAQSDGGKHQIDYLQGFIPRHSLIFSDLIINI
TVFGSYKSWKHLPKQIKDLLFWGKPDFIAYDPKNDKILFAVEETGAVPTGNQALQRC
ERIYGSARKQIPFWYLLSEFGQHKDGGTRRDSIWPTIMGLKLTQLVKTPSIILHYSD
INNPEDYNSGNGLKFLFKSLLQIIINYCTLKNPLKGMLELLSIQYENMLEFIKSQWK
EQIDFLPGEEILNTKTKELARMYASLAIGQTVKIPEELFNWPRTDKVNFKSPQGLIK
YDELCYQLEKAVGSKKAYCLSNNAGAKPQKLESLKEWINSQKKLFDKAPKLTPPAEF
NMKLDAFPVTSNNNYYVTTSKNILYLFDYWKDLRIAIETAFPRLKGKLPTDIDEKPA
LIYICNSVKPGRLFGDPFTGQLSAFSTIFGKKNIDMPRIVVAYYPHQIYSQALPKNN
KSNKGITLKKELTDFLIFHGGVVVKLNEGKAY

R2.BsrDI DNA sequence (SEQ ID NO:57)

ATGACTGATTATAGATATTCATTTGAACTAAGTGAAGAGATTGCAAGATGGGCATTC
GAAATAAAAAACAAAAAAATACAGATTGGTTTGTAGCTTTTTCTAATCCAACGGCTGGT
CCTTGGAAAAGAGTAATGGCAATAGATAAGGCTTCTAATAGAGAAGGAGAAGTACAT
AGATTTGGAAGAGAAGATGAGCGTCCTGATATTATTCTAGTTAATGATAATATATCA
TTAATATTGATATTGGAGGCCAAAGAAAAATTGAACCAGTTAATCAGTAAATCGCAA
GTAGATAAATCAGTTGATGTGTTTTTAACTCTCTCCAGTATTCTGAAAGAAAAGTCT
GATAATAATTATTGGGGAGATAGAACAAAGTACATAAATGTGTTAGGAATTCTATGG
GGAAGCGAACAAGAAACTTCCCAAAAAGATATTGATAATGCGTTTAGAGTTTATAGA
GATTCCCTAGTTAAAAATTTAAAAGAAATCAACCCTACACCTACCAATATTTGTACG

Figure 2-23

GATATTTTAGTACGTGTAGAGTCTATCAAGAACAAAAAAGAAGAAATATCTATTAAA
ATTCATGTTTCTAATATATATGCGGAAATATATCCTAAATTTACTGGAAAACATCTT
CTGGAAAAGTTAGCTGTTCTGAATTAG

R2.BsrDI amino acid sequence (SEQ ID NO:58)

MTDYRYSFELSEEIARWAFEIKTKNTDWFVAFSNPTAGPWKRVMAIDKASNREGEVH
RFGREDERPDIILVNDNISLILILEAKEKLNQLISKSQVDKSVDVFLTLSSILKEKS
DNNYWGDRTKYINVLGILWGSEQETSQKDIDNAFRVYRDSLVKNLKEINPTPTNICT
DILVGVESIKNKKEEISIKIHVSNIYAEIYPKFTGKHLLEKLAVLN

BsrI DNA sequence (SEQ ID NO:59)

ATGAGAAATATTCGTATCTATTCTGAAGTAAAGGAACAAGGGATATTTTTTAAAGAA
GTAATTCAATCTGTTTTAGAAAAAGCTAACGTTGAAGTAGTTTTAGTAAATTCAGCG
ATGTTGGATTATAGTGACGTATCTGTCATTTCTTTGATACGTAATCAAAAGAAGTTT
GATTTGTTAGTATCGGAAGTTAGGGATAAACGCGAAATTCCTATTGTTATGGTTGAA
TTCTCAACGGCAGTAACTACAGATGATCATGAACTTCAACGAGCAGATGCAATGTTT
TGGGCATACAAGTATAAAATACCATATTTAAAAATATCACCTATGGAGAAAAAATCA
CAGACAGCAGATGATAAATTTGGTGGCGGAAGGCTTTTAAGTGTAAATGACCAGATT
ATTCACATGTATAGAACGGATGGTGTAATGTATCATATTGAATGGGAATCAATGGAT
AATTCTGCATATGTGAAGAATGCGGAACTATATCCTTCTTGTCCTGATTGTGCACCG
GAATTAGCGTCTCTATTTAGATGTCTTTTGGAAACAATTGAGAAATGTGAGAATATA
GAAGATTATTATAGGATTTTGTTAGATAAGTTAGGTAAACAAAAAGTGGCCGTAAAA
TGGGGGAATTTCCGTGAAGAAAAAACACTTGAACAGTGGAAGCATGAAAAATTTGAT
TTATTGGAGCGCTTTAGTAAAAGTTCTTCACGTATGGAGTATGATAAAGACAAAAAA
GAGTTAAAAATTAAAGTTAATCGATATGGCCACGCGATGGATCCGGAACGAGGCATT
CTGGCCTTTTGGAAACTAGTTCTTGGAGACGAATGGAAGATTGTTGCGGAATTTCAG
TTGCAACGCAAAACACTCAAGGGGAGACAATCTTATCAATCGCTTTTTGATGAAGTT
TCTCAAGAAGAAAAATTAATGAACATAGCATCTGAAATTATAAAGAATGGAAATGTT
ATTTCTCCTGATAAAGCAATAGAAATTCACAAATTAGCTACTTCTTCCACAATGATT
AGTACAATTGATTTGGGAACTCCAGAACGTAAATATATTACAGATGACTCTTTAAAA
GGGTATTTGCAACATGGATTAATTACGAATATTTACAAAAATTTGCTTTATTATGTA
GATGAAATTCGATTTACAGATTTACAAAGAAAAACAATCGCTTCTTTGACATGGAAT
AAGGAGATTGTAAATGATTATTATAAATCATTAATGGATCAGTTGTTAGATAAGAAC
TTAAGAGTATTACCGTTGACATCAATCAAGAATATTTCTGAAGACTTGATTACATGG
TCTAGTAAAGAAATTCTTATAAATCTTGGATATAAGATTTTAGCAGCTAGTTATCCA
GAGGCTCAAGGAGATCGTTGTATTTTAGTTGGTCCTACTGGCAAGAAGACTGAAAGA
AAGTTTATTGACTTAATTGCTATTTCTCCTAAAAGTAAAGGGGTTATATTATTAGAA
TGTAAGGATAAGTTGAGTAAATCGAAAGATGATTGTGAAAAAATGAATGATCTTCTT
AATCATAACTATGATAAAGTTACGAAATTAATAAATGTATTGAATATTAACAATTAT
AATTATAATAATATTATATATACAGGAGTAGCAGGTCTAATTGGAAGGAAAAATGTT
GACAATCTTCCTGTAGATTTCGTGATTAAATTTAAATATGATGCTAAAAACCTCAAA
CTAAATTGGGAAATAAATAGTGATATTTTAGGTAAACATAGTGGCAGTTTTAGTATG
GAAGATGTAGCAGTAGTGCGAAAACGATCATAA

BsrI amino acid sequence (SEQ ID NO:60)

MRNIRIYSEVKEQGIFFKEVIQSVLEKANVEVVLVNSAMLDYSDVSVISLIRNQKKF
DLLVSEVRDKREIPIVMVEFSTAVTTDDHELQRADAMFWAYKYKIPYLKISPMEKKS
QTADDKFGGGRLLSVNDQIIHMYRTDGVMYHIEWESMDNSAYVKNAELYPSCPDCAP
ELASLFRCLLETIEKCENIEDYYRILLDKLGKQKVAVKWGNFREEKTLEQWKHEKFD

Figure 2-24

LLRFSKSSSRMEYDKDKKELKIKVNRYGHAMDPERGILAFWKLVLGDEWKIVAEFQL
QRKTLKGRQSYQSLFDEVSQEEKLMNIASEIIKNGNVISPDKAIEIHKLATSSTMIS
TIDLGTPERKYITDDSLKGYLQHGLITNIYKNLLYYVDEIRFTDLQRKTIASLTWNK
EIVNDYYKSLMDQLLDKNLRVLPLTSIKNISEDLITWSSKEILINLGYKILAASYPE
AQGDRCILVGPTGKKTERKFIDLIAISPKSKGVILLECKDKLSKSKDDCEKMNDLLN
HNYDKVTKLINVLNINNYNYNNIIYTGVAGLIGRKNVDNLPVDFVIKFKYDAKNLKL
NWEINSDILGKHSGSFSMEDVAVVRKRS

BstEII DNA sequence (SEQ ID NO:61)

ATGATAAAAAACTTTAGAGACTATCAACGAGTAGCAGCTAAATACATAACATTTATT
GAATCAGAATTTTACCCTGACTATCTAGATAATGCTCGTTTTTATATGGGGAAGTA
TTAAATAAATTCTATGAATTAGTAAATAGCTCTTCTAGCTCTATAGAGTTGTTGGAA
AATATTTCAAAAACAAAAGATCCTGTCCGAACTCAACTGTTACGGATTTTTAGAAAG
TATGTTTCACCTGATACTTCAGTTGAAATGTTAAAAAGAAAACAGAGAATTCCCGAT
ATTATTAAAGAGTTTGGAACAAGATTTCGGGACATTAAAATAGTAAGACAAAAAATT
GCTACTCGCAATCATCCTGATGAAACCATAATGGCTCTCCTTTACGAATACAAAGAT
CGAGGAAAAAAAGGATATGAATTGACTGATGCATTTTTTACATGGTTTGAACAGAAG
TTTCCTAATTACGAAATCATTGGACCAAGAGGGGCTGGTAAAGATATACTACTAAAT
GAAGTATTACCAGGATTTCCATCAAAAATCCCTGCAGATTTCCTAATATATAGAAGA
TCTGATAAAACCCCTATAGTAGTTGGATTTGCAAGATATGATTCAGATAGAGGAGGT
GCTCAAGAAGATGATAGAACAGGTGGCAATAGAGATAAAATCACCGAAATAAAAAAG
TATGCTGCGGAGCATAACATTCCTTTAAAAATTTTATTTTTAAATGACGGTCCTGGA
TTACTTTTAGGTTCTATGTGGAATGATTACTCCGCATTAGAAGATTATGGTGAAGGG
TGCGTTATGGTTTGTACATTAAAAATGTTGGAGGAGCGTTTTACAATCGATTGGCTT
GAAAATTTATAA

BstEII amino acid sequence (SEQ ID NO:62)

MIKNFRDYQRVAAKYITFIESEFYPDYLDNARFLYGEVLNKFYELVNSSSSSIELLE
NISKTKDPVRTQLLRIFRKYVSPDTSVEMLKRKQRIPDIIKEFGTRFRDIKIVRQKI
ATRNHPDETIMALLYEYKDRGKKGYELTDAFFTWFEQKFPNYEIIGPRGAGKDILLN
EVLPGFPSKIPADFLIYRRSDKTPIVVGFARYDSDRGGAQEDDRTGGNRDKITEIKK
YAAEHNIPLKILFLNDGPGLLLGSMWNDYSALEDYGEGCVMVCTLKMLEERFTIDWL
ENL

BsuFI DNA sequence (SEQ ID NO:63)

ATGAATAAAGACAATCAAATCAAAAATGAATCTGGTAAACAAGCCAAAATTCTTGTA
TCAGAAATCGTAAATAATCTTAAAAATGAATTAGGGATTAATATAGAAATTGAAGAA
GGGTACTCTATAGGTTACCCAAATCAAGAAAAGCAATTTAAAATGGATTTTCTTGTT
CAATTTACTGACTTTGATAACGAACAATGGTTAATAAAATCAACTAACTCTATAAGG
GAACGTATATACGGTACAGAATTTTTTGCACAAAACATCAGGCTTATCGATGAGAAA
GTAAAAAATATATATGTTGTTGTTCCAGATTCTATATCTTCAGCTGAAATGAAAAAG
AAAAGAAACTACTCCGTAAAAATAAACGGAACAACATATACTTCCTTTTTAACTGAT
GTTTTAACCGTTAATGAATTGCGACAAAAAATTGTAGAAAAGGCATCTCAAAACATA
GCGCAGGGCTTACGTGCTAATGTGCTTGGTAATGATGCTGAAACCAGTATTGTTAAC
CTGCTTAATGATTTGAAAAATAAAGCATTATGGAATGATTATCAAAACGCTCAACAA
ACCATCAAATCATCAACATACAAGATATACAAAGAGATCCTTGAAAAAATTGATCTA
AAGGAAGGCTTTGATAAGATACTTGAAGTTACCGCTACAAATGATATTCCTCTATTA
TCCAATAGGGGAAAACCGAAAACAGATGTATCAGTTACAATCAAAACAAATACAAAA
GAATTAATTAGGAATATCAGTATAAAAAACACTCGTGAAAAAACTGTCACTATACAT

Figure 2-25

GAAGGTAGTGTTTCGGATTTGATTTCTCGATTAAAATTATCGGAAACGGACCCACTA
TCGCAAGCACTTATACATTTTGAAAAAGTCGGTAGCAAAAAAAAATTAATTGCAGAG
CATCCTAACTCAGATAAAATTTTAGAGGAAAACTTAAAATTGTATAATAGAGAACTT
ATTGAATTCTTACATAGCCCTTTACTCAATGACAAGATACAAATGGTAGATTTAATT
ATATTTACAAATAAATTTGCTGTTTGGAATCGTGATGATTATATTAAACATTACATC
GAAGAATATAGTGGAAAAGGACAATTTGGAACTCCTTTTAAATGGACTTATCCAAGC
AAAAAGCGTGGTCAAAAAATACAGATTAAAGGTTTTTCAAACAATTAA

BsuFI amino acid sequence (SEQ ID NO:64)

MNKDNQIKNESGKQAKILVSEIVNNLKNELGINIEIEEGYSIGYPNQEKQFKMDFLV
QFTDFDNEQWLIKSTNSIRERIYGTEFFAQNIRLIDEKVKNIYVVVPDSISSAEMKK
KRNYSVKINGTTYTSFLTDVLTVNELRQKIVEKASQNIAQGLRANVLGNDAETSIVN
LLNDLKNKALWNDYQNAQQTIKSSTYKIYKEILEKIDLKEGFDKILEVTATNDIPLL
SNRGKPKTDVSVTIKTNTKELIRNISIKNTREKTVTIHEGSVSDLISRLKLSETDPL
SQALIHFEKVGSKKKLIAEHPNSDKILEENLKLYNRELIEFLHSPLLNDKIQMVDLI
IFTNKFAVWNRDDYIKHYIEEYSGKGQFGTPFKWTYPSKKRGQKIQIKGFSNN

Bsu36I DNA sequence (SEQ ID NO:65)

ATGACAACCTATATATATCCTACCCCACATAAAGATAAATTAGTTGCCCTATTACTA
AACGATAAATTACCAGTAGAAGATAAACCAAGAGTTGAAGAGGCAATTGTGGTTTAT
ACAAATTGGATAAAAAACTTAAACATTATTACAAGTGCCGGTCTTCCTCCCCAACAG
ACTTTAAATAAAATGATTGAGCTTCTAAATGAATATAAATTCTATATAGATTTAAAT
TTGGTATTTGATAGCCCAAGAGATTTCCTTTATAGACAAAAAGGGCAATTAAAAATT
GACAATACTATTATTGAAGAATTTTTACCCCGTTTAGCTCATCCGTCTGTTATTCCT
GAAATAATCGATATGGATGTAACGGTTGGACCAAAAAAGTGTTTTTCTTCAGTTTAC
TTTGAATCTAGTCTTGATGCGCCAGCAATTGGAGGAGGACTAAGAGTAAGAAGCAAA
GACCAAGACTTTGCAATAAGCAAAAAATTATTCTTAAAAGCGTCACACACACAAGAT
TATAAAGAGAGTTTGGAAACAGAAACATTCTTATCTTATGTGTCTGCTGAGTGTAAA
ACAAATCTTGATAAGACAATGTTTCAAGAAGGATGTGCTACAGCTCATGATACGAAG
GTAGCTGTACCAGGTTCTAAATATTTCTTGCTATGTGAATGGTTAGATATGACACCA
TTAAGTACAGCTCCTACAGATATTGATGAAATTCTACTTCTCCGTAAAGCCAAAAGA
TTAAATTCTAATATAAGAAAAAAGTTTTCTTCTTATAGTGGGAGACAAGAAAAACGG
GATTATTTCATCAATTATCTCAAATCACATCCATTTAGAGTAGAGGTTTTTGAAAGA
TTTATTGAACACATTAGAAAACTTATCCAAAATGAAGTTCCGGTTGAACATAATGTT
ATGGAATTAGGTTATTTTTAA

Bsu36I amino acid sequence (SEQ ID NO:66)

MTTYIYPTPHKDKLVALLLNDKLPVEDKPRVEEAIVVYTNWIKNLNIITSAGLPPQQ
TLNKMIELLNEYKFYIDLNLVFDSPRDFLYRQKGQLKIDNTIIEEFLPRLAHPSVIP
EIIDMDVTVGPKKCFSSVYFESSLDAPAIGGGLRVRSKDQDFAISKKLFLKASHTQD
YKESLETETFLSYVSAECKTNLDKTMFQEGCATAHDTKVAVPGSKYFLLCEWLDMTP
LSTAPTDIDEILLLRKAKRLNSNIRKKFSSYSGRQEKRDYFINYLKSHPFRVEVFER
FIEHIRKLIQNEVPVEHNVMELGYF

Cac8I DNA sequence (SEQ ID NO:67)

ATACATACTTTATTTGAAAAAGAAATTATTAACTCCAATCATGAATACTATATACCA
CAATTATCTAATTCAATAGAAAATTTTTATTTATTGAATGCAGATTTAAATCGAATA
CCAAGCTCAACAGCGGACATGCTTTTAGTTTTCCAACGTTTGTTTGATAAAGCACTT

Figure 2-26

AAAAATGATTTTACATCATTATCAATAATTAATTACATGCATAATAATTTAACAGAT
GAATCTAAAGCTAAACGTAAAGTTACTGCTAGAGATATTGAAGATTTTATTGCTGAT
CTTTTCGAAGGAACTGTAACTGATGAAGAAAGTAGACAAAATCTCACTTCAACTATA
GATATTGTAGACTCTTATATATCAAGTAACTACAGGGAAAAATGTGATATTCAATTC
AATAATTCATATAAATTATCAATAAAAAGCTTTATAAGCGATAACAAAGAAATCAAT
TGTGGTTCTTTTGCTAGAGAAGCTCTATTTAAAGATATAGTTGAAAATTATGGCGGT
GAAAGAAAAAATGGATTAGGGTCTAAAGGGCAATTTCTAGATTTATTTGAAAAAATC
AAAGATAATGGAAAATGGACAGACTTTACTAATCGCTTTACTTATATGACTAATAAT
ATATTTAAAGATGACTTATTAATTTTTATTAAAGGTGGTAATAATGTTGATATCTAT
TTAGTTGATAGTGAAAAATTTAGGAATACATTAATTTCTGCTGTTTCATCAGGGCCT
AAATTTGCAGTTTCAGTTTTAAATAGATATGAAGGAAATTCTATACGAATTGAAAGA
GATATTTTCCTTTCACCTAAAATCAGTACACATATTGGTTTAAATTTTAATAAAACT
AATGAAAATGCCCTTAATAAAATAGATGTTGAACTACAAAAACTGAAAGATGTGACA
TTAAATTTTATATCAAATGATACTGCTTCTTTAAATAATTATAGCCAATTAATATCT
ACATTTAACTCTTCTTATCAGAATACTATTTCTGATTTACTTTCATTGAAATCAATG
ACTTTATCTTCAGATGCATTAATTACATCTTTCCATCAAAATGTTCTTAATCTTTAT
TCATCAAATAAGTTGTCAATTATTGATATGAAAAAGAAGAAAAGAGGAAATTCATAT
AGTATTGTAAGGGAATTATAA

Cac8I amino acid sequence (SEQ ID NO:68)

MHTLFEKEIINSNHEYYIPQLSNSIENFYLLNADLNRIPSSTADMLLVFQRLFDKAL
KNDFTSLSIINYMHNNLTDESKAKRKVTARDIEDFIADLFEGTVTDEESRQNLTSTI
DIVDSYISSNYREKCDIQFNNSYKLSIKSFISDNKEINCGSFAREALFKDIVENYGG
ERKNGLGSKGQFLDLFEKIKDNGKWTDFTNRFTYMTNNIFKDDLLIFIKGGNNVDIY
LVDSEKFRNTLISAVSSGPKFAVSVLNRYEGNSIRIERDIFLSPKISTHIGLNFNKT
NENALNKIDVELQKLKDVTLNFISNDTASLNNYSQLISTFNSSYQNTISDLLSLKSM
TLSSDALITSFHQNVLNLYSSNKLSIIDMKKKKRGNSYSIVREL

ClaI DNA sequence (SEQ ID NO:69)

ATGACTTATTTAATTTTAAGGAGGCAACAACGTATGAAGAACTCTGCACAAATGATT
AAAGATAACATCATGAAAGAACAGTTAACAATTTATCATGAAATCGAAGTAGGTGAT
CCTGAATTTTGGTACTCTACTGAACAAATGGAAGAACTATTAAATGAAGCTCTTCAA
GGCACAGATTTGAACGGGATGGCTTTAAGAACTCGTTCAAAGTTTGTAAAAGTCAAA
ATTTGTGAAGCTTTTGGATATCAGGTGCCCAAATCGTTTAAAAAAACACAACCACGT
TTTTTATCTCAAAAATTTGATGTATATAATCAAAAATCAAATAATCTCCAAATTTGG
AATGAAGAAATTTCTCCTTCAAGAAGATATGTTTTAATAAAAATTTCTTTCGATGAT
ATTATTACTCAGGTGAAAGTAGTTACTGGTGATGTTTTAGCGACGTTAGATAGTACA
GGAACATTAACTCAAAAATATCAAGCGAAATATGCTGGTGTACATGAAAGAAAGGCT
ACACTTCTAAGTGAATGCGATACAGACTTTATTCAAAGCATTACTCAATCATACAAT
AGTTTTGACGAATTTACAGCTCCTGATACAAATCCAAAAGAAGACGAATTAATGGGA
ATTGACGAAATTTTTGATAAGCTAAAGGATTTAATCGGAACTAAGATTCCATATATA
GGTGCTACTCAAGAAAGAAATCGAGGGGGTCATTTACACAAGATGATTTGTGATGCC
CTTGGTTATAATAATTTTAAAGAGAACGGGCAGTTTCCAGATATAAAACATCAACTA
TTAGAAGTGAAGCTGCAAACGTCGGAAACTATAGATTTAGGATTATTTACGCCCAAT
AGTTATGAGCTATTAGACATCCCTCAATTAAATAACGAGTCTATTTCAATGTTAGAT
GTGCGTTATGCTATATTTTATGGTGATGTTATAGAAGACACTATTACTATTACACAT
TTTTATTTAGTTACAGGTGAAGACTTCTTCACGTATTTTAAACCCTTTGGTGGGAAA
GGGATTAATAAGAAAATTCAAATTCCTTTAAATGAAGAATTTTGGAATCTTTAA

Figure 2-27

ClaI amino acid sequence (SEQ ID NO:70)

MTYLILRRQQRMKNSAQMIKDNIMKEQLTIYHEIEVGDPEFWYSTEQMEELLNEALQ
GTDLNGMALRTRSKFVKVKICEAFGYQVPKSFKKTQPRFLSQKFDVYNQKSNNLQIW
NEEISPSRRYVLIKISFDDIITQVKVVTGDVLATLDSTGTLTQKYQAKYAGVHERKA
TLLSECDTDFIQSITQSYNSFDEFTAPDTNPKEDELMGIDEIFDKLKDLIGTKIPYI
GATQERNRGGHLHKMICDALGYNNFKENGQFPDIKHQLLEVKLQTSETIDLGLFTPN
SYELLDIPQLNNESISMLDVRYAIFYGDVIEDTITITHFYLVTGEDFFTYFKPFGGK
GINKKIQIPLNEEFWNL

CviKI DNA sequence (SEQ ID NO:71)

ATGTCTTTTCGCACGTTAGAACTATTCGCCGGTATAGCTGGTATTTCACATGGCCTC
AGAGGTATATCTACACCAGTTGCATTCGTAGAAATTAATGAAGACGCACAAAAATTC
TTGAAAACAAAGTTTTCAGATGCATCTGTATTCAATGACGTTACGAAATTTACCAAA
TCGGACTTCCCAGAAGACATAGACATGATTACTGCGGGATTCCCGTGCACTGGGTTT
AGTATTGCAGGTTCTAGAACTGGATTCGAACACAAGGAATCCGGTCTCTTTGCTGAT
GTTGTGCGAATCACGGAAGAGTATAAACCTAAAATAGTGTTTTTGGAAAACTCCCAT
ATGTTGTCCCACACTTACAATCTCGATGTCGTCGTAAAAAAGATGGATGAAATTGGT
TATTTCTGCAAGTGGGTAACTTGTCGGGCATCAATTATAGGAGCCCATCATCAACGC
CACCGGTGGTTTTGTCTCGCGATTCGAAAAGATTATGAACCAGAAGAAATAATTGTA
TCTGTGAATGCTACAAAGTTCGACTGGGAAAATAATGAACCACCGTGTCAAGTAGAC
AATAAGAGTTACGAGAATTCAACTCTTGTTCGTCTGGCAGGATATTCCGTGGTCCCC
GACCAGATCAGATATGCTTTCACCGGTCTATTTACAGGTGATTTTGAGTCATCGTGG
AAAACTACCTTGACACCTGGGACAATAATTGGCACGGAACACAAAAAAATGAAAGGA
ACTTACGATAAAGTCATAAACGGGTATTATGAGAACGATGTGTATTATTCTTTTTCA
AGGAAAGAAGTTCATCGCGCTCCTCTAAATATATCCGTGAAACCACGTGATATTCCG
GAGAAACATAACGGAAAAACACTCGTAGATCGCGAAATGATCAAGAAATATTGGTGC
ACACCATGTGCTAGTTATGGCACTGCTACTGCTGGATGCAATGTTCTGACAGACCGT
CAGTCACATGCACTTCCTACACAAGTCAGGTTTTCATATAGGGGTGTATGTGGACGA
CATTTGTCTGGTATATGGTGTGCATGGTTGATGGGGTATGACCAAGAATATCTTGGT
TATTTGGTTCAATATGATTAAAATATTTTGATACACTAAATGGATATAAGAAGAAAA
CGTTTTACAATAGAAGGGGCTAAACGTATAATACTCGAAAAAAAGAGACTTGAAGAG
AAAAAACGAATTGCGGAAGAGAAAAAAAGAATTGCACTTATAGAAAAACAACGAATT
GCGGAAGAGAAAAAAAGAATTGCGGAAGAGAAAAAACGATTCGCACTTGAAGAGAAA
AAACGAATTGCGGAAGAAAAAAAACGAATCGCGGAAGAGAAAAAACGAATCGTGGAA
GAGAAAAAAAGACTTGCACTTATAGAAAAACAACGAATTGCGGAAGAGAAAATTGCG
TCGGGGAGAAAAATTAGAAAGAGGATCTCTACAAATGCAACAAAACATGAAAGAGAA
TTTGTCAAAGTTATAAATTCAATGTTCGTCGGACCCGCTACTTTTGTATTCGTAGAT
ATAAAAGGTAATAAATCCAGAGAAATCCACAACGTTGTAAGATTCAGACAATTACAA
GGCAGTAAAGCGAAATCCCCGACCGCGTATGTTGATAGAGAATATAACAAACCTAAA
GCGGATATAGCAGCGGTAGACATAACCGGTAAAGATGTGGCATGGATATCCCATAAA
GCATCTGAAGGATATCAACAATATCTAAAAATTTCTGGAAAGAACCTCAAGTTCACA
GGAAAAGAATTAGAAGAAGTTCTATCGTTCAAGAGAAAAGTAGTTAGTATGGCACCG
GTATCTAAAATATGGCCTGCTAATAAGACCGTATGGTCTCCTATCAAGTCAAATTTG
ATTAAAAATCAAGCAATATTCGGATTTGATTACGGTAAGAAACCAGGAAGGGACAAT
GTAGACATCATAGGTCAAGGACGACCAATTATAACAAAAAGAAGTTCCATATTATAT
CTTACATTCACTGGTTTTAGCGCATTAAATGGGCACTTGGAGAATTTTACTGGGAAA
CATGAACCCGTTTTCTATGTAAGAACAGAACGGAGTAGTAGCGGGAGAAGTATAACA
ACTGTCGTCAATGGTGTCACTTATAAAAATTTAAGATTCTTTATACATCCATACAAC
TTTGTTTCTTCAAAAACACAACGTATTATGTAG

Figure 2-28

CviKI amino acid sequence (SEQ ID NO:72)

MEEKKRLALIEKQRIAEEKIASGRKIRKRISTNATKHEREFVKVINSMFVGPATFVF
VDIKGNKSREIHNVVRFRQLQGSKAKSPTAYVDREYNKPKADIAAVDITGKDVAWIS
HKASEGYQQYLKISGKNLKFTGKELEEVLSFKRKVVSMAPVSKIWPANKTVWSPIKS
NLIKNQAIFGFDYGKKPGRDNVDIIGQGRPIITKRSSILYLTFTGFSALNGHLENFT
GKHEPVFYVRTERSSSGRSITTVVNGVTYKNLRFFIHPYNFVSSKTQRIM

DraI DNA sequence (SEQ ID NO:73)

ATGAGTGAAATTGACAACTTGGTGAACTTTATCCTTTCTAAAGATGGAATTGGTGAC
AAATCCATTCTTGAGAAAGAAGTGATTGAAAGATTTTCATTAACGAGGGATAGGTCT
GTTTACTACTGCACAGATTTTGCTATACGATTTAGTTCCTCGAAATCAGCAGCATTT
AGCAACACAGTCCTATCGCTATCCAATCTCAGAAAATTTGATAGCAAGCCCTTTATT
GTTTGCCTCATAACTCCTGCAAAAAATTACCTTTTTTTGGCAAACACTAGCTTTCTG
AAAAAAATCAGCCATAGTTCACAGACCTTAACGAGCAACAATATTAGAGGCAGTTTC
AATGGAAGCGACATATATAAGGATTTCGATGGTATACCCAATTCCCCTGAGAACTTC
GAATATCTGTTTAGAATACACGCAGAAACTACATTTGAAGAGAATCTAATTCGTTTA
GCAGAAGCAACCAACGATATTGCACCTAGCGGTAAGAAGTTCGTTCCCTCACCCCAA
GGTGAAGAAAATATATATCTAGCCCCCAAGAGAGCAAGTGAGTTTATCGCCTCCGAT
AATTACAGGCAGCTGCTGCAAGAATTGGATGATATAGTAAGGCATTATACCAATGAA
ATCATTATTGCATCCATGATAAACAACGTAAATATCAGGGGCAGAGTAATCGAATAT
CTAGTGGCCGGAGAAGATGATCTTCTGAGACAAAACATAATTTATAAGCTCAGAAAT
GGCGGTACAAATCTACCCCAATTCAAAACAGATAATTCGTTAGGAGATTACTCAAAA
GCTTTTGAAGGCTTTGATACAGAAACAGATGTGAAAACAAAAATTATGCTCCTTAAT
TCCAATCCAAAAGCATACAACTTAGATAAGATTCTTAATTTCTTATCGAGCGATAAG
AGCGTATTTCTTTTCTATTTCATTGGAATAGATTCTGATAACTCTCTTAAGACATGT
CTTGTGACTATGTTTAATGAGGAGTTGTTACGAGGTACAATTACTCTCAGGCATTGG
GCAGGCAGGAATTCTAGAGGCGTTTCCCAGTTCGATGGAAAAATCATCAACAATATA
ATTCTTAATCCGTCAAATAAAATTGATAAGGCTCAAGCTCGGGAATTCCTTACCAGA
ATTTTATCTTTATAA

DraI amino acid sequence (SEQ ID NO:74)

MSEIDNLVNFILSKDGIGDKSILEKEVIERFSLTRDRSVYYCTDFAIRFSSSKSAAF
SNTVLSLSNLRKFDSKPFIVCLITPAKNYLFLANTSFLKKISHSSQTLTSNNIRGSF
NGSDIYKDFDGIPNSPENFEYLFRIHAETTFEENLIRLAEATNDIAPSGKKFVPSPQ
GEENIYLAPKRASEFIASDNYRQLLQELDDIVRHYTNEIIIASMINNVNIRGRVIEY
LVAGEDDLLRQNIIYKLRNGGTNLPQFKTDNSLGDYSKAFEGFDTETDVKTKIMLLN
SNPKAYNLDKILNFLSSDKSVFLFYFIGIDSDNSLKTCLVTMFNEELLRGTITLRHW
AGRNSRGVSQFDGKIINNIILNPSNKIDKAQAREFLTRILSL

EagI DNA sequence (SEQ ID NO:75)

ATGAAAAAAAGAAGAGATTTGGTTGAAGTATTTGGCTATAACCCCTATGGACCTTAGC
CCTGAAGTCAGGGCTCTTTGGAACTTGGGAGCATGCCCATTTCTTAATAAAGAATGC
ATAAAAATAAATCATGATCAAACAATAATTTATGGCACATGCAGTGTAACGTCTCCT
TATGGAGACGTTATTATTTGTCCAAATAGGCTTTATGCTAATGACTATGAAACCTTG
CATAAAGTCAGTCGCGATGCATTTGGCGATGATGTCCCTTTTTTTGACTTATAGTAAT
TTCATAAAATATAGGGCGACTTACAAAGACTGTATCGTAGCCCTCGGTAAAAACTCA
GGGAAAGAAGTTCAAGTTGGCAGGGCTCTATCGATGGACTGGGTTTTGGTCAGAATC
ACTGACGGGGAACTTAAAGAATACGTAGGCGTAGAAATACAAAGCATTGATATAACT

Figure 2-29

GGAAATTACAGAGATGCTTGGCATGCTTACAAAAACCTCAAACCTATAGATATCATT
GATAACTTACCAACTTCACAACATGGACTGAATTGGGCTAATGTACACAAAAGACTC
ATACCACAAATAATAAGAAAAGGAGTTGTTTACTCTCGATCAAATTATGTAAAAAAA
GGTCTTTATTTTATATTACCTGAGATTGTCTATAATAAATTTGAAGATGTTATTGGT
GCAGACATACCTCTTTTGAAAACACAAACGAATAAAAGCATAACAGTTCATACATAC
TCCTTAGGTGAGCCAGCTGCAAATGGTGAACAACGAAAACTAATCAGTGAAAGAGAA
ATCATTTTCGATTTAGACGAATTTTCAAAAAGATTCACGACTGGCCCCAACTTGCCA
AAAGGAGATGATTTGGACGCAGTAATTAAAAAAGCGTTAGGAATGATGTAA

EagI amino acid sequence (SEQ ID NO:76)

MKKRRDLVEVFGYNPMDLSPEVRALWNLGACPFLNKECIKINHDQTIIYGTCSVTSP
YGDVIICPNRLYANDYETLHKVSRDAFGDDVPFLTYSNFIKYRATYKDCIVALGKNS
GKEVQVGRALSMDWVLVRITDGELKEYVGVEIQSIDITGNYRDAWHAYKNLKPIDII
DNLPTSQHGLNWANVHKRLIPQIIRKGVVYSRSNYVKKGLYFILPEIVYNKFEDVIG
ADIPLLKTQTNKSITVHTYSLGEPAANGEQRKLISEREIIFDLDEFSKRFTTGPNLP
KGDDLDAVIKKALGMM

EarI DNA sequence (SEQ ID NO:77)

GATCATACATTGCCTGTATATTACTTATGGCCTTTGACTACTAATAATGCCACATTG
CTCTGTAAAGTACATAATGGAGAAAAAGCAGAGAAATGGCCTGGCGAGTTTTATTCA
AGGCAAGAATTGGCATCACTCTCAAGATTGACCGGGGTTGAAGCTCGTGTTTTGGCT
GGGGCACCAATATTTAATCCAGAAGCAATTGATATTTTAAAAAATCCTAAATTCGTT
GAAGGTTTAGTCGATAAGTTTTCCAGATATCCGAATGAGGTATATAATTTACGCAAT
CGAATTAAGAGAGTTACAGGGTTCGATTTCTTCGATAACCCTAATTTGAAAATTTCT
GCCAATTGGGTTATCGAAGCCGATAAACTTATCTAA

EarI amino acid sequence (SEQ ID NO:78)

DHTLPVYYLWPLTTNNATLLCKVHNGEKAEKWPGEFYSRQELASLSRLTGVEARVLA
GAPIFNPEAIDILKNPKFVEGLVDKFSRYPNEVYNLRNRIKRVTGFDFFDNPNLKIS
ANWVIEADKLI

EsaBC3I DNA sequence (SEQ ID NO:79)

ATGCTCAAGACCACCTCAACCTTTTCCCCCTCAACCGTCAAATTCCCCAAAAAACCC
GCGCTCACAATATCCTTCCCATCCACCATTATACCCTTTAAGATCTCCAAAGCCTTC
TTTGATGTCATACATAGAATTCTAAAGGCGGAGAGGCAATGCTTTCCCAACTTTATA
ATAACGAGAAGGAAAATGCTAAGCTTAAACCTTAGGGGATTATCAAAACCTTCTTTG
ATAGCCCTTTACATAGACCTTCTGACGCTCTACTTTAAAACCACCTTGTGGGTGTGC
GGTTTTCAACCCAACACGGAAAAACTTGGATACAACGGTTATAGGATGGATGCAGAT
ACAGGCAAGAGAATTGATTGCGAGGTAAAACCACAAAATACCGATAACCGTAGAAAA
AAATTGACTGGAGGTGGAAGTTTTAACGATTATACGGTAGAAAGGTTTAAAAAGGAT
TTAGAAAACAATCCTGCAATTTTGGTTAGTGGTTTTGTAGGAGGGAAACTCATATAC
ATCTTTGAGTTTAGGTTTGAATGCTTAAGGGAAAAACTTAAAGGTTTGCTTGAACGT
AGATTTCCAAGGGGCCACAGAAGGGAAGGTGAATACTTACGTTCCGCGAACTTTTCT
TTCGATACTTTGAGGGTCTTGAAAGATGAAGGGTTTGGAAAGGTTCATAAATCAAGT
TATACACGGTGA

Figure 2-30

EsaBC3I amino acid sequence (SEQ ID NO:80)

MLKTTSTFSPSTVKFPKKPALTISFPSTIIPFKISKAFFDVIHRILKAERQCFPNFI
ITRRKMLSLNLRGLSKPSLIALYIDLLTLYFKTTLWVCGFQPNTEKLGYNGYRMDAD
TGKRIDCEVKPQNTDNRRKKLTGGGSFNDYTVERFKKDLENNPAILVSGFVGGKLIY
IFEFRFECLREKLKGLLERRFPRGHRREGEYLRSANFSFDTLRVLKDEGFGKVHKSS
YTR

EsaBC4I DNA sequence (SEQ ID NO:81)

ATGGACCTGTTGGCTGAAATAAGAGGTATAAAATATAAGCCGTTTCTTTGTAGAGAC
CTGGTACCTTTTGAGTTTAGCAGGTTAGAAGATGCTATTGCCTCCTCTCCATCTTTT
ATTTTAGAAGTTGATGAAAAAAATAGGGTTGCTGTAAGTTGGTGGGTTTCACCTAAA
CGCACTCGCTCCTATCCATACGCAAGAGTTTACGATACTTTAGGTTTTTCCGGAAAG
AAAATAACAATCATTCCAATCATGAAAGACGAAGGTGAAGGAGGGGATAGAGATTTT
TTACAATGGGATACTGTTTCACTTATGAGTTTGTTAGGAGTTTATGTGATTATTGCT
TATTATAACAAGGCCGAGCCGAGTAAAAGGTATAAAAACAAGATCACAAATCAACGA
TTTGATATTGATTACATTAAAGAAAAAATTAAAAGCATTATTTCTTACCAATCGGAT
GCTTTACACTGGAATCTTTATGAAGTTGAAAATGTGGGAGAAATTGGAGAAAGAGCT
CTGAAGGCTTATGACTTAATTTCAATGGAGTTAAATATAAGAATGCATTCACGAAAA
ACTGCAGAAAAAAGAATTAAAGAATTATTAAAAGGGAAAGAAAAGTTTATGAGTCTT
TCACGAACTTTAGCGGAGAAAGCACAAAGAAGAGAGAAATTGACTATTCAGCCAAAA
GAAAATCTTTCTGGATCAAAAGCTTCTATTACAATAAAGAATTATCTAGGTGGTTTT
TATTATCTCACTGTTGATGAAGTAAAAGTTATAGGAAATAAAGTTTTGCTAATTGAG
GCGAAGCATAGCAAGACAAATTCCTTACCGTCGCTGGAAGATATAAAAGATGGTCTG
TTAAAGATGATTTTATTTACTAATCTCGAAAATGTAGAAATAGAAAGTAAAAATTAT
AAGCCAGAAGCTGTGTTAAAACTAACTGTTGAAGGTGGTTTTAACGAGAGTAGACTT
TCACCTTCACAAAAAAAGACTTTAAAACTCTTACAAGAAGAAGCCGAAAGCAATAAT
TTTCAAATTCAACTAATATGA

EsaBC4I amino acid sequence (SEQ ID NO:82)

MDLLAEIRGIKYKPFLCRDLVPFEFSRLEDAIASSPSFILEVDEKNRVAVSWWVSPK
RTRSYPYARVYDTLGFSGKKITIIPIMKDEGEGGDRDFLQWDTVSLMSLLGVYVIIA
YYNKAEPSKRYKNKITNQRFDIDYIKEKIKSIISYQSDALHWNLYEVENVGEIGERA
LKAYDLISMELNIRMHSRKTAEKRIKELLKGKEKFMSLSRTLAEKAQRREKLTIQPK
ENLSGSKASITIKNYLGGFYYLTVDEVKVIGNKVLLIEAKHSKTNSLPSLEDIKDGL
LKMILFTNLENVEIESKNYKPEAVLKLTVEGGFNESRLSPSQKKTLKLLQEEAESNN
FQIQLI

EsaBS9I DNA sequence (SEQ ID NO:83)

ATGGCAGAGAGAGGTTTGAGTTGGCGGTTGGCAACTATCAACGAACTCGGTTGGCGG
GGCAAAAACCGAAAGCAGCGACTCTGGTGCAACGCCGCGACGGGTCGTTCTATCTGC
AAATTAGTTGAAAAAATCCAACACAAACTTCCAAAGCTATTTCACTTAGCAGAATTA
GAGAGTTCAAGAGCTGGTAAGATAGGGATGGAAGTAGGTTCTATTAGGGAAAAGATT
ATCGTCGCTTTGTTGATACACAAGTTTGGTGAAGAAAATGTTAAGACCGATATTCCG
ATTACTGAAGCAGAAGTAGATGTTGAAGTATTTGGAAATCCGCTTTCCATAAAGACT
ATTACAGGAAAAAAATCTATCGGGTGTAAAGCTAATATGGACTGTTGATGCCGCTAAA
TCAAAAGAATTTCGTGAGACTTATTTACCTTTCTGCGATATGATTTTAATACAGGTC
AACTGGGGTAGTAACGGCGGATTTTACCTTATTCCAAAAGAAACGCAACTTGACGTA
TTGAACAACTTAGGCAGAACAACATACATAAAACTCCCCAAAACTGGGACAAATCCA

Figure 2-31

AGAGGCGTTGAGTTGAGCAGGCAGGCTTTACAGGAGTTAGTGCGGCACAAAGACACA
ATGATAATACCTATTGATTGGAAAAAGAAGAAATAGACTTTAAACCACTTAAAAGA
TGGATTGAATTATGGGAGAAAGAGTAA

EsaBS9I amino acid sequence (SEQ ID NO:84)

MAERGLSWRLATINELGWRGKNRKQRLWCNAATGRSICKLVEKIQHKLPKLFHLAEL
ESSRAGKIGMEVGSIREKIIVALLIHKFGEENVKTDIPITEAEVDVEVFGNPLSIKT
ITGKNLSGVKLIWTVDAAKSKEFRETYLPFCDMILIQVNWGSNGGFYLIPKETQLDV
LNNLGRTTYIKLPKTGTNPRGVELSRQALQELVRHKDTMIIPIDWKKEEIDFKPLKR
WIELWEKE

EsaDix6IP DNA sequence (SEQ ID NO:85)

ATGAAAGATCCAATTGAAGACCTAAAAAGGTATCGTGATTTTCTTGAAAGCATACCT
TTAGACGAGTATAGAAAACAATTAAAAGGTATTAAATGGGTAGAGCAAGACTTACCC
AAAGAAATTTTACCCCTTGCCTCAATATTCAAATATTACTGGGAGATTAGAAAATTT
TTAAATTTTGATGAATGGTTCGATAAATTTTGGAGAGAGATAAATACCAATCTAGAA
AGTAAGAAGACACTTGAAGAATTCAAAAGATATTTCTTCAATAAGTCACTTGAAGAA
AATGATTGGTTTAGGAAAGGATTTAAAGCAAGAATGTATAGAACTTGGGTATCTGTT
CTTACTCAATTAGACTTTTGTTATATGTTTGAATATGTCTGTGCTAAAAAGGGAATA
AATTTAAAATTAGAGTGCAATGCAGAGTTAGATGCAAGAGGAATTGATGCTAAGGTT
AATGATATTTGTTTTCAGGTAGCGAAAATAAGTCAAAGAAAAGAAGCAAGGACTGTA
GGTAGAAAGAAAACAATTATTACTATACCTTATGCTGTATTTAACATAGAAGAGTTT
AAAAGAAGGATTGCAAGTCCGCGGGTTAAAGACAAAAGTAGCTATCAAAAAGCCTTA
AAGGCGTTTCATAAGTACTTTGATCTTCTTAAAAATGGCTTTGTTGTTTTTAAGAAA
GATTATATAAAGAAGATAATAAATAACATAGACGATGTTGAAAAACTGAGACAAGCG
GTTAATGAAATCTCACGAGAATTATGTGGAGAAATTTAA

EsaDix6IP amino acid sequence (SEQ ID NO:86)

MKDPIEDLKRYRDFLESIPLDEYRKQLKGIKWVEQDLPKEILPLASIFKYYWEIRKF
LNFDEWFDKFWREINTNLESKKTLEEFKRYFFNKSLEENDWFRKGFKARMYRTWVSV
LTQLDFCYMFEYVCAKKGINLKLECNAELDARGIDAKVNDICFQVAKISQRKEARTV
GRKKTIITIPYAVFNIEEFKRRIASPRVKDKSSYQKALKAFHKYFDLLKNGFVVFKK
DYIKKIINNIDDVEKLRQAVNEISRELCGEI

EsaLHCI DNA sequence (SEQ ID NO:89)

GCAAAGGGAAACATCAATTCATTCAAAGGCATTCACAAAGTTTTCCATGAATTCGAG
CCAATTCAGACCACTGTGGTATGGCCTTACAAAAAGAGCTTACTTAACGAGTACAAT
ACAAGCGAAAGCAACATTTTATCTGTAGCAAATAATCAAAGAATTTTGCATCACTTC
TTGTTTGGAAAAGATACAGAATTTGATAGCTTAGACATTACAAAACGACCTAAAACC
TATTTTCCACATAGAACAAAAATGAGTTTTTTCTATAGCTTTGGAAAAGATTTACAG
ATTGAGTTGAAGAACATACAAATAGAAATTGATTTAACTATTGAGTTTCAAGGCATA
ATCGGAATTTTTGAAGCAAAGAATGGCAGTCCTAGTAATTTTGCAATTTATCAGCTT
TATCATCCTTTTTTATACTATTACAACGCCAATCAAATCTCCGAGATAAAAGGCGAA
ATCAAAAACATTTATGGTGTTTATGTTGTTAGAAACATAGAACGTAGGATTACAAAC
CTAAAAATGTGGGCATATACTTTTGAGAATCCATTGGATATTACTAGTATAAAGTTT
GTAAAATCTGCTTGCTACCAACTAAAAGTCTAA

Figure 2-32

EsaLHCI amino acid sequence (SEQ ID NO:90)

AKGNINSFKGIHKVFHEFEPIQTTVVWPYKKSLLNEYNTSESNILSVANNQRILHHF
LFGKDTEFDSLDITKRPKTYFPHRTKMSFFYSFGKDLQIELKNIQIEIDLTIEFQGI
IGIFEAKNGSPSNFAIYQLYHPFLYYYNANQISEIKGEIKNIYGVYVVRNIERRITN
LKMWAYTFENPLDITSIKFVKSACYQLKV

EsaS1IP DNA sequence (SEQ ID NO:91)

TTAAACTTAGAACCCCGTATTGTTGAAAGTACAACTGACATTTTAGAGTTGCTTATA
CAAACCGACTCCAAAGGGAGAGAAGGTGATGTACGAGATATATTAATAATTCGGCGA
GATATTCAGTGGGAAATAGGGCTAAGCCTTAAGCATAATCATTTTGCTGTAAAGCAT
AGCCGTCTAAGTCGAAAATTGGATTTTGGAAATGAATGGTATGGCATTTCATGCTCG
GAGGCTTATTGGAAAGGAGTTAATCCTGTATTTGATTATCTAGTTGTCGAAAAAAGT
AAACATAAAAAATTCAATGAACTCAAAAATAAAGAAGAAGTCGTTTACGTTCCTTTG
CTAAAAGCTTTTATAGATGAAATCAAGCAACAATGCCAAGTCCATAAAGATATTCCT
AGTAAATTGGTACAATACCTTTTAGGAAAGTATGACTTTTATAAAATAATTAGCATA
GATAAAGAGCGGATGACTCAAATTCAATCCTATAATTTACACGGTACACTCAACAAA
AACAGCGAATCGAAAAAAGCATCCATTCGAATTCCACTAGCATCCTTGCCAACGCGT
ATAGTGAGTTTGGACTTTGTTCCGGGGAAGACAAACACTGTTGAACTTTATATGGAT
GGTGGTTGGCAATTTTCTTTTCGCATACATAACGCAGAAACTTATGTTGCGCCGACC
TTGAAGTTTGATATTCAAATAGTAGGTATGCCTACTGCTATAATCACAATAAATTGT
CTTTGGAAATAA

EsaS1IP amino acid sequence (SEQ ID NO:92)

MNLEPRIVESTTDILELLIQTDSKGREGDVRDILIIRRDIQWEIGLSLKHNHFAVKH
SRLSRKLDFGNEWYGISCSEAYWKGVNPVFDYLVVEKSKHKKFNELKNKEEVVYVPL
LKAFIDEIKQQCQVHKDIPSKLVQYLLGKYDFYKIISIDKERMTQIQSYNLHGTLNK
NSESKKASIRIPLASLPTRIVSLDFVPGKTNTVELYMDGGWQFSFRIHNAETYVAPT
LKFDIQIVGMPTAIITINCLWK

FseI DNA sequence (SEQ ID NO:93)

ATGACCGACGAGTTGTTTCCTATCCCGGAGCCATTGGTCAGACCAGTCATCGCACTC
CCCCCTCATCTGAAGGAATTGATCGATCTACTCCCATTGAATACGCCGGTACATCGC
CGAGATCTCGAAGCGAAGTATGGGCGCTCCAACTATGCTAGACGCATACGAAAGATT
ATCAGTGAATACGGTTGGGAAATCGAGAGTCGCCGCCAGTCGGAAGGCGCCAATGAC
GATTGGTACATCCGTCGGTCCGACGGCCCCGTGCGACCGCAGCGTATTAGACGGGAG
GTACCAAGACGCAGCCGCGAGACCGTCTACAGACGTGACGACTGGATCTGCCAGATT
TGTCGGATGAAAACCGACCCGGAGCGTGGATCTCTCGTTCCGCAGTGCGATCACAAG
ATTCCGGCGGACCGCGGAGGGGATTCTGATGAAGAAAATCTTCAGACGCTTTGCACG
CGTTGCAATCTCAAGAAGAGGCAGGCCTGCGGTGGATGCGCTCTGGCCAGCTGTGCG
GATTGTCCATTTGCGTATCCAGAAAAGTTTGATGATGTGCTGATTCTGCACCTCGAC
AGGGAGCACCTTAAGAGGATTATGACCACGGCATACGCTCGAAATGTCACGGCCAGT
GCAGTCGTCAGCGACCTATCCGACCTGCTCTAG

FseI amino acid sequence (SEQ ID NO:94)

MTDELFPIPEPLVRPVIALPPHLKELIDLLPLNTPVHRRDLEAKYGRSNYARRIRKI
ISEYGWEIESRRQSEGANDDWYIRRSDGPVRPQRIRREVPRRSRETVYRRDDWICQI

Figure 2-33

CRMKTDPERGSLVPQCDHKIPADRGGDSDEENLQTLCTRCNLKKRQACGGCALASCA
DCPFAYPEKFDDVLILHLDREHLKRIMTTAYARNVTASAVVSDLSDLL

FspI DNA sequence (SEQ ID NO:95)

GTGTTGACAAACAACGAGATTGAAAGATTAAGGCAAGCCATTATCGCGACCATTGCA
TCTCCTGTAATTGGCTCGATAGAAGATTATACATGGGAAGCAATTTTTCATTATGTT
AAGGATATTCCTTTATCAGATCCCGCTCTGGGACGCAGCAAGCTTCTCTATGATGCT
GTTGACGTAGTTACTAAAACTGGTTGGTCACTCAAATCCCTCCAATTGAAGAGCCTT
AACTTTAAAAGCCCATTTTTATTTGTTATTCAGAGAGCAGATATCCTTAAGAAGTCT
GTCCAGCTGGGTTTTCCTGGTCTGACTGAGCAATCTTCGCCGGATGAGCTTGGAGCA
GCCATTATCCAACATTGGAATGAGAAGATTATTTTGAGTCAGGCAGCACAAAGCGTT
GTAAATAGTTATGAAGGCATATTACTGAAAACTATCAAAGGTTACGAGTATATCTAT
TGTGAGTTTCCACTCGATCCTCTTGATCCAAGCACGTTTTCTTGGGCTTGGACGGTG
GACAAAACTACTGGCGGTGCAGGGGTAGGGCTACAAGGTAGCATTGTGGGCAAAACA
GAATTAGTGTGGTATAAAAATCAGAAACAACTTTTCAGAGCTAGGACTATTCCCGCA
CAAGCGGTTCGTATTACAGTTGAAAGAACTCGTCTTACTCTTGATCGATATGTAAAG
ACAGTTATCTTTGCTTTGCAAGATCAAATCAACATGCAGTTTTCTGAGAATGAGCCT
GAAGAATAG

FspI amino acid sequence (SEQ ID NO:96)

MLTNNEIERLRQAIIATIASPVIGSIEDYTWEAIFHYVKDIPLSDPALGRSKLLYDA
VDVVTKTGWSLKSLQLKSLNFKSPFLFVIQRADILKKSVQLGFPGLTEQSSPDELGA
AIIQHWNEKIILSQAAQSVVNSYEGILLKTIKGYEYIYCEFPLDPLDPSTFSWAWTV
DKTTGGAGVGLQGSIVGKTELVWYKNQKQLFRARTIPAQAVRITVERTRLTLDRYVK
TVIFALQDQINMQFSENEPEE

HhaI DNA sequence (SEQ ID NO:97)

ATGAATTGGAAAGAATTTGAAGTTTTTTGTGTTACTTATTTAAATAAAACTTATGGA
AACAAATTTGCGAAAAAAGGCGAAAGTGATTCTACAACAAGTGATATTCTTTTTACA
GGAAATAATCCATTCTATATAGAAGCAAAAATGCCACATTCCCAATGCGGTCAATTT
GTTTTAATTCCTAATAGAGCTAAATATAAATTTGATTATTCACCGAAAAATAAGAGT
GAAATAAATCCCTATACTCAAAAAATAATGCAATTTATGTCAGAAAACTTCTCTGAA
TATGCTAATTTATCTACTAAAGGGAAAATTATTCCATTACCTGAATCTGTATTTGTA
AATTGGATTAAGGAATATTATAAAAGTAAAAGTGTGAAATTCTTTATTACTTCTAAT
GGTGATTTTATTATATTTCCTATTGAACACTTCGAGCATTACTTTAACGTATCTTGT
ACATACAGAATTAAAAAAAGCGGTCCAAGACATCTCAATTCGAAAAGCCTTCCTGAT
TTCAAACAGGCGTTAGATAAAAAAGGCATCTCTTATACGATGAGGGGGTTGGAACTG
CATTCTGACGAGAACATTCACGATAAAAGAATTTCAGGAGATGATAAGGATTTTTTA
ATTAAAGAGAATAATGGAGCTTATCACGTTAAGATTTTATCTAATACTTTTAATGCT
AATGTTATAATTTTCAATATCATTAAAAAATAA

HhaI amino acid sequence (SEQ ID NO:98)

MNWKEFEVFCVTYLNKTYGNKFAKKGESDSTTSDILFTGNNPFYIEAKMPHSQCGQF
VLIPNRAKYKFDYSPKNKSEINPYTQKIMQFMSENFSEYANLSTKGKIIPLPESVFV
NWIKEYYKSKSVKFFITSNGDFIIFPIEHFEHYFNVSCTYRIKKSGPRHLNSKSLPD
FKQALDKKGISYTMRGLELHSDENIHDKRISGDDKDFLIKENNGAYHVKILSNTFNA
NVIIFNIIKK

Figure 2-34

HinP1I DNA sequence (SEQ ID NO:99)

ATGAATCTGGTAGAATTAGGATCTAAAACAGCTAAAGATGGTTTTAAAAACGAAAAA
GATATTGCAGATAGATTTGAAAATTGGAAAGAGAATTCAGAAGCCCAAGATTGGTTA
GTTACAATGGGACATAACTTAGATGAAATCAAATCTGTTAAAGCTGTTGTATTAAGT
GGATATAAATCAGATATAAATGTTCAAGTTTTAGTTTTTTATAAAGACGCGTTAGAT
ATTCATAATATTCAAGTTAAGCTCGTTAGTAATAAACGTGGTTTTAATCAGATAGAT
AAACACTGGCTTGCTCATTATCAGGAAATGTGGAAATTTGATGATAATCTATTAAGA
ATATTAAGACATTTTACGGGTGAACTTCCTCCATATCATTCAAATACAAAAGATAAG
CGAAGAATGTTTATGACAGAATTTTCCCAAGAAGAGCAAAATATCGTTCTTAATTGG
TTAGAAAAGAACAGAGTTCTTGTGCTAACCGATATATTAAGAGGAAGAGGCGATTTT
GCCGCTGAATGGGTGCTTGTAGCACAAAAAGTAAGTAATAATGCAAGATGGATATTG
AGAAATATTAATGAGGTTTTACAACACTATGGTTCAGGCGATATTTCTCTTTCCCCA
AGAGGCTCTATTAACTTTGGTCGAGTAACTATTCAAAGAAAAGGGGGCGATAATGGT
AGAGAAACCGCAAATATGTTGCAATTCAAAATTGATCCAACAGAGTTATTTGATATT
TAG

HinP1I amino acid sequence (SEQ ID NO:100)

MNLVELGSKTAKDGFKNEKDIADRFENWKENSEAQDWLVTMGHNLDEIKSVKAVVLS
GYKSDINVQVLVFYKDALDIHNIQVKLVSNKRGFNQIDKHWLAHYQEMWKFDDNLLR
ILRHFTGELPPYHSNTKDKRRMFMTEFSQEEQNIVLNWLEKNRVLVLTDILRGRGDF
AAEWVLVAQKVSNNARWILRNINEVLQHYGSGDISLSPRGSINFGRVTIQRKGGDNG
RETANMLQFKIDPTELFDI

MfeI DNA sequence (SEQ ID NO:101)

ATGGGTAAATCTGAATTAAGTGGAAGATTAAATTGGCAAGCATTGGCTGGATTAAAA
GCTAGTGGTGCTGAACAAAACTTATATAACGTGTTTAACGCTGTTTTTGAAGGAACT
AAATACGTTTTATACGAGAAGCCAAAGCACCTTAAAAATCTATACGCTCAAGTAGTC
TTACCTGATGATGTTATTAAAGAAATTTTTAATCCTTTAATTGATTTATCAACTACT
CAATGGGGTGTTTCTCCAGATTTCGCAATAGAAAATACAGAAACGCATAAAATTCTT
TTTGGTGAAATTAAAAGACAAGATGGATGGGTAGAAGGTAAAGATCCTAGTGCTGGC
AGGGGTAATGCACATGAGAGATCTTGTAAATTATTTACTCCTGGATTATTAAAAGCT
TATAGAACAATTGGTGGAATTAACGATGAAGAGATATTGCCATTCTGGGTTGTATTC
GAAGGTGATATAACACGAGATCCCAAAAGAGTAAGAGAAATTACTTTCTGGTATGAC
CACTATCAAGATAATTATTTCATGTGGCGACCAAATGAATCAGGCGAAAAATTAGTT
CAACACTTCAATGAAAAATTAAAAAAATATTTAGATTAA

MfeI amino acid sequence (SEQ ID NO:102)

MGKSELSGRLNWQALAGLKASGAEQNLYNVFNAVFEGTKYVLYEKPKHLKNLYAQVV
LPDDVIKEIFNPLIDLSTTQWGVSPDFAIENTETHKILFGEIKRQDGWVEGKDPSAG
RGNAHERSCKLFTPGLLKAYRTIGGINDEEILPFWVVFEGDITRDPKRVREITFWYD
HYQDNYFMWRPNESGEKLVQHFNEKLKKYLD

MluI DNA sequence (SEQ ID NO:103)

GTGAGCGCTCCCGAAGTCGACAGCGCCCGGGATGCCCGCTACGTCGAGATCCTCCTG
GCTCCCCTTCGAAAGTGTGGGACCTACCTGCCGAAGATGGGCGGGTCCGGCGAAGTG
GATCTCGCTGGCTTCACCGCGGCCTACGGGGCTGATCCGCTCTATCACTGGATGGGG
CTCGACTCGCCTCTCATGTTCGCTGCGCACAAGGCCGCCGGCGGTATGACCTCGATC

Figure 2-35

TACCGCCAGCTCGGTATCGGATCCGAGCGCCTCTTCCGCCAGGTCCTGCGGGACGAG
CTCAATCTCACAGCCGACCAGGTCAAGTGGTCCTACAAGATGCTGCCCGAGCTTGAT
GCGGAGCACGCGAACGAGTCGGTCAAAGCTCGAGTCCTCTCGTTGGACGGGAGGGTG
GAGCTCGAGGATCTGGAGGATCAGCAGGCTCGCGAGCGCGTCGAAGCTTGGATAGAA
GTACAGCGCCGTCGTCTCAACATCACCGCACCCCTCAAGGGCGCCGTCTTCGAGGTT
CGCCAAGGGTACAAGTCAGCTGACAGCAAGCGGCAGAACGCCGACCTCGCCAACGCG
GCGCAAGCCCTCGGGCACCAGTACCTTCCGGTGCTCGTCATCATGTCCACCCAGATC
AACGAGGTCGTCCACGCCCGCTACACGACGGGCAACTGGTCCGTACTCATGGGCACG
GTTGGGGCCTCGGACCCGGTGGGCAGTACCTACGACTTCCTTGATCAGGTCGTAGGT
TACGACCTAGCCGCGTTCTTCGAGCGCAACAAGGCTCTCCGCGCTGGCACCGAGGGC
ATTCTCACTGATCTTCTGGAGGCCCGGTGA

MluI amino acid sequence (SEQ ID NO:104)

MSAPEVDSARDARYVEILLAPLRKCGTYLPKMGGSGEVDLAGFTAAYGADPLYHWMG
LDSPLMFAAHKAAGGMTSIYRQLGIGSERLFRQVLRDELNLTADQVKWSYKMLPELD
AEHANESVKARVLSLDGRVELEDLEDQQARERVEAWIEVQRRRLNITAPLKGAVFEV
RQGYKSADSKRQNADLANAAQALGHQYLPVLVIMSTQINEVVHARYTTGNWSVLMGT
VGASDPVGSTYDFLDQVVGYDLAAFFERNKAALRAGTEGILTDLLEAR

MmeII DNA sequence (SEQ ID NO:105)

ATGAGTGAAACTAATCTTAATCAATTAGCTTGGACATCGTTATTTGAAAAATACGAT
ATTTTCAATCAATTAGAAACACATAATTTCTTTAATATCACCTCTACACAAATAAAC
CAATTTCGTGAAGCAAGGTTAATGACTAAGTTTGATAATACTAGTCAACTTCCTAAT
ATTTTTTCTAAAAATGGTATTGGAATATTGCCAACCTCTCGTGGCTCTTACACATTA
GGAAAATTTAATATTTTCCATAAATTTGAAGAAATACCAGAAGAAGTAGAGCATTAT
AGATTTTGCAATATTTATGAAAGCCTAGATTTCAATAATATTAGTTCGGAGTCAACA
GCTATAAGCTGCGCTTCTATATCAAAAATATTAGACGATTTTATTGGTGAAGAATTA
GTTTCAACTGTTTCAGGCAGAATGGGAACAAGCACTTTTGAATTCAGTTTAGATAAA
TTTCATACTAAAAAAATCACAGTTGAAAAAGCACAAATTGAAATTGACGGAGGATAT
GAAGGCGAAAAATCTTTTGTATTGATTGAAGCTAAAAACTACATATCCGACGATTTC
ATTATTAGACAGCTTTATTATCCATTTAGAAAATGGAAAGAAACAATTCAAAAAGAG
GTAAAAAATGTTTACCTCACTTATTCAAATGGAGTATTTGAATTAAGAGAGTATGCT
TTTACAGATATTGAAGGCTATAACTCTATCTATCTCGTTAAAAGTAAGAGGTATGCT
ATTTACAATATTGTGATCAATGTTGAAATAATACAGCAATTAATTTTAGCTACTGCC
ATAGAGCCAGAGCCATTAGATACACCTTTCCCACAAGCCGACTCTTTTGAAAGAGTA
ATCAAGTTATGTGAATTGATTAACACTTCCGAAATATTGAGCAAAGACGAAATTACA
GAAAACTACGACTTTGACTCTCGGCAAACTGATTACTATTTGAATGCTTGCAAATAT
CTAGGCTTAACAGAAAAGGCATTTAAAGACGGTGGTATAGCTGCCTGTCTCAGTAGC
AAAGGAAAAGCGATATTTAAAAAGGATATTAGCTCTCGTAGACTTGATTTTATTAAG
CTGATATTGGCTAAAACCGTATTTAGAAAAACATTAGAGTTATATTTCAATAAAGCC
AGCATGCCCACCAAAGACGAAGTTGTATTGATAATGAAAGAGTCAAAACTAAATAAA
GTAACTTCCGAAGAAACATACAGCAGAAGAGCTTCTACTGTATTGGGCTGGACAAAC
TGGATAATTAATCAAATAGAAGAATAG

MmeII amino acid sequence (SEQ ID NO:106)

MSETNLNQLAWTSLFEKYDIFNQLETHNFFNITSTQINQFREARLMTKFDNTSQLPN
IFSKNGIGILPTSRGSYTLGKFNIFHKFEEIPEEVEHYRFCNIYESLDFNNISSEST
AISCASISKILDDFIGEELVSTVSGRMGTSTFEFSLDKFHTKKITVEKAQIEIDGGY

Figure 2-36

EGEKSFVLIEAKNYISDDFIIRQLYYPFRKWKETIQKEVKNVYLTYSNGVFELREYA
FTDIEGYNSIYLVKSKRYAIYNIVINVEIIQQLILATAIEPEPLDTPFPQADSFERV
IKLCELINTSEILSKDEITENYDFDSRQTDYYLNACKYLGLTEKAFKDGGIAACLSS
KGKAIFKKDISSRRLDFIKLILAKTVFRKTLELYFNKASMPTKDEVVLIMKESKLNK
VTSEETYSRRASTVLGWTNWIINQIEE

MscI DNA sequence (SEQ ID NO:107)

ATGGGCGACATGGCGTACAGGGACCGACCGCTCAACGCAGAGGAGATGGAGGCTCTC
CGCCTCGTCCTAAGCACGTACCGGGATTCCTCGGGACAGAACCAAACCAAATACGGG
TCTATGCCTGGGTTCCGCGACTTCGAGCGAGGTCTGGCGAGCGTGCTGGGCGGTACC
GCCGCGGAGAACAAGGGTGTCTTCGACATCATCGTCACACCTAGCGACGGCAGCACA
GCCTTCGGAATCTCGTGCAAGATGGCCCGGTTCGCGCCGAAGGCACAGAACGCGGCG
TTCGTTGAACTCTCCAACGCGGCCGCGAAGTTCCGGGCGCACCTCTTGGAGCGCCAG
ATCAACTGGGCCACCGACCCCATGCTCGCAGGACCGGCGATCATCGAGTTGGTCACG
AAGTGGCACACCGATGACGCCAACGAGCATGGGCTGGACCTCGATAAGAGCGCCTAC
GCCGTACTAAGCCGGAGCAGTGATTGGTCCACTTACCAGTTGTCCACTTTCCCGCTG
GACCTCTATGGCTTCAACCCGATTGGGGACATCGCGTGGACGGCAACGACCAAGCGC
ATAGATGGGCACGTGGAGATCAACGGCCAGCCCCATCTGCTATGGCAGTGGTACCCC
ACCAGTGGGGGTCAGTTGAAGTGGTGGCCTCCGCTCTCCTGGGCTACGTGGTCGACT
GAGCCTTTTACTTTGGAGGAGCCGCCGTTGGTTCGCCCGGTGGAACGCGCGGAGGAG
TACTTCCCAGACCTGTGGCCTCACGGATTCACTCCTTCTGCTTGA

MscI amino acid sequence (SEQ ID NO:108)

MGDMAYRDRPLNAEEMEALRLVLSTYRDSSGQNQTKYGSMPGFRDFERGLASVLGGT
AAENKGVFDIIVTPSDGSTAFGISCKMARFAPKAQNAAFVELSNAAAKFRAHLLERQ
INWATDPMLAGPAIIELVTKWHTDDANEHGLDLDKSAYAVLSRSSDWSTYQLSTFPL
DLYGFNPIGDIAWTATTKRIDGHVEINGQPHLLWQWYPTSGGQLKWWPPLSWATWST
EPFTLEEPPLVRPVERAEEYFPDLWPHGFTPSA

NdeI DNA sequence (SEQ ID NO:109)

ATGAAAAACTTATCTTTCTCACAATTAGACTCTTTTTTAGAAAAGATGATTTTCCA
AGTATTGAGAGACATCAATATGGCATTAGGTATTTAAAATTAAGAAGTATGTCTCGT
AAAGAAATTATGGAAGAATTTTTTCAGGAATATGAAATTGACATCTCTAAGCTTAAG
TCAAAAGAATATTTTAGATATGCTTTTGAGAACATTGATATAACCATAGAAAGTATA
AATAGTTTTATTGAAAAGAAATACCAAATAGAGCGTACCGATAGACTTCTACAAGAA
GATTATTTAGTAGATCAACTGAGCAGATTACAATACTTCGATTGGGGCGGTTCATTT
GGTAATAGTCTTGAAAAAAACATTGTCGATAATTATGTCAAAAAAATACAATCTTTT
GACATAATTAACAAAAAAATAGAAACTGAGCTATTTTCAAGTTTACAGGGATACACT
CTAAATTCTTGGTATAATCACTGGACTTCAATTTTAATTGAAGATATTTTTAAAGAT
CATGCTAATGTATTGCCAACCATCGGACTTATAAAAAAGATTGATTTCTTTATAAAT
GAGATACCTTTTGATTTAAAGGTTACTTATTTTCCTGAGCAGTTCTTAGCTGAAAAA
TTGAAGCAAAAGGGGTTTGGCAATGAGTTAACTAGATTAAAACAAATATGTAGAAAA
CTGAACATTTTAATTCCTAATGACATGTCTGACAAAAACTTAAAACTGCATTTATAC
ACAAAAGTTTCAGAATGTCATCATAAAGAAGCTAAAGAATTAATAAATGAATTAAAT
AAGTTAAAAAAACAAATTATTCGTGAAGCCGAACAAAATTCAGATGAATTAAAAGTA
TGGCTTTATGAAAATCAGGGTGAAGCCCGTTTTGACGCTTCAAATAGATTTTTTTA
ATTCTCACGGACGAGACCAATATCAATGATAGTTGGAAACTTAAAAGAAACATTAAA
TTCCTAAGAGAGAAAATTCACTCTCATCTAGATTCTATAAAACTGGATCTTAATAAA

Figure 2-37

CTAAATACAAAATTTTACTGGAAGAAAACAAATGAACATTTTAATTGTAAGTCTGAT
ATACTTTTTATAAAACAGACTTAA

NdeI amino acid sequence (SEQ ID NO:110)

MKNLSFSQLDSFFRKDDFPSIERHQYGIRYLKLRSMSRKEIMEEFFQEYEIDISKLK
SKEYFRYAFENIDITIESINSFIEKKYQIERTDRLLQEDYLVDQLSRLQYFDWGGSF
GNSLEKNIVDNYVKKIQSFDIINKKIETELFSSLQGYTLNSWYNHWTSILIEDIFKD
HANVLPTIGLIKKIDFFINEIPFDLKVTYFPEQFLAEKLKQKGFGNELTRLKQICRK
LNILIPNDMSDKNLKLHLYTKVSECHHKEAKELINELNKLKKQIIREAEQNSDELKV
WLYENQGEARFDASNRFFLILTDETNINDSWKLKRNIKFLREKIHSHLDSIKLDLNK
LNTKFYWKKTNEHFNCKSDILFIKQT

NgoMX DNA sequence (SEQ ID NO:111)

ATGAGCGGTTTTAATTACGAGAAAAACCAGCCGCACCAAATGCGGGCGGTTTCGGCG
GTTTTGGGCGTGTTTGACGGGGCAACGCCCAAATATCGGACGGCAGACGAAAATCCC
GAACTTTTGTTTGCTGCAAAACAATACGCAAACAATATCCTGAAAGTGCAAAGCCAA
AACGGTATAGACGGCCGATTCCCCGACCGTTCGGACGACCAAAATATCCTTGATATT
TCCATGGAAACGGGCACGGGCAAAACCTATACCTACACACAAACCATGTTCGAGCTG
CACCGTTGGCTGGGCGTGTTCAAATTTATCGTGGTCGTGCCGACTTTGTCCATTAAG
GCGGGAACACAGCAGTTTTTGCAAAGCAAGGCTTTGGCAGAGCATTTTGAACAGGAT
TTCGGCGGCGATTATGAAGGCGTACGCCTGAAAACCTATGTGGTGGAAAGCGCGAAA
AAGAATAAGGGCAAAAAGTCCAATGCGCCCATAACGATTGAGCAATTTGTCAAAGCG
GAAAACAAAAAGGAAATTCATGTGCTGCTGATTAACGCGGGCATGGTTAATTCGTCG
TCCATGAACGATACGGGCGACAAGGCATTGAAGGATTTGTTTGACAATCCCGTTGAT
GCATTGGCTGCCGTGCGCCCGTTTATGATTGTGGACGAACCGCATAAATTCCCCGACC
CGAGATAGCGCGAAAACGTGGGGCAATATCAAACGCTTAAAACCGCAATATATTTTG
CGCTACGGTGCAACATTTAACGATGAATATTACAACTTGCTTTACCGTTTGACGGCA
GTAGACGCGTTTAACGACGGGCTGGTCAAAGGCGTGCGCGTGTTTCAGGAAGAAATG
CAGGGCGGCATGGATGCGGCGGTAAAACTGGTGTCGTCGGACGGCAAAGAAGCGAAA
TTTGAATTAAACGAAAAGGACAAAAAGCAGACGTTCAAACTGGCAAAAGGCGAAGAT
TTGGCGCAAATCCATCCGGCTATTTCGGATTTGAAAATCGACAAAATGAATAAAACC
GTGGTGGTGTTAAGCAACGGCTTGGAGTTGAAAACGGGTGCCGTCATCAACCCTTAT
TCCTATTCGCAAACGGTGCAGGATGCGATGATGCAGCGGGCGGTTGCCGAACATTTC
AAGCTGGAACGCGCGCTTTTGGCAGAACGCGCGCTACAGCCCAAAATCAAGCCGCTG
ACGCTGTTTTTTATTGACGATATCGCGGGCTACCGCAGCGGCAACGAGCTTTCAGGC
AGCCTGAAAGATAAATTTGAAAGCTGGATTCGCGCGGAAGCCGCACGCCGTCTGAAA
ACGGAAAGCGACCCGTTTTACCGCGATTACCTGCAAAAGACGTTGGACGATGTATCC
GCCTGCCACGGCGGCTATTTTTCCAAAGACAATACAGACAGCGACGATAGAATCGAG
CAGGAAATCAATGAAATCCTGCACGATAAGGAAAAACTGCTGTCTTTGGACAACCCG
CGCCGCTTTATTTTTTCCAAATGGACGCTGCGCGAAGGCTGGGACAATCCCAACGTT
TTCCAGATTTGCAAACTGCGTTCCAGCGGCAGCACGACTTCCAAGCTGCAAGAAGTC
GGACGCGGCCTGCGCCTGCCGGTAAACGAGCTGATGGCGCGGGTGCGCGATGTACCG
TACAAACTGAATTATTTTGTCGATAGCAGCGAAAAAGACTTTGTGAAGCAGCTTGTC
GGCGAAATCAACGACAATTCTTTTCAGGAAGAAATCTCCAAAAAGTTTACCGAAGAG
CTGAAACAAAAAATATTGCAAAAATACCCCGATATCAAACCGCTGGTATTGGTAAAC
CAACTGTTTTCAGACGGCATCATTGACGACAATGAAAACTTTGCCGAAGACGGCTAT
GACAAATTAAAAGCCGCCTATCCCGAAGCCTTCCCCAAAGGTTTGGACAAAGGCAAA
GTCAGCAACGCCAAAGACGAGGGCAAAGACACCATCATCATGCGCGAAGGCAAATAT
GAAGAACTCAAAGCCTTGTGGGAGCTGATTCACCATAAAGCCGTTTTGCAGTACAAA
ATCAAAGATGAAGCCGAATTTGTCGATTTATTTACCGCCTATTTGCGTGAAAACGCC

Figure 2-38

GCCAAATTCCCGCAGGCAGGCATATGCACGGCGGTAAACGAAGCTTATATCAACAAC
GGGCTTATGCTTTCCCGCCGCATAGACAGTATTGAAGATGAAGATTTTATCCGTTTC
AACACAATGACTTACCGTGAGTTTCTGGAAAAACTGGCACAAACGGCAAAAATCCAG
ATGCAGACTTTGCATCAGGCGTTTTACCGCGTCCGCGACGAACTGAACATTGGCGAT
TTTTTGAATATGCAGACCATCGCCCAAATCAAAAACGGCTTCAACCGGTTTTTGCTT
CATCATTCCTTCCATAAATTCGAACTGGATTACCGGCTTGTCGGCAGCAAAATCCAT
CCGACCAAATTTACCAATAAAGACGGCAAACCGCGCGCGGTGAAAAAAGCAGATTTC
GGCAGATTTGAAGATACGGAGCACCGGCCTGCCGCCGGCTATCTCTTCGGCGAGATT
TTCTACGATTCGGATATAGAACATGAAAATGTCGCCAACAACCAAATTGAAGGCGTA
ATCGTATTTACCAAAATACCGAGAAACTCCATCAAAATCCCTGTTGCCGGCGGCGGC
ACGTATTCGCCCGACTTTGCCTATATCGTGAAAACCAAAAGCGGCGAGATTCTGAAC
TTTGTGATTGAAGCCAAAGGGACTGACGGGGCGGAAGATTTGCGAAAAAGCGAAGAG
CGGAAAATCAAACATGCCGAAAAGCTGTTTGCCGAGATTTCCAAAGAAATCAAGGTG
GTGTTCAAAACGCAGTTTGACGGCGAGAGGATAGCCGAACTGATCGGGCAAAATATG
CCAGCAGGCGGGCATTCTGAAAACGGACACTGA

NgoMX amino acid sequence (SEQ ID NO:112)

MSGFNYEKNQPHQMRAVSAVLGVFDGATPKYRTADENPELLFAAKQYANNILKVQSQ
NGIDGRFPDRSDDQNILDISMETGTGKTYTYTQTMFELHRWLGVFKFIVVVPTLSIK
AGTQQFLQSKALAEHFEQDFGGDYEGVRLKTYVVESAKKNKGKKSNAPITIEQFVKA
ENKKEIHVLLINAGMVNSSSMNDTGDKALKDLFDNPVDALAAVRPFMIVDEPHKFPT
RDSAKTWGNIKRLKPQYILRYGATFNDEYYNLLYRLTAVDAFNDGLVKGVRVFQEEM
QGGMDAAVKLVSSDGKEAKFELNEKDKKQTFKLAKGEDLAQIHPAISDLKIDKMNKT
VVVLSNGLELKTGAVINPYSYSQTVQDAMMQRAVAEHFKLERALLAERALQPKIKPL
TLFFIDDIAGYRSGNELSGSLKDKFESWIRAEAARRLKTESDPFYRDYLQKTLDDVS
ACHGGYFSKDNTDSDDRIEQEINEILHDKEKLLSLDNPRRFIFSKWTLREGWDNPNV
FQICKLRSSGSTTSKLQEVGRGLRLPVNELMARVRDVPYKLNYFVDSSEKDFVKQLV
GEINDNSFQEEISKKFTEELKQKILQKYPDIKPLVLVNQLFSDGIIDDNENFAEDGY
DKLKAAYPEAFPKGLDKGKVSNAKDEGKDTIIMREGKYEELKALWELIHHKAVLQYK
IKDEAEFVDLFTAYLRENAAKFPQAGICTAVNEAYINNGLMLSRRIDSIEDEDFIRF
NTMTYREFLEKLAQTAKIQMQTLHQAFYRVRDELNIGDFLNMQTIAQIKNGFNRFLL
HHSFHKFELDYRLVGSKIHPTKFTNKDGKPRAVKKADFGRFEDTEHRPAAGYLFGEI
FYDSDIEHENVANNQIEGVIVFTKIPRNSIKIPVAGGGTYSPDFAYIVKTKSGEILN
FVIEAKGTDGAEDLRKSEERKIKHAEKLFAEISKEIKVVFKTQFDGERIAELIGQNM
PAGGHSENGH

NotI DNA sequence (SEQ ID NO:113)

ATGCGGTCAGATACGTCGGTGGAGCCAGAGGGCGCCAACTTCATCGCGGAATTTTTC
GGGCATCGTGTGTACCCCGAAGTCCGTCAGCACTGAAGCTGCGAGGAATGACCAGGCG
ACGGGGACCTGCCCTTTCTTGACGGCTGCCAAGCTGGTTGAAACTTCATGCGTAAAG
GCCGAGACCTCGCGCGGGGTTTGCGTGGTCAACACAGCTGTAGACAACGAGCGCTAC
GACTGGTTGGTGTGTCCCAACCGAGCGTTAGACCCCCTGTTCATGTCCGCAGCTTCG
AGGAAGCTTTTTGGCTACGGACCCACAGAACCGCTTCAGTTCATCGCGGCGCCCGACG
TTAGCCGATCAGGCGGTGCGCGACGGAATCCGGGAATGGCTGGATCGTGGAGTCCAC
GTGGTCGCTTACTTCCAGGAGAAACTCGGTGGCGAGCTGAGCATCAGCAAGACCGAT
AGCTCGCCGGAGTTTTCATTCGACTGGACTCTTGCCGAAGTCGAGTCTATCTACCCC
GTGCCGAAGATCAAGCGGTACGGGGTCCTTGAGATCCAGACTATGGACTTCCACGGC
TCGTACAAGCATGCTGTCGGTGCTATCGACATTGCCTTAGTGGAGGGAATTGATTTC
CACGGCTGGTTGCCCACACCAGCGGGTCGTGCCGCTCTCTCGAAGAAGATGGAGGGC
CCAAACCTCTCCAATGTGTTCAAGCGCACGTTCTACCAGATGGCATACAAATTCGCT

Figure 2-39

CTGAGTGGTCATCAACGATGTGCCGGGACCGGGTTCGCGATTCCGCAGAGTGTCTGG
AAAAGCTGGCTGAGACATCTGGCCAACCCAACGCTGATAGACAACGGGGATGGCACC
TTCTCTCTGGGGGATACCCGGAATGATAGTGAAAACGCTTGGATATTCGTATTCGAA
CTAGATCCGGATACTGATGCCTCGCCGCGCCCATTGGCGCCCCACCTTGAGATTCGA
GTGAACGTGGACACGTTGATTGATCTCGCGCTGAGAGAATCGCCCAGGGCTGCTCTT
GGCCCGTCTGGGCCGGTGGCTACGTTCACCGACAAGGTCGAGGCGCGGATGTTAAGG
TTCTGGCCGAAGACTCGCCGCCGTCGCTCGACGACACCAGGGGGGCAGCGGGGGCTG
TTCGATGCATGA

NotI amino acid sequence (SEQ ID NO:114)

MRSDTSVEPEGANFIAEFFGHRVYPEVVSTEAARNDQATGTCPFLTAAKLVETSCVK
AETSRGVCVVNTAVDNERYDWLVCPNRALDPLFMSAASRKLFGYGPTEPLQFIAAPT
LADQAVRDGIREWLDRGVHVVAYFQEKLGGELSISKTDSSPEFSFDWTLAEVESIYP
VPKIKRYGVLEIQTMDFHGSYKHAVGAIDIALVEGIDFHGWLPTPAGRAALSKKMEG
PNLSNVFKRTFYQMAYKFALSGHQRCAGTGFAIPQSVWKSWLRHLANPTLIDNGDGT
FSLGDTRNDSENAWIFVFELDPDTDASPRPLAPHLEIRVNVDTLIDLALRESPRAAL
GPSGPVATFTDKVEARMLRFWPKTRRRRSTTPGGQRGLFDA

PacI DNA sequence (SEQ ID NO:115)

ATGACGCAATGTCCAAGGTGCCAGCGCAATCTCGCAGCTGACGAGTTCTATGCTGGC
TCTAGCAAAATGTGCAAGGGTTGCATGACTTGGCAAAACCTAAGCTACAACGCGAAT
AAGGAAGGTCATGCCAACACCTTCACCAAAGCGACATTTTTGGCGTGGTACGGCTTA
TCAGCACAGCGGCATTGTGGGTATTGCGGTATATCGGAGGCAGGTTTTACATCCTTG
CACAGGACTAATCCACGCGGCTACCACATACAGTGTTTGGGTGTTGATCGCTCAGAT
TCGTTCGAAGGCTATTCACCTCAAAACGCTCGGCTCGCCTGTTTTATATGCAACAGG
ATAAAATCAAACATCTTCAGCGCCAGTGAGATGGACGTTCTAGGTGAGGCCATTTCA
AAAGCGTGGCATGGTCGAGGAATTGCCTAA

PacI amino acid sequence (SEQ ID NO:116)

MTQCPRCQRNLAADEFYAGSSKMCKGCMTWQNLSYNANKEGHANTFTKATFLAWYGL
SAQRHCGYCGISEAGFTSLHRTNPRGYHIQCLGVDRSDSFEGYSPQNARLACFICNR
IKSNIFSASEMDVLGEAISKAWHGRGIA

PflMI DNA sequence (SEQ ID NO:117)

ATGCGTGGACTGGAGATCGGTGTAAACGCATTAGTTTTTTATCAGACACGCACTGAG
TGGAACGTAAATAATCCTGAAAACTTGGGATGGGAGCCCGCGGAGAACAGGATAAGC
CCTCTAGGTGGGCAGTATGTTGCGCGTATCGCCGCAACCACTGCGTTAGATAATGGC
GAAAAAATTATCCGTGGTTTCACGACATCTAAAGTAAAAGGCGCTGGAATTCGGTTA
TTTGAATACGCGGGAGAAAAGGATATTAGGGCGTGTCGTCTCCAGCTTGAGGCTCTT
TTTTGGATGTGCCGCGACTCAACGGAAGTTGCGATAATTAACGGTATGACTGCTCAG
GACGCGTTGTCTAGAAGTACCTATAACGCAGCTGAGTGCCAAAAAATATGATTTGCTT
GATTTAAATCGACTTCATGAAGCGCGCATCATAAATACAGATGGTAGAACCATCTGT
CCTCTCTGTCTTGAAGAGCTTTCTGGTGAAGGCTTTTTGAGTCGGTTGGAGCAAGCA
GAAGGTCGAGAGGTACACGACCTTACTGTTACAAAGTTAAACTTGTTTCATATTTCA
GAGCTCCGTTTTGGAGTCTATAACCATAAGCCATACAACCTAGGTTGGGGGCATCAC
CACTGTAACGTCGTTGTTAAAGACTCGGGGATAATCGAGACATTACAATGGATGTAT
GAGGTGGTTCATCGAAATATCAACGATGGTCACTTTGCTCCTGAGAACAATCCGAAC
TGA

Figure 2-40

PflMI amino acid sequence (SEQ ID NO:118)

MRGLEIGVNALVFYQTRTEWNVNNPENLGWEPAENRISPLGGQYVARIAATTALDNG
EKIIRGFTTSKVKGAGIRLFEYAGEKDIRACRLQLEALFWMCRDSTEVAIINGMTAQ
DALSRSTYNAAECQKYDLLDLNRLHEARIINTDGRTICPLCLEELSGEGFLSRLEQA
EGREVHDLTVTKLNLFHISELRFGVYNHKPYNLGWGHHHCNVVVKDSGIIETLQWMY
EVVHRNINDGHFAPENNPN

PmeI DNA sequence (SEQID NO:119)

ATGACAACAAACTCCCCCTCAGACGTCGGCATGATCGACGAGTGTCTGTCCATCGTC
CGAACGTCGCTTGCACGATGTTTCCAACAGCAGGCCCCAAGCATTCAAGCCTCATGG
CCACTTTCAGGACGCGCCGTATCTGAGATTGGAGGCCGCCTAGTCGAGAGTTTCGTT
TTAGCACGACTCCCGCATGAACTGAGCACCACGCCTTTTGACGGCCAGATTCTATGT
GAAATACCTGAATCCGGCAGAGCGATGGAAGACATTGCGGTGACCTTCATCGGCCCA
CATGGAAGGGCTCGACTACTCATCGACGTCAAGGGTCATAACGAATACCGCACGGGA
TCGAGACCCAATTTGGCTTCGATCCGAAAATGTCTGGAACTCTATCGCAGCTCCTCA
CATACCGTTGATGAGCTCGTTGTCTTCTTCTGCCGTTACCGCCCATCCGTCCACCCG
GATCATCACGCACAAGCGGTCGAATATCACGTTCTGCCCGAGTCGTTYAATGAGCAG
GGAMTTTTCCTGCTTCGTGCCCTGAGCGAAAGCAACCTGGATCCAGCCAATATCGGA
GTGGCGGCCAGTTGCTGCTTGCCAGGGAAAACAACATACGGTTAGTGAATCGTTCAA
GGTCGGAGTTCGTTCAACTTCTAGAGGGTCTCCAGTCACGCCTTCAACGGGGGCGAA
GTACGGTTTGA

PmeI amino acid sequence (SEQ ID NO:120)

MTTNSPSDVGMIDECLSIVRTSLARCFQQQAPSIQASWPLSGRAVSEIGGRLVESFV
LARLPHELSTTPFDGQILCEIPESGRAMEDIAVTFIGPHGRARLLIDVKGHNEYRTG
SRPNLASIRKCLELYRSSSHTVDELVVFFCRYRPSVHPDHHAQAVEYHVLPESFNEQ
GLFLLRALSESNLDPANIGSGGQLLLARENNIRLVNRSRSEFVQLLEGLQSRLQRGR
STV

PshAI DNA sequence (SEQ ID NO:121)

ATGTCGATTTTAGATAATGAAAAACAATTGAGAATATTGAACATAATTAACGAGGGT
GTTACTCCTGCCATAATACCAGAGCTTCATTCGCTAGTTGATGACAGGATTACTAAC
GAAGAAATCGAATTGCTACATAAGAAAGTCTCTACACTTATCGGGCTTTCAATACCC
GTGCTAAATATTCCCCGTGACATTTTAAAGGCTTTTGAACCTTCCCAGATTGGAACA
ATTGTTGGAACAGTCATGGATGCTTGTATTCCTCAGCTAGATTCAATTATTGAGGAT
TCAAAAGTTATAGCGGATATTGGTTTGCAAAAACACGAAGGGATTCTTGGGGAAAGA
GAAGGTTACCCAGATTATAAGACTAATGATGGGTACAGGCTTGAGCTCAAACTACTA
TATGTTGATCCTGATGATGTTGAGATGAAAAAGCCCCCTACACCAAGAGAGGCATCT
GCGAGACTGACTCAAAAAGTAACCTATAAGAATGTCGATACAAGCAAAGACCTATTA
ATGGTTGTCGCGTATCAGTTTCGTGAAACACATGACCAAATATATTCGCCAACAATA
ATTGATGTTGGAATTTTCCCAGTAATTGATTGTATCTTGGCAAGAGATGTTCGTCTT
TCTTTATCGCCTGGTCGATGGTTTGGAAATTTTGAAACACCTGCAATATTGAGCAAT
GCTGGCAAAATTAAAAATTCTAACGGCGATCCACTAAATAAGTCCGTATACGGAAGA
AAAGAATCCGAAGGCTTGGACTTCAATGAAGATACAAATGTAGGAAAGCTAGCAAGA
AAACCATTAAAAACCTTGCAAGAATTTCTTAAGAAAAATAACACTAAGTATGCCAGC
AGAGGGGTCTATCCATCAGCCTGGACAATCCGA

Figure 2-41

PshAI amino acid sequence (SEQ ID NO:122)

MSILDNEKQLRILNIINEGVTPAIIPELHSLVDDRITNEEIELLHKKVSTLIGLSIP
VLNIPRDILKAFEPSQIGTIVGTVMDACIPQLDSIIEDSKVIADIGLQKHEGILGER
EGYPDYKTNDGYRLELKLLYVDPDDVEMKKPPTPREASARLTQKVTYKNVDTSKDLL
MVVAYQFRETHDQIYSPTIIDVGIFPVIDCILARDVRLSLSPGRWFGNFETPAILSN
AGKIKNSNGDPLNKSVYGRKESEGLDFNEDTNVGKLARKPLKTLQEFLKKNNTKYAS
RGVYPSAWTIR

PstII DNA sequence (SEQ ID NO:123)

ATGAGCCGAAGCAACGCCATAAAAATTGCCAATAAGATTAGTGCACGACTGTCACTA
CGCGATCCCCAAGATGAATCATTGCGTATCTTATGCAACGTACTTGAACAATTCAGT
CTCAGTAAAGATCCCGATCTTAATCGCTGGATTGAATTGCTAAGCCAACAGTACCCT
ACAGTGAAAGGGTTTGAACGAGCCTTTCCTTCATTATGCTTCGCACTGGCTACTGGT
GTGGGTAAAACACGCTTAATGGGTGCAATGATTACTTGGCTATATTTAACCGGACGC
AGCCGTCATTTCTTCATACTATCTCCAAATTTAACCATCTATGAAAAACTTAAGATG
GATTTTTTACCCGGTTCACCAAAGTATGTTTTCCAAGGTATTCCTGAACTTGCACAA
ACACCTCCGGTTCTAATCACTGGTGATGACTATCAGGAAGGGCGGGGTGTTCGTCTA
GATTATGCAATTGCCGAAAGCAAAACGGGTGATCTTTTTGACAATGAAACCGCTCCA
CACATTAATATCTTCAATATTTCCAAAATAAACGCACTGGAAAATGCCAAAGGTGCT
GCTAAATCTAAGGTCGCTAAAATTCGAAGAATACAGGAATACATCGGAGAATCTTAT
TTTAGCTACCTAGCGAATCTACCTGATTTAGTTATTTTGATGGATGAAGCTCACCGT
TATTATGCCAGCGCAGGCGCACAGGCACTTAACGATCTGAATCCAGTATTGGGTATT
GAATTAACTGCCACGCCGAAAACTGTGGGAGCAAACCCGCGCGATTTTAAAAATATT
ATTTATCACTATCCTCTCTCACGGGCATTAAAAGATGGATATGTAAAAATCCCGGCG
GTTGCCACACGTAAAGAGTTCCGCGCCGCAAATTACTCTGAAGAACAACTAGAAAAA
ATAAAGTTGGAAGACGGTATCCATCATCATGAATATGTGAAAACAGAGCTAACCAGC
TTCGCTAACAATACCGGTAACAAATTAATTAAACCTTTTATGCTAGTTGTTGCACAG
GATACCGACCATGCAGACAGCCTAAAAGTACGTATTGAACACGACGATTTCTTCAAC
GGTGCCTACAAAGGCAAAGTAATCACCGTTCATTCGAACCAAACGGGTGAAGAATCA
GAAGAGACTATGCAGCGACTTTTGGCCGTTGAGTATGATAAAGATACAGAAATAGTC
ATTCATGTCAATAAGTTAAAAGAGGGTTGGGATGTTACCAACCTGTATACTATTGTT
CCATTACGTGCTTCTGCTTCTGAAATCCTGACTGAGCAAACCATAGGGCGAGGGCTA
CGCCTACCGTACGGTAAAAGAACAGGCGTCGAAGCTGTTGATCGTCTGACAATCATT
GCCCATGATCGTTTTCAAGATATTATCGACCGTGCCAATAATGATGACTCGATTATT
AAAAAAGTCCTTTATATAGGGTTAGATGATGATGAAAATGGTATTCCAGAAGTAAAA
CCTCAGCAAATTGTCGTACCATCAATGGCAGAATTTCTACTGGGAAATCAAGTTATT
GATAATAATTTGCAGGTGTGTGAACCTCAGGCAATATATCAAACGAATTCTATATCA
AAACCGGTGCTCACCACGAACACAGAACGTAAAGTTGCAGAACTCACGTTCAAAGTA
GTCTCAGAAGAAGCTAAACGGTTAACCAGTAGCCACCAACTCAGCACCCCAGAGGTG
AAAGCAAGCGTAACTCGGCGAGTACAACAAGCCTTACGTGAATGGGAAATTTCCCAA
TCTCAAATTTCATCCACTTCGGAACAGAGCGATCTGACAGAAATAATTGAAAAGCAA
GTTGAACAGTCGAATTCCCTATCAATGGAAGATACGGAAGTTCAGGAGTTAGTCGGA
ACGATTACCGAAAAACTGATGGAATATACTATCGATATTCCTCGAATCGTGGTTTTG
CCAGAACGCGAAGTCAATTACGGATTTAATGATTTTAACCTTTCCCAGTTAGATCGT
ATTGCGCTAAAACCAGGTAGCAAAGAACTCTTACTCACGCATCTGGAGAATAACGAA
CAACGTACAATCAGTTGGCAGGAAGGCGGAGAAGAGGAAGAACGACTTGAAAATTAC
CTCATTCGCTATCTGCTCGACCACGATGAAATTGATTACGATGAACATGCCGACATG
CTCTATAAACTGGCCGGACAAATGGTGGGGCATTTATGTAGTTATCAGTCCCAAGAA
GATGCTGAATCCGTTCTGAAAAATGCAGGTCGGCAGTTGGCAGAATTTATATGGGTG

Figure 2-42

CAAATCAAACAAAATATGTGGACAACGCCAACGGGCTATACTGGACGTATAATACAG
GGTTTTGATGTAATACATCCAGCCACATTCAATTTTGCTGGTAATGAAAGACCGAGA
GATTTCCGTGTTGTGATTCCAGCAGGAGAAAAAAATAAAGTTCGCCAGATGATTTTC
ACTGGTTTTACTAAGTGCTGTTATCCTTATCAGAAATTTGACTCTGTAGATGGGGAG
CTCCGTCTCGCACAAATACTTGAGAATGATCCTTCAGTGATTCGCTGGATGAAACCT
CGGCCAGGTCAATTCCGCATTGAGTATGCTAATGGTAAAAATTATGAACCTGATTTT
GTTGTCGAAACGGATAATGGCTATTGTTTAATCGAACCCAAAAAAGCGACAGAAATC
GACACGCCTGAAGTTAAAGCCAAAGCACAAGCGGCTATCCGGTGGTGTGAGTTTGCA
AATCAAAATGCAGATAAACTTAAAGGGAAAACTTGGCAATATGCTCTTATTCCTCAT
AATGAGATTGAATTAAGTCGTTCAATCTCAGGATTACTAACTGATTTTAAGATGTCA
TTTCAATAG

PstII amino acid sequence (SEQ ID NO:124)

MSRSNAIKIANKISARLSLRDPQDESLRILCNVLEQFSLSKDPDLNRWIELLSQQYP
TVKGFERAFPSLCFALATGVGKTRLMGAMITWLYLTGRSRHFFILSPNLTIYEKLKM
DFLPGSPKYVFQGIPELAQTPPVLITGDDYQEGRGVRLDYAIAESKTGDLFDNETAP
HINIFNISKINALENAKGAAKSKVAKIRRIQEYIGESYFSYLANLPDLVILMDEAHR
YYASAGAQALNDLNPVLGIELTATPKTVGANPRDFKNIIYHYPLSRALKDGYVKIPA
VATRKEFRAANYSEEQLEKIKLEDGIHHHEYVKTELTSFANNTGNKLIKPFMLVVAQ
DTDHADSLKVRIEHDDFFNGAYKGKVITVHSNQTGEESEETMQRLLAVEYDKDTEIV
IHVNKLKEGWDVTNLYTIVPLRASASEILTEQTIGRGLRLPYGKRTGVEAVDRLTII
AHDRFQDIIDRANNDDSIIKKVLYIGLDDDENGIPEVKPQQIVVPSMAEFLLGNQVI
DNNLQVCEPQAIYQTNSISKPVLTTNTERKVAELTFKVVSEEAKRLTSSHQLSTPEV
KASVTRRVQQALREWEISQSQISSTSEQSDLTEIIEKQVEQSNSLSMEDTEVQELVG
TITEKLMEYTIDIPRIVVLPEREVNYGFNDFNLSQLDRIALKPGSKELLLTHLENNE
QRTISWQEGGEEEERLENYLIRYLLDHDEIDYDEHADMLYKLAGQMVGHLCSYQSQE
DAESVLKNAGRQLAEFIWVQIKQNMWTTPTGYTGRIIQGFDVIHPATFNFAGNERPR
DFRVVIPAGEKNKVRQMIFTGFTKCCYPYQKFDSVDGELRLAQILENDPSVIRWMKP
RPGQFRIEYANGKNYEPDFVVETDNGYCLIEPKKATEIDTPEVKAKAQAAIRWCEFA
NQNADKLKGKTWQYALIPHNEIELSRSISGLLTDFKMSFQ

PsuNI DNA sequence (SEQ ID NO:125)

ATGCCTTACTCCTTTGATCATTCGGAAGTTTGCCATAACTGTCCTTTCGGAAGTTGC
TTTGAGGACAGAAGGGATAATCCGGTAAGGAATCGAGATACAAAATTTCGGTTTCGC
CAAACTGCCGCAATGAGCTGTACATTCGCAGACTTCATCCCTGGGACGGATAGTGAC
CCCATCCCCCAAAGAAGCTTCGAAGAGTATCTAAAAAAGTTCACCTCGAATGCCATG
CTGGCAGGTGAAACTCTGTTTGGTGGTGAGTTCAACGTTAAGGGTGCGGCCATCGCC
AAAGTCGAAGGTGATGTCTTTGAACTCCTTGAGGCTGCGGCGCTGTGGAATGCTACA
GCGGCTTGGAACAGGCTTATGGACTCCGGTTCGTGGGGCGCATCTGTATTCACTTGT
CCTCAATCGGCTGTGCCTACGCCGACCCGTAAAATTGCCGTAGTAACCCTTCCAAGA
GGGTATGATGCAACAAAGCTATTTCGGGACGAAATTCGCAGCAGCATCCGTGCTCAC
GAGGAGGCTCTTCATCTAAGAGGGTTGTCTCTTGGGTTGTCAAGTCCTGACATTGTT
GGTGTTCGGCTTCCTTGCCCGCTTCCGGAAGAGCTTGGTTGCTTCATGGAGCCTATC
GAAAACCTTGGTGAAGAAAACAGGGTAAAGCTTGAAGAGGCTTACAAGCTGCTTGAA
GGCAAGATTGAGGCAACAGGTTTCCTCTTTGCTATTGCCGTAAAGAGAACCATTCGG
AGTGATAGGCTTTACCAGCCGCTTTTCGAAGCCAATGTGTTGAAGTATCTGATTGAG
GTGGTGCTCAAGGGGGCTGCGTTCAGGTTCTACGCTCACTTCAATTCATTTGAAGGT
GCGGATGTGGAAGGTCACTACAAGGCGGCATCGCTAATCTCGCTAGCCAGGGGTGGC
ACTCCTACAAAAGCGATTGACGTTCTCCACCTTGCGGAGTCTCCCCTTGCATCGGCA
CAGGCTGTGCTTAATGACTTTCCCCTGTTCCATCTTTAA

Figure 2-43

PsuNI amino acid sequence (SEQ ID NO:126)

MPYSFDHSEVCHNCPFGSCFEDRRDNPVRNRDTKFRFRQTAAMSCTFADFIPGTDSD
PIPQRSFEEYLKKFTSNAMLAGETLFGGEFNVKGAAIAKVEGDVFELLEAAALWNAT
AAWNRLMDSGSWGASVFTCPQSAVPTPTRKIAVVTLPRGYDATKLFRDEIRSSIRAH
EEALHLRGLSLGLSSPDIVGVRLPCPLPEELGCFMEPIENLGEENRVKLEEAYKLLE
GKIEATGFLFAIAVKRTIRSDRLYQPLFEANVLKYLIEVVLKGAAFRFYAHFNSFEG
ADVEGHYKAASLISLARGGTPTKAIDVLHLAESPLASAQAVLNDFPLFHL

SacII DNA sequence (SEQ ID NO:127)

ATGGCGCCGGTGGTGAGCCCCGACGATGGCACGCAGTACCACAAGGACTTCACTCTC
AGCATCACGAAGGCGCTCGGTGACCAGCTGGCAGCGGCTCTGGACGGGCTAGACAGG
GCCCCCCTGACGGACCGGAGCATCGCGGCCCTCAAGGAAAAGCCCGGCGTCTACCAG
CTCTACTTGAACGGCAGCTTCGTCTACGTCGGCAAGGCTGATAGGTCGTTGCCCGCG
CGGCTCCGCAACCATAAGCGCAAGATCTCGGGGCGTCGGAGGATTTCGCTCGACGAG
ATGGCCTTCTCCTGTCTCTACGTGGCCGAAGACTTCTCGGCACTCGCCCCCGAACAG
CTCCTGATCAGCCACCACAAGGGCATGGGAGACATTCCCTGGAACAACAACGGGTTC
GGCAATAAGGACCCCGGGCGCCAGCGGGACAGCACCGTACTAAAGCGGAATCACTTT
GACGTGCTATTCCCCATCGACCTCGACCGGTCGAGGGCCTACGAGCCGGGGAAACGA
CACTGCAGGAGCTCCTGGAAGCGGTTAAGGTCGGTTTGCCCTACAACTTCCGCTATG
GGAAGCATGACGGCTTCAAGAGTCGATATGTGA

SacII amino acid sequence (SEQ ID NO:128)

MAPVVSPDDGTQYHKDFTLSITKALGDQLAAALDGLDRAPLTDRSIAALKEKPGVYQ
LYLNGSFVYVGKADRSLPARLRNHKRKISGRRRISLDEMAFSCLYVAEDFSALAPEQ
LLISHHKGMGDIPWNNNGFGNKDPGRQRDSTVLKRNHFDVLFPIDLDRSRAYEPGKR
HCRSSWKRLRSVCPTTSAMGSMTASRVDM

SfoI DNA sequence (SEQ ID NO:129)

ATGAATAATACATTGGATGAGGCCTTTGCTTTCTATGCCAGCCATATCTATGACGAA
GAAAAAATTAATCTGTTGAGGTCACATAACCTCAAAGTTGCGGGGCATGTTCCCTCT
GTCTTATGGGAGCTGTTTGGTTCAATTCTTACAGGACGTCGTGGTAATGGCATTACT
GGGGCAGACCTTCAAGGCTGGGAGGTTAAGTCGTCCACATTGAGGAGCTCTTTCGAG
TATCAGTATCACTTGAATACAGGCGAAGCTAAGCTTTTGGAAGATTGCGAAGTTAAT
CATCTCTTTTGCTCCTATTCAACTGATTATCGTGATCTTATCGTCAAAGCGATTCCG
GGTGAGGAACTTAAAGAGACCTTTTTTGAAGCTTGGTTGCCAGAATATAGAGCGAAT
TATGACCGTACTGTAGGTAGCACTTCTAGGCGCCAACGTTTTAGGAAGGCAATACCA
TATGGTTTTGTTCAAGTACATGGTCGTACAATCCTTGAAGTTAAAGCTGGTGAAATG
TACAGTAGAAATGATAGTCTTTTAGAAGAGTTCAATAGATTGGTAGGCTAG

SfoI amino acid sequence (SEQ ID NO:130)

MNNTLDEAFAFYASHIYDEEKINLLRSHNLKVAGHVPSVLWELFGSILTGRRGNGIT
GADLQGWEVKSSTLRSSFEYQYHLNTGEAKLLEDCEVNHLFCSYSTDYRDLIVKAIP
GEELKETFFEAWLPEYRANYDRTVGSTSRRQRFRKAIPYGFVQVHGRTILEVKAGEM
YSRNDSLLEEFNRLVG

Figure 2-44

SpeI DNA sequence (SEQ ID NO:131)

ATGTCAATCGATCCCAACAAGCTAAACAGCGCCCTTTACGCGATTCTTGGAGGCTAC
AGAGGAAAATTCTCCAATAAGGTCTATAACGGCGAAAACGATGAGTTCGACATTTTA
ATGGAAATTTTCGGAATTTCCCCATTATTGAAACGCGAGAGCCGCCAGTACTGGGGC
CGAGAGCTTGGCATGTGCTGGCCACGACTTGTTGTGGAAATTTGCAAACAGACGCGA
AATGACTTCGGATCTGCTTTACAAATTGATGGCGGCGAGCCTTGTGATTTGATAGTA
GGCGGTTTGGCGATCGAAACCAAGTATAGAATAGGGTCCGGCGATGCAGGCACCTTG
AAAAAGTTCCAAGCTTACGGCTCTCTGCTTAGTTCAATGGGGTATGAGCCAGTACTC
TTGATAGTTCGTGAAGACAACCTTGGTGCAGCAATCACAGCGTGCCACGCAGGCGGC
TGGACCGTTATAACAGGGCAACGCACCTTCGACTACCTTCGCGACCTTACAGGAATT
AACATTAAGGAACTACTCCTGCAGCGTGCCGGAAAATTTCCTGTTGTCCGGTGA

SpeI amino acid sequence (SEQ ID NO:132)

MSIDPNKLNSALYAILGGYRGKFSNKVYNGENDEFDILMEIFGISPLLKRESRQYWG
RELGMCWPRLVVEICKQTRNDFGSALQIDGGEPCDLIVGGLAIETKYRIGSGDAGTL
KKFQAYGSLLSSMGYEPVLLIVREDNLGAAITACHAGGWTVITGQRTFDYLRDLTGI
NIKELLLQRAGKFPVVR

TliI DNA sequence (SEQ ID NO:133)

ATGGAAACTAGCGTTTGCCATACTTTGAAGAGCCCTGTTATTAAGAAGTTCTGTGAG
TCTATAACTGAATTGGCCAGAACCTCTAGGGGATACTTCGAGCCTATTCAGGACGAT
TTTCTGAAAGCATACTATCAAATCGTTGAAAAAGCTCGTATTAACGGCAGACTTCCA
GAGGGAGAATACCGACAGAAAGGAAACGCATTTAGAGATTTTATCAGCGAATTGATT
TACATAAGATCTGGGGGAATCTACCGCCTAACAGATAGAAGAATTCCTGGCTATTCT
GAGAGAACTCATGACGTTGATCTCGCTTATGTGAGGGACGCTACTGTTTTGGTGGCT
GGCGAAGTCAAAATGACAGGTAGCCCAAGGCATAAGAAGGGAACAACGGTTCAGAAG
GAAAGAAAGACGCAGAGCGATCTAGATAAAAGATTAAAAGAAGTCAAGTTCACCGCA
GTGGATTTAAAACTTCGCTACACTCCCGAAGAGGCCATAATAAATGCCTTAAACTCC
AAGAATACTTTTTCTGAAGTTTCTAATAACAGTTGGTGGATGCGATGGATTCATACC
TCCATTCCCGGCTTTTACTCGTTCTGGGCATCCAGGCTTGCCTCGGGCCGTCTTGAC
AAGAAAACAGGAAGGAGAGTAGACTTTGATAATCCCGATCTTCTTCTCGAAAAATTC
AGGAATCTACTAAAATACAACAACGCAGTAGGTCTTTTCATGTTCCGGGAGGAGAAT
GGCAGATACGTTCCCGTTGAAACTGAGAGAATCAAAAGGGAAAGAATTTCAATAGAC
GACGCGGTGAAGGATCTTATAAAGTTCCTAGATACTCACTTGGATTAG

TliI amino acid sequence (SEQ ID NO:134)

METSVCHTLKSPVIKKFCESITELARTSRGYFEPIQDDFLKAYYQIVEKARINGRLP
EGEYRQKGNAFRDFISELIYIRSGGIYRLTDRRIPGYSERTHDVDLAYVRDATVLVA
GEVKMTGSPRHKKGTTVQKERKTQSDLDKRLKEVKFTAVDLKLRYTPEEAIINALNS
KNTFSEVSNNSWWMRWIHTSIPGFYSFWASRLASGRLDKKTGRRVDFDNPDLLLEKF
RNLLKYNNAVGLFMFREENGRYVPVETERIKRERISIDDAVKDLIKFLDTHLD

TseI DNA sequence (SEQ ID NO:135)

ATGAAAAGATTAGCAGGCTTAATAAGCTTAGCAGACTTAATACAAGGTGATACTGAG
TTTAAGATAAGCTGGGAAAAACCGAGGGAAAAAGGCGCTCACTCTTCTGGCCGAGAAG
GCAGGCATCAGATGCGACGAGCAGCTAGATGATCTTCTGTCGCAAGCCCTGGATCTT
GCAAGGAGCACGCTTACCTCCGGCAAAAATCCTGATGCTGACATCGCTCACTTCTGG

Figure 2-45

GAGGAGGTCGAAAAAAACGCCACCCTCTTAACGAAAAACGACTACCTCCGAGCGGCT
GTAGTAGCTCTTTCGTTTGCCCACCGCTTTGCCCGAACAGACTACGGATCGTCAAGG
CAACGCGGCTTCGGGCAACTCTGGGCAGATGCGATTCAAGGCTTCCTTGGTGAAATT
GCCTTCCAGAAGTTTATGAGGTCAGCCACGTCTGGGAGGACCATCCCTATTTTAGAC
GCCAGCGAAGAAGATCTTGGAGTCGCCCTAAGCGCTGACATAGTTGAAGTCATCACA
GAGGGGAAATCAATAAAGCCCTCAAAAAGAATCAGCATCAAGACTACGAAGCTCCAT
GGGCGCTGGTTAGATGTACCCTACGCTCAAAATAAGCACAGCGACATTTACGTTCTG
GTTAAAGTCGGGACTGACGCCGATGCGCTTTTCAACTTTCTGGCAAGCGTAGGGGCG
CTTGAGAAAGTCTTAACCGCCTATCAAGAGGGCGGTCTTGCTGAAGGCGAGCTTCCT
TTTCTCAACGAAGGCGAAGCGCTCAAAAGAGCTAAGGAAGAGGTAGAAAAAATCAAG
GAAAAAAACATGCTTTTTTTAGCCTTTATAGCTGGCTGGAAGGAGAAGGATCGGCTC
AGCCAAACCTTCGAAGCTCACGAGCACAACGCCCAAAGAGCCCGCACAAAAATCACT
GTCTACAGCGGAGTTGGTACAATTTCATCTGGTAGCGTGCGAACAAAGCAAATCACC
TTTCGCGGTCCCCTCCCTAAAAACAATCTGCTGGTTGAGTTTTATCCAATAGGAAAA
TTCTCCAAAAGCCAGCATGCACTGTGCAGCACAGATCTGCTTGTGAAGGATCTCAAT
AAGATAGCAGAACTTCTCTCTGCTCCTGAAGAGGGGGATGAATGCGCACAGTAA

TseI amino acid sequence (SEQ ID NO:136)

MKRLAGLISLADLIQGDTEFKISWENRGKKALTLLAEKAGIRCDEQLDDLLSQALDL
ARSTLTSGKNPDADIAHFWEEVEKNATLLTKNDYLRAAVVALSFAHRFARTDYGSSR
QRGFGQLWGDAIQGFLGEIAFQKFMRSATSGRTIPILDASEEDLGVALSADIVEVIT
EGKSIKPSKRISIKTTKLHGRWLDVPYAQNKHSDIYVLVKVGTDADALFNFLASVGA
LEKVLTAYQEGGLAEGELPFLNEGEALKRAKEEVEKMKEKNMLFLAFIAGWKEKDRL
SQTFEAHEHNAQRARTKITVYSGVGTISSGSVRTKQITFRGPLPKNNLLVEFYPIGK
FSKSQHALCSTDLLVKDLNKIAELLSAPEEGDECAQ

Tsp509I DNA sequence (SEQ ID NO:137)

ATGAACGAAATGTACGAGATTGCCAAAGGAGTGGCCTCATTTGAAGGTGCTCCTACC
TTACCAGGACGTACGACAGGTGAGGCTAGAGGGGGCCGAGAGTTTGAAGCTGTTGTT
GCGGAAGGTCTTCTGAAATATGGCCGATTGCTGGTCACCGCCGTTCCCTCATTAAGA
TTACGCCCGGTTGCTGCAGAAGGAACTTCAAGACAAAACCATCTGGCTGACGCTCTT
GCAGTCGTAAACGAAGAAAATAAAAGAGTCTTGGTGTTCAGATTACCTGCATTCAGG
CACAATCCTCTCTTTGCTGAGATTACTTCAGGCGCGCTACAGAACGATTTCGTTCGA
GTTCCGGACTCATTTTTGAAAAGGGAGTTCGTTGTGGAGGAGTGGTATACCCCCAAG
TTAGGGGAACTAGCAGAAAGAGGATGGATTCCTGAAGAGGATGAACCTTATCCTTTT
TCCGGGACTAACTATCCAGAACTGTATAGGCGTAAGCGCACCCAGTTCGACGGTGTG
ATTATCTTCTTGGAAAGTGGCACGCTAAGGGAAAAAGCCCTGCTAGAAATAAAATCT
CTGAAGTCTTCTGAGGGGGCCAGGGTCGATGGTAACGCCCACGAACGGTTTGCGTAC
CAGAATCTAGACTATCTCGAGATAGGGGCCCTATATCCTCGCACAACGCTCTTGCTA
CTTACAAACGATGCCATTCTCAAGTACAGAAACAAATACCACACGGGAATCGGTGTA
CATGCATTACGGCTAAGCTATGCGTTTTGCTGGTACAAGTTTGAGATGGTTAGCTCC
GTTCGACAGTACCTTCGCCTCTTTTCTTTGTGGAAGGAATGGCTGGAGGGCAAATGA

Tsp509I amino acid sequence (SEQ ID NO:138)

MNEMYEIAKGVASFEGAPTLPGRTTGEARGGREFEAVVAEGLLKYGRLLVTAVPSLR
LRPVAAEGTSRQNHLADALAVVNEENKRVLVFRLPAFRHNPLFAEITSGALQNDFVR
VPDSFLKREFVVEEWYTPKLGELAERGWIPEEDEPYPFSGTNYPELYRRKRTQFDGV
IIFLESGTLREKALLEIKSLKSSEGARVDGNAHERFAYQNLDYLEIGALYPRTTLLL
LTNDAILKYRNKYHTGIGVHALRLSYAFCWYKFEMVSSVRQYLRLFSLWKEWLEGK

Figure 2-46

Tth111I DNA sequence (SEQ ID NO:139)

ATGGCGAATACTCTTGAGGACCATATTACTCAAGTATTGGAGAGCTTTAAGGGCGAA
GAAATAAACAGAGTTATAGCGATTTATAAGCCGCCGGATCTCGAGTTAGCAATTTTT
TACTCAAAAATCATATCCAAGTTGTCCCCGATAATCGGTAACGTGCTTGAAAGATCC
GTTGCAAAGGAATTGGGGGTTCGATTGAAGGCCCCATATAAGAGGCAAGATCCGGAA
TTTCCAGATGTTGTTGTGGAATTGGGAAAAGATAAAAGGATAGGCTTTGAAATAAAA
GCGTGGTATGCTCTTTCAACAGAAGCGGCTGCCCGGTTCAGAACAAGCCAAAAGGAG
CTCTCAAGCGGGGCTTACGAGGAGGTTTATCTAGTCGTAATAGCTTGGACAATGAGC
AAGCTGTTTTATGGAAAACCTAAAATAATCAATCTTTTCTTTGAAAAAGCCATTGAG
ATTGCCCGGACACGTGACCAAAAGTACCACAATCCTCCATGGAATATAGTTTTAGAG
CCTGTAGACACATCAGCGAGAACAATAAACCTACAACAGAAAGTAGTCATCGGTAAA
AAACTACAAGAAGAAAATCTTCCAGAAGGTGTACAAGCCGAAGAAGAGCTTAAAAAG
CTTGCTCAGGACAAAAAAATAAAAGACTATAAGGTCTATTCAACGCAAGAAGATTAT
GTTGATTTCATACGAAATCTGGAAAGAGTTTTGCCTTATCGCGAAGACTCCAATTTT
GGCAAGATAGATCGCATTCCTCATGAAAGGCTTTCATCTTTCCTCAAAAACACCAAG
AAATTAAAGCTATTAGGGCTCACTTTGAAGGACTGGATCAAGGTCATGGAGTACATA
TCAAATCAGGAGGAAAAATCTGCTCAAAAATCTAAAAAAAAGAAGGAGTTAGAGGAT
CTAGTGGAAAAAGCACTAAAAAAGCTCGGTTACCCTAACACATACTGA

Tth111I amino acid sequence (SEQ ID NO:140)

MANTLEDHITQVLESFKGEEINRVIAIYKPPDLELAIFYSKIISKLSPIIGNVLERS
VAKELGVRLKAPYKRQDPEFPDVVVELGKDKRIGFEIKAWYALSTEAAARFRTSQKE
LSSGAYEEVYLVVIAWTMSKLFYGKPKIINLFFEKAIEIARTRDQKYHNPPWNIVLE
PVDTSARTINLQQKVVIGKKLQEENLPEGVQAEEELKKLAQDKKIKDYKVYSTQEDY
VDFIRNLERVLPYREDSNFGKIDRIPHERLSSFLKNTKKLKLLGLTLKDWIKVMEYI
SNQEEKSAQKSKKKKELEDLVEKALKKLGYPNTY

XcmI DNA sequence (SEQ ID NO:141)

ATGCCAGTAACACCTCCACAAGACTTGATCGATTTTATCGATGATATTCTCTCGGAT
TTGCTTACAAACAATCCGCTTGCCACTTCCTCAGAGGCGTATGTGCAAAACCACATC
GAATTTGAGCTTGTGAGGAGGAATCACAATCCTAAGTATTATTTGAGGATCGGCATC
AACTACCATGGGGAGAAAGTCCAGCATATCATGGTCGACCCGCTCACAGGGAAGCTA
ATTGGCTGGAACCCTGCGGGAGATGCGCTCGGCACCGGTGCAAACGCGAAAATGCTA
CTCGCGAATTACACAATATTTGATCGTGCGCCTGGCGAACACATGATGACCGACTGC
AAAGTTGGCGGCGGCCCCCTCGCGGCGGGTCAGTACGTCCGCGCCGAGTTCAAGGTG
AGGGGATGGCTTGGCAAAACAAAGAATCTGGATGGCAAGCAATTTCAGAAAGATTTG
GACCTCATGGGCGCCGATAAAGCGGACCTGCTTGTTTGGTGCCTGTCAGAAACCGCT
CATTGCAAGTTCCGCGGCGAAGGACCTGCACATCAAGCGGGTCGACGAACAGGATGC
CAGGATTTCGCACCCATTCTCCTGCCCACTAATCAAATCGGGATCGCTCCTGTAACC
CGGCAGGTCCCATATCGCCGGATCGAGACCGCAAATTTGCCAGCCGCGCAAGCTTTG
TGGATCAACACGCAAAATTGGGTCGTTCGCAGTCGGAAGGTGACGGCTGCGCCGGGC
TCACTGATGCCCGGCGCAGAGCACTACGTCACGATGTGCTGGCGCGTGTAG

XcmI amino acid sequence (SEQ ID NO:142)

MPVTPPQDLIDFIDDILSDLLTNNPLATSSEAYVQNHIEFELVRRNHNPKYYLRIGI
NYHGEKVQHIMVDPLTGKLIGWNPAGDALGTGANAKMLLANYTIFDRAPGEHMMTDC
KVGGGPLAAGQYVRAEFKVRGWLGKTKNLDGKQFQKDLDLMGADKADLLVWCLSETA

Figure 2-47

HCKFRGEGPAHQAGRRTGCQDFAPILLPTNQIGIAPVTRQVPYRRIETANLPAAQAL
WINTQNWVVRSRKVTAAPGSLMPGAEHYVTMCWRV

XhoII DNA sequence (SEQ ID NO:143)

TTGAAAGTCGCAAAAATCTACTCACATCTGAACGGCCTGGAATTTTTAAAAGTTCAC
CATGAAAAGGTGATTTTGGAGCTGGATCGGGTCATTACCCGTATAGACGCTGAGGCT
TGCCGCACCAAAGAAACAAAAGAGGCAAGAAAGGCAGGGCGGTTCGCTGATGGTCTT
CTGTATAGCCCGGTAGCACTGAATGAAGCTTTTAACGATGCTCTGTCGCAGCTTCAC
TGGTATGAAGATCGCTATTCCTACTTCGTGACCGATGACGCTAGGCTCATTAGAGCG
ACATTAGGGTTGGACAGAGCGGAGCAAAAGCGAATAATTGAGGATGCAGGTCATAAG
GCGATTGCAACCTACAATCAGACGGATTTTGTGAAAGACAGGGTGGCCATAGAAGTG
CAGTTTGGAAAGTATTCGTTTGTAGCTTACGATCTTTTTGTCAAACACATGGCATTT
TATGTTGGTGACAAAATTGACGTCGGCATAGAAATTCTGCCAATGAAATCTTTGCAG
GAGAATATGTCTTCGGGAATTGCTTACTACGAAAGTGAGCTTTCCAATCTTGTAAGG
CAAGGCCGAGGTGTGCCCGCTGTTCCTCTGGTGCTGATGGGCATAGAGCCTTAA

XhoII amino acid sequence (SEQ ID NO:144)

LKVAKIYSHLNGLEFLKVHHEKVILELDRVITRIDAEACRTKETKEARKAGRFADGL
LYSPVALNEAFNDALSQLHWYEDRYSYFVTDDARLIRATLGLDRAEQKRIIEDAGHK
AIATYNQTDFVKDRVAIEVQFGKYSFVAYDLFVKHMAFYVGDKIDVGIEILPMKSLQ
ENMSSGIAYYESELSNLVRQGRGVPAVPLVLMGIEP

Acc65I DNA sequence (SEQ ID NO:149)

ATGAAATTAAATGCTGAGAATTTAAGTATTCAGGAACAATTAGCAGAATTTGATCAA
TGGCTCACAGCTAGACTAGATAAAATCAAAGATTCAGAAAAATTCAATTCAGAAATT
AACTCCCTCTGTAATTGTATTACCGTATTATCTCCTCTTTTAGAAAACTTCAGTGAT
CCTTCCACCTGTACAATTCATAGCTTAGTGAATGCGGTTATAGAAGCCAGCAATAGA
ATAGTCTCTGGTAGTAGTTTTGGAGGTGATGAAGCTGCTCTCAACAACTTTTATGAG
TCTTTTTTTAACTTGCTATTCCTAACCAGTGGGGCAACAGATAACAACCTAAAGAAT
CATTTTCTAATTAAACTTAATGAAGACGATATTACACCTCTCATACCTAAACGTGGT
TCAATAAAGAAACAGATCACATTCAAACTTTATGAAATTCCTACAACTACTAAATCT
GACTTTATCGCTCGTACCTTAGCAAGTTGTTTTACAGGAACTAAATATCCCCTCCTA
GTAAAGACAGAACCATTTTTCGATCTTGAAACATACTTTAAAATTTTTTTAGAAGAA
TACATTAAGCTTATTCTTGATGATGAAGAAGATTTATTACAACTCTGGGCTATCTGC
CACTCATTTGTTGAATTATCCACTAACCCTCATGGTTCCAATTTGGGTAAATATTTA
TTAAATTCTTGTACGATTTTTAAAGTTAGAGGTAGTGTATCAGCATCAGGTGGTCAC
GTTACTGAATCTATACTTAGGGAAAAGTTATCAAACATCGGGTTAAGAGCTGATATT
GATTACAATAATAATGATGTCAAAATTGGTGATGATGAAATTATTGAAGACGGGAAA
AGAAAAAAGAAAACTCGTGCGTATGACTTTATAATTCCTTATAAAATAGATAACTGG
GAACCAAAACCTAAGCTATTTATCCAATCACAATTTTACGCTGGGGATTCTGGCAGT
GTATCTCATAAAGTCGTAGATCAAACTCAAAGTTCAAGAGTATTTACACTAACCAAA
TATCCGAATGCTAAATTTGTTGAATATTTAGATGGTGCTGGTTACTACGCTTCTTTA
AGAGGTGATTTACAGCACATGCTATCTTTCAGCAATACAGAATCTTTTTTTCAAGTA
AAAAGTATTCTTTTACGTTTAAGACGTGAATTCCAAAAGATCGATTTTTTAACAGCT
ATTGAAATTCAGCATGCTGTACTAATCAGCAAATCTCGGACTCATAAAGATCTCCAA
AATCTTCTTATAAAAGATAACTATTCTATCCAAGAAATAGAAAGAGCTATTCAAACC
AATTTAGAACTAGGTCTTATTACTAAAAATGAATCAGATGAAATTGTAATACCTACA
GAACATATTTGTATCGCCCGGAGACTTTTAATTTTAGATATTGCTGCAAACTATTCA
TGCTCTATTACTCAGGCAGAAAAGTCTAGCCAAAAAATATTTATTAGTACCGGGCAAT

Figure 2-48

GGGGCCAATAAAGGAATTAAGGAGTCTAAGCTAGCTGAGTTAGCTTTTGACTTATGT
AAAGATATTAATATAACACCGACTGAATTTATTGAAGACATCGAATGGCTCTTAGAT
GAGGGAGTAATTAAACGATTTTAG

ACC65I amino acid sequence (SEQ ID NO:150)

MKLNAENLSIQEQLAEFDQWLTARLDKIKDSEKFNSEINSLCNCITVLSPLLENFSD
PSTCTIHSLVNAVIEASNRIVSGSSFGGDEAALNNFYESFFNLLFLTSGATDNNLKN
HFLIKLNEDDITPLIPKRGSIKKQITFKLYEIPTTTKSDFIARTLASCFTGTKYPLL
VKTEPFFDLETYFKIFLEEYIKLILDDEEDLLQLWAICHSFVELSTNPHGSNLGKYL
LNSCTIFKVRGSVSASGGHVTESILREKLSNIGLRADIDYNNNDVKIGDDEIIEDGK
RKKKTRAYDFIIPYKIDNWEPKPKLFIQSQFYAGDSGSVSHKVVDQTQSSRVFTLTK
YPNAKFVEYLDGAGYYASLRGDLQHMLSFSNTESFFQVKSILLRLRREFQKIDFLTA
IEIQHAVLISKSRTHKDLQNLLIKDNYSIQEIERAIQTNLELGLITKNESDEIVIPT
EHICIARRLLILDIAANYSCSITQAEKSSQKYLLVPGNGANKGIKESKLAELAFDLC
KDINITPTEFIEDIEWLLDEGVIKRF

BsaAI DNA sequence (SEQ ID NO:151)

ATGTACAATTATTTATTAAACGAAAATGCAGATATAATTTATGATGGAAAGGTTATA
CTCACAAAAGAACAAGTTGTTGAAGCAATTATTATAACAAATACAAACTTAAAGAAA
CTTAATGACATTACGAAAGAGTCTGGTGTCGAAGTGTTTGAAGCATTAGGAATGAGA
AACCTAAGTGGTTTTATTGGTGAGTTTTTCGTAAGCAGTCTCGAACAAGTATCAAAT
AAGAACTTAGTTAAAAATCCACATCAAGATGGATATCCAGATTTGTTGCTCGTAGAT
TCTCCTAAAGCTGCCTCATACTTTAATTCAATAGTCGAAATAGTTGATGGAAAATTA
TATCCAAAAGAAAAAAGTCTGTTTAGCCCATTTAAATATGGTGGATTAGAGGTAAAA
GCCACTTGTGGTTCTACACCTTCAGCAAAAGTTATGCCTAAGCCATTGATTGGCGAG
CAGAGAATTCACATCTTAACTGGATTAGATTGGAAGGCCCATCATAGAGGTACTAAC
AATCTAATAGGAATATATTGGGATTTTTTAGATGAGTTACCAACCATTTGCGCTGTA
TTTTATAGAAACGACCTAACCGAAGATGATTGGGGAAAAATTGTTCGCCCTAAAGAA
GGTGGGGGAAGAACCACAAGTGTATCCATTATGAACTCAAAGGGTGTCAAAAAAATG
TGCAAGAACTGGATTGCTATTATTGATAACGAAGATTATATAAACGCATTTTCTAAT
AAAAAATGGATAGGATATAATGTAAAAAACTCATCAAATTAG

BsaAI amino acid sequence (SEQ ID NO:152)

MYNYLLNENADIIYDGKVILTKEQVVEAIIITNTNLKKLNDITKESGVEVFEALGMR
NLSGFIGEFFVSSLEQVSNKNLVKNPHQDGYPDLLLVDSPKAASYFNSIVEIVDGKL
YPKEKSLFSPFKYGGLEVKATCGSTPSAKVMPKPLIGEQRIHILTGLDWKAHHRGTN
NLIGIYWDFLDELPTICAVFYRNDLTEDDWGKIVRPKEGGGRTTSVSIMNSKGVKKM
CKNWIAIIDNEDYINAFSNKKWIGYNVKNSSN

BsmFI DNA sequence (SEQ ID NO:153)

ATGTTGAGTACCATAACAAGGTTGCCTGTATATGATGATGATGAAGTAGGAGTTTTC
CATCCTATTTGCGAGTCTGCATTAAATCAGGCTCTGTCTAATCTTGGCTTGGATAAA
GAGTTTAAAGTTTTACATCATGAAGCCGTTGGTAGTCTTGAAGCAGATTTTGCATTA
ATACGGGAGTCAACAAGAAAATATGTTTTATTCATTGAGGTGAAGAGGAAACCAGCC
GCTGTAAGTAGTACAAGATATAGAATACAAGCACAGTCATATGTTCAAGAAGCAAAA
ACAGCAGTAGAAAAACCTTATTATGCTATTACTAATTTAGAAGTACTGGATATTTTT
AAGTATGATAGTAGCAGGCCTTCAGTTACTCAGCAAATAATTGAACCAAGTCCAGTT
CGTATAGGTACATTTTCCGACAATCCCGTAGAATTTTTTAATAACTTAGTTAAAACT

Figure 2-49

TTTGAGGATATTATCACTATTGTTGTAAATGACAGTGGTACATACAAAGAACTAACT
GGAAGTTTTATTCCATTACTAGAAAATAATAAAACTAATCAACAACGTTGGCATCAA
AGTTTATTAGTTGCCGGATATGAATATATTAGAGGTGTAATGCAAGCAAGTAAAAGA
AATATGACATGGAAAGCAGCCTTGAATTACAAAAATAGACCTAATAAATTAGTTGAG
AATATTCGATCAGTAAATTTTAGTTCATTAGTTGTTCCACCGTTACCTGCTAGTAAA
GATAGTGAAATTTGGAATACATCGATGTTAGAGGACTTGGTAGAGTTAGGAAAAAAA
ACAATGAGTGGTGATGGACTGGCTGAATTAGTTCATTCAATTGCTGTTTCCGGGAGG
GAGCACGAGGGTTTAGTACCTACAGACTTAGAGTTGGCTAATATTTTGGCTATTTTA
TCAAAATATGTTCTCGGTAGAGAGTTAAATGAAAATGAGATTATATGCGATCCAGCA
GCGGGAAGTGGAAATTTGTTAGCAGCCATCAGGGCAGGATTTGATACAATAAATCCA
AAACAATTATGGGCAAATGATAAAGAGCAGTTATTTCTTGAACTACTTTCTATTAGA
TTAGGTTTGATGTTTCCACTAATAGTCTCACCTACAAACTCACCTTTAGTTACAGGA
AAAGATATTTGTGACCTTAATAAGAACGATTTTACGAATGTTAGTGTAGTTCTTATG
AATCCTCCATATGTTTCAGGGGTAAAGGACCCTATAACTAAGAAAAAAGTTGCCAAA
CGTATATTTGATATTAGTGGAACAATGTCCAAGACTAATATTGGACAAGTAGGAATA
GAAGCACCATTCTTAGAACTAATTACAAACTTGGTGAAAGATAATACAATTATAGGT
GTGGTTTTCCCAAAACAGTATTTAACCGCGAGAGGTAGAGAGGCAGAAGCATTAAGA
AATTATTTATTAAATGATTTCGGTTTAAACCTTATTTTTATATATCCGAGAGAAGGA
ATATTCAAAGATGTAACAAAAGATACTGTAGTACTAATAGGGAGAAAGAATAATCCT
TCTAGCAAAGTGAAAGTTATAAAAAGCGAAATTCCACTTGCAGAAATAAATCTTACA
AAATTTAAACAAGGCTTGAATAATTTAAAAACAAATAGTTCAATACATTCTCTTGCA
TATGGAGTTGATGTAAGGGAACTTAATGCAAATGAATTGCATCAGAAAGTTAAAGAT
GGATGGAGAAGTCTTACAAATGTTGGTCAAAAAAATAGATAATTGGATTAATAGTACT
CTTATTCCAATTAGTGAGAAATTATCTGGAGTTCATAATTTAAAAAAAGGAAGAATT
GGAAATGCAGGTGCCTCGGACTTATTATTTATAAACTCAAATCATAAATTATGGGAA
TTGGTTAAGCATATTATTCCAAAAGATTGGTTATATCCAGCCCTTCGACTTGTAAAA
GATATTAATAACGTATTTGTTAATTCATCTACTACGGATGTTCGTTTTCTTGCCCCA
TGTGAAAAAGCGTTTCAAACAGGTACAAAAGAATATAGTATTTTAGAAGAAATATTA
GATATATACGAAGAAGTAAAAGCAGAATCCTTAGTAAAAACAAAACAACCAAAGAAA
ATAAAGACTAAGGAAGAATTGCGAAAGATATTAAATAGAGAAAGAAAGAAAATAACT
AGTCCTTATACTATTTTAATTCCTCGTAATATTAGAAGATATGCTAGGGTATTTATT
ACAACTGAAAGTGCATACATATCAACAAATGTAATTGAGGTAACTGGTGGAACAAAG
GATCAAAAGTGGATCACGTTTTCATGGTTGTTAAGTATATTTTCGCAACTTCAATTA
GAAGTAATGTCAAAAGAGCAAGAAGGTGCAAGAAAGACAGAAGTAGGTAGTATTAAG
GATTTACTTTTACCTAAGTTCGAAAACATTGATAACAAAATAGTCGAAAAACTAATA
AATGAGACTGAAACTAGAATAGGATTTTTGGATTTATGTAATCCATCAACTACTACA
ATTGATAAGTTATGGGCTGAAGTTTTATCTTCTTCGAAACCAGAAGAGATACTGAAT
CAAGCATTGTTTTTATTAGAAGAAAAAGTGAATGAGAGATATCCTGAGTATTTAGTA
TCAGATGATGATGAATAA

BsmFI amino acid sequence (SEQ ID NO:156)

MLSTITRLPVYDDDEVGVFHPICESALNQALSNLGLDKEFKVLHHEAVGSLEADFAL
IRESTRKYVLFIEVKRKPAAVSSTRYRIQAQSYVQEAKTAVEKPYYAITNLEVLDIF
KYDSSRPSVTQQIIEPSPVRIGTFSDNPVEFFNNLVKTFEDIITIVVNDSGTYKELT
GSFIPLLENNKTNQQRWHQSLLVAGYEYIRGVMQASKRNMTWKAALNYKNRPNKLVE
NIRSVNFSSLVVPPLPASKDSEIWNTSMLEDLVELGKKTMSGDGLAELVHSIAVSGR
EHEGLVPTDLELANILAILSKYVLGRELNENEIICDPAAGSGNLLAAIRAGFDTINP
KQLWANDKEQLFLELLSIRLGLMFPLIVSPTNSPLVTGKDICDLNKNDFTNVSVVLM
NPPYVSGVKDPITKKKVAKRIFDISGTMSKTNIGQVGIEAPFLELITNLVKDNTIIG
VVFPKQYLTARGREAEALRNYLLNDFGLNLIFIYPREGIFKDVTKDTVVLIGRKNNP
SSKVKVIKSEIPLAEINLTKFKQGLNNLKTNSSIHSLAYGVDVRELNANELHQKVKD

Figure 2-50

GWRSLTNVGQKIDNWINSTLIPISEKLSGVHNLKKGRIGNAGASDLLFINSNHKLWE
LVKHIIPKDWLYPALRLVKDINNVFVNSSTTDVRFLAPCEKAFQTGTKEYSILEEIL
DIYEEVKAESLVKTKQPKKIKTKEELRKILNRERKKITSPYTILIPRNIRRYARVFI
TTESAYISTNVIEVTGGTKDQKWITFSWLLSIFSQLQLEVMSKEQEGARKTEVGSIK
DLLLPKFENIDNKIVEKLINETETRIGFLDLCNPSTTTIDKLWAEVLSSSKPEEILN
QALFLLEEKVNERYPEYLVSDDDE

BspEI DNA sequence (SEQ ID NO:157)

ATGATTGAAACGGTGTTAGAGAAAGTTACAAATAAAAACAATTTTGTTACATTACAA
AATTATACGGATTTTGCTTTATATTTTTAGAGTATATTCAGAAGAATAAACAAGCT
ACAATTGTTTCACAAAATGAACATGTATATAACTTTTATCAATATAATAGTGAAGCG
AATTATCAAGTAACTCGCCCTTTCAATTCAAAAATTTTATATTCTCACCAAGATTTT
TTGGATAACCTAGGGGAATTCAATAAAATATTGAAGGATTTGAAAAGCGACCGTAAT
CATGCAAAAATTTTGGATAGAAGTATTATTAATAGAACAATTTATACGGTACAACAA
ACAATAGGTTTTGCATTGGACGGTCTTGACGCAAATAGGACAAATGTAGCTCGAAAA
CTGAATGGAGACTATTTCGAGCAGTTAATTTTATTACTGCTGCGAGAAATCGGTGCT
CCCGCGAATAACGGGGTTGTAAAAGTCCCTGTAAATATGGAAGACAAACAACTATTC
AATATGAGTTATCAACACGATCTTATACTTAAAGACAAAAAAGGCGAGGTAAAATTG
ATTGGTTCTGTTAAAACAACTTCAAAGGATAGAATTGGAAAGATTTTTGTCGATAAG
TTTCTATATTCGAAATTAACGGAAACAACAGTACCCCACATTGCAATTTTCTTACAT
GATGTTCAAAGAAAGAGGAATAAAGATCCGCAAAAATTCGGGATAAATGGCACCTTT
TTAGCAGGACATTTTAAAGGTTACACGGTTAAATTAAATCCCCTTGATGGAGTGTAT
TATTTCGACCCACGCCCACAAATGCAAACTGATGTTCTATTGAGTGAACATATACAA
ACGTTCGACCATTTGCTTTGCGATGATATTTGGAGTTATGTTGATTGA

BspEI amino acid sequence (SEQ ID NO:158)

MIETVLEKVTNKNNFVTLQNYTDFALYFLEYIQKNKQATIVSQNEHVYNFYQYNSEA
NYQVTRPFNSKILYSHQDFLDNLGEFNKILKDLKSDRNHAKILDRSIINRTIYTVQQ
TIGFALDGLDANRTNVARKLNGDYFEQLILLLLREIGAPANNGVVKVPVNMEDKQLF
NMSYQHDLILKDKKGEVKLIGSVKTTSKDRIGKIFVDKFLYSKLTETTVPHIAIFLH
DVQRKRNKDPQKFGINGTFLAGHFKGYTVKLNPLDGVYYFDPRPQMQTDVLLSEHIQ
TFDHLLCDDIWSYVD

BtsCI DNA sequence (SEQ ID NO:159)

ATGAAAATAACAGAGGGAATCGTCCATGTTGCAATGCGGCACTTTCTAAAATCAAAT
GGCTGGAAATTAATTGCTGGGCAATACCCTGGTGGAAGCGATGACGAATTGACTGCA
CTTAATATTGTTGATCCTGTGGTAGCTCGTGATAATAGTCCTGATCCTCGCCGTCAT
AGTTTAGGTAAAATTGTTCCTGACCTAATAGCTTATAAAAACGATGATTTACTCGTT
ATTGAAGCAAAGCCGAAATATTCGCAGGATGATAGGGATAAATTACTTTACTTGCTT
TCAGAAAGAAAACATGACTTTTACGCGGCTTTAGAAAAATTCGCTACTGAAAGGAAT
CACCCAGAACTACTGCCGGTATCTAAGCTGAATATTTATACCTGGGTTAGCGTTTTCC
GCTTCAGAAAACAAATTCAAAAAGGATCCCGGATTCGTTTACATAAGAGTATCTGGG
ATCTTTGAAGCATTTATGGAGGGCTATGATTGGGGGTGA

BtsCI amino acid sequence (SEQ ID NO:160)

MKRILYLLTEERPKINIIHQIINLEYKATLHFGAKIVPVMNEENKFTFIYHVKGIEV
EGFDAVLIKIVSGHSSFVDYLVFDSNDLKPEKNTITLFDLDQYELDLSYYFGKGWIV
RIPSPSDLPKYVVEETKTDDHESRNTNAYQRSSKFVFCELYYGKEVKKYMLYDISDG

Figure 2-51

RTLSGTDTHNFGMRMLVTNNVNLVGVPNMYLPFTDIKEFINEKNRIADNGPSHNVPI
RLKLDKEKNVIYISAKLDKGNGKNKNKISNDPNIGAVAIISATLRNLNWKGDIEIIN
HNLLPSSISSRSNGNKLLYIMKKLGVRFNNINVNWNNIKNNINYFFYNITSEKIVSI
YYHLYVEDKLSNARVIFDNHAGCGKSYFRTLNNKIIPVGKEIPLPDLVIFDSDQNIV
KVIEAEKAENVYNGVEQLSTFDKFIESYINKYYPGAAVECSVITWGKSSNPYVSFYL
DKDGSAVFL

BtsIA DNA sequence (SEQ ID NO:161)

ATGAAAATAACAGAGGGAATCGTCCATGTTGCAATGCGGCACTTTCTAAAATCAAAT
GGCTGGAAATTAATTGCTGGGCAATACCCTGGTGGAAGCGATGACGAATTGACTGCA
CTTAATATTGTTGATCCTGTGGTAGCTCGTGATAATAGTCCTGATCCTCGCCGTCAT
AGTTTAGGTAAAATTGTTCCTGACCTAATAGCTTATAAAAACGATGATTTACTCGTT
ATTGAAGCAAAGCCGAAATATTCGCAGGATGATAGGGATAAATTACTTTACTTGCTT
TCAGAAAGAAAACATGACTTTTACGCGGCTTTAGAAAAATTCGCTACTGAAAGGAAT
CACCCAGAACTACTGCCGGTATCTAAGCTGAATATTATACCTGGGTTAGCGTTTTCC
GCTTCAGAAAACAAATTCAAAAAGGATCCCGGATTCGTTTACATAAGAGTATCTGGG
ATCTTTGAAGCATTTATGGAGGGCTATGATTGGGGGTGA

BtsIA amino acid sequence (SEQ ID NO:162)

MKITEGIVHVAMRHFLKSNGWKLIAGQYPGGSDDELTALNIVDPVVARDNSPDPRRH
SLGKIVPDLIAYKNDDLLVIEAKPKYSQDDRDKLLYLLSERKHDFYAALEKFATERN
HPELLPVSKLNIIPGLAFSASENKFKKDPGFVYIRVSGIFEAFMEGYDWG

BtsIB DNA sequence (SEQ ID NO:163)

ATGCAGATCGAACAATTAATGAAAAGTCTCACAATCTATTTTGACGACATACAAGAG
GGTTTATGGTTTAAAAACTTGCATCCTCTATTAGAATCCGCGTCTCTTGAGGCGATT
ACTGGATCCCTAAAAAGAAATCCAAACTTAGCTGATGTTTTAAAATATGATAGACCC
GATATCATTCTTACCTTGAATCAAACACCCATATTAGTAATAGAGCGAACAATTGAG
GTTCCAAGTGGGCATAATGTCGGACAAAGATATGGGAGATTAGCCGCAGCATCGGAA
GCAGGAGTTCCTTTAGTCTACTTTGGTCCTTACGCTGCCAGAAAACATGGTGGGGCT
ACTGAAGGACCACGATACATGAACTTGCGTTTATTTTATGCCCTGGATGTAATGCAA
AAGGTAAACGGTTCTGCTATTACCACTATAAATTGGCCTGTAGATCAGAATTTCGAA
ATACTCCAAGATCCATCTAAAGATAAGAGAATGAAGGAGTATTTAGAAATGTTCTTC
GATAATCTTTTGAAATACGGAATAGCCGGTATAAATTTAGCGATTAGAAATTCCTCT
TTTCAAGCTGAGCAATTAGCTGAAAGAGAAAAATTTGTGGAAACTATGATAACTAAC
CCTGAACAATACGATGTCCCGCCCGATTCGGTCCAAATTCTTAATGCTGAAAGGTTC
TTCAATGAATTAGGTATATCAGAAAATAAGAGAATAATCTGTGATGAGGTTGTTTTA
TATCAAGTAGGAATGACATACGTCAGATCAGACCCATATACTGGAATGGCCCTTTTA
TATAAGTATCTTTATATACTTGGGAGCGAACGAAATAGATGTCTTATTTTAAAGTTC
CCTAATATTACAACTGATATGTGGAAAAAGGTGGCTTTTGGAAGTAGAGAGCGGAAA
GACGTAAGAATCTACCGAAGTGTCTCAGATGGAATATTGTTTGCAGATGGTTATTTA
TCAAAAGAAGAGTTGTAA

BtsIB amino acid sequence (SEQ ID NO:164)

MQIEQLMKSLTIYFDDIQEGLWFKNLHPLLESASLEAITGSLKRNPNLADVLKYDRP
DIILTLNQTPILVIERTIEVPSGHNVGQRYGRLAAASEAGVPLVYFGPYAARKHGGA
TEGPRYMNLRLFYALDVMQKVNGSAITTINWPVDQNFEILQDPSKDKRMKEYLEMFF
DNLLKYGIAGINLAIRNSSFQAEQLAEREKFVETMITNPEQYDVPPDSVQILNAERF

Figure 2-52

FNELGISENKRIICDEVVLYQVGMTYVRSDPYTGMALLYKYLYILGSERNRCLILKF
PNITTDMWKKVAFGSRERKDVRIYRSVSDGILFADGYLSKEEL

EcoNI DNA sequence (SEQ ID NO:165)

ATGAATATTGGTTTATACCCAAATGATAGTAGAGATTGGGGAGAAGACGATTGGCAT
CAATTTTTGCAAGAATTAGTTAATAATAATTTAGTGTCATATGAGCAGATCACTTCT
CTCGTTTTGGGGCATTTAAACCCATCTCAAGTTGGTACATCAATAGCCTCTAAAAAA
ACATTTCAGGCGCATTATCCTCCTCGTCAATGTTGGGCTGCTGTTCGTTCTTGGCAT
TTTGAGCAGTCGGGGCGATGCATCGACTGTGGAACTCGCCTTGAATTACAGGCAGAT
CATGTGCTTCCGCGAGAATTACTAGGTGATGAAGCTGATCGGCTTGATAATATGGCT
TTGAGATGTCGAAGGTGCAACGTTATAAGAAGGCCAAGTCATAGAAACGGTGGAATA
GCTCATCTTACTACCGAATCAGCACTAATGTGGTTGCTCTTTACTCGTCAGCCTACA
AATTATCAAACATATCGAGATTTGTGTCGTGCATATGGAATGACTATGGCAAGTATC
CGTTTCGAAGAAGCATGGGCTATGGCAAGATGGCTGGAAAGAGAAGGTTTGTATTAT
ATAGACGAAACTTCTATTTTTTGA

EcoNI amino acid sequence (SEQ ID NO:166)

MNIGLYPNDSRDWGEDDWHQFLQELVNNNLVSYEQITSLVLGHLNPSQVGTSIASKK
TFQAHYPPRQCWAAVRSWHFEQSGRCIDCGTRLELQADHVLPRELLGDEADRLDNMA
LRCRRCNVIRRPSHRNGGIAHLTTESALMWLLFTRQPTNYQTYRDLCRAYGMTMASI
RFEEAWAMARWLEREGLYYIDETSIF

Fnu4HI DNA sequence (SEQ ID NO:167)

ATGAGTGATATAAAAAAAATAACAGATGTTGAGTATAAAATGGTAATTTCGCTTTAT
CCTATTTGGAAAGAACTAAATAGTTCTATAAAAAGCATATATTCTCGTGGTGTTAAT
TTTCATGAAGTTTTTTCTGAATTTATTGTATGCTATATAAATAATTACTATCATAGT
CTTGGGAGTGGTTCAGAAGATGCTTATACAAGTGATATGAAAAAAAAGGTTCAAGTA
AAAGCTAGTTCTAATTTTAATAGTGATTTAACTAGTTTTGGTCCAACTAGTGAATTT
GATATTCTAGAATTTGCTCGTTTAAATCAAGAAGAAAATAAATTATATCTATATAAA
ATTCCAATAGATAATTTATATAATATAAATGTAAATTCTAACGAAACATTTAAAGAA
CAACAACAAAGTGGAAGAAGACCAAGATTTTCTATTATAGAAAAATATATAAAAGAA
TATAATCTAAAGCACTATGCAGTTGTTGATATGATAACTGGTCTTTATTTTTAA

Fnu4HI amino acid sequence (SEQ ID NO:168)

MSDIKKITDVEYKMVISLYPIWKELNSSIKSIYSRGVNFHEVFSEFIVCYINNYYHS
LGSGSEDAYTSDMKKKVQVKASSNFNSDLTSFGPTSEFDILEFARLNQEENKLYLYK
IPIDNLYNINVNSNETFKEQQQSGRRPRFSIIEKYIKEYNLKHYAVVDMITGLYF

KasI DNA sequence (SEQ ID NO:169)

ATGAGCGTTATTCCGTGTAAAAAGGACCTTCAGCTAAAAAAATTGATTGAATCCTAT
GCAGAAGCCTTGAAAGTTGAGGCCCATAAGCTAGGAGAGCATGGATTAACTGAAGCT
GAATTTTATGATAGCGGCCTCTTTCGGGGGGCTATCGAGCGAATTCGAGGACAGTTC
TCCGCGACCATGCGGGAGAAAAGAAATTTCGTTAAGCATGTTTTAAATTACATGCAG
GATAACGACTACATTGCTGATTGGGAGTCGGCTGGTGAATCGAATCGCCATGATTAT
ATGGTAACTCTCAATTCTGGGCGCAAAGCTGCTATTGAGCTGAAAGGGTGCCTTGAT
GGCAATAACACTAACATCTTTGATCGCCCCCCTCAGGCAGAAGAATTTGTTATCTGG
AGTGTATGCACAAATCCTGGTGCTGACCCTCAGCATAATGTTTGGTCTGGGCTTCAC

Figure 2-53

ACCAGACTAAGTGCTGAAATCATTTCACGGGAGCAAAGGATTGATGGAATGGTCATT
TGGGACTGGGCTTGTGGAACAGTCGGAAGGCCATGCCCCAAAATAGCAACTGAACCT
GAGCGGGCTGTAACATTTGGGCCGTTCAAATTGCCGCCACCATGTTTGTATCTTTTA
CCTTCGACGATTCCAAGCCCAAGAAACAACCCGTCTCCAAGAGCTCAGCAGATTGAA
GACGTGCAGCTAATCAAAGCGTTTCACGATTGTTTTGGGTGCCGGTCTGAAGAAGTT
AATTTCGTTAACTTTGATGTTGGTTATCATGGTAAAGATACCGTCCGTAAAACGACT
ATCATTCGAAACGGCATGGTGGAGCGTGAATCGGAAATGACGGCAATAAGGCGGTCT
TAA

KasI amino acid sequence (SEQ ID NO:170)

MSVIPCKKDLQLKKLIESYAEALKVEAHKLGEHGLTEAEFYDSGLFRGAIERIRGQF
SATMREKRNFVKHVLNYMQDNDYIADWESAGESNRHDYMVTLNSGRKAAIELKGCLD
GNNTNIFDRPPQAEEFVIWSVCTNPGADPQHNVWSGLHTRLSAEIISREQRIDGMVI
WDWACGTVGRPCPKIATEPERAVTFGPFKLPPPCLYLLPSTIPSPRNNPSPRAQQIE
DVQLIKAFHDCFGCRSEEVNFVNFDVGYHGKDTVRKTTIIRNGMVERESEMTAIRRS

McaTI DNA sequence (SEQ ID NO:171)

ATGACAAAAGAAGAATTTGAAAGCTATTTGGACGACATCGCCTCTAAGCTCAGGGAC
GAAGCCAGAAAGACGCCATTTGCCGCAGCCAAGCAGTTCGAGCAACGTGTTCGGGAA
ATCACCAAGGAAACGATCCAAGCTCCCGGGATCGAGATCGATTTCAACCCACACCCT
CAAGCATTCCCCGACATAGAAATCGGTCAGTTCGGAATTGAGGTGAAATTCACGACA
AACGACGAATGGAGGAGCGTCGCCAACAGCGTGCTGGAAACCAACCGTATCGAATCC
GTGCAGCACGTGTACATCATGTTCGGAAAGATGGGTGGCAATCCGGACGTGAGATGG
GGTGAATACGAGAAATGCGTCATGCATGTCAGAACATCCCACGTCCCTCGCTTCGAG
GTGCAGATCGATGCCACTCGATCCTTATTCGAGATCATGGGCATTTCTTACGATCAA
TTCCGGGTGCTCGAAATGCACGAGAAGATGCAGTACATCCGGAAATACGCAAGAAGC
AGGCTGAAGAACGGAGAACGCTTATGGTGGCTGGAAGATTCGCCCGGCGAAGCCCAT
ACCTTGCCTATGCAAGCTCGACTATTCACTGAGCTAGAGCAGTCCGAGAAGATTCGA
CTTCGCGCCGAAGCAATCCTACTTTGTCCTCAAATCGTTCAATCTGGCAGAGCCCGG
CATAAGTACGATGACGTCGCGTTATTCATGCTGACCTATCACGGCGTGATCTGCCAT
CAGACCAGAGATATGTTCTCTGCCGGTAGCGTTGGAAACCCGGAGAATGACGATAAC
GGCGGACTCTACATCGCGCGCATGCTCAAGCTGATGGAAGCCGAGTTGGAGAAGGCA
GCGGCGCGCATGGATGCCGCGCTGTTTGAGGAATATTGGGGCGTGGCTGTCCCACCT
GAGGAAAGAATAGCGGAATGGCTGCGTCGCGCAGACAAGTTCGCGTCGGGAATTTGG
AAGCCATCTGAAGAGTTGTTCGATGGTAGATACGCTCAGCCAAGAGGAGCGTAG

McaTI amino acid sequence (SEQ ID NO:172)

MTKEEFESYLDDIASKLRDEARKTPFAAAKQFEQRVREITKETIQAPGIEIDFNPHP
QAFPDIEIGQFGIEVKFTTNDEWRSVANSVLETNRIESVQHVYIMFGKMGGNPDVRW
GEYEKCVMHVRTSHVPRFEVQIDATRSLFEIMGISYDQFRVLEMHEKMQYIRKYARS
RLKNGERLWWLEDSPGEAHTLPMQARLFTELEQSEKIRLRAEAILLCPQIVQSGRAR
HKYDDVALFMLTYHGVICHQTRDMFSAGSVGNPENDDNGGLYIARMLKLMEAELEKA
AARMDAALFEEYWGVAVPPEERIAEWLRRADKFASGIWKPSEELFDGRYAQPRGA

NciI DNA sequence (SEQ ID NO:173)

ATGAAAATAAATAAATTTAATTTAGAAAAAATTTTAAATAAATTTATATGCGGTGAT
TCTTTGCAAAAAATGAAAAAATTACCTAGTAAATCAATCGATTTAATTTTTACTTCC
CCTCCTTATAATTTAAAAAATTCAACTGGTAATGGAATGAAAGATGGTAGAGGCGGA

Figure 2-54

AAATGGTCAAATGCCAGATTAATTGAAGGGTATGACAACCATGATGATTGTATGCCA
CATGATGAGTATGTGAAATGGCAACGTAAATGTTTAAAAGAAATGCTTCGTCTGATA
AAAGATGATGGTGCTATTTTTTATAATCATAAATGGAGAGTACAAAATGGTCTATTA
CAAGATAGAGCAGACATTGTAAAAGGCTTTCCTGTTCGCCAAATTATTATTTGGAAA
AGAAAGGGAGGAATTAATTTTAATCCTGGATATTTTTTGCCAACTTATGAAGTAATT
TATTTAATTTGCAAGAAACCTTTTAAATTGGCAAAAGGTGCAAATTCATTTGGAGAT
ATTTGGGAATTCACGCAAGATATGAATAATGAACATCCTGCACCATTTCCTTTAGAA
TTAGCTAAGCGAGTTGTACAAAGTACAAATGCTCAAATAGTGCTTGATCCATTTATG
GGAAGTGGAACAACTGCTATTGCAGCAGCACTATTAGACAGAAAGTTTATTGGCATT
GAACTTTCATCTGAATATGTCAAGATATCTAAAAAAAGATATAACAATATTTTTGGT
AATTTATTTGGAGTAGATATGAAAACTTTTACAAAAGAATCTTTAATTCAAGAGCTA
AAGGAAATTAAAAATAAAGGTCCGGTTCTTAATAACAGAGGAAGTAACAATGGGGCT
TCCGGGAATGTTTTAGAAGATTTGCTGGGAATTGAAGAAAATAATCTCCCTTTAGCA
AATGCTGCAGAATGGGAAATAAAAACCAAAAAAAGATCATCCAATTCACTGGTAACA
CTATTTCATGTTGAACCCTCTCCAACCGCATGTAAATTTGTCCCAAATATATTATTA
CCTAAATACGGATGGAAACATAAAGAGGCTGGAAAAAAATATCCTGACACTGAAAAA
AGTTTTAGACAAACTATTAAGTGTGGTTTATTTTCTGATAGAGGATTTTCTATAAAA
CTTAATGATAGCGAAGAAAAAATTGAAGTAAATTTTAGATATGATCTAATAGATCAA
AAGCATAATGAATGGAAGCAGGATATTTCTACCTTTCAGACATTGGATACAATACCA
TACTGGGGATTTAATGATATATATCATAAACTTGGTGCAAAATTGCATAACTGTTTT
TTTGCGATAGTAGATGTTTGTAAAAGAGGAGATGATGAATATTTTACCTATAGTGAA
ATTTATATGCTCCGTAATTTATCGAAAGATAAATTTATATCTGCAATCCGAGATGGA
AAGATATATATAGATTTTGATGCTAGAACAGGACATAATCATGGAACAAAATTTAGG
ATAAAAGAAAAAGATATTTTTGACCTCTATGAAGAATGCATCGAAATATCAAACTTA
TAG

NciI amino acid sequence (SEQ ID NO:174)

MKINKFNLEKILNKFICGDSLQKMKKLPSKSIDLIFTSPPYNLKNSTGNGMKDGRGG
KWSNARLIEGYDNHDDCMPHDEYVKWQRKCLKEMLRLIKDDGAIFYNHKWRVQNGLL
QDRADIVKGFPVRQIIIWKRKGGINFNPGYFLPTYEVIYLICKKPFKLAKGANSFGD
IWEFTQDMNNEHPAPFPLELAKRVVQSTNAQIVLDPFMGSGTTAIAAALLDRKFIGI
ELSSEYVKISKKRYNNIFGNLFGVDMKTFTKESLIQELKEIKNKGPVLNNRGSNNGA
SGNVLEDLLGIEENNLPLANAAEWEIKTKKRSSNSLVTLFHVEPSPTACKFVPNILL
PKYGWKHKEACKKYPDTEKSFRQTIKCGLFSDRGFSIKLNDSEEKIEVNFRYDLIDQ
KHNEWKQDISTFQTLDTIPYWGFNDIYHKLGAKLHNCFFAIVDVCKRGDDEYFTYSE
IYMLRNLSKDKFISAIRDGKIYIDFDARTGHNHGTKFRIKEKDIFDLYEECIEISNL

NruI DNA sequence (SEQ ID NO:175)

ATGGGATTTCTTGAAGACTGGGACCTCAGCTACGACGAGATCAACGAGCTTCTCACT
GACAACCCCAGCCTTCGATCGTTCGTGATGGGGTACGCAGCGGAGATCAAGTGTCGC
AACATGTTCTTCGTTGATCATCCACATATCACCAACATTTACAAGCCCGATGATCAC
GATCGCACTGAAAAGGGCGACTGGATCATCAACTACAAGGGACACCGGATCGGGGTC
GAGGTCAAGAGTCTCCAGACGAACTCACTGCGGCTTCGCCGAGATGGCAGTGTCCGA
CCAAACTACCAGTGCGACGCTTCGGATGCCCGCACCGTGATCTTCGCTGACGGTAGC
GAAGTTCATACGACCGCTCTGTTGGTCGGAGAATTTGACGTAGTTGCAGTCAATATC
CATGCGTTCGAAAATAAGTGGGATTTTGCGTTCGCTAAGAACGAGGATCTCATCACG
ATGGAGGGTGCGACCAGGGGCGCAGCGAAAGACTACACCGAACTCCAGAAACGCAAT
CTCATCAAGACTCTCCAACCGATGCCTATGGACGTGCCAGCCCCGTACACTCGAGAT
CCCTTCAAACTCTTCGACGAGATCATCGAAGAGCGCATGAAGGGTGAGCAGCCTCAG
CTCAAGGCGAAGATCATCGAAGACGAAGAGTGA

Figure 2-55

NruI amino acid sequence (SEQ ID NO:176)

MGFLEDWDLSYDEINELLTDNPSLRSFVMGYAAEIKCRNMFFVDHPHITNIYKPDDH
DRTEKGDWIINYKGHRIGVEVKSLQTNSLRLRRDGSVRPNYQCDASDARTVIFADGS
EVHTTALLVGEFDVVAVNIHAFENKWDFAFAKNEDLITMEGATRGAAKDYTELQKRN
LIKTLQPMPMDVPAPYTRDPFKLFDEIIEERMKGEQPQLKAKIIEDEE

Sbo13I DNA sequence (SEQ ID NO:177)

ATGAGAGAACCCTCGATTCTAGAAAGATGGGAAATAAGCGAAGAAAAATTAACTGAC
TTGGTTGATAAAAACCCCTCTCTTAGAGGAATGATTTTAGGTTATGTTGCTGAGGAT
AAATTTCACGAGCTATTCCTTGAAGATGAAAGAGTAAAGGAGGTTTCTAAAGACGAC
GATCATGACAGAAAGAAAAAAGGAGATAGAACCTTTATTTACAAAGGTAAAAAATTT
ACAGTTGAAGTTAAAAGCTTGCAAACCGCAATGTGCAAGAAAAATGAAGACGGAACT
TATTCAGGAAAAGCCCAAGTAGACGGCAGTGATCGAAGAATAGTAAAATTCCCAGAC
AATTCAGAATTAAATACGACGTTACTCTTGAAAGGAGAGTTTGATCTATTAGCCGTT
AATTGCTTTGCTTTTGGTGAAGGATGGAAATTTGCTTTTGCAAAAAATTCTGACCTT
CCCACCTCAACATTCAAAAAATACACAGAAGAACAAAGGAAACAACTTATTGCCTCA
CTGATTCCTGTAACTTGGCCACCAAAGCCACCATTCAGTGATGACCCATTCCACCTT
CTGGACGAGATGATTGCAGCGCCAGAAGAGGAACCGGTGATAGAAGAAAGTAGTGAA
TTAAAAGAAGTAAAAGAAGATATAGATGTAGTTAAAGTGAAATCATAA

Sbo13I amino acid sequence (SEQ ID NO:178)

MREPSILERWEISEEKLTDLVDKNPSLRGMILGYVAEDKFHELFLEDERVKEVSKDD
DHDRKKKGDRTFIYKGKKFTVEVKSLQTAMCKKNEDGTYSGKAQVDGSDRRIVKFPD
NSELNTTLLLKGEFDLLAVNCFAFGEGWKFAFAKNSDLPTSTFKKYTEEQRKQLIAS
LIPVTWPPKPPFSDDPFHLLDEMIAAPEEEPVIEESSELKEVKEDIDVVKVKS

SfcI DNA sequence (SEQ ID NO:179)

ATGAATTACTCTATCAATGAACAATTATTAAGATTTAAATTTTTAATTGAAGATTCA
ATAAAAGAAGGTGGTACAATAGGAAAAACTTCTATGATTAGATCTTCAAAAATGATT
AACCTCATTCATGATGCTACAAAGCAAGAATTGATATGTAACGGTGTTAACCCCGAT
AATATCCGTCCACCGCTTGGACATTCAAAACCTGAATTAAAAATTGCTGGCATACTT
AAACAGAAAGACCAAGATGTTTGTGTTATTCCAACCGGCATATACCCCACCCCAACC
CCTATTACTTGGGGACCTCTGGCTTTTAATAAAAAAATCGATCCTTACGGTTTTGAA
TTTAGTGAAAAAACTTTAATCATCAATGTTCGTAGCCAAATGAGTAGCTTAGCCAAA
AATGCAGACACTTTGTTTGAAAGAACCTTTGCAGAAGCACAAAATTTGCACTTAAGA
TATCCTAATGCCGTTTTAGGAGAGGTATATCTAATTCCAGTTAATGAATATGATGAT
GCTCTTGTATCTAAACATCAAGTAGGTTTTAAAACTCGTCAGACTGATTTAGAAAAA
TACATTAGCTTCTTTACTGAAATCAATAATCGTTCTATTGGTGAACCTCCACATTCT
TATGAGCGGTGTGCATTATTGATCGTTGATTTTAATCAACCTCAACCTCTTCTATTT
TCGAATAGTGATGAATTAAAAGCTGCTGGTTACATCTCTTCTGATTTTGATATTGAA
TATGCAAATATTAATTTTCAAAATTTTGCCTCAGATATTTTAAGCATCTATGATCAG
CGTTTTGACATCAATTATCTAATATAA

SfcI amino acid sequence (SEQ ID NO:180)

MNYSINEQLLRFKFLIEDSIKEGGTIGKTSMIRSSKMINLIHDATKQELICNGVNPD
NIRPPLGHSKPELKIAGILKQKDQDVCVIPTGIYPTPTPITWGPLAFNKKIDPYGFE

Figure 2-56

FSEKTLIINVRSQMSSLAKNADTLFERTFAEAQNLHLRYPNAVLGEVYLIPVNEYDD
ALVSKHQVGFKTRQTDLEKYISFFTEINNRSIGEPPHSYERCALLIVDFNQPQPLLF
SNSDELKAAGYISSDFDIEYANINFQNFASDILSIYDQRFDINYLI

StuI DNA sequence (SEQ ID NO:181)

GTGTCAGTGAGTGCGGTCGAACAGGTATTTTTGGAATGCGAGCGCGCTCGGGCAGAC
GGTGACTTGATTCAGCGGGTCTCCGCCAGTGATAAGGAGTACCACTTTCAGAATTGG
GTGCAGGCCCGCATAGAGGCATGCAGGCTTTCGTACGATGATCCTGGCCGGAACACC
TATCCGGACTTCCGGCTCATCCATCACCCGGAAGGGTATGAGGTCAAGGGCCTGGAG
TTTCCCGGCCGCGAGGCGGACTACGACTCAAACTCCCAGGTGCCCACCGGTAACCAC
GGCGGCCGTGAGGTCTTCTACGTGTTCGGTCGCTACCCGAAGGCAGAGCGCGGCGTC
GATGAGTATCCAGTTGTAGATCTGGTGGTGTGCCACGGCAGCTTCCTCAATGCCGAT
AGTGAGTACGTTCATAAGAACAAGTCGTTCCGTGGCTTTGGCTCGTACGGAGACATC
CTGGTCCGCGACCGCAAAATGTACGTCGTGCCAACGCCGTTCGCACTAGCTTCCGGA
ACCGCAGGGCTCGCGACCCTGATCGTGCCTACTGAATTCGAGCCACAGTCGGATACT
CTCGTTCAGGTGGGTGAACTTGATCGGACCGAGGTTGACGAGGTCATCGTGTCGTAC
GAGTTCAACCTTCAGACAAATGAGATGGTGACGCATAAGGCGCCGAATCTCAATGCA
GGTAAGGTCCACAGTTTCCGAGCATATCGCTCGCGCGGTGCGGGCGATTCTAAGCCG
GTTTCCCTCGCAGGGGGTCGGCTGTGA

StuI amino acid sequence (SEQ ID NO:182)

MSVSAVEQVFLECERARADGDLIQRVSASDKEYHFQNWVQARIEACRLSYDDPGRNT
YPDFRLIHHPEGYEVKGLEFPGREADYDSNSQVPTGNHGGREVFYVFGRYPKAERGV
DEYPVVDLVVCHGSFLNADSEYVHKNKSFRGFGSYGDILVRDRKMYVVPTPFALASG
TAGLATLIVPTEFEPQSDTLVQVGELDRTEVDEVIVSYEFNLQTNEMVTHKAPNLNA
GKVHSFRAYRSRGAGDSKPVSLAGGRL

StyI DNA sequence (SEQ ID NO:183)

TTGTTTTTAACTGTCATTTTTCCTAACTATCGATCTGTTACCATACAACCTGCTATC
TTAGCATCTCATTTTTACTATGTCCATGGTGAGGATATGAATTTCAAGGATAAAAAT
TGTTTCCCTAACGAACTCATAGCGTTGGCGAAAATTTCAAAAAATGATGTTTTAGAT
AAGTTCGGAACGGATGTTTTTAAAAAGGTTGTTTATGATGTTTTAACAGGTAAAAAT
GTTCGCGAATTCACTGAAATACTAACTCGTACTAGATTGTTAGAAAGCAATCTCTCT
TTTTTTGACTTTTTTGTGGATAAAATGAAAGAGGGGATAACGCCAAAGCAGCTTTAT
CTCTATGCAAAAAATGCATTATCGAACAAGTCTTATGTTAAGTATAATCAACCTGTT
CTCGAGTGGATGGTTATGATGACAAATAAACAGACCCAAAATGTTTTAAGAGATGAG
CATGGGGATGGTTTTGATAGGCTTGCTTTAAGGACGCAAGAAGAAATACTTAAAATA
AAAAACGGGTATGAAGATAAAATTGGAGAGATATCTATTGGTGGGCAAAAGGTGTCT
TTAGAAGATTTTTGCTATATTATTTTATCTCTTGGTTCGCAAACTTTAACTATTAGG
GGATCTGAGAAATCTCTTCATGGTAAATATTTTGAAAAGCTAATACTCGGTTCTTTA
TTTACAATAATGGGTTTTGAATATAAAGAAAAAATTGAAGAAGGGTTAAATGCTAAA
TGTTTTACTCTTTCAACAAGAGCTGATGACAGGGAGTCTGATGCTACTCTTATTTTT
AATGGGAAGGCGATTAGGGTTGATATTGGTTTTATTGGTAGGGGTAACACAGAAATA
AGTTTGGATAAAGTATCTAGATTTAGACGAATGGATGATATTGGCGGAGTGATGCAT
AATATAAGCACAATGGTTATTGTTGACGTTATTGGTGATAGAAGTAGAATAGTTAAT
ATGGCTGAAGAGATTGATGGTAAAGTTGTTGCGATGAGTGACCCGTATTGGGTTGCA
AAGGTCTCTTCCTATATTAGTTCGAAACTGAATGTAGATGATCTTTTAGAGGATAAA
CCTCAACTTAAATACATACAGTCTTTTATATCTGATGCATTAGAGAATGTAGATCTG
GAAAAATACATTAAATTATAA

Figure 2-57

StyI amino acid sequence (SEQ ID NO:184)

MFLTVIFPNYRSVTIQPAILASHFYYVHGEDMNFKDKNCFPNELIALAKISKNDVLD
KFGTDVFKKVVYDVLTGKNVREFTEILTRTRLLESNLSFFDFFVDKMKEGITPKQLY
LYAKNALSNKSYVKYNQPVLEWMVMMTNKQTQNVLRDEHGDGFDRLALRTQEEILKI
KNGYEDKIGEISIGGQKVSLEDFCYIILSLGSQTLTIRGSEKSLHGKYFEKLILGSL
FTIMGFEYKEKIEEGLNAKCFTLSTRADDRESDATLIFNGKAIRVDIGFIGRGNTEI
SLDKVSRFRRMDDIGGVMHNISTMVIVDVIGDRSRIVNMAEEIDGKVVAMSDPYWVA
KVSSYISSKLNVDDLLEDKPQLKYIQSFISDALENVDLEKYIKL

BsiWI DNA sequence (SEQ ID NO:185)

ATGACAAAAGTTAAAGAATTGTTTGGATTGAATACAAGTGTTAAAGGGACTGATTGG
GGAAAAGTTGTTACAGAACAGCATTGCCCCTTTTTGAATAAAAAGTGTATAAAAAAT
AGAAAGAGTCAGGCAGAAATAGCAATTGGCACATGTACTATGAGTTATGGCAAAGTA
AGTAAAGATATAATTATCTGTCCACATAGATTACTAGAAAACAGAAAAATATTCATA
GATTGTATTCATTTACTAACAATGCATGAGCCTGGTAATGAGTTACATGTTGTATCA
GAAGTGTCTATTCCAGGAGGTAATGTAGATTACTTTTTAGTCTCAGCAAAAGATGGT
AAAGTAAAAGATTTTGTTGGGATTGAGCTACAGACTATGGATACCACAGGTACTGTA
TGGCCTGAAAGAGAAAGGTTTCTAAAAGATGCTGGATATAGTGGATATGATAAAGAG
GCAATAGACTCTGATAAGTCCTTTGGAATGAATTGGAAGCATACAGCAAAAACTATT
CTTGTACAGTTACATCATAAGGTCAAAACCTTTGAGCATGTTAATAAAAAATTGGTC
TTAGTGATACAAGAACCTTTAATAGATTATATGAAAAAAGAATTTAGTTTTTCTCAT
GTAGGAAATGCTAAGTTAGGTGACCCACTACATTTTCACCCATATTCCTTAGATACT
AGAGAAGATAATCAATTACATTTAAATTTAAAAACTAGACTTAGTACAGACTCAGAT
GGAATGGCAATGTGTTTAGGATTACAAGCTGAGGCAAAAGTTGAATTAACAGAAATT
ATTGCTAAATTAGAAGAAAAAATGAAAAATGCTACAGTCAGTACATTATTAACTTTG
TAA

BsiWI amino acid sequence (SEQ ID NO:186)

MTKVKELFGLNTSVKGTDWGKVVTEQHCPFLNKKCIKNRKSQAEIAIGTCTMSYGKV
SKDIIICPHRLLENRKIFIDCIHLLTMHEPGNELHVVSEVSIPGGNVDYFLVSAKDG
KVKDFVGIELQTMDTTGTVWPERERFLKDAGYSGYDKEAIDSDKSFGMNWKHTAKTI
LVQLHHKVKTFEHVNKKLVLVIQEPLIDYMKKEFSFSHVGNAKLGDPLHFHPYSLDT
REDNQLHLNLKTRLSTDSDGMAMCLGLQAEAKVELTEIIAKLEEKMKNATVSTLLTL

BspQI DNA sequence (SEQ ID NO:187)

ATGAGACGATTAGCAAAAAATTCACGGAACGACAGTTATTTAAGTAATAGGGATTAC
CAGGAAATCGTGAGGGAAAATACCACTACAATATCGTTTCCCTTAAAAGAAAAACAT
ACTCTGACTTTAACGAAAAAAATAGGGCTAAATCAGACTGCTGGATTCGGAGGATGG
TTTTTCCCTGATTCACCATGTTTATTAACAGTAACTGTACTATCCTCTTTCGGTACA
AAGGTAACTTCTAAAACCTTTAGCCTTTCTAAAGATTGGAATCGTGTTGGGCTTGCT
TGGATTAACGAGCATTCGAGTGACACCATAGCATTGTCCTAGAGTTTAGTGATGTGG
AAATAGTTCATACATGGGGACTTACATGTGATGTTTTTAATGTCCATGAATTAATTA
TTGATGCTATAGAAGATCAAAATAAACTAATAGACGTGCTAAATCAAGAACATTTAT
CTCCTGAAACATATTATTTAAACCATGACTCTGATACTGATTTAATTGAGAATTTGG
AATCTACAGAAGAGATAAAGATAGTTAACCAAAGCCAAAAGCAAATCTCTTTAAAAA
AATGCTGTTATTGTCAACGTTATATGCCTGTGAACATATTAGTTCGTTCAAATTCAT
CATTTCATAAACACAAGAGTAAGAAAACTGGTTTTCAAAATGAATGTCGGGCTTGTA

Figure 2-58

AGAAGTGGAGAATAAATAATTCATTCAATCCAGTCAGAACAAAAGACCAACTACATG
AATCAGCAGTTATTACACGTGAAAAAAAAATATTACTTAAAGAACCTGAAATATTAC
AGAAAATCAAAAATAGAAATAACGGTGAGGGCTTAAAAAGTATTATATGGAAAAAAT
TTGATAAAAAATGCTTTAATTGTGAAAAAGAATTAACCATTGAAGAGGTACGCCTAG
ACCATACAAGACCACTTGCTTATCTGTGGCCTATCGATGAACACGCAACTTGTTTAT
GTGAAAAATGCAACAATACAAAACATGATATGTTTCCTATCGATTTTTATCAAGGGG
ACGAAGACAAATTAAGACGTTTAGCTAGAATTACGGGGTTAGATTATGAATCTCTAG
TTAAGAGGGACGTAAATGAAGTTGAACTTGCAAGAATAATCAATAACATTGAAGACT
TTGCAACTAATGTAGAGGCACGTACTTTTCGCTCAATAAGAAATAAAGTAAAAGAAG
TACGTCCCGATACTGACCTATTTGAAATTCTTAAATCTAAAAATATTAATTTATATA
ATGAACTTCAATATGAACTTCTTACCCGTAAGGATTAA

BspQI amino acid sequence (SEQ ID NO:188)

MRRLAKNSRNDSYLSNRDYQEIVRENTTTISFPLKEKHTLTLTKKIGLNQTAGFGGW
FFPDSPCLLTVTVLSSFGTKVTSKTFSLSKDWNRVGLAWINEHSSDTMSIVLEFSDV
EIVHTWGLTCDVFNVHELIIDAIEDQNKLIDVLNQEHLSPETYYLNHDSDTDLIENL
ESTEEIKIVNQSQKQISLKKCCYCQRYMPVNILVRSNSSFHKHKSKKTGFQNECRAC
KKWRINNSFNPVRTKDQLHESAVITREKKILLKEPEILQKIKNRNNGEGLKSIIWKK
FDKKCFNCEKELTIEEVRLDHTRPLAYLWPIDEHATCLCEKCNNTKHDMFPIDFYQG
DEDKLRRLARITGLDYESLVKRDVNEVELARIINNIEDFATNVEARTFRSIRNKVKE
VRPDTDLFEILKSKNINLYNELQYELLTRKD

Figure 3-1

| Enzyme | x= 10 | 9 | 8 | 7 | 6 | 5 | 4 | 3 | 2 | 1 | Length of amino acid sequence |
|---|---|---|---|---|---|---|---|---|---|---|---|
| Acc65I | 1 | 1 | 1 | 1 | 1 | 1 | 1 | 1 | 1 | 1 | 539 |
| AciI | 0 | 0 | 0 | 0 | 0 | 0 | 0 | 0 | 3 | 17 | 529 |
| AclI | 0 | 0 | 0 | 0 | 0 | 0 | 0 | 0 | 0 | 0 | 323 |
| AflII | 0 | 0 | 0 | 0 | 0 | 0 | 0 | 0 | 0 | 0 | 310 |
| AflIII | 1 | 1 | 1 | 1 | 1 | 1 | 1 | 1 | 1 | 1 | 233 |
| ApaI | 0 | 0 | 0 | 0 | 0 | 0 | 0 | 0 | 0 | 0 | 355 |
| ApoI | 0 | 0 | 0 | 0 | 1 | 1 | 6 | 6 | 6 | 6 | 237 |
| AscI | 1 | 1 | 1 | 1 | 1 | 1 | 1 | 1 | 1 | 1 | 455 |
| AseI | 0 | 0 | 0 | 0 | 0 | 0 | 0 | 0 | 0 | 0 | 244 |
| AspCNI | 6 | 6 | 6 | 6 | 6 | 7 | 7 | 9 | 12 | 15 | 334 |
| AvrII | 1 | 1 | 1 | 1 | 1 | 1 | 1 | 1 | 1 | 2 | 358 |
| BbvCIA | 3 | 3 | 3 | 3 | 3 | 3 | 4 | 6 | 7 | 7 | 275 |
| BbvCIB | 6 | 6 | 6 | 6 | 6 | 7 | 7 | 10 | 10 | 10 | 285 |
| BbvI | 2 | 2 | 2 | 2 | 2 | 2 | 3 | 3 | 5 | 14 | 539 |
| BccI | 13 | 14 | 15 | 15 | 15 | 16 | 16 | 17 | 17 | 18 | 535 |
| BceAI | 2 | 2 | 2 | 2 | 2 | 2 | 3 | 3 | 4 | 6 | 591 |
| BclI | 2 | 2 | 2 | 2 | 2 | 2 | 2 | 2 | 2 | 2 | 285 |
| BfaIA | 2 | 2 | 2 | 2 | 2 | 2 | 2 | 2 | 2 | 2 | 205 |
| BfaIB | 2 | 2 | 2 | 2 | 2 | 2 | 2 | 2 | 2 | 3 | 196 |
| BfuAI | 0 | 0 | 0 | 0 | 0 | 0 | 0 | 0 | 0 | 0 | 486 |
| BlpI | 7 | 7 | 8 | 10 | 10 | 10 | 10 | 10 | 11 | 12 | 289 |
| BmrI | 2 | 2 | 2 | 2 | 2 | 2 | 2 | 2 | 2 | 3 | 358 |
| BsaAI | 1 | 1 | 1 | 1 | 1 | 1 | 1 | 1 | 1 | 1 | 260 |
| BsaJI | 4 | 4 | 4 | 4 | 4 | 4 | 4 | 4 | 4 | 4 | 307 |
| BscGI | 0 | 0 | 0 | 0 | 0 | 0 | 0 | 0 | 4 | 8 | 457 |
| BseYIA | 0 | 0 | 0 | 0 | 0 | 0 | 0 | 0 | 0 | 0 | 513 |
| BseYIB | 0 | 0 | 0 | 0 | 0 | 0 | 0 | 0 | 0 | 0 | 322 |
| BsgI | 64 | 64 | 64 | 64 | 64 | 64 | 64 | 64 | 64 | 64 | 1035 |
| BsiWI | 4 | 4 | 4 | 4 | 4 | 6 | 7 | 8 | 8 | 8 | 285 |
| BsmFI | 1 | 1 | 1 | 1 | 1 | 2 | 5 | 12 | 21 | 51 | 879 |
| BspCNI | 2 | 3 | 4 | 5 | 10 | 13 | 20 | 31 | 61 | 64 | 918 |
| BspEI | 1 | 1 | 1 | 1 | 1 | 1 | 2 | 2 | 2 | 5 | 300 |
| BspHI | 0 | 0 | 0 | 0 | 0 | 0 | 1 | 2 | 2 | 8 | 381 |
| BspMI | 0 | 0 | 0 | 0 | 0 | 0 | 0 | 0 | 0 | 0 | 496 |
| BspQI | 3 | 3 | 3 | 3 | 3 | 3 | 3 | 3 | 4 | 5 | 429 |
| BsrBI | 0 | 0 | 0 | 0 | 0 | 0 | 0 | 0 | 0 | 1 | 437 |
| BsrI | 0 | 0 | 0 | 0 | 0 | 0 | 0 | 0 | 0 | 0 | 599 |
| BstEII | 0 | 0 | 0 | 0 | 0 | 0 | 0 | 0 | 0 | 3 | 288 |
| Bsu36I | 2 | 2 | 4 | 6 | 7 | 7 | 8 | 8 | 8 | 8 | 310 |
| BsuFI | 2 | 2 | 2 | 2 | 3 | 3 | 5 | 6 | 12 | 29 | 395 |
| BtsCI | 2 | 2 | 2 | 2 | 2 | 2 | 2 | 2 | 11 | 30 | 465 |
| BtsIA | 1 | 1 | 1 | 1 | 1 | 1 | 1 | 1 | 1 | 2 | 164 |
| BtsIB | 1 | 1 | 1 | 1 | 1 | 1 | 1 | 1 | 1 | 2 | 328 |
| Cac8I | 1 | 1 | 1 | 1 | 1 | 1 | 2 | 3 | 15 | 50 | 386 |
| ClaI | 1 | 1 | 1 | 1 | 1 | 1 | 1 | 1 | 2 | 4 | 359 |
| DraI | 0 | 0 | 0 | 0 | 0 | 0 | 0 | 0 | 0 | 0 | 384 |
| EagI | 1 | 1 | 1 | 2 | 2 | 4 | 6 | 7 | 7 | 10 | 301 |
| EarI | 3 | 3 | 3 | 3 | 3 | 3 | 3 | 3 | 3 | 3 | 334 |
| EcoNI | 0 | 0 | 0 | 0 | 0 | 0 | 0 | 0 | 1 | 3 | 197 |
| EsaBC3I | 0 | 0 | 0 | 0 | 0 | 0 | 0 | 0 | 0 | 0 | 231 |
| EsaBC4I | 3 | 3 | 3 | 3 | 3 | 4 | 4 | 4 | 4 | 7 | 348 |

Figure 3-2

| | | | | | | | | | | | |
|---|---|---|---|---|---|---|---|---|---|---|---|
| EsaBS9I | 2 | 2 | 2 | 2 | 2 | 2 | 2 | 2 | 2 | 2 | 236 |
| EsaDix6IP | 8 | 8 | 8 | 8 | 8 | 8 | 8 | 8 | 8 | 10 | 259 |
| EsaLHCI | 0 | 0 | 0 | 0 | 0 | 1 | 3 | 4 | 5 | 11 | 200 |
| EsaS1IP | 4 | 4 | 4 | 4 | 4 | 4 | 4 | 4 | 4 | 5 | 250 |
| Fnu4HI | 3 | 3 | 3 | 3 | 3 | 3 | 3 | 3 | 3 | 4 | 169 |
| FseI | 0 | 0 | 0 | 1 | 2 | 5 | 8 | 33 | 64 | 64 | 219 |
| FspI | 1 | 1 | 1 | 1 | 1 | 1 | 1 | 1 | 1 | 1 | 249 |
| HhaI | 0 | 0 | 0 | 0 | 0 | 0 | 0 | 0 | 0 | 0 | 238 |
| HinP1I | 5 | 5 | 5 | 5 | 5 | 5 | 5 | 5 | 5 | 9 | 247 |
| KasI | 0 | 0 | 0 | 0 | 0 | 0 | 0 | 0 | 0 | 0 | 285 |
| McaTI | 7 | 7 | 8 | 8 | 8 | 8 | 8 | 8 | 8 | 8 | 340 |
| MfeI | 2 | 2 | 2 | 2 | 2 | 2 | 2 | 2 | 2 | 2 | 202 |
| MluI | 0 | 0 | 0 | 0 | 0 | 0 | 0 | 0 | 0 | 0 | 276 |
| MmeII | 10 | 10 | 10 | 10 | 10 | 10 | 10 | 10 | 10 | 15 | 426 |
| MscI | 1 | 1 | 1 | 1 | 1 | 1 | 1 | 1 | 1 | 1 | 261 |
| NciI | 64 | 64 | 64 | 64 | 64 | 64 | 64 | 64 | 64 | 64 | 513 |
| NdeI | 2 | 2 | 2 | 2 | 3 | 3 | 4 | 5 | 11 | 24 | 368 |
| NgoMX | 64 | 64 | 64 | 64 | 64 | 64 | 64 | 64 | 64 | 64 | 979 |
| NruI | 0 | 0 | 0 | 0 | 0 | 0 | 0 | 0 | 0 | 0 | 219 |
| PacI | 0 | 0 | 0 | 0 | 0 | 1 | 2 | 2 | 2 | 2 | 142 |
| PflMI | 2 | 2 | 2 | 2 | 2 | 2 | 3 | 3 | 3 | 3 | 247 |
| PmeI | 0 | 0 | 0 | 0 | 0 | 0 | 0 | 0 | 0 | 0 | 231 |
| PshAI | 1 | 1 | 1 | 1 | 1 | 1 | 1 | 1 | 1 | 1 | 296 |
| PstII | 33 | 36 | 39 | 47 | 55 | 64 | 64 | 64 | 64 | 64 | 952 |
| PsuNI | 1 | 1 | 1 | 1 | 1 | 2 | 3 | 4 | 4 | 4 | 335 |
| R1.BsrDI | 0 | 0 | 0 | 0 | 0 | 0 | 0 | 0 | 0 | 1 | 488 |
| R2.BsrDI | 0 | 0 | 0 | 0 | 0 | 0 | 0 | 0 | 0 | 1 | 217 |
| SacII | 1 | 1 | 1 | 1 | 1 | 1 | 1 | 1 | 1 | 2 | 200 |
| Sbo13I | 0 | 0 | 0 | 0 | 0 | 0 | 0 | 0 | 0 | 0 | 224 |
| SfcI | 2 | 2 | 2 | 2 | 2 | 2 | 2 | 2 | 2 | 4 | 274 |
| SfoI | 0 | 0 | 0 | 0 | 0 | 0 | 0 | 0 | 0 | 0 | 187 |
| SpeI | 0 | 0 | 0 | 0 | 0 | 0 | 0 | 0 | 0 | 0 | 188 |
| StuI | 1 | 1 | 1 | 2 | 2 | 2 | 2 | 2 | 3 | 3 | 255 |
| StyI | 3 | 3 | 3 | 3 | 3 | 3 | 3 | 3 | 3 | 3 | 386 |
| TliI | 0 | 0 | 0 | 0 | 0 | 0 | 0 | 0 | 0 | 0 | 281 |
| TseI | 2 | 2 | 2 | 2 | 2 | 2 | 2 | 2 | 2 | 2 | 378 |
| Tsp509I | 0 | 0 | 0 | 0 | 0 | 0 | 0 | 0 | 0 | 0 | 284 |
| Tth111I | 0 | 0 | 0 | 0 | 0 | 0 | 0 | 0 | 1 | 5 | 319 |
| XhoII | 4 | 4 | 4 | 4 | 4 | 4 | 4 | 4 | 4 | 5 | 207 |

For each enzyme did the following steps:

1. GenBank's NR database (July, 2006 release) was queried with the enzyme's amino acid sequence using the BLAST program [1] with its low complexity filter turned off.
2. The first 64 hits were taken from BLAST's output and counted the number of hits with e-values lower than $10^{-x}$ (x=10, 9, ..., 1).

Reference:

1. BLASTP 2.2.10 [Oct-19-2004]
   Reference: Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

Figure 4A

```
                                                                      Score     E
Sequences producing significant alignments:                           (Bits)  Value

gi|27657790|gb|AAO18218.1|  Yga2E [Corynebacterium glutamicum]...      431    2e-119
gi|68248271|gb|EAN30354.1|  hypothetical protein Mmc1DRAFT_368...      242    1e-62

Sequences with E-value WORSE than threshold

gi|89286118|gb|EAR84121.1|  hypothetical protein TTHERM_007230...     37.0    0.94
gi|38570107|ref|NP_073622.2|  CAP-binding protein complex inte...     36.3    1.6
gi|8670820|emb|CAA71749.1|  CAP-binding protein complex intera...     36.3    1.7
```

Figure 4B

```
gi|27657790|gb|AAO18218.1| Gene info Yga2E [Corynebacterium glutamicum]
gi|27764619|ref|NP_776241.1| Gene info Yga2E [Corynebacterium glutamicum]
Length=306

Score = 431 bits (1108), Expect = 2e-119, Method: Composition-based stats.
Identities = 100/306 (32%), Positives = 160/306 (52%), Gaps = 41/306 (13%)

Query 1 MQPNPKFINKSSAFWAYAKLLSEQLGYSKDGVVISYSEAQARAKLKKLGINVKE------- 54
        M+  PK+IN+   FW Y +++S+ LGY++ G +  +          L++L ++V
Sbjct 1 MKAEPKWINRPPQFWHYVRVISQHLGYARKGEIYRHEPEAIERALRELELSVDALRLTPI 60

Query 55 -GI-FKDVLRYLKYRAELLNKH-KDYLMDVEEARKYFQVALK---------QHQQNNYTCK 103
          G+   ++  Y  +RA+L++       L +  EA+K F+  ++       ' Q +       +
Sbjct 61 FGLSVGELAEYFDFRADLIHGTIAANLQNASEAKKTFEQVVEKFTTGMTPQFKGGKENSR 120

Query 104 L------------PLNKQKNEKKDYAYFTCIINIIAETELRYFANNNGLVYGKDIYFDDNP 152
         L            P NKQK +K+D  + T   NI+    L Y+                FD +P
Sbjct 121 LYRVNGGVPVVVPYNKQKGDKRDIDFLTGTTNIL----LSYYLGGES---------FDQDP 168

Query 153 MNLSYILNFNRELEGIMSRRFDGAFPSTVNPILIWEIKEYYYTTTFGSRIADGVYETQLD 212
           L  ++  +  + G MSRR DGA+P +VNP  IWE K YYYTTTFGS+I+D VY T LD
Sbjct 169 RQLP-VVTEDGVVSGSMSRRMDGAYPDSVNPSAIWEFKCYYYTTTFGSKISDAVYITDLD 227

Query 213 GYEIKTIREETNKNIQHIYFIDDYNTWWNMGKSYLCRIIDMLHMGLVDEVIMGKEVFERW 272
         GYE   I + ++K +++  F+D Y+ +   G S+L R++DML  G VD ++ GKEV
Sbjct 228 GYERGEILKASHKRVENNVFLDAYSVFMEQGLSFLVRLVDMLQRGAVDNLVFGKEVLTAV 287

Query 273 PQILRA 278 (SEQ ID NO:189)
         P+I++
Sbjct 288 PEIVKG 293 (SEQ ID NO:190)

gi|68248271|gb|EAN30354.1| hypothetical protein Mmc1DRAFT_3688 [Magnetococcus sp. MC-1]
gi|69255906|ref|ZP_00605648.1| hypothetical protein Mmc1DRAFT_3688 [Magnetococcus sp. MC-
1]
Length=266
Score = 242 bits (618), Expect = 1e-62, Method: Composition-based stats.
Identities = 58/137 (42%), Positives = 79/137 (57%), Gaps = 3/137 (2%)

Query 144 KDIYFDDNPMNLSYILNFNRELEGIMSRRFDGAFPSTVNPILIWEIKEYYYTTTFGSRIA 203
          K I FD +P N     +N NR     + SR  DGA P   NP +IWEIKEY+  T   GS+++
Sbjct 133 KGIQFDFDPQNRCVWINDNRL--HVTSRNLDGAIPGLTNPEIIWEIKEYWGKTKGGSKMS 190

Query 204 DGVYETQLDGYEIKTIREETNKNIQHIYFIDDYNTWWNMGKSYLCRIIDMLHMGLVDEVI 263
          D VYE QL G E++   E+ NK I H  F+D +   W+  KS L R ID+   GL+D +
Sbjct 191 DAVYECQLVGRELREYEEKCNKKIMHFVFLDGKDQ-WSHRKSDLKRFIDLWCQGLIDTLF 249

Query 264 MGKEVFERWPQILRAVL 280 (SEQ ID NO:191)
          +GK+V   W + L  +L
Sbjct 250 VGKQVESLWEKTLEKLL 266 (SEQ ID NO:192)
```

Figure 4C

```
                                                                 Score    E
Sequences producing significant alignments:                      (Bits)  Value

gi|76260977|ref|ZP_00768602.1|  conserved hypothetical protein...  344    3e-93
gi|84686807|ref|ZP_01014694.1|  hypothetical protein RB2654_22...  337    4e-91
gi|67939563|ref|ZP_00532060.1|  hypothetical protein CphamnIDR...  328    3e-88
gi|78171892|gb|ABB28988.1|  hypothetical protein Cag_1737 [Chl...  299    9e-80
gi|89055379|ref|YP_510830.1|  hypothetical protein Jann_2888 [...  288    2e-76
gi|86211168|gb|ABC87270.1|  NotI restriction endonuclease [Nocard  286    6e-76
gi|56677682|gb|AAV94348.1|  hypothetical protein SPO1048 [Sili...  286    1e-75
gi|71901748|ref|ZP_00683819.1|  conserved hypothetical protein...  268    2e-70
gi|9105516|gb|AAF83450.1|  hypothetical protein XF_0640 [Xylel...  266    8e-70
gi|70779363|gb|AAZ08143.1|  ORF2 [Burkholderia cepacia]            266    1e-69
gi|78773885|gb|ABB51232.1|  unknown [Arthrospira platensis]        266    1e-69
gi|53688392|ref|ZP_00345702.1|  hypothetical protein Npun02002...  260    6e-68
gi|71491000|gb|EAO23340.1|  hypothetical protein SwolDRAFT_003...  222    1e-56
gi|67935692|ref|ZP_00528711.1|  hypothetical protein Cpha266DR...  211    3e-53

Sequences with E-value WORSE than threshold

gi|3660495|emb|CAA57707.1|  R.EcoHK31I protein [Escherichia coli]  43.8   0.008
gi|2760956|gb|AAB95338.1|  EaeI restriction endonuclease [Enterob  42.3   0.028
gi|89300400|gb|EAR98388.1|  cyclic nucleotide-binding domain c...  39.2   0.22
gi|21355217|ref|NP_651245.1|  CG5728-PA [Drosophila melanogast...  38.0   0.48
```

Figure 4D

```
gi|76260977|ref|ZP_00768602.1|  conserved hypothetical protein [Chloroflexus aurantiacus
J-10-fl]
gi|76164166|gb|EAO58321.1|  conserved hypothetical protein [Chloroflexus aurantiacus J-
10-fl]
Length=294

 Score =  344 bits (884),  Expect = 3e-93, Method: Composition-based stats.
 Identities = 64/305 (20%), Positives = 115/305 (37%), Gaps = 37/305 (12%)

Query  2    KKRRDLVEVFGYNPMDLSPEVRALWNLGACPFLN--KECIKINHDQTIIYGTCSVTSPYG  59
            + ++ L EVFGY   D S       +   CPF    ++C K   +  +  G C++
Sbjct  8    QTQQPLAEVFGYQITDQSEAAARCRSARLCPFQGQDRKCTKDKANNPL--GVCAIYHNNE  65

Query  60   DVIICPNRLYANDYETLHKVSRDAFGDDVPFLTYSNFIKYRATYKDCIVALGKNSGKEVQ  119
             VI CP R   N               D     +    ++    +   + L    GK
Sbjct  66   PVITCPIRFRQN----------WLIAQDAALFFFGEGTRWSILTE---IRLPDAFGK---  109

Query  120  VGRALSMDWVLVRITD-GELKEYVGVEIQSIDITGNYRDAWHAYKNLKP----IDIIDNL  174
               A ++D VLV   D G + ++  +EIQ++ I+GN R  +  Y          D I
Sbjct  110  --SAGNIDVVLVSYDDEGRITDFGAIEIQAVYISGNVRSFFEHYMRDPQGYIVGDWIGET  167

Query  175  PTSQHGLNWANVHKRLIPQIIRKGVVYSRSNYVKKGLYFILPEIVYNKFEDVIGADIPLL  234
            P  +     ++  KRL+PQ++ KG +    N   K +  ++ E  +     +
Sbjct  168  PVPRPDY-LSSSRKRLVPQLMYKGAILRAWN---KKMAVVVDEQFFQTLPQLASIP----  219

Query  235  KTQTNKSITVHTYSLGEPAANGEQRKLISE-REIIFDLDEFSKRFTTGPNLPKGDDLDAV  293
                N +  ++    G  A  G +R  + +  E+  D ++  +  TT     + +D
Sbjct  220  PQDANMAWFIYRLMPGRQAHEGTERYYLEKVTEVFTDFEQVIRVMTTSSPG-RSEDFIKF  278

Query  294  IKKAL  298 (SEQ ID NO:193)
            ++  L
Sbjct  279  LQAKL  283 (SEQ ID NO:194)
```

Figure 4D continued

```
>gi|84686807|ref|ZP_01014694.1| hypothetical protein RB2654_22558 [Rhodobacterales
bacterium HTCC2654]
gi|84665238|gb|EAQ11717.1| hypothetical protein RB2654_22558 [Rhodobacterales bacterium
HTCC2654]
Length=304

 Score = 337 bits (865), Expect = 4e-91, Method: Composition-based stats.
 Identities = 86/308 (27%), Positives = 146/308 (47%), Gaps = 25/308 (8%)

Query  7    LVEVFGYNPMDLSPEVRALWNLGACPFLNKECIKINHDQTIIYGTCSVTSPY-GDVIICP  65
            + E FGY   D S    +    +   CP    + C K  +D  ++ G C++        VI CP
Sbjct  5    IFEFFGYRADDRSDIAKHAADTEVCPISGETCQKSFND-GVVSGVCAIKPITSEPVICCP  63

Query  66   NRLYANDYETLHKVSRDAFGDDVPFLTYSNFIKYRATYKD-CIVALGKNSGKEVQVGR--  122
             RLYA+DY  L  ++    FG ++  +    + + Y    ++ C+   GK  G E+++ +
Sbjct  64   IRLYADDYRILSDIADRVFGPNLKLVAGRDAVNYSIDNREACVAVFGKGWGGELRLPQKS  123

Query  123  ---ALSMDWVLVRI-TDGELKEYVGVEIQSIDITGNYRDAWHAYKNLKPIDIIDNLPTSQ  178
                +DWVL +I   +G+L E+V VE+Q+ID TG YR  + A K    ++          +
Sbjct  124  KKGGYFVDWVLAKISEEGDLVEFVAVEVQTIDTTGTYRPGYDALKQDGLVE-------KTT  177

Query  179  HGLNWANVHKRLIPQIIRKGVVYSRSNYVKKGLYFILPEIVYNKFEDVIGADIPLLKTQT  238
             GLNW NV KR++PQ+I KG +   R     K GL+F+ PE V+ +  + +G     L++
Sbjct  178  AGLNWENVAKRILPQLIYKGQILQREELCKNGLFFVCPEPVFRRIMERLGGQEGLVRYAL  237

Query  239  N---KSITVHTYSLGEPAANGEQRKL---ISEREIIFDLDEFSKRFTTGPNLPKGDDLDA  292
                +  V+ Y          ++         L    ++       ++ + E       T     LP   +
Sbjct  238  QPASITFAVYDYDFSSEPSDETLVPLKNTLNHSTTVYKVQEAFNNVT-----LPIENVYRD  293

Query  293  VIKKALGM  300 (SEQ ID NO:195)
             I++ALG+
Sbjct  294  AIRRALGI  301 (SEQ ID NO:196)

>gi|67939563|ref|ZP_00532060.1| hypothetical protein Cphamn1DRAFT_2148 [Chlorobium
phaeobacteroides BS1]
 gi|67914217|gb|EAM63568.1| hypothetical protein Cphamn1DRAFT_2148 [Chlorobium
phaeobacteroides BS1]
Length=293

 Score = 328 bits (841), Expect = 3e-88, Method: Composition-based stats.
 Identities = 67/313 (21%), Positives = 117/313 (37%), Gaps = 55/313 (17%)

Query  2    KKRRDLVEVFGYNPMDLSPEVRALWNLGACPFLNK--ECIKINHDQTIIYGTCSVTSPYG  59
            K   + L EVFG+    D S         +    CPF NK    C K       +  G CS+
Sbjct  3    KNAQPLAEVFGHPVTDASSRADRYRSQRLCPFNNKVPNCTKDKAKSPL--GVCSIQHDGS  60

Query  60   DVIICPNRLYANDYETLHKVSRDAFGDDVPFLTYSNFIKYRATYKDCIVALGKNSGKEVQ  119
             VI CP R               DD       +      K+ +   +   + L     +GK
Sbjct  61   PVITCPIRFR-----------EDWLITDDAASFFFPEGTKWSSLTE---IRLNDGNGK---  104

Query  120  VGRALSMDWVLVRITD-GELKEYVGVEIQSIDITGNYRDAWHAYKNLKPIDIIDNLPTSQ  178
              A ++D VLV    D G++K++   +EIQ++  I+GN RD          P +       P  +
Sbjct  105  --SAGNIDIVLVAYDDNGKVKDFGALEIQAVYISGNVRD---------PFEYFMEEPKGR  153

Query  179  HGLNWAN------------VHKRLIPQIIRKGVVYSRSNYVKKGLYFILPEIVYNKFEDV  226
             ++W+N             KRL+PQ+  KG +         KK      L +  ++      +
Sbjct  154  AFMDWSNQPNYPRPDYLSSSRKRLVPQLFFKGGILHSW---KKKSAVALNKSFFDTLPPL  210

Query  227  IGADIPLLKTQTNKSITVHTYSLGEPAANGEQRKLISE-REIIFDLDEFSKRFTTGPNLP  285
                  + + + +  ++     L    A   +R   + +   E+   + +            TT
Sbjct  211  TTVS-----RKKADIAWLIYDIELCGSGAE--KRYRLKKVDEVFTEFEPALLSITTPVPG-  263

Query  286  KGDDLDAVIKKAL  298 (SEQ ID NO:197)
            + DD    +++   +
Sbjct  264  RIDDFMNMLQVKI  276 (SEQ ID NO:198)
```

Figure 4D continued

```
>gi|78171892|gb|ABB28988.1| Gene info hypothetical protein Cag_1737 [Chlorobium
chlorochromatii CaD3]
 gi|78189693|ref|YP_380031.1| Gene info hypothetical protein Cag_1737 [Chlorobium
chlorochromatii CaD3]
Length=498

 Score =  299 bits (767),  Expect = 9e-80, Method: Composition-based stats.
 Identities = 52/302 (17%), Positives = 109/302 (36%), Gaps = 56/302 (18%)

Query  6    DLVEVFGYNPMDLSPEVRALWNLGACPFLNK--ECIKINHDQTIIYGTCSVTSPYGDVII  63
             L EVFG+   D SP+ +    +    CPF NK    C    + +  +  G CS+        +I
Sbjct  228  PLGEVFGFAATDQSPKAQRYRSHRHCPFNNKSPNCTNSHTENPL--GVCSILHNNKAIIT  285

Query  64   CPNRLYANDYETLHKVSRDAFGDDVPFLTYSNFIKYRATYKDCIVALGKNSGKEVQVGRA  123
             CP R                    DD     +   +++ +        V L    +G        A
Sbjct  286  CPIRFR----------EDWLITDDAASFFFEPGVRWSSLTD---VRLADANG-----TSA  327

Query  124  LSMDWVLVRIT-DGELKEYVGVEIQSIDITGNYRDAWHAYKNLKPIDIIDNLPTSQHGLN  182
             +MD +LV     +G++ ++   ++IQ+  I GN R+              P +       P +     ++
Sbjct  328  GNMDVMLVAYDKEGKIIDFGAIQIQTAHIDGNVRE---------PFECYMKDPKTNAMMD  378

Query  183  W------------ANVHKRLIPQIIRKGVVYSRSNYVKKGLYFILPEIVYNKFEDVIGAD  230
     W             + +    ++P+++ KG +       N     K +    + + ++          +
Sbjct  379  WTRQPNYPEPDFLSAMRTSVVPELLYKGGILHSWN---KKMAIAINKSMFETLPPLTRV-  434

Query  231  IPLLKTQTNKSITVHTYSLGEPAANGE-QRKLISEREIIFD-LDEFSKRFTTGPNLPKGD  288
          K  + + +    ++             +GE  +     + + E+++               T                D
Sbjct  435  ---KKDEADIAWLLYELE---AVNDGEKEAYQLKKSEVVYTAFQPTLLALTAIAPGNVND  488

Query  289  DL  290 (SEQ ID NO:199)
             +
Sbjct  489  FM  490 (SEQ ID NO:200)

>gi|89055379|ref|YP_510830.1| Gene info hypothetical protein Jann_2888 [Jannaschia sp.
CCS1]
 gi|88864928|gb|ABD55805.1| Gene info conserved hypothetical protein [Jannaschia sp.
CCS1]
Length=341

 Score =  288 bits (739),  Expect = 2e-76, Method: Composition-based stats.
 Identities = 52/300 (17%), Positives = 94/300 (31%), Gaps = 49/300 (16%)

Query  18   LSPEVRALWNLGACPFLNK-----ECIKINHDQTIIYGTCSVTSPYGD--VI---------  62
             S    +           CPF                C K           G CS+         +  VI
Sbjct  69   RSKLAQQQAEELPCPFRTDSPHPTCTK--------PGGVCSIRIYREEAGVIAPIDGERGR  121

Query  63   ---ICPNRLYANDYETLHKVSRDAFGDDVPFLTYSNFIKYRATYKDCIVALGKNSGKEVQ  119
                +CP R +  D       K+        D  P                  + +      L     +G++V
Sbjct  122  LRALCPWRFHQ-DGTAFDKIGESLLADPSPLRAGEVG-------FLESTGNLDSAAGEDV-  173

Query  120  VGRALSMDWVLVRIT--DGELKEYVGVEIQSIDITGNYRDAWHAYKNLKPIDIIDNLPTS  177
               +D +LV+    DG    ++V VE+Q++   +G            +    L          +
Sbjct  174  ----GRIDMILVKSNSVDGAPMDWVAVEVQAVYFSGKKMSIEFDHLKLTQGRLSMAQEKR  229

Query  178  QHGLNWANVHKRLIPQIIRKGVVYSRSNYVKKGLYFILPEIVYNKFEDVIGADIPLLKTQ  237
          +        + V KRL+PQ++ K       R          K +   ++        +         +
Sbjct  230  RPDYRSSGV-KRLMPQLLTKVPTLRRWG---KKMAVVVDAPFFYSMGKMERVPHLS---N  282

Query  238  TNKSITVHTYSLGEPAANGEQRKLISEREIIFDLDEFSKRFTTGPNLPKGDDLDAVIKKA  297
(SEQ ID NO:201)
             +      +   +      + AA G     +L          E          L+   +          T G    + +G            +   KA
Sbjct  283  ADIVWFLVDF---KQAAPGAPFQLEVVEEFYTTLESATLGLTGGVPVSQGAFEARITAKA  339
(SEQ ID NO:202)
```

Figure 4D continued

```
>gi|86211168|gb|ABC87270.1|  NotI restriction endonuclease [Nocardia otitidiscaviarum]
Length=383

 Score =  286 bits (734),  Expect = 6e-76, Method: Composition-based stats.
 Identities = 69/353 (19%), Positives = 120/353 (33%), Gaps = 68/353 (19%)

Query  7    LVEVFGYNPMDL---SPEVRALWNLGACPFL-------NKECIKINHDQTIIYGTCSVTSP  57
            + E FG+        +   R     G CPFL          C+K   + +     +V +
Sbjct  15   IAEFFGHRVYPEVVSTEAARNDQATGTCPFLTAAKLVETSCVKAETSRGVCVVNTAVDNE  74

Query  58   YGDVIICPNRLYANDYETLHKVSRDAFG-------------DDVPFLTYSNFI-KYRATYK  104
              D ++CPNR  A D   +   SR  FG              +       + I ++
Sbjct  75   RYDWLVCPNR--ALDPLFMSAASRKLFGYGPTEPLQFIAAPTLADQAVRDGIREWLDRGV  132

Query  105  DCIVALGKNSGKEVQVG------RALSMDWVLVRITD----GELKEYVGVEIQSIDITGNY  155
              +    +  G E+ +          S DW L +        ++K Y  +EIQ++D  G+Y
Sbjct  133  BVVAYFQEKLGGELSISKTDSSPEFSFDWTLAEVESIYPVPKIKRYGVLEIQTMDFHGSY  192

Query  156  RDAWHAYKNLKPIDIID-------------NLPTSQHGLNWANVHKRLIPQIIRKGVVYSR  203
            + A  A  ++  ++ ID              L     G N +NV KR   Q+  K  +
Sbjct  193  KHAVGAI-DIALVEGIDFHGWLPTPAGRAALSKKMEGPNLSNVFKRTFYQMAYKFALSGH  251

Query  204  SNYVKKGLYFILPEIVYNKFEDVIG-----------ADIPLLKTQTNKSITVHTYSLGEP  252
                  G  F +P+ V+   +   +              +   +  +  +  +  + L +P
Sbjct  252  QRCAGTG--FAIPQSVWKSWLRHLANPTLIDNGDGTFSLGDTRNDSENAW-IFVFEL-DP  307

Query  253  AANGEQRKLISEREIIFDLDEFSK-------RFTTGPNLPKGDDLDAVIKKAL  298
(SEQ ID NO:203)
              +   R L    EI  ++D           R   GP+ P     D V  + L
Sbjct  308  DTDASPRPLAPHLEIRVNVDTLIDLALRESPRAALGPSGPVATFTDKVEARML  360
(SEQ ID NO:204)


>gi|56677682|gb|AAV94348.1| Gene info hypothetical protein SPO1048 [Silicibacter pomeroyi
DSS-3]
 gi|56695945|ref|YP_166299.1| Gene info hypothetical protein SPO1048 [Silicibacter
pomeroyi DSS-3]
Length=341

 Score =  286 bits (732),  Expect = 1e-75, Method: Composition-based stats.
 Identities = 51/302 (16%), Positives = 94/302 (31%), Gaps = 49/302 (16%)

Query  18   LSPEVRALWNLGACPFL-----NKECIKINHDQTIIYGTCSVT------SPYGDVI-----  62
                 R       CPF      N  C K         G CS+       +    +
Sbjct  69   RDKLTRQQAEEIPCPFRPDTPNATCTK--------PGGVCSIRVYRGEKNRVEPITGERGR  121

Query  63   ---ICPNRLYANDYETLHKVSRDAFGDDVPFLTYSNFIKYRATYKDCIVALGKNSGKEVQ  119
               +CP R +  D +   +V +    D  P             + +    L  + G++V
Sbjct  122  LRALCPWRFHQ-DGKAFSEVGKRLLNDPDPIKAGEVG------FLESSGNLDSDPGEDV-  173

Query  120  VGRALSMDWVLVRIT--DGELKEYVGVEIQSIDITGNYRDAWHAYKNLKPIDIIDNLPTS  177
                  +D +LV+    +G   ++V VE+Q++  +G        +       I
Sbjct  174  ----GRIDMILVKSNGVEGAPMDWVAVEVQAVYFSGKKMSIEFDHLIKTQGKISMAREKR  229

Query  178  QHGLNWANVHKRLIPQIIRKGVVYSRSNYVKKGLYFILPEIVYNKFEDVIGADIPLLKTQ  237
            +     + V KRL+PQ+  K     R     K +  ++    +    ++
Sbjct  230  RPDYRSSGV-KRLMPQLQTKVPTLRRWG---KKMAVVVDAPFFYSMGEMARERDVS---N  282

Query  238  TNKSITVHTYSLGEPAANGEQRKLISEREIIFDLDEFSKRFTTGPNLPKGDDLDAVIKKA  297
             +    +  +   +   NG   KL    E    L+  +   T G  + +GD    +  K
Sbjct  283  ADIIWFLADF---KEDLNGGGFKLEIVEEFYTTLESATLGLTGGTPVSQGDFEARIRAKT  339

Query  298  LG  299 (SEQ ID NO:205)
             G
Sbjct  340  DG  341 (SEQ ID NO:206)
```

Figure 4D continued

```
>gi|71901748|ref|ZP_00683819.1| conserved hypothetical protein [Xylella fastidiosa Ann-
1]
 gi|71728488|gb|EAO30648.1| conserved hypothetical protein [Xylella fastidiosa Ann-1]
 gi|71274521|ref|ZP_00650809.1| conserved hypothetical protein [Xylella fastidiosa
Dixon]
 gi|71164253|gb|EAO13967.1| conserved hypothetical protein [Xylella fastidiosa Dixon]
Length=283

 Score = 268 bits (686), Expect = 2e-70, Method: Composition-based stats.
 Identities = 61/274 (22%), Positives = 104/274 (37%), Gaps = 51/274 (18%)

Query  7    LVEVFGYNPM----DLSPEVRALWNLGACPFLNKECIKINHDQT-IIYGTCSVTSPYGD-  60
            +VE+FG        D   E+         CPFL K C K+       I  G+C+V
Sbjct  4    VVELFGKAADAPGIDWQNEIADQQ----CPFLGKRCYKVRKSNPEISIGSCTVLYGREPE  59

Query  61   -VIICPNRLYANDYETLHKVSRDAFGDDVPFLTYSNFIKYRATYKDCIVALGKN-SGKEV  118
             +IICP RL                             I+     + DC+  L  +  G E+
Sbjct  60   PIIICPTRL-----------------------------IQRGQIFTDCLHLLTSHEPGNEL  91

Query  119  QVGRA------LSMDWVLVRITDGELKEYVGVEIQSIDITGNYRDAWHAYKNLKPIDIIDN  173
             +           S+D+VLV   +G+++++VG+E+Q++D TG                +   DN
Sbjct  92   HLVSEVTVPGGSIDYVLVSAKEGKVRDFVGIELQTLDTTGTVWPERQRLLKELGVARGDN  151

Query  174  LPTSQH--GLNWANVHKRLIPQIIRKGVVYSRSNYVKKGLYFILPEIVYNKFEDVIGADI  231
              S    G+NW     K ++ Q+   K    +      +V + L  ++ +               D
Sbjct  152  GEESDKSFGMNWKMTAKTILVQMHHKVQTFE---HVNRKLVLVVQDKFLAYMTKEFKFDH  208

Query  232  PLLKTQTNKSITVHTYSLGEPAANGEQRKLISER  265 (SEQ ID NO:207)
                      S+ +H+Y +    A +G  R  ++ R
Sbjct  209  MKNPAAVGDSMHLHSYRMAR-ADDGNFRLSMASR  241 (SEQ ID NO:208)

>gi|9105516|gb|AAF83450.1| Gene info hypothetical protein XF_0640 [Xylella fastidiosa
9a5c]
 gi|15837242|ref|NP_297930.1| Gene info hypothetical protein XF0640 [Xylella fastidiosa
9a5c]
Length=283

 Score = 266 bits (681), Expect = 9e-70, Method: Composition-based stats.
 Identities = 60/274 (21%), Positives = 103/274 (37%), Gaps = 51/274 (18%)

Query  7    LVEVFGYNPM----DLSPEVRALWNLGACPFLNKECIKINHDQT-IIYGTCSVTSPYGD-  60
            +VE+FG        D   E+         CPFL K C  +       I  G+C+V
Sbjct  4    VVELFGKAADAPGIDWQNEIADQQ----CPFLGKRCYNVRKSNPEISIGSCTVLYGREPE  59

Query  61   -VIICPNRLYANDYETLHKVSRDAFGDDVPFLTYSNFIKYRATYKDCIVALGKN-SGKEV  118
             +IICP RL                             I+     + DC+  L  +  G E+
Sbjct  60   PIIICPTRL-----------------------------IQRGQIFTDCLHLLTSHEPGNEL  91

Query  119  QVGRA------LSMDWVLVRITDGELKEYVGVEIQSIDITGNYRDAWHAYKNLKPIDIIDN  173
            +           S+D+VLV   +G+++++VG+E+Q++D TG                +   DN
Sbjct  92   HLVSEVTVPGGSIDYVLVSAKEGKVRDFVGIELQTLDTTGTVWPERQRLLKELGVARGDN  151

Query  174  LPTSQH--GLNWANVHKRLIPQIIRKGVVYSRSNYVKKGLYFILPEIVYNKFEDVIGADI  231
              S    G+NW     K ++ Q+   K    +      +V + L  ++ +               D
Sbjct  152  GEESDKSFGMNWKMTAKTILVQMHHKVQTFE---HVNRKLVLVVQDKFLAYMTKEFKFDH  208

Query  232  PLLKTQTNKSITVHTYSLGEPAANGEQRKLISER  265 (SEQ ID NO:209)
                      S+ +H+Y +    A +G  R  ++ R
Sbjct  209  MKNPAAVGDSMHLHSYRMAR-ADDGNFRLSMASR  241 (SEQ ID NO:210)
```

Figure 4D continued

```
>gi|70779363|gb|AAZ08143.1|  ORF2 [Burkholderia cepacia]
Length=355

 Score =  266 bits (680),  Expect = 1e-69, Method: Composition-based stats.
 Identities = 53/329 (16%), Positives = 99/329 (30%), Gaps = 69/329 (20%)

Query  7     LVEVFGYNPMDLSPEVRAL-----------WNLGACPFLNKE----CIKINHDQTIIYGT  51
             + E FG+N   LS E R                  CPF ++     C K         G
Sbjct  14    IGEWFGFNLTQLSGEERRQLAAEVLKPKKERTPQPCPFQARKTGAVCSKD-------GGV  66

Query  52    CSVT-------SPYGDVI-------------ICPNRLYANDYETLHKVSRDAFGDDVPFL  91
             CS+           G  +              CP R +                 D   +
Sbjct  67    CSLRLYSYNTHPDNGRAVGVPVEGKQGDLRATCPYRFHDELDVFKWVGETILGDPDPLLV  126

Query  92    TYSNFIKYRATYKDCIVALGKNSGKEVQVGRALSMDWVLVRITDGE--LKEYVGVEIQSI  149
                 F++  A+          + G +        +D VLV     +     +  +EIQ++
Sbjct  127   GEVGFLEAGAST--------DSEGGD----DVGRIDMVLVSSKTPKEAPMNWAALEIQAV  174

Query  150   DITGNYRDAWHAYKNLKPIDIIDNLPTSQHGLNWANVH-KRLIPQIIRKGVVYSRSNYVK  208
               +GN         N   +D +   P  +   ++ +   KRL+PQ+  K     R
Sbjct  175   YFSGNAMKGEFEAFNDDAVDWV-IFPAGRRRPDYRSSGPKRLMPQLQIKVPTLRRWG---  230

Query  209   KGLYFILPEIVYNKFEDVIGADIPLLKTQTNKSITVHTYSLGEPAANGEQRKLISEREI-  267
             K + ++    ++    ++            + +  +  +        G++R  I   E+
Sbjct  231   KKMAVVVDRAFFDSIGEMDNVADIS---NADIAWFIVRFE----EVEGQKRTRIVRDEVR  283

Query  268   IFDLDEFSKRFTTGPNLPKGDDLDAVIKK  296 (SEQ ID NO:211)
                L+   +  T G  +P       +  K
Sbjct  284   YTTLERSVEGLTGGKPVPLPVFETRITDK  312 (SEQ ID NO:212)


>gi|78773885|gb|ABB51232.1|  unknown [Arthrospira platensis]
Length=270

 Score =  266 bits (680),  Expect = 1e-69, Method: Composition-based stats.
 Identities = 59/264 (22%), Positives = 107/264 (40%), Gaps = 51/264 (19%)

Query  7     LVEVFGYN-----PMDLSPEVRALWNLGACPFLNKECIKINHDQT-IIYGTCSVTSPYG-  59
             ++E+FGY+      +D +  +R       CP+L + CIK+   Q  I  GTCSV
Sbjct  4     IIEIFGYSINQPEHIDWTSLIR----EQHCPYLQRRCIKVRKSQPDISIGTCSVIYGKNA  59

Query  60    -DVIICPNRLYANDYETLHKVSRDAFGDDVPFLTYSNFIKYRATYKDCIVALGKN-SGKE  117
               VIICP+RL                            ++ +  + DC+  L  +  G E
Sbjct  60    IPVIICPHRL----------------------------LERKQIFIDCLHLLTNHEPGNE  91

Query  118   VQVGRA-----LSMDWVLVRITDGELKEYVGVEIQSIDITGNYRDAWHAYKNLKPIDIID  172
             + +         ++D+ LV   + ++K++VG+E+Q++D TG              +   D
Sbjct  92    LHLVSEISIPGGNVDYFLVSALNNKVKDFVGIELQTLDTTGTVWPERQRLLEELGVPTED  151

Query  173   NLPTSQH--GLNWANVHKRLIPQIIRKGVVYSRSNYVKKGLYFILPEIVYNKFEDVIGAD  230
             N   SQ   G+NW    K ++ Q+  K   +    ++ K L  ++ +   +  +
Sbjct  152   NQSQSQKTFGMNWKMTAKTILIQLHHKIETFE---HINKKLVLVIQDCFLDYIQREFSFS  208

Query  231   IPLLKTQTNKSITVHTYSLGEPAA  254 (SEQ ID NO:213)
                 + Q   S+ +H Y + E
Sbjct  209   HISHQAQLGDSMHIHAYQMTEQPD  232 (SEQ ID NO:214)
```

Figure 4D continued

```
>gi|53688392|ref|ZP_00345702.1|  hypothetical protein Npun02002587 [Nostoc punctiforme
PCC 73102]
Length=295

 Score =  260 bits (665),  Expect = 6e-68, Method: Composition-based stats.
 Identities = 49/259 (18%), Positives = 106/259 (40%), Gaps = 44/259 (16%)

Query  7     LVEVFGYNPMDLSPEVRALWNLGACPFLNKECIKINHDQT-IIYGTCSVTSPYG--DVII  63
             +VE++G NP + S     + +   CPFL+++C+K    +  +  G+C+V+      ++II
Sbjct  4     VVELYG-NPTNQSLIWSDIASSQNCPFLSRKCLKNRKSEPDLTIGSCTVSYGREARNIII  62

Query  64    CPNRLYANDYETLHKVSRDAFGDDVPFLTYSNFIKYRATYKDCIVALG-KNSGKEVQVGR  122
             CP RL                            ++    + DCI  L     G E+++
Sbjct  63    CPFRL----------------------------LERSQIFTDCIHLLTLHEPGNELRIVP  94

Query  123   A-----LSMDWVLVRITDGELKEYVGVEIQSIDITGNYRDAWHAYKNLKPIDI--IDNLP  175
                    S+D+ L  +  G++ +++ +E+Q++D TG        +     + +  +D
Sbjct  95    EIAVPGGSIDYCLASVRSGKVIDFISIELQTLDTTGTVWPERQRFLQRHGVSVRDVDVAS  154

Query  176   TSQHGLNWANVHKRLIPQIIRKGVVYSRSNYVKKGLYFILPEIVYNKFEDVIGADIPLLK  235
                 G+NW    K ++ Q+  K   +    ++ K L  ++ + + +  +     +
Sbjct  155   GKGFGMNWKMTAKTILMQLHHKIHTFE---HLSKHLVLVVQDCLIDYMQREFSFEHI-QD  210

Query  236   TQTNKSITVHTYSLGEPAA  254 (SEQ ID NO:215)
              +    +  H+Y L   A+
Sbjct  211   ARLGNPMHFHSYELLTEAS  229 (SEQ ID NO:216)

>gi|71491000|gb|EAO23340.1|  hypothetical protein SwolDRAFT_0030 [Syntrophomonas wolfei
subsp.
wolfei str. Goettingen]
 gi|71542547|ref|ZP_00664130.1|  hypothetical protein SwolDRAFT_0030 [Syntrophomonas
wolfei str.
Goettingen]
Length=223

 Score =  222 bits (568),  Expect = 1e-56, Method: Composition-based stats.
 Identities = 44/221 (19%), Positives = 82/221 (37%), Gaps = 25/221 (11%)

Query  83    AFGDDVPFLTYSNFIKYRATYKDCIVALGKNSGKEVQVGRALSMDWVLVRITD-GELKEY  141
                 D     +S   K+    +   V L   +G       A ++D VLV   D G++ ++
Sbjct  1     MVTIDAASFFFSPGTKWTTLTE---VRLNDINGH-----TAGNIDIVLVAYDDYGKITDF  52

Query  142   VGVEIQSIDITGNYRDAWHAYKNLKPI----DIIDNLPTSQHGLNWANVHKRLIPQIIRK  197
               +EIQS+ I+GN R  + AY     +    D +      +     ++  KRL+PQ+I K
Sbjct  53    GALEIQSVYISGNIRRPFEAYIQEPELMYNMDWLSKPNYPRPDY-LSSSRKRLVPQLIYK  111

Query  198   GVVYSRSNYVKKGLYFILPEIVYNKFEDVIGADIPLLKTQTNKSITVHTYSLGEPAANGE  257
             G + +      K +   L   ++     +          +   +  ++   L +
Sbjct  112   GKILNVW---SKKIAVALHSGFFSTLPQLPRVS----ADKAEIAWLIYDIELKQE----T  160

Query  258   QRKLISEREIIFDLDEFSKRFTTGPNLPKGDDLDAVIKKAL  298 (SEQ ID NO:217)
              R  +   + I+ L + S      P     DD   V++  L
Sbjct  161   NRYNLVHTDTIYTLFQNSLDRIVTPESGLIDDFIEVLQGKL  201 (SEQ ID NO:218)
```

Figure 4D continued

```
>gi|67935692|ref|ZP_00528711.1|  hypothetical protein Cpha266DRAFT_1693 [Chlorobium
phaeobacteroides
DSM 266]
 gi|67775417|gb|EAM35084.1|  hypothetical protein Cpha266DRAFT_1693 [Chlorobium
phaeobacteroides
DSM 266]
Length=258

 Score =  211 bits (538),  Expect = 3e-53, Method: Composition-based stats.
 Identities = 41/218 (18%), Positives = 81/218 (37%), Gaps = 40/218 (18%)

Query  83    AFGDDVPFLTYSNFIKYRATYKDCIVALGKNSGKEVQVGRALSMDWVLVRIT-DGELKEY  141
                DD      +     + +  +   V L    GK       A + D VLV     G++ ++
Sbjct  1     MITDDAASFFFDESTTWSSLTE---VRLNDAYGK------SAGNTDVVLVAYDKTGKVIDF  52

Query  142   VGVEIQSIDITGNYRDAWHAYKNLKPIDIIDNLPTSQHGLNW-------------ANVHKR  189
                +EIQ++ I+GN R+         P +     P +   +NW             ++  KR
Sbjct  53    GALEIQAVYISGNVRE----------PFEQFMKEPETHENMNWTTQPNYPRPDYLSSSRKR  103

Query  190   LIPQIIRKGVVYSRSNYVKKGLYFILPEIVYNKFEDVIGADIPLLKTQTNKSITVHTYSL  249
              L PQ++ KG +     N  KK       + +  ++         +     K++    +  V+    L
Sbjct  104   LAPQLLFKGGIL---NIRKKKTAVAINKSFFDTLPSFKQVE----KSKATIAWIVYDLEL  156

Query  250   GEPAANGEQRKLISE-REIIFDLDEFSKRFTTGPNLPK  286 (SEQ ID NO:219)
               +    +G +R  + +  E+  + +       TT     +
Sbjct  157   SDE-DGLERYHLKKIDEVYTEFEPALVAITTATPGKR (SEQ ID NO:220)
```

RESTRICTION ENDONUCLEASES, DNA ENCODING THESE ENDONUCLEASES AND METHODS FOR INDENTIFYING NEW ENDONUCLEASES WITH THE SAME OR VARIED SPECIFICITY

CROSS REFERENCE

This application is a divisional of U.S. application Ser. No. 11/997,614, filed on Feb. 1, 2008 which is a §371 application of international application number PCT/US2006/030419 filed on Aug. 3, 2006, which claims priority from U.S. provisional application No. 60/705,504 filed on Aug. 4, 2005, herein incorporated by reference.

BACKGROUND

Restriction endonucleases are enzymes that occur naturally in certain unicellular microbes—mainly bacteria and archaea—and that function to protect those organisms from infections by viruses and other parasitic DNA elements. These enzymes bind to specific sequences of nucleotides ('recognition sequence') in double-stranded DNA molecules (dsDNA) and cleave the DNA, usually within or close to the recognition sequence, disrupting the DNA and triggering its destruction. Restriction endonucleases commonly occur with one or more companion enzymes termed modification DNA methyltransferases. DNA methyltransferases bind to the same sequences in dsDNA as the restriction endonucleases they accompany, but instead of cleaving the DNA, they alter it by the addition of a methyl group to one of the bases within the sequence. This modification ('methylation') prevents the restriction endonuclease from binding to that site thereafter, rendering the site resistant to cleavage. Methyltransferases function as cellular antidotes to the restriction endonucleases they accompany, protecting the cell's own DNA from destruction by its restriction endonucleases. Together, a restriction endonuclease and its companion modification methyltransferase(s) form a restriction-modification (R-M) system, an enzymatic partnership that accomplishes for microbes what the immune system accomplishes, in some respects, for multicellular organisms.

A large and varied class of restriction endonucleases has been classified as 'Type II' class of restriction endonucleases. These enzymes cleave DNA at defined positions, and when purified can be used to cut DNA molecules into precise fragments for gene cloning and analysis.

New Type II restriction endonucleases can be discovered by a number of methods. The traditional approach to screening for restriction endonucleases, pioneered by Roberts et al. and others in the early to mid 1970's (e.g. Smith, H. O. and Wilcox, K. W., *J. Mol. Biol.* 51:379-391 (1970); Kelly, T. J. Jr. and Smith, H. O., *J. Mol. Biol.* 51:393-409, (1970); Middleton, J. H. et al., *J. Virol.* 10:42-50 (1972); and Roberts, R. J. et al., *J. Mol. Biol.* 91:121-123, (1975)), was to grow small cultures of individual strains, prepare cell extracts and then test the crude cell extracts for their ability to produce specific fragments on small DNA molecules (see Schildkraut, I. S., "Screening for and Characterizing Restriction Endonucleases", in Genetic Engineering, Principles and Methods, Vol. 6, pp. 117-140, Plenum Press, NY, N.Y. (1984)). Using this approach, about 12,000 strains have been screened worldwide to yield the current harvest of almost 3,600 restriction endonucleases (Roberts, R. J. et al., *Nucl. Acids. Res.* 33:D230-D232 (2005)). Roughly, one in four of all strains examined, using a biochemical approach, show the presence of a Type II restriction enzyme.

An in silico screening technique to identify restriction-modification systems has also been described and has been successfully used to identify novel restriction endonucleases (US-2004-0137576-A1). This method relies on identifying new methylases by their consensus sequences. Methylases have much more conservation of amino acid sequence, because they all must bind the methyl donor cofactor S-adenosyl methionine (SAM) and bind the nucleotide to be methylated, either an adenine or a cytosine base, and then perform the methyl transfer chemistry. Although there are several classes of methyltransferases, there are many sequenced examples of methylases and these have well conserved motifs that can be used to identify a protein sequence in a database as a methylase. In this method, identifying restriction endonucleases relies on testing any or all open reading frame (ORF) protein sequences located near the identified methylases.

Since the various Type II restriction enzymes appear to perform similar biological roles and share the biochemistry of causing dsDNA breaks, it might be thought that they would closely resemble one another in amino acid sequence. Experience shows this not to be true, however. Surprisingly, far from sharing significant amino acid similarity with one another, most enzymes appear unique, with their amino acid sequences resembling neither other restriction enzymes nor any other known proteins. Thus the Type II restriction endonucleases seem either to have arisen independently of each other during evolution or to be evolving very rapidly thereby losing apparent sequence similarity, so that today's enzymes represent a heterogeneous collection rather than one or a few distinct families.

Restriction endonucleases are biochemically diverse in their function: some act as homodimers, some as monomers, others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins; at other times they are fused. The orders and orientations of restriction and modification genes vary, with all possible organizations occurring. Given this great diversity among restriction endonucleases, it is perhaps not surprising that it has not been possible to form consensus sequences that can be used for in silico searches that are able to identify Type II restriction endonucleases, as has been successfully done for DNA methyltransferases. Thus there is no general common amino acid sequence motif(s) that can be used to identify restriction endonucleases from translated raw DNA sequence ab initio.

Although restriction endonucleases lack conserved sequence motifs and generally have highly diverged DNA and amino acid sequences, some restriction endonucleases are in fact related to one another and, though they may diverge in function, these endonucleases or families of related endonucleases share significant sequence similarity with one another. The key to unlocking these families of endonucleases is to obtain the sequence of one of the members of the related enzymes; from this sequence the other members of the family can be identified. With the advent of whole genome sequencing, many prokaryotic DNA sequences, and from the DNA sequence many amino acid sequences, have become available. Thus there are many amino acid sequences in the database with no known function. This pool of sequences undoubtedly contains numerous restriction endonucleases.

The problem is how to identify which genes encode restriction endonucleases, and then how to characterize the function of these genes.

SUMMARY

In an embodiment of the invention, a DNA segment encoding a restriction endonuclease and the corresponding amino acid sequence is described where the DNA has at least 90% sequence identity with a DNA sequence selected from SEQ ID NOS: 1, 3, 5, 7, 9, 11, 13, 15, 17, 19, 21, 23, 25, 27, 29, 31, 33, 35, 37, 39, 41, 43 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 157, 159, 161, 163, 165, 167, 169, 171, 173, 175, 177, 179, 181, 183, 185, and 187 or the amino acid sequence has at least 90% sequence identity with an amino acid sequence selected from SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 156, 158, 160, 162, 164, 166, 168, 170, 172, 174, 176, 178, 180, 182, 184, 186 and 188.

In an additional embodiment of the invention, an identified restriction endonuclease is provided which has an amino acid sequence identified by an Expectation value of less than or equal to e−02 in a BLAST search when an amino acid sequence having at least 90% sequence identity to the amino acid sequences listed above is used for searching the database. In the context of the embodiments of the invention, "an" is not intended to be limited to "one."

In an additional embodiment of the invention, a method is provided for identifying a restriction endonuclease, that includes: (a) selecting one or more probes having at least 90% sequence identity to a sequence selected from SEQ ID NOS: 1-153 and 156-188; (b) comparing the one or more probes with a database of sequences by a sequence similarity analysis to identify a sequence match; and (c) identifying the restriction endonuclease from the sequence match.

Examples of a sequence similarity analysis include a BLAST search and a PSI Blast search using an expectation value, E of less than or equal to e−02 (E≤e−02).

The sequence similarity analysis may further include analyzing the expectation value assigned to a sequence match and the distribution of sequence similarity between the probe and the sequence match.

In another embodiment, the sequence similarity analysis utilizes sequence comparisons such that, where the amino acid sequence match is in a genome sequence within the database, a methyltransferase sequence adjacent to the restriction endonuclease sequence can be identified and characterized by sequence similarity analysis to provide information about the restriction endonuclease.

In another embodiment of the invention, the restriction endonuclease is further characterized by biochemistry to determine the recognition and cleavage sites for the restriction endonuclease. The functional characteristics of the restriction endonuclease may further be characterized by thermostability, pH range and optima, star activity, etc. using methodology described in the prior art.

In a further embodiment of the invention, a method for identifying a restriction endonuclease is provided that includes: (a) selecting one or more probes having at least 90% sequence identity to a known restriction endonuclease sequence; (b) comparing the one or more probes with a database of sequences by a sequence similarity analysis to identify a sequence match, wherein a sequence match is any sequence producing an expectation value, E≤e−02; and (c) identifying the restriction endonuclease from the sequence match.

DETAILED DESCRIPTION OF THE DRAWINGS

FIG. 1-1 to 1-6 shows a list of restriction enzymes and their respective recognition sequences.

FIG. 2-1 to 2-58 shows the DNA and amino acid sequences of the restriction enzymes listed in FIG. 1-1 to 1-6.

FIG. 3-1 to 3-2 shows the number of observed matches at Expectation values ranging from E=e−01 to E=e−10 using targeting sequences selected from FIG. 2-1 to 2-58 in a sequence similarity analysis using the GENBANK non-redundant database and a BLAST similarity search.

For each enzyme, the following steps were performed:

1. GenBank's NR database (July, 2006 release) was queried with the enzyme's amino acid sequence using the BLAST program [1] with its low complexity filter turned off.
2. The first 64 hits were taken from BLAST's output and counted the number of hits with e-values lower than $10^{-x}$ (x=10, 9, . . . , 1).

REFERENCES

1. BLASTP 2.2.10 [Oct. 19, 2004]

Reference: Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402.

FIGS. 4A-4D provide a list of restriction endonucleases identified by PSI BLAST searches using BclI and EagI amino acid sequences.

FIG. 4A shows sequences with significant alignments to BclI.

FIG. 4B shows PSI-BLAST alignments between BclI, "query" sequence, and the restriction endonucleases identified, the "Sbjct" sequences. Identities and positives (similar amino acids) are shown between the query and subject sequences.

FIG. 4C shows PSI-BLAST significant alignments to EagI.

FIG. 4D shows PSI-BLAST alignments between EagI, "query" sequence, and the restriction endonucleases identified, the "Sbjct" sequences. Identities and positives (similar amino acids) are shown between the query and subject sequences.

DETAILED DESCRIPTION OF THE EMBODIMENTS

The amino acid sequences for a group of restriction enzymes are described herein for the first time. The use of these sequences and corresponding DNA sequences are described in a novel method for finding restriction endonucleases in a sequence database. Statistically significant sequence similarity between known restriction endonucleases and sequences in the database can reveal new and useful tools for molecular biology in the form of isochizomers, neoschizomers and restriction endonucleases with novel recognition sequences.

Embodiments of the method are based on finding at least a minimum amount of sequence similarity between an amino acid or DNA sequence in a sequence database and a probe. (A "probe" may refer to an amino acid sequence or significant portion thereof (or a DNA sequence or significant portion thereof) of the specified restriction endonuclease). The identified sequence having similarity to a probe may be referred to as "a sequence match". In one embodiment, the sequence match is assumed to be a restriction endonuclease if an expectation value requirement of E=e≤−02 is met. Analysis of sequence similarity between the probe and the sequence match indicates whether the newly identified restriction endonuclease is likely to be an isochizomer of a known restriction endonuclease, or a new restriction endonuclease recognizing and/or cleaving at a previously unknown site(s). In addition, the determination of the amino acid or DNA sequence similarity of any methyltransferase encoded by a DNA sequence that is located at an adjacent site on a genome to a gene encoding the newly identified restriction endonuclease can assist in classifying the restriction endonuclease. Confirmation of the recognition and cleavage sites of a restriction endonuclease identified by sequence similarity analysis can be achieved by biochemistry methods described herein as well as the biochemical properties of the enzyme such as pH and heat sensitivity.

In silico screening has established that similarity occurs between restriction enzyme gene sequences only when the two enzymes are related to one another. Such related restriction endonucleases may be isoschizomers; i.e. they recognize exactly the same sequence and cut at the same position, but come from different microorganisms (e.g. Lubys, A. et al., *Gene* 141:85-89 (1994); Withers, B. E. et al., *Nucl. Acids. Res.* 20:6267-6273 (1992)); have related recognition sequences (i.e., they recognize sequences that may be subsets of each other (e.g. HincII GTYRAC and MjaIV GTNNAC (US-2004-0137576-A1)) or share several common nucleotides (e.g., BsaI GGTCTC and BsmBI CGTCTC), or have similar catalytic properties but recognize different DNA sequences, such as MmeI [TCCRACN20/N18 (SEQ ID NO:154)] and CstMI [AAGGAGN20/N18 (SEQ ID NO:155)].

Although restriction endonucleases cannot be identified from common sequence motifs, a method is provided herein to search a sequence database for significant matches (sequence matches) to sequences of specified restriction endonucleases (probes). It is anticipated that sequence matches and probes may be derived from a common ancestor. Some of the sequence matches may be isoschizomers. However probes can be used to successfully identify novel restriction endonucleases that recognize and/or cleave DNA sequences that are different from that recognized and/or cleaved by the probes, and which may be novel DNA recognition sequences. In principle, any amino acid sequence of a restriction endonuclease having at least 90% identity with a sequence of a specified restriction endonuclease can be tested in databases to discover previously unknown restriction endonucleases. A limitation on discovery of novel restriction endonucleases in sequence databases is thus the availability of probes.

The likelihood that a sequence identified by this method will in fact be a restriction endonuclease depends on the choice of the level of statistical significance used for the identification of restriction endonuclease candidates; i.e. a less stringent threshold of statistical significance will result in more false positive hits (sequences that are not restriction endonucleases), but will include those restriction endonucleases (true positives) that are more highly diverged from the known restriction endonuclease and thus perhaps more likely to have a different recognition sequence or different biochemical characteristics. Conversely, a more stringent threshold will insure that most or all of the hits are restriction endonuclease genes (few false positives), but will likely exclude some restriction endonucleases (false negatives) having relatively less sequence similarity. Thus, selection of the probability functions determines the stringency of the selection and the likelihood that candidate sequences identified are in fact restriction endonucleases. We use the Expectation value of the BLAST program to set the cutoff for finding restriction endonucleases. When the Expectation value is E=e−02 or less, the sequence match can be predictably identified as a restriction endonuclease. Close proximity to a methylase is further confirmation that the sequence is an endonuclease, and the methylase can be used to protect host cells when expressing the potential endonuclease in a new host.

The specified amino acid and nucleic acid sequences for the restriction endonucleases provided in FIG. 2-1 to 2-58 are previously unknown and result from the cloning and sequencing of these restriction endonucleases, along with, in most cases, their methyltransferase(s) using biochemical methods. Biochemical methods for obtaining purified restriction enzymes and their sequences include the methylase selection method (see U.S. Pat. No. 5,179,015, U.S. Pat. No. 5,137,823, U.S. Pat. No. 5,180,673, U.S. Pat. No. 5,200,333, U.S. Pat. No. 5,320,957), while specific examples of cloning and/or purification for individual restriction endonucleases are U.S. Pat. No. 5,405,768, U.S. Pat. No. 5,004,691, U.S. Pat. No. 5,030,569, U.S. Pat. No. 5,366,882, U.S. Pat. No. 5,137,823, U.S. Pat. No. 5,198,354, U.S. Pat. No. 5,434,068, U.S. Pat. No. 5,354,680, U.S. Pat. No. 4,996,151, U.S. Pat. No. 4,999,294, U.S. Pat. No. 5,196,332, U.S. Pat. No. 4,987,074, U.S. Pat. No. 4,999,293, U.S. Pat. No. RE: 35,248, U.S. Pat. No. 5,215,906, U.S. Pat. No. 4,983,522, U.S. Pat. No. 5,298,404, U.S. Pat. No. 5,147,794, U.S. Pat. No. 5,196,331, U.S. Pat. No. 5,053,330, U.S. Pat. No. 5,292,651, U.S. Pat. No. 5,202,248, U.S. Pat. No. 5,139,942, U.S. Pat. No. 5,278,060, U.S. Pat. No. 5,075,232, U.S. Pat. No. 5,371,006, U.S. Pat. No. 5,288,696, U.S. Pat. No. 5,637,476, U.S. Pat. No. 5,262,318, U.S. Pat. No. 5,296,371, U.S. Pat. No. 5,208,157, U.S. Pat. No. 4,983,542, U.S. Pat. No. 5,002,882, U.S. Pat. No. 5,516,678, U.S. Pat. No. 5,543,308, U.S. Pat. No. 5,532,153, U.S. Pat. No. 5,731,185, U.S. Pat. No. 5,616,484, U.S. Pat. No. 5,721,126, U.S. Pat. No. 5,824,529, U.S. Pat. No. 5,663,067, U.S. Pat. No. 5,786,195, U.S. Pat. No. 5,945,326, U.S. Pat. No. 5,849,558, U.S. Pat. No. 5,866,422, U.S. Pat. No. 5,866,398, U.S. Pat. No. 5,945,288, U.S. Pat. No. 5,885,818, U.S. Pat. No. 6,004,793, U.S. Pat. No. 6,027,929, U.S. Pat. No. 6,025,179, U.S. Pat. No. 6,048,731, U.S. Pat. No. 6,258,583, U.S. Pat. No. 6,238,901, U.S. Pat. No. 6,130,078, U.S. Pat. No. 6,048,719, U.S. Pat. No. 6,133,008, U.S. Pat. No. 6,245,545, U.S. Pat. No. 6,066,487, U.S. Pat. No. 6,194,188, U.S. Pat. No. 6,133,009, U.S. Pat. No. 6,335,190, U.S. Pat. No. 6,403,354, U.S. Pat. No. 6,395,531, U.S. Pat. No. 6,391,608, U.S. Pat. No. 6,514,737, U.S. Pat. No. 6,764,843, U.S. Pat. No. 6,596,524, U.S. Pat. No. 6,593,122, U.S. Pat. No. 6,589,769, U.S. Pat. No. 6,586,220, U.S. Pat. No. 6,673,588, U.S. Pat. No. 6,723,546, U.S. Pat. No. 6,794,172, U.S. Pat. No. 6,869,786. Methods of sequencing are well known in the art.

In Silico Searching for Restriction Endonucleases

There is no characteristic consensus amino acid sequence for type II restriction enzymes that can be used to identify a new example from a database, even though all restriction endonucleases recognize and cleave dsDNA.

There is an "endonuclease motif" that many of the restriction endonucleases share, consisting of ((DIE) $X_{6-20}$ (D/E) XK). However, this motif does not contain enough specified sequence to be used for database searching (Anderson, J. E.; *Curr. Opin. Struct. Biol.* 3: 24-30 (1993)).

As illustrated in the Examples, candidate sequences that produce Expectation values of equal to or less than e−02 when compared to any of the restriction endonuclease sequences specified in this application are likely to be restriction endonucleases. Restriction endonucleases identified from sequence matches are likely to recognize the same or related DNA sequences as the specified endonuclease with which they share significant similarity. Nonetheless, enzymes thus identified may differ in useful ways from the known restriction endonuclease with which they share sequence similarity, including having different recognition sequences, different biochemical properties, such as reaction conditions, temperature optima, methylation sensitivity, etc., or other different characteristics from the previously known endonuclease. One example of isoschizomers, which have different properties, is an isochizomer of thermolabile SapI identified as BspQI, which is the thermostable.

Accordingly, sequence matches may correspond to restriction endonucleases that are isoschizomers, which recognize an identical sequence and cleave at the same position; neoschizomers, which recognize the same DNA sequence but cleave at a different position within the DNA; or restriction endonucleases that have similar but different recognition sequences. An example of the latter is BsaI, which produces a BLAST E-value of $e^{-66}$ (NR Genbank database) with BsmBI, yet differs subtly in the recognition sequence as follows:

| | |
|---|---|
| BsaI: | GGTCTC |
| BsmBI: | CGTCTC |

Although certain restriction enzymes listed in FIG. 1-1 to 1-6 have been identified from a variety of organisms and their recognition sequences determined, the DNA and amino acid sequences of these enzymes have not previously been obtained. These sequences are here provided in FIG. 2-1 to 2-58 and may be used not only for cloning the identified naturally occurring restriction enzymes, but also for discovering related enzymes using sequence databases such as GenBank (Benson et al., *Nucleic Acids Research* 32:D23-D26 (2004)) using a suitable search algorithm. Sequence similarity may be determined using in silico sequence matching programs such as BLAST ((web site: http://www.ncbi.nlm.nih.gov/BLAST/), Altschul, S. F., et al., *J. Mol. Biol.* 215:403-410 (1990) or Smith, T. F. and Waterman, M. S., *J. Mol. Biol.* 147(1): 195-7 (1981), or PSI-BLAST ((web site: http://www.ncbi.nlm.nih.gov/BLAST/), Altschul et al. *Nucleic Acids Res.* 25:3389-3402 (1997)) available in the art, or by in vitro biochemical assays such as Southern hybridization assays. An example of a search methodology is provided in Example I.

Significant sequence similarity between any one of the amino acid sequences or DNA sequences of the restriction endonuclease listed in FIG. 2-1 to 2-58 or more generally in REBASE (http://rebase.neb.com) and an unknown sequence in the database suggests that the unknown sequence is a restriction endonuclease also. Sequence similarity can be determined from alignment algorithms described above, where an Expectation value of less than e−02 is considered significant, and thus the sequence is a restriction endonuclease.

Any single alignment producing an Expectation value of less than e−02 between an amino acid sequence of FIG. 2-1 to 2-58 and an unknown sequence in the database, particularly where the unknown sequence does not appear to have sequence similarity with other sequences in the database, suggests a strong presumption that the unknown sequence is a restriction endonuclease (FIG. 3-1 to 3-2). When Expectation values are greater than e−02 but less than 2 between two sequences, the unknown sequence identified by the method may be presumed to be an endonuclease if there is additional supporting information, such as that the unknown sequence is located next to a methylase in its genome sequence context. The presence of a methylase gene adjacent or close to the unknown sequence identified by the method strengthens the likelihood that the unknown sequence is indeed an endonuclease.

DNA and amino acid sequences of specified restriction endonucleases and methylases provided in FIG. 2-1 to 2-58 are as follows.

AciI (SEQ ID NOS:1 and 2), AclI (SEQ ID NOS:3 and 4), AflII (SEQ ID NOS:5 and 6), AflIII (SEQ ID NOS:7 and 8), ApaI (SEQ ID NOS:9 and 10), ApoI (SEQ ID NOS:11 and 12), AscI (SEQ ID NOS:13 and 14), AseI (SEQ ID NOS:15 and 16), AspCNI (SEQ ID NOS:17 and 18), AvrII (SEQ ID NOS:19 and 20), BbvI (SEQ ID NOS:21 and 22), BbvCIA (SEQ ID NOS:23 and 24), BbvCIB (SEQ ID NOS:145 and 146), BccI (SEQ ID NOS:25 and 26), BceAI (SEQ ID NOS: 27 and 28), BclI (SEQ ID NOS:29 and 30), BfaIA (SEQ ID NOS:31 and 32), BfaIB (SEQ ID NOS:147 and 148), BfuAI (SEQ ID NOS:33 and 34), BlpI (SEQ ID NOS:35 and 36), BmrI (SEQ ID NOS:37 and 38), BsaJI (SEQ ID NOS:39 and 40), BscGI (SEQ ID NOS:41 and 42), BseYIA (SEQ ID NOS:43 and 44), BseYIB (SEQ ID NOS:87 and 88), BsgI (SEQ ID NOS:45 and 46), BspCNI (SEQ ID NOS:47 and 48), BspHI (SEQ ID NOS:49 and 50), BspMI (SEQ ID NOS:51 and 52), BsrBI (SEQ ID NOS:53 and 54), R1.BsrDI (SEQ ID NOS:55 and 56), R2.BsrDI (SEQ ID NOS:57 and 58), BsrI (SEQ ID NOS:59 and 60), BstEII (SEQ ID NOS:61 and 62), BsuFI (SEQ ID NOS:63 and 64), Bsu36I (SEQ ID NOS:65 and 66), Cac8I (SEQ ID NOS:67 and 68), ClaI (SEQ ID NOS:69 and 70), CviKI (SEQ ID NOS:71 and 72), DraI (SEQ ID NOS:73 and 74), EagI (SEQ ID NOS:75 and 76), EarI (SEQ ID NOS:77 and 78), EsaBC3I (SEQ ID NOS:79 and 80), EsaBC4I (SEQ ID NOS:81 and 82), EsaBS9I (SEQ ID NOS:83 and 84), EsaDix6IP (SEQ ID NOS:85 and 86), EsaLHCI (SEQ ID NOS:89 and 90), EsaS1IP (SEQ ID NOS:91 and 92), FseI (SEQ ID NOS:93 and 94), FspI (SEQ ID NOS: 95 and 96), HhaI (SEQ ID NOS:97 and 98), HinP1I (SEQ ID NOS:99 and 100), MfeI (SEQ ID NOS:101 and 102), MluI (SEQ ID NOS:103 and 104), MmeII (SEQ ID NOS:105 and 106), MscI (SEQ ID NOS:107 and 108), NdeI (SEQ ID NOS:109 and 110), NgoMX (SEQ ID NOS:111 and 112), NotI (SEQ ID NOS:113 and 114), PacI (SEQ ID NOS:115 and 116), PflMI (SEQ ID NOS:117 and 118), PmeI (SEQ ID NOS:119 and 120), PshAI (SEQ ID NOS:121 and 122), PstII (SEQ ID NOS:123 and 124), PsuNI (SEQ ID NOS:125 and 126), SacII (SEQ ID NOS:127 and 128), SfoI (SEQ ID NOS: 129 and 130), SpeI (SEQ ID NOS:131 and 132), TliI (SEQ ID NOS:133 and 134), TseI (SEQ ID NOS:135 and 136), Tsp509I (SEQ ID NOS:137 and 138), Tth111I (SEQ ID NOS:139 and 140), XcmI (SEQ ID NOS:141 and 142), XhoII (SEQ ID NOS:143 and 144), Acc65I (SEQ ID NOS:149 and 150), BsaAI (SEQ ID NOS:151 and 152), BsmFI (SEQ ID NOS:153 and 156), BspEI (SEQ ID NOS:157 and 158), BtsCI (SEQ ID NOS:159 and 160), BtsIA (SEQ ID NOS:161 and 162), BtsIB (SEQ ID NOS:163 and 164), EcoNI (SEQ ID NOS:165 and 166), Fnu4HI (SEQ ID NOS:167 and 168), KasI (SEQ ID NOS:169 and 170), McaTI (SEQ ID NOS:171 and 172), NciI (SEQ ID NOS:173 and 174), NruI (SEQ ID NOS:175 and 176), Sbo13I (SEQ ID NOS:177 and 178), SfcI (SEQ ID NOS:179 and 180), StuI (SEQ ID NOS:181 and 182), StyI (SEQ ID NOS:183 and 184), BsiWI (SEQ ID NOS:185 and 186), and BspQI (SEQ ID NOS:187 and 188).

All references described herein, as well as U.S. provisional application Ser. No. 60/705,504, are incorporated by reference. The examples are not intended to be limiting.

EXAMPLES

Example 1

Method of Identifying Potential Restriction Endonuclease Using the Sequences Provided in this Application The amino acid sequence of one of the known restriction endonucleases is used to perform a protein to protein (blastp) BLAST search, a protein to translated database (tblastn) BLAST search, or is used to perform a protein to protein PSI-BLAST iterative similarity search. For example, such a search may be performed through the NCBI web server: http://www.ncbi.nlm.nih.gov/blast/ selecting the blastp (or tblastn) program, and searching against the NR (non-redundant) database of "all organisms," using the standard preset values, which consist of Expect=10, word size=3, using the BLOSUM62 matrix and with gap costs of Existence=11, extension=1. The low complexity filter can be turned off for the search, as restriction endonucleases are prokaryotic proteins and generally do not contain repeats or regions of low complexity. These parameters can be varied by those skilled in the art to obtain slightly varied search results. The PSI-BLAST search can be performed for several iterations until convergence is achieved.

The output returned by the BLAST search is examined for sequences that give Expectation scores of less than or equal to e−02. These sequences are presumed to be restriction endonucleases.

The sequence context of the restriction endonucleases identified is examined to see if there is a DNA methyltransferase adjacent to or near (within one or two ORFs) the restriction endonuclease. The presence of such a methyltransferase is highly suggestive that the sequence identified using the known endonuclease sequence is an endonuclease.

The degree of similarity between the known endonuclease sequence (probe) and the sequence match can suggest whether the two sequences are isoschizomers (indicated by a high degree of similarity, for example E<e−50), or may recognize related but different sequences (indicated by a lesser degree of similarity, for example, e−10<E<e−02).

The sequence match is tested to see if it encodes a functional restriction endonuclease by any convenient methods of expressing protein from the sequence and testing that protein for endonucleolytic function, such as the methods described in Example 3. For example, the identified sequence may by amplified by PCR. The gene may then be expressed either in a cell-free in vitro transcription/translation system and the protein produced tested for endonuclease activity, or the gene may be introduced into a vector and cloned into a host cell, such as *E. coli*. The transformed host cells are then grown to allow the identified endonuclease gene to express protein, and a cell free lysate is prepared and tested for endonuclease activity.

Example 2

Search Results for Several of the Enzymes of this Application

A. The alignments produced by standard BLAST or PSI-BLAST is here used to predict whether a sequence match encodes or represents a newly identified restriction endonuclease and whether this restriction endonuclease is likely to have a similar substrate specificity or whether it is likely to recognize a different DNA sequence to that of the restriction endonuclease corresponding to the probe (specified restriction endonuclease). The level of sequence similarity between the probe and the sequence match and the distribution of the similarity can be used to predict whether two restriction endonucleases recognize the same or different sites on a DNA substrate. A sequence match with significant similarity to the probe spread throughout the sequences is likely to be an isoschizomer that recognizes the same DNA substrate as the specified restriction endonuclease, with the likelihood increasing as the level of similarity increases. However, a newly identified restriction endonuclease that shares significant similarity with the specified restriction endonuclease in only a portion of its sequence is less likely to be isoschizomer. In addition, a comparison of a methyltransferase encoded by a gene adjacent to the sequence match, if there is one, with methyltransferases of known DNA recognition specificity, can assist in this analysis. If the adjacent methyltransferase is most similar to methyltransferase(s) that recognize the same sequence as the specified restriction endonuclease, the likelihood that the two restriction endonucleases are isoschizomers is increased; however if the methyltransferase is most similar to methyltransferase(s) recognizing different sequences from the specified restriction endonuclease, then the likelihood that the identified restriction endonuclease differs from the recognition sequence of the specified restriction endonuclease is increased.

Results for searching using the BclI amino acid sequence on 25 Jul. 2006 (scores will change slightly as the size of the database increases, and new hits may be found as new sequences are added to the database daily). The BclI amino acid sequence from FIG. 2-1 to 2-58 was copied and pasted into the NCBI Blast web server at: http://www.ncbi/nlm.nih.gov/BLAST/ using the "Protein—protein BLAST (blastp) program. The default values for the search were used and the low complexity filter was turned off. The best scoring results are reported below:

| Sequences producing significant alignments: | Score (Bits) | E Value |
|---|---|---|
| gi \| 27657790 \| gb \| AAO18218.1 \| Yga2E [*Corynebacterium glutamicum*] . . . | 159 | 1e−37 |
| gi \| 68248271 \| gb \| EAN30354.1 \| hypothetical protein Mmc1DRAFT_368 . . . | 103 | 7e−21 |
| gi \| 110287792 \| sp \| Q29L39 \| POE_DROPS Proteinpurity of essence >g . . . | 36.2 | 1.6 |
| gi \| 90302769 \| gb \| EAS32400.1 \| hypothetical protein CIMG_03424 [Cocc | 35.0 | 3.8 |
| gi \| 89286118 \| gb \| EAR84121.1 \| hypothetical protein TTHERM_007230 . . . | 34.7 | 5.4 |
| gi \| 4426611 \| gb \| AAD20450.1 \| pushover [*Drosophila melanogaster*] | 34.3 | 6.9 |

The first two hits have E values of 1e−37 and 7e−21, both of which would indicate that these are highly likely to be restriction endonucleases. Note that the both sequences identified using BclI are reported as "hypothetical proteins," since without a sequence of a known endonuclease with which to identify these sequences, such as the BclI sequence specified in this application, the nature of these ORFs was not known. Both of these ORFs are adjacent to an ORF identified as a methyltransferase, which strengthens the case that they are endonucleases. These ORFs can be confirmed as endonucleases, and their characteristics determined, by the techniques described in Example 3. The third and subsequent hits are outside the threshold value of E value<e−02. Note the very sharp drop off in E value results between the two endonuclease hits and the next best scoring sequences, which are outside the level of significance for identifying endonucleases described herein.

Similar results are obtained using the PSI-BLAST program with the BclI sequence. PSI-BLAST is able to detect more distant similarities among protein sequences than standard BLAST. The expectation values produced after several iterations of PSI-BLAST are often smaller than the single pass results from standard BLAST. PSI-BLAST may detect restriction endonuclease candidate genes whose sequence is more distantly similar to the input restriction endonuclease sequence; however, PSI-BLAST errors may be amplified by the iteration process and so marginal hits with PSI-BLAST require more careful examination. A PSI-BLAST search with the BclI amino acid sequence yields the same two hits as the standard BLAST search, although the E values are now much smaller. The BclI amino acid sequence from FIG. 2-1 to 2-58 was copied and pasted into the NCBI Blast web server at: http://www.ncbi/nlm.nih.gov/BLAST/ using the PSI-BLAST program. The default values for the search were used. The best scoring results are reported below:

| | Score (Bits) | E Value |
|---|---|---|
| Sequences producing significant alignments: | | |
| gi \| 27657790 \| gb \| AAO18218.1 \| Yga2E [*Corynebacterium glutamicum*] . . . | 431 | 2e−119 |
| gi \| 68248271 \| gb \| EAN30354.1 \| hypothetical protein Mmc1DRAFT 368 . . . | 242 | 1e−62 |
| Sequences with E-value WORSE than threshold | | |
| gi \| 89286118 \| gb \| EAR84121.1 \| hypothetical protein TTHERM_007230 . . . | 37.0 | 0.93 |
| gi \| 38570107 \| ref \| NP_073622.2 \| CAP-binding protein complex inte . . . | 36.3 | 1.6 |
| gi \| 8670820 \| emb \| CAA71749.1 \| CAP-binding protein complex intera . . . | 36.3 | 1.7 |

Using the BclI sequence of FIG. 2-1 to 2-58 in the method described clearly identifies two restriction endonuclease genes.

The PSI-BLAST output returns the alignment that produced the E values given. This alignment may be used to predict whether the restriction endonuclease identified will be an isoschizomer of BclI or will recognize a differing sequence. Here the best scoring sequence, gi:27657790 Yga2E hypothetical protein has highly significant similarity (E=2e−119) that extends over nearly the entire sequence of BclI (from amino acids 1 to 277 out of a total length of 285 amino acids) and over nearly the entire length of Yga2E (amino acids 1 to 292 out of a total length of 306 amino acids). The adjacent methyltransferase sequence best matches the M.BclI methyltransferase sequence, at an E value of e−72, having similarity throughout the sequence, and in particular in the TRD (Target (DNA) Recognition Domain) of the methyltransferase. This evidence combines to make it very likely that this restriction endonuclease gene will recognize the same sequence, TGATCA, as BclI, though it may differ in other characteristics, such as temperature optima and sensitivity, buffer optima, etc. However, the second hit, gi:68248271 hypothetical protein Mmc1DRAFT_3688, appears likely to recognize a different sequence than BclI and is thus a good candidate for a new DNA specificity. This restriction endonuclease sequence has significant similarity to BclI (E=1e−62), but in contrast to the first hit, this similarity is only to the carboxy half of BclI. The approximately first half of each restriction endonuclease does not share significant similarity. In addition, the adjacent methyltransferase has significant similarity in a standard BLAST search to methyltransferases recognizing many different, though related, DNA sequences, and the similarity is at similar levels of E value and distribution throughout the methyltransferase sequence. For example, a BLAST search with this methyltransferase, Mmc1DRAFT_3689, gave E value scores of e−57 to M.EacI which recognizes GGATC, e−54 to M.ThaII, recognizing GATC, e−26 to M1.BstSE1, recognizing GAGTC, e−26 to M.BstNBI, recognizing GASTC, e−20 to M.CviBI, recognizing GANTC, e−19 to M.EcoRV, recognizing GATATC and e−14 to M.TfiI, recognizing GAWTC, among many other methyltransferases. The E value for this adjacent methyltransferase and the BclI methyltransferase, M.BclI, was E=e−12. This significant but relatively equal similarity to enzymes with a wide range of recognition sequences, coupled with the finding that the significant similarity between the identified and input RE sequenced was limited to only one half of the restriction endonuclease genes indicates that the identified Mmc1DRAFT_3688 is likely to recognize a different sequence than the input restriction endonuclease, BclI.

B. Results for searching using the EagI amino acid sequence of FIG. 2-1 to 2-58 on 25 Jul. 2006 as in A above. The best scoring results from a BLAST search are reported below:

| | Score (Bits) | E Value |
|---|---|---|
| Sequences producing significant alignments: | | |
| gi \| 84686807 \| ref \| ZP_01014694.1 \| hypothetical protein RB2654_22 . . . | 127 | 8e−28 |
| gi \| 78773885 \| gb \| ABB51232.1 \| unknown [*Arthrospira platensis*] | 63.2 | 1e−08 |
| gi \| 67939563 \| ref \| ZP_00532060.1 \| hypothetical protein Cphamn1DR . . . | 55.5 | 3e−06 |
| gi \| 71901748 \| ref \| ZP_00683819.1 \| conserved hypothetical protein . . . | 53.9 | 8e−06 |
| gi \| 9105516 \| gb \| AAF83450.1 \| hypothetical protein XF_0640 [Xylel . . . | 52.0 | 3e−05 |
| gi \| 76260977 \| ref \| ZP_00768602.1 \| conserved hypothetical protein . . . | 51.2 | 5e−05 |
| gi \| 53688392 \| ref \| ZP 00345702.1 \| hypothetical protein Npun02002 . . . | 48.9 | 3e−04 |
| gi \| 78171892 \| gb \| ABB28988.1 \| hypothetical protein Cag_1737 [Chl . . . | 43.1 | 0.015 |
| gi \| 71491000 \| gb \| EAO23340.1 \| hypothetical protein SwolDRAFT_003 . . . | 42.7 | 0.019 |
| gi \| 86211168 \| gb \| ABC87270.1 \| NotI restriction endonuclease [Nocard | 42.0 | 0.033 |
| gi \| 20988646 \| gb \| AAH29858.1 \| Leucine rich repeat containing 23 [Ho | 37.7 | 0.62 |
| gi \| 89300041 \| gb \| EAR98029.1 \| hypothetical protein TTHERM_002842 . . . | 37.4 | 0.81 |

The first seven hits have E values of less than e−02, indicating that these are likely to be restriction endonucleases. Note that the sequences identified are reported as "hypothetical protein," "unknown" or "conserved hypothetical protein," since the nature of these ORFs is not known. Because the E values are not very small, with the exception of the first hit, it is more likely that these endonucleases may have some-what different recognition sequences from EagI, and indeed may recognize novel DNA sequences. All seven of these ORFs are adjacent to an ORF identified as a methyltransferase. Interestingly, the methyltransferases are of different types, with the 8e−28 hit (gi:84686807) having a 5-methyl cytosine-methyltransferase like EagI, while the other 6 hits are adjacent to an amino-methyltransferase that could modify either N4C or N6A, which is different from the EagI R-M system. These seven ORFs can be confirmed as endonucleases by the techniques described in Example 3.

The subsequent hits are outside the cut off value of E value<e−02, however two of the next best three hits are of interest. The first such hit, cag__1737 (gi:78171892) is not next to an identified methylase: however, there is a methylase motif, DPPY, in the sequence adjacent to cag__1737, perhaps indicating this is a R-M system that is degenerated or partially disrupted. The next best hit, SwolDRAFT__0030 (gi: 71491000), does have a methyltransferase adjacent to it. Even though the similarity is less than the described cut off, this gene is likely a restriction endonuclease, albeit one that is more highly diverged from EagI. The next best scoring sequence is a known restriction endonuclease, NotI. The further best scoring sequences do not appear to be restriction endonucleases. This example demonstrates that had we set the Expectation value threshold to a less stringent value, such as E<0.1, we would have included two additional true positive finds, while also including one false positive sequence (cag__1737). Setting the cut off threshold at E less than or equal to e−02 ensures that the sequences identified are very likely to be restriction endonucleases.

When a PSI-BLAST similarity analysis was performed, the results were broadly similar to the BLAST search, but the differences demonstrated the increased sensitivity obtained using PSI-BLAST. After three iterations of PSI-BLAST, no additional new hits are obtained. The best scoring results from the fourth iteration are:

| | Score (Bits) | E Value |
|---|---|---|
| Sequences producing significant alignments: | | |
| gi \| 76260977 \| ref \| ZP_00768602.1 \| conserved hypothetical protein . . . | 344 | 3e−93 |
| gi \| 84686807 \| ref \| ZP_01014694.1 \| hypothetical protein RB2654_22 . . . | 337 | 4e−91 |
| gi \| 67939563 \| ref \| ZP_00532060.1 \| hypothetical protein Cphamn1DR . . . | 328 | 3e−88 |
| gi \| 78171892 \| gb \| ABB28988.1 \| hypothetical protein Cag_1737 [Chl . . . | 299 | 9e−80 |
| gi \| 89055379 \| ref \| YP_510830.1 \| hypothetical protein Jann_2888 [ . . . | 288 | 2e−76 |
| gi \| 86211168 \| gb \| ABC87270.1 \| NotI restriction endonuclease [Nocard | 286 | 6e−76 |
| gi \| 56677682 \| gb \| AAV94348.1 \| hypothetical protein SPO1048 [Sili . . . | 286 | 1e−75 |
| gi \| 71901748 \| ref \| ZP_00683819.1 \| conserved hypothetical protein . . . | 268 | 2e−70 |
| gi \| 91055161 \| gb \| AAF83450.1 \| hypothetical protein XF_0640 [Xylel . . . | 266 | 8e−70 |
| gi \| 70779363 \| gb \| AAZ08143.1 \| ORF2 [*Burkholderia cepacia*] | 266 | 1e−69 |
| gi \| 78773885 \| gb \| ABB51232.1 \| unknown [*Arthrospira platensis*] | 266 | 1e−69 |
| gi \| 53688392 \| ref \| ZP_00345702.1 \| hypothetical protein Npun02002 . . . | 260 | 6e−68 |
| gi \| 71491000 \| gb \| EAO23340.1 \| hypothetical protein SwolDRAFT_003 . . . | 222 | 1e−56 |
| gi \| 67935692 \| ref \| ZP_00528711.1 \| hypothetical protein Cpha266DR . . . | 211 | 3e−53 |

-continued

| | Score (Bits) | E Value |
|---|---|---|
| Sequences with E-value WORSE than threshold | | |
| gi \| 3660495 \| emb \| CAA57707.1 \| R. EcoHK31I protein [*Escherichia coli*] | 43.8 | 0.008 |
| gi \| 2760956 \| gb \| AAB95338.1 \| EaeI restriction endonuclease [Enterob | 42.3 | 0.028 |
| gi \| 893004001\| gb \| EAR98388.1 \| cyclic nucleotide-binding domain c . . . | 39.2 | 0.22 |
| gi \| 21355217 \| ref \| NP_651245.1 \| CG5728-PA [*Drosophila* melanogast . . . | 38.0 | 0.48 |

The seven restriction endonuclease hits identified using standard BLAST were also identified by PSI-BLAST, while the more sensitive PSI-BLAST identified seven additional restriction endonucleases, three of which were the three hits just outside of the e−02 cutoff from the standard BLAST and four of which were new to the PSI-BLAST results.

The fourteen restriction endonuclease hits form five groups of related sequences. The first group consists of those sequences that appear likely to recognize the same recognition sequence as EagI. Only three of the fourteen sequences fall into this group: hypothetical proteins RB2654__22558, Jann__2888 and SPO1048. These three sequences are considered likely to share the EagI recognition sequence because they are adjacent to methyltransferases that are very highly similar to the EagI R-M system methyltransferase, M.EagI, with E value scores of E=0.0 using standard BLAST against the REBASE database and significant similarity through the genes, including in the region of the TRD (target recognition domain). Interestingly, only one of these sequences was identified in the EagI standard BLAST results, RB2564__22558, where it is the highest scoring sequence. Because Jann__2888 and SPO1048 are only identified by the PSI-BLAST, it is more likely that they may have differences in functional properties with EagI.

The second grouping includes four sequences, two of which are nearly identical, being found in the same genus and species though different strains: XF__0640 and XfasoDRAFT__0198, along with *Arthrospira platensis* ORF2 and Npun02002587. This group is likely to recognize a different sequence than EagI, which demonstrates the ability of this method to identify restriction endonucleases having different recognition sequences. All four restriction endonucleases of this group are adjacent to methyltransferases that are very highly similar (E=0.0) to the BsiWI methyltransferase, and all are significantly similar to the BsiWI RE sequence (E=2e−92 to E=9e−99 when using standard BLAST at NCBI searching the Genbank database with the BsiWI probes—SEQ ID. 185 and 186). Additionally, all four have a large gap in the PSI-BLAST alignment with EagI from amino acid position 69 to 96, which is a relatively large region of difference indicating a different function for the proteins. EagI and BsiWI recognize related sequences, differing only in the internal two bases recognized: CGGCCG (EagI) and CGTACG (BsiWI). It is interesting that the sequence similarity observed implies a common ancestor for the EagI restrcition endonuclease (and family members) and the BsiWI restriction endonuclease (and these four family members).

The third grouping is characterized by: the similarity of the sequences in a standard BLAST analysis compared with other identified restriction endonuclease sequences; and the high degree of similarity of adjacent methyltransferases, while only moderately similar to methyltransferases of known specificity in a standard BLAST. This group consists of CaurDRAFT__2301, Cphamn1DRAFT__2148, Burkholderia cepacia ORF2, SwolDRAFT__0030 and Cpha266DRAFT__1693. These five sequences are good candidates to recognize sequences different from that recognized by EagI, even though the first sequence (CaurDRAFT__2301) scores the best in the PSI-BLAST results, because the adjacent methylases do not closely match any other methylase of known specificity, and because the restriction endonucleases have multiple small gaps in the alignments. In the case of Cpha266DRAFT__1693, there is no adjacent methyltransferase gene. However, the C-terminal portion of the sequence has significant similarity to the methyltransferases adjacent to the other members of this group, while the N-terminal portion of this sequence matches the identified restriction endonucleases of this group. This may be a case of poor sequence data because the sequence is reported as a DRAFT, or it may be that this R-M system is degraded. The region of this gene could be amplified by PCR and sequenced to determine which is the case.

The last two groups have only one member. The first case is the cag__1737 sequence. This sequence is significantly larger than EagI, at 498 amino acids versus 301 for EagI. Similarity to EagI occurs in the carboxy terminal half of the sequence, while the amino terminal portion does not have high similarity to EagI or to methyltransferases. There is no adjacent readily identifiable methyltransferase to be found near cag__1737. The lack of methyltransferase and unique N-terminal half of this sequence makes it likely to be different than EagI. This would be an interesting candidate to characterize, though it is possible this may not be functioning as a typical type II restriction endonuclease.

The last group is the case of the identified NotI RE. NotI recognizes a more specific sequence, GCGGCCGC, than EagI, CGGCCG, wherein the internal six bases of the NotI recognition sequence are the same as the EagI recognition sequence. It is thus not surprising that the NotI sequence can be identified using the EagI sequence as they are likely descended from a common ancestor. Clues that the NotI gene identified might be different from EagI are that the NotI sequence is longer (383 amino acids versus 301 amino acids), that there are eight gaps in EagI sequence in the alignment with NotI, and that the methyltransferases adjacent to NotI and EagI are of different classes, wherein the M.NotI is an amino methyltransferase, while the EagI methyltransferase, M.EagI, is a 5 methyl-cytosine class methylase. Finding this restriction endonuclease having a different recognition sequence demonstrates the ability of the method to identify novel and useful new restriction endonucleases.

C. Results of searching using the Mmell amino acid sequence of FIG. 2-1 to 2-58 on 25 Jul. 2006 with the standard BLAST blastp program.

| | Score (Bits) | E Value |
|---|---|---|
| Sequences producing significant alignments: | | |
| gi \| 67916884 \| ref \| ZP_00510572.1 \| conserved hypothetical protein . . . | 384 | 3e−105 |
| gi \| 28210143 \| ref \| NP_781087.1 \| hypothetical protein CTC00388 [C . . . | 355 | 2e−96 |
| gi \| 109647707 \| ref \| ZP_01371610.1 \| conserved hypothetical protei . . . | 348 | 3e−94 |
| gi \| 89892981 \| ref \| YP_516468.1 \| hypothetical protein DSY0235 [De . . . | 344 | 4e−93 |
| gi \| 89209832 \| ref \| ZP_01188226.1 \| conserved hypothetical protein . . . | 316 | 1e−84 |

-continued

| | Score (Bits) | E Value |
|---|---|---|
| gi \| 89201678 \| ref \| ZP_01180415.1 \| conserved hypothetical protein . . . | 316 | 1e−84 |
| gi \| 11016839 \| gb \| ABG52939.1 \| conserved hypothetical protein [T . . . | 293 | 1e−77 |
| gi \| 77412887 \| ref \| ZP_00789091.1 \| conserved hypothetical protein . . . | 259 | 2e−67 |
| gi \| 81427752 \| ref \| YP_394751.1 \| hypothetical protein [Lactobacil . . . | 216 | 1e−54 |
| gi \| 56295584 \| emb \| CAH04826.1 \| conserved hypothetical protein [uncu | 163 | 2e−38 |
| gi \| 110620011 \| emb \| CAJ35289.1 \| conserved hypothetical protein [ . . . | 159 | 4e−37 |
| gi \| 76260023 \| ref \| ZP_00767665.1 \| hypothetical protein CaurDRAFT . . . | 36.2 | 2.7 |
| gi \| 19921772 \| ref \| NP_1610333.1 \| CG8728-PA [*Drosophila* melanogast... | 36.2 | 3.2 |
| gi \| 68544761 \| ref \| ZP_00584368.1 \| Globin:Oxidoreductase FAD/NAD ( . . . | 35.4 | 5.5 |
| gi \| 44891709 \| tpg \| DAA02258.1 \| TPA: TPA_exp: S6 sporozoite-induced | 35.0 | 6.9 |
| gi \| 82594327 \| ref \| XP_725378.1 \| hypothetical protein PY04986 [Pl . . . | 35.0 | 6.9 |
| gi \| 68139991 \| gb \| EAM93304.1 \| Glycine hydroxymethyltransferase [ . . . | 34.7 | 9.9 |

Note that the first eleven hits are highly significant, with E values ranging from 3e−105 to 4e−37. All are adjacent to DNA methyltransferases. Note the very sharp drop off in E value results between the eleven restriction endonuclease hits and the remainder of the hits, which are outside the level of significance for identifying endonucleases described herein. Also note that the endonucleases identified are reported as “hypothetical proteins” or “conserved hypothetical proteins.” Without the input of the known Mmell sequence these ORFs are not identified as endonucleases. These eleven ORFs can be confirmed as endonucleases by the techniques described in Example 3.

The same search using the sequence of MmeII in the PSI-BLAST program initially identifies the same eleven genes (first iteration), but after five iterations, an additional 5 restriction endonuclease genes are found. No new sequence hits were added at the sixth iteration. The PSI-BLAST results (sixth iteration) for MmeII are:

| | Score (Bits) | E Value |
|---|---|---|
| Sequences producing significant alignments: | | |
| gi \| 28210143 \| ref \| NP_781087.1 \| hypothetical protein CTC00388 [C . . . | 674 | 0.0 |
| gi \| 67916884 \| ref \| ZP_00510572.1 \| conserved hypothetical protein . . . | 667 | 0.0 |
| gi \| 89201678 \| ref \| ZP_01180415.1 \| conserved hypothetical protein . . . | 646 | 0.0 |
| gi \| 89209832 \| ref \| ZP_01188226.1 \| conserved hypothetical protein . . . | 642 | 0.0 |
| gi \| 110168399 \| gb \| ABG52939.1 \| conserved hypothetical protein [T . . . | 620 | 4e−176 |
| gi \| 109647707 \| ref \| ZP_01371610.1 \| conserved hypothetical protei . . . | 617 | 2e−175 |
| gi \| 89892981 \| ref \| YP_516468.1 \| hypothetical protein DSY0235 [De . . . | 607 | 4e−172 |
| gi \| 77412887 \| ref \| ZP_00789091.1 \| conserved hypothetical protein . . . | 605 | 2e−171 |
| gi \| 81427752 \| ref \| YP_394751.1 \| hypothetical protein [Lactobacil . . . | 564 | 3e−159 |
| gi \| 56295584 \| emb \| CAH04826.1 \| conserved hypothetical protein [uncu | 530 | 5e−149 |

-continued

| | Score (Bits) | E Value |
|---|---|---|
| gi \| 110620011 \|emb \| CAJ35289.1 \| conserved hypothetical protein [ . . . | 526 | 9e−148 |
| gi \| 16329761 \| ref \| NP_1440489.1 \| hypothetical protein slr1033 [Sy . . . | 169 | 3e−40 |
| gi \| 76260023 \| ref \| ZP_00767665.1 \| hypothetical protein CaurDRAFT . . . | 166 | 2e−39 |
| gi \| 71143791 \| gb \| AAZ24264.1 \| hypothetical protein CPS_0499 [Col . . . | 164 | 5e−39 |
| gi \| 106890764 \| ref \| ZP_01357956.1 \| hypothetical protein RoseRSDR . . . | 155 | 4e−36 |
| gi \| 78195585 \| gb \| ABB33352.1 \| hypothetical protein Gmet_3139 [Ge . . . | 137 | 7e−31 |
| Sequences with E-value WORSE than threshold | | |
| gi \| 47565512 \| ref \| ZP_00236553.1 \| hypothetical protein protein [ . . . | 41.2 | 0.091 |
| gi \| 89295649 \| gb \| EAR93637.1 \| cation channel family protein [Tetrah | 40.9 | 0.12 |
| gi\| 34763083 \| ref \| ZP_00144055.1 \| RNA polymerase sigma-54 factor . . . | 40.5 | 0.16 |

The highest scoring hits (9e−148 and smaller E values) are the same eleven hits found by standard BLAST. There is still a dramatic drop off from E=7e−31 to the next best scoring sequence at E=0.091. The five additional sequence hits identified through PSI-BLAST all align with only the carboxy portion of MmeII (amino acids 248 to 423), so they likely differ from MmeII. Two have methyltransferases adjacent to them, gi:78195585 Gmet_3139 and gi:71143791 CPS_0499, although the methyltransferase next to CPS_0499 is not labeled as a methyltransferase in the sequence annotation. The other three do not have a good adjacent methyltransferase candidate gene. These three could be restriction endonucleases like PacI or PmeI that do not have a methylase partner; they could be inactive or fragmentary restriction endonucleases; they could have a methylase partner located at some distance in their genome; or they could be false positive hits. These sixteen ORFs can be confirmed as endonucleases by the techniques described in Example 3.

Note that while BclI, EagI and MmeII identify several restriction endonuclease sequences in the Genbank database, many of the restriction endonuclease sequences of FIG. 2-1 to 2-58 currently have no matches in the database at the specified E value, indicating the very unique nature of these restriction endonuclease gene sequences. As more sequences are added to the database, however, these currently unique restriction endonuclease sequences may be used to identify restriction endonucleases with which they share significant sequence similarity.

Example 3

Method of Determining Whether a Sequence Identified According to Example I has Endonuclease Activity Various methods can be employed to determine whether a DNA sequence identified as a potential endonuclease gene encodes an active endonuclease. Several such methods are described herein.

(a) In vitro transcription and translation of the identified ORF may be used to produce the protein encoded by that identified ORF (see for example, U.S. Pat. No. 6,689,573 U.S. Pat. No. 6,905,837, U.S. Pat. No. 6,383,770). The protein thus produced is then used in standard restriction endonuclease assays to see if it cleaves DNA. If DNA cleavage is observed, the restriction endonuclease and position of DNA strand breakage within or near the recognition sequence is determined by the methods described below. In vitro transcription-translation has an advantage that there is no requirement for host DNA protection by the companion DNA methyltransferase in order to express the endonuclease, as is usually the case when cloning the restriction endonuclease into a naïve host, such as typical laboratory *E. coli* strains. In vitro transcription and translation systems that have minimal endogenous, non-specific nucleases are preferable, such as the rabbit reticulocyte system.

(b) The candidate genes can be cloned and expressed in a host cell. *E. coli* is often used as a host for such cloning, but any host cell with a genetic transformation system could be used as well, such as *Bacillus subtilis* or yeast strains. Typically, the methyltransferase gene for the potential restriction system is cloned into a vector that has an origin of replication compatible with a second vector, which will be used for the endonuclease gene. The methyltransferase gene may be amplified by PCR using suitable primers, which primers often include a termination codon to end expression of the vector protein into which the methyltransferase gene is being inserted, a ribosome binding sequence to allow initiation of translation at the start of the methyltransferase ORF, and restriction sites to facilitate cloning. The methyltransferase gene can then be introduced into the host. Host cells expressing the methyltransferase are then grown and made competent.

If the potential endonuclease being cloned is an isoschizomer or a neoschizomer of a known enzyme, the known endonuclease can be used to test whether expression of the newly identified potential methyltransferase prevents cleavage by the known endonuclease. DNA from the methyltransferase expressing host, either the vector and methyltransferase gene or total host DNA, can be purified and digested with the known endonuclease. If the potential methyltransferase methylates the same recognition sequence as the known endonuclease, it will prevent cleavage by the known endonuclease if the methylation occurs at the same base position as methylated by the known restriction system methyltransferase.

It may be, however, that the potential methyltransferase modifies the same DNA sequence at a different position, i.e., either a different base within the recognition sequence, or at a different position on the same base, such as 5-methyl cytosine versus N4-methyl cytosine. If the base position modified is different, it may be that the potential methyltransferase modifies the host DNA but fails to protect against cleavage by the known endonuclease. This is more likely in the case of neoschizomers but can also occur with isoschizomers. Differences in methylation sensitivity can lead to new and potentially advantageous uses for isoschizomers or neoschizomers identified by the method of this application. If the potential restriction system being investigated has a different recognition sequence than the known endonuclease, it is likely that the cloned potential methyltransferase gene will not prevent cleavage by the known endonuclease. An exception to this would be if the known restriction system recognizes a sequence that is a subset of that recognized by potential restriction system. For example, MjaIV, recognizing GTNNAC, was observed to have weak similarity to HincII, recognizing GTYRAC. While MjaIV has a different recognition sequence to HincII, all HincII recognition sites are also MjaIV recognition sites, so MjaIV methylation will block HincII cutting even though MjaIV has a different recognition sequence. Once the methylase is introduced and expressed so as to protect the host cell, the endonuclease can then be introduced into those cells.

For cloning, the endonuclease gene is amplified by PCR using suitable primers, as for the methyltransferase, inserted into a vector compatible in the same host cell as the vector encoding the cognate methyltransferase, and transformed into the competent host cells already expressing the methyltransferase. Transformed host cells are then grown and a protein extract is made by appropriate methods, such as sonication or pressure disruption (french press). The protein extract is then assayed for restriction endonuclease activity by mixing various dilutions of the protein extract with standard DNAs, for example phage lambda DNA, phage T7 DNA, phage PhiX174 DNA, pBR322 DNA or pUC19 DNA, in a standard buffer, such as NEBuffer 2 or NEBuffer 4 (New England Biolabs, Inc., Ipswich, Mass.). The reaction products are electrophoresed on agarose gels and examined to see if the DNA has been cleaved.

The specific DNA sequence recognized by the endonuclease (the 'recognition sequence'), and the exact position of strand cleavage within or near the recognition sequence, are then determined for the endonuclease (see Schildkraut, I. S., "Screening for and Characterizing Restriction Endonucleases", in Genetic Engineering, Principles and Methods, Vol. 6, pp. 117-140, Plenum Press (1984)), U.S. Pat. No. 5,030,569, U.S. Pat. No. 5,200,337, U.S. Pat. No. 5,192,676, U.S. Pat. No. 5,100,793, U.S. Pat. No. 4,996,151, U.S. Pat. No. 5,543,308, U.S. Pat. No. 4,999,293, U.S. Pat. No. 5,139,942, U.S. Pat. No. 5,371,006, U.S. Pat. No. 5,098,839, U.S. Pat. No. 5,196,330, U.S. Pat. No. 5,824,529, U.S. Pat. No. 5,288,696, U.S. Pat. No. 5,945,326).

For example, to determine the recognition sequence of the endonuclease, the size of the fragments generated from digestion of several of the known standard DNAs, such as lambda DNA or PhiX174 DNA, can be estimated by comparison of the fragments produced by the unknown enzyme to DNA molecular weight standards (such as NEB catalog #N3012 lambda DNA-HindIII digest, NEB cat #N3026 PhiX174 DNA-HaeIII digest, NEB cat #N3232 1 kb DNA Ladder or other DNA size standards (New England Biolabs, Inc., Ipswich, Mass.)). The approximate sizes of the fragments can be entered into a program such as REBpredictor (http://tools.neb.com/REBpredictor/index.php), which will generate possible recognition sequences matching the fragment size input data. The output of this program is usually a list of multiple possible recognition sequences, only one of which is correct. The correct recognition sequence can be determined by mapping several positions at which the unknown endonuclease cuts the standard DNAs. Mapping is done by standard techniques in which the DNA is cut with the unknown enzyme and a known endonuclease. By using several known endonucleases, which cut at various positions in the DNA, the position(s) of cleavage of the unknown enzyme can be estimated. The correct recognition sequence predicted by a program such as REBpredictor will occur at the positions determined by the mapping experiment. When a candidate recognition sequence is determined, it can be confirmed by comparing the observed sizes of DNA fragments generated by cutting with the unknown endonuclease on various DNAs to the computer predicted sizes of fragments generated in silico by cutting at the predicted recognition sequence (for example, see U.S. Pat. No. 5,030,569, U.S. Pat. No. 5,200,337, U.S. Pat. No. 5,192,676, U.S. Pat. No. 5,100,793, U.S. Pat. No. 4,996,151, U.S. Pat. No. 5,543,308, U.S. Pat. No. 4,999,293, U.S. Pat. No. 5,139,942, U.S. Pat. No. 5,371,006, U.S. Pat. No. 5,098,839, U.S. Pat. No. 5,196,330, U.S. Pat. No. 5,824,529, U.S. Pat. No. 5,288,696, U.S. Pat. No. 5,945,326).

The position of DNA strand cleavage relative to the recognition sequence can be determined by standards methods, such as that of cleavage of a primer extension product, which can then be electrophoresed alongside a set of standard dideoxy sequencing reactions produced from the same primer and template. Such an approach is exemplified in Example II of U.S. Pat. No. 6,194,188. Alternatively, a DNA can be cut by the endonuclease and then a standard sequencing reaction is performed using a primer located within 500 bases of the endonuclease-cutting site. The sequencing reaction will give normal sequence until it runs off the end of the template at the site of the endonuclease cut. Sequencing must be performed in both directions to observe the cleavage position of each DNA strand. Such an approach is exemplified in Example II of U.S. application Ser. No. 10/617,361.

The biochemical characteristics of the new restriction endonucleases identified by this method can be determined by standard techniques. Properties to be examined would include thermostability, activity in various buffer conditions, level of star activity and sensitivity to methylation at various positions within the recognition sequence. Endonucleases that differ from previously known isoschizomers in some or other of these biochemical characteristics may have uses that differ from the previously known endonucleases.

What is claimed is:

1. An isolated protein having at least 90% amino acid sequence identity with SEQ ID NO: 14.

2. An isolated protein having an amino acid sequence identified by an Expectation value of less than or equal to e−05 in a BLAST search for detecting sequence similarity using the amino acid sequence of SEQ ID NO:14.

3. The isolated protein according to claim 2, having restriction endonuclease activity.

4. The isolated protein of claim 1, wherein the protein is present in a buffer.

5. The isolated protein of claim 2, wherein the protein is present in a buffer.

* * * * *

SEQUENCE LISTING

<160> NUMBER OF SEQ ID NOS: 220

<210> SEQ ID NO 1
<211> LENGTH: 1590
<212> TYPE: DNA
<213> ORGANISM: Arthrobacter citreus

<400> SEQUENCE: 1
atgttcatga atgaacacat aaagggatct aattcgcatg gtaatagcaa tgagttggaa 60
ttggtttatg cgtttgatgg caagaaagtt aaggatttaa acactaattt aaaaaatttt 120
gtacaattca ttgcaaacga taacaatata aaaattaata atgatacaaa attatttgcg 180
aagtatgttt ctaataacaa attaaaacaa gattttattg tatcgtttaa tgaaagagat 240
ttttacatta gtttaaaaat gggttcagga aatagtgttc atcaagaacc gattgaagat 300

```
tttattaaat acttgaatac gaattatgaa gtaactgaga aaatttgtaa tgatttaagg    360

ttttttattt gggcagatgg tacgttagat ggaaaaggaa aatttgagaa tagatttgac    420

gctagatatt ttaaaaagaa ttatcctgaa aaacgaagag agttattaca atttttcgaa    480

aaaaataagg tagaactaat taagcatttt atgtttgttg gtaaacataa tagtagagtt    540

gattatcttt atcatggaac gacttcgaat ggggcgtgga tgtcaacaaa acaaataatt    600

gattacaata ttcaaaacca aatagatact aacaaaggta attctcctac tttaagcgtc    660

ggaagaatgt caattcaagc atggaatgtt gcaaagtctg gaagcgagtc agcagaaaag    720

aaacgaggag aaatccaggt aaaatacgga aaacttaaag aagattttaa ggaggtatta    780

aaattaaatt cctcgaacaa aggaactttg tttggagatc atgaggaatt tgatatttct    840

ggaactttaa ataaaaataa aaatcatttt tattggaaga tgatagcaag agatttgaat    900

ttaaatcaag aagaactgaa taatttatat gttgttcgtg tttcttcaaa agttatgtca    960

tctctcagta agaaaaaggt tcttccaaaa tcggatgctt atataattag agctgatctc   1020

tctaaatctt ttttactatc taaagaatac aaactatctg aagatgattt ggtaggtata   1080

atatataaaa aagtaggacg tagtggcatt tcagtaaaaa gagctgattc gaagaaatat   1140

actattgtaa aacttacagt tgcttcattt gaaaagtgct ttgaaatcga gccagagata   1200

aaaaaaataa ttgctggact tttgttatat agtaaagaga aggatatgta taaaaatctt   1260

gaaattttaa ataagattgg tatatctgaa cttgaattga taaattatac aaatcgattt   1320

attgtagata aagttatttc gtgcaatgat cccaaaaatg tcgatataat caggagtacg   1380

atgcaagaac ggactcgaac actaattgaa aaaaatttag aaatcaaaaa agcactattt   1440

atgggtgaag gctggtatga agaaccctat tgcatcaatt atatttttaa agatgggaaa   1500

ttatcaaatg atgtattttc tgagtatatt attactacag gttcaggccg ttcaaagggc   1560

aattatacaa ttgcgttgaa gcctaagtaa                                    1590


<210> SEQ ID NO 2
<211> LENGTH: 529
<212> TYPE: PRT
<213> ORGANISM: Arthrobacter citreus

<400> SEQUENCE: 2

Met Phe Met Asn Glu His Ile Lys Gly Ser Asn Ser His Gly Asn Ser
1               5                   10                  15

Asn Glu Leu Glu Leu Val Tyr Ala Phe Asp Gly Lys Lys Val Lys Asp
            20                  25                  30

Leu Asn Thr Asn Leu Lys Asn Phe Val Gln Phe Ile Ala Asn Asp Asn
        35                  40                  45

Asn Ile Lys Ile Asn Asn Asp Thr Lys Leu Phe Ala Lys Tyr Val Ser
    50                  55                  60

Asn Asn Lys Leu Lys Gln Asp Phe Ile Val Ser Phe Asn Glu Arg Asp
65                  70                  75                  80

Phe Tyr Ile Ser Leu Lys Met Gly Ser Gly Asn Ser Val His Gln Glu
                85                  90                  95

Pro Ile Glu Asp Phe Ile Lys Tyr Leu Asn Thr Asn Tyr Glu Val Thr
            100                 105                 110

Glu Lys Ile Cys Asn Asp Leu Arg Phe Phe Ile Trp Ala Asp Gly Thr
        115                 120                 125

Leu Asp Gly Lys Gly Lys Phe Glu Asn Arg Phe Asp Ala Arg Tyr Phe
    130                 135                 140
```

-continued

```
Lys Lys Asn Tyr Pro Glu Lys Arg Arg Glu Leu Leu Gln Phe Phe Glu
145                 150                 155                 160

Lys Asn Lys Val Glu Leu Ile Lys His Phe Met Phe Val Gly Lys His
                165                 170                 175

Asn Ser Arg Val Asp Tyr Leu Tyr His Gly Thr Thr Ser Asn Gly Ala
            180                 185                 190

Trp Met Ser Thr Lys Gln Ile Ile Asp Tyr Asn Ile Gln Asn Gln Ile
        195                 200                 205

Asp Thr Asn Lys Gly Asn Ser Pro Thr Leu Ser Val Gly Arg Met Ser
    210                 215                 220

Ile Gln Ala Trp Asn Val Ala Lys Ser Gly Ser Glu Ser Ala Glu Lys
225                 230                 235                 240

Lys Arg Gly Glu Ile Gln Val Lys Tyr Gly Lys Leu Lys Glu Asp Phe
                245                 250                 255

Lys Glu Val Leu Lys Leu Asn Ser Ser Asn Lys Gly Thr Leu Phe Gly
            260                 265                 270

Asp His Glu Glu Phe Asp Ile Ser Gly Thr Leu Asn Lys Asn Lys Asn
        275                 280                 285

His Phe Tyr Trp Lys Met Ile Ala Arg Asp Leu Asn Leu Asn Gln Glu
    290                 295                 300

Glu Leu Asn Asn Leu Tyr Val Val Arg Val Ser Ser Lys Val Met Ser
305                 310                 315                 320

Ser Leu Ser Lys Lys Lys Val Leu Pro Lys Ser Asp Ala Tyr Ile Ile
                325                 330                 335

Arg Ala Asp Leu Ser Lys Ser Phe Leu Leu Ser Lys Glu Tyr Lys Leu
            340                 345                 350

Ser Glu Asp Asp Leu Val Gly Ile Ile Tyr Lys Lys Val Gly Arg Ser
        355                 360                 365

Gly Ile Ser Val Lys Arg Ala Asp Ser Lys Lys Tyr Thr Ile Val Lys
    370                 375                 380

Leu Thr Val Ala Ser Phe Glu Lys Cys Phe Glu Ile Glu Pro Glu Ile
385                 390                 395                 400

Lys Lys Ile Ile Ala Gly Leu Leu Leu Tyr Ser Lys Glu Lys Asp Met
                405                 410                 415

Tyr Lys Asn Leu Glu Ile Leu Asn Lys Ile Gly Ile Ser Glu Leu Glu
            420                 425                 430

Leu Ile Asn Tyr Thr Asn Arg Phe Ile Val Asp Lys Val Ile Ser Cys
        435                 440                 445

Asn Asp Pro Lys Asn Val Asp Ile Ile Arg Ser Thr Met Gln Glu Arg
    450                 455                 460

Thr Arg Thr Leu Ile Glu Lys Asn Leu Glu Ile Lys Lys Ala Leu Phe
465                 470                 475                 480

Met Gly Glu Gly Trp Tyr Glu Glu Pro Tyr Cys Ile Asn Tyr Ile Phe
                485                 490                 495

Lys Asp Gly Lys Leu Ser Asn Asp Val Phe Ser Glu Tyr Ile Ile Thr
            500                 505                 510

Thr Gly Ser Gly Arg Ser Lys Gly Asn Tyr Thr Ile Ala Leu Lys Pro
        515                 520                 525

Lys
```

<210> SEQ ID NO 3
<211> LENGTH: 972
<212> TYPE: DNA
<213> ORGANISM: Acinetobacter calcoaceticus M4

<400> SEQUENCE: 3

```
ttgggaaaac ttaaaaaaat tttagcgggt actgctggtc gaaatactgg tcatgcatat     60
gaagaatatc tagcagataa tattaattca ttaaatgttc cattaaatat atcaatacaa    120
ccactaccga tagtaggttc ttatcaaaat gtcttttctt caaataatga agctttcaca    180
ttaatcactt atttggctaa agcatataat atttctcaaa ttactagaat ttatgctgtt    240
gcaacagggg gattagcaac atccgctaac agtcagggtg tccattttaa tggacaaata    300
attaaaaaat gtaaaagtga tattttaatt gaaatcgaag accaatctaa tcaaattcat    360
cgtattggga tatctgtaaa acaatgtaac aatcagagac ctcttaatgc tcaagttttt    420
tgttccacag cttcagggtt ttctaaccta ttaagacaac ataacattcc agtttctatt    480
ttagctgaaa atgaattacg taaattctgt ggtcatcctg gaagctctcc aatagatcac    540
aatattcatt tgacccgtgt aattgatcat agaagatact tttgggaaga actagatatt    600
aatgcatcac aggagtggca aaatattttt gataattaca acgctgaaat agctagaatt    660
ttattgcaaa aagcatatag taacgaacct tatccacctg agtttttatt acataaaaca    720
aagagaacct caggaaatca ggaaattgct atttttgaaa ttgctgattt aatagtaaaa    780
agttttcagt atcaatgctt tacaacatca ctctatagag taaaaaaagg aacttttaaa    840
gaagctaaaa ctatgggaga tacacacgag gctcctagtt ttggaatatt tcaaatgcaa    900
cgcttaggaa atactcaaaa tgcacatcaa ttgcaattta atttaaaagc cggctatttt    960
tatcatattt aa                                                        972
```

<210> SEQ ID NO 4
<211> LENGTH: 323
<212> TYPE: PRT
<213> ORGANISM: Acinetobacter calcoaceticus M4

<400> SEQUENCE: 4

```
Met Gly Lys Leu Lys Lys Ile Leu Ala Gly Thr Ala Gly Arg Asn Thr
1               5                   10                  15

Gly His Ala Tyr Glu Glu Tyr Leu Ala Asp Asn Ile Asn Ser Leu Asn
            20                  25                  30

Val Pro Leu Asn Ile Ser Ile Gln Pro Leu Pro Ile Val Gly Ser Tyr
        35                  40                  45

Gln Asn Val Phe Ser Ser Asn Asn Glu Ala Phe Thr Leu Ile Thr Tyr
    50                  55                  60

Leu Ala Lys Ala Tyr Asn Ile Ser Gln Ile Thr Arg Ile Tyr Ala Val
65                  70                  75                  80

Ala Thr Gly Gly Leu Ala Thr Ser Ala Asn Ser Gln Gly Val His Phe
                85                  90                  95

Asn Gly Gln Ile Ile Lys Lys Cys Lys Ser Asp Ile Leu Ile Glu Ile
            100                 105                 110

Glu Asp Gln Ser Asn Gln Ile His Arg Ile Gly Ile Ser Val Lys Gln
        115                 120                 125

Cys Asn Asn Gln Arg Pro Leu Asn Ala Gln Val Phe Cys Ser Thr Ala
    130                 135                 140

Ser Gly Phe Ser Asn Leu Leu Arg Gln His Asn Ile Pro Val Ser Ile
145                 150                 155                 160

Leu Ala Glu Asn Glu Leu Arg Lys Phe Cys Gly His Pro Gly Ser Ser
                165                 170                 175

Pro Ile Asp His Asn Ile His Leu Thr Arg Val Ile Asp His Arg Arg
            180                 185                 190
```

```
Tyr Phe Trp Glu Glu Leu Asp Ile Asn Ala Ser Gln Glu Trp Gln Asn
        195                 200                 205

Ile Phe Asp Asn Tyr Asn Ala Glu Ile Ala Arg Ile Leu Leu Gln Lys
    210                 215                 220

Ala Tyr Ser Asn Glu Pro Tyr Pro Pro Glu Phe Leu Leu His Lys Thr
225                 230                 235                 240

Lys Arg Thr Ser Gly Asn Gln Glu Ile Ala Ile Phe Glu Ile Ala Asp
                245                 250                 255

Leu Ile Val Lys Ser Phe Gln Tyr Gln Cys Phe Thr Thr Ser Leu Tyr
            260                 265                 270

Arg Val Lys Lys Gly Thr Phe Lys Glu Ala Lys Thr Met Gly Asp Thr
        275                 280                 285

His Glu Ala Pro Ser Phe Gly Ile Phe Gln Met Gln Arg Leu Gly Asn
    290                 295                 300

Thr Gln Asn Ala His Gln Leu Gln Phe Asn Leu Lys Ala Gly Tyr Phe
305                 310                 315                 320

Tyr His Ile
```

<210> SEQ ID NO 5
<211> LENGTH: 933
<212> TYPE: DNA
<213> ORGANISM: Anabaena flos-aquae

<400> SEQUENCE: 5

```
atgacatttc aaataactcc agaaaatacc caaaataaat ctgctttgtt ggaatatttt      60

agagaattag gaaatgaaaa actttctgaa attagaagag aagtcggtaa taaaaattat     120

caaaaaataa ctcctcatat caataaagca atcaataaaa ctaagaatga ttttttacat     180

acaattattg aaactgcaaa tcaaaataat tggaatgatc aagataaact ttcctcactt     240

cttttcacta cttattgcgc tcatgtagta atgcttgatt tacgtcatga agtgtggcct     300

tatgaatata tggcattttc tcgacgaatt ggtgagcttt gggaaaattt tgtaagatta     360

ccatttttgt acccgccaaa agcagcagaa ttaacctctt ttgtaccacc actttttttct     420

gaagtcagaa aaaatctaaa aaaagatatt gaagaatata ttgatacttt gttcatttct     480

caagaacaaa aatatgaact tatcaattat tatgaaaaag tatgggtgct agtagattct     540

ggtgaaataa gtcttgagtt agattttcat gctattatta gaggtaaaag attcaatata     600

gattttaaaa gtggatttgg ctcaaatgag aaaggaaata ccaaccgact gcttatggta     660

gcaactattt attgtaattt agaagatgaa tatagtaata ttctgctcgt tcgcgctaaa     720

gaagatttga ataacaatta ctttagaact ttaaaaaagt ctcatgtttg gaatgcatat     780

tgtggtgatg aagcttatga aaaaattggt gattttacaa attttgatat gcgaacctgg     840

ataaattcaa gtattgattg gcaaaatgat ttattaagta caacagtaag tgattttgag     900

aaatttaatt taatgggata tttacaatgg taa                                  933
```

<210> SEQ ID NO 6
<211> LENGTH: 310
<212> TYPE: PRT
<213> ORGANISM: Anabaena flos-aquae

<400> SEQUENCE: 6

```
Met Thr Phe Gln Ile Thr Pro Glu Asn Thr Gln Asn Lys Ser Ala Leu
1               5                   10                  15

Leu Glu Tyr Phe Arg Glu Leu Gly Asn Glu Lys Leu Ser Glu Ile Arg
            20                  25                  30
```

-continued

```
Arg Glu Val Gly Asn Lys Asn Tyr Gln Lys Ile Thr Pro His Ile Asn
        35                  40                  45

Lys Ala Ile Asn Lys Thr Lys Asn Asp Phe Leu His Thr Ile Ile Glu
    50                  55                  60

Thr Ala Asn Gln Asn Asn Trp Asn Asp Gln Asp Lys Leu Ser Ser Leu
65                  70                  75                  80

Leu Phe Thr Thr Tyr Cys Ala His Val Val Met Leu Asp Leu Arg His
                85                  90                  95

Glu Val Trp Pro Tyr Glu Tyr Met Ala Phe Ser Arg Arg Ile Gly Glu
            100                 105                 110

Leu Trp Glu Asn Phe Val Arg Leu Pro Phe Leu Tyr Pro Pro Lys Ala
        115                 120                 125

Ala Glu Leu Thr Ser Phe Val Pro Pro Leu Phe Ser Glu Val Arg Lys
    130                 135                 140

Asn Leu Lys Lys Asp Ile Glu Glu Tyr Ile Asp Thr Leu Phe Ile Ser
145                 150                 155                 160

Gln Glu Gln Lys Tyr Glu Leu Ile Asn Tyr Tyr Glu Lys Val Trp Val
                165                 170                 175

Leu Val Asp Ser Gly Glu Ile Ser Leu Glu Leu Asp Phe His Ala Ile
            180                 185                 190

Ile Arg Gly Lys Arg Phe Asn Ile Asp Phe Lys Ser Gly Phe Gly Ser
        195                 200                 205

Asn Glu Lys Gly Asn Thr Asn Arg Leu Leu Met Val Ala Thr Ile Tyr
    210                 215                 220

Cys Asn Leu Glu Asp Glu Tyr Ser Asn Ile Leu Leu Val Arg Ala Lys
225                 230                 235                 240

Glu Asp Leu Asn Asn Asn Tyr Phe Arg Thr Leu Lys Lys Ser His Val
                245                 250                 255

Trp Asn Ala Tyr Cys Gly Asp Glu Ala Tyr Glu Lys Ile Gly Asp Phe
            260                 265                 270

Thr Asn Phe Asp Met Arg Thr Trp Ile Asn Ser Ser Ile Asp Trp Gln
        275                 280                 285

Asn Asp Leu Leu Ser Thr Thr Val Ser Asp Phe Glu Lys Phe Asn Leu
    290                 295                 300

Met Gly Tyr Leu Gln Trp
305                 310
```

<210> SEQ ID NO 7
<211> LENGTH: 702
<212> TYPE: DNA
<213> ORGANISM: Anabaena flos-aquae

<400> SEQUENCE: 7

```
atgataaatg aagatgattt actgaatata gctatagtaa atattagaaa agtttcaaaa     60

tttaaacctt ataaaagcta ttctggtgtc aataacaaag aggaatttca gcaattaata    120

gctaatgatc ctgcttttgg ctctttaggt ttggacgacg aaagatacat tattgccaga    180

gtgggaggaa atcttgtaac ctccttacat cgcaaacttg gtgatatgta tgagaattta    240

tttgcctatt tattaaaaga gagttttgga ttaaatgaga atgaactaca ctttagtgtc    300

aatgttaaaa ttggtaaacg tgaccaggtt cgatccactg atggattaat cagaaaagat    360

aagttcaatc aaaatattcc ctcagattgg attaaatatg aaggaatagg atttgaagtc    420

cgttcatgct atcaaattgg tgattctaaa agaattcagg ctgattatga tatgtccttg    480

gctttgaagt cttacgaaat tctgcctgta atgttaattt tctgcaatac atctttaaaa    540
```

-continued

```
agccctgtac ttagattatc aaagagttgg gaactctatg aaggaagaaa cagttttgat    600

ttagttcata ctattactgg tttcgacctt tataatttcc ttcagataaa ttcagagttg    660

ttgaaaaaag agatagataa tattttctca tattttctct aa                       702


<210> SEQ ID NO 8
<211> LENGTH: 233
<212> TYPE: PRT
<213> ORGANISM: Anabaena flos-aquae

<400> SEQUENCE: 8

Met Ile Asn Glu Asp Asp Leu Leu Asn Ile Ala Ile Val Asn Ile Arg
1               5                   10                  15

Lys Val Ser Lys Phe Lys Pro Tyr Lys Ser Tyr Ser Gly Val Asn Asn
            20                  25                  30

Lys Glu Glu Phe Gln Gln Leu Ile Ala Asn Asp Pro Ala Phe Gly Ser
        35                  40                  45

Leu Gly Leu Asp Asp Glu Arg Tyr Ile Ile Ala Arg Val Gly Gly Asn
    50                  55                  60

Leu Val Thr Ser Leu His Arg Lys Leu Gly Asp Met Tyr Glu Asn Leu
65                  70                  75                  80

Phe Ala Tyr Leu Leu Lys Glu Ser Phe Gly Leu Asn Glu Asn Glu Leu
                85                  90                  95

His Phe Ser Val Asn Val Lys Ile Gly Lys Arg Asp Gln Val Arg Ser
            100                 105                 110

Thr Asp Gly Leu Ile Arg Lys Asp Lys Phe Asn Gln Asn Ile Pro Ser
        115                 120                 125

Asp Trp Ile Lys Tyr Glu Gly Ile Gly Phe Glu Val Arg Ser Cys Tyr
    130                 135                 140

Gln Ile Gly Asp Ser Lys Arg Ile Gln Ala Asp Tyr Asp Met Ser Leu
145                 150                 155                 160

Ala Leu Lys Ser Tyr Glu Ile Leu Pro Val Met Leu Ile Phe Cys Asn
                165                 170                 175

Thr Ser Leu Lys Ser Pro Val Leu Arg Leu Ser Lys Ser Trp Glu Leu
            180                 185                 190

Tyr Glu Gly Arg Asn Ser Phe Asp Leu Val His Thr Ile Thr Gly Phe
        195                 200                 205

Asp Leu Tyr Asn Phe Leu Gln Ile Asn Ser Glu Leu Leu Lys Lys Glu
    210                 215                 220

Ile Asp Asn Ile Phe Ser Tyr Phe Leu
225                 230


<210> SEQ ID NO 9
<211> LENGTH: 1068
<212> TYPE: DNA
<213> ORGANISM: Acetobacter pasteurianus sub. pasteurianus

<400> SEQUENCE: 9

atggcccgca acgtgttagt tgaacgtgcg gtggacgctg cgcttgaacg gctggacgcc     60

ttcattgaag gcgagaagct ggcaaagttg cccgatgctg cgacccgagc attactggac    120

gaccagcttg gccacggatc taacagcgtt cgattagcat cgctgttctt tgtcttctat    180

gcgtcagttg atctggcatg ggattgcaat tcaatcccga ccggaattcg cggcacctac    240

ggcgacaagc ggttggcgac gcaacttggg cttcgtagca tcacgcttca caatgccatt    300

acggccttcg gagaaaacct tggctggaaa ggaaacgtta ctaattcgcg ccttcagaac    360

gacgtgcgat tcgacggatt tggccgaact cttactggcc tgaacgtcga acagcggacg    420
```

-continued

```
ctatgcgctg actatatggc cgcacggttt gccgaaagcc ggaaagtcat tgcaccgtta    480

ccaccagtcg ccgatgacgt gttgacctac gcccgtgcgc ggaagctgtt ctattcactg    540

atcgcccttc catccgaagg taacgttcag caattcctta tcgccgcact gttgttcgtt    600

catcgccagc gatacggtta tgacattcga acccatcacg ttcatgcttc agaccgcttc    660

gatacgacag cgggcgatat tgaggaactg ctgaacggcg accttgtgcg cgcctacgaa    720

gtgacagttc gacccgattg gaagaaccgc atgggcgact tccgaaaaaa gatggatggt    780

gcgagccttc gcaaatacac catcattgcg tcgaacgtga acagcgacga cgatcttgcc    840

gaacccgccg acatgatccg cttccttacg ccctatggcc gcgacattgc gatcgtggat    900

attcacgatt tcatcaacgt gttcgcaatg gaattgatcg tcgacgaact gtgtcgggct    960

gtcacgcaaa cctacaacta tcttacaacg ccaagcttgt gcggacgtgc tgatattatc   1020

gataagttca acgctaccgt cgaaggttgg ttggatgaag taacctaa                1068
```

<210> SEQ ID NO 10
<211> LENGTH: 355
<212> TYPE: PRT
<213> ORGANISM: Acetobacter pasteurianus sub. pasteurianus

<400> SEQUENCE: 10

```
Met Ala Arg Asn Val Leu Val Glu Arg Ala Val Asp Ala Ala Leu Glu
1               5                   10                  15

Arg Leu Asp Ala Phe Ile Glu Gly Glu Lys Leu Ala Lys Leu Pro Asp
            20                  25                  30

Ala Ala Thr Arg Ala Leu Leu Asp Asp Gln Leu Gly His Gly Ser Asn
        35                  40                  45

Ser Val Arg Leu Ala Ser Leu Phe Phe Val Phe Tyr Ala Ser Val Asp
    50                  55                  60

Leu Ala Trp Asp Cys Asn Ser Ile Pro Thr Gly Ile Arg Gly Thr Tyr
65                  70                  75                  80

Gly Asp Lys Arg Leu Ala Thr Gln Leu Gly Leu Arg Ser Ile Thr Leu
                85                  90                  95

His Asn Ala Ile Thr Ala Phe Gly Glu Asn Leu Gly Trp Lys Gly Asn
            100                 105                 110

Val Thr Asn Ser Arg Leu Gln Asn Asp Val Arg Phe Asp Gly Phe Gly
        115                 120                 125

Arg Thr Leu Thr Gly Leu Asn Val Glu Gln Arg Thr Leu Cys Ala Asp
    130                 135                 140

Tyr Met Ala Ala Arg Phe Ala Glu Ser Arg Lys Val Ile Ala Pro Leu
145                 150                 155                 160

Pro Pro Val Ala Asp Asp Val Leu Thr Tyr Ala Arg Ala Arg Lys Leu
                165                 170                 175

Phe Tyr Ser Leu Ile Ala Leu Pro Ser Glu Gly Asn Val Gln Gln Phe
            180                 185                 190

Leu Ile Ala Ala Leu Leu Phe Val His Arg Gln Arg Tyr Gly Tyr Asp
        195                 200                 205

Ile Arg Thr His His Val His Ala Ser Asp Arg Phe Asp Thr Thr Ala
    210                 215                 220

Gly Asp Ile Glu Glu Leu Leu Asn Gly Asp Leu Val Arg Ala Tyr Glu
225                 230                 235                 240

Val Thr Val Arg Pro Asp Trp Lys Asn Arg Met Gly Asp Phe Arg Lys
                245                 250                 255

Lys Met Asp Gly Ala Ser Leu Arg Lys Tyr Thr Ile Ile Ala Ser Asn
```

-continued

```
            260                 265                 270

Val Asn Ser Asp Asp Asp Leu Ala Glu Pro Ala Asp Met Ile Arg Phe
        275                 280                 285

Leu Thr Pro Tyr Gly Arg Asp Ile Ala Ile Val Asp Ile His Asp Phe
    290                 295                 300

Ile Asn Val Phe Ala Met Glu Leu Ile Val Asp Glu Leu Cys Arg Ala
305                 310                 315                 320

Val Thr Gln Thr Tyr Asn Tyr Leu Thr Thr Pro Ser Leu Cys Gly Arg
                325                 330                 335

Ala Asp Ile Ile Asp Lys Phe Asn Ala Thr Val Glu Gly Trp Leu Asp
            340                 345                 350

Glu Val Thr
        355


<210> SEQ ID NO 11
<211> LENGTH: 714
<212> TYPE: DNA
<213> ORGANISM: Arthrobacter protophormiae

<400> SEQUENCE: 11

atggcgcaga aggcacgact tcggcagaac cgctacggga ctgtcatcaa tacgacctcg      60

tctaagcagg agctgcagct cggtgacgcg cttgtcgatg ccaccgagcg ccttacggcg     120

aagttcggta tcgccttcac gcacgagaag aaggtgatgc tcgctgatat cgtcacctcc     180

ctccgccgca gcttcccgac ggtgtcgttc gatgacccgc tcccgaacac ttacatgagc     240

cccgacggcg gcatcctctc aatcatggcg gcggacggcg agcgcacatt ccctgtactg     300

atcacggagg tgaagaacca ggggaccaac gacctgcggg ctcaggaggg gctgaagaag     360

caagcgatgg gtaatgccat cgagcgcctc gggaagaacg tgatcggatt ccgcgcaatg     420

atgctggagg acggaatcat cccgttcgtg tgctttggct acggctggga tttccacgag     480

ggtagttcga ttctcgacag ggtgaagacc atcgctatgt tcggcgagct gaatcaggtg     540

aacgtcatcc ctgaagggga ggaggggctc ttcaatcgag gcagcttctt cttccggatg     600

gagccttggt ccttggaaga gatgtcggat gtgatgtttg acgtcgggag ccgtgcgatt     660

cactactact tcgctaagtt cggcgattct gcgttcaaaa tgattggttc ctaa           714


<210> SEQ ID NO 12
<211> LENGTH: 237
<212> TYPE: PRT
<213> ORGANISM: Arthrobacter protophormiae

<400> SEQUENCE: 12

Met Ala Gln Lys Ala Arg Leu Arg Gln Asn Arg Tyr Gly Thr Val Ile
1               5                   10                  15

Asn Thr Thr Ser Ser Lys Gln Glu Leu Gln Leu Gly Asp Ala Leu Val
            20                  25                  30

Asp Ala Thr Glu Arg Leu Thr Ala Lys Phe Gly Ile Ala Phe Thr His
        35                  40                  45

Glu Lys Lys Val Met Leu Ala Asp Ile Val Thr Ser Leu Arg Arg Ser
    50                  55                  60

Phe Pro Thr Val Ser Phe Asp Asp Pro Leu Pro Asn Thr Tyr Met Ser
65                  70                  75                  80

Pro Asp Gly Gly Ile Leu Ser Ile Met Ala Ala Asp Gly Glu Arg Thr
                85                  90                  95

Phe Pro Val Leu Ile Thr Glu Val Lys Asn Gln Gly Thr Asn Asp Leu
            100                 105                 110
```

-continued

```
Arg Ala Gln Glu Gly Leu Lys Lys Gln Ala Met Gly Asn Ala Ile Glu
        115                 120                 125

Arg Leu Gly Lys Asn Val Ile Gly Phe Arg Ala Met Met Leu Glu Asp
    130                 135                 140

Gly Ile Ile Pro Phe Val Cys Phe Gly Tyr Gly Trp Asp Phe His Glu
145                 150                 155                 160

Gly Ser Ser Ile Leu Asp Arg Val Lys Thr Ile Ala Met Phe Gly Glu
                165                 170                 175

Leu Asn Gln Val Asn Val Ile Pro Glu Gly Glu Glu Gly Leu Phe Asn
            180                 185                 190

Arg Gly Ser Phe Phe Phe Arg Met Glu Pro Trp Ser Leu Glu Glu Met
        195                 200                 205

Ser Asp Val Met Phe Asp Val Gly Ser Arg Ala Ile His Tyr Tyr Phe
    210                 215                 220

Ala Lys Phe Gly Asp Ser Ala Phe Lys Met Ile Gly Ser
225                 230                 235


<210> SEQ ID NO 13
<211> LENGTH: 1368
<212> TYPE: DNA
<213> ORGANISM: Arthrobacter species

<400> SEQUENCE: 13

gtgattgaat ttcccgagta tcgagacagc tcggccgcgc caaagatttc agaccttgaa     60

aggctgatgg atcgctcctt gaccaactcg cagtacgtgg atggggcgaa cgcagctcgc    120

ttgctaggca catttatccg gtcatttcgt agcgtcattg gtagcgccga ggagtcggcc    180

actcgagcca atttagttga ggcgcacgac gaggcgaaac tcttcgggtt gatgctatcc    240

gcgggattcg acctaatttg taatgcagaa tatgtccacg ggcgattggt caacaataag    300

tggatctact gccaccgagg gggtgagccg gctgtcgcct attactcttt cctgaaacag    360

tgtcctcggt gctgccttga ccgaggcttg gaggggcggc tgagtggcgc acagcacaag    420

ccgacgagcc atcacatcgg tgagataacc accgtcgcga tcgcccttct tctccagttg    480

gtggctgccg ctaacgagaa tccgttcgaa atcgccacga tcacaaaaca gtcgcatgac    540

gttgatgcca ttggcttccg tgacgatctt ttggtccttt tcgagattaa agcttcccca    600

atggtctcct ttcctctggt gactgaactg gaagaaccaa tgctgcagga gggccccgac    660

ggcccagtag agtaccggca acactcattg gtggatttaa cgctgcaagg ccgagaattc    720

gctgtagcta tcccgcacgc agagacggca atccctctcg gtgaacgaga gggggagtct    780

tggccctatg aaccgctgat cgactacttc tcagtacccg ccaatgccgc tagttatctg    840

caggcgtgga tcgagctgta cgcggcttac agaaccccca agacgcaaag agcgggccgg    900

actgctgcgc tcgcgtatct cgtgaacggc tggggtgacg agatcgactc caataagact    960

aagcctgggc ttgggcggac tgatgacgta aaaaaaggca cttatcagtt gttgaagttc   1020

ggttcctact atagggacga cgccgcaagt gtgcctgtaa ggggtgctct ggtcgccaac   1080

cttgatccgc tctttctgcg ccctggttac atcgatggac tgtctgacgt gcgctggggc   1140

cacgggcgcg atttcacgct tgaggagggt gaatacagga tcgcggaagg atcgctgcgg   1200

catctgtacg atgcgatact tgcgttcaac gacccgctgt taaacgaccc gctccttcaa   1260

gagatattcg atcttggtgc cgtggagagg aaactggcca atggcgacct ggaagcactc   1320

ttggacaaat ggattgcgcg acccgagata gtgcttgacc ctagttga                 1368
```

-continued

<210> SEQ ID NO 14
<211> LENGTH: 455
<212> TYPE: PRT
<213> ORGANISM: Arthrobacter species

<400> SEQUENCE: 14

```
Val Ile Glu Phe Pro Glu Tyr Arg Asp Ser Ser Ala Ala Pro Lys Ile
1               5                   10                  15

Ser Asp Leu Glu Arg Leu Met Asp Arg Ser Leu Thr Asn Ser Gln Tyr
            20                  25                  30

Val Asp Gly Ala Asn Ala Ala Arg Leu Leu Gly Thr Phe Ile Arg Ser
        35                  40                  45

Phe Arg Ser Val Ile Gly Ser Ala Glu Glu Ser Ala Thr Arg Ala Asn
    50                  55                  60

Leu Val Glu Ala His Asp Glu Ala Lys Leu Phe Gly Leu Met Leu Ser
65                  70                  75                  80

Ala Gly Phe Asp Leu Ile Cys Asn Ala Glu Tyr Val His Gly Arg Leu
                85                  90                  95

Val Asn Asn Lys Trp Ile Tyr Cys His Arg Gly Gly Glu Pro Ala Val
            100                 105                 110

Ala Tyr Tyr Ser Phe Leu Lys Gln Cys Pro Arg Cys Cys Leu Asp Arg
        115                 120                 125

Gly Leu Glu Gly Arg Leu Ser Gly Ala Gln His Lys Pro Thr Ser His
    130                 135                 140

His Ile Gly Glu Ile Thr Thr Val Ala Ile Ala Leu Leu Leu Gln Leu
145                 150                 155                 160

Val Ala Ala Ala Asn Glu Asn Pro Phe Glu Ile Ala Thr Ile Thr Lys
                165                 170                 175

Gln Ser His Asp Val Asp Ala Ile Gly Phe Arg Asp Asp Leu Leu Val
            180                 185                 190

Leu Phe Glu Ile Lys Ala Ser Pro Met Val Ser Phe Pro Leu Val Thr
        195                 200                 205

Glu Leu Glu Glu Pro Met Leu Gln Glu Gly Pro Asp Gly Pro Val Glu
    210                 215                 220

Tyr Arg Gln His Ser Leu Val Asp Leu Thr Leu Gln Gly Arg Glu Phe
225                 230                 235                 240

Ala Val Ala Ile Pro His Ala Glu Thr Ala Ile Pro Leu Gly Glu Arg
                245                 250                 255

Glu Gly Glu Ser Trp Pro Tyr Glu Pro Leu Ile Asp Tyr Phe Ser Val
            260                 265                 270

Pro Ala Asn Ala Ala Ser Tyr Leu Gln Ala Trp Ile Glu Leu Tyr Ala
        275                 280                 285

Ala Tyr Arg Thr Pro Lys Thr Gln Arg Ala Gly Arg Thr Ala Ala Leu
    290                 295                 300

Ala Tyr Leu Val Asn Gly Trp Gly Asp Glu Ile Asp Ser Asn Lys Thr
305                 310                 315                 320

Lys Pro Gly Leu Gly Arg Thr Asp Asp Val Lys Lys Gly Thr Tyr Gln
                325                 330                 335

Leu Leu Lys Phe Gly Ser Tyr Tyr Arg Asp Asp Ala Ala Ser Val Pro
            340                 345                 350

Val Arg Gly Ala Leu Val Ala Asn Leu Asp Pro Leu Phe Leu Arg Pro
        355                 360                 365

Gly Tyr Ile Asp Gly Leu Ser Asp Val Arg Trp Gly His Gly Arg Asp
    370                 375                 380

Phe Thr Leu Glu Glu Gly Glu Tyr Arg Ile Ala Glu Gly Ser Leu Arg
```

-continued

```
385                 390                 395                 400

His Leu Tyr Asp Ala Ile Leu Ala Phe Asn Asp Pro Leu Leu Asn Asp
                405                 410                 415

Pro Leu Leu Gln Glu Ile Phe Asp Leu Gly Ala Val Glu Arg Lys Leu
            420                 425                 430

Ala Asn Gly Asp Leu Glu Ala Leu Leu Asp Lys Trp Ile Ala Arg Pro
        435                 440                 445

Glu Ile Val Leu Asp Pro Ser
    450                 455


<210> SEQ ID NO 15
<211> LENGTH: 735
<212> TYPE: DNA
<213> ORGANISM: Aquaspirillum serpens

<400> SEQUENCE: 15

atgttgagag gactaactgt ggaactttta gaattaaaaa atagaataac cacctcattt      60

agcggtaccg aggatgattt aagagaagtt ctagacttga tagagcaaga tcagcctgtg     120

tttccgttta atgagtatga gcatctcatt tgtaatctta tcgaaaaggg tggtcttaat     180

tataatcaat atattgaaat tagatcggaa tatatcagtc aaaacccgaa cttatggatt     240

tttgaaatat cagcccctag aggatttggt gagaaatttg cccaaacata tgtgaaaggt     300

aagtgttcaa aactaaaaac ccccatccaaa aaattagacc caaattatgc tggagaatat     360

gatctttggc tcgacggaat tactattgag gtaaaagcat ctagagcagt agatagtaat     420

agtgaagaac ctctttatgt gaaagcatta gcaagagata caaacaggca attcattatg     480

aattttcagc aactgaaacc gcaatactgt gatgtattta tatgggttgc cgtctttcgg     540

gatgaaattg tgttatggat aatgagttca gatgaggttg aaaaaaatcc tttttattca     600

aaagggcaac atagaggcaa caaaggaaac gaagggcagt tgcatataaa acatgacaaa     660

atccacttat tctcaaagta tgagcttaag gatgatgatt tggagggggc aatacggaaa     720

gcagcaaaag gataa                                                       735


<210> SEQ ID NO 16
<211> LENGTH: 244
<212> TYPE: PRT
<213> ORGANISM: Aquaspirillum serpens

<400> SEQUENCE: 16

Met Leu Arg Gly Leu Thr Val Glu Leu Leu Glu Leu Lys Asn Arg Ile
1               5                   10                  15

Thr Thr Ser Phe Ser Gly Thr Glu Asp Asp Leu Arg Glu Val Leu Asp
            20                  25                  30

Leu Ile Glu Gln Asp Gln Pro Val Phe Pro Phe Asn Glu Tyr Glu His
        35                  40                  45

Leu Ile Cys Asn Leu Ile Glu Lys Gly Gly Leu Asn Tyr Asn Gln Tyr
    50                  55                  60

Ile Glu Ile Arg Ser Glu Tyr Ile Ser Gln Asn Pro Asn Leu Trp Ile
65                  70                  75                  80

Phe Glu Ile Ser Ala Pro Arg Gly Phe Gly Glu Lys Phe Ala Gln Thr
                85                  90                  95

Tyr Val Lys Gly Lys Cys Ser Lys Leu Lys Thr Pro Ser Lys Lys Leu
            100                 105                 110

Asp Pro Asn Tyr Ala Gly Glu Tyr Asp Leu Trp Leu Asp Gly Ile Thr
        115                 120                 125
```

-continued

```
Ile Glu Val Lys Ala Ser Arg Ala Val Asp Ser Asn Ser Glu Glu Pro
    130                 135                 140

Leu Tyr Val Lys Ala Leu Ala Arg Asp Thr Asn Arg Gln Phe Ile Met
145                 150                 155                 160

Asn Phe Gln Gln Leu Lys Pro Gln Tyr Cys Asp Val Phe Ile Trp Val
                165                 170                 175

Ala Val Phe Arg Asp Glu Ile Val Leu Trp Ile Met Ser Ser Asp Glu
            180                 185                 190

Val Glu Lys Asn Pro Phe Tyr Ser Lys Gly Gln His Arg Gly Asn Lys
        195                 200                 205

Gly Asn Glu Gly Gln Leu His Ile Lys His Asp Lys Ile His Leu Phe
    210                 215                 220

Ser Lys Tyr Glu Leu Lys Asp Asp Asp Leu Glu Gly Ala Ile Arg Lys
225                 230                 235                 240

Ala Ala Lys Gly


<210> SEQ ID NO 17
<211> LENGTH: 372
<212> TYPE: DNA
<213> ORGANISM: Acinetobacter species 1690

<400> SEQUENCE: 17

aatttaaacg tgtattttgg taaaggtaga gaaaataaac aaactggaaa gatcattcct      60

cgtccgtggt atgaaataga gatcatttct agtaacgata tcaatagttt acctgattat     120

ccaaaaggtg acttctatgc atatacggat gatggcttaa ttattcctat gagaactcaa     180

ggggactatt ttaaaaattt aagatcaaaa gatagcctgc aaatttttgg tatgtggctg     240

aagggaaaac tagaaaaagc gggagtgtta aaaaaatata cgcctgttac gattgacact     300

ttaagggagt atggtaatag caagctaaca ctttataaaa taagtgaaaa tgagtatttt     360

atggattttt ag                                                         372


<210> SEQ ID NO 18
<211> LENGTH: 334
<212> TYPE: PRT
<213> ORGANISM: Acinetobacter species 1690

<400> SEQUENCE: 18

Met Phe Thr Asn Leu Asp Lys His His Gly Gly Asn Phe Arg Asp Val
1               5                   10                  15

Leu Glu Tyr Asn Leu Val Thr Ala Lys Lys Val Arg Ile Ala Ser Gly
            20                  25                  30

Tyr Val Ser Leu His Thr Ile Gln Ala Tyr Arg Thr Gln Leu Glu Asp
        35                  40                  45

Ile Ala Cys Arg Tyr Gly Asn Val Gln Leu Met Leu Gly Met Ala Phe
    50                  55                  60

Tyr Glu Gly Leu Ser Val Lys Gln Leu Asp Ala Cys Leu Asp Leu His
65                  70                  75                  80

Asn Ser Leu Ser Leu His Pro Asn Ser Gly Val Tyr Val Ala His Gly
                85                  90                  95

Arg Arg Tyr His Gly Lys Ile Tyr Asp Phe Asn Glu Gly Val Asp Asn
            100                 105                 110

Lys Ile Phe Val Gly Ser Ser Asn Phe Ser Pro Ser Gly Leu Ala Gly
        115                 120                 125

Asn Ile Glu Cys Thr Val Glu Val Ile Asp Arg Ser Gln Lys Ala Gln
    130                 135                 140
```

-continued

```
Val Asn Asn Phe Leu Asp Thr Leu Phe Asp Lys His Ser Glu Lys Ile
145                 150                 155                 160

Asn Asn Val Val Ile Asn Thr Gly Thr Lys Arg Val Val Ser Leu Ser
                165                 170                 175

Ile Asp Glu Lys Tyr Arg Lys Leu Leu Arg His Ser Arg Thr Ile Asn
            180                 185                 190

Thr Ala Leu Asn Lys Val Glu Ile Asp Leu Glu Arg Ile Ala Glu Lys
        195                 200                 205

Pro Ser Ser Asn Leu Asn Val Tyr Phe Gly Lys Gly Arg Glu Asn Lys
    210                 215                 220

Gln Thr Gly Lys Ile Ile Pro Arg Pro Trp Tyr Glu Ile Glu Ile Ile
225                 230                 235                 240

Ser Ser Asn Asp Ile Asn Ser Leu Pro Asp Tyr Pro Lys Gly Asp Phe
                245                 250                 255

Tyr Ala Tyr Thr Asp Asp Gly Leu Ile Ile Pro Met Arg Thr Gln Gly
            260                 265                 270

Asp Tyr Phe Lys Asn Leu Arg Ser Lys Asp Ser Leu Gln Ile Phe Gly
        275                 280                 285

Met Trp Leu Lys Gly Lys Leu Glu Lys Ala Gly Val Leu Lys Lys Tyr
    290                 295                 300

Thr Pro Val Thr Ile Asp Thr Leu Arg Glu Tyr Gly Asn Ser Lys Leu
305                 310                 315                 320

Thr Leu Tyr Lys Ile Ser Glu Asn Glu Tyr Phe Met Asp Phe
                325                 330
```

<210> SEQ ID NO 19
<211> LENGTH: 1077
<212> TYPE: DNA
<213> ORGANISM: Anabaena variabilis uw

<400> SEQUENCE: 19

```
atggaagaag accttgattt atctgaaaat atcgaagctg catctgcgga gcttacgact     60

ctttatcagg tagctgctga tgctatgaaa gattatattg aaatctatct tgcgctgagt    120

aaacagtctg atgggttttc aaatattaac aatcttgact taacttctcg taacaggcgt    180

ttggtagtta tacatggact ttcgttagag ttagatccag atacttcgac tccagaggaa    240

attaaacgtg aagctgaacg aatgctagcg atagctcttg atacagagtc agcaattacg    300

gcaggagtat atgaaaaaat gcgtctcttc gcaagctctt tagtagatca gctatttgaa    360

caaacggatg aacttaattc attatcatcg gaatatttgt cagcaaatcc aggatttttg    420

ccgtttttcc agcagttggc ggggcttaga agtaaatcag agttaaagag agaagtagga    480

aatgcctctg acaatagtat ttctaaagcg gttgcagaga gaatattaga gcgcattata    540

cgtaacttga gaattcgcac tttttccaaa gagaaactat tacaagctgt tgagcctact    600

ttagaaggaa tagtcaggga tctcgtagga aaagtgttat tggaaaatat agttgctgat    660

gctttatctg atttacaagt tcctttcatg cgtgaatcag agtatcaaag ccttaaagga    720

gtgatttatg atttccgcgc tgattttgtg ataccagacg cacaaaatcc aattgctttt    780

atcgaggtgc gaaaaagctc tacacgacat gcgtcactct atgccaagga taagatgttt    840

tcagcgatta attggaaagg aaaaaataaa aggcttttgg gtattttggt tgtggaagga    900

ccttggacaa gagaaactct tcgcgtcatg gcaaatgtgt ttgattacgt tacaccttta    960

actcgtgttt cccaagttgc agaagctatc agagcatatc tagatgggga taaaacgaga   1020

ctgaagtggt tagttaattt cagtattgaa gaagcagacc acgacaacat aacctaa      1077
```

<210> SEQ ID NO 20
<211> LENGTH: 358
<212> TYPE: PRT
<213> ORGANISM: Anabaena variabilis uw

<400> SEQUENCE: 20

```
Met Glu Glu Asp Leu Asp Leu Ser Glu Asn Ile Glu Ala Ala Ser Ala
1               5                   10                  15

Glu Leu Thr Thr Leu Tyr Gln Val Ala Ala Asp Ala Met Lys Asp Tyr
            20                  25                  30

Ile Glu Ile Tyr Leu Ala Leu Ser Lys Gln Ser Asp Gly Phe Ser Asn
        35                  40                  45

Ile Asn Asn Leu Asp Leu Thr Ser Arg Asn Arg Arg Leu Val Val Ile
    50                  55                  60

His Gly Leu Ser Leu Glu Leu Asp Pro Asp Thr Ser Thr Pro Glu Glu
65                  70                  75                  80

Ile Lys Arg Glu Ala Glu Arg Met Leu Ala Ile Ala Leu Asp Thr Glu
                85                  90                  95

Ser Ala Ile Thr Ala Gly Val Tyr Glu Lys Met Arg Leu Phe Ala Ser
            100                 105                 110

Ser Leu Val Asp Gln Leu Phe Glu Gln Thr Asp Glu Leu Asn Ser Leu
        115                 120                 125

Ser Ser Glu Tyr Leu Ser Ala Asn Pro Gly Phe Leu Pro Phe Phe Gln
    130                 135                 140

Gln Leu Ala Gly Leu Arg Ser Lys Ser Glu Leu Lys Arg Glu Val Gly
145                 150                 155                 160

Asn Ala Ser Asp Asn Ser Ile Ser Lys Ala Val Ala Glu Arg Ile Leu
                165                 170                 175

Glu Arg Ile Ile Arg Asn Leu Arg Ile Arg Thr Phe Ser Lys Glu Lys
            180                 185                 190

Leu Leu Gln Ala Val Glu Pro Thr Leu Glu Gly Ile Val Arg Asp Leu
        195                 200                 205

Val Gly Lys Val Leu Leu Glu Asn Ile Val Ala Asp Ala Leu Ser Asp
    210                 215                 220

Leu Gln Val Pro Phe Met Arg Glu Ser Glu Tyr Gln Ser Leu Lys Gly
225                 230                 235                 240

Val Ile Tyr Asp Phe Arg Ala Asp Phe Val Ile Pro Asp Ala Gln Asn
                245                 250                 255

Pro Ile Ala Phe Ile Glu Val Arg Lys Ser Ser Thr Arg His Ala Ser
            260                 265                 270

Leu Tyr Ala Lys Asp Lys Met Phe Ser Ala Ile Asn Trp Lys Gly Lys
        275                 280                 285

Asn Lys Arg Leu Leu Gly Ile Leu Val Val Glu Gly Pro Trp Thr Arg
    290                 295                 300

Glu Thr Leu Arg Val Met Ala Asn Val Phe Asp Tyr Val Thr Pro Leu
305                 310                 315                 320

Thr Arg Val Ser Gln Val Ala Glu Ala Ile Arg Ala Tyr Leu Asp Gly
                325                 330                 335

Asp Lys Thr Arg Leu Lys Trp Leu Val Asn Phe Ser Ile Glu Glu Ala
            340                 345                 350

Asp His Asp Asn Ile Thr
        355
```

<210> SEQ ID NO 21
<211> LENGTH: 1620

<212> TYPE: DNA
<213> ORGANISM: Bacillus brevis
<220> FEATURE:
<221> NAME/KEY: misc_feature
<222> LOCATION: (64)..(64)
<223> OTHER INFORMATION: r= g or a
<220> FEATURE:
<221> NAME/KEY: misc_feature
<222> LOCATION: (116)..(116)
<223> OTHER INFORMATION: k= g or t/u

<400> SEQUENCE: 21

```
atgacagaaa gaaaagtctg gtttattaca agaccggagc gtgatccaaa gtttcacagg     60
gaarcccttc tggctctgca gaaagcaaca aacggcttca cagtaaagtg gtccgkaaac    120
cgcacagcac atctcgcata tgagcaggcg ctggccgatg ctgaggtaaa gcgtccaaac    180
atcagtaatg atggctctgg tggacgaaca tgggccgcaa tgctgaagac atttgcctac    240
tgctatacaa acgaagaggg ctaccttgta ccgaccaaag tcggagaagc actgttaaaa    300
aggcacaaag tattcgacaa cgttaaaaaa cagattctca ctcttcagat tccgaatgcc    360
tattttctgg aggccggatt ccggccaaaa tttgatgaat ctttccgtat tcgtccagcc    420
cggttcctga tccgcctagt aaatcaagag gagctggcct accacgtcac gaaagaagaa    480
attactttct ttgcgctaac agcatcaaag gacagccagt tgtcagagat tacagcaaaa    540
atcaaagcat ttcgcgttgc ttcttctgct gaaagactag aaatgaaagc agacatcgct    600
gctcaatatg accatcgtga gcgaacagat aaaggggcgc gcgattttga gactgctcac    660
tctgatgttg cccatacctt tatgctaatc tgcgacgcca caggaatggt tgagtacatt    720
cgcggtcaat ccctgagggt aaatccagaa gaaaatcaga agcttagcca ggagttggag    780
gagctggagg cacggtatcc cttcaacaac cgatacaaaa tttccctaga acggatggca    840
gaaaacaatg gtcttgatgt cgaaagctac aaggcgagcc gtaatagcgg aaaaggacaa    900
gcgacaaatg cagcaaagag actgagaaaa ataaacgaaa tcatgaacgc gtatcccaat    960
cccgctgctt tgccgcagga agaactggag agaatcctcg cagaagaggt cggtccgcgt   1020
gaagctcaaa agtatgcatt cgaattaaaa gaaagtcagg tagccttcag cggactgaat   1080
acagagttcg tagagagtta tctgtatgaa gaagacaatc tccgattcga agacaaaaca   1140
ggggaagtgc tcaaagcgat cggttttgac gttgaaatgc ggcccaaacc tgcatccatg   1200
gagcgaacag aaattgagat catggtgaag tatggcgata ggcagtgcgg tattattgat   1260
gccaagaact accggcaaaa gtttgctctt tctgcctcac tgacatcgca tatggcatcc   1320
gagtatatac cgaactatca gggatacaag gggcttaatg tacagttttt tggatatgta   1380
accgctgctg acttttctgg cgaaaaaaat cttgaaaaaa tcagcaataa agtacaggaa   1440
cacacttcta gcagagacat aaaaggacta atgctcagcg ctaaagtatt gcttggattt   1500
cttgattact gcttagagaa cgatattccc gaaaacgaac gtgtgaatct gtttatacgc   1560
gctgtccaaa accggggcta caaaacgctg ggagagatgc tgaaagaagc taaatactaa   1620
```

<210> SEQ ID NO 22
<211> LENGTH: 539
<212> TYPE: PRT
<213> ORGANISM: Bacillus brevis
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 22

```
Met Thr Glu Arg Lys Val Trp Phe Ile Thr Arg Pro Glu Arg Asp Pro
1               5                   10                  15

Lys Phe His Arg Glu Xaa Leu Leu Ala Leu Gln Lys Ala Thr Asn Gly
            20                  25                  30

Phe Thr Val Lys Trp Ser Xaa Asn Arg Thr Ala His Leu Ala Tyr Glu
        35                  40                  45

Gln Ala Leu Ala Asp Ala Glu Val Lys Arg Pro Asn Ile Ser Asn Asp
    50                  55                  60

Gly Ser Gly Gly Arg Thr Trp Ala Ala Met Leu Lys Thr Phe Ala Tyr
65                  70                  75                  80

Cys Tyr Thr Asn Glu Glu Gly Tyr Leu Val Pro Thr Lys Val Gly Glu
                85                  90                  95

Ala Leu Leu Lys Arg His Lys Val Phe Asp Asn Val Lys Lys Gln Ile
            100                 105                 110

Leu Thr Leu Gln Ile Pro Asn Ala Tyr Phe Leu Glu Ala Gly Phe Arg
        115                 120                 125

Pro Lys Phe Asp Glu Ser Phe Arg Ile Arg Pro Ala Arg Phe Leu Ile
    130                 135                 140

Arg Leu Val Asn Gln Glu Glu Leu Ala Tyr His Val Thr Lys Glu Glu
145                 150                 155                 160

Ile Thr Phe Phe Ala Leu Thr Ala Ser Lys Asp Ser Gln Leu Ser Glu
                165                 170                 175

Ile Thr Ala Lys Ile Lys Ala Phe Arg Val Ala Ser Ser Ala Glu Arg
            180                 185                 190

Leu Glu Met Lys Ala Asp Ile Ala Ala Gln Tyr Asp His Arg Glu Arg
        195                 200                 205

Thr Asp Lys Gly Ala Arg Asp Phe Glu Thr Ala His Ser Asp Val Ala
    210                 215                 220

His Thr Phe Met Leu Ile Cys Asp Ala Thr Gly Met Val Glu Tyr Ile
225                 230                 235                 240

Arg Gly Gln Ser Leu Arg Val Asn Pro Glu Glu Asn Gln Lys Leu Ser
                245                 250                 255

Gln Glu Leu Glu Glu Leu Glu Ala Arg Tyr Pro Phe Asn Asn Arg Tyr
            260                 265                 270

Lys Ile Ser Leu Glu Arg Met Ala Glu Asn Asn Gly Leu Asp Val Glu
        275                 280                 285

Ser Tyr Lys Ala Ser Arg Asn Ser Gly Lys Gly Gln Ala Thr Asn Ala
    290                 295                 300

Ala Lys Arg Leu Arg Lys Ile Asn Glu Ile Met Asn Ala Tyr Pro Asn
305                 310                 315                 320

Pro Ala Ala Leu Pro Gln Glu Glu Leu Glu Arg Ile Leu Ala Glu Glu
                325                 330                 335

Val Gly Pro Arg Glu Ala Gln Lys Tyr Ala Phe Glu Leu Lys Glu Ser
            340                 345                 350

Gln Val Ala Phe Ser Gly Leu Asn Thr Glu Phe Val Glu Ser Tyr Leu
        355                 360                 365

Tyr Glu Glu Asp Asn Leu Arg Phe Glu Asp Lys Thr Gly Glu Val Leu
    370                 375                 380

Lys Ala Ile Gly Phe Asp Val Glu Met Arg Pro Lys Pro Ala Ser Met
385                 390                 395                 400

Glu Arg Thr Glu Ile Glu Ile Met Val Lys Tyr Gly Asp Arg Gln Cys
                405                 410                 415
```

```
Gly Ile Ile Asp Ala Lys Asn Tyr Arg Gln Lys Phe Ala Leu Ser Ala
            420                 425                 430

Ser Leu Thr Ser His Met Ala Ser Glu Tyr Ile Pro Asn Tyr Gln Gly
        435                 440                 445

Tyr Lys Gly Leu Asn Val Gln Phe Phe Gly Tyr Val Thr Ala Ala Asp
    450                 455                 460

Phe Ser Gly Glu Lys Asn Leu Glu Lys Ile Ser Asn Lys Val Gln Glu
465                 470                 475                 480

His Thr Ser Ser Arg Asp Ile Lys Gly Leu Met Leu Ser Ala Lys Val
                485                 490                 495

Leu Leu Gly Phe Leu Asp Tyr Cys Leu Glu Asn Asp Ile Pro Glu Asn
            500                 505                 510

Glu Arg Val Asn Leu Phe Ile Arg Ala Val Gln Asn Arg Gly Tyr Lys
        515                 520                 525

Thr Leu Gly Glu Met Leu Lys Glu Ala Lys Tyr
    530                 535
```

<210> SEQ ID NO 23
<211> LENGTH: 840
<212> TYPE: DNA
<213> ORGANISM: Bacillus brevis

<400> SEQUENCE: 23

```
atgggggtag taatgattaa cgaggacttt tttatttatg agcaattgtc tcacaagaaa      60

aatttagagc aaaaggggaa aaatgcattt gatgaagaga cggaggaact tgtaaggcaa     120

gccaaaagtg gctatcatgc ctttattgaa ggaataaatt atgacgaagt aacaaaactg     180

gatctcaata gttctgtagc tgcattagaa gattacatct ccattgcgaa agaaatagag     240

aaaaaacata aaatgtttaa ctggcgaagt gactatgctg gaagcattat tccagaattt     300

ttgtatagaa ttgtgcatgt agcaactgtg aaagctgggt taaaacctat tttctctacg     360

agaaatacaa ttattgagat cagtggagcg gcacataggg aaggattaca aatacgacgt     420

aaaaacgaag attttgcgtt gggttttcat gaggtagacg ttaaaattgc aagtgagagt     480

catagagtta ttagtttagc cgtcgcatgt gaagttaaaa caaatatcga taaaaacaaa     540

cttaatgggt tagacttttc ggctgagcgg atgaaacgca catatccagg ttctgcttat     600

tttttaataa ccgagaccct agatttttcc ccagatgaga atcattcatc tggtctcatc     660

gatgaaattt atgttcttcg aaaacaagtg cgcaccaaaa accgagttca gaaggcaccg     720

ctatgcccta gtgtttttgc agagttgttg gaagacattc ttgaaatatc ataccgtgca     780

tctaatgtaa aaggacatgt ttatgatcgt ttggagggag ggaagttaat acgtgtttaa     840
```

<210> SEQ ID NO 24
<211> LENGTH: 279
<212> TYPE: PRT
<213> ORGANISM: Bacillus brevis

<400> SEQUENCE: 24

```
Met Gly Val Val Met Ile Asn Glu Asp Phe Phe Ile Tyr Glu Gln Leu
1               5                   10                  15

Ser His Lys Lys Asn Leu Glu Gln Lys Gly Lys Asn Ala Phe Asp Glu
            20                  25                  30

Glu Thr Glu Glu Leu Val Arg Gln Ala Lys Ser Gly Tyr His Ala Phe
        35                  40                  45

Ile Glu Gly Ile Asn Tyr Asp Glu Val Thr Lys Leu Asp Leu Asn Ser
    50                  55                  60
```

```
Ser Val Ala Ala Leu Glu Asp Tyr Ile Ser Ile Ala Lys Glu Ile Glu
65                  70                  75                  80

Lys Lys His Lys Met Phe Asn Trp Arg Ser Asp Tyr Ala Gly Ser Ile
                85                  90                  95

Ile Pro Glu Phe Leu Tyr Arg Ile Val His Val Ala Thr Val Lys Ala
            100                 105                 110

Gly Leu Lys Pro Ile Phe Ser Thr Arg Asn Thr Ile Ile Glu Ile Ser
        115                 120                 125

Gly Ala Ala His Arg Glu Gly Leu Gln Ile Arg Arg Lys Asn Glu Asp
    130                 135                 140

Phe Ala Leu Gly Phe His Glu Val Asp Val Lys Ile Ala Ser Glu Ser
145                 150                 155                 160

His Arg Val Ile Ser Leu Ala Val Ala Cys Glu Val Lys Thr Asn Ile
                165                 170                 175

Asp Lys Asn Lys Leu Asn Gly Leu Asp Phe Ser Ala Glu Arg Met Lys
            180                 185                 190

Arg Thr Tyr Pro Gly Ser Ala Tyr Phe Leu Ile Thr Glu Thr Leu Asp
        195                 200                 205

Phe Ser Pro Asp Glu Asn His Ser Ser Gly Leu Ile Asp Glu Ile Tyr
    210                 215                 220

Val Leu Arg Lys Gln Val Arg Thr Lys Asn Arg Val Gln Lys Ala Pro
225                 230                 235                 240

Leu Cys Pro Ser Val Phe Ala Glu Leu Leu Glu Asp Ile Leu Glu Ile
                245                 250                 255

Ser Tyr Arg Ala Ser Asn Val Lys Gly His Val Tyr Asp Arg Leu Glu
            260                 265                 270

Gly Gly Lys Leu Ile Arg Val
        275
```

```
<210> SEQ ID NO 25
<211> LENGTH: 1608
<212> TYPE: DNA
<213> ORGANISM: Bacteroides caccae

<400> SEQUENCE: 25

atgcctagaa aacctgaata taagccgttg ctttacacga ctacgatacg aaatcctgag     60

cgttttaaag atttcatgca catacttaaa cgattcaatg gccggatact taataataaa    120

acagtcgagt tgttcgagag agaactgttt aaggttggct tgtatcgacc aatgaagcgc    180

ccggaaacag ttcaggataa gtggaaatca acaaagaacg gggaattagc cagcaaacca    240

ttaacagatg aagaaacgaa agatgtgtat cagcagaatg atccccaagt caacaaaagt    300

ataaagggac ataaagaagc agggtttcct aaagggtggc cgagtcgatt tgacacacaa    360

ttcaaattga tgaaagttct gggctttgta tattatgaat ggggaaagcc tataaacttc    420

tctcaaacag gtaactatct tgcagatact gtatccattg aaatagattc aggagcaata    480

tctcgcgaga ttgtaaatcc acagaatgag caaattgcat ttatgcaagc ttttgccaag    540

caacaaagat gcaatccgtt tatttgtgaa ttaaatgata atattccact gatattattg    600

cttgaagtta taaagaagtt aaactctgat ccagattata atggttcggg aatctcatat    660

aaggagatac ctttagttat cttttggaaa gataatgatg cggaatcttt gtatcagcgt    720

attaaacttc tgcgaaagga acataggtac aatccttcaa atgaagtgat agaggatata    780

tgtgtaaacg aaatacttgg gggattcaag aaatttgatc ttgactctat tgtgtccgaa    840

tatcccgatg aatttgtccg caaaatgaga atgacaggac ttatatcatt tagagggggt    900
```

```
ggtcgattta tcgacattaa ccataatgaa gatgataaga taaattatat actggctaat    960

tatgccacat atcgcaagta cacttcaaaa gaagaatatt ttgactatat gtcagacatt   1020

gatgatgcat tgtttgcatt aaaagctgtc gaaatcccca aaaatgtcgc agctgataaa   1080

ttagctaaac tcgtgggtga ttactcatgg gattctatta aaaaagaact tacccatttg   1140

gcgaaaaaaa catcatcaag ccacaatatt ttaaggttta ttgcagctcc ggcaagatta   1200

gagttcctga ccgcccttgc tattaagtca aaactgcctg ctgttgaggt aattcccaat   1260

tatccatgtg acgatgaagg tctgccaacc tctacggctg gtggggatat tggagatatt   1320

gagtgtttcg aggcttctaa cagtatattg gtggaagtca caatgtctga agggcgtcag   1380

cagacaatga tggaagtatg gcctattgcg agacatttaa aggagcttag agaaaaatat   1440

gaatgtgaaa atttccaatg tgtgtttctg gcaccaagta tatttgttga ttctgagaat   1500

cagatagact gggttaagga taaaaagcag cttgttattc gtccatacaa gattgtagat   1560

tttattaact atctggatac agcagcatct ttatatcaga ttgtataa                1608
```

<210> SEQ ID NO 26
<211> LENGTH: 535
<212> TYPE: PRT
<213> ORGANISM: Bacteroides caccae

<400> SEQUENCE: 26

```
Met Pro Arg Lys Pro Glu Tyr Lys Pro Leu Leu Tyr Thr Thr Thr Ile
1               5                   10                  15

Arg Asn Pro Glu Arg Phe Lys Asp Phe Met His Ile Leu Lys Arg Phe
            20                  25                  30

Asn Gly Arg Ile Leu Asn Asn Lys Thr Val Glu Leu Phe Glu Arg Glu
        35                  40                  45

Leu Phe Lys Val Gly Leu Tyr Arg Pro Met Lys Arg Pro Glu Thr Val
    50                  55                  60

Gln Asp Lys Trp Lys Ser Thr Lys Asn Gly Glu Leu Ala Ser Lys Pro
65                  70                  75                  80

Leu Thr Asp Glu Glu Thr Lys Asp Val Tyr Gln Gln Asn Asp Pro Gln
                85                  90                  95

Val Asn Lys Ser Ile Lys Gly His Lys Glu Ala Gly Phe Pro Lys Gly
            100                 105                 110

Trp Pro Ser Arg Phe Asp Thr Gln Phe Lys Leu Met Lys Val Leu Gly
        115                 120                 125

Phe Val Tyr Tyr Glu Trp Gly Lys Pro Ile Asn Phe Ser Gln Thr Gly
    130                 135                 140

Asn Tyr Leu Ala Asp Thr Val Ser Ile Glu Ile Asp Ser Gly Ala Ile
145                 150                 155                 160

Ser Arg Glu Ile Val Asn Pro Gln Asn Glu Gln Ile Ala Phe Met Gln
                165                 170                 175

Ala Phe Ala Lys Gln Gln Arg Cys Asn Pro Phe Ile Cys Glu Leu Asn
            180                 185                 190

Asp Asn Ile Pro Leu Ile Leu Leu Leu Glu Val Ile Lys Lys Leu Asn
        195                 200                 205

Ser Asp Pro Asp Tyr Asn Gly Ser Gly Ile Ser Tyr Lys Glu Ile Pro
    210                 215                 220

Leu Val Ile Phe Trp Lys Asp Asn Asp Ala Glu Ser Leu Tyr Gln Arg
225                 230                 235                 240

Ile Lys Leu Leu Arg Lys Glu His Arg Tyr Asn Pro Ser Asn Glu Val
                245                 250                 255
```

```
Ile Glu Asp Ile Cys Val Asn Glu Ile Leu Gly Gly Phe Lys Lys Phe
            260                 265                 270

Asp Leu Asp Ser Ile Val Ser Glu Tyr Pro Asp Glu Phe Val Arg Lys
        275                 280                 285

Met Arg Met Thr Gly Leu Ile Ser Phe Arg Gly Gly Gly Arg Phe Ile
    290                 295                 300

Asp Ile Asn His Asn Glu Asp Asp Lys Ile Asn Tyr Ile Leu Ala Asn
305                 310                 315                 320

Tyr Ala Thr Tyr Arg Lys Tyr Thr Ser Lys Glu Glu Tyr Phe Asp Tyr
                325                 330                 335

Met Ser Asp Ile Asp Asp Ala Leu Phe Ala Leu Lys Ala Val Glu Ile
            340                 345                 350

Pro Lys Asn Val Ala Ala Asp Lys Leu Ala Lys Leu Val Gly Asp Tyr
        355                 360                 365

Ser Trp Asp Ser Ile Lys Lys Glu Leu Thr His Leu Ala Lys Lys Thr
    370                 375                 380

Ser Ser Ser His Asn Ile Leu Arg Phe Ile Ala Ala Pro Ala Arg Leu
385                 390                 395                 400

Glu Phe Leu Thr Ala Leu Ala Ile Lys Ser Lys Leu Pro Ala Val Glu
                405                 410                 415

Val Ile Pro Asn Tyr Pro Cys Asp Asp Glu Gly Leu Pro Thr Ser Thr
            420                 425                 430

Ala Gly Gly Asp Ile Gly Asp Ile Glu Cys Phe Glu Ala Ser Asn Ser
        435                 440                 445

Ile Leu Val Glu Val Thr Met Ser Glu Gly Arg Gln Gln Thr Met Met
    450                 455                 460

Glu Val Trp Pro Ile Ala Arg His Leu Lys Glu Leu Arg Glu Lys Tyr
465                 470                 475                 480

Glu Cys Glu Asn Phe Gln Cys Val Phe Leu Ala Pro Ser Ile Phe Val
                485                 490                 495

Asp Ser Glu Asn Gln Ile Asp Trp Val Lys Asp Lys Lys Gln Leu Val
            500                 505                 510

Ile Arg Pro Tyr Lys Ile Val Asp Phe Ile Asn Tyr Leu Asp Thr Ala
        515                 520                 525

Ala Ser Leu Tyr Gln Ile Val
    530                 535
```

<210> SEQ ID NO 27
<211> LENGTH: 1776
<212> TYPE: DNA
<213> ORGANISM: Bacillus cereus 1315

<400> SEQUENCE: 27

```
atggtacaaa aaaatagaag taaagaggta tggcttgttc caaaaagagg aagttttcac      60

caaacgattt gtttaataga atcccttata aataggaatt atgatcaaac acgttggaat     120

gagcaaaaac aaaataatat tggaaatgat ttaagaaaac gtggggcagt aagggaaaaa     180

agatcccctt caaatcaatc tattcgtact ttacttgctt caattccaca gtatttaggg     240

tttttataca tagatagcaa tacaacgcct aatactgtaa aaatcacaga tgctggtaga     300

tacctatata attttcataa agatagcatt gagaatatcg gaaccttagg ggaaggtaaa     360

aaaagtggag gtttaattga aacttcatcg gtatttcttg aacaatttga aaaacttcaa     420

atcactaatc cggtaatatt aaaagattgt gaaaatattt tagtctttcc atttagagtt     480

attttaaagt tattaattga attaaattat cttgatcgag aggaattggc gtattttgta     540
```

-continued

```
ttttcgatta gggatgaaag tgaaattcca cttacaatag agaaaataaa aaagtacagg    600
aaacaagatt taatggaacg agatactgaa attaaacttt ttaaggaaac acatataggt    660
aatattactc ttgtaaaggc atcttcagca tcttattttg aaaacctgtg ttatagtacg    720
gggattattg agagatttaa aattcagata ccgaaccctg gaagctctga ttccaataaa    780
ttacctgcaa ttaaaattaa agatgaacaa gaagtttatg ttaaagaggt tttaagtagt    840
aaatatgaaa attcacaagt atataatttt ggtaataatt taaagttatg ggtggattac    900
attggaaatc ctaatagaaa gataccacca agggatattg agattgaaaa taaaggaaat    960
agcaatttaa taataattat tgaacaaaat ggggtaatga taaaaggtga tttaataaaa   1020
agtggttact cattagtttc tccaatgttc ataaatgaga attatgacat tatttttata   1080
agcccggtgg atggaactgt tttggaaagg gctacaatca agccggatta tttaagtgga   1140
aaatatgaat ttaatattaa ctcaaacctt agtattacta ataatgaaaa tatagatgaa   1200
ataggacaaa tcatcaatga acactctgcg gcaaaaacat ttgataagaa ttatttgtct   1260
tatctaggaa ttataggaga cattatagga gctgatttaa ccaataataa aaaccttagg   1320
ggagcttatt atgaatattt attttataaa ttattggagc agctacgaaa agaaaaaata   1380
atagatgatg tgtattggaa tggtaaagta ggggaatttg gtcttccaag accagcgcct   1440
ggggggaaga caggaacccc agattttatt tttattatta atgatgaatt ctttatatta   1500
gaattaccaa caattaaggc taattctgca caatttagtg ctgaaggttc ttcattacca   1560
gaccacatta atttatttgc ggaagaacct tctgaggcaa ttgtctatgg aatttatact   1620
gcacccacta ttcatgatcg gaatacatct gccatgaaag cgattcttga tccactagaa   1680
attaatttaa aatgtattga agatagagaa ttagtagatt tgttattatc taaagataga   1740
aatctcattt acagtgaatt aacaagtggt aaataa                             1776
```

<210> SEQ ID NO 28
<211> LENGTH: 591
<212> TYPE: PRT
<213> ORGANISM: Bacillus cereus 1315

<400> SEQUENCE: 28

```
Met Val Gln Lys Asn Arg Ser Lys Glu Val Trp Leu Val Pro Lys Arg
1               5                   10                  15

Gly Ser Phe His Gln Thr Ile Cys Leu Ile Glu Ser Leu Ile Asn Arg
            20                  25                  30

Asn Tyr Asp Gln Thr Arg Trp Asn Glu Gln Lys Gln Asn Asn Ile Gly
        35                  40                  45

Asn Asp Leu Arg Lys Arg Gly Ala Val Arg Glu Lys Arg Ser Pro Ser
    50                  55                  60

Asn Gln Ser Ile Arg Thr Leu Leu Ala Ser Ile Pro Gln Tyr Leu Gly
65                  70                  75                  80

Phe Leu Tyr Ile Asp Ser Asn Thr Thr Pro Asn Thr Val Lys Ile Thr
                85                  90                  95

Asp Ala Gly Arg Tyr Leu Tyr Asn Phe His Lys Asp Ser Ile Glu Asn
            100                 105                 110

Ile Gly Thr Leu Gly Glu Gly Lys Lys Ser Gly Gly Leu Ile Glu Thr
        115                 120                 125

Ser Ser Val Phe Leu Glu Gln Phe Glu Lys Leu Gln Ile Thr Asn Pro
    130                 135                 140

Val Ile Leu Lys Asp Cys Glu Asn Ile Leu Val Phe Pro Phe Arg Val
145                 150                 155                 160
```

```
Ile Leu Lys Leu Leu Ile Glu Leu Asn Tyr Leu Asp Arg Glu Glu Leu
                165                 170                 175

Ala Tyr Phe Val Phe Ser Ile Arg Asp Glu Ser Glu Ile Pro Leu Thr
            180                 185                 190

Ile Glu Lys Ile Lys Lys Tyr Arg Lys Gln Asp Leu Met Glu Arg Asp
        195                 200                 205

Thr Glu Ile Lys Leu Phe Lys Glu Thr His Ile Gly Asn Ile Thr Leu
    210                 215                 220

Val Lys Ala Ser Ser Ala Ser Tyr Phe Glu Asn Leu Cys Tyr Ser Thr
225                 230                 235                 240

Gly Ile Ile Glu Arg Phe Lys Ile Gln Ile Pro Asn Pro Gly Ser Ser
                245                 250                 255

Asp Ser Asn Lys Leu Pro Ala Ile Lys Ile Lys Asp Glu Gln Glu Val
            260                 265                 270

Tyr Val Lys Glu Val Leu Ser Ser Lys Tyr Glu Asn Ser Gln Val Tyr
        275                 280                 285

Asn Phe Gly Asn Asn Leu Lys Leu Trp Val Asp Tyr Ile Gly Asn Pro
    290                 295                 300

Asn Arg Lys Ile Pro Pro Arg Asp Ile Glu Ile Glu Asn Lys Gly Asn
305                 310                 315                 320

Ser Asn Leu Ile Ile Ile Ile Glu Gln Asn Gly Val Met Ile Lys Gly
                325                 330                 335

Asp Leu Ile Lys Ser Gly Tyr Ser Leu Val Ser Pro Met Phe Ile Asn
            340                 345                 350

Glu Asn Tyr Asp Ile Ile Phe Ile Ser Pro Val Asp Gly Thr Val Leu
        355                 360                 365

Glu Arg Ala Thr Ile Lys Pro Asp Tyr Leu Ser Gly Lys Tyr Glu Phe
    370                 375                 380

Asn Ile Asn Ser Asn Leu Ser Ile Thr Asn Asn Glu Asn Ile Asp Glu
385                 390                 395                 400

Ile Gly Gln Ile Ile Asn Glu His Ser Ala Ala Lys Thr Phe Asp Lys
                405                 410                 415

Asn Tyr Leu Ser Tyr Leu Gly Ile Ile Gly Asp Ile Ile Gly Ala Asp
            420                 425                 430

Leu Thr Asn Asn Lys Asn Leu Arg Gly Ala Tyr Tyr Glu Tyr Leu Phe
        435                 440                 445

Tyr Lys Leu Leu Glu Gln Leu Arg Lys Glu Lys Ile Ile Asp Asp Val
    450                 455                 460

Tyr Trp Asn Gly Lys Val Gly Glu Phe Gly Leu Pro Arg Pro Ala Pro
465                 470                 475                 480

Gly Gly Lys Thr Gly Thr Pro Asp Phe Ile Phe Ile Ile Asn Asp Glu
                485                 490                 495

Phe Phe Ile Leu Glu Leu Pro Thr Ile Lys Ala Asn Ser Ala Gln Phe
            500                 505                 510

Ser Ala Glu Gly Ser Ser Leu Pro Asp His Ile Asn Leu Phe Ala Glu
        515                 520                 525

Glu Pro Ser Glu Ala Ile Val Tyr Gly Ile Tyr Thr Ala Pro Thr Ile
    530                 535                 540

His Asp Arg Asn Thr Ser Ala Met Lys Ala Ile Leu Asp Pro Leu Glu
545                 550                 555                 560

Ile Asn Leu Lys Cys Ile Glu Asp Arg Glu Leu Val Asp Leu Leu Leu
                565                 570                 575

Ser Lys Asp Arg Asn Leu Ile Tyr Ser Glu Leu Thr Ser Gly Lys
```

-continued 580 585 590

<210> SEQ ID NO 29
<211> LENGTH: 858
<212> TYPE: DNA
<213> ORGANISM: Bacillus caldolyticus

<400> SEQUENCE: 29

```
atgcaaccaa atcctaaatt tataaataaa agctctgcat tttgggctta tgcaaaactg      60

ttgtctgaac agttaggata ttctaaagat ggagtagtca ttagttattc agaggcacag     120

gcaagagcaa aacttaaaaa actaggtata aatgtaaaag agggtatttt taaagatgta     180

ttgaggtacc tgaaatacag agcagaatta ctaaataaac ataaggacta tctaatggat     240

gtagaagaag caaggaaata tttccaagta gcacttaagc aacatcagca gaataattat     300

acttgcaaac ttccgcttaa caaacagaaa aatgaaaaga aagattatgc ttactttaca     360

tgcattatta atattattgc agaaacggag ctaaggtatt ttgcaaacaa taatggttta     420

gtttatggaa aagacattta ttttgatgat aatcctatga atctatcata tatattaaat     480

ttcaatagag aattggaagg tataatgtcc cggcgttttg atggtgcttt tccaagtaca     540

gtaaatccga ttctaatttg ggaaattaaa gagtattatt acacaaccac ttttggaagt     600

cgaattgccg atggggttta tgaaactcag ttagatggct acgaaataaa aacaatcagg     660

gaagaaacaa acaagaatat tcaacatata tactttattg atgactataa tacttggtgg     720

aacatgggta agtcttatct ttgtcggatc attgatatgt tacatatggg attagtggac     780

gaggtaatta tggggaaaga ggttttcgaa agatggcctc agattttaag agcagtactt     840

aatcaatact ataaataa                                                   858
```

<210> SEQ ID NO 30
<211> LENGTH: 285
<212> TYPE: PRT
<213> ORGANISM: Bacillus caldolyticus

<400> SEQUENCE: 30

```
Met Gln Pro Asn Pro Lys Phe Ile Asn Lys Ser Ser Ala Phe Trp Ala
1               5                   10                  15

Tyr Ala Lys Leu Leu Ser Glu Gln Leu Gly Tyr Ser Lys Asp Gly Val
            20                  25                  30

Val Ile Ser Tyr Ser Glu Ala Gln Ala Arg Ala Lys Leu Lys Lys Leu
        35                  40                  45

Gly Ile Asn Val Lys Glu Gly Ile Phe Lys Asp Val Leu Arg Tyr Leu
    50                  55                  60

Lys Tyr Arg Ala Glu Leu Leu Asn Lys His Lys Asp Tyr Leu Met Asp
65                  70                  75                  80

Val Glu Glu Ala Arg Lys Tyr Phe Gln Val Ala Leu Lys Gln His Gln
                85                  90                  95

Gln Asn Asn Tyr Thr Cys Lys Leu Pro Leu Asn Lys Gln Lys Asn Glu
            100                 105                 110

Lys Lys Asp Tyr Ala Tyr Phe Thr Cys Ile Ile Asn Ile Ile Ala Glu
        115                 120                 125

Thr Glu Leu Arg Tyr Phe Ala Asn Asn Asn Gly Leu Val Tyr Gly Lys
    130                 135                 140

Asp Ile Tyr Phe Asp Asp Asn Pro Met Asn Leu Ser Tyr Ile Leu Asn
145                 150                 155                 160

Phe Asn Arg Glu Leu Glu Gly Ile Met Ser Arg Arg Phe Asp Gly Ala
                165                 170                 175
```

```
Phe Pro Ser Thr Val Asn Pro Ile Leu Ile Trp Glu Ile Lys Glu Tyr
            180                 185                 190

Tyr Tyr Thr Thr Thr Phe Gly Ser Arg Ile Ala Asp Gly Val Tyr Glu
        195                 200                 205

Thr Gln Leu Asp Gly Tyr Glu Ile Lys Thr Ile Arg Glu Glu Thr Asn
    210                 215                 220

Lys Asn Ile Gln His Ile Tyr Phe Ile Asp Asp Tyr Asn Thr Trp Trp
225                 230                 235                 240

Asn Met Gly Lys Ser Tyr Leu Cys Arg Ile Ile Asp Met Leu His Met
                245                 250                 255

Gly Leu Val Asp Glu Val Ile Met Gly Lys Glu Val Phe Glu Arg Trp
            260                 265                 270

Pro Gln Ile Leu Arg Ala Val Leu Asn Gln Tyr Tyr Lys
        275                 280                 285


<210> SEQ ID NO 31
<211> LENGTH: 618
<212> TYPE: DNA
<213> ORGANISM: Bacteroides fragilis

<400> SEQUENCE: 31

atggcaaagt caaagataaa atttaatgat gtgtcttctg ctaatggtac tcagaaaata      60

cagcttccaa aatactcttc tcaagttatt aaccttgcaa atggttattc aaaggcaacc     120

agaccggcaa acgttggaca ggtatctgaa gatataaaaa ctttcagaga tgatgagact     180

cttataggat atacaaacca agattggata aactggcata aaaataaata tccagagggc     240

atacaaaagg ctactgatgc aacatgggtt atgttccaaa agatggtaca aagtctcaat     300

actgtaacta aagaagatat tcaaaagtgg gaagaggatt ttgtattttc gaaaacctat     360

gatggattaa tggtccaaaa tgccatcgtt aagaaaatag cagaagagat aaacactcaa     420

aactatcggt tagcttcacc cgaggaagaa cgacaaggta ttgatggcta cataaataat     480

catccagtcc aaattaagtc agatacatat gatagaacgg gaagacttca taacgaagaa     540

atgcaatgtg ttgtaatatc ataccaaaaa agcaataaga ctataatatt tgactacaat     600

ccagaagatt ttcaataa                                                   618


<210> SEQ ID NO 32
<211> LENGTH: 205
<212> TYPE: PRT
<213> ORGANISM: Bacteroides fragilis

<400> SEQUENCE: 32

Met Ala Lys Ser Lys Ile Lys Phe Asn Asp Val Ser Ser Ala Asn Gly
1               5                   10                  15

Thr Gln Lys Ile Gln Leu Pro Lys Tyr Ser Ser Gln Val Ile Asn Leu
            20                  25                  30

Ala Asn Gly Tyr Ser Lys Ala Thr Arg Pro Ala Asn Val Gly Gln Val
        35                  40                  45

Ser Glu Asp Ile Lys Thr Phe Arg Asp Asp Glu Thr Leu Ile Gly Tyr
    50                  55                  60

Thr Asn Gln Asp Trp Ile Asn Trp His Lys Asn Lys Tyr Pro Glu Gly
65                  70                  75                  80

Ile Gln Lys Ala Thr Asp Ala Thr Trp Val Met Phe Gln Lys Met Val
                85                  90                  95

Gln Ser Leu Asn Thr Val Thr Lys Glu Asp Ile Gln Lys Trp Glu Glu
            100                 105                 110
```

```
Asp Phe Val Phe Ser Lys Thr Tyr Asp Gly Leu Met Val Gln Asn Ala
        115                 120                 125

Ile Val Lys Lys Ile Ala Glu Glu Ile Asn Thr Gln Asn Tyr Arg Leu
    130                 135                 140

Ala Ser Pro Glu Glu Glu Arg Gln Gly Ile Asp Gly Tyr Ile Asn Asn
145                 150                 155                 160

His Pro Val Gln Ile Lys Ser Asp Thr Tyr Asp Arg Thr Gly Arg Leu
                165                 170                 175

His Asn Glu Glu Met Gln Cys Val Val Ile Ser Tyr Gln Lys Ser Asn
            180                 185                 190

Lys Thr Ile Ile Phe Asp Tyr Asn Pro Glu Asp Phe Gln
        195                 200                 205
```

<210> SEQ ID NO 33
<211> LENGTH: 1461
<212> TYPE: DNA
<213> ORGANISM: Bacillus fusiformis 1083

<400> SEQUENCE: 33

```
atgagccatg atctgctggc ttcaatatca agtgcttcaa ttgctaacat tttaacagat     60

caatcaacat tatttacttc agaaacaata aataacctct ctatttatgc tagtagagaa    120

gggaaaactt catggccttt tgcggatgga gtaattgtaa ttgaagaaga ggcaaccgta    180

aaatataaga tggcagttga atttaaaaga gttaatgaag gaattcacgg aattttaact    240

gcattaggcc aatcacaagc gtatttaaaa aaaggttata atggaacaat cataataatt    300

ccagaagtgt ataatactca tgaagcacct ggtgagtatt taaaaagtgt tcttgattta    360

gttggtgaag atttaccaat aatgattttt acttataaaa taaatggaga aaatgattta    420

gaagttaact gtatccgcaa tattgatctt tctacgacgg ctatcgattc tgacgatact    480

accaatcaaa ctaatacaat tagtacacag tgggcacact tacgagaggg aagcacagag    540

ccagatactt tttatagata tttacaaatg gcaaaaagaa tagatttaac agagttaaat    600

gaacctacaa ttgaattccc tattgaactc ttaaacgcat tgccgaatga tgtagatcct    660

ctgaaatact tatcaaatgc acctggggat acttatcatg attttgtttg gaggcacttt    720

tggtttacat atatcattaa cgaaagaaca ttgcctttat ttactttaga aggggactta    780

tacaaggtat gtgatgctag ttcttcttta ttaaaaaatg atggtttacc taagtatttt    840

ttggtgggta aaagtaactc tccaaaaaat aaaattatag gaaaattaaa tgctggtacc    900

attaacgagg aacaagcttg ggtagaatat gcccagaaaa taaaagacag agcacatagc    960

tttagagaag atatagattc ttcactctat catataggta tgattgatga agatggaaag   1020

cctacaagta taggttacaa atttgtagat gcttgtgaaa gaaatagaaa tgatagtata   1080

aatggtactc cgctagctat ttttgaaaca gcaataatcc agcacgggga attaggtgca   1140

tttattcatt acataagctt agcctcacaa aagattttta aagacactcc attaaagtat   1200

agtgtgatag aaggaaatga atttaagtca tttaattcga ataattattt aaaagaagta   1260

gaagaaatat tagctaatga tataaaagtt attagaaaag tttctttacg tggaggagtg   1320

gggagaaaac ctttccaagc agaattagca gttttaggtt ttttaggttt ctttaaaaaa   1380

ggtagaaata gatttaaacc tgttgttgga ttagatatcg attgggagaa agtatataca   1440

gctttaaacc gagaaattta a                                             1461
```

<210> SEQ ID NO 34
<211> LENGTH: 486

<212> TYPE: PRT
<213> ORGANISM: Bacillus fusiformis 1083

<400> SEQUENCE: 34

```
Met Ser His Asp Leu Leu Ala Ser Ile Ser Ser Ala Ser Ile Ala Asn
1               5                   10                  15

Ile Leu Thr Asp Gln Ser Thr Leu Phe Thr Ser Glu Thr Ile Asn Asn
            20                  25                  30

Leu Ser Ile Tyr Ala Ser Arg Glu Gly Lys Thr Ser Trp Pro Phe Ala
        35                  40                  45

Asp Gly Val Ile Val Ile Glu Glu Glu Ala Thr Val Lys Tyr Lys Met
    50                  55                  60

Ala Val Glu Phe Lys Arg Val Asn Glu Gly Ile His Gly Ile Leu Thr
65                  70                  75                  80

Ala Leu Gly Gln Ser Gln Ala Tyr Leu Lys Lys Gly Tyr Asn Gly Thr
                85                  90                  95

Ile Ile Ile Ile Pro Glu Val Tyr Asn Thr His Glu Ala Pro Gly Glu
            100                 105                 110

Tyr Leu Lys Ser Val Leu Asp Leu Val Gly Glu Asp Leu Pro Ile Met
        115                 120                 125

Ile Phe Thr Tyr Lys Ile Asn Gly Glu Asn Asp Leu Glu Val Asn Cys
    130                 135                 140

Ile Arg Asn Ile Asp Leu Ser Thr Thr Ala Ile Asp Ser Asp Asp Thr
145                 150                 155                 160

Thr Asn Gln Thr Asn Thr Ile Ser Thr Gln Trp Ala His Leu Arg Glu
                165                 170                 175

Gly Ser Thr Glu Pro Asp Thr Phe Tyr Arg Tyr Leu Gln Met Ala Lys
            180                 185                 190

Arg Ile Asp Leu Thr Glu Leu Asn Glu Pro Thr Ile Glu Phe Pro Ile
        195                 200                 205

Glu Leu Leu Asn Ala Leu Pro Asn Asp Val Asp Pro Leu Lys Tyr Leu
    210                 215                 220

Ser Asn Ala Pro Gly Asp Thr Tyr His Asp Phe Val Trp Arg His Phe
225                 230                 235                 240

Trp Phe Thr Tyr Ile Ile Asn Glu Arg Thr Leu Pro Leu Phe Thr Leu
                245                 250                 255

Glu Gly Asp Leu Tyr Lys Val Cys Asp Ala Ser Ser Ser Leu Leu Lys
            260                 265                 270

Asn Asp Gly Leu Pro Lys Tyr Phe Leu Val Gly Lys Ser Asn Ser Pro
        275                 280                 285

Lys Asn Lys Ile Ile Gly Lys Leu Asn Ala Gly Thr Ile Asn Glu Glu
    290                 295                 300

Gln Ala Trp Val Glu Tyr Ala Gln Lys Ile Lys Asp Arg Ala His Ser
305                 310                 315                 320

Phe Arg Glu Asp Ile Asp Ser Ser Leu Tyr His Ile Gly Met Ile Asp
                325                 330                 335

Glu Asp Gly Lys Pro Thr Ser Ile Gly Tyr Lys Phe Val Asp Ala Cys
            340                 345                 350

Glu Arg Asn Arg Asn Asp Ser Ile Asn Gly Thr Pro Leu Ala Ile Phe
        355                 360                 365

Glu Thr Ala Ile Ile Gln His Gly Glu Leu Gly Ala Phe Ile His Tyr
    370                 375                 380

Ile Ser Leu Ala Ser Gln Lys Ile Phe Lys Asp Thr Pro Leu Lys Tyr
385                 390                 395                 400
```

```
Ser Val Ile Glu Gly Asn Glu Phe Lys Ser Phe Asn Ser Asn Asn Tyr
                405                 410                 415

Leu Lys Glu Val Glu Glu Ile Leu Ala Asn Asp Ile Lys Val Ile Arg
            420                 425                 430

Lys Val Ser Leu Arg Gly Gly Val Gly Arg Lys Pro Phe Gln Ala Glu
        435                 440                 445

Leu Ala Val Leu Gly Phe Leu Gly Phe Phe Lys Lys Gly Arg Asn Arg
    450                 455                 460

Phe Lys Pro Val Val Gly Leu Asp Ile Asp Trp Glu Lys Val Tyr Thr
465                 470                 475                 480

Ala Leu Asn Arg Glu Ile
                485
```

<210> SEQ ID NO 35
<211> LENGTH: 870
<212> TYPE: DNA
<213> ORGANISM: Bacillus species lp

<400> SEQUENCE: 35

```
atgttcgttc atggagataa tttaacgcaa aaagaaaatc atcgtacaaa atatacagat      60

ggtttgtcta aacaatattt aacagaaata agagaaaaat ataatgaatg gaaaaaagcc     120

aacgaagaat tgataggtcc ttttgctgag gcaacgcctg aagatgaagc aatagtgaaa     180

aaaagagtag aattgctgaa tgattataaa gattttgtag accaacaaca ctatgcggaa     240

aaatttgatt cacgttcgaa cctacattcc tcaattttag aagaatttgt ctactacctg     300

tttaaggata tagcaaaaag ttttaatgat gaagccattg taggtaaatc acatgctttt     360

aaagatttgt ttataaatcc tagtagttat aaagatatgg taactcaacc aaatgtaaag     420

gtagaaatta aggaccatga ttttattatt ggtgtaggaa ttgaagcaaa aatgattgtc     480

aaaggttcaa ctgaaattga aaatcatact ttagaagtag cggcggttgc gattgaatgt     540

aaaacatatt tagataaaac aatgctagag ggttcatcag ttgccgcaga acaattgaaa     600

agtaggaatc ctaacgcaaa atatattgta gtatcagaat ggttaaagct atctgaacaa     660

gtaaaccttc agaaatataa agttgaccaa atttatgttt tgagaaaaca aaaaaatact     720

gatagagaat ttagatatgc tgacacgtac gtgaaaaatg ctattcatga agatgtagtt     780

ttacatttat tccatacaat aagattacac ttaactactg aatgggatgg gtctattagc     840

catggtattg atagaggtta cctactatag                                      870
```

<210> SEQ ID NO 36
<211> LENGTH: 289
<212> TYPE: PRT
<213> ORGANISM: Bacillus species lp

<400> SEQUENCE: 36

```
Met Phe Val His Gly Asp Asn Leu Thr Gln Lys Glu Asn His Arg Thr
1               5                   10                  15

Lys Tyr Thr Asp Gly Leu Ser Lys Gln Tyr Leu Thr Glu Ile Arg Glu
            20                  25                  30

Lys Tyr Asn Glu Trp Lys Lys Ala Asn Glu Glu Leu Ile Gly Pro Phe
        35                  40                  45

Ala Glu Ala Thr Pro Glu Asp Glu Ala Ile Val Lys Lys Arg Val Glu
    50                  55                  60

Leu Leu Asn Asp Tyr Lys Asp Phe Val Asp Gln Gln His Tyr Ala Glu
65                  70                  75                  80

Lys Phe Asp Ser Arg Ser Asn Leu His Ser Ser Ile Leu Glu Glu Phe
```

```
                85                  90                  95

Val Tyr Tyr Leu Phe Lys Asp Ile Ala Lys Ser Phe Asn Asp Glu Ala
            100                 105                 110

Ile Val Gly Lys Ser His Ala Phe Lys Asp Leu Phe Ile Asn Pro Ser
        115                 120                 125

Ser Tyr Lys Asp Met Val Thr Gln Pro Asn Val Lys Val Glu Ile Lys
    130                 135                 140

Asp His Asp Phe Ile Ile Gly Val Gly Ile Glu Ala Lys Met Ile Val
145                 150                 155                 160

Lys Gly Ser Thr Glu Ile Glu Asn His Thr Leu Glu Val Ala Ala Val
                165                 170                 175

Ala Ile Glu Cys Lys Thr Tyr Leu Asp Lys Thr Met Leu Glu Gly Ser
            180                 185                 190

Ser Val Ala Ala Glu Gln Leu Lys Ser Arg Asn Pro Asn Ala Lys Tyr
        195                 200                 205

Ile Val Val Ser Glu Trp Leu Lys Leu Ser Glu Gln Val Asn Leu Gln
    210                 215                 220

Lys Tyr Lys Val Asp Gln Ile Tyr Val Leu Arg Lys Gln Lys Asn Thr
225                 230                 235                 240

Asp Arg Glu Phe Arg Tyr Ala Asp Thr Tyr Val Lys Asn Ala Ile His
                245                 250                 255

Glu Asp Val Val Leu His Leu Phe His Thr Ile Arg Leu His Leu Thr
            260                 265                 270

Thr Glu Trp Asp Gly Ser Ile Ser His Gly Ile Asp Arg Gly Tyr Leu
        275                 280                 285

Leu
```

<210> SEQ ID NO 37
<211> LENGTH: 1077
<212> TYPE: DNA
<213> ORGANISM: Bacillus megaterium GC subgroup A

<400> SEQUENCE: 37

```
ttgaactatt tctctttgca tcctaacgta tacgcaactg gtagaccaaa aggattaata     60

aatatgttag aatccgtgtg gatatcaaac caaaaacccg gtgacgggac tatgtattta    120

atttctggat ttgcaaatta taatggtgga ataagattct acgaaacatt tacagaacat    180

attaaccatg gtggtaaagt tatcgccatt ttaggaggca gcacctccca aagattgtca    240

agtaaacaag ttgtagcaga attggtatct cgaggtgtag atgtatacat cattaataga    300

aaacgacttc ttcatgctaa actatatggt tccagcagta attctggaga atctttagta    360

gtttcttctg gtaactttac tggtccaggc atgtctcaaa atgttgaagc ctcattattg    420

ttagataata atacaacctc atcgatggga ttttcttgga atggtatggt caattcaatg    480

cttgatcaga aatggcaaat tcataatttg agcaattcca accctacatc acctagttgg    540

aatttattgt atgacgaacg cacaacaaat ctaactttag atgatactca gaaagtgacc    600

ttaattctta ccttaggtca tgcggatacc gcaagaattc aggctgcacc aaaaagtaag    660

gctggagagg gatctcaata cttttggtta agtaaagata gttatgactt ttttccacct    720

ttaacaatcc gaaataaacg tgggactaaa gcaacttatt cttgccttat aaacatgaac    780

tatttagaca taaaatatat tgatagcgaa tgtagagtca cttttgaagc agaaaacaat    840

ttcgatttta ggttaggaac aggaaaactt agatacacaa atgtagcagc aagtgatgac    900

atagctgcaa ttactcgtgt aggtgattca gattatgaat taagaataat taaaaaagga    960
```

-continued

```
agttctaatt atgatgcact tgattcagct gcagtaaatt ttataggtaa tagaggaaaa   1020

agatacggat acatacctaa tgatgagttt gggagaatca taggagctaa gttttga      1077


<210> SEQ ID NO 38
<211> LENGTH: 357
<212> TYPE: PRT
<213> ORGANISM: Bacillus megaterium GC subgroup A

<400> SEQUENCE: 38

Met Asn Tyr Phe Ser Leu His Pro Asn Val Tyr Ala Thr Gly Arg Pro
1               5                   10                  15

Lys Gly Leu Ile Asn Met Leu Glu Ser Val Trp Ile Ser Asn Gln Lys
            20                  25                  30

Pro Gly Asp Gly Thr Met Tyr Leu Ile Ser Gly Phe Ala Asn Tyr Asn
        35                  40                  45

Gly Gly Ile Thr Phe Tyr Glu Thr Phe Thr Glu His Ile Asn His Gly
    50                  55                  60

Gly Lys Val Ile Ala Ile Leu Gly Gly Ser Thr Ser Gln Arg Leu Ser
65                  70                  75                  80

Ser Lys Gln Val Val Ala Glu Leu Val Ser Arg Gly Val Asp Val Tyr
            85                  90                  95

Ile Ile Asn Arg Lys Arg Leu Leu His Ala Lys Leu Tyr Gly Ser Ser
            100                 105                 110

Ser Asn Ser Gly Glu Ser Leu Val Val Ser Ser Gly Asn Phe Thr Gly
        115                 120                 125

Pro Gly Met Ser Gln Asn Val Glu Ser Ser Leu Leu Leu Tyr Asn Asn
    130                 135                 140

Thr Thr Ser Ser Met Gly Phe Ser Trp Asn Gly Met Val Asn Ser Met
145                 150                 155                 160

Leu Asp Gln Lys Trp Gln Ile His Asn Leu Ser Asn Ser Asn Pro Thr
                165                 170                 175

Ser Pro Ser Trp Asn Leu Leu Tyr Asp Glu Arg Thr Thr Asn Thr Leu
            180                 185                 190

Asp Asp Thr Gln Lys Val Thr Phe Ile Leu Thr Leu Cys His Ala Asp
        195                 200                 205

Thr Ala Arg Ile Gln Ala Ala Pro Lys Ile Lys Ala Gly Glu Gly Ser
    210                 215                 220

Gln Tyr Phe Trp Leu Ser Lys Asp Ser Tyr Asp Phe Phe Pro Pro Leu
225                 230                 235                 240

Thr Ile Arg Asn Lys Arg Gly Thr Lys Ala Thr Tyr Ser Cys Leu Ile
                245                 250                 255

Asn Met Asn Tyr Leu Asp Ile Lys Tyr Ile Asp Ser Glu Cys Arg Val
            260                 265                 270

Thr Phe Glu Ala Glu Asn Asn Phe Asp Phe Arg Leu Gly Thr Gly Lys
        275                 280                 285

Leu Ile Tyr Thr Asn Val Ala Ala Ser Asp Asp Ile Ala Ala Ile Thr
    290                 295                 300

Arg Val Gly Asp Ser Asp Tyr Glu Leu Arg Ile Ile Lys Lys Gly Ser
305                 310                 315                 320

Ser Asn Tyr Asp Ala Leu Asp Ser Ala Ala Val Asn Phe Ile Gly Asn
                325                 330                 335

Arg Gly Lys Arg Tyr Gly Tyr Ile Pro Asn Asp Glu Phe Gly Arg Ile
            340                 345                 350

Ile Gly Ala Lys Phe
        355
```

<210> SEQ ID NO 39
<211> LENGTH: 924
<212> TYPE: DNA
<213> ORGANISM: Bacillus stearothermophilus J695

<400> SEQUENCE: 39

```
atgacttttg ataaaattgc agtcaaacag atcttgttaa ggcttctaaa aggtgaagat     60

tatagaggag aagtacttaa cattattaat gctgactttt tagactttgc tttgcagttt    120

tttaaagatg tcgctttagc aaaacttcaa aatgaagagt taaccgatga ttggtataaa    180

aaatatttta ttcaaaatcc atctctcaca aaagaaaagg ttgctattta ctcaggttta    240

aacatgaaga caataagtaa tacctataaa actacagcaa agaatgtagt tgttgatgcg    300

tcattagagc attacgatgc atttgtaaaa acgatccaag aattaataga aattgatgat    360

tctttagaac taatgttaac tattaagtat aacaaggtta gtgttgaact tactcttagt    420

gagtctttaa tagtaatgaa tgtattagca gttaaaaggg cagctattag aggaggagca    480

tggagtacag cgggaaaacg agttgaaaaa cttttaatgc taacattgtg taagctattt    540

agggtaccgg ataaacatta taaaagtatt tatgtagcgc aattaaaaga tgagaacgat    600

tttagtagag aaattgattt ttatttgatt gaccaaaaca acaatgaatt aaaatgcgag    660

gtcaaattaa tgggaaaagg aaatccagaa agtgctgatg cggtaatcgc tcgtgacagt    720

aagatttttg tagcagatac attatcagaa acaaataaga aacaattaga tttttttaaaa    780

gttgagtggg ttgagcttag aagcgaaaaa ggctatgaaa aatttaaaac tattctttct    840

aacagaggaa ttccatatga agatatagaa gaaatcactc cagaatatct agaaaaagtc    900

attgatgagt ctttaggaat ttaa                                           924
```

<210> SEQ ID NO 40
<211> LENGTH: 306
<212> TYPE: PRT
<213> ORGANISM: Bacillus stearothermophilus J695

<400> SEQUENCE: 40

```
Met Thr Phe Asp Lys Ile Ala Val Lys Gln Ile Leu Leu Arg Leu Leu
1               5                   10                  15

Lys Gly Glu Asp Tyr Arg Gly Glu Val Leu Asn Ile Ile Asn Ala Asp
            20                  25                  30

Phe Leu Asp Phe Ala Leu Gln Phe Phe Lys Asp Val Ala Leu Ala Lys
        35                  40                  45

Leu Gln Asn Glu Glu Leu Thr Asp Asp Trp Tyr Lys Lys Tyr Phe Ile
    50                  55                  60

Gln Asn Pro Ser Leu Thr Lys Glu Lys Val Ala Ile Tyr Ser Gly Leu
65                  70                  75                  80

Asn Met Lys Thr Ile Ser Asn Thr Tyr Lys Thr Thr Ala Lys Asn Val
                85                  90                  95

Val Val Asp Ala Ser Leu Glu His Tyr Asp Ala Phe Val Lys Thr Ile
            100                 105                 110

Gln Glu Leu Ile Glu Ile Asp Asp Ser Leu Glu Leu Met Leu Thr Ile
        115                 120                 125

Lys Tyr Asn Lys Val Ser Val Glu Leu Thr Leu Ser Glu Ser Leu Ile
    130                 135                 140

Val Met Asn Val Leu Ala Val Lys Arg Ala Ala Ile Arg Gly Gly Ala
145                 150                 155                 160

Trp Ser Thr Ala Gly Lys Arg Val Glu Lys Leu Leu Met Leu Thr Leu
```

-continued

```
                165                 170                 175

Cys Lys Leu Phe Arg Val Pro Asp Lys His Tyr Lys Ser Ile Val Ala
            180                 185                 190

Gln Leu Lys Asp Glu Asn Asp Phe Ser Arg Glu Ile Asp Phe Tyr Leu
        195                 200                 205

Ile Asp Gln Asn Asn Asn Glu Leu Lys Cys Glu Val Lys Leu Met Gly
    210                 215                 220

Lys Gly Asn Pro Glu Ser Ala Asp Ala Val Ile Ala Arg Asp Ser Lys
225                 230                 235                 240

Ile Phe Val Ala Asp Thr Leu Ser Glu Thr Asn Lys Lys Gln Leu Asp
                245                 250                 255

Phe Leu Lys Val Glu Trp Val Glu Leu Arg Ser Glu Lys Gly Tyr Glu
            260                 265                 270

Lys Phe Lys Thr Ile Leu Ser Asn Arg Gly Ile Pro Tyr Glu Asp Ile
        275                 280                 285

Glu Glu Ile Thr Pro Glu Tyr Leu Glu Lys Val Ile Asp Glu Ser Leu
    290                 295                 300

Gly Ile
305
```

<210> SEQ ID NO 41
<211> LENGTH: 1374
<212> TYPE: DNA
<213> ORGANISM: Bacillus smithii

<400> SEQUENCE: 41

```
atgaggtaca atccagcaga gcaatttaga tgtactatta ttagaggaaa agcgaaaaat     60

gctcttgata acctattgcc agcttatgcc aagatcattt ctgatatttg cccatgtagt    120

aagaaagagt tcccttcggc attcaatcaa aggcttaacg aggttcttgg tgagagcacg    180

aaaaaaactt tagataatca cagaacagaa attgctggta aattatttgg aatgttttat    240

gaggatgaca atgggatagt tttttcttct gagagaactg aaaagtattt aaaggactca    300

gaccagccag ctttcttcaa agatttgtgt tttaagttcc agtttcccaa tggtatggat    360

aagatagata acgtattaga aaaaatgcga tttaaaatat caattaggca gtttccttat    420

attcttcagc ttttattgtt agctagtgaa aaaggaatta aattaacaaa ggatgaagta    480

gggtattatg ttttaaattc tcttcacgtt ttacaagggc aaatacatcc gactattgta    540

ttggaacaaa tcattgctga tcgaagggca ggaaatataa agaaagtaat ggttcctggt    600

aaagcctctt cttattctgt acagcatata aacgagcaat taaactattt agaattggct    660

aacttgatta ggattgatga taaagttatt tccattaatt ttaaggaatc tgaaacaatt    720

gaattgatgg catctttttg gaataaaaag cctgagttcg atgcatataa atacaatttg    780

gaagatagag aacaaagaaa aagattttat aaggattggc aattatatta ttctaattta    840

aataaagtga aagagttcca aacgacagtt gaatccctta acatctcact tgatacttct    900

actccttcta cccatattga taaaactgct attggggatg aaggagagaa ttttgtttta    960

gaatatgaga agaaaagagt tagtaagttc gacccaagat tggtacaaaa ggtagtacct   1020

ttaggtaaaa ccagaggatt agggtatgat attcaatctg tgattgctga gcctggagaa   1080

aatgctgagt tcgttaagta tattgaggtt aaaacaacta agcgagttac tgtcccagat   1140

gtcaatgatc caacttggat tgataccatt aatttaacta gaaatgagtg gattgcagct   1200

gcacaacata gagagttcta ttctgtatac agggtttatc taactccaga aagggttact   1260

gtatttgtaa taaatgatcc atttactaaa aataaagaca acataattaa atgcaaacct   1320
```

```
ttaacatata ggttagattt ttcacacgta gcaattgata atgttttgca atag         1374


<210> SEQ ID NO 42
<211> LENGTH: 457
<212> TYPE: PRT
<213> ORGANISM: Bacillus smithii

<400> SEQUENCE: 42

Met Arg Tyr Asn Pro Ala Glu Gln Phe Arg Cys Thr Ile Ile Arg Gly
1               5                   10                  15

Lys Ala Lys Asn Ala Leu Asp Asn Leu Leu Pro Ala Tyr Ala Lys Ile
            20                  25                  30

Ile Ser Asp Ile Cys Pro Cys Ser Lys Lys Glu Phe Pro Ser Ala Phe
        35                  40                  45

Asn Gln Arg Leu Asn Glu Val Leu Gly Glu Ser Thr Lys Lys Thr Leu
    50                  55                  60

Asp Asn His Arg Thr Glu Ile Ala Gly Lys Leu Phe Gly Met Phe Tyr
65                  70                  75                  80

Glu Asp Asp Asn Gly Ile Val Phe Ser Ser Glu Arg Thr Glu Lys Tyr
                85                  90                  95

Leu Lys Asp Ser Asp Gln Pro Ala Phe Phe Lys Asp Leu Cys Phe Lys
            100                 105                 110

Phe Gln Phe Pro Asn Gly Met Asp Lys Ile Asp Asn Val Leu Glu Lys
        115                 120                 125

Met Arg Phe Lys Ile Ser Ile Arg Gln Phe Pro Tyr Ile Leu Gln Leu
    130                 135                 140

Leu Leu Leu Ala Ser Glu Lys Gly Ile Lys Leu Thr Lys Asp Glu Val
145                 150                 155                 160

Gly Tyr Tyr Val Leu Asn Ser Leu His Val Leu Gln Gly Gln Ile His
                165                 170                 175

Pro Thr Ile Val Leu Glu Gln Ile Ile Ala Asp Arg Arg Ala Gly Asn
            180                 185                 190

Ile Lys Lys Val Met Val Pro Gly Lys Ala Ser Ser Tyr Ser Val Gln
        195                 200                 205

His Ile Asn Glu Gln Leu Asn Tyr Leu Glu Leu Ala Asn Leu Ile Arg
    210                 215                 220

Ile Asp Asp Lys Val Ile Ser Ile Asn Phe Lys Glu Ser Glu Thr Ile
225                 230                 235                 240

Glu Leu Met Ala Ser Phe Trp Asn Lys Lys Pro Glu Phe Asp Ala Tyr
                245                 250                 255

Lys Tyr Asn Leu Glu Asp Arg Glu Gln Arg Lys Arg Phe Tyr Lys Asp
            260                 265                 270

Trp Gln Leu Tyr Tyr Ser Asn Leu Asn Lys Val Lys Glu Phe Gln Thr
        275                 280                 285

Thr Val Glu Ser Leu Asn Ile Ser Leu Asp Thr Ser Thr Pro Ser Thr
    290                 295                 300

His Ile Asp Lys Thr Ala Ile Gly Asp Glu Gly Glu Asn Phe Val Leu
305                 310                 315                 320

Glu Tyr Glu Lys Lys Arg Val Ser Lys Phe Asp Pro Arg Leu Val Gln
                325                 330                 335

Lys Val Val Pro Leu Gly Lys Thr Arg Gly Leu Gly Tyr Asp Ile Gln
            340                 345                 350

Ser Val Ile Ala Glu Pro Gly Glu Asn Ala Glu Phe Val Lys Tyr Ile
        355                 360                 365
```

Glu Val Lys Thr Thr Lys Arg Val Thr Val Pro Asp Val Asn Asp Pro
    370                 375                 380

Thr Trp Ile Asp Thr Ile Asn Leu Thr Arg Asn Glu Trp Ile Ala Ala
385                 390                 395                 400

Ala Gln His Arg Glu Phe Tyr Ser Val Tyr Arg Val Tyr Leu Thr Pro
                405                 410                 415

Glu Arg Val Thr Val Phe Val Ile Asn Asp Pro Phe Thr Lys Asn Lys
            420                 425                 430

Asp Asn Ile Ile Lys Cys Lys Pro Leu Thr Tyr Arg Leu Asp Phe Ser
        435                 440                 445

His Val Ala Ile Asp Asn Val Leu Gln
    450                 455

<210> SEQ ID NO 43
<211> LENGTH: 1542
<212> TYPE: DNA
<213> ORGANISM: Bacillus species 2521

<400> SEQUENCE: 43
atgaaattgg gtgaaataaa tctaaaaaag tttttggagg aaaaaaaagg aatagtttac 60
ggcgaactcg ttcaagatgc taaactacgc tggtatacga gagaatatga atatgcgata 120
ttgaaagata ataaaatgga gatatggccg aagggtaaag tagcaaataa aatcgttcta 180
ccaaccaaaa taattttgga ttcagaattg gttaccttct ttggattata tagtggtgac 240
ggcgcaaaag gcacggaaat tataaataaa cccgggagaa ttacaacttc tatctctttt 300
tctcaaaagg aacctcattt aattaaattt gctataaatc aattcaggaa aatttttggg 360
gataatattt ggtttgattt ttctttaggt gaggacagtg cttatttcat ggatgaggat 420
gggcataata gaattaaatc tgttctaaat gatgatgtac cattggtaat ggagtctctt 480
aatgaattaa atgttaattt aagtgcggca gatataatat atttaaatga gcaaaggaat 540
gtttcaatta ctaacgaaga agccttggca tttcattatc aatataataa tgaaatgcaa 600
aaatatttaa tagatgtaaa aatgaatgat ttaaatgatg ttggaattac acttggtcct 660
aatgaccgag taaatgcatc tttacgtcgg ccattcaaaa aaggcgcaag aacaatgggg 720
ggaagtagca gatctgatga actctatgtt aaaggggttt ctttatttgg ggagctattt 780
ttaaaaattc tccatagtat agaggaatct attttgaatg atacacaaga atcaacagac 840
actttaataa aatgggatgg taaaccatct acgatagggg aagttattga cctaaaaaat 900
cactttttgg aaagtcctta tgcagaaatt aatggttcta agccaatatt agaagaggaa 960
gcactctacc taattggaaa atatccaaga ggttcgttgg tgaaattaaa taaacggttg 1020
cgtcaaactc cattatggct gtatgctgcg gggctttatt tagcagaggg atctactgca 1080
aaagaaaaaa tgtttcagat gtatacaagt agagctagag ggctatcact aagctttact 1140
tcttctgaac cgtatagcct agaaattata attaaagcgt tagagctatt atttttcgac 1200
gagcaaattt taagtagctg gaaagtaaaa gttggatccc agtattttcc tgaactagtc 1260
accacagggt taaaacttgg tgtccctatg ttaagggggg ggctaagtgg tgacgggaag 1320
ttgagaacta tggaaatttc acttagtatt aagagatggg cattggagat tgtacccttt 1380
ttcagcaaat atgaggatag gtttagccat gttgaaccta caggcgcagg ggtagcaaga 1440
atagattttt caggatcatc aaaactatgt aaatggtatt ttgggttaat aatttattcg 1500
gcatttaaga atactactaa agatccaaaa ggggaatttt aa 1542

<210> SEQ ID NO 44

<211> LENGTH: 513
<212> TYPE: PRT
<213> ORGANISM: Bacillus species 2521

<400> SEQUENCE: 44

```
Met Lys Leu Gly Glu Ile Asn Leu Lys Lys Phe Leu Glu Glu Lys Lys
1               5                   10                  15

Gly Ile Val Tyr Gly Glu Leu Val Gln Asp Ala Lys Leu Arg Trp Tyr
            20                  25                  30

Thr Arg Glu Tyr Glu Tyr Ala Ile Leu Lys Asp Asn Lys Met Glu Ile
        35                  40                  45

Trp Pro Lys Gly Lys Val Ala Asn Lys Ile Val Leu Pro Thr Lys Ile
    50                  55                  60

Ile Leu Asp Ser Glu Leu Val Thr Phe Phe Gly Leu Tyr Ser Gly Asp
65                  70                  75                  80

Gly Ala Lys Gly Thr Glu Ile Ile Asn Lys Pro Gly Arg Ile Thr Thr
                85                  90                  95

Ser Ile Ser Phe Ser Gln Lys Glu Pro His Leu Ile Lys Phe Ala Ile
            100                 105                 110

Asn Gln Phe Arg Lys Ile Phe Gly Asp Asn Ile Trp Phe Asp Phe Ser
        115                 120                 125

Leu Gly Glu Asp Ser Ala Tyr Phe Met Asp Glu Asp Gly His Asn Arg
    130                 135                 140

Ile Lys Ser Val Leu Asn Asp Asp Val Pro Leu Val Met Glu Ser Leu
145                 150                 155                 160

Asn Glu Leu Asn Val Asn Leu Ser Ala Ala Asp Ile Ile Tyr Leu Asn
                165                 170                 175

Glu Gln Arg Asn Val Ser Ile Thr Asn Glu Glu Ala Leu Ala Phe His
            180                 185                 190

Tyr Gln Tyr Asn Asn Glu Met Gln Lys Tyr Leu Ile Asp Val Lys Met
        195                 200                 205

Asn Asp Leu Asn Asp Val Gly Ile Thr Leu Gly Pro Asn Asp Arg Val
    210                 215                 220

Asn Ala Ser Leu Arg Arg Pro Phe Lys Lys Gly Ala Arg Thr Met Gly
225                 230                 235                 240

Gly Ser Ser Arg Ser Asp Glu Leu Tyr Val Lys Gly Val Ser Leu Phe
                245                 250                 255

Gly Glu Leu Phe Leu Lys Ile Leu His Ser Ile Glu Glu Ser Ile Leu
            260                 265                 270

Asn Asp Thr Gln Glu Ser Thr Asp Thr Leu Ile Lys Trp Asp Gly Lys
        275                 280                 285

Pro Ser Thr Ile Gly Glu Val Ile Asp Leu Lys Asn His Phe Leu Glu
    290                 295                 300

Ser Pro Tyr Ala Glu Ile Asn Gly Ser Lys Pro Ile Leu Glu Glu Glu
305                 310                 315                 320

Ala Leu Tyr Leu Ile Gly Lys Tyr Pro Arg Gly Ser Leu Val Lys Leu
                325                 330                 335

Asn Lys Arg Leu Arg Gln Thr Pro Leu Trp Leu Tyr Ala Ala Gly Leu
            340                 345                 350

Tyr Leu Ala Glu Gly Ser Thr Ala Lys Glu Lys Met Phe Gln Met Tyr
        355                 360                 365

Thr Ser Arg Ala Arg Gly Leu Ser Leu Ser Phe Thr Ser Ser Glu Pro
    370                 375                 380

Tyr Ser Leu Glu Ile Ile Ile Lys Ala Leu Glu Leu Leu Phe Phe Asp
385                 390                 395                 400
```

-continued

```
Glu Gln Ile Leu Ser Ser Trp Lys Val Lys Val Gly Ser Gln Tyr Phe
                405                 410                 415

Pro Glu Leu Val Thr Thr Gly Leu Lys Leu Gly Val Pro Met Leu Arg
            420                 425                 430

Gly Gly Leu Ser Gly Asp Gly Lys Leu Arg Thr Met Glu Ile Ser Leu
        435                 440                 445

Ser Ile Lys Arg Trp Ala Leu Glu Ile Val Pro Phe Phe Ser Lys Tyr
    450                 455                 460

Glu Asp Arg Phe Ser His Val Glu Pro Thr Gly Ala Gly Val Ala Arg
465                 470                 475                 480

Ile Asp Phe Ser Gly Ser Ser Lys Leu Cys Lys Trp Tyr Phe Gly Leu
                485                 490                 495

Ile Ile Tyr Ser Ala Phe Lys Asn Thr Thr Lys Asp Pro Lys Gly Glu
            500                 505                 510

Phe


<210> SEQ ID NO 45
<211> LENGTH: 3108
<212> TYPE: DNA
<213> ORGANISM: Bacillus sphaericus GC subgroup

<400> SEQUENCE: 45

atgaatagag tagaatctaa aaaaaaatta gaacaattag ttcaacagtt cgagaagtat     60

gaaagtacat atagcgcttc ggattataaa gaggcaactt taagatctag tttttagat    120

cccttttttg aactttttgg atgggaaatg cgccctgaaa gaataactaa tccagcagac    180

ttagaagtga ttatagaaga aagtttagaa acggaaaaat ctactaagta tatagattat    240

gtttttaaaa ttaatagaac gactcagttt ttggtagaag ctaaaaagcc agctgaaagt    300

ctttctaaaa aagatcatat ttttcaggct aaaagttatg catttactac ggagattcca    360

tttgtcattt taacaaattt taaagagttc agattttatg acgtttcaac tgaaccttta    420

cacaatcaac cggatacaga taaagtggaa gaatattgtt ttgattataa agaatatgtt    480

caaaactttg ataagttatg ggaattattc agcagagaag cagttgctaa cagaagttta    540

gccaagtttt atgctaaaag aagaaatata gtagatagtc cagatttaat ttttaaactt    600

aattatcaaa ttgataaagg tgcatcatta ctggatatat ctttcttaaa aaatttgaaa    660

atatggagaa aatcattagc tgaaaatatc tttaataata attcacttaa tgttaacgta    720

attaatgaag tagttcagag aatattagat agactgatat ttatccgtat cattgaagac    780

agaaatattg aatctaaaga gtttttaaaa gaaattgtag aaatgcacga acaagataat    840

tcgatttcag tgaaaaatga actagataaa ctatgtattg aattaaataa gaaatttaat    900

gggttagttt tccatgacca cacatttgtt aacgaagcgt tgatagataa cgaaatttta    960

atagttatta ttgacaattt atattatcca aagtctcctt ataactttag attaattaag   1020

ccagaaattt taggacgaat attcgagcaa tttttgggtg aaaaaattga aataatcgat   1080

ggaaaaataa cgttaggatt aaaagatatt aataaaaaat caggaggtgt ttattataca   1140

ccttcatata tagttgaaaa aatagtagaa aatacattat ccaaaaaatt acataatgat   1200

attactattg aaaatttaga acagataaaa atagctgaca tagcttgtgg ttcaggaagc   1260

tttttaattt catcatataa atatttaatt gataaatttc aatatattta ttccaaatgt   1320

tcggaagcgg atgttcaaac attaattagt aataacttag tatttataga caatggtaaa   1380

ttaatgttaa caatggaaca taaaaagggg atacttcagc aaaatatttt tggggtagat   1440
```

-continued

```
atagattcac aagcaattca ggtagcgaaa ttaagtcttt atataaccat gttagaagaa   1500

ggatacagag aaggtacatt aagacctata ttaccagact taaatgataa tattaaacat   1560

ggtaactcaa taatagataa tgaaatttta tttgaagatg atataaatta cgatattgat   1620

gcaacattac cattcgattg ggaatatgct tttcctgata ttatagataa cggaggtttt   1680

gatgtaatat taggcaatcc accctatata agaattcaaa tttttgaaga gttatatgga   1740

aaagatgtag ttaattattt gaaaaaaaaa tacgtttctg ccgaaaaatt taactttgat   1800

atatatgtcg tgtttataga aaaagcattg tcactcttga atgaccaggg gatattggga   1860

tatattgtga tgaacaaatt ttttactaca caatatggag aaaaattgcg cgagttaata   1920

acttcacaaa aattattata tgaaatcatt gattttggaa ttaatgaaat atttaataat   1980

gctactactt atacttgtat attaatttta gacaaaacta atccagatga aataattatt   2040

gaaagagtga ttgatttaaa tacttggaaa gctggagaat cttcagatcg gaaagtggta   2100

gatcataccg aattcactag tactccttgg tatttatcaa gcaatactga tgaagaaatt   2160

tacaaattct ttgaagaaaa tatggtttta cttgaaacca ttagtgatag ggtttttgtt   2220

ggtgttcaga cagactgtga tccagtatat attttagaag aagtttatga agaagaaaat   2280

tatttatatt gtaagtcaga atatactact gaagtacaca agtttgaaaa agatcattta   2340

aaaccatttt taaaaggttc tctagatata aagaaatata ctttttcaaa tgttaataag   2400

tggttacttt tcccttatac caattcggaa aatacttctg atttaattcc cgaaacaact   2460

tacaaacagt atttcccaga aacatggaaa tacttagagt cttgtaaaga aagattagca   2520

aaaagaaaaa gtattgaaag agaattggat attaatccga attataatga gtggtataaa   2580

tatatttaca aaaagaatca cacgaggatg gaccaattaa aaatagtatt tcctgcgata   2640

tcgaagggta gtagcttttg ttatgattcg gatggagagt actattttgt aggaagtggt   2700

gctggaggcg gtggtggagg cgcaatagtc ttgccagatc aatctgatta taattattta   2760

tccttacttg gaattctaaa ttcagaagta gtttcatatc aaattgtaag aagaggttca   2820

aaacataaag gttcttatta tggtgtagat aaaaagagaa tagaaaatct atatgtgcca   2880

ttgattaatg aggataataa aaatttattt agtaatattt caaaaatggt agctcaaatt   2940

cttgatgcgt ttcaaaaaat gcatcaagca gggacaacgg atgttggtaa agaacaactt   3000

caacaaagaa taaaaatgct taatgctaga ataaatgagc tggtatatag actgtataat   3060

ttaccagtag aatataaaga atatattaaa aatgccttag aaaattaa                3108
```

<210> SEQ ID NO 46
<211> LENGTH: 1035
<212> TYPE: PRT
<213> ORGANISM: Bacillus sphaericus GC subgroup

<400> SEQUENCE: 46

```
Met Asn Arg Val Glu Ser Lys Lys Lys Leu Glu Gln Leu Val Gln Gln
1               5                   10                  15

Phe Glu Lys Tyr Glu Ser Thr Tyr Ser Ala Ser Asp Tyr Lys Glu Ala
            20                  25                  30

Thr Leu Arg Ser Ser Phe Leu Asp Pro Phe Phe Glu Leu Phe Gly Trp
        35                  40                  45

Glu Met Arg Pro Glu Arg Ile Thr Asn Pro Ala Asp Leu Glu Val Ile
    50                  55                  60

Ile Glu Glu Ser Leu Glu Thr Glu Lys Ser Thr Lys Tyr Ile Asp Tyr
65                  70                  75                  80

Val Phe Lys Ile Asn Arg Thr Thr Gln Phe Leu Val Glu Ala Lys Lys
```

-continued

```
                85                  90                  95

Pro Ala Glu Ser Leu Ser Lys Lys Asp His Ile Phe Gln Ala Lys Ser
            100                 105                 110

Tyr Ala Phe Thr Thr Glu Ile Pro Phe Val Ile Leu Thr Asn Phe Lys
        115                 120                 125

Glu Phe Arg Phe Tyr Asp Val Ser Thr Glu Pro Leu His Asn Gln Pro
    130                 135                 140

Asp Thr Asp Lys Val Glu Glu Tyr Cys Phe Asp Tyr Lys Glu Tyr Val
145                 150                 155                 160

Gln Asn Phe Asp Lys Leu Trp Glu Leu Phe Ser Arg Glu Ala Val Ala
                165                 170                 175

Asn Arg Ser Leu Ala Lys Phe Tyr Ala Lys Arg Arg Asn Ile Val Asp
            180                 185                 190

Ser Pro Asp Leu Ile Phe Lys Leu Asn Tyr Gln Ile Asp Lys Gly Ala
        195                 200                 205

Ser Leu Leu Asp Ile Ser Phe Leu Lys Asn Leu Lys Ile Trp Arg Lys
    210                 215                 220

Ser Leu Ala Glu Asn Ile Phe Asn Asn Asn Ser Leu Asn Val Asn Val
225                 230                 235                 240

Ile Asn Glu Val Val Gln Arg Ile Leu Asp Arg Leu Ile Phe Ile Arg
                245                 250                 255

Ile Ile Glu Asp Arg Asn Ile Glu Ser Lys Glu Phe Leu Lys Glu Ile
            260                 265                 270

Val Glu Met His Glu Gln Asp Asn Ser Ile Ser Val Lys Asn Glu Leu
        275                 280                 285

Asp Lys Leu Cys Ile Glu Leu Asn Lys Lys Phe Asn Gly Leu Val Phe
    290                 295                 300

His Asp His Thr Phe Val Asn Glu Ala Leu Ile Asp Asn Glu Ile Leu
305                 310                 315                 320

Ile Val Ile Ile Asp Asn Leu Tyr Tyr Pro Lys Ser Pro Tyr Asn Phe
                325                 330                 335

Arg Leu Ile Lys Pro Glu Ile Leu Gly Arg Ile Phe Glu Gln Phe Leu
            340                 345                 350

Gly Glu Lys Ile Glu Ile Ile Asp Gly Lys Ile Thr Leu Gly Leu Lys
        355                 360                 365

Asp Ile Asn Lys Lys Ser Gly Gly Val Tyr Tyr Thr Pro Ser Tyr Ile
    370                 375                 380

Val Glu Lys Ile Val Glu Asn Thr Leu Ser Lys Lys Leu His Asn Asp
385                 390                 395                 400

Ile Thr Ile Glu Asn Leu Glu Gln Ile Lys Ile Ala Asp Ile Ala Cys
                405                 410                 415

Gly Ser Gly Ser Phe Leu Ile Ser Ser Tyr Lys Tyr Leu Ile Asp Lys
            420                 425                 430

Phe Gln Tyr Ile Tyr Ser Lys Cys Ser Glu Ala Asp Val Gln Thr Leu
        435                 440                 445

Ile Ser Asn Asn Leu Val Phe Ile Asp Asn Gly Lys Leu Met Leu Thr
    450                 455                 460

Met Glu His Lys Lys Gly Ile Leu Gln Gln Asn Ile Phe Gly Val Asp
465                 470                 475                 480

Ile Asp Ser Gln Ala Ile Gln Val Ala Lys Leu Ser Leu Tyr Ile Thr
                485                 490                 495

Met Leu Glu Glu Gly Tyr Arg Glu Gly Thr Leu Arg Pro Ile Leu Pro
            500                 505                 510
```

Asp Leu Asn Asp Asn Ile Lys His Gly Asn Ser Ile Ile Asp Asn Glu
515 520 525

Ile Leu Phe Glu Asp Asp Ile Asn Tyr Asp Ile Asp Ala Thr Leu Pro
530 535 540

Phe Asp Trp Glu Tyr Ala Phe Pro Asp Ile Ile Asp Asn Gly Gly Phe
545 550 555 560

Asp Val Ile Leu Gly Asn Pro Pro Tyr Ile Arg Ile Gln Ile Phe Glu
565 570 575

Glu Leu Tyr Gly Lys Asp Val Val Asn Tyr Leu Lys Lys Lys Tyr Val
580 585 590

Ser Ala Glu Lys Phe Asn Phe Asp Ile Tyr Val Val Phe Ile Glu Lys
595 600 605

Ala Leu Ser Leu Leu Asn Asp Gln Gly Ile Leu Gly Tyr Ile Val Met
610 615 620

Asn Lys Phe Phe Thr Thr Gln Tyr Gly Glu Lys Leu Arg Glu Leu Ile
625 630 635 640

Thr Ser Gln Lys Leu Leu Tyr Glu Ile Ile Asp Phe Gly Ile Asn Glu
645 650 655

Ile Phe Asn Asn Ala Thr Thr Tyr Thr Cys Ile Leu Ile Leu Asp Lys
660 665 670

Thr Asn Pro Asp Glu Ile Ile Ile Glu Arg Val Ile Asp Leu Asn Thr
675 680 685

Trp Lys Ala Gly Glu Ser Ser Asp Arg Lys Val Val Asp His Thr Glu
690 695 700

Phe Thr Ser Thr Pro Trp Tyr Leu Ser Ser Asn Thr Asp Glu Glu Ile
705 710 715 720

Tyr Lys Phe Phe Glu Glu Asn Met Val Leu Leu Glu Thr Ile Ser Asp
725 730 735

Arg Val Phe Val Gly Val Gln Thr Asp Cys Asp Pro Val Tyr Ile Leu
740 745 750

Glu Glu Val Tyr Glu Glu Glu Asn Tyr Leu Tyr Cys Lys Ser Glu Tyr
755 760 765

Thr Thr Glu Val His Lys Phe Glu Lys Asp His Leu Lys Pro Phe Leu
770 775 780

Lys Gly Ser Leu Asp Ile Lys Lys Tyr Thr Phe Ser Asn Val Asn Lys
785 790 795 800

Trp Leu Leu Phe Pro Tyr Thr Asn Ser Glu Asn Thr Ser Asp Leu Ile
805 810 815

Pro Glu Thr Thr Tyr Lys Gln Tyr Phe Pro Glu Thr Trp Lys Tyr Leu
820 825 830

Glu Ser Cys Lys Glu Arg Leu Ala Lys Arg Lys Ser Ile Glu Arg Glu
835 840 845

Leu Asp Ile Asn Pro Asn Tyr Asn Glu Trp Tyr Lys Tyr Ile Tyr Lys
850 855 860

Lys Asn His Thr Arg Met Asp Gln Leu Lys Ile Val Phe Pro Ala Ile
865 870 875 880

Ser Lys Gly Ser Ser Phe Cys Tyr Asp Ser Asp Gly Glu Tyr Tyr Phe
885 890 895

Val Gly Ser Gly Ala Gly Gly Gly Gly Gly Gly Ala Ile Val Leu Pro
900 905 910

Asp Gln Ser Asp Tyr Asn Tyr Leu Ser Leu Leu Gly Ile Leu Asn Ser
915 920 925

Glu Val Val Ser Tyr Gln Ile Val Arg Arg Gly Ser Lys His Lys Gly
930 935 940

```
Ser Tyr Tyr Gly Val Asp Lys Lys Arg Ile Glu Asn Leu Tyr Val Pro
945                 950                 955                 960

Leu Ile Asn Glu Asp Asn Lys Asn Leu Phe Ser Asn Ile Ser Lys Met
                965                 970                 975

Val Ala Gln Ile Leu Asp Ala Phe Gln Lys Met His Gln Ala Gly Thr
            980                 985                 990

Thr Asp Val Gly Lys Glu Gln Leu  Gln Gln Arg Ile Lys  Met Leu Asn
        995                 1000                1005

Ala Arg  Ile Asn Glu Leu Val  Tyr Arg Leu Tyr Asn  Leu Pro Val
    1010                 1015                1020

Glu Tyr  Lys Glu Tyr Ile Lys  Asn Ala Leu Glu Asn
    1025                 1030                1035


<210> SEQ ID NO 47
<211> LENGTH: 2757
<212> TYPE: DNA
<213> ORGANISM: Bacillus species 1310

<400> SEQUENCE: 47

atgaaaaaag tgggagcaac gcgtgataat gaacgtagtt gggctattga tctaatatca     60

aggattaatt caggtgccat tgtttgtaaa gaagatagta tgatacaaca tgcaggagga    120

gagatggggc tatcaacagg tagcggctct cttttccctg atgttctttt atttggagat    180

aagggcaaaa caagggtctt acaaggttgg gaattaaaat accctgatac accaatagat    240

gatagagaat tatttataaa tgctgtaaaa aaggcagagc ttctaggagt aaacagtttc    300

ttattatgga atgtatcggt tgctcatcta tacgttaaaa atgaagaaag tggaaaatat    360

gaactattaa agaaatggga tgacctaaaa catattacta aacgttctga agttgcttat    420

agtatggctg aaataaatca agtgttagaa agtatcttga aggatttaga atactacttt    480

cgaaatggta cattacgtac cgaaaaaata cttaactcaa ttgttaatga gcaaatgctc    540

tcgttggcgt tcaataatat tgaagattgt gcactttcat taaaaaatgc ttctgcaaaa    600

gatagtgatt ttaatgatga aataatactt tggtgggaaa cagaaggctt gagctatgga    660

aagaaagctg ataggtggat tgagttatca agattagcta tcatttcgct tatgaataaa    720

ttgatatttg caaatattct aaagaagtat aattctcatg cacagattat agatcaggtt    780

aacgattcac ttacagtaga agagtgccta gatatcctta atgaaatatc tgagaagtgt    840

gacttttata atatttttga agaaaaacca ggggaaagat atattgatgt agctacgtta    900

aaagtactaa caaactttaa tgattatatt atgaatttag atttcaatag ttatagtgat    960

aggttacttg aagaattatt aaatattgta gtgacaagaa gtaagcggaa agttgctggt   1020

caattctcaa caccaaaaga attagctatg attttgacct ctttaacgat gacggataaa   1080

tcatcaagaa tttctgatcc gtgttgtgga acaggaacaa ttgtaaaagc agcttatgat   1140

cttaaattgg tttcgggtat tgatagcagc gatgctatag atcaaatttg ggcaggcgat   1200

aaatttagat atccactaca gtttgctatg cttgcattat catccccaga aaatttaggt   1260

aagcagataa atatatacaa agatgatgta tttaacctaa acgcaagcca taaggtagaa   1320

ctccatagtc caatcagtaa ggaaacttat gaagttgatc tgggagagtt tgatactgtg   1380

gtttcgaact tacctttgt  tcaacaagag accctagctg aattaaatcc agaagctatt   1440

agatttattg aagaattaaa tgaagcattc aacggtagaa gtgacttata tgcatacata   1500

gcattaaaaa tagatgaaat acttccagaa aaagggacag ctggtttaat agtatctaat   1560

tcttggcttg gaacagaatt tggagaaaga ttctttgatg agctaaagaa aagatatcat   1620
```

```
attaaatata tattaacatc tggaaaaggt cgatggttcc aaaatgctga tgtagtaaca   1680

aacatcattg tgttagaaaa aggaaatact tcccctgaca aaaaagttaa tttcataact   1740

ctaaaaaaga ctcttcaaga aattgtcgtt gagggagaga aggagcaaca atttgagaat   1800

gttgcaacaa tggttgcaaa aattcggagg gatatgcctt cagaattata tgagagtaac   1860

agttattctt atggtgaaat tgagggcttg aataaacttg gtgtaattaa aaatgctctt   1920

tttgcagatt gtagttggct tttgattttt gaggataatt tagtcccatt aacggagttt   1980

ttcaatgtta aacgtggaga acgtcggggg tggaatcctc tattctatcc gaagaatcac   2040

aacattgaac ctgattatat agtacctgta atgaaaaaac tggatacatc ctcttatata   2100

atgaatctta gcgcttcaat agaaggtttt agttgtagta gaaccattga agagcttgaa   2160

gcactaaatc acagtggaac attagagtgg ataaagagtt ttgaaacagt taaaaatggt   2220

agaggtgtgt tactaacaga agatttgcct agaaagaatg tacattggta tgaaatgcca   2280

ctaaagaaga cctttgacat cggtttgtta attaatcctg atgagaggtt gtttttctca   2340

aaagcacctc aaccagtatt ttttgaccaa agattaacag gtcttgttag gaagaatcct   2400

caagatgact tagatatatt gacagcatta ttaaacagca ttgttggagt atactacatt   2460

gaggcaattg gtttcggaag aggtctaggt gcattagact taaataaaaa taaagttgaa   2520

gataaattta aaatgttgaa tccttcttta attagtgaac aagataaatt aataattttg   2580

gaactgtata gagaactaga aaaacgtcag gttttgccat tacttcaaga agttcaacaa   2640

agagaccgat atgatttgga tatggctgtg ttaaaagctt ttggtttaga aaagcattat   2700

gatagtataa aaaattctct tatgcagtta tttgcaatac gtaaatctgt gagataa      2757
```

```
<210> SEQ ID NO 48
<211> LENGTH: 918
<212> TYPE: PRT
<213> ORGANISM: Bacillus species 1310

<400> SEQUENCE: 48

Met Lys Lys Val Gly Ala Thr Arg Asp Asn Glu Arg Ser Trp Ala Ile
1               5                   10                  15

Asp Leu Ile Ser Arg Ile Asn Ser Gly Ala Ile Val Cys Lys Glu Asp
            20                  25                  30

Ser Met Ile Gln His Ala Gly Gly Glu Met Gly Leu Ser Thr Gly Ser
        35                  40                  45

Gly Ser Leu Phe Pro Asp Val Leu Leu Phe Gly Asp Lys Gly Lys Thr
    50                  55                  60

Arg Val Leu Gln Gly Trp Glu Leu Lys Tyr Pro Asp Thr Pro Ile Asp
65                  70                  75                  80

Asp Arg Glu Leu Phe Ile Asn Ala Val Lys Lys Ala Glu Leu Leu Gly
                85                  90                  95

Val Asn Ser Phe Leu Leu Trp Asn Val Ser Val Ala His Leu Tyr Val
            100                 105                 110

Lys Asn Glu Glu Ser Gly Lys Tyr Glu Leu Leu Lys Lys Trp Asp Asp
        115                 120                 125

Leu Lys His Ile Thr Lys Arg Ser Glu Val Ala Tyr Ser Met Ala Glu
    130                 135                 140

Ile Asn Gln Val Leu Glu Ser Ile Leu Lys Asp Leu Glu Tyr Tyr Phe
145                 150                 155                 160

Arg Asn Gly Thr Leu Arg Thr Glu Lys Ile Leu Asn Ser Ile Val Asn
                165                 170                 175
```

```
Glu Gln Met Leu Ser Leu Ala Phe Asn Asn Ile Glu Asp Cys Ala Leu
            180                 185                 190

Ser Leu Lys Asn Ala Ser Ala Lys Asp Ser Asp Phe Asn Asp Glu Ile
        195                 200                 205

Ile Leu Trp Trp Glu Thr Glu Gly Leu Ser Tyr Gly Lys Lys Ala Asp
    210                 215                 220

Arg Trp Ile Glu Leu Ser Arg Leu Ala Ile Ile Ser Leu Met Asn Lys
225                 230                 235                 240

Leu Ile Phe Ala Asn Ile Leu Lys Lys Tyr Asn Ser His Ala Gln Ile
                245                 250                 255

Ile Asp Gln Val Asn Asp Ser Leu Thr Val Glu Glu Cys Leu Asp Ile
            260                 265                 270

Leu Asn Glu Ile Ser Glu Lys Cys Asp Phe Tyr Asn Ile Phe Glu Glu
        275                 280                 285

Lys Pro Gly Glu Arg Tyr Ile Asp Val Ala Thr Leu Lys Val Leu Thr
    290                 295                 300

Asn Phe Asn Asp Tyr Ile Met Asn Leu Asp Phe Asn Ser Tyr Ser Asp
305                 310                 315                 320

Arg Leu Leu Glu Glu Leu Leu Asn Ile Val Val Thr Arg Ser Lys Arg
                325                 330                 335

Lys Val Ala Gly Gln Phe Ser Thr Pro Lys Glu Leu Ala Met Ile Leu
            340                 345                 350

Thr Ser Leu Thr Met Thr Asp Lys Ser Ser Arg Ile Ser Asp Pro Cys
        355                 360                 365

Cys Gly Thr Gly Thr Ile Val Lys Ala Ala Tyr Asp Leu Lys Leu Val
    370                 375                 380

Ser Gly Ile Asp Ser Ser Asp Ala Ile Asp Gln Ile Trp Ala Gly Asp
385                 390                 395                 400

Lys Phe Arg Tyr Pro Leu Gln Phe Ala Met Leu Ala Leu Ser Ser Pro
                405                 410                 415

Glu Asn Leu Gly Lys Gln Ile Asn Ile Tyr Lys Asp Asp Val Phe Asn
            420                 425                 430

Leu Asn Ala Ser His Lys Val Glu Leu His Ser Pro Ile Ser Lys Glu
        435                 440                 445

Thr Tyr Glu Val Asp Leu Gly Glu Phe Asp Thr Val Val Ser Asn Leu
    450                 455                 460

Pro Phe Val Gln Gln Glu Thr Leu Ala Glu Leu Asn Pro Glu Ala Ile
465                 470                 475                 480

Arg Phe Ile Glu Glu Leu Asn Glu Ala Phe Asn Gly Arg Ser Asp Leu
                485                 490                 495

Tyr Ala Tyr Ile Ala Leu Lys Ile Asp Glu Ile Leu Pro Glu Lys Gly
            500                 505                 510

Thr Ala Gly Leu Ile Val Ser Asn Ser Trp Leu Gly Thr Glu Phe Gly
        515                 520                 525

Glu Arg Phe Phe Asp Glu Leu Lys Lys Arg Tyr His Ile Lys Tyr Ile
    530                 535                 540

Leu Thr Ser Gly Lys Gly Arg Trp Phe Gln Asn Ala Asp Val Val Thr
545                 550                 555                 560

Asn Ile Ile Val Leu Glu Lys Gly Asn Thr Ser Pro Asp Lys Lys Val
                565                 570                 575

Asn Phe Ile Thr Leu Lys Lys Thr Leu Gln Glu Ile Val Val Glu Gly
            580                 585                 590

Glu Lys Glu Gln Gln Phe Glu Asn Val Ala Thr Met Val Ala Lys Ile
        595                 600                 605
```

-continued

```
Arg Arg Asp Met Pro Ser Glu Leu Tyr Glu Ser Asn Ser Tyr Ser Tyr
    610                 615                 620

Gly Glu Ile Glu Gly Leu Asn Lys Leu Gly Val Ile Lys Asn Ala Leu
625                 630                 635                 640

Phe Ala Asp Cys Ser Trp Leu Phe Asp Phe Glu Asp Asn Leu Val Pro
                645                 650                 655

Leu Thr Glu Phe Phe Asn Val Lys Arg Gly Glu Arg Arg Gly Trp Asn
            660                 665                 670

Pro Leu Phe Tyr Pro Lys Asn His Asn Ile Glu Pro Asp Tyr Ile Val
        675                 680                 685

Pro Val Met Lys Lys Leu Asp Thr Ser Ser Tyr Ile Met Asn Leu Ser
    690                 695                 700

Ala Ser Ile Glu Gly Phe Ser Cys Ser Arg Thr Ile Glu Glu Leu Glu
705                 710                 715                 720

Ala Leu Asn His Ser Gly Thr Leu Glu Trp Ile Lys Ser Phe Glu Thr
                725                 730                 735

Val Lys Asn Gly Arg Gly Val Leu Leu Thr Glu Asp Leu Pro Arg Lys
            740                 745                 750

Asn Val His Trp Tyr Glu Met Pro Leu Lys Lys Thr Phe Asp Ile Gly
        755                 760                 765

Leu Leu Ile Asn Pro Asp Glu Arg Leu Phe Phe Ser Lys Ala Pro Gln
    770                 775                 780

Pro Val Phe Phe Asp Gln Arg Leu Thr Gly Leu Val Arg Lys Asn Pro
785                 790                 795                 800

Gln Asp Asp Leu Asp Ile Leu Thr Ala Leu Leu Asn Ser Ile Val Gly
                805                 810                 815

Val Tyr Tyr Ile Glu Ala Ile Gly Phe Gly Arg Gly Leu Gly Ala Leu
            820                 825                 830

Asp Leu Asn Lys Asn Lys Val Glu Asp Lys Phe Lys Met Leu Asn Pro
        835                 840                 845

Ser Leu Ile Ser Glu Gln Asp Lys Leu Ile Ile Leu Glu Leu Tyr Arg
    850                 855                 860

Glu Leu Glu Lys Arg Gln Val Leu Pro Leu Leu Gln Glu Val Gln Gln
865                 870                 875                 880

Arg Asp Arg Tyr Asp Phe Asp Met Ala Val Leu Lys Ala Phe Gly Leu
                885                 890                 895

Glu Lys His Tyr Asp Ser Ile Lys Asn Ser Leu Met Gln Leu Phe Ala
            900                 905                 910

Ile Arg Lys Ser Val Arg
        915
```

<210> SEQ ID NO 49
<211> LENGTH: 1146
<212> TYPE: DNA
<213> ORGANISM: Bacillus species H

<400> SEQUENCE: 49

```
gtgtcgaaat tatccgatgt ttttaaatat atatctttct atagaagtgc tggtcatcaa      60

atagggcgaa aggttgggga tatgttagaa gtgctaacat atggagcttt acattacgat     120

caaaatctga aaaaaagatt acatattgaa cctaacttat acggcttttc tgatgcaggg     180

cataaagttg agtttttaat tacaaaagat gtaaatgaga atttacttaa gggagggagt     240

gttactaatc tagaaaatta tataggtttt attgaatgta aaaaggtagg agtcgagcaa     300

acagtctcaa cttcatttaa aaataaattt aaagattatg aaaataaaca gactaagaaa     360
```

```
tatgatttaa aattagatag tatttttaat atcggttttt caagtcatgg tatgaataga    420

cacaagttat ctgtatcttt tgcaaattgt gataataatt tattcattaa tgtaaaaaat    480

gaaatcaata atgaaatcat ttttaatgaa caagtcaaag atcattatag acttatagtt    540

gcacaatgta gtgataatag tatagatata ataggaaata gtcgaagttt aagagaattc    600

aatttaccat taaataactg tcgtatatta gaaatatcta attttaattt acaggagaat    660

agaatatctt tagttcttaa taattgttta gctggtccgc aaacaccaga aaaagcaaaa    720

caggcttcat ttgttgcttt agatgttcgt aagaagagat ttggatcatt tgataaggtt    780

gatgatccaa gctttaaaag tattttagtg ttaactgaat ttgcacactg ggaaagaaaa    840

agcagaaata tgattagtgc ttgtattgat atcaatcttg tagtaccaga tagtatatta    900

atcgaggctt tcgaagtatt taatcaatat tttgaaagaa atggcgcaac ggtatcaaat    960

ttatatgatc taataacaaa agataacttt gaaaagaata aagagataca agatcttatt   1020

atgagtatat taacagaata tgatggtaaa attttccaac aacttaagtc agatggtact   1080

catattgaag aacttgtatc tctaaattac ttaaataata gtttatctat tatttctgaa   1140

agataa                                                              1146


<210> SEQ ID NO 50
<211> LENGTH: 381
<212> TYPE: PRT
<213> ORGANISM: Bacillus species H

<400> SEQUENCE: 50

Val Ser Lys Leu Ser Asp Val Phe Lys Tyr Ile Ser Phe Tyr Arg Ser
1               5                   10                  15

Ala Gly His Gln Ile Gly Arg Lys Val Gly Asp Met Leu Glu Val Leu
            20                  25                  30

Thr Tyr Gly Ala Leu His Tyr Asp Gln Asn Leu Lys Lys Arg Leu His
        35                  40                  45

Ile Glu Pro Asn Leu Tyr Gly Phe Ser Asp Ala Gly His Lys Val Glu
    50                  55                  60

Phe Leu Ile Thr Lys Asp Val Asn Glu Asn Leu Leu Lys Gly Gly Ser
65                  70                  75                  80

Val Thr Asn Leu Glu Asn Tyr Ile Gly Phe Ile Glu Cys Lys Lys Val
                85                  90                  95

Gly Val Glu Gln Thr Val Ser Thr Ser Phe Lys Asn Lys Phe Lys Asp
            100                 105                 110

Tyr Glu Asn Lys Gln Thr Lys Lys Tyr Asp Leu Lys Leu Asp Ser Ile
        115                 120                 125

Phe Asn Ile Gly Phe Ser Ser His Gly Met Asn Arg His Lys Leu Ser
    130                 135                 140

Val Ser Phe Ala Asn Cys Asp Asn Asn Leu Phe Ile Asn Val Lys Asn
145                 150                 155                 160

Glu Ile Asn Asn Glu Ile Ile Phe Asn Glu Gln Val Lys Asp His Tyr
                165                 170                 175

Arg Leu Ile Val Ala Gln Cys Ser Asp Asn Ser Ile Asp Ile Ile Gly
            180                 185                 190

Asn Ser Arg Ser Leu Arg Glu Phe Asn Leu Pro Leu Asn Asn Cys Arg
        195                 200                 205

Ile Leu Glu Ile Ser Asn Phe Asn Leu Gln Glu Asn Arg Ile Ser Leu
    210                 215                 220

Val Leu Asn Asn Cys Leu Ala Gly Pro Gln Thr Pro Glu Lys Ala Lys
```

-continued

```
225                 230                 235                 240

Gln Ala Ser Phe Val Ala Leu Asp Val Arg Lys Lys Arg Phe Gly Ser
                245                 250                 255

Phe Asp Lys Val Asp Asp Pro Ser Phe Lys Ser Ile Leu Val Leu Thr
            260                 265                 270

Glu Phe Ala His Trp Glu Arg Lys Ser Arg Asn Met Ile Ser Ala Cys
        275                 280                 285

Ile Asp Ile Asn Leu Val Val Pro Asp Ser Ile Leu Ile Glu Ala Phe
    290                 295                 300

Glu Val Phe Asn Gln Tyr Phe Glu Arg Asn Gly Ala Thr Val Ser Asn
305                 310                 315                 320

Leu Tyr Asp Leu Ile Thr Lys Asp Asn Phe Glu Lys Asn Lys Glu Ile
                325                 330                 335

Gln Asp Leu Ile Met Ser Ile Leu Thr Glu Tyr Asp Gly Lys Ile Phe
            340                 345                 350

Gln Gln Leu Lys Ser Asp Gly Thr His Ile Glu Glu Leu Val Ser Leu
        355                 360                 365

Asn Tyr Leu Asn Asn Ser Leu Ser Ile Ile Ser Glu Arg
    370                 375                 380


<210> SEQ ID NO 51
<211> LENGTH: 1490
<212> TYPE: DNA
<213> ORGANISM: Bacillus species M

<400> SEQUENCE: 51

gcgataccac aatgagtcat gatttatatg ctgcttgggc agctacagaa attactaata     60

ttttgcaaac aaatccccgt tttttagtga gtgacggtat atctagaaat tttactgttt    120

atgctagtaa agaaggaaga accaagtggc ctattgctga tggtgttatt cttgttgaag    180

aaaatggccg agtggtttat gagatagcaa tagagttcaa acgacgaaac gagggagtgc    240

acggtgtact tactgccctt ggccaggctc atgcctattt acataaagga tatcgaggat    300

cgataattgt tattccagaa gcctacgata cccataataa tccatcaggg catttaaaag    360

aaataattga atatactagc gatcaagtcc ctattggagt attcagttat aaagatcctg    420

atgtcactaa gacttctccg tttaatggta aaattacatg tattagacat ttgaatttga    480

atactgggct aggttctgtt gttaggtcct ctagccctca aaattttgtt aaaactcaat    540

gggctcattt gagggagggt agtagtgatc ctgatgcatt ttttcgatac ttacaaacat    600

ctaagcagct agcaattgat agcttaattg agccatcagt aaatttcccc ccgagtctag    660

ttcaggctat tcaagatata caaccaggtg caaacccact aaaatacttg tctaattcaa    720

taggcaatga tctacatgat atagtatgga gaaatttttg gtttaattac attcttaccg    780

acgaggccat acctatttgg aataattctg aaggtaacta tgtaattaat gattcatcta    840

caaaaatagt taaaccagac gagagcggga acaagatgtt ttttgctggt cgttcagatt    900

caataaaaaa tcgattagtg aacgatctga atatgggaaa tatctcagag tctgaagcat    960

ggaaaaaata cgctctaaag attcgtgaaa gagcacatag ctatagggag gatatagact   1020

ctggtttaga tcatattgga ttacttgaaa gtgatggtaa accttcagag cttggatacc   1080

gctttgttga tgcatgtgaa agaactagaa atagtaattc aggcagtcct aaggctcttt   1140

taggagctgc aattcttaaa aatggaaatt taggggcgtt tttgcattat atataccgtc   1200

tttcagaaga aaaatttaat gcagacccct tggcctttac aaaacaaaac aattcatcag   1260

gacgcttaca atttctgcat aaggaatatt tgcaatggtt agagaatgaa ttggctacta   1320
```

```
atctaaaagt tatgaggaaa gttagtatta ggggaggagc aagtagacag cctttccaag   1380

gtgaacttgc tattctgagg aattatgaat ttgtaggaaa ctttcgggta ggtacaggat   1440

taaaaataaa ctggcccaaa atccaaaatg cttatgaagt agagatataa              1490


<210> SEQ ID NO 52
<211> LENGTH: 496
<212> TYPE: PRT
<213> ORGANISM: Bacillus species M

<400> SEQUENCE: 52

Gly Asp Thr Thr Met Ser His Asp Leu Tyr Ala Ala Trp Ala Ala Thr
1               5                   10                  15

Glu Ile Thr Asn Ile Leu Gln Thr Asn Pro Arg Phe Leu Val Ser Asp
            20                  25                  30

Gly Ile Ser Arg Asn Phe Thr Val Tyr Ala Ser Lys Glu Gly Arg Thr
        35                  40                  45

Lys Trp Pro Ile Ala Asp Gly Val Ile Leu Val Glu Glu Asn Gly Arg
    50                  55                  60

Val Val Tyr Glu Ile Ala Ile Glu Phe Lys Arg Arg Asn Glu Gly Val
65                  70                  75                  80

His Gly Val Leu Thr Ala Leu Gly Gln Ala His Ala Tyr Leu His Lys
                85                  90                  95

Gly Tyr Arg Gly Ser Ile Ile Val Ile Pro Glu Ala Tyr Asp Thr His
            100                 105                 110

Asn Asn Pro Ser Gly His Leu Lys Glu Ile Ile Glu Tyr Thr Ser Asp
        115                 120                 125

Gln Val Pro Ile Gly Val Phe Ser Tyr Lys Asp Pro Asp Val Thr Lys
    130                 135                 140

Thr Ser Pro Phe Asn Gly Lys Ile Thr Cys Ile Arg His Leu Asn Leu
145                 150                 155                 160

Asn Thr Gly Leu Gly Ser Val Val Arg Ser Ser Ser Pro Gln Asn Phe
                165                 170                 175

Val Lys Thr Gln Trp Ala His Leu Arg Glu Gly Ser Ser Asp Pro Asp
            180                 185                 190

Ala Phe Phe Arg Tyr Leu Gln Thr Ser Lys Gln Leu Ala Ile Asp Ser
        195                 200                 205

Leu Ile Glu Pro Ser Val Asn Phe Pro Pro Ser Leu Val Gln Ala Ile
    210                 215                 220

Gln Asp Ile Gln Pro Gly Ala Asn Pro Leu Lys Tyr Leu Ser Asn Ser
225                 230                 235                 240

Ile Gly Asn Asp Leu His Asp Ile Val Trp Arg Asn Phe Trp Phe Asn
                245                 250                 255

Tyr Ile Leu Thr Asp Glu Ala Ile Pro Ile Trp Asn Asn Ser Glu Gly
            260                 265                 270

Asn Tyr Val Ile Asn Asp Ser Ser Thr Lys Ile Val Lys Pro Asp Glu
        275                 280                 285

Ser Gly Asn Lys Met Phe Phe Ala Gly Arg Ser Asp Ser Ile Lys Asn
    290                 295                 300

Arg Leu Val Asn Asp Leu Asn Met Gly Asn Ile Ser Glu Ser Glu Ala
305                 310                 315                 320

Trp Lys Lys Tyr Ala Leu Lys Ile Arg Glu Arg Ala His Ser Tyr Arg
                325                 330                 335

Glu Asp Ile Asp Ser Gly Leu Asp His Ile Gly Leu Leu Glu Ser Asp
            340                 345                 350
```

```
Gly Lys Pro Ser Glu Leu Gly Tyr Arg Phe Val Asp Ala Cys Glu Arg
        355                 360                 365

Thr Arg Asn Ser Asn Ser Gly Ser Pro Lys Ala Leu Leu Gly Ala Ala
    370                 375                 380

Ile Leu Lys Asn Gly Asn Leu Gly Ala Phe Leu His Tyr Ile Tyr Arg
385                 390                 395                 400

Leu Ser Glu Glu Lys Phe Asn Ala Asp Pro Leu Ala Phe Thr Lys Gln
                405                 410                 415

Asn Asn Ser Ser Gly Arg Leu Gln Phe Leu His Lys Glu Tyr Leu Gln
            420                 425                 430

Trp Leu Glu Asn Glu Leu Ala Thr Asn Leu Lys Val Met Arg Lys Val
        435                 440                 445

Ser Ile Arg Gly Gly Ala Ser Arg Gln Pro Phe Gln Gly Glu Leu Ala
    450                 455                 460

Ile Leu Arg Asn Tyr Glu Phe Val Gly Asn Phe Arg Val Gly Thr Gly
465                 470                 475                 480

Leu Lys Ile Asn Trp Pro Lys Ile Gln Asn Ala Tyr Glu Val Glu Ile
                485                 490                 495


<210> SEQ ID NO 53
<211> LENGTH: 1314
<212> TYPE: DNA
<213> ORGANISM: Bacillus stearothermophilus CPW193

<400> SEQUENCE: 53

atgagtgata aggttaattt ttcttctaac aatattgacc aaaactatag tattgagata      60

tccgaatttg agtttggaac tggaagaatt gccgatataa tcagggcact caaagattat     120

tatggcgttg aatctttgga aaatttaaca catagtcaaa agcttgatgg tctgtgtaaa     180

gctcttcagt ttactccatc tcaactggat cgtttaatag ctcaaaattc tcctgtactt     240

cgtaccatta agggccatgc atttgagaga gtttttgatg aaattcttaa aatgaatgga     300

tatgaggtaa ctgaagtcgg aggagacagt ggagttgata gaattgtaaa taataaaacc     360

cttcagctaa aaactcctaa taaggctgga acaaaggaaa atgtcgtaga atacaaaaca     420

cataaaactc atggtgctaa atctgagagg gagtctttag attactacta tagtaaagaa     480

gactttgctg attatttagt tggtcttgtt tcatatgagc cttttaacat tctctttata     540

cctcgggagg aattgccgac aatttccaaa gattcatcaa agattaagag tccatttaag     600

gtagaatggg actcaaaccc aggtttaaac tcctttaaat ctattggtat agacaatatt     660

gttatatcag aaaaaattta taaacctgca catgggaatg aacttttacc tttatcatca     720

aggaaactcc aactaaaaag cgagataata attgatgtga ttttaaatga aagtaatttc     780

cgtatatggg atatgaatat gagaggattt gctagagaaa tggcttttgt cgagtatcta     840

tcatcttttg ggattagagt atttaaccct gcaaattgca gaaaagaaag ggcagataag     900

gctgacatag cattaaaatc tgcccaaaat ggcaactttt cttttctaca aattaaaggt     960

attacattag atttagataa tttccggggg agagaatcaa ttgttgatgt tgagacacag    1020

ctttcacgtg gacgggtaaa tgatcatcca acacaaagta ggctctatct tgaaactgat    1080

tttgattatt taattgtctg tatagaccca tgttattcaa aactttactc taaagaaatt    1140

ggcaagccta attgttttga ctgggagttt tatgctatcc ctaacaatgt tttagaacgt    1200

catccaaaat acactcgtcg aataaaatca catcaaaaga taaaatatgt tgaattacag    1260

agatatagaa tagatgatac ttggattaat ttgtgggaaa aaggagctaa ctaa          1314
```

-continued

<210> SEQ ID NO 54
<211> LENGTH: 437
<212> TYPE: PRT
<213> ORGANISM: Bacillus stearothermophilus CPW193

<400> SEQUENCE: 54

```
Met Ser Asp Lys Val Asn Phe Ser Ser Asn Asn Ile Asp Gln Asn Tyr
1               5                   10                  15

Ser Ile Glu Ile Ser Glu Phe Glu Phe Gly Thr Gly Arg Ile Ala Asp
            20                  25                  30

Ile Ile Arg Ala Leu Lys Asp Tyr Tyr Gly Val Glu Ser Leu Glu Asn
        35                  40                  45

Leu Thr His Ser Gln Lys Leu Asp Gly Leu Cys Lys Ala Leu Gln Phe
    50                  55                  60

Thr Pro Ser Gln Leu Asp Arg Leu Ile Ala Gln Asn Ser Pro Val Leu
65                  70                  75                  80

Arg Thr Ile Lys Gly His Ala Phe Glu Arg Val Phe Asp Glu Ile Leu
                85                  90                  95

Lys Met Asn Gly Tyr Glu Val Thr Glu Val Gly Gly Asp Ser Gly Val
            100                 105                 110

Asp Arg Ile Val Asn Asn Lys Thr Leu Gln Leu Lys Thr Pro Asn Lys
        115                 120                 125

Ala Gly Thr Lys Glu Asn Val Val Glu Tyr Lys Thr His Lys Thr His
    130                 135                 140

Gly Ala Lys Ser Glu Arg Glu Ser Leu Asp Tyr Tyr Tyr Ser Lys Glu
145                 150                 155                 160

Asp Phe Ala Asp Tyr Leu Val Gly Leu Val Ser Tyr Glu Pro Phe Asn
                165                 170                 175

Ile Leu Phe Ile Pro Arg Glu Glu Leu Pro Thr Ile Ser Lys Asp Ser
            180                 185                 190

Ser Lys Ile Lys Ser Pro Phe Lys Val Glu Trp Asp Ser Asn Pro Gly
        195                 200                 205

Leu Asn Ser Phe Lys Ser Ile Gly Ile Asp Asn Ile Val Ile Ser Glu
    210                 215                 220

Lys Ile Tyr Lys Pro Ala His Gly Asn Glu Leu Leu Pro Leu Ser Ser
225                 230                 235                 240

Arg Lys Leu Gln Leu Lys Ser Glu Ile Ile Ile Asp Val Ile Leu Asn
                245                 250                 255

Glu Ser Asn Phe Arg Ile Trp Asp Met Asn Met Arg Gly Phe Ala Arg
            260                 265                 270

Glu Met Ala Phe Val Glu Tyr Leu Ser Ser Phe Gly Ile Arg Val Phe
        275                 280                 285

Asn Pro Ala Asn Cys Arg Lys Glu Arg Ala Asp Lys Ala Asp Ile Ala
    290                 295                 300

Leu Lys Ser Ala Gln Asn Gly Asn Phe Ser Phe Leu Gln Ile Lys Gly
305                 310                 315                 320

Ile Thr Leu Asp Leu Asp Asn Phe Arg Gly Arg Glu Ser Ile Val Asp
                325                 330                 335

Val Glu Thr Gln Leu Ser Arg Gly Arg Val Asn Asp His Pro Thr Gln
            340                 345                 350

Ser Arg Leu Tyr Leu Glu Thr Asp Phe Asp Tyr Leu Ile Val Cys Ile
        355                 360                 365

Asp Pro Cys Tyr Ser Lys Leu Tyr Ser Lys Glu Ile Gly Lys Pro Asn
    370                 375                 380
```

```
Cys Phe Asp Trp Glu Phe Tyr Ala Ile Pro Asn Asn Val Leu Glu Arg
385                 390                 395                 400

His Pro Lys Tyr Thr Arg Arg Ile Lys Ser His Gln Lys Ile Lys Tyr
                405                 410                 415

Val Glu Leu Gln Arg Tyr Arg Ile Asp Asp Thr Trp Ile Asn Leu Trp
            420                 425                 430

Glu Lys Gly Ala Asn
        435
```

<210> SEQ ID NO 55
<211> LENGTH: 1467
<212> TYPE: DNA
<213> ORGANISM: Bacillus stearothermophilus D70

<400> SEQUENCE: 55

```
atgacagaat atgacttaca tttatatgct gatagtttcc atgaaggaca ttggtgttgt     60

gaaaacttag caaaaattgc acaatcagat ggaggaaaac accaaattga ttatcttcaa    120

gggtttatac ctagacattc tttaatattc agcgatttaa taattaatat tactgtattc    180

ggttcttaca aatcatggaa acatttacct aaacaaatta aagacctttt attctggggg    240

aaacctgatt ttatagcata tgacccaaaa aatgataaaa tcttgtttgc agttgaagaa    300

acgggagcag ttccaacagg taatcaggct ttacaaagat gcgaaagaat ctacggaagc    360

gcaagaaaac aaataccttt ctggtattta ttaagtgagt tcggtcaaca taaggatggt    420

ggaacccgtc gtgattccat ttggcctact ataatgggat taaagttaac acagttagta    480

aaaacacctt cgattatatt acactattca gatatcaata atcccgaaga ttataattct    540

ggtaatggtc taaaattttt gtttaaatct ctactacaaa ttattatcaa ttactgcact    600

cttaaaaatc ctttaaaagg tatgttggaa ttactgtcta ttcaatacga aaatatgtta    660

gaattcatta aatcccaatg gaaagagcag attgacttct taccaggaga agaaatttta    720

aatacaaaaa caaaagaact agctcgcatg tacgcatctt tagcaatagg acaaacagtg    780

aagattccag aagaattgtt taattggcca agaacagaca aagttaattt caagagtcca    840

cagggattaa ttaagtatga tgagttatgt tatcaattag aaaaagctgt aggaagcaaa    900

aaagcttatt gtttatctaa taatgctgga gctaaaccac aaaaattaga atctttaaaa    960

gaatggataa atagtcaaaa gaaattattt gataaagctc caaaactaac acctccagca   1020

gaatttaata tgaagttaga tgcttttcct gttacatcaa acaataatta ttatgttact   1080

acttctaaaa atattttata tctattcgat tattggaaag acttacgcat tgctatagaa   1140

accgcttttc ctagattaaa aggtaagttg ccaactgata ttgatgagaa acctgctcta   1200

atctatatct gtaatagcgt taagccaggt cgattatttg gagatccttt tactggtcaa   1260

ctttctgcat tttctactat ttttggaaaa aaaaatattg acatgccacg aatagtggta   1320

gcttattatc cacatcaaat ttatagtcaa gctcttccaa agaataacaa atctaataaa   1380

ggaataactt taaaaaagga gttaaccgat ttcttaattt ttcatggggg agtagttgtt   1440

aaattaaatg aagggaaggc atattaa                                        1467
```

<210> SEQ ID NO 56
<211> LENGTH: 488
<212> TYPE: PRT
<213> ORGANISM: Bacillus stearothermophilus D70

<400> SEQUENCE: 56

```
Met Thr Glu Tyr Asp Leu His Leu Tyr Ala Asp Ser Phe His Glu Gly
1               5                   10                  15
```

```
His Trp Cys Cys Glu Asn Leu Ala Lys Ile Ala Gln Ser Asp Gly Gly
            20                  25                  30

Lys His Gln Ile Asp Tyr Leu Gln Gly Phe Ile Pro Arg His Ser Leu
        35                  40                  45

Ile Phe Ser Asp Leu Ile Ile Asn Ile Thr Val Phe Gly Ser Tyr Lys
    50                  55                  60

Ser Trp Lys His Leu Pro Lys Gln Ile Lys Asp Leu Leu Phe Trp Gly
65                  70                  75                  80

Lys Pro Asp Phe Ile Ala Tyr Asp Pro Lys Asn Asp Lys Ile Leu Phe
                85                  90                  95

Ala Val Glu Glu Thr Gly Ala Val Pro Thr Gly Asn Gln Ala Leu Gln
            100                 105                 110

Arg Cys Glu Arg Ile Tyr Gly Ser Ala Arg Lys Gln Ile Pro Phe Trp
        115                 120                 125

Tyr Leu Leu Ser Glu Phe Gly Gln His Lys Asp Gly Gly Thr Arg Arg
    130                 135                 140

Asp Ser Ile Trp Pro Thr Ile Met Gly Leu Lys Leu Thr Gln Leu Val
145                 150                 155                 160

Lys Thr Pro Ser Ile Ile Leu His Tyr Ser Asp Ile Asn Asn Pro Glu
                165                 170                 175

Asp Tyr Asn Ser Gly Asn Gly Leu Lys Phe Leu Phe Lys Ser Leu Leu
            180                 185                 190

Gln Ile Ile Ile Asn Tyr Cys Thr Leu Lys Asn Pro Leu Lys Gly Met
        195                 200                 205

Leu Glu Leu Leu Ser Ile Gln Tyr Glu Asn Met Leu Glu Phe Ile Lys
    210                 215                 220

Ser Gln Trp Lys Glu Gln Ile Asp Phe Leu Pro Gly Glu Glu Ile Leu
225                 230                 235                 240

Asn Thr Lys Thr Lys Glu Leu Ala Arg Met Tyr Ala Ser Leu Ala Ile
                245                 250                 255

Gly Gln Thr Val Lys Ile Pro Glu Glu Leu Phe Asn Trp Pro Arg Thr
            260                 265                 270

Asp Lys Val Asn Phe Lys Ser Pro Gln Gly Leu Ile Lys Tyr Asp Glu
        275                 280                 285

Leu Cys Tyr Gln Leu Glu Lys Ala Val Gly Ser Lys Lys Ala Tyr Cys
    290                 295                 300

Leu Ser Asn Asn Ala Gly Ala Lys Pro Gln Lys Leu Glu Ser Leu Lys
305                 310                 315                 320

Glu Trp Ile Asn Ser Gln Lys Lys Leu Phe Asp Lys Ala Pro Lys Leu
                325                 330                 335

Thr Pro Pro Ala Glu Phe Asn Met Lys Leu Asp Ala Phe Pro Val Thr
            340                 345                 350

Ser Asn Asn Asn Tyr Tyr Val Thr Thr Ser Lys Asn Ile Leu Tyr Leu
        355                 360                 365

Phe Asp Tyr Trp Lys Asp Leu Arg Ile Ala Ile Glu Thr Ala Phe Pro
    370                 375                 380

Arg Leu Lys Gly Lys Leu Pro Thr Asp Ile Asp Glu Lys Pro Ala Leu
385                 390                 395                 400

Ile Tyr Ile Cys Asn Ser Val Lys Pro Gly Arg Leu Phe Gly Asp Pro
                405                 410                 415

Phe Thr Gly Gln Leu Ser Ala Phe Ser Thr Ile Phe Gly Lys Lys Asn
            420                 425                 430

Ile Asp Met Pro Arg Ile Val Val Ala Tyr Tyr Pro His Gln Ile Tyr
```

-continued

```
        435                 440                 445

Ser Gln Ala Leu Pro Lys Asn Asn Lys Ser Asn Lys Gly Ile Thr Leu
    450                 455                 460

Lys Lys Glu Leu Thr Asp Phe Leu Ile Phe His Gly Gly Val Val Val
465                 470                 475                 480

Lys Leu Asn Glu Gly Lys Ala Tyr
                485


<210> SEQ ID NO 57
<211> LENGTH: 654
<212> TYPE: DNA
<213> ORGANISM: Bacillus stearothermophilus D70

<400> SEQUENCE: 57

atgactgatt atagatattc atttgaacta agtgaagaga ttgcaagatg ggcattcgaa     60

ataaaaacaa aaaatacaga ttggtttgta gctttttcta atccaacggc tggtccttgg    120

aaaagagtaa tggcaataga taaggcttct aatagagaag gagaagtaca tagatttgga    180

agagaagatg agcgtcctga tattattcta gttaatgata atatatcatt aatattgata    240

ttggaggcca aagaaaaatt gaaccagtta atcagtaaat cgcaagtaga taaatcagtt    300

gatgtgtttt taactctctc cagtattctg aaagaaaagt ctgataataa ttattgggga    360

gatagaacaa agtacataaa tgtgttagga attctatggg gaagcgaaca agaaacttcc    420

caaaaagata ttgataatgc gtttagagtt tatagagatt ccctagttaa aaatttaaaa    480

gaaatcaacc ctacacctac caatatttgt acggatattt tagtaggtgt agagtctatc    540

aagaacaaaa aagaagaaat atctattaaa attcatgttt ctaatatata tgcggaaata    600

tatcctaaat ttactggaaa acatcttctg gaaaagttag ctgttctgaa ttag          654


<210> SEQ ID NO 58
<211> LENGTH: 217
<212> TYPE: PRT
<213> ORGANISM: Bacillus stearothermophilus D70

<400> SEQUENCE: 58

Met Thr Asp Tyr Arg Tyr Ser Phe Glu Leu Ser Glu Glu Ile Ala Arg
1               5                   10                  15

Trp Ala Phe Glu Ile Lys Thr Lys Asn Thr Asp Trp Phe Val Ala Phe
            20                  25                  30

Ser Asn Pro Thr Ala Gly Pro Trp Lys Arg Val Met Ala Ile Asp Lys
        35                  40                  45

Ala Ser Asn Arg Glu Gly Glu Val His Arg Phe Gly Arg Glu Asp Glu
    50                  55                  60

Arg Pro Asp Ile Ile Leu Val Asn Asp Asn Ile Ser Leu Ile Leu Ile
65                  70                  75                  80

Leu Glu Ala Lys Glu Lys Leu Asn Gln Leu Ile Ser Lys Ser Gln Val
                85                  90                  95

Asp Lys Ser Val Asp Val Phe Leu Thr Leu Ser Ser Ile Leu Lys Glu
            100                 105                 110

Lys Ser Asp Asn Asn Tyr Trp Gly Asp Arg Thr Lys Tyr Ile Asn Val
        115                 120                 125

Leu Gly Ile Leu Trp Gly Ser Glu Gln Glu Thr Ser Gln Lys Asp Ile
    130                 135                 140

Asp Asn Ala Phe Arg Val Tyr Arg Asp Ser Leu Val Lys Asn Leu Lys
145                 150                 155                 160

Glu Ile Asn Pro Thr Pro Thr Asn Ile Cys Thr Asp Ile Leu Val Gly
```

-continued

```
            165                 170                 175

Val Glu Ser Ile Lys Asn Lys Lys Glu Glu Ile Ser Ile Lys Ile His
        180                 185                 190

Val Ser Asn Ile Tyr Ala Glu Ile Tyr Pro Lys Phe Thr Gly Lys His
    195                 200                 205

Leu Leu Glu Lys Leu Ala Val Leu Asn
    210                 215


<210> SEQ ID NO 59
<211> LENGTH: 1800
<212> TYPE: DNA
<213> ORGANISM: Bacillus stearothermophilus

<400> SEQUENCE: 59

atgagaaata ttcgtatcta ttctgaagta aaggaacaag ggatattttt taaagaagta      60

attcaatctg ttttagaaaa agctaacgtt gaagtagttt tagtaaattc agcgatgttg     120

gattatagtg acgtatctgt catttctttg atacgtaatc aaaagaagtt tgatttgtta     180

gtatcggaag ttagggataa acgcgaaatt cctattgtta tggttgaatt ctcaacggca     240

gtaactacag atgatcatga acttcaacga gcagatgcaa tgttttgggc atacaagtat     300

aaaataccat atttaaaaat atcacctatg gagaaaaaat cacagacagc agatgataaa     360

tttggtggcg gaaggctttt aagtgtaaat gaccagatta ttcacatgta tagaacggat     420

ggtgtaatgt atcatattga atgggaatca atggataatt ctgcatatgt gaagaatgcg     480

gaactatatc cttcttgtcc tgattgtgca ccggaattag cgtctctatt tagatgtctt     540

ttggaaacaa ttgagaaatg tgagaatata gaagattatt ataggatttt gttagataag     600

ttaggtaaac aaaaagtggc cgtaaaatgg gggaatttcc gtgaagaaaa aacacttgaa     660

cagtggaagc atgaaaaatt tgatttattg gagcgcttta gtaaaagttc ttcacgtatg     720

gagtatgata aagacaaaaa agagttaaaa attaaagtta atcgatatgg ccacgcgatg     780

gatccggaac gaggcattct ggccttttgg aaactagttc ttggagacga atggaagatt     840

gttgcggaat ttcagttgca acgcaaaaca ctcaagggga gacaatctta tcaatcgctt     900

tttgatgaag tttctcaaga agaaaaatta atgaacatag catctgaaat tataaagaat     960

ggaaatgtta tttctcctga taaagcaata gaaattcaca aattagctac ttcttccaca    1020

atgattagta caattgattt gggaactcca gaacgtaaat atattacaga tgactcttta    1080

aaagggtatt tgcaacatgg attaattacg aatatttaca aaaatttgct ttattatgta    1140

gatgaaattc gatttacaga tttacaaaga aaaacaatcg cttctttgac atggaataag    1200

gagattgtaa atgattatta taaatcatta atggatcagt tgttagataa gaacttaaga    1260

gtattaccgt tgacatcaat caagaatatt tctgaagact tgattacatg gtctagtaaa    1320

gaaattctta taaatcttgg atataagatt ttagcagcta gttatccaga ggctcaagga    1380

gatcgttgta ttttagttgg tcctactggc aagaagactg aaagaaagtt tattgactta    1440

attgctattt ctcctaaaag taaaggggtt atattattag aatgtaagga taagttgagt    1500

aaatcgaaag atgattgtga aaaaatgaat gatcttctta atcataacta tgataaagtt    1560

acgaaattaa taaatgtatt gaatattaac aattataatt ataataatat tatatataca    1620

ggagtagcag gtctaattgg aaggaaaaat gttgacaatc ttcctgtaga tttcgtgatt    1680

aaatttaaat atgatgctaa aaacctcaaa ctaaattggg aaataaatag tgatatttta    1740

ggtaaacata gtggcagttt tagtatggaa gatgtagcag tagtgcgaaa acgatcataa    1800
```

<210> SEQ ID NO 60
<211> LENGTH: 598
<212> TYPE: PRT
<213> ORGANISM: Bacillus stearothermophilus

<400> SEQUENCE: 60

```
Met Arg Asn Ile Arg Ile Tyr Ser Glu Val Lys Glu Gln Gly Ile Phe
1               5                   10                  15

Phe Lys Glu Val Ile Gln Ser Val Leu Glu Lys Ala Asn Val Glu Val
            20                  25                  30

Val Leu Val Asn Ser Ala Met Leu Asp Tyr Ser Asp Val Ser Val Ile
        35                  40                  45

Ser Leu Ile Arg Asn Gln Lys Lys Phe Asp Leu Leu Val Ser Glu Val
    50                  55                  60

Arg Asp Lys Arg Glu Ile Pro Ile Val Met Val Glu Phe Ser Thr Ala
65                  70                  75                  80

Val Thr Thr Asp Asp His Glu Leu Gln Arg Ala Asp Ala Met Phe Trp
                85                  90                  95

Ala Tyr Lys Tyr Lys Ile Pro Tyr Leu Lys Ile Ser Pro Met Glu Lys
            100                 105                 110

Lys Ser Gln Thr Ala Asp Asp Lys Phe Gly Gly Gly Arg Leu Leu Ser
        115                 120                 125

Val Asn Asp Gln Ile Ile His Met Tyr Arg Thr Asp Gly Val Met Tyr
    130                 135                 140

His Ile Glu Trp Glu Ser Met Asp Asn Ser Ala Tyr Val Lys Asn Ala
145                 150                 155                 160

Glu Leu Tyr Pro Ser Cys Pro Asp Cys Ala Pro Glu Leu Ala Ser Leu
                165                 170                 175

Phe Arg Cys Leu Leu Glu Thr Ile Glu Lys Cys Glu Asn Ile Glu Asp
            180                 185                 190

Tyr Tyr Arg Ile Leu Leu Asp Lys Leu Gly Lys Gln Lys Val Ala Val
        195                 200                 205

Lys Trp Gly Asn Phe Arg Glu Glu Lys Thr Leu Glu Gln Trp Lys His
    210                 215                 220

Glu Lys Phe Asp Leu Leu Arg Phe Ser Lys Ser Ser Ser Arg Met Glu
225                 230                 235                 240

Tyr Asp Lys Asp Lys Lys Glu Leu Lys Ile Lys Val Asn Arg Tyr Gly
                245                 250                 255

His Ala Met Asp Pro Glu Arg Gly Ile Leu Ala Phe Trp Lys Leu Val
            260                 265                 270

Leu Gly Asp Glu Trp Lys Ile Val Ala Glu Phe Gln Leu Gln Arg Lys
        275                 280                 285

Thr Leu Lys Gly Arg Gln Ser Tyr Gln Ser Leu Phe Asp Glu Val Ser
    290                 295                 300

Gln Glu Glu Lys Leu Met Asn Ile Ala Ser Glu Ile Ile Lys Asn Gly
305                 310                 315                 320

Asn Val Ile Ser Pro Asp Lys Ala Ile Glu Ile His Lys Leu Ala Thr
                325                 330                 335

Ser Ser Thr Met Ile Ser Thr Ile Asp Leu Gly Thr Pro Glu Arg Lys
            340                 345                 350

Tyr Ile Thr Asp Asp Ser Leu Lys Gly Tyr Leu Gln His Gly Leu Ile
        355                 360                 365

Thr Asn Ile Tyr Lys Asn Leu Leu Tyr Tyr Val Asp Glu Ile Arg Phe
    370                 375                 380

Thr Asp Leu Gln Arg Lys Thr Ile Ala Ser Leu Thr Trp Asn Lys Glu
```

```
385                 390                 395                 400

Ile Val Asn Asp Tyr Tyr Lys Ser Leu Met Asp Gln Leu Leu Asp Lys
                405                 410                 415

Asn Leu Arg Val Leu Pro Leu Thr Ser Ile Lys Asn Ile Ser Glu Asp
            420                 425                 430

Leu Ile Thr Trp Ser Ser Lys Glu Ile Leu Ile Asn Leu Gly Tyr Lys
        435                 440                 445

Ile Leu Ala Ala Ser Tyr Pro Glu Ala Gln Gly Asp Arg Cys Ile Leu
    450                 455                 460

Val Gly Pro Thr Gly Lys Lys Thr Glu Arg Lys Phe Ile Asp Leu Ile
465                 470                 475                 480

Ala Ile Ser Pro Lys Ser Lys Gly Val Ile Leu Leu Glu Cys Lys Asp
                485                 490                 495

Lys Leu Ser Lys Ser Lys Asp Asp Cys Glu Lys Met Asn Asp Leu Leu
            500                 505                 510

Asn His Asn Tyr Asp Lys Val Thr Lys Leu Ile Asn Val Leu Asn Ile
        515                 520                 525

Asn Asn Tyr Asn Tyr Asn Asn Ile Ile Tyr Thr Gly Val Ala Gly Leu
    530                 535                 540

Ile Gly Arg Lys Asn Val Asp Asn Leu Pro Val Asp Phe Val Ile Lys
545                 550                 555                 560

Phe Lys Tyr Asp Ala Lys Asn Leu Lys Leu Asn Trp Glu Ile Asn Ser
                565                 570                 575

Asp Ile Leu Gly Lys His Ser Gly Ser Phe Ser Met Glu Asp Val Ala
            580                 585                 590

Val Val Arg Lys Arg Ser
        595
```

<210> SEQ ID NO 61
<211> LENGTH: 867
<212> TYPE: DNA
<213> ORGANISM: Bacillus stearothermophilus ET

<400> SEQUENCE: 61

```
atgataaaaa actttagaga ctatcaacga gtagcagcta aatacataac atttattgaa      60

tcagaatttt accctgacta tctagataat gctcgttttt tatatgggga agtattaaat     120

aaattctatg aattagtaaa tagctcttct agctctatag agttgttgga aaatatttca     180

aaaacaaaag atcctgtccg aactcaactg ttacggattt ttagaaagta tgtttcacct     240

gatacttcag ttgaaatgtt aaaaagaaaa cagagaattc ccgatattat taaagagttt     300

ggaacaagat ttcgggacat taaaatagta agacaaaaaa ttgctactcg caatcatcct     360

gatgaaacca taatggctct cctttacgaa tacaaagatc gaggaaaaaa aggatatgaa     420

ttgactgatg catttttttac atggtttgaa cagaagtttc ctaattacga aatcattgga     480

ccaagagggg ctggtaaaga tatactacta aatgaagtat taccaggatt tccatcaaaa     540

atccctgcag atttcctaat atatagaaga tctgataaaa cccctatagt agttggattt     600

gcaagatatg attcagatag aggaggtgct caagaagatg atagaacagg tggcaataga     660

gataaaatca ccgaaataaa aaagtatgct gcggagcata acattccttt aaaaatttta     720

tttttaaatg acggtcctgg attactttta ggttctatgt ggaatgatta ctccgcatta     780

gaagattatg gtgaagggtg cgttatggtt tgtacattaa aaatgttgga ggagcgtttt     840

acaatcgatt ggcttgaaaa tttataa                                         867
```

<210> SEQ ID NO 62
<211> LENGTH: 288
<212> TYPE: PRT
<213> ORGANISM: Bacillus stearothermophilus ET

<400> SEQUENCE: 62

```
Met Ile Lys Asn Phe Arg Asp Tyr Gln Arg Val Ala Ala Lys Tyr Ile
1               5                   10                  15

Thr Phe Ile Glu Ser Glu Phe Tyr Pro Asp Tyr Leu Asp Asn Ala Arg
            20                  25                  30

Phe Leu Tyr Gly Glu Val Leu Asn Lys Phe Tyr Glu Leu Val Asn Ser
        35                  40                  45

Ser Ser Ser Ser Ile Glu Leu Leu Glu Asn Ile Ser Lys Thr Lys Asp
    50                  55                  60

Pro Val Arg Thr Gln Leu Leu Arg Ile Phe Arg Lys Tyr Val Ser Pro
65                  70                  75                  80

Asp Thr Ser Val Glu Met Leu Lys Arg Lys Gln Arg Ile Pro Asp Ile
                85                  90                  95

Ile Lys Glu Phe Gly Thr Arg Phe Arg Asp Ile Lys Ile Val Arg Gln
            100                 105                 110

Lys Ile Ala Thr Arg Asn His Pro Asp Glu Thr Ile Met Ala Leu Leu
        115                 120                 125

Tyr Glu Tyr Lys Asp Arg Gly Lys Lys Gly Tyr Glu Leu Thr Asp Ala
    130                 135                 140

Phe Phe Thr Trp Phe Glu Gln Lys Phe Pro Asn Tyr Glu Ile Ile Gly
145                 150                 155                 160

Pro Arg Gly Ala Gly Lys Asp Ile Leu Leu Asn Glu Val Leu Pro Gly
                165                 170                 175

Phe Pro Ser Lys Ile Pro Ala Asp Phe Leu Ile Tyr Arg Arg Ser Asp
            180                 185                 190

Lys Thr Pro Ile Val Val Gly Phe Ala Arg Tyr Asp Ser Asp Arg Gly
        195                 200                 205

Gly Ala Gln Glu Asp Asp Arg Thr Gly Gly Asn Arg Asp Lys Ile Thr
    210                 215                 220

Glu Ile Lys Lys Tyr Ala Ala Glu His Asn Ile Pro Leu Lys Ile Leu
225                 230                 235                 240

Phe Leu Asn Asp Gly Pro Gly Leu Leu Leu Gly Ser Met Trp Asn Asp
                245                 250                 255

Tyr Ser Ala Leu Glu Asp Tyr Gly Glu Gly Cys Val Met Val Cys Thr
            260                 265                 270

Leu Lys Met Leu Glu Glu Arg Phe Thr Ile Asp Trp Leu Glu Asn Leu
        275                 280                 285
```

<210> SEQ ID NO 63
<211> LENGTH: 1188
<212> TYPE: DNA
<213> ORGANISM: Bacillus subtilis

<400> SEQUENCE: 63

```
atgaataaag acaatcaaat caaaaatgaa tctggtaaac aagccaaaat tcttgtatca      60

gaaatcgtaa ataatcttaa aaatgaatta gggattaata tagaaattga agaagggtac     120

tctataggtt acccaaatca agaaaagcaa tttaaaatgg attttcttgt tcaatttact     180

gactttgata acgaacaatg gttaataaaa tcaactaact ctataaggga acgtatatac     240

ggtacagaat tttttgcaca aaacatcagg cttatcgatg agaaagtaaa aaatatatat     300

gttgttgttc cagattctat atcttcagct gaaatgaaaa agaaaagaaa ctactccgta     360
```

aaaataaacg gaacaacata tacttccttt ttaactgatg ttttaaccgt taatgaattg 420
cgacaaaaaa ttgtagaaaa ggcatctcaa aacatagcgc agggcttacg tgctaatgtg 480
cttggtaatg atgctgaaac cagtattgtt aacctgctta atgatttgaa aaataaagca 540
ttatggaatg attatcaaaa cgctcaacaa accatcaaat catcaacata caagatatac 600
aaagagatcc ttgaaaaaat tgatctaaag gaaggctttg ataagatact tgaagttacc 660
gctacaaatg atattcctct attatccaat aggggaaaac cgaaaacaga tgtatcagtt 720
acaatcaaaa caaatacaaa agaattaatt aggaatatca gtataaaaaa cactcgtgaa 780
aaaactgtca ctatacatga aggtagtgtt tcggatttga tttctcgatt aaaattatcg 840
gaaacggacc cactatcgca agcacttata cattttgaaa aagtcggtag caaaaaaaaa 900
ttaattgcag agcatcctaa ctcagataaa attttagagg aaaacttaaa attgtataat 960
agagaactta ttgaattctt acatagccct ttactcaatg acaagataca aatggtagat 1020
ttaattatat ttacaaataa atttgctgtt tggaatcgtg atgattatat taaacattac 1080
atcgaagaat atagtggaaa aggacaattt ggaactcctt ttaaatggac ttatccaagc 1140
aaaaagcgtg gtcaaaaaat acagattaaa ggtttttcaa acaattaa 1188

<210> SEQ ID NO 64
<211> LENGTH: 395
<212> TYPE: PRT
<213> ORGANISM: Bacillus subtilis

<400> SEQUENCE: 64

Met Asn Lys Asp Asn Gln Ile Lys Asn Glu Ser Gly Lys Gln Ala Lys
1               5                   10                  15

Ile Leu Val Ser Glu Ile Val Asn Asn Leu Lys Asn Glu Leu Gly Ile
            20                  25                  30

Asn Ile Glu Ile Glu Glu Gly Tyr Ser Ile Gly Tyr Pro Asn Gln Glu
        35                  40                  45

Lys Gln Phe Lys Met Asp Phe Leu Val Gln Phe Thr Asp Phe Asp Asn
    50                  55                  60

Glu Gln Trp Leu Ile Lys Ser Thr Asn Ser Ile Arg Glu Arg Ile Tyr
65                  70                  75                  80

Gly Thr Glu Phe Phe Ala Gln Asn Ile Arg Leu Ile Asp Glu Lys Val
                85                  90                  95

Lys Asn Ile Tyr Val Val Val Pro Asp Ser Ile Ser Ser Ala Glu Met
            100                 105                 110

Lys Lys Lys Arg Asn Tyr Ser Val Lys Ile Asn Gly Thr Thr Tyr Thr
        115                 120                 125

Ser Phe Leu Thr Asp Val Leu Thr Val Asn Glu Leu Arg Gln Lys Ile
    130                 135                 140

Val Glu Lys Ala Ser Gln Asn Ile Ala Gln Gly Leu Arg Ala Asn Val
145                 150                 155                 160

Leu Gly Asn Asp Ala Glu Thr Ser Ile Val Asn Leu Leu Asn Asp Leu
                165                 170                 175

Lys Asn Lys Ala Leu Trp Asn Asp Tyr Gln Asn Ala Gln Gln Thr Ile
            180                 185                 190

Lys Ser Ser Thr Tyr Lys Ile Tyr Lys Glu Ile Leu Glu Lys Ile Asp
        195                 200                 205

Leu Lys Glu Gly Phe Asp Lys Ile Leu Glu Val Thr Ala Thr Asn Asp
    210                 215                 220

Ile Pro Leu Leu Ser Asn Arg Gly Lys Pro Lys Thr Asp Val Ser Val

```
225                 230                 235                 240

Thr Ile Lys Thr Asn Thr Lys Glu Leu Ile Arg Asn Ile Ser Ile Lys
                245                 250                 255

Asn Thr Arg Glu Lys Thr Val Thr Ile His Glu Gly Ser Val Ser Asp
            260                 265                 270

Leu Ile Ser Arg Leu Lys Leu Ser Glu Thr Asp Pro Leu Ser Gln Ala
        275                 280                 285

Leu Ile His Phe Glu Lys Val Gly Ser Lys Lys Lys Leu Ile Ala Glu
    290                 295                 300

His Pro Asn Ser Asp Lys Ile Leu Glu Glu Asn Leu Lys Leu Tyr Asn
305                 310                 315                 320

Arg Glu Leu Ile Glu Phe Leu His Ser Pro Leu Leu Asn Asp Lys Ile
                325                 330                 335

Gln Met Val Asp Leu Ile Ile Phe Thr Asn Lys Phe Ala Val Trp Asn
            340                 345                 350

Arg Asp Asp Tyr Ile Lys His Tyr Ile Glu Glu Tyr Ser Gly Lys Gly
        355                 360                 365

Gln Phe Gly Thr Pro Phe Lys Trp Thr Tyr Pro Ser Lys Lys Arg Gly
    370                 375                 380

Gln Lys Ile Gln Ile Lys Gly Phe Ser Asn Asn
385                 390                 395
```

<210> SEQ ID NO 65
<211> LENGTH: 933
<212> TYPE: DNA
<213> ORGANISM: Bacillus subtilis 36

<400> SEQUENCE: 65

```
atgacaacct atatatatcc taccccacat aaagataaat tagttgccct attactaaac      60

gataaattac cagtagaaga taaaccaaga gttgaagagg caattgtggt ttatacaaat     120

tggataaaaa acttaaacat tattacaagt gccggtcttc ctccccaaca gactttaaat     180

aaaatgattg agcttctaaa tgaatataaa ttctatatag atttaaattt ggtatttgat     240

agcccaagag atttccttta tagacaaaaa gggcaattaa aaattgacaa tactattatt     300

gaagaatttt taccccgttt agctcatccg tctgttattc ctgaaataat cgatatggat     360

gtaacggttg gaccaaaaaa gtgtttttct tcagtttact ttgaatctag tcttgatgcg     420

ccagcaattg gaggaggact aagagtaaga agcaaagacc aagactttgc aataagcaaa     480

aaattattct taaaagcgtc acacacacaa gattataaag agagtttgga aacagaaaca     540

ttcttatctt atgtgtctgc tgagtgtaaa acaaatcttg ataagacaat gtttcaagaa     600

ggatgtgcta cagctcatga tacgaaggta gctgtaccag gttctaaata tttcttgcta     660

tgtgaatggt tagatatgac accattaagt acagctccta cagatattga tgaaattcta     720

cttctccgta aagccaaaag attaaattct aatataagaa aaaagtttc ttcttatagt     780

gggagacaag aaaaacggga ttatttcatc aattatctca aatcacatcc atttagagta     840

gaggttttg aaagatttat tgaacacatt agaaaactta tccaaaatga agttccggtt     900

gaacataatg ttatggaatt aggttatttt taa                                  933
```

<210> SEQ ID NO 66
<211> LENGTH: 310
<212> TYPE: PRT
<213> ORGANISM: Bacillus subtilis 36

<400> SEQUENCE: 66

```
Met Thr Thr Tyr Ile Tyr Pro Thr Pro His Lys Asp Lys Leu Val Ala
1               5                   10                  15

Leu Leu Leu Asn Asp Lys Leu Pro Val Glu Asp Lys Pro Arg Val Glu
            20                  25                  30

Glu Ala Ile Val Val Tyr Thr Asn Trp Ile Lys Asn Leu Asn Ile Ile
        35                  40                  45

Thr Ser Ala Gly Leu Pro Pro Gln Gln Thr Leu Asn Lys Met Ile Glu
    50                  55                  60

Leu Leu Asn Glu Tyr Lys Phe Tyr Ile Asp Leu Asn Leu Val Phe Asp
65                  70                  75                  80

Ser Pro Arg Asp Phe Leu Tyr Arg Gln Lys Gly Gln Leu Lys Ile Asp
                85                  90                  95

Asn Thr Ile Ile Glu Glu Phe Leu Pro Arg Leu Ala His Pro Ser Val
            100                 105                 110

Ile Pro Glu Ile Ile Asp Met Asp Val Thr Val Gly Pro Lys Lys Cys
        115                 120                 125

Phe Ser Ser Val Tyr Phe Glu Ser Ser Leu Asp Ala Pro Ala Ile Gly
    130                 135                 140

Gly Gly Leu Arg Val Arg Ser Lys Asp Gln Asp Phe Ala Ile Ser Lys
145                 150                 155                 160

Lys Leu Phe Leu Lys Ala Ser His Thr Gln Asp Tyr Lys Glu Ser Leu
                165                 170                 175

Glu Thr Glu Thr Phe Leu Ser Tyr Val Ser Ala Glu Cys Lys Thr Asn
            180                 185                 190

Leu Asp Lys Thr Met Phe Gln Glu Gly Cys Ala Thr Ala His Asp Thr
        195                 200                 205

Lys Val Ala Val Pro Gly Ser Lys Tyr Phe Leu Leu Cys Glu Trp Leu
    210                 215                 220

Asp Met Thr Pro Leu Ser Thr Ala Pro Thr Asp Ile Asp Glu Ile Leu
225                 230                 235                 240

Leu Leu Arg Lys Ala Lys Arg Leu Asn Ser Asn Ile Arg Lys Lys Phe
                245                 250                 255

Ser Ser Tyr Ser Gly Arg Gln Glu Lys Arg Asp Tyr Phe Ile Asn Tyr
            260                 265                 270

Leu Lys Ser His Pro Phe Arg Val Glu Val Phe Glu Arg Phe Ile Glu
        275                 280                 285

His Ile Arg Lys Leu Ile Gln Asn Glu Val Pro Val Glu His Asn Val
    290                 295                 300

Met Glu Leu Gly Tyr Phe
305                 310
```

<210> SEQ ID NO 67
<211> LENGTH: 1161
<212> TYPE: DNA
<213> ORGANISM: Clostridium acetobutylicum ABKn8

<400> SEQUENCE: 67

```
atacatactt tatttgaaaa agaaattatt aactccaatc atgaatacta tataccacaa     60

ttatctaatt caatagaaaa tttttattta ttgaatgcag atttaaatcg aataccaagc    120

tcaacagcgg acatgctttt agttttccaa cgtttgtttg ataaagcact taaaaatgat    180

tttacatcat tatcaataat taattacatg cataataatt taacagatga atctaaagct    240

aaacgtaaag ttactgctag agatattgaa gattttattg ctgatctttt cgaaggaact    300

gtaactgatg aagaaagtag acaaaatctc acttcaacta tagatattgt agactcttat    360
```

```
atatcaagta actacaggga aaaatgtgat attcaattca ataattcata taaattatca    420

ataaaaagct ttataagcga taacaaagaa atcaattgtg gttcttttgc tagagaagct    480

ctatttaaag atatagttga aaattatggc ggtgaaagaa aaaatggatt agggtctaaa    540

gggcaatttc tagatttatt tgaaaaaatc aaagataatg gaaaatggac agactttact    600

aatcgcttta cttatatgac taataatata tttaaagatg acttattaat ttttattaaa    660

ggtggtaata atgttgatat ctatttagtt gatagtgaaa aatttaggaa tacattaatt    720

tctgctgttt catcagggcc taaatttgca gtttcagttt taaatagata tgaaggaaat    780

tctatacgaa ttgaaagaga tattttcctt tcacctaaaa tcagtacaca tattggttta    840

aattttaata aaactaatga aaatgccctt aataaaatag atgttgaact acaaaaactg    900

aaagatgtga cattaaattt tatatcaaat gatactgctt ctttaaataa ttatagccaa    960

ttaatatcta catttaactc ttcttatcag aatactattt ctgatttact ttcattgaaa   1020

tcaatgactt tatcttcaga tgcattaatt acatctttcc atcaaaatgt tcttaatctt   1080

tattcatcaa ataagttgtc aattattgat atgaaaaaga agaaaagagg aaattcatat   1140

agtattgtaa gggaattata a                                             1161
```

```
<210> SEQ ID NO 68
<211> LENGTH: 386
<212> TYPE: PRT
<213> ORGANISM: Clostridium acetobutylicum ABKn8

<400> SEQUENCE: 68

Met His Thr Leu Phe Glu Lys Glu Ile Ile Asn Ser Asn His Glu Tyr
1               5                   10                  15

Tyr Ile Pro Gln Leu Ser Asn Ser Ile Glu Asn Phe Tyr Leu Leu Asn
            20                  25                  30

Ala Asp Leu Asn Arg Ile Pro Ser Ser Thr Ala Asp Met Leu Leu Val
        35                  40                  45

Phe Gln Arg Leu Phe Asp Lys Ala Leu Lys Asn Asp Phe Thr Ser Leu
    50                  55                  60

Ser Ile Ile Asn Tyr Met His Asn Asn Leu Thr Asp Glu Ser Lys Ala
65                  70                  75                  80

Lys Arg Lys Val Thr Ala Arg Asp Ile Glu Asp Phe Ile Ala Asp Leu
                85                  90                  95

Phe Glu Gly Thr Val Thr Asp Glu Glu Ser Arg Gln Asn Leu Thr Ser
            100                 105                 110

Thr Ile Asp Ile Val Asp Ser Tyr Ile Ser Ser Asn Tyr Arg Glu Lys
        115                 120                 125

Cys Asp Ile Gln Phe Asn Asn Ser Tyr Lys Leu Ser Ile Lys Ser Phe
    130                 135                 140

Ile Ser Asp Asn Lys Glu Ile Asn Cys Gly Ser Phe Ala Arg Glu Ala
145                 150                 155                 160

Leu Phe Lys Asp Ile Val Glu Asn Tyr Gly Gly Glu Arg Lys Asn Gly
                165                 170                 175

Leu Gly Ser Lys Gly Gln Phe Leu Asp Leu Phe Glu Lys Ile Lys Asp
            180                 185                 190

Asn Gly Lys Trp Thr Asp Phe Thr Asn Arg Phe Thr Tyr Met Thr Asn
        195                 200                 205

Asn Ile Phe Lys Asp Asp Leu Leu Ile Phe Ile Lys Gly Gly Asn Asn
    210                 215                 220

Val Asp Ile Tyr Leu Val Asp Ser Glu Lys Phe Arg Asn Thr Leu Ile
225                 230                 235                 240
```

Ser Ala Val Ser Ser Gly Pro Lys Phe Ala Val Ser Val Leu Asn Arg
245 250 255

Tyr Glu Gly Asn Ser Ile Arg Ile Glu Arg Asp Ile Phe Leu Ser Pro
260 265 270

Lys Ile Ser Thr His Ile Gly Leu Asn Phe Asn Lys Thr Asn Glu Asn
275 280 285

Ala Leu Asn Lys Ile Asp Val Glu Leu Gln Lys Leu Lys Asp Val Thr
290 295 300

Leu Asn Phe Ile Ser Asn Asp Thr Ala Ser Leu Asn Asn Tyr Ser Gln
305 310 315 320

Leu Ile Ser Thr Phe Asn Ser Ser Tyr Gln Asn Thr Ile Ser Asp Leu
325 330 335

Leu Ser Leu Lys Ser Met Thr Leu Ser Ser Asp Ala Leu Ile Thr Ser
340 345 350

Phe His Gln Asn Val Leu Asn Leu Tyr Ser Ser Asn Lys Leu Ser Ile
355 360 365

Ile Asp Met Lys Lys Lys Lys Arg Gly Asn Ser Tyr Ser Ile Val Arg
370 375 380

Glu Leu
385

<210> SEQ ID NO 69
<211> LENGTH: 1080
<212> TYPE: DNA
<213> ORGANISM: Caryophanon latum L

<400> SEQUENCE: 69
atgacttatt taattttaag gaggcaacaa cgtatgaaga actctgcaca aatgattaaa 60
gataacatca tgaaagaaca gttaacaatt tatcatgaaa tcgaagtagg tgatcctgaa 120
ttttggtact ctactgaaca aatggaagaa ctattaaatg aagctcttca aggcacagat 180
ttgaacggga tggctttaag aactcgttca aagtttgtaa aagtcaaaat ttgtgaagct 240
tttggatatc aggtgcccaa atcgtttaaa aaaacacaac cacgtttttt atctcaaaaa 300
tttgatgtat ataatcaaaa atcaaataat ctccaaattt ggaatgaaga aatttctcct 360
tcaagaagat atgttttaat aaaaatttct ttcgatgata ttattactca ggtgaaagta 420
gttactggtg atgttttagc gacgttagat agtacaggaa cattaactca aaaatatcaa 480
gcgaaatatg ctggtgtaca tgaaagaaag gctacacttc taagtgaatg cgatacagac 540
tttattcaaa gcattactca atcatacaat agttttgacg aatttacagc tcctgataca 600
aatccaaaag aagacgaatt aatgggaatt gacgaaattt ttgataagct aaaggattta 660
atcggaacta agattccata tataggtgct actcaagaaa gaaatcgagg gggtcattta 720
cacaagatga tttgtgatgc ccttggttat aataatttta aagagaacgg gcagtttcca 780
gatataaaac atcaactatt agaagtgaag ctgcaaacgt cggaaactat agatttagga 840
ttatttacgc ccaatagtta tgagctatta gacatccctc aattaaataa cgagtctatt 900
tcaatgttag atgtgcgtta tgctatattt tatggtgatg ttatagaaga cactattact 960
attacacatt tttatttagt tacaggtgaa gacttcttca cgtattttaa accctttggt 1020
gggaaaggga ttaataagaa aattcaaatt cctttaaatg aagaattttg gaatctttaa 1080

<210> SEQ ID NO 70
<211> LENGTH: 359
<212> TYPE: PRT
<213> ORGANISM: Caryophanon latum L

<400> SEQUENCE: 70

Met Thr Tyr Leu Ile Leu Arg Arg Gln Gln Arg Met Lys Asn Ser Ala
1 5 10 15

Gln Met Ile Lys Asp Asn Ile Met Lys Glu Gln Leu Thr Ile Tyr His
20 25 30

Glu Ile Glu Val Gly Asp Pro Glu Phe Trp Tyr Ser Thr Glu Gln Met
35 40 45

Glu Glu Leu Leu Asn Glu Ala Leu Gln Gly Thr Asp Leu Asn Gly Met
50 55 60

Ala Leu Arg Thr Arg Ser Lys Phe Val Lys Val Lys Ile Cys Glu Ala
65 70 75 80

Phe Gly Tyr Gln Val Pro Lys Ser Phe Lys Lys Thr Gln Pro Arg Phe
85 90 95

Leu Ser Gln Lys Phe Asp Val Tyr Asn Gln Lys Ser Asn Asn Leu Gln
100 105 110

Ile Trp Asn Glu Glu Ile Ser Pro Ser Arg Arg Tyr Val Leu Ile Lys
115 120 125

Ile Ser Phe Asp Asp Ile Ile Thr Gln Val Lys Val Val Thr Gly Asp
130 135 140

Val Leu Ala Thr Leu Asp Ser Thr Gly Thr Leu Thr Gln Lys Tyr Gln
145 150 155 160

Ala Lys Tyr Ala Gly Val His Glu Arg Lys Ala Thr Leu Leu Ser Glu
165 170 175

Cys Asp Thr Asp Phe Ile Gln Ser Ile Thr Gln Ser Tyr Asn Ser Phe
180 185 190

Asp Glu Phe Thr Ala Pro Asp Thr Asn Pro Lys Glu Asp Glu Leu Met
195 200 205

Gly Ile Asp Glu Ile Phe Asp Lys Leu Lys Asp Leu Ile Gly Thr Lys
210 215 220

Ile Pro Tyr Ile Gly Ala Thr Gln Glu Arg Asn Arg Gly Gly His Leu
225 230 235 240

His Lys Met Ile Cys Asp Ala Leu Gly Tyr Asn Asn Phe Lys Glu Asn
245 250 255

Gly Gln Phe Pro Asp Ile Lys His Gln Leu Leu Glu Val Lys Leu Gln
260 265 270

Thr Ser Glu Thr Ile Asp Leu Gly Leu Phe Thr Pro Asn Ser Tyr Glu
275 280 285

Leu Leu Asp Ile Pro Gln Leu Asn Asn Glu Ser Ile Ser Met Leu Asp
290 295 300

Val Arg Tyr Ala Ile Phe Tyr Gly Asp Val Ile Glu Asp Thr Ile Thr
305 310 315 320

Ile Thr His Phe Tyr Leu Val Thr Gly Glu Asp Phe Phe Thr Tyr Phe
325 330 335

Lys Pro Phe Gly Gly Lys Gly Ile Asn Lys Lys Ile Gln Ile Pro Leu
340 345 350

Asn Glu Glu Phe Trp Asn Leu
355

<210> SEQ ID NO 71
<211> LENGTH: 2199
<212> TYPE: DNA
<213> ORGANISM: Chlorella strain NC64A (CA-1A)

<400> SEQUENCE: 71

-continued

```
atgtcttttc gcacgttaga actattcgcc ggtatagctg gtatttcaca tggcctcaga     60
ggtatatcta caccagttgc attcgtagaa attaatgaag acgcacaaaa attcttgaaa    120
acaaagtttt cagatgcatc tgtattcaat gacgttacga aatttaccaa atcggacttc    180
ccagaagaca tagacatgat tactgcggga ttcccgtgca ctgggtttag tattgcaggt    240
tctagaactg gattcgaaca caaggaatcc ggtctctttg ctgatgttgt gcgaatcacg    300
gaagagtata aacctaaaat agtgtttttg gaaaactccc atatgttgtc ccacacttac    360
aatctcgatg tcgtcgtaaa aaagatggat gaaattggtt atttctgcaa gtgggtaact    420
tgtcgggcat caattatagg agcccatcat caacgccacc ggtggttttg tctcgcgatt    480
cgaaaagatt atgaaccaga agaaataatt gtatctgtga atgctacaaa gttcgactgg    540
gaaaataatg aaccaccgtg tcaagtagac aataagagtt acgagaattc aactcttgtt    600
cgtctggcag gatattccgt ggtccccgac cagatcagat atgctttcac cggtctattt    660
acaggtgatt ttgagtcatc gtggaaaact accttgacac ctgggacaat aattggcacg    720
gaacacaaaa aaatgaaagg aacttacgat aaagtcataa acgggtatta tgagaacgat    780
gtgtattatt ctttttcaag gaaagaagtt catcgcgctc ctctaaatat atccgtgaaa    840
ccacgtgata ttccggagaa acataacgga aaaacactcg tagatcgcga aatgatcaag    900
aaatattggt gcacaccatg tgctagttat ggcactgcta ctgctggatg caatgttctg    960
acagaccgtc agtcacatgc acttcctaca caagtcaggt tttcatatag gggtgtatgt   1020
ggacgacatt tgtctggtat atggtgtgca tggttgatgg ggtatgacca agaatatctt   1080
ggttatttgg ttcaatatga ttaaaatatt ttgatacact aaatggatat aagaagaaaa   1140
cgttttacaa tagaaggggc taaacgtata atactcgaaa aaaagagact tgaagagaaa   1200
aaacgaattg cggaagagaa aaaaagaatt gcacttatag aaaaacaacg aattgcggaa   1260
gagaaaaaaa gaattgcgga agagaaaaaa cgattcgcac ttgaagagaa aaaacgaatt   1320
gcggaagaaa aaaaacgaat cgcggaagag aaaaaacgaa tcgtggaaga gaaaaaaaga   1380
cttgcactta tagaaaaaca acgaattgcg gaagagaaaa ttgcgtcggg gagaaaaatt   1440
agaaagagga tctctacaaa tgcaacaaaa catgaaagag aatttgtcaa agttataaat   1500
tcaatgttcg tcggacccgc tacttttgta ttcgtagata taaaaggtaa taaatccaga   1560
gaaatccaca acgttgtaag attcagacaa ttacaaggca gtaaagcgaa atccccgacc   1620
gcgtatgttg atagagaata taacaaacct aaagcggata tagcagcggt agacataacc   1680
ggtaaagatg tggcatggat atcccataaa gcatctgaag gatatcaaca atatctaaaa   1740
atttctggaa agaacctcaa gttcacagga aaagaattag aagaagttct atcgttcaag   1800
agaaaagtag ttagtatggc accggtatct aaaatatggc ctgctaataa gaccgtatgg   1860
tctcctatca agtcaaattt gattaaaaat caagcaatat tcggatttga ttacggtaag   1920
aaaccaggaa gggacaatgt agacatcata ggtcaaggac gaccaattat aacaaaaaga   1980
agttccatat tatatcttac attcactggt tttagcgcat taaatgggca cttggagaat   2040
tttactggga aacatgaacc cgttttctat gtaagaacag aacggagtag tagcgggaga   2100
agtataacaa ctgtcgtcaa tggtgtcact tataaaaatt taagattctt tatacatcca   2160
tacaactttg tttcttcaaa aacacaacgt attatgtag                          2199
```

<210> SEQ ID NO 72
<211> LENGTH: 278
<212> TYPE: PRT
<213> ORGANISM: Chlorella strain NC64A (CA-1A)

<400> SEQUENCE: 72

Met Glu Glu Lys Lys Arg Leu Ala Leu Ile Glu Lys Gln Arg Ile Ala
1               5                   10                  15

Glu Glu Lys Ile Ala Ser Gly Arg Lys Ile Arg Lys Arg Ile Ser Thr
            20                  25                  30

Asn Ala Thr Lys His Glu Arg Glu Phe Val Lys Val Ile Asn Ser Met
        35                  40                  45

Phe Val Gly Pro Ala Thr Phe Val Phe Val Asp Ile Lys Gly Asn Lys
    50                  55                  60

Ser Arg Glu Ile His Asn Val Val Arg Phe Arg Gln Leu Gln Gly Ser
65                  70                  75                  80

Lys Ala Lys Ser Pro Thr Ala Tyr Val Asp Arg Glu Tyr Asn Lys Pro
                85                  90                  95

Lys Ala Asp Ile Ala Ala Val Asp Ile Thr Gly Lys Asp Val Ala Trp
            100                 105                 110

Ile Ser His Lys Ala Ser Glu Gly Tyr Gln Gln Tyr Leu Lys Ile Ser
        115                 120                 125

Gly Lys Asn Leu Lys Phe Thr Gly Lys Glu Leu Glu Glu Val Leu Ser
    130                 135                 140

Phe Lys Arg Lys Val Val Ser Met Ala Pro Val Ser Lys Ile Trp Pro
145                 150                 155                 160

Ala Asn Lys Thr Val Trp Ser Pro Ile Lys Ser Asn Leu Ile Lys Asn
                165                 170                 175

Gln Ala Ile Phe Gly Phe Asp Tyr Gly Lys Lys Pro Gly Arg Asp Asn
            180                 185                 190

Val Asp Ile Ile Gly Gln Gly Arg Pro Ile Ile Thr Lys Arg Ser Ser
        195                 200                 205

Ile Leu Tyr Leu Thr Phe Thr Gly Phe Ser Ala Leu Asn Gly His Leu
    210                 215                 220

Glu Asn Phe Thr Gly Lys His Glu Pro Val Phe Tyr Val Arg Thr Glu
225                 230                 235                 240

Arg Ser Ser Ser Gly Arg Ser Ile Thr Thr Val Val Asn Gly Val Thr
                245                 250                 255

Tyr Lys Asn Leu Arg Phe Phe Ile His Pro Tyr Asn Phe Val Ser Ser
            260                 265                 270

Lys Thr Gln Arg Ile Met
        275

<210> SEQ ID NO 73
<211> LENGTH: 1155
<212> TYPE: DNA
<213> ORGANISM: Deinococcus radiophilus

<400> SEQUENCE: 73
atgagtgaaa ttgacaactt ggtgaacttt atcctttcta aagatggaat tggtgacaaa 60
tccattcttg agaaagaagt gattgaaaga ttttcattaa cgagggatag gtctgtttac 120
tactgcacag attttgctat acgatttagt tcctcgaaat cagcagcatt tagcaacaca 180
gtcctatcgc tatccaatct cagaaaattt gatagcaagc cctttattgt ttgcctcata 240
actcctgcaa aaaattacct ttttttggca aacactagct ttctgaaaaa aatcagccat 300
agttcacaga ccttaacgag caacaatatt agaggcagtt tcaatggaag cgacatatat 360
aaggatttcg atggtatacc caattcccct gagaacttcg aatatctgtt tagaatacac 420
gcagaaacta catttgaaga gaatctaatt cgtttagcag aagcaaccaa cgatattgca 480

```
cctagcggta agaagttcgt tccctcaccc caaggtgaag aaaatatata tctagccccc    540

aagagagcaa gtgagtttat cgcctccgat aattacaggc agctgctgca agaattggat    600

gatatagtaa ggcattatac caatgaaatc attattgcat ccatgataaa caacgtaaat    660

atcaggggca gagtaatcga atatctagtg gccggagaag atgatcttct gagacaaaac    720

ataatttata agctcagaaa tggcggtaca aatctacccc aattcaaaac agataattcg    780

ttaggagatt actcaaaagc ttttgaaggc tttgatacag aaacagatgt gaaaacaaaa    840

attatgctcc ttaattccaa tccaaaagca tacaacttag ataagattct taatttctta    900

tcgagcgata agagcgtatt tcttttctat ttcattggaa tagattctga taactctctt    960

aagacatgtc ttgtgactat gtttaatgag gagttgttac gaggtacaat tactctcagg   1020

cattgggcag gcaggaattc tagaggcgtt tcccagttcg atggaaaaat catcaacaat   1080

ataattctta atccgtcaaa taaaattgat aaggctcaag ctcgggaatt ccttaccaga   1140

attttatctt tataa                                                    1155


<210> SEQ ID NO 74
<211> LENGTH: 384
<212> TYPE: PRT
<213> ORGANISM: Deinococcus radiophilus

<400> SEQUENCE: 74

Met Ser Glu Ile Asp Asn Leu Val Asn Phe Ile Leu Ser Lys Asp Gly
1               5                   10                  15

Ile Gly Asp Lys Ser Ile Leu Glu Lys Glu Val Ile Glu Arg Phe Ser
            20                  25                  30

Leu Thr Arg Asp Arg Ser Val Tyr Tyr Cys Thr Asp Phe Ala Ile Arg
        35                  40                  45

Phe Ser Ser Ser Lys Ser Ala Ala Phe Ser Asn Thr Val Leu Ser Leu
    50                  55                  60

Ser Asn Leu Arg Lys Phe Asp Ser Lys Pro Phe Ile Val Cys Leu Ile
65                  70                  75                  80

Thr Pro Ala Lys Asn Tyr Leu Phe Leu Ala Asn Thr Ser Phe Leu Lys
                85                  90                  95

Lys Ile Ser His Ser Ser Gln Thr Leu Thr Ser Asn Asn Ile Arg Gly
            100                 105                 110

Ser Phe Asn Gly Ser Asp Ile Tyr Lys Asp Phe Asp Gly Ile Pro Asn
        115                 120                 125

Ser Pro Glu Asn Phe Glu Tyr Leu Phe Arg Ile His Ala Glu Thr Thr
    130                 135                 140

Phe Glu Glu Asn Leu Ile Arg Leu Ala Glu Ala Thr Asn Asp Ile Ala
145                 150                 155                 160

Pro Ser Gly Lys Lys Phe Val Pro Ser Pro Gln Gly Glu Glu Asn Ile
                165                 170                 175

Tyr Leu Ala Pro Lys Arg Ala Ser Glu Phe Ile Ala Ser Asp Asn Tyr
            180                 185                 190

Arg Gln Leu Leu Gln Glu Leu Asp Asp Ile Val Arg His Tyr Thr Asn
        195                 200                 205

Glu Ile Ile Ile Ala Ser Met Ile Asn Asn Val Asn Ile Arg Gly Arg
    210                 215                 220

Val Ile Glu Tyr Leu Val Ala Gly Glu Asp Asp Leu Leu Arg Gln Asn
225                 230                 235                 240

Ile Ile Tyr Lys Leu Arg Asn Gly Gly Thr Asn Leu Pro Gln Phe Lys
                245                 250                 255
```

-continued

```
Thr Asp Asn Ser Leu Gly Asp Tyr Ser Lys Ala Phe Glu Gly Phe Asp
            260                 265                 270

Thr Glu Thr Asp Val Lys Thr Lys Ile Met Leu Leu Asn Ser Asn Pro
        275                 280                 285

Lys Ala Tyr Asn Leu Asp Lys Ile Leu Asn Phe Leu Ser Ser Asp Lys
    290                 295                 300

Ser Val Phe Leu Phe Tyr Phe Ile Gly Ile Asp Ser Asp Asn Ser Leu
305                 310                 315                 320

Lys Thr Cys Leu Val Thr Met Phe Asn Glu Glu Leu Leu Arg Gly Thr
                325                 330                 335

Ile Thr Leu Arg His Trp Ala Gly Arg Asn Ser Arg Gly Val Ser Gln
            340                 345                 350

Phe Asp Gly Lys Ile Ile Asn Asn Ile Ile Leu Asn Pro Ser Asn Lys
        355                 360                 365

Ile Asp Lys Ala Gln Ala Arg Glu Phe Leu Thr Arg Ile Leu Ser Leu
    370                 375                 380
```

<210> SEQ ID NO 75
<211> LENGTH: 906
<212> TYPE: DNA
<213> ORGANISM: Enterobacter agglomerans

<400> SEQUENCE: 75

```
atgaaaaaaa gaagagattt ggttgaagta tttggctata accctatgga ccttagccct      60

gaagtcaggg ctctttggaa cttgggagca tgcccatttc ttaataaaga atgcataaaa     120

ataaatcatg atcaaacaat aatttatggc acatgcagtg taacgtctcc ttatggagac     180

gttattattt gtccaaatag gctttatgct aatgactatg aaaccttgca taaagtcagt     240

cgcgatgcat ttggcgatga tgtccctttt ttgacttata gtaatttcat aaaatatagg     300

gcgacttaca aagactgtat cgtagccctc ggtaaaaact cagggaaaga agttcaagtt     360

ggcagggctc tatcgatgga ctgggttttg gtcagaatca ctgacgggga acttaaagaa     420

tacgtaggcg tagaaataca aagcattgat ataactggaa attacagaga tgcttggcat     480

gcttacaaaa acctcaaacc tatagatatc attgataact taccaacttc acaacatgga     540

ctgaattggg ctaatgtaca caaaagactc ataccacaaa taataagaaa aggagttgtt     600

tactctcgat caaattatgt aaaaaaaggt ctttatttta tattacctga gattgtctat     660

aataaatttg aagatgttat tggtgcagac atacctcttt tgaaaacaca aacgaataaa     720

agcataacag ttcatacata ctccttaggt gagccagctg caaatggtga acaacgaaaa     780

ctaatcagtg aaagagaaat cattttcgat ttagacgaat tttcaaaaag attcacgact     840

ggccccaact tgccaaaagg agatgatttg gacgcagtaa ttaaaaaagc gttaggaatg     900

atgtaa                                                                 906
```

<210> SEQ ID NO 76
<211> LENGTH: 301
<212> TYPE: PRT
<213> ORGANISM: Enterobacter agglomerans

<400> SEQUENCE: 76

```
Met Lys Lys Arg Arg Asp Leu Val Glu Val Phe Gly Tyr Asn Pro Met
1               5                   10                  15

Asp Leu Ser Pro Glu Val Arg Ala Leu Trp Asn Leu Gly Ala Cys Pro
            20                  25                  30

Phe Leu Asn Lys Glu Cys Ile Lys Ile Asn His Asp Gln Thr Ile Ile
        35                  40                  45
```

```
Tyr Gly Thr Cys Ser Val Thr Ser Pro Tyr Gly Asp Val Ile Ile Cys
    50                  55                  60

Pro Asn Arg Leu Tyr Ala Asn Asp Tyr Glu Thr Leu His Lys Val Ser
65                  70                  75                  80

Arg Asp Ala Phe Gly Asp Asp Val Pro Phe Leu Thr Tyr Ser Asn Phe
                85                  90                  95

Ile Lys Tyr Arg Ala Thr Tyr Lys Asp Cys Ile Val Ala Leu Gly Lys
            100                 105                 110

Asn Ser Gly Lys Glu Val Gln Val Gly Arg Ala Leu Ser Met Asp Trp
        115                 120                 125

Val Leu Val Arg Ile Thr Asp Gly Glu Leu Lys Glu Tyr Val Gly Val
    130                 135                 140

Glu Ile Gln Ser Ile Asp Ile Thr Gly Asn Tyr Arg Asp Ala Trp His
145                 150                 155                 160

Ala Tyr Lys Asn Leu Lys Pro Ile Asp Ile Ile Asp Asn Leu Pro Thr
                165                 170                 175

Ser Gln His Gly Leu Asn Trp Ala Asn Val His Lys Arg Leu Ile Pro
            180                 185                 190

Gln Ile Ile Arg Lys Gly Val Val Tyr Ser Arg Ser Asn Tyr Val Lys
        195                 200                 205

Lys Gly Leu Tyr Phe Ile Leu Pro Glu Ile Val Tyr Asn Lys Phe Glu
    210                 215                 220

Asp Val Ile Gly Ala Asp Ile Pro Leu Leu Lys Thr Gln Thr Asn Lys
225                 230                 235                 240

Ser Ile Thr Val His Thr Tyr Ser Leu Gly Glu Pro Ala Ala Asn Gly
                245                 250                 255

Glu Gln Arg Lys Leu Ile Ser Glu Arg Glu Ile Ile Phe Asp Leu Asp
            260                 265                 270

Glu Phe Ser Lys Arg Phe Thr Thr Gly Pro Asn Leu Pro Lys Gly Asp
        275                 280                 285

Asp Leu Asp Ala Val Ile Lys Lys Ala Leu Gly Met Met
    290                 295                 300
```

<210> SEQ ID NO 77
<211> LENGTH: 378
<212> TYPE: DNA
<213> ORGANISM: Enterobacter aerogenes

<400> SEQUENCE: 77

```
gatcatacat tgcctgtata ttacttatgg cctttgacta ctaataatgc cacattgctc     60

tgtaaagtac ataatggaga aaaagcagag aaatggcctg gcgagtttta ttcaaggcaa    120

gaattggcat cactctcaag attgaccggg gttgaagctc gtgttttggc tggggcacca    180

atatttaatc cagaagcaat tgatatttta aaaaatccta aattcgttga aggtttagtc    240

gataagtttt ccagatatcc gaatgaggta tataatttac gcaatcgaat taagagagtt    300

acagggttcg atttcttcga taaccctaat ttgaaaattt ctgccaattg ggttatcgaa    360

gccgataaac ttatctaa                                                  378
```

<210> SEQ ID NO 78
<211> LENGTH: 125
<212> TYPE: PRT
<213> ORGANISM: Enterobacter aerogenes

<400> SEQUENCE: 78

```
Asp His Thr Leu Pro Val Tyr Tyr Leu Trp Pro Leu Thr Thr Asn Asn
```

-continued

```
1               5                   10                  15

Ala Thr Leu Leu Cys Lys Val His Asn Gly Glu Lys Ala Glu Lys Trp
            20                  25                  30

Pro Gly Glu Phe Tyr Ser Arg Gln Glu Leu Ala Ser Leu Ser Arg Leu
        35                  40                  45

Thr Gly Val Glu Ala Arg Val Leu Ala Gly Ala Pro Ile Phe Asn Pro
    50                  55                  60

Glu Ala Ile Asp Ile Leu Lys Asn Pro Lys Phe Val Glu Gly Leu Val
65                  70                  75                  80

Asp Lys Phe Ser Arg Tyr Pro Asn Glu Val Tyr Asn Leu Arg Asn Arg
                85                  90                  95

Ile Lys Arg Val Thr Gly Phe Asp Phe Phe Asp Asn Pro Asn Leu Lys
            100                 105                 110

Ile Ser Ala Asn Trp Val Ile Glu Ala Asp Lys Leu Ile
        115                 120                 125
```

<210> SEQ ID NO 79
<211> LENGTH: 696
<212> TYPE: DNA
<213> ORGANISM: Environmental sample BC3

<400> SEQUENCE: 79

```
atgctcaaga ccacctcaac cttttccccc tcaaccgtca aattccccaa aaaacccgcg      60

ctcacaatat ccttcccatc caccattata ccctttaaga tctccaaagc cttctttgat     120

gtcatacata gaattctaaa ggcggagagg caatgctttc ccaactttat aataacgaga     180

aggaaaatgc taagcttaaa ccttagggga ttatcaaaac cttctttgat agccctttac     240

atagaccttc tgacgctcta ctttaaaacc accttgtggg tgtgcggttt tcaacccaac     300

acggaaaaac ttggatacaa cggttatagg atggatgcag atacaggcaa gagaattgat     360

tgcgaggtaa aaccacaaaa taccgataac cgtagaaaaa aattgactgg aggtggaagt     420

tttaacgatt atacggtaga aaggtttaaa aaggatttag aaaacaatcc tgcaattttg     480

gttagtggtt ttgtaggagg gaaactcata tacatctttg agtttaggtt tgaatgctta     540

agggaaaaac ttaaaggttt gcttgaacgt agatttccaa ggggccacag aagggaaggt     600

gaatacttac gttccgcgaa cttttctttc gatactttga gggtcttgaa agatgaaggg     660

tttggaaagg ttcataaatc aagttataca cggtga                               696
```

<210> SEQ ID NO 80
<211> LENGTH: 231
<212> TYPE: PRT
<213> ORGANISM: Environmental sample BC3

<400> SEQUENCE: 80

```
Met Leu Lys Thr Thr Ser Thr Phe Ser Pro Ser Thr Val Lys Phe Pro
1               5                   10                  15

Lys Lys Pro Ala Leu Thr Ile Ser Phe Pro Ser Thr Ile Ile Pro Phe
            20                  25                  30

Lys Ile Ser Lys Ala Phe Phe Asp Val Ile His Arg Ile Leu Lys Ala
        35                  40                  45

Glu Arg Gln Cys Phe Pro Asn Phe Ile Ile Thr Arg Arg Lys Met Leu
    50                  55                  60

Ser Leu Asn Leu Arg Gly Leu Ser Lys Pro Ser Leu Ile Ala Leu Tyr
65                  70                  75                  80

Ile Asp Leu Leu Thr Leu Tyr Phe Lys Thr Thr Leu Trp Val Cys Gly
                85                  90                  95
```

```
Phe Gln Pro Asn Thr Glu Lys Leu Gly Tyr Asn Gly Tyr Arg Met Asp
            100                 105                 110

Ala Asp Thr Gly Lys Arg Ile Asp Cys Glu Val Lys Pro Gln Asn Thr
        115                 120                 125

Asp Asn Arg Arg Lys Lys Leu Thr Gly Gly Gly Ser Phe Asn Asp Tyr
    130                 135                 140

Thr Val Glu Arg Phe Lys Lys Asp Leu Glu Asn Asn Pro Ala Ile Leu
145                 150                 155                 160

Val Ser Gly Phe Val Gly Gly Lys Leu Ile Tyr Ile Phe Glu Phe Arg
                165                 170                 175

Phe Glu Cys Leu Arg Glu Lys Leu Lys Gly Leu Leu Glu Arg Arg Phe
            180                 185                 190

Pro Arg Gly His Arg Arg Glu Gly Glu Tyr Leu Arg Ser Ala Asn Phe
        195                 200                 205

Ser Phe Asp Thr Leu Arg Val Leu Lys Asp Glu Gly Phe Gly Lys Val
    210                 215                 220

His Lys Ser Ser Tyr Thr Arg
225                 230
```

<210> SEQ ID NO 81
<211> LENGTH: 1047
<212> TYPE: DNA
<213> ORGANISM: Environmental sample BC4

<400> SEQUENCE: 81

```
atggacctgt tggctgaaat aagaggtata aaatataagc cgtttctttg tagagacctg      60

gtaccttttg agtttagcag gttagaagat gctattgcct cctctccatc ttttatttta     120

gaagttgatg aaaaaaatag ggttgctgta agttggtggg tttcacctaa acgcactcgc     180

tcctatccat acgcaagagt ttacgatact ttaggttttt ccggaaagaa aataacaatc     240

attccaatca tgaaagacga aggtgaagga ggggatagag attttttaca atgggatact     300

gtttcactta tgagtttgtt aggagtttat gtgattattg cttattataa caaggccgag     360

ccgagtaaaa ggtataaaaa caagatcaca aatcaacgat ttgatattga ttacattaaa     420

gaaaaaatta aaagcattat ttcttaccaa tcggatgctt tacactggaa tctttatgaa     480

gttgaaaatg tgggagaaat tggagaaaga gctctgaagg cttatgactt aatttcaatg     540

gagttaaata taagaatgca ttcacgaaaa actgcagaaa aaagaattaa agaattatta     600

aaagggaaag aaaagtttat gagtctttca cgaactttag cggagaaagc acaaagaaga     660

gagaaattga ctattcagcc aaaagaaaat ctttctggat caaaagcttc tattacaata     720

aagaattatc taggtggttt ttattatctc actgttgatg aagtaaaagt tataggaaat     780

aaagttttgc taattgaggc gaagcatagc aagacaaatt ccttaccgtc gctggaagat     840

ataaaagatg gtctgttaaa gatgatttta tttactaatc tcgaaaatgt agaaatagaa     900

agtaaaaatt ataagccaga agctgtgtta aaactaactg ttgaaggtgg ttttaacgag     960

agtagacttt caccttcaca aaaaaagact ttaaaactct tacaagaaga agccgaaagc    1020

aataattttc aaattcaact aatatga                                        1047
```

<210> SEQ ID NO 82
<211> LENGTH: 348
<212> TYPE: PRT
<213> ORGANISM: Environmental sample BC4

<400> SEQUENCE: 82

-continued

```
Met Asp Leu Leu Ala Glu Ile Arg Gly Ile Lys Tyr Lys Pro Phe Leu
1               5                   10                  15

Cys Arg Asp Leu Val Pro Phe Glu Phe Ser Arg Leu Glu Asp Ala Ile
            20                  25                  30

Ala Ser Ser Pro Ser Phe Ile Leu Glu Val Asp Glu Lys Asn Arg Val
        35                  40                  45

Ala Val Ser Trp Trp Val Ser Pro Lys Arg Thr Arg Ser Tyr Pro Tyr
    50                  55                  60

Ala Arg Val Tyr Asp Thr Leu Gly Phe Ser Gly Lys Lys Ile Thr Ile
65                  70                  75                  80

Ile Pro Ile Met Lys Asp Glu Gly Glu Gly Gly Asp Arg Asp Phe Leu
                85                  90                  95

Gln Trp Asp Thr Val Ser Leu Met Ser Leu Leu Gly Val Tyr Val Ile
            100                 105                 110

Ile Ala Tyr Tyr Asn Lys Ala Glu Pro Ser Lys Arg Tyr Lys Asn Lys
        115                 120                 125

Ile Thr Asn Gln Arg Phe Asp Ile Asp Tyr Ile Lys Glu Lys Ile Lys
    130                 135                 140

Ser Ile Ile Ser Tyr Gln Ser Asp Ala Leu His Trp Asn Leu Tyr Glu
145                 150                 155                 160

Val Glu Asn Val Gly Glu Ile Gly Glu Arg Ala Leu Lys Ala Tyr Asp
                165                 170                 175

Leu Ile Ser Met Glu Leu Asn Ile Arg Met His Ser Arg Lys Thr Ala
            180                 185                 190

Glu Lys Arg Ile Lys Glu Leu Leu Lys Gly Lys Glu Lys Phe Met Ser
        195                 200                 205

Leu Ser Arg Thr Leu Ala Glu Lys Ala Gln Arg Arg Glu Lys Leu Thr
    210                 215                 220

Ile Gln Pro Lys Glu Asn Leu Ser Gly Ser Lys Ala Ser Ile Thr Ile
225                 230                 235                 240

Lys Asn Tyr Leu Gly Gly Phe Tyr Tyr Leu Thr Val Asp Glu Val Lys
                245                 250                 255

Val Ile Gly Asn Lys Val Leu Leu Ile Glu Ala Lys His Ser Lys Thr
            260                 265                 270

Asn Ser Leu Pro Ser Leu Glu Asp Ile Lys Asp Gly Leu Leu Lys Met
        275                 280                 285

Ile Leu Phe Thr Asn Leu Glu Asn Val Glu Ile Glu Ser Lys Asn Tyr
    290                 295                 300

Lys Pro Glu Ala Val Leu Lys Leu Thr Val Glu Gly Gly Phe Asn Glu
305                 310                 315                 320

Ser Arg Leu Ser Pro Ser Gln Lys Lys Thr Leu Lys Leu Leu Gln Glu
                325                 330                 335

Glu Ala Glu Ser Asn Asn Phe Gln Ile Gln Leu Ile
            340                 345
```

<210> SEQ ID NO 83
<211> LENGTH: 711
<212> TYPE: DNA
<213> ORGANISM: Environmental sample BS #9

<400> SEQUENCE: 83

```
atggcagaga gaggtttgag ttggcggttg gcaactatca acgaactcgg ttggcggggc      60

aaaaaccgaa agcagcgact ctggtgcaac gccgcgacgg gtcgttctat ctgcaaatta     120

gttgaaaaaa tccaacacaa acttccaaag ctatttcact tagcagaatt agagagttca     180
```

-continued

```
agagctggta agatagggat ggaagtaggt tctattaggg aaaagattat cgtcgctttg    240

ttgatacaca agtttggtga agaaaatgtt aagaccgata ttccgattac tgaagcagaa    300

gtagatgttg aagtatttgg aaatccgctt tccataaaga ctattacagg aaaaaatcta    360

tcgggtgtaa agctaatatg gactgttgat gccgctaaat caaaagaatt tcgtgagact    420

tatttacctt tctgcgatat gattttaata caggtcaact ggggtagtaa cggcggattt    480

taccttattc caaaagaaac gcaacttgac gtattgaaca acttaggcag aacaacatac    540

ataaaactcc ccaaaactgg gacaaatcca agaggcgttg agttgagcag gcaggcttta    600

caggagttag tgcggcacaa agacacaatg ataataccta ttgattggaa aaaagaagaa    660

atagacttta aaccacttaa aagatggatt gaattatggg agaaagagta a             711
```

<210> SEQ ID NO 84
<211> LENGTH: 236
<212> TYPE: PRT
<213> ORGANISM: Environmental sample BS #9

<400> SEQUENCE: 84

```
Met Ala Glu Arg Gly Leu Ser Trp Arg Leu Ala Thr Ile Asn Glu Leu
1               5                   10                  15

Gly Trp Arg Gly Lys Asn Arg Lys Gln Arg Leu Trp Cys Asn Ala Ala
            20                  25                  30

Thr Gly Arg Ser Ile Cys Lys Leu Val Glu Lys Ile Gln His Lys Leu
        35                  40                  45

Pro Lys Leu Phe His Leu Ala Glu Leu Glu Ser Ser Arg Ala Gly Lys
    50                  55                  60

Ile Gly Met Glu Val Gly Ser Ile Arg Glu Lys Ile Ile Val Ala Leu
65                  70                  75                  80

Leu Ile His Lys Phe Gly Glu Glu Asn Val Lys Thr Asp Ile Pro Ile
                85                  90                  95

Thr Glu Ala Glu Val Asp Val Glu Val Phe Gly Asn Pro Leu Ser Ile
            100                 105                 110

Lys Thr Ile Thr Gly Lys Asn Leu Ser Gly Val Lys Leu Ile Trp Thr
        115                 120                 125

Val Asp Ala Ala Lys Ser Lys Glu Phe Arg Glu Thr Tyr Leu Pro Phe
    130                 135                 140

Cys Asp Met Ile Leu Ile Gln Val Asn Trp Gly Ser Asn Gly Gly Phe
145                 150                 155                 160

Tyr Leu Ile Pro Lys Glu Thr Gln Leu Asp Val Leu Asn Asn Leu Gly
                165                 170                 175

Arg Thr Thr Tyr Ile Lys Leu Pro Lys Thr Gly Thr Asn Pro Arg Gly
            180                 185                 190

Val Glu Leu Ser Arg Gln Ala Leu Gln Glu Leu Val Arg His Lys Asp
        195                 200                 205

Thr Met Ile Ile Pro Ile Asp Trp Lys Lys Glu Glu Ile Asp Phe Lys
    210                 215                 220

Pro Leu Lys Arg Trp Ile Glu Leu Trp Glu Lys Glu
225                 230                 235
```

<210> SEQ ID NO 85
<211> LENGTH: 780
<212> TYPE: DNA
<213> ORGANISM: Environmental sample Dixie, Nevada

<400> SEQUENCE: 85

```
atgaaagatc caattgaaga cctaaaaagg tatcgtgatt ttcttgaaag catacccttta     60
```

gacgagtata gaaaacaatt aaaaggtatt aaatgggtag agcaagactt acccaaagaa 120
attttacccc ttgcctcaat attcaaatat tactgggaga ttagaaaatt tttaaatttt 180
gatgaatggt tcgataaatt ttggagagag ataaatacca atctagaaag taagaagaca 240
cttgaagaat tcaaaagata tttcttcaat aagtcacttg aagaaaatga ttggtttagg 300
aaaggattta aagcaagaat gtatagaact tgggtatctg ttcttactca attagacttt 360
tgttatatgt ttgaatatgt ctgtgctaaa aagggaataa atttaaaatt agagtgcaat 420
gcagagttag atgcaagagg aattgatgct aaggttaatg atatttgttt tcaggtagcg 480
aaaataagtc aaagaaaaga agcaaggact gtaggtagaa agaaaacaat tattactata 540
ccttatgctg tatttaacat agaagagttt aaaagaagga ttgcaagtcc gcgggttaaa 600
gacaaaagta gctatcaaaa agccttaaag gcgtttcata agtactttga tcttcttaaa 660
aatggctttg ttgtttttaa gaaagattat ataaagaaga taataaataa catagacgat 720
gttgaaaaac tgagacaagc ggttaatgaa atctcacgag aattatgtgg agaaatttaa 780

<210> SEQ ID NO 86
<211> LENGTH: 259
<212> TYPE: PRT
<213> ORGANISM: Environmental sample Dixie, Nevada

<400> SEQUENCE: 86

Met Lys Asp Pro Ile Glu Asp Leu Lys Arg Tyr Arg Asp Phe Leu Glu
1 5 10 15

Ser Ile Pro Leu Asp Glu Tyr Arg Lys Gln Leu Lys Gly Ile Lys Trp
20 25 30

Val Glu Gln Asp Leu Pro Lys Glu Ile Leu Pro Leu Ala Ser Ile Phe
35 40 45

Lys Tyr Tyr Trp Glu Ile Arg Lys Phe Leu Asn Phe Asp Glu Trp Phe
50 55 60

Asp Lys Phe Trp Arg Glu Ile Asn Thr Asn Leu Glu Ser Lys Lys Thr
65 70 75 80

Leu Glu Glu Phe Lys Arg Tyr Phe Phe Asn Lys Ser Leu Glu Glu Asn
85 90 95

Asp Trp Phe Arg Lys Gly Phe Lys Ala Arg Met Tyr Arg Thr Trp Val
100 105 110

Ser Val Leu Thr Gln Leu Asp Phe Cys Tyr Met Phe Glu Tyr Val Cys
115 120 125

Ala Lys Lys Gly Ile Asn Leu Lys Leu Glu Cys Asn Ala Glu Leu Asp
130 135 140

Ala Arg Gly Ile Asp Ala Lys Val Asn Asp Ile Cys Phe Gln Val Ala
145 150 155 160

Lys Ile Ser Gln Arg Lys Glu Ala Arg Thr Val Gly Arg Lys Lys Thr
165 170 175

Ile Ile Thr Ile Pro Tyr Ala Val Phe Asn Ile Glu Glu Phe Lys Arg
180 185 190

Arg Ile Ala Ser Pro Arg Val Lys Asp Lys Ser Ser Tyr Gln Lys Ala
195 200 205

Leu Lys Ala Phe His Lys Tyr Phe Asp Leu Leu Lys Asn Gly Phe Val
210 215 220

Val Phe Lys Lys Asp Tyr Ile Lys Lys Ile Ile Asn Asn Ile Asp Asp
225 230 235 240

Val Glu Lys Leu Arg Gln Ala Val Asn Glu Ile Ser Arg Glu Leu Cys
245 250 255

Gly Glu Ile

<210> SEQ ID NO 87
<211> LENGTH: 969
<212> TYPE: DNA
<213> ORGANISM: Bacillus species 2521

<400> SEQUENCE: 87
atggttatta atcatttatt attgcctaat ttaaatatta ataatgaaaa agcagtcccg 60
gaagtatata aacgtatttt ggaagggtat ttagattatt taaatacagc cctcgaatac 120
gaatcaattg ctatgtctga ggtagttgct ggagttataa gtgaattaat tttatataat 180
gaaattaagc atgactggtt tttaattata aaagacttac tagaatatga tgaattaccg 240
atatcttatt ctaagaatta tggtgaaaaa ttatatggat ttaattcaca gtggttacaa 300
catactgttc atgccactta taatcatagt tttattatga atttgttaaa taagagccaa 360
tttgattact caagtattat attagattta gttcaacctg atggatatat ttataacaag 420
aaggttagtg caaccaatcc ccgaacccgc atgaaaagtg agctattaat gtctttaact 480
atggggttat cgttaattga ttctagtcga attcctgaac agtgtatcgt taagataaag 540
acatttgata aaacagaatt tgtaacagca gagtatttta agttgttctg tttaaagctt 600
ttgaaaatag ataacttaga aacgtattgc aactacaatg atatattatt agaaagatgt 660
tttaccggta ctggatatgc tgattttaat gttcaagata aagtcgatga ttacatggga 720
acattaaaac gaactgctag agataaatct gttgcatcac ccttaataac ggtttacgca 780
ggagaaattg ctgaagtatt aggttcttct acgttagatt tgtataattc taacaaggaa 840
aagtatattc aacatttatc tttgaacccg ctagacatta ccgcttataa aatgagagat 900
cttaatgcag attttgggga aagtattacc ccttttgaaa ttttttccac tataattctg 960
aataattaa 969

<210> SEQ ID NO 88
<211> LENGTH: 322
<212> TYPE: PRT
<213> ORGANISM: Bacillus species 2521

<400> SEQUENCE: 88

Met Val Ile Asn His Leu Leu Leu Pro Asn Leu Asn Ile Asn Asn Glu
1               5                   10                  15

Lys Ala Val Pro Glu Val Tyr Lys Arg Ile Leu Glu Gly Tyr Leu Asp
            20                  25                  30

Tyr Leu Asn Thr Ala Leu Glu Tyr Glu Ser Ile Ala Met Ser Glu Val
        35                  40                  45

Val Ala Gly Val Ile Ser Glu Leu Ile Leu Tyr Asn Glu Ile Lys His
    50                  55                  60

Asp Trp Phe Leu Ile Ile Lys Asp Leu Leu Glu Tyr Asp Glu Leu Pro
65                  70                  75                  80

Ile Ser Tyr Ser Lys Asn Tyr Gly Glu Lys Leu Tyr Gly Phe Asn Ser
                85                  90                  95

Gln Trp Leu Gln His Thr Val His Ala Thr Tyr Asn His Ser Phe Ile
            100                 105                 110

Met Asn Leu Leu Asn Lys Ser Gln Phe Asp Tyr Ser Ser Ile Ile Leu
        115                 120                 125

Asp Leu Val Gln Pro Asp Gly Tyr Ile Tyr Asn Lys Lys Val Ser Ala
    130                 135                 140

```
Thr Asn Pro Arg Thr Arg Met Lys Ser Glu Leu Leu Met Ser Leu Thr
145                 150                 155                 160

Met Gly Leu Ser Leu Ile Asp Ser Ser Arg Ile Pro Glu Gln Cys Ile
                165                 170                 175

Val Lys Ile Lys Thr Phe Asp Lys Thr Glu Phe Val Thr Ala Glu Tyr
            180                 185                 190

Phe Lys Leu Phe Cys Leu Lys Leu Leu Lys Ile Asp Asn Leu Glu Thr
        195                 200                 205

Tyr Cys Asn Tyr Asn Asp Ile Leu Leu Glu Arg Cys Phe Thr Gly Thr
    210                 215                 220

Gly Tyr Ala Asp Phe Asn Val Gln Asp Lys Val Asp Asp Tyr Met Gly
225                 230                 235                 240

Thr Leu Lys Arg Thr Ala Arg Asp Lys Ser Val Ala Ser Pro Leu Ile
                245                 250                 255

Thr Val Tyr Ala Gly Glu Ile Ala Glu Val Leu Gly Ser Ser Thr Leu
            260                 265                 270

Asp Leu Tyr Asn Ser Asn Lys Glu Lys Tyr Ile Gln His Leu Ser Leu
        275                 280                 285

Asn Pro Leu Asp Ile Thr Ala Tyr Lys Met Arg Asp Leu Asn Ala Asp
    290                 295                 300

Phe Gly Glu Ser Ile Thr Pro Phe Glu Ile Phe Ser Thr Ile Ile Leu
305                 310                 315                 320

Asn Asn


<210> SEQ ID NO 89
<211> LENGTH: 603
<212> TYPE: DNA
<213> ORGANISM: Environmental sample LHC

<400> SEQUENCE: 89

gcaaagggaa acatcaattc attcaaaggc attcacaaag ttttccatga attcgagcca      60

attcagacca ctgtggtatg gccttacaaa aagagcttac ttaacgagta caatacaagc     120

gaaagcaaca ttttatctgt agcaaataat caaagaattt tgcatcactt cttgtttgga     180

aaagatacag aatttgatag cttagacatt acaaaacgac ctaaaaccta ttttccacat     240

agaacaaaaa tgagtttttt ctatagcttt ggaaaagatt tacagattga gttgaagaac     300

atacaaatag aaattgattt aactattgag tttcaaggca taatcggaat tttgaagca      360

aagaatggca gtcctagtaa ttttgcaatt tatcagcttt atcatccttt tttatactat     420

tacaacgcca atcaaatctc cgagataaaa ggcgaaatca aaaacattta tggtgtttat     480

gttgttagaa acatagaacg taggattaca aacctaaaaa tgtgggcata tacttttgag     540

aatccattgg atattactag tataaagttt gtaaaatctg cttgctacca actaaaagtc     600

taa                                                                   603


<210> SEQ ID NO 90
<211> LENGTH: 200
<212> TYPE: PRT
<213> ORGANISM: Environmental sample LHC

<400> SEQUENCE: 90

Ala Lys Gly Asn Ile Asn Ser Phe Lys Gly Ile His Lys Val Phe His
1               5                   10                  15

Glu Phe Glu Pro Ile Gln Thr Thr Val Val Trp Pro Tyr Lys Lys Ser
            20                  25                  30

Leu Leu Asn Glu Tyr Asn Thr Ser Glu Ser Asn Ile Leu Ser Val Ala
```

-continued

```
        35                  40                  45

Asn Asn Gln Arg Ile Leu His His Phe Leu Phe Gly Lys Asp Thr Glu
    50                  55                  60

Phe Asp Ser Leu Asp Ile Thr Lys Arg Pro Lys Thr Tyr Phe Pro His
65                  70                  75                  80

Arg Thr Lys Met Ser Phe Phe Tyr Ser Phe Gly Lys Asp Leu Gln Ile
                85                  90                  95

Glu Leu Lys Asn Ile Gln Ile Glu Ile Asp Leu Thr Ile Glu Phe Gln
            100                 105                 110

Gly Ile Ile Gly Ile Phe Glu Ala Lys Asn Gly Ser Pro Ser Asn Phe
        115                 120                 125

Ala Ile Tyr Gln Leu Tyr His Pro Phe Leu Tyr Tyr Tyr Asn Ala Asn
    130                 135                 140

Gln Ile Ser Glu Ile Lys Gly Glu Ile Lys Asn Ile Tyr Gly Val Tyr
145                 150                 155                 160

Val Val Arg Asn Ile Glu Arg Arg Ile Thr Asn Leu Lys Met Trp Ala
                165                 170                 175

Tyr Thr Phe Glu Asn Pro Leu Asp Ile Thr Ser Ile Lys Phe Val Lys
            180                 185                 190

Ser Ala Cys Tyr Gln Leu Lys Val
        195                 200


<210> SEQ ID NO 91
<211> LENGTH: 753
<212> TYPE: DNA
<213> ORGANISM: Environmental sample S1

<400> SEQUENCE: 91

ttaaacttag aaccccgtat tgttgaaagt acaactgaca ttttagagtt gcttatacaa      60

accgactcca aagggagaga aggtgatgta cgagatatat taataattcg gcgagatatt     120

cagtgggaaa tagggctaag ccttaagcat aatcattttg ctgtaaagca tagccgtcta     180

agtcgaaaat tggattttgg aaatgaatgg tatggcattt catgctcgga ggcttattgg     240

aaaggagtta atcctgtatt tgattatcta gttgtcgaaa aaagtaaaca taaaaaattc     300

aatgaactca aaaataaaga agaagtcgtt tacgttcctt tgctaaaagc ttttatagat     360

gaaatcaagc aacaatgcca agtccataaa gatattccta gtaaattggt acaatacctt     420

ttaggaaagt atgactttta taaaataatt agcatagata aagagcggat gactcaaatt     480

caatcctata atttacacgg tacactcaac aaaaacagcg aatcgaaaaa agcatccatt     540

cgaattccac tagcatcctt gccaacgcgt atagtgagtt tggactttgt tccggggaag     600

acaaacactg ttgaacttta tatggatggt ggttggcaat tttcttttcg catacataac     660

gcagaaactt atgttgcgcc gaccttgaag tttgatattc aaatagtagg tatgcctact     720

gctataatca caataaattg tctttggaaa taa                                  753


<210> SEQ ID NO 92
<211> LENGTH: 250
<212> TYPE: PRT
<213> ORGANISM: Environmental sample S1

<400> SEQUENCE: 92

Met Asn Leu Glu Pro Arg Ile Val Glu Ser Thr Thr Asp Ile Leu Glu
1               5                   10                  15

Leu Leu Ile Gln Thr Asp Ser Lys Gly Arg Glu Gly Asp Val Arg Asp
            20                  25                  30
```

-continued

```
Ile Leu Ile Ile Arg Arg Asp Ile Gln Trp Glu Ile Gly Leu Ser Leu
        35                  40                  45

Lys His Asn His Phe Ala Val Lys His Ser Arg Leu Ser Arg Lys Leu
    50                  55                  60

Asp Phe Gly Asn Glu Trp Tyr Gly Ile Ser Cys Ser Glu Ala Tyr Trp
65                  70                  75                  80

Lys Gly Val Asn Pro Val Phe Asp Tyr Leu Val Val Glu Lys Ser Lys
                85                  90                  95

His Lys Lys Phe Asn Glu Leu Lys Asn Lys Glu Glu Val Val Tyr Val
            100                 105                 110

Pro Leu Leu Lys Ala Phe Ile Asp Glu Ile Lys Gln Gln Cys Gln Val
        115                 120                 125

His Lys Asp Ile Pro Ser Lys Leu Val Gln Tyr Leu Leu Gly Lys Tyr
    130                 135                 140

Asp Phe Tyr Lys Ile Ile Ser Ile Asp Lys Glu Arg Met Thr Gln Ile
145                 150                 155                 160

Gln Ser Tyr Asn Leu His Gly Thr Leu Asn Lys Asn Ser Glu Ser Lys
                165                 170                 175

Lys Ala Ser Ile Arg Ile Pro Leu Ala Ser Leu Pro Thr Arg Ile Val
            180                 185                 190

Ser Leu Asp Phe Val Pro Gly Lys Thr Asn Thr Val Glu Leu Tyr Met
        195                 200                 205

Asp Gly Gly Trp Gln Phe Ser Phe Arg Ile His Asn Ala Glu Thr Tyr
    210                 215                 220

Val Ala Pro Thr Leu Lys Phe Asp Ile Gln Ile Val Gly Met Pro Thr
225                 230                 235                 240

Ala Ile Ile Thr Ile Asn Cys Leu Trp Lys
                245                 250


<210> SEQ ID NO 93
<211> LENGTH: 660
<212> TYPE: DNA
<213> ORGANISM: Frankia species Eul1b

<400> SEQUENCE: 93

atgaccgacg agttgtttcc tatcccggag ccattggtca gaccagtcat cgcactcccc      60

cctcatctga aggaattgat cgatctactc ccattgaata cgccggtaca tcgccgagat     120

ctcgaagcga agtatgggcg ctccaactat gctagacgca tacgaaagat tatcagtgaa     180

tacggttggg aaatcgagag tcgccgccag tcggaaggcg ccaatgacga ttggtacatc     240

cgtcggtccg acggccccgt gcgaccgcag cgtattagac gggaggtacc aagacgcagc     300

cgcgagaccg tctacagacg tgacgactgg atctgccaga tttgtcggat gaaaaccgac     360

ccggagcgtg gatctctcgt tccgcagtgc gatcacaaga ttccggcgga ccgcggaggg     420

gattctgatg aagaaaatct tcagacgctt tgcacgcgtt gcaatctcaa gaagaggcag     480

gcctgcggtg gatgcgctct ggccagctgt gcggattgtc catttgcgta tccagaaaag     540

tttgatgatg tgctgattct gcacctcgac agggagcacc ttaagaggat tatgaccacg     600

gcatacgctc gaaatgtcac ggccagtgca gtcgtcagcg acctatccga cctgctctag     660


<210> SEQ ID NO 94
<211> LENGTH: 219
<212> TYPE: PRT
<213> ORGANISM: Frankia species Eul1b

<400> SEQUENCE: 94
```

-continued

```
Met Thr Asp Glu Leu Phe Pro Ile Pro Glu Pro Leu Val Arg Pro Val
1               5                   10                  15

Ile Ala Leu Pro Pro His Leu Lys Glu Leu Ile Asp Leu Leu Pro Leu
            20                  25                  30

Asn Thr Pro Val His Arg Arg Asp Leu Glu Ala Lys Tyr Gly Arg Ser
        35                  40                  45

Asn Tyr Ala Arg Arg Ile Arg Lys Ile Ile Ser Glu Tyr Gly Trp Glu
    50                  55                  60

Ile Glu Ser Arg Arg Gln Ser Glu Gly Ala Asn Asp Asp Trp Tyr Ile
65                  70                  75                  80

Arg Arg Ser Asp Gly Pro Val Arg Pro Gln Arg Ile Arg Arg Glu Val
                85                  90                  95

Pro Arg Arg Ser Arg Glu Thr Val Tyr Arg Arg Asp Asp Trp Ile Cys
            100                 105                 110

Gln Ile Cys Arg Met Lys Thr Asp Pro Glu Arg Gly Ser Leu Val Pro
        115                 120                 125

Gln Cys Asp His Lys Ile Pro Ala Asp Arg Gly Gly Asp Ser Asp Glu
    130                 135                 140

Glu Asn Leu Gln Thr Leu Cys Thr Arg Cys Asn Leu Lys Lys Arg Gln
145                 150                 155                 160

Ala Cys Gly Gly Cys Ala Leu Ala Ser Cys Ala Asp Cys Pro Phe Ala
                165                 170                 175

Tyr Pro Glu Lys Phe Asp Asp Val Leu Ile Leu His Leu Asp Arg Glu
            180                 185                 190

His Leu Lys Arg Ile Met Thr Thr Ala Tyr Ala Arg Asn Val Thr Ala
        195                 200                 205

Ser Ala Val Val Ser Asp Leu Ser Asp Leu Leu
    210                 215
```

<210> SEQ ID NO 95
<211> LENGTH: 750
<212> TYPE: DNA
<213> ORGANISM: Fischerella species

<400> SEQUENCE: 95

```
gtgttgacaa acaacgagat tgaaagatta aggcaagcca ttatcgcgac cattgcatct     60

cctgtaattg gctcgataga agattataca tgggaagcaa tttttcatta tgttaaggat    120

attcctttat cagatcccgc tctgggacgc agcaagcttc tctatgatgc tgttgacgta    180

gttactaaaa ctggttggtc actcaaatcc ctccaattga agagccttaa ctttaaaagc    240

ccatttttat ttgttattca gagagcagat atccttaaga agtctgtcca gctgggtttt    300

cctggtctga ctgagcaatc ttcgccggat gagcttggag cagccattat ccaacattgg    360

aatgagaaga ttattttgag tcaggcagca caaagcgttg taaatagtta tgaaggcata    420

ttactgaaaa ctatcaaagg ttacgagtat atctattgtg agtttccact cgatcctctt    480

gatccaagca cgttttcttg ggcttggacg gtggacaaaa ctactggcgg tgcaggggta    540

gggctacaag gtagcattgt gggcaaaaca gaattagtgt ggtataaaaa tcagaaacaa    600

cttttcagag ctaggactat tcccgcacaa gcggttcgta ttacagttga aagaactcgt    660

cttactcttg atcgatatgt aaagacagtt atctttgctt tgcaagatca aatcaacatg    720

cagttttctg agaatgagcc tgaagaatag                                     750
```

<210> SEQ ID NO 96
<211> LENGTH: 249
<212> TYPE: PRT

-continued

<213> ORGANISM: Fischerella species

<400> SEQUENCE: 96

```
Met Leu Thr Asn Asn Glu Ile Glu Arg Leu Arg Gln Ala Ile Ile Ala
1               5                   10                  15

Thr Ile Ala Ser Pro Val Ile Gly Ser Ile Glu Asp Tyr Thr Trp Glu
            20                  25                  30

Ala Ile Phe His Tyr Val Lys Asp Ile Pro Leu Ser Asp Pro Ala Leu
        35                  40                  45

Gly Arg Ser Lys Leu Leu Tyr Asp Ala Val Asp Val Val Thr Lys Thr
    50                  55                  60

Gly Trp Ser Leu Lys Ser Leu Gln Leu Lys Ser Leu Asn Phe Lys Ser
65                  70                  75                  80

Pro Phe Leu Phe Val Ile Gln Arg Ala Asp Ile Leu Lys Lys Ser Val
                85                  90                  95

Gln Leu Gly Phe Pro Gly Leu Thr Glu Gln Ser Ser Pro Asp Glu Leu
            100                 105                 110

Gly Ala Ala Ile Ile Gln His Trp Asn Glu Lys Ile Ile Leu Ser Gln
        115                 120                 125

Ala Ala Gln Ser Val Val Asn Ser Tyr Glu Gly Ile Leu Leu Lys Thr
    130                 135                 140

Ile Lys Gly Tyr Glu Tyr Ile Tyr Cys Glu Phe Pro Leu Asp Pro Leu
145                 150                 155                 160

Asp Pro Ser Thr Phe Ser Trp Ala Trp Thr Val Asp Lys Thr Thr Gly
                165                 170                 175

Gly Ala Gly Val Gly Leu Gln Gly Ser Ile Val Gly Lys Thr Glu Leu
            180                 185                 190

Val Trp Tyr Lys Asn Gln Lys Gln Leu Phe Arg Ala Arg Thr Ile Pro
        195                 200                 205

Ala Gln Ala Val Arg Ile Thr Val Glu Arg Thr Arg Leu Thr Leu Asp
    210                 215                 220

Arg Tyr Val Lys Thr Val Ile Phe Ala Leu Gln Asp Gln Ile Asn Met
225                 230                 235                 240

Gln Phe Ser Glu Asn Glu Pro Glu Glu
                245
```

<210> SEQ ID NO 97
<211> LENGTH: 717
<212> TYPE: DNA
<213> ORGANISM: Haemophilus haemolyticus

<400> SEQUENCE: 97

```
atgaattgga aagaatttga agttttttgt gttacttatt taaataaaac ttatggaaac     60

aaatttgcga aaaaaggcga aagtgattct acaacaagtg atattctttt tacaggaaat    120

aatccattct atatagaagc aaaaaatgcca cattcccaat gcggtcaatt tgttttaatt    180

cctaatagag ctaaatataa atttgattat tcaccgaaaa ataagagtga aataaatccc    240

tatactcaaa aaataatgca atttatgtca gaaaacttct ctgaatatgc taatttatct    300

actaaaggga aaattattcc attacctgaa tctgtatttg taaattggat taaggaatat    360

tataaaagta aaagtgtgaa attctttatt acttctaatg gtgattttat tatatttcct    420

attgaacact tcgagcatta ctttaacgta tcttgtacat acagaattaa aaaaagcggt    480

ccaagacatc tcaattcgaa aagccttcct gatttcaaac aggcgttaga taaaaaaggc    540

atctcttata cgatgagggg gttggaactg cattctgacg agaacattca cgataaaaga    600
```

atttcaggag atgataagga ttttttaatt aaagagaata atggagctta tcacgttaag 660
attttatcta atacttttaa tgctaatgtt ataattttca atatcattaa aaaataa 717

<210> SEQ ID NO 98
<211> LENGTH: 238
<212> TYPE: PRT
<213> ORGANISM: Haemophilus haemolyticus

<400> SEQUENCE: 98

```
Met Asn Trp Lys Glu Phe Glu Val Phe Cys Val Thr Tyr Leu Asn Lys
1               5                   10                  15

Thr Tyr Gly Asn Lys Phe Ala Lys Lys Gly Glu Ser Asp Ser Thr Thr
            20                  25                  30

Ser Asp Ile Leu Phe Thr Gly Asn Asn Pro Phe Tyr Ile Glu Ala Lys
        35                  40                  45

Met Pro His Ser Gln Cys Gly Gln Phe Val Leu Ile Pro Asn Arg Ala
    50                  55                  60

Lys Tyr Lys Phe Asp Tyr Ser Pro Lys Asn Lys Ser Glu Ile Asn Pro
65                  70                  75                  80

Tyr Thr Gln Lys Ile Met Gln Phe Met Ser Glu Asn Phe Ser Glu Tyr
                85                  90                  95

Ala Asn Leu Ser Thr Lys Gly Lys Ile Ile Pro Leu Pro Glu Ser Val
            100                 105                 110

Phe Val Asn Trp Ile Lys Glu Tyr Tyr Lys Ser Lys Ser Val Lys Phe
        115                 120                 125

Phe Ile Thr Ser Asn Gly Asp Phe Ile Ile Phe Pro Ile Glu His Phe
    130                 135                 140

Glu His Tyr Phe Asn Val Ser Cys Thr Tyr Arg Ile Lys Lys Ser Gly
145                 150                 155                 160

Pro Arg His Leu Asn Ser Lys Ser Leu Pro Asp Phe Lys Gln Ala Leu
                165                 170                 175

Asp Lys Lys Gly Ile Ser Tyr Thr Met Arg Gly Leu Glu Leu His Ser
            180                 185                 190

Asp Glu Asn Ile His Asp Lys Arg Ile Ser Gly Asp Asp Lys Asp Phe
        195                 200                 205

Leu Ile Lys Glu Asn Asn Gly Ala Tyr His Val Lys Ile Leu Ser Asn
    210                 215                 220

Thr Phe Asn Ala Asn Val Ile Ile Phe Asn Ile Ile Lys Lys
225                 230                 235
```

<210> SEQ ID NO 99
<211> LENGTH: 744
<212> TYPE: DNA
<213> ORGANISM: Haemophilus influenzae P1

<400> SEQUENCE: 99
atgaatctgg tagaattagg atctaaaaca gctaaagatg gttttaaaaa cgaaaaagat 60
attgcagata gatttgaaaa ttggaaagag aattcagaag cccaagattg gttagttaca 120
atgggacata acttagatga aatcaaatct gttaaagctg ttgtattaag tggatataaa 180
tcagatataa atgttcaagt tttagttttt tataaagacg cgttagatat tcataatatt 240
caagttaagc tcgttagtaa taaacgtggt tttaatcaga tagataaaca ctggcttgct 300
cattatcagg aaatgtggaa atttgatgat aatctattaa gaatattaag acattttacg 360
ggtgaacttc ctccatatca ttcaaataca aaagataagc gaagaatgtt tatgacagaa 420
ttttcccaag aagagcaaaa tatcgttctt aattggttag aaaagaacag agttcttgtg 480
ctaaccgata tattaagagg aagaggcgat tttgccgctg aatgggtgct tgtagcacaa 540
aaagtaagta ataatgcaag atggatattg agaaatatta atgaggtttt acaacactat 600
ggttcaggcg atatttctct ttccccaaga ggctctatta actttggtcg agtaactatt 660
caaagaaaag gggcgataa tggtagagaa accgcaaata tgttgcaatt caaaattgat 720
ccaacagagt tatttgatat ttag 744

<210> SEQ ID NO 100
<211> LENGTH: 247
<212> TYPE: PRT
<213> ORGANISM: Haemophilus influenzae P1

<400> SEQUENCE: 100

Met Asn Leu Val Glu Leu Gly Ser Lys Thr Ala Lys Asp Gly Phe Lys
1 5 10 15

Asn Glu Lys Asp Ile Ala Asp Arg Phe Glu Asn Trp Lys Glu Asn Ser
20 25 30

Glu Ala Gln Asp Trp Leu Val Thr Met Gly His Asn Leu Asp Glu Ile
35 40 45

Lys Ser Val Lys Ala Val Val Leu Ser Gly Tyr Lys Ser Asp Ile Asn
50 55 60

Val Gln Val Leu Val Phe Tyr Lys Asp Ala Leu Asp Ile His Asn Ile
65 70 75 80

Gln Val Lys Leu Val Ser Asn Lys Arg Gly Phe Asn Gln Ile Asp Lys
85 90 95

His Trp Leu Ala His Tyr Gln Glu Met Trp Lys Phe Asp Asp Asn Leu
100 105 110

Leu Arg Ile Leu Arg His Phe Thr Gly Glu Leu Pro Pro Tyr His Ser
115 120 125

Asn Thr Lys Asp Lys Arg Arg Met Phe Met Thr Glu Phe Ser Gln Glu
130 135 140

Glu Gln Asn Ile Val Leu Asn Trp Leu Glu Lys Asn Arg Val Leu Val
145 150 155 160

Leu Thr Asp Ile Leu Arg Gly Arg Gly Asp Phe Ala Ala Glu Trp Val
165 170 175

Leu Val Ala Gln Lys Val Ser Asn Asn Ala Arg Trp Ile Leu Arg Asn
180 185 190

Ile Asn Glu Val Leu Gln His Tyr Gly Ser Gly Asp Ile Ser Leu Ser
195 200 205

Pro Arg Gly Ser Ile Asn Phe Gly Arg Val Thr Ile Gln Arg Lys Gly
210 215 220

Gly Asp Asn Gly Arg Glu Thr Ala Asn Met Leu Gln Phe Lys Ile Asp
225 230 235 240

Pro Thr Glu Leu Phe Asp Ile
245

<210> SEQ ID NO 101
<211> LENGTH: 609
<212> TYPE: DNA
<213> ORGANISM: Mycoplasma fermentans

<400> SEQUENCE: 101
atgggtaaat ctgaattaag tggaagatta aattggcaag cattggctgg attaaaagct 60
agtggtgctg aacaaaactt atataacgtg tttaacgctg tttttgaagg aactaaatac 120
gttttatacg agaagccaaa gcaccttaaa aatctatacg ctcaagtagt cttacctgat 180
gatgttatta aagaaatttt taatccttta attgatttat caactactca atggggtgtt 240
tctccagatt tcgcaataga aaatacagaa acgcataaaa ttctttttgg tgaaattaaa 300
agacaagatg gatgggtaga aggtaaagat cctagtgctg gcaggggtaa tgcacatgag 360
agatcttgta aattatttac tcctggatta ttaaaagctt atagaacaat tggtggaatt 420
aacgatgaag agatattgcc attctgggtt gtattcgaag gtgatataac acgagatccc 480
aaaagagtaa gagaaattac tttctggtat gaccactatc aagataatta tttcatgtgg 540
cgaccaaatg aatcaggcga aaaattagtt caacacttca atgaaaaatt aaaaaaatat 600
ttagattaa 609

<210> SEQ ID NO 102
<211> LENGTH: 202
<212> TYPE: PRT
<213> ORGANISM: Mycoplasma fermentans

<400> SEQUENCE: 102

Met Gly Lys Ser Glu Leu Ser Gly Arg Leu Asn Trp Gln Ala Leu Ala
1 5 10 15

Gly Leu Lys Ala Ser Gly Ala Glu Gln Asn Leu Tyr Asn Val Phe Asn
20 25 30

Ala Val Phe Glu Gly Thr Lys Tyr Val Leu Tyr Glu Lys Pro Lys His
35 40 45

Leu Lys Asn Leu Tyr Ala Gln Val Val Leu Pro Asp Asp Val Ile Lys
50 55 60

Glu Ile Phe Asn Pro Leu Ile Asp Leu Ser Thr Thr Gln Trp Gly Val
65 70 75 80

Ser Pro Asp Phe Ala Ile Glu Asn Thr Glu Thr His Lys Ile Leu Phe
85 90 95

Gly Glu Ile Lys Arg Gln Asp Gly Trp Val Glu Gly Lys Asp Pro Ser
100 105 110

Ala Gly Arg Gly Asn Ala His Glu Arg Ser Cys Lys Leu Phe Thr Pro
115 120 125

Gly Leu Leu Lys Ala Tyr Arg Thr Ile Gly Gly Ile Asn Asp Glu Glu
130 135 140

Ile Leu Pro Phe Trp Val Val Phe Glu Gly Asp Ile Thr Arg Asp Pro
145 150 155 160

Lys Arg Val Arg Glu Ile Thr Phe Trp Tyr Asp His Tyr Gln Asp Asn
165 170 175

Tyr Phe Met Trp Arg Pro Asn Glu Ser Gly Glu Lys Leu Val Gln His
180 185 190

Phe Asn Glu Lys Leu Lys Lys Tyr Leu Asp
195 200

<210> SEQ ID NO 103
<211> LENGTH: 828
<212> TYPE: DNA
<213> ORGANISM: Micrococcus luteus

<400> SEQUENCE: 103
gtgagcgctc ccgaagtcga cagcgcccgg gatgcccgct acgtcgagat cctcctggct 60
ccccttcgaa agtgtgggac ctacctgccg aagatgggcg ggtccggcga agtggatctc 120
gctggcttca ccgcggccta cggggctgat ccgctctatc actggatggg gctcgactcg 180
cctctcatgt tcgctgcgca caaggccgcc ggcggtatga cctcgatcta ccgccagctc 240

```
ggtatcggat ccgagcgcct cttccgccag gtcctgcggg acgagctcaa tctcacagcc    300

gaccaggtca agtggtccta caagatgctg cccgagcttg atgcggagca cgcgaacgag    360

tcggtcaaag ctcgagtcct ctcgttggac gggagggtgg agctcgagga tctggaggat    420

cagcaggctc gcgagcgcgt cgaagcttgg atagaagtac agcgccgtcg tctcaacatc    480

accgcacccc tcaagggcgc cgtcttcgag gttcgccaag ggtacaagtc agctgacagc    540

aagcggcaga acgccgacct cgccaacgcg gcgcaagccc tcgggcacca gtaccttccg    600

gtgctcgtca tcatgtccac ccagatcaac gaggtcgtcc acgcccgcta cacgacgggc    660

aactggtccg tactcatggg cacggttggg gcctcggacc cggtgggcag tacctacgac    720

ttccttgatc aggtcgtagg ttacgaccta gccgcgttct tcgagcgcaa caaggctctc    780

cgcgctggca ccgagggcat tctcactgat cttctggagg cccggtga                 828
```

```
<210> SEQ ID NO 104
<211> LENGTH: 276
<212> TYPE: PRT
<213> ORGANISM: Micrococcus luteus

<400> SEQUENCE: 104

Met Ser Ala Pro Glu Val Asp Ser Ala Arg Asp Ala Arg Tyr Val Glu
1               5                   10                  15

Ile Leu Leu Ala Pro Leu Arg Lys Cys Gly Thr Tyr Leu Pro Lys Met
            20                  25                  30

Gly Gly Ser Gly Glu Val Asp Leu Ala Gly Phe Thr Ala Ala Tyr Gly
        35                  40                  45

Ala Asp Pro Leu Tyr His Trp Met Gly Leu Asp Ser Pro Leu Met Phe
    50                  55                  60

Ala Ala His Lys Ala Ala Gly Gly Met Thr Ser Ile Tyr Arg Gln Leu
65                  70                  75                  80

Gly Ile Gly Ser Glu Arg Leu Phe Arg Gln Val Leu Arg Asp Glu Leu
                85                  90                  95

Asn Leu Thr Ala Asp Gln Val Lys Trp Ser Tyr Lys Met Leu Pro Glu
            100                 105                 110

Leu Asp Ala Glu His Ala Asn Glu Ser Val Lys Ala Arg Val Leu Ser
        115                 120                 125

Leu Asp Gly Arg Val Glu Leu Glu Asp Leu Glu Asp Gln Gln Ala Arg
    130                 135                 140

Glu Arg Val Glu Ala Trp Ile Glu Val Gln Arg Arg Arg Leu Asn Ile
145                 150                 155                 160

Thr Ala Pro Leu Lys Gly Ala Val Phe Glu Val Arg Gln Gly Tyr Lys
                165                 170                 175

Ser Ala Asp Ser Lys Arg Gln Asn Ala Asp Leu Ala Asn Ala Ala Gln
            180                 185                 190

Ala Leu Gly His Gln Tyr Leu Pro Val Leu Val Ile Met Ser Thr Gln
        195                 200                 205

Ile Asn Glu Val Val His Ala Arg Tyr Thr Thr Gly Asn Trp Ser Val
    210                 215                 220

Leu Met Gly Thr Val Gly Ala Ser Asp Pro Val Gly Ser Thr Tyr Asp
225                 230                 235                 240

Phe Leu Asp Gln Val Val Gly Tyr Asp Leu Ala Ala Phe Phe Glu Arg
                245                 250                 255

Asn Lys Ala Ala Leu Arg Ala Gly Thr Glu Gly Ile Leu Thr Asp Leu
            260                 265                 270

Leu Glu Ala Arg
```

275

<210> SEQ ID NO 105
<211> LENGTH: 1281
<212> TYPE: DNA
<213> ORGANISM: Methylophilus methylotrophus

<400> SEQUENCE: 105
atgagtgaaa ctaatcttaa tcaattagct tggacatcgt tatttgaaaa atacgatatt 60
ttcaatcaat tagaaacaca taatttcttt aatatcacct ctacacaaat aaaccaattt 120
cgtgaagcaa ggttaatgac taagtttgat aatactagtc aacttcctaa tatttttttct 180 aaaaatggta ttggaatatt gccaacctct cgtggctctt acacattagg aaaatttaat 240
attttccata aatttgaaga aataccagaa gaagtagagc attatagatt ttgcaatatt 300
tatgaaagcc tagatttcaa taatattagt tcggagtcaa cagctataag ctgcgcttct 360
atatcaaaaa tattagacga ttttattggt gaagaattag tttcaactgt ttcaggcaga 420
atgggaacaa gcacttttga attcagttta gataaatttc atactaaaaa aatcacagtt 480
gaaaaagcac aaattgaaat tgacggagga tatgaaggcg aaaaatcttt tgtattgatt 540
gaagctaaaa actacatatc cgacgatttc attattagac agctttatta tccatttaga 600
aaatggaaag aaacaattca aaaagaggta aaaaatgttt acctcactta ttcaaatgga 660
gtatttgaat taagagagta tgcttttaca gatattgaag gctataactc tatctatctc 720
gttaaaagta agaggtatgc tatttacaat attgtgatca atgttgaaat aatacagcaa 780
ttaattttag ctactgccat agagccagag ccattagata cacctttccc acaagccgac 840
tcttttgaaa gagtaatcaa gttatgtgaa ttgattaaca cttccgaaat attgagcaaa 900
gacgaaatta cagaaaacta cgactttgac tctcggcaaa ctgattacta tttgaatgct 960
tgcaaatatc taggcttaac agaaaaggca tttaaagacg gtggtatagc tgcctgtctc 1020
agtagcaaag gaaaagcgat atttaaaaag gatattagct ctcgtagact tgattttatt 1080
aagctgatat tggctaaaac cgtatttaga aaaacattag agttatattt caataaagcc 1140
agcatgccca ccaaagacga agttgtattg ataatgaaag agtcaaaact aaataaagta 1200
acttccgaag aaacatacag cagaagagct tctactgtat tgggctggac aaactggata 1260
attaatcaaa tagaagaata g 1281

<210> SEQ ID NO 106
<211> LENGTH: 426
<212> TYPE: PRT
<213> ORGANISM: Methylophilus methylotrophus

<400> SEQUENCE: 106

Met Ser Glu Thr Asn Leu Asn Gln Leu Ala Trp Thr Ser Leu Phe Glu
1 5 10 15

Lys Tyr Asp Ile Phe Asn Gln Leu Glu Thr His Asn Phe Phe Asn Ile
20 25 30

Thr Ser Thr Gln Ile Asn Gln Phe Arg Glu Ala Arg Leu Met Thr Lys
35 40 45

Phe Asp Asn Thr Ser Gln Leu Pro Asn Ile Phe Ser Lys Asn Gly Ile
50 55 60

Gly Ile Leu Pro Thr Ser Arg Gly Ser Tyr Thr Leu Gly Lys Phe Asn
65 70 75 80

Ile Phe His Lys Phe Glu Glu Ile Pro Glu Glu Val Glu His Tyr Arg
85 90 95

-continued

```
Phe Cys Asn Ile Tyr Glu Ser Leu Asp Phe Asn Asn Ile Ser Ser Glu
            100                 105                 110

Ser Thr Ala Ile Ser Cys Ala Ser Ile Ser Lys Ile Leu Asp Asp Phe
        115                 120                 125

Ile Gly Glu Glu Leu Val Ser Thr Val Ser Gly Arg Met Gly Thr Ser
    130                 135                 140

Thr Phe Glu Phe Ser Leu Asp Lys Phe His Thr Lys Lys Ile Thr Val
145                 150                 155                 160

Glu Lys Ala Gln Ile Glu Ile Asp Gly Gly Tyr Glu Gly Glu Lys Ser
                165                 170                 175

Phe Val Leu Ile Glu Ala Lys Asn Tyr Ile Ser Asp Asp Phe Ile Ile
            180                 185                 190

Arg Gln Leu Tyr Tyr Pro Phe Arg Lys Trp Lys Glu Thr Ile Gln Lys
        195                 200                 205

Glu Val Lys Asn Val Tyr Leu Thr Tyr Ser Asn Gly Val Phe Glu Leu
    210                 215                 220

Arg Glu Tyr Ala Phe Thr Asp Ile Glu Gly Tyr Asn Ser Ile Tyr Leu
225                 230                 235                 240

Val Lys Ser Lys Arg Tyr Ala Ile Tyr Asn Ile Val Ile Asn Val Glu
                245                 250                 255

Ile Ile Gln Gln Leu Ile Leu Ala Thr Ala Ile Glu Pro Glu Pro Leu
            260                 265                 270

Asp Thr Pro Phe Pro Gln Ala Asp Ser Phe Glu Arg Val Ile Lys Leu
        275                 280                 285

Cys Glu Leu Ile Asn Thr Ser Glu Ile Leu Ser Lys Asp Glu Ile Thr
    290                 295                 300

Glu Asn Tyr Asp Phe Asp Ser Arg Gln Thr Asp Tyr Tyr Leu Asn Ala
305                 310                 315                 320

Cys Lys Tyr Leu Gly Leu Thr Glu Lys Ala Phe Lys Asp Gly Gly Ile
                325                 330                 335

Ala Ala Cys Leu Ser Ser Lys Gly Lys Ala Ile Phe Lys Lys Asp Ile
            340                 345                 350

Ser Ser Arg Arg Leu Asp Phe Ile Lys Leu Ile Leu Ala Lys Thr Val
        355                 360                 365

Phe Arg Lys Thr Leu Glu Leu Tyr Phe Asn Lys Ala Ser Met Pro Thr
    370                 375                 380

Lys Asp Glu Val Val Leu Ile Met Lys Glu Ser Lys Leu Asn Lys Val
385                 390                 395                 400

Thr Ser Glu Glu Thr Tyr Ser Arg Arg Ala Ser Thr Val Leu Gly Trp
                405                 410                 415

Thr Asn Trp Ile Ile Asn Gln Ile Glu Glu
            420                 425
```

<210> SEQ ID NO 107
<211> LENGTH: 786
<212> TYPE: DNA
<213> ORGANISM: Micrococcus species

<400> SEQUENCE: 107

```
atgggcgaca tggcgtacag ggaccgaccg ctcaacgcag aggagatgga ggctctccgc      60

ctcgtcctaa gcacgtaccg ggattcctcg ggacagaacc aaaccaaata cgggtctatg     120

cctgggttcc gcgacttcga gcgaggtctg gcgagcgtgc tgggcggtac cgccgcggag     180

aacaagggtg tcttcgacat catcgtcaca cctagcgacg gcagcacagc cttcggaatc     240

tcgtgcaaga tggcccggtt cgcgccgaag gcacagaacg cggcgttcgt tgaactctcc     300
```

```
aacgcggccg cgaagttccg ggcgcacctc ttggagcgcc agatcaactg ggccaccgac    360

cccatgctcg caggaccggc gatcatcgag ttggtcacga agtggcacac cgatgacgcc    420

aacgagcatg ggctggacct cgataagagc gcctacgccg tactaagccg gagcagtgat    480

tggtccactt accagttgtc cactttcccg ctggacctct atggcttcaa cccgattggg    540

gacatcgcgt ggacggcaac gaccaagcgc atagatgggc acgtggagat caacggccag    600

ccccatctgc tatggcagtg gtaccccacc agtgggggtc agttgaagtg gtggcctccg    660

ctctcctggg ctacgtggtc gactgagcct tttactttgg aggagccgcc gttggttcgc    720

ccggtggaac gcgcggagga gtacttccca gacctgtggc ctcacggatt cactccttct    780

gcttga                                                               786
```

<210> SEQ ID NO 108
<211> LENGTH: 261
<212> TYPE: PRT
<213> ORGANISM: Micrococcus species

<400> SEQUENCE: 108

```
Met Gly Asp Met Ala Tyr Arg Asp Arg Pro Leu Asn Ala Glu Glu Met
1               5                   10                  15

Glu Ala Leu Arg Leu Val Leu Ser Thr Tyr Arg Asp Ser Ser Gly Gln
            20                  25                  30

Asn Gln Thr Lys Tyr Gly Ser Met Pro Gly Phe Arg Asp Phe Glu Arg
        35                  40                  45

Gly Leu Ala Ser Val Leu Gly Gly Thr Ala Ala Glu Asn Lys Gly Val
    50                  55                  60

Phe Asp Ile Ile Val Thr Pro Ser Asp Gly Ser Thr Ala Phe Gly Ile
65                  70                  75                  80

Ser Cys Lys Met Ala Arg Phe Ala Pro Lys Ala Gln Asn Ala Ala Phe
                85                  90                  95

Val Glu Leu Ser Asn Ala Ala Ala Lys Phe Arg Ala His Leu Leu Glu
            100                 105                 110

Arg Gln Ile Asn Trp Ala Thr Asp Pro Met Leu Ala Gly Pro Ala Ile
        115                 120                 125

Ile Glu Leu Val Thr Lys Trp His Thr Asp Asp Ala Asn Glu His Gly
    130                 135                 140

Leu Asp Leu Asp Lys Ser Ala Tyr Ala Val Leu Ser Arg Ser Ser Asp
145                 150                 155                 160

Trp Ser Thr Tyr Gln Leu Ser Thr Phe Pro Leu Asp Leu Tyr Gly Phe
                165                 170                 175

Asn Pro Ile Gly Asp Ile Ala Trp Thr Ala Thr Thr Lys Arg Ile Asp
            180                 185                 190

Gly His Val Glu Ile Asn Gly Gln Pro His Leu Leu Trp Gln Trp Tyr
        195                 200                 205

Pro Thr Ser Gly Gly Gln Leu Lys Trp Trp Pro Pro Leu Ser Trp Ala
    210                 215                 220

Thr Trp Ser Thr Glu Pro Phe Thr Leu Glu Glu Pro Pro Leu Val Arg
225                 230                 235                 240

Pro Val Glu Arg Ala Glu Glu Tyr Phe Pro Asp Leu Trp Pro His Gly
                245                 250                 255

Phe Thr Pro Ser Ala
            260
```

<210> SEQ ID NO 109

<211> LENGTH: 1107
<212> TYPE: DNA
<213> ORGANISM: Neisseria denitrificans

<400> SEQUENCE: 109

```
atgaaaaact tatctttctc acaattagac tcttttttta gaaaagatga ttttccaagt     60

attgagagac atcaatatgg cattaggtat ttaaaattaa gaagtatgtc tcgtaaagaa    120

attatggaag aatttttca ggaatatgaa attgacatct ctaagcttaa gtcaaaagaa    180

tattttagat atgcttttga gaacattgat ataaccatag aaagtataaa tagttttatt    240

gaaaagaaat accaaataga gcgtaccgat agacttctac aagaagatta tttagtagat    300

caactgagca gattacaata cttcgattgg ggcggttcat ttggtaatag tcttgaaaaa    360

aacattgtcg ataattatgt caaaaaaata caatcttttg acataattaa caaaaaaata    420

gaaactgagc tattttcaag tttacaggga tacactctaa attcttggta taatcactgg    480

acttcaattt taattgaaga tatttttaaa gatcatgcta atgtattgcc aaccatcgga    540

cttataaaaa agattgattt ctttataaat gagatacctt ttgatttaaa ggttacttat    600

tttcctgagc agttcttagc tgaaaaattg aagcaaaagg ggtttggcaa tgagttaact    660

agattaaaac aaatatgtag aaaactgaac attttaattc ctaatgacat gtctgacaaa    720

aacttaaaac tgcatttata cacaaaagtt tcagaatgtc atcataaaga agctaaagaa    780

ttaataaatg aattaaataa gttaaaaaaa caaattattc gtgaagccga acaaaattca    840

gatgaattaa aagtatggct ttatgaaaat cagggtgaag cccgttttga cgcttcaaat    900

agattttttt taattctcac ggacgagacc aatatcaatg atagttggaa acttaaaaga    960

aacattaaat tcctaagaga gaaaattcac tctcatctag attctataaa actggatctt   1020

aataaactaa atacaaaatt ttactggaag aaaacaaatg aacattttaa ttgtaagtct   1080

gatatacttt ttataaaaca gacttaa                                        1107
```

<210> SEQ ID NO 110
<211> LENGTH: 368
<212> TYPE: PRT
<213> ORGANISM: Neisseria denitrificanse

<400> SEQUENCE: 110

```
Met Lys Asn Leu Ser Phe Ser Gln Leu Asp Ser Phe Phe Arg Lys Asp
1               5                   10                  15

Asp Phe Pro Ser Ile Glu Arg His Gln Tyr Gly Ile Arg Tyr Leu Lys
            20                  25                  30

Leu Arg Ser Met Ser Arg Lys Glu Ile Met Glu Glu Phe Phe Gln Glu
        35                  40                  45

Tyr Glu Ile Asp Ile Ser Lys Leu Lys Ser Lys Glu Tyr Phe Arg Tyr
    50                  55                  60

Ala Phe Glu Asn Ile Asp Ile Thr Ile Glu Ser Ile Asn Ser Phe Ile
65                  70                  75                  80

Glu Lys Lys Tyr Gln Ile Glu Arg Thr Asp Arg Leu Leu Gln Glu Asp
                85                  90                  95

Tyr Leu Val Asp Gln Leu Ser Arg Leu Gln Tyr Phe Asp Trp Gly Gly
            100                 105                 110

Ser Phe Gly Asn Ser Leu Glu Lys Asn Ile Val Asp Asn Tyr Val Lys
        115                 120                 125

Lys Ile Gln Ser Phe Asp Ile Ile Asn Lys Lys Ile Glu Thr Glu Leu
    130                 135                 140

Phe Ser Ser Leu Gln Gly Tyr Thr Leu Asn Ser Trp Tyr Asn His Trp
```

```
145                 150                 155                 160

Thr Ser Ile Leu Ile Glu Asp Ile Phe Lys Asp His Ala Asn Val Leu
                165                 170                 175

Pro Thr Ile Gly Leu Ile Lys Lys Ile Asp Phe Phe Ile Asn Glu Ile
            180                 185                 190

Pro Phe Asp Leu Lys Val Thr Tyr Phe Pro Glu Gln Phe Leu Ala Glu
        195                 200                 205

Lys Leu Lys Gln Lys Gly Phe Gly Asn Glu Leu Thr Arg Leu Lys Gln
    210                 215                 220

Ile Cys Arg Lys Leu Asn Ile Leu Ile Pro Asn Asp Met Ser Asp Lys
225                 230                 235                 240

Asn Leu Lys Leu His Leu Tyr Thr Lys Val Ser Glu Cys His His Lys
                245                 250                 255

Glu Ala Lys Glu Leu Ile Asn Glu Leu Asn Lys Leu Lys Lys Gln Ile
            260                 265                 270

Ile Arg Glu Ala Glu Gln Asn Ser Asp Glu Leu Lys Val Trp Leu Tyr
        275                 280                 285

Glu Asn Gln Gly Glu Ala Arg Phe Asp Ala Ser Asn Arg Phe Phe Leu
    290                 295                 300

Ile Leu Thr Asp Glu Thr Asn Ile Asn Asp Ser Trp Lys Leu Lys Arg
305                 310                 315                 320

Asn Ile Lys Phe Leu Arg Glu Lys Ile His Ser His Leu Asp Ser Ile
                325                 330                 335

Lys Leu Asp Leu Asn Lys Leu Asn Thr Lys Phe Tyr Trp Lys Lys Thr
            340                 345                 350

Asn Glu His Phe Asn Cys Lys Ser Asp Ile Leu Phe Ile Lys Gln Thr
        355                 360                 365


<210> SEQ ID NO 111
<211> LENGTH: 2940
<212> TYPE: DNA
<213> ORGANISM: Neisseria gonorrhoeae MS11

<400> SEQUENCE: 111

atgagcggtt ttaattacga gaaaaaccag ccgcaccaaa tgcgggcggt ttcggcggtt      60

ttgggcgtgt ttgacggggc aacgcccaaa tatcggacgg cagacgaaaa tcccgaactt     120

ttgtttgctg caaaacaata cgcaaacaat atcctgaaag tgcaaagcca aaacggtata     180

gacggccgat tccccgaccg ttcggacgac caaaatatcc ttgatatttc catggaaacg     240

ggcacgggca aaacctatac ctacacacaa accatgttcg agctgcaccg ttggctgggc     300

gtgttcaaat ttatcgtggt cgtgccgact ttgtccatta aggcgggaac acagcagttt     360

ttgcaaagca aggctttggc agagcatttt gaacaggatt tcggcggcga ttatgaaggc     420

gtacgcctga aacctatgt ggtggaaagc gcgaaaaaga ataagggcaa aaagtccaat     480

gcgcccataa cgattgagca atttgtcaaa gcggaaaaca aaaaggaaat tcatgtgctg     540

ctgattaacg cgggcatggt taattcgtcg tccatgaacg atacgggcga caaggcattg     600

aaggatttgt ttgacaatcc cgttgatgca ttggctgccg tgcgcccgtt tatgattgtg     660

gacgaaccgc ataaattccc gacccgagat agcgcgaaaa cgtggggcaa tatcaaacgc     720

ttaaaaccgc aatatatttt gcgctacggt gcaacattta acgatgaata ttacaacttg     780

ctttaccgtt tgacggcagt agacgcgttt aacgacgggc tggtcaaagg cgtgcgcgtg     840

tttcaggaag aaatgcaggg cggcatggat gcggcggtaa aactggtgtc gtcggacggc     900

aaagaagcga aatttgaatt aaacgaaaag gacaaaaagc agacgttcaa actggcaaaa     960
```

ggcgaagatt tggcgcaaat ccatccggct atttcggatt tgaaaatcga caaaatgaat 1020
aaaaccgtgg tggtgttaag caacggcttg gagttgaaaa cgggtgccgt catcaaccct 1080
tattcctatt cgcaaacggt gcaggatgcg atgatgcagc gggcggttgc cgaacatttc 1140
aagctggaac gcgcgctttt ggcagaacgc gcgctacagc ccaaaatcaa gccgctgacg 1200
ctgtttttta ttgacgatat cgcgggctac cgcagcggca acgagctttc aggcagcctg 1260
aaagataaat ttgaaagctg gattcgcgcg gaagccgcac gccgtctgaa aacggaaagc 1320
gacccgtttt accgcgatta cctgcaaaag acgttggacg atgtatccgc ctgccacggc 1380
ggctattttt ccaaagacaa tacagacagc gacgatagaa tcgagcagga aatcaatgaa 1440
atcctgcacg ataaggaaaa actgctgtct ttggacaacc cgcgccgctt tatttttttcc 1500 aaatggacgc tgcgcgaagg ctgggacaat cccaacgttt tccagatttg caaactgcgt 1560
tccagcggca gcacgacttc caagctgcaa gaagtcggac gcggcctgcg cctgccggta 1620
aacgagctga tggcgcgggt gcgcgatgta ccgtacaaac tgaattattt tgtcgatagc 1680
agcgaaaaag actttgtgaa gcagcttgtc ggcgaaatca acgacaattc ttttcaggaa 1740
gaaatctcca aaaagtttac cgaagagctg aaacaaaaaa tattgcaaaa ataccccgat 1800
atcaaaccgc tggtattggt aaaccaactg ttttcagacg gcatcattga cgacaatgaa 1860
aactttgccg aagacggcta tgacaaatta aaagccgcct atcccgaagc cttccccaaa 1920
ggtttggaca aaggcaaagt cagcaacgcc aaagacgagg gcaaagacac catcatcatg 1980
cgcgaaggca aatatgaaga actcaaagcc ttgtgggagc tgattcacca taaagccgtt 2040
ttgcagtaca aaatcaaaga tgaagccgaa tttgtcgatt tatttaccgc ctatttgcgt 2100
gaaaacgccg ccaaattccc gcaggcaggc atatgcacgg cggtaaacga agcttatatc 2160
aacaacgggc ttatgctttc ccgccgcata gacagtattg aagatgaaga ttttatccgt 2220
ttcaacacaa tgacttaccg tgagtttctg gaaaaactgg cacaaacggc aaaaatccag 2280
atgcagactt tgcatcaggc gttttaccgc gtccgcgacg aactgaacat tggcgatttt 2340
ttgaatatgc agaccatcgc ccaaatcaaa aacggcttca accggttttt gcttcatcat 2400
tccttccata aattcgaact ggattaccgg cttgtcggca gcaaaatcca tccgaccaaa 2460
tttaccaata aagacggcaa accgcgcgcg gtgaaaaaag cagatttcgg cagatttgaa 2520
gatacggagc accggcctgc cgccggctat ctcttcggcg agattttcta cgattcggat 2580
atagaacatg aaaatgtcgc caacaaccaa attgaaggcg taatcgtatt taccaaaata 2640
ccgagaaact ccatcaaaat ccctgttgcc ggcggcggca cgtattcgcc cgactttgcc 2700
tatatcgtga aaaccaaaag cggcgagatt ctgaactttg tgattgaagc caaagggact 2760
gacggggcgg aagatttgcg aaaaagcgaa gagcggaaaa tcaaacatgc cgaaaagctg 2820
tttgccgaga tttccaaaga aatcaaggtg gtgttcaaaa cgcagtttga cggcgagagg 2880
atagccgaac tgatcgggca aaatatgcca gcaggcgggc attctgaaaa cggacactga 2940

<210> SEQ ID NO 112
<211> LENGTH: 979
<212> TYPE: PRT
<213> ORGANISM: Neisseria gonorrhoeae MS11

<400> SEQUENCE: 112

Met Ser Gly Phe Asn Tyr Glu Lys Asn Gln Pro His Gln Met Arg Ala
1 5 10 15

Val Ser Ala Val Leu Gly Val Phe Asp Gly Ala Thr Pro Lys Tyr Arg
20 25 30

```
Thr Ala Asp Glu Asn Pro Glu Leu Leu Phe Ala Ala Lys Gln Tyr Ala
        35                  40                  45

Asn Asn Ile Leu Lys Val Gln Ser Gln Asn Gly Ile Asp Gly Arg Phe
    50                  55                  60

Pro Asp Arg Ser Asp Asp Gln Asn Ile Leu Asp Ile Ser Met Glu Thr
65                  70                  75                  80

Gly Thr Gly Lys Thr Tyr Thr Tyr Thr Gln Thr Met Phe Glu Leu His
                85                  90                  95

Arg Trp Leu Gly Val Phe Lys Phe Ile Val Val Val Pro Thr Leu Ser
            100                 105                 110

Ile Lys Ala Gly Thr Gln Gln Phe Leu Gln Ser Lys Ala Leu Ala Glu
        115                 120                 125

His Phe Glu Gln Asp Phe Gly Gly Asp Tyr Glu Gly Val Arg Leu Lys
    130                 135                 140

Thr Tyr Val Val Glu Ser Ala Lys Lys Asn Lys Gly Lys Lys Ser Asn
145                 150                 155                 160

Ala Pro Ile Thr Ile Glu Gln Phe Val Lys Ala Glu Asn Lys Lys Glu
                165                 170                 175

Ile His Val Leu Leu Ile Asn Ala Gly Met Val Asn Ser Ser Ser Met
            180                 185                 190

Asn Asp Thr Gly Asp Lys Ala Leu Lys Asp Leu Phe Asp Asn Pro Val
        195                 200                 205

Asp Ala Leu Ala Ala Val Arg Pro Phe Met Ile Val Asp Glu Pro His
    210                 215                 220

Lys Phe Pro Thr Arg Asp Ser Ala Lys Thr Trp Gly Asn Ile Lys Arg
225                 230                 235                 240

Leu Lys Pro Gln Tyr Ile Leu Arg Tyr Gly Ala Thr Phe Asn Asp Glu
                245                 250                 255

Tyr Tyr Asn Leu Leu Tyr Arg Leu Thr Ala Val Asp Ala Phe Asn Asp
            260                 265                 270

Gly Leu Val Lys Gly Val Arg Val Phe Gln Glu Glu Met Gln Gly Gly
        275                 280                 285

Met Asp Ala Ala Val Lys Leu Val Ser Ser Asp Gly Lys Glu Ala Lys
    290                 295                 300

Phe Glu Leu Asn Glu Lys Asp Lys Lys Gln Thr Phe Lys Leu Ala Lys
305                 310                 315                 320

Gly Glu Asp Leu Ala Gln Ile His Pro Ala Ile Ser Asp Leu Lys Ile
                325                 330                 335

Asp Lys Met Asn Lys Thr Val Val Val Leu Ser Asn Gly Leu Glu Leu
            340                 345                 350

Lys Thr Gly Ala Val Ile Asn Pro Tyr Ser Tyr Ser Gln Thr Val Gln
        355                 360                 365

Asp Ala Met Met Gln Arg Ala Val Ala Glu His Phe Lys Leu Glu Arg
    370                 375                 380

Ala Leu Leu Ala Glu Arg Ala Leu Gln Pro Lys Ile Lys Pro Leu Thr
385                 390                 395                 400

Leu Phe Phe Ile Asp Asp Ile Ala Gly Tyr Arg Ser Gly Asn Glu Leu
                405                 410                 415

Ser Gly Ser Leu Lys Asp Lys Phe Glu Ser Trp Ile Arg Ala Glu Ala
            420                 425                 430

Ala Arg Arg Leu Lys Thr Glu Ser Asp Pro Phe Tyr Arg Asp Tyr Leu
        435                 440                 445

Gln Lys Thr Leu Asp Asp Val Ser Ala Cys His Gly Gly Tyr Phe Ser
```

```
    450                 455                 460

Lys Asp Asn Thr Asp Ser Asp Asp Arg Ile Glu Gln Glu Ile Asn Glu
465                 470                 475                 480

Ile Leu His Asp Lys Glu Lys Leu Leu Ser Leu Asp Asn Pro Arg Arg
                485                 490                 495

Phe Ile Phe Ser Lys Trp Thr Leu Arg Glu Gly Trp Asp Asn Pro Asn
            500                 505                 510

Val Phe Gln Ile Cys Lys Leu Arg Ser Ser Gly Ser Thr Thr Ser Lys
        515                 520                 525

Leu Gln Glu Val Gly Arg Gly Leu Arg Leu Pro Val Asn Glu Leu Met
    530                 535                 540

Ala Arg Val Arg Asp Val Pro Tyr Lys Leu Asn Tyr Phe Val Asp Ser
545                 550                 555                 560

Ser Glu Lys Asp Phe Val Lys Gln Leu Val Gly Glu Ile Asn Asp Asn
                565                 570                 575

Ser Phe Gln Glu Glu Ile Ser Lys Lys Phe Thr Glu Glu Leu Lys Gln
            580                 585                 590

Lys Ile Leu Gln Lys Tyr Pro Asp Ile Lys Pro Leu Val Leu Val Asn
        595                 600                 605

Gln Leu Phe Ser Asp Gly Ile Ile Asp Asp Asn Glu Asn Phe Ala Glu
    610                 615                 620

Asp Gly Tyr Asp Lys Leu Lys Ala Ala Tyr Pro Glu Ala Phe Pro Lys
625                 630                 635                 640

Gly Leu Asp Lys Gly Lys Val Ser Asn Ala Lys Asp Glu Gly Lys Asp
                645                 650                 655

Thr Ile Ile Met Arg Glu Gly Lys Tyr Glu Glu Leu Lys Ala Leu Trp
            660                 665                 670

Glu Leu Ile His His Lys Ala Val Leu Gln Tyr Lys Ile Lys Asp Glu
        675                 680                 685

Ala Glu Phe Val Asp Leu Phe Thr Ala Tyr Leu Arg Glu Asn Ala Ala
    690                 695                 700

Lys Phe Pro Gln Ala Gly Ile Cys Thr Ala Val Asn Glu Ala Tyr Ile
705                 710                 715                 720

Asn Asn Gly Leu Met Leu Ser Arg Arg Ile Asp Ser Ile Glu Asp Glu
                725                 730                 735

Asp Phe Ile Arg Phe Asn Thr Met Thr Tyr Arg Glu Phe Leu Glu Lys
            740                 745                 750

Leu Ala Gln Thr Ala Lys Ile Gln Met Gln Thr Leu His Gln Ala Phe
        755                 760                 765

Tyr Arg Val Arg Asp Glu Leu Asn Ile Gly Asp Phe Leu Asn Met Gln
    770                 775                 780

Thr Ile Ala Gln Ile Lys Asn Gly Phe Asn Arg Phe Leu Leu His His
785                 790                 795                 800

Ser Phe His Lys Phe Glu Leu Asp Tyr Arg Leu Val Gly Ser Lys Ile
                805                 810                 815

His Pro Thr Lys Phe Thr Asn Lys Asp Gly Lys Pro Arg Ala Val Lys
            820                 825                 830

Lys Ala Asp Phe Gly Arg Phe Glu Asp Thr Glu His Arg Pro Ala Ala
        835                 840                 845

Gly Tyr Leu Phe Gly Glu Ile Phe Tyr Asp Ser Asp Ile Glu His Glu
    850                 855                 860

Asn Val Ala Asn Asn Gln Ile Glu Gly Val Ile Val Phe Thr Lys Ile
865                 870                 875                 880
```

Pro Arg Asn Ser Ile Lys Ile Pro Val Ala Gly Gly Gly Thr Tyr Ser
885 890 895

Pro Asp Phe Ala Tyr Ile Val Lys Thr Lys Ser Gly Glu Ile Leu Asn
900 905 910

Phe Val Ile Glu Ala Lys Gly Thr Asp Gly Ala Glu Asp Leu Arg Lys
915 920 925

Ser Glu Glu Arg Lys Ile Lys His Ala Glu Lys Leu Phe Ala Glu Ile
930 935 940

Ser Lys Glu Ile Lys Val Val Phe Lys Thr Gln Phe Asp Gly Glu Arg
945 950 955 960

Ile Ala Glu Leu Ile Gly Gln Asn Met Pro Ala Gly Gly His Ser Glu
965 970 975

Asn Gly His

<210> SEQ ID NO 113
<211> LENGTH: 1152
<212> TYPE: DNA
<213> ORGANISM: Nocardia otitidis-caviarum

<400> SEQUENCE: 113
atgcggtcag atacgtcggt ggagccagag ggcgccaact tcatcgcgga atttttcggg 60
catcgtgtgt accccgaagt cgtcagcact gaagctgcga ggaatgacca ggcgacgggg 120
acctgccctt tcttgacggc tgccaagctg gttgaaactt catgcgtaaa ggccgagacc 180
tcgcgcgggg tttgcgtggt caacacagct gtagacaacg agcgctacga ctggttggtg 240
tgtcccaacc gagcgttaga ccccctgttc atgtccgcag cttcgaggaa gctttttggc 300
tacggaccca cagaaccgct tcagttcatc gcggcgccga cgttagccga tcaggcggtg 360
cgcgacggaa tccgggaatg gctggatcgt ggagtccacg tggtcgctta cttccaggag 420
aaactcggtg gcgagctgag catcagcaag accgatagct cgccggagtt ttcattcgac 480
tggactcttg ccgaagtcga gtctatctac cccgtgccga agatcaagcg gtacggggtc 540
cttgagatcc agactatgga cttccacggc tcgtacaagc atgctgtcgg tgctatcgac 600
attgccttag tggagggaat tgatttccac ggctggttgc ccacaccagc gggtcgtgcc 660
gctctctcga agaagatgga gggcccaaac ctctccaatg tgttcaagcg cacgttctac 720
cagatggcat acaaattcgc tctgagtggt catcaacgat gtgccgggac cgggttcgcg 780
attccgcaga gtgtctggaa aagctggctg agacatctgg ccaacccaac gctgatagac 840
aacggggatg gcaccttctc tctgggggat acccggaatg atagtgaaaa cgcttggata 900
ttcgtattcg aactagatcc ggatactgat gcctcgccgc gcccattggc gccccacctt 960
gagattcgag tgaacgtgga cacgttgatt gatctcgcgc tgagagaatc gcccagggct 1020
gctcttggcc cgtctgggcc ggtggctacg ttcaccgaca aggtcgaggc gcggatgtta 1080
aggttctggc cgaagactcg ccgccgtcgc tcgacgacac cagggggggca gcgggggctg 1140 ttcgatgcat ga 1152

<210> SEQ ID NO 114
<211> LENGTH: 383
<212> TYPE: PRT
<213> ORGANISM: Nocardia otitidis-caviarum

<400> SEQUENCE: 114

Met Arg Ser Asp Thr Ser Val Glu Pro Glu Gly Ala Asn Phe Ile Ala
1 5 10 15

Glu Phe Phe Gly His Arg Val Tyr Pro Glu Val Val Ser Thr Glu Ala

-continued

```
            20                  25                  30

Ala Arg Asn Asp Gln Ala Thr Gly Thr Cys Pro Phe Leu Thr Ala Ala
        35                  40                  45

Lys Leu Val Glu Thr Ser Cys Val Lys Ala Glu Thr Ser Arg Gly Val
    50                  55                  60

Cys Val Val Asn Thr Ala Val Asp Asn Glu Arg Tyr Asp Trp Leu Val
65                  70                  75                  80

Cys Pro Asn Arg Ala Leu Asp Pro Leu Phe Met Ser Ala Ala Ser Arg
                85                  90                  95

Lys Leu Phe Gly Tyr Gly Pro Thr Glu Pro Leu Gln Phe Ile Ala Ala
            100                 105                 110

Pro Thr Leu Ala Asp Gln Ala Val Arg Asp Gly Ile Arg Glu Trp Leu
        115                 120                 125

Asp Arg Gly Val His Val Val Ala Tyr Phe Gln Glu Lys Leu Gly Gly
    130                 135                 140

Glu Leu Ser Ile Ser Lys Thr Asp Ser Ser Pro Glu Phe Ser Phe Asp
145                 150                 155                 160

Trp Thr Leu Ala Glu Val Glu Ser Ile Tyr Pro Val Pro Lys Ile Lys
                165                 170                 175

Arg Tyr Gly Val Leu Glu Ile Gln Thr Met Asp Phe His Gly Ser Tyr
            180                 185                 190

Lys His Ala Val Gly Ala Ile Asp Ile Ala Leu Val Glu Gly Ile Asp
        195                 200                 205

Phe His Gly Trp Leu Pro Thr Pro Ala Gly Arg Ala Ala Leu Ser Lys
    210                 215                 220

Lys Met Glu Gly Pro Asn Leu Ser Asn Val Phe Lys Arg Thr Phe Tyr
225                 230                 235                 240

Gln Met Ala Tyr Lys Phe Ala Leu Ser Gly His Gln Arg Cys Ala Gly
                245                 250                 255

Thr Gly Phe Ala Ile Pro Gln Ser Val Trp Lys Ser Trp Leu Arg His
            260                 265                 270

Leu Ala Asn Pro Thr Leu Ile Asp Asn Gly Asp Gly Thr Phe Ser Leu
        275                 280                 285

Gly Asp Thr Arg Asn Asp Ser Glu Asn Ala Trp Ile Phe Val Phe Glu
    290                 295                 300

Leu Asp Pro Asp Thr Asp Ala Ser Pro Arg Pro Leu Ala Pro His Leu
305                 310                 315                 320

Glu Ile Arg Val Asn Val Asp Thr Leu Ile Asp Leu Ala Leu Arg Glu
                325                 330                 335

Ser Pro Arg Ala Ala Leu Gly Pro Ser Gly Pro Val Ala Thr Phe Thr
            340                 345                 350

Asp Lys Val Glu Ala Arg Met Leu Arg Phe Trp Pro Lys Thr Arg Arg
        355                 360                 365

Arg Arg Ser Thr Thr Pro Gly Gly Gln Arg Gly Leu Phe Asp Ala
    370                 375                 380
```

<210> SEQ ID NO 115
<211> LENGTH: 429
<212> TYPE: DNA
<213> ORGANISM: Pseudomonas alcaligenes

<400> SEQUENCE: 115

```
atgacgcaat gtccaaggtg ccagcgcaat ctcgcagctg acgagttcta tgctggctct      60

agcaaaatgt gcaagggttg catgacttgg caaaacctaa gctacaacgc gaataaggaa     120
```

```
ggtcatgcca acaccttcac caaagcgaca tttttggcgt ggtacggctt atcagcacag    180

cggcattgtg ggtattgcgg tatatcggag gcaggtttta catccttgca caggactaat    240

ccacgcggct accacataca gtgtttgggt gttgatcgct cagattcgtt cgaaggctat    300

tcacctcaaa acgctcggct cgcctgtttt atatgcaaca ggataaaatc aaacatcttc    360

agcgccagtg agatggacgt tctaggtgag gccatttcaa aagcgtggca tggtcgagga    420

attgcctaa                                                            429
```

<210> SEQ ID NO 116
<211> LENGTH: 142
<212> TYPE: PRT
<213> ORGANISM: Pseudomonas alcaligenes
<220> FEATURE:
<221> NAME/KEY: MISC_FEATURE
<222> LOCATION: (116)..(116)
<223> OTHER INFORMATION: k= g or t/u

<400> SEQUENCE: 116

```
Met Thr Gln Cys Pro Arg Cys Gln Arg Asn Leu Ala Ala Asp Glu Phe
1               5                   10                  15

Tyr Ala Gly Ser Ser Lys Met Cys Lys Gly Cys Met Thr Trp Gln Asn
            20                  25                  30

Leu Ser Tyr Asn Ala Asn Lys Glu Gly His Ala Asn Thr Phe Thr Lys
        35                  40                  45

Ala Thr Phe Leu Ala Trp Tyr Gly Leu Ser Ala Gln Arg His Cys Gly
    50                  55                  60

Tyr Cys Gly Ile Ser Glu Ala Gly Phe Thr Ser Leu His Arg Thr Asn
65                  70                  75                  80

Pro Arg Gly Tyr His Ile Gln Cys Leu Gly Val Asp Arg Ser Asp Ser
                85                  90                  95

Phe Glu Gly Tyr Ser Pro Gln Asn Ala Arg Leu Ala Cys Phe Ile Cys
            100                 105                 110

Asn Arg Ile Lys Ser Asn Ile Phe Ser Ala Ser Glu Met Asp Val Leu
        115                 120                 125

Gly Glu Ala Ile Ser Lys Ala Trp His Gly Arg Gly Ile Ala
    130                 135                 140
```

<210> SEQ ID NO 117
<211> LENGTH: 744
<212> TYPE: DNA
<213> ORGANISM: Pseudomonas fluorescens

<400> SEQUENCE: 117

```
atgcgtggac tggagatcgg tgtaaacgca ttagtttttt atcagacacg cactgagtgg     60

aacgtaaata atcctgaaaa cttgggatgg gagcccgcgg agaacaggat aagccctcta    120

ggtgggcagt atgttgcgcg tatcgccgca accactgcgt tagataatgg cgaaaaaatt    180

atccgtggtt tcacgacatc taaagtaaaa ggcgctggaa ttcggttatt tgaatacgcg    240

ggagaaaagg atattagggc gtgtcgtctc cagcttgagg ctcttttttg gatgtgccgc    300

gactcaacgg aagttgcgat aattaacggt atgactgctc aggacgcgtt gtctagaagt    360

acctataacg cagctgagtg ccaaaaatat gatttgcttg atttaaatcg acttcatgaa    420

gcgcgcatca taaatacaga tggtagaacc atctgtcctc tctgtcttga agagctttct    480

ggtgaaggct ttttgagtcg gttggagcaa gcagaaggtc gagaggtaca cgaccttact    540

gttacaaagt taaacttgtt tcatatttca gagctccgtt ttggagtcta taaccataag    600

ccatacaacc taggttgggg gcatcaccac tgtaacgtcg ttgttaaaga ctcggggata    660
```

atcgagacat tacaatggat gtatgaggtg gttcatcgaa atatcaacga tggtcacttt 720
gctcctgaga acaatccgaa ctga 744

<210> SEQ ID NO 118
<211> LENGTH: 247
<212> TYPE: PRT
<213> ORGANISM: Pseudomonas fluorescens

<400> SEQUENCE: 118

Met Arg Gly Leu Glu Ile Gly Val Asn Ala Leu Val Phe Tyr Gln Thr
1 5 10 15

Arg Thr Glu Trp Asn Val Asn Asn Pro Glu Asn Leu Gly Trp Glu Pro
20 25 30

Ala Glu Asn Arg Ile Ser Pro Leu Gly Gly Gln Tyr Val Ala Arg Ile
35 40 45

Ala Ala Thr Thr Ala Leu Asp Asn Gly Glu Lys Ile Ile Arg Gly Phe
50 55 60

Thr Thr Ser Lys Val Lys Gly Ala Gly Ile Arg Leu Phe Glu Tyr Ala
65 70 75 80

Gly Glu Lys Asp Ile Arg Ala Cys Arg Leu Gln Leu Glu Ala Leu Phe
85 90 95

Trp Met Cys Arg Asp Ser Thr Glu Val Ala Ile Ile Asn Gly Met Thr
100 105 110

Ala Gln Asp Ala Leu Ser Arg Ser Thr Tyr Asn Ala Ala Glu Cys Gln
115 120 125

Lys Tyr Asp Leu Leu Asp Leu Asn Arg Leu His Glu Ala Arg Ile Ile
130 135 140

Asn Thr Asp Gly Arg Thr Ile Cys Pro Leu Cys Leu Glu Glu Leu Ser
145 150 155 160

Gly Glu Gly Phe Leu Ser Arg Leu Glu Gln Ala Glu Gly Arg Glu Val
165 170 175

His Asp Leu Thr Val Thr Lys Leu Asn Leu Phe His Ile Ser Glu Leu
180 185 190

Arg Phe Gly Val Tyr Asn His Lys Pro Tyr Asn Leu Gly Trp Gly His
195 200 205

His His Cys Asn Val Val Val Lys Asp Ser Gly Ile Ile Glu Thr Leu
210 215 220

Gln Trp Met Tyr Glu Val Val His Arg Asn Ile Asn Asp Gly His Phe
225 230 235 240

Ala Pro Glu Asn Asn Pro Asn
245

<210> SEQ ID NO 119
<211> LENGTH: 695
<212> TYPE: DNA
<213> ORGANISM: Pseudomonas mendocina
<220> FEATURE:
<221> NAME/KEY: misc_feature
<222> LOCATION: (104)..(104)
<223> OTHER INFORMATION: y= t/u or c
<220> FEATURE:
<221> NAME/KEY: misc_feature
<222> LOCATION: (117)..(117)
<223> OTHER INFORMATION: m= a or c

<400> SEQUENCE: 119
atgacaacaa actccccctc agacgtcggc atgatcgacg agtgtctgtc catcgtccga 60
acgtcgcttg cacgatgttt ccaacagcag gccccaagca ttcaagcctc atggccactt 120
tcaggacgcg ccgtatctga gattggaggc cgcctagtcg agagtttcgt tttagcacga 180
ctcccgcatg aactgagcac cacgcctttt gacggccaga ttctatgtga aatacctgaa 240
tccggcagag cgatggaaga cattgcggtg accttcatcg gcccacatgg aagggctcga 300
ctactcatcg acgtcaaggg tcataacgaa taccgcacgg gatcgagacc caatttggct 360
tcgatccgaa aatgtctgga actctatcgc agctcctcac ataccgttga tgagctcgtt 420
gtcttcttct gccgttaccg cccatccgtc cacccggatc atcacgcaca agcggtcgaa 480
tatcacgttc tgcccgagtc gttyaatgag cagggamttt tcctgcttcg tgccctgagc 540
gaaagcaacc tggatccagc caatatcgga gtggcggcca gttgctgctt gccagggaaa 600
acaacatacg gttagtgaat cgttcaaggt cggagttcgt tcaacttcta gagggtctcc 660
agtcacgcct tcaacggggg cgaagtacgg tttga 695

<210> SEQ ID NO 120
<211> LENGTH: 231
<212> TYPE: PRT
<213> ORGANISM: Pseudomonas mendocina

<400> SEQUENCE: 120

Met Thr Thr Asn Ser Pro Ser Asp Val Gly Met Ile Asp Glu Cys Leu
1 5 10 15

Ser Ile Val Arg Thr Ser Leu Ala Arg Cys Phe Gln Gln Gln Ala Pro
20 25 30

Ser Ile Gln Ala Ser Trp Pro Leu Ser Gly Arg Ala Val Ser Glu Ile
35 40 45

Gly Gly Arg Leu Val Glu Ser Phe Val Leu Ala Arg Leu Pro His Glu
50 55 60

Leu Ser Thr Thr Pro Phe Asp Gly Gln Ile Leu Cys Glu Ile Pro Glu
65 70 75 80

Ser Gly Arg Ala Met Glu Asp Ile Ala Val Thr Phe Ile Gly Pro His
85 90 95

Gly Arg Ala Arg Leu Leu Ile Asp Val Lys Gly His Asn Glu Tyr Arg
100 105 110

Thr Gly Ser Arg Pro Asn Leu Ala Ser Ile Arg Lys Cys Leu Glu Leu
115 120 125

Tyr Arg Ser Ser Ser His Thr Val Asp Glu Leu Val Val Phe Phe Cys
130 135 140

Arg Tyr Arg Pro Ser Val His Pro Asp His His Ala Gln Ala Val Glu
145 150 155 160

Tyr His Val Leu Pro Glu Ser Phe Asn Glu Gln Gly Leu Phe Leu Leu
165 170 175

Arg Ala Leu Ser Glu Ser Asn Leu Asp Pro Ala Asn Ile Gly Ser Gly
180 185 190

Gly Gln Leu Leu Leu Ala Arg Glu Asn Asn Ile Arg Leu Val Asn Arg
195 200 205

Ser Arg Ser Glu Phe Val Gln Leu Leu Glu Gly Leu Gln Ser Arg Leu
210 215 220

Gln Arg Gly Arg Ser Thr Val
225 230

<210> SEQ ID NO 121
<211> LENGTH: 888
<212> TYPE: DNA
<213> ORGANISM: Plesiomonas shigelloides 319-73

<400> SEQUENCE: 121

```
atgtcgattt tagataatga aaaacaattg agaatattga acataattaa cgagggtgtt     60
actcctgcca taataccaga gcttcattcg ctagttgatg acaggattac taacgaagaa    120
atcgaattgc tacataagaa agtctctaca cttatcgggc tttcaatacc cgtgctaaat    180
attccccgtg acattttaaa ggcttttgaa ccttcccaga ttggaacaat tgttggaaca    240
gtcatggatg cttgtattcc tcagctagat tcaattattg aggattcaaa agttatagcg    300
gatattggtt tgcaaaaaca cgaagggatt cttggggaaa gagaaggtta cccagattat    360
aagactaatg atgggtacag gcttgagctc aaactactat atgttgatcc tgatgatgtt    420
gagatgaaaa agccccctac accaagagag gcatctgcga gactgactca aaaagtaacc    480
tataagaatg tcgatacaag caaagaccta ttaatggttg tcgcgtatca gtttcgtgaa    540
acacatgacc aaatatattc gccaacaata attgatgttg gaattttccc agtaattgat    600
tgtatcttgg caagagatgt tcgtctttct ttatcgcctg gtcgatggtt tggaaatttt    660
gaaacacctg caatattgag caatgctggc aaaattaaaa attctaacgg cgatccacta    720
aataagtccg tatacggaag aaaagaatcc gaaggcttgg acttcaatga agatacaaat    780
gtaggaaagc tagcaagaaa accattaaaa accttgcaag aatttcttaa gaaaaataac    840
actaagtatg ccagcagagg ggtctatcca tcagcctgga caatccga                 888
```

<210> SEQ ID NO 122
<211> LENGTH: 296
<212> TYPE: PRT
<213> ORGANISM: Plesiomonas shigelloides 319-73

<400> SEQUENCE: 122

```
Met Ser Ile Leu Asp Asn Glu Lys Gln Leu Arg Ile Leu Asn Ile Ile
1               5                   10                  15

Asn Glu Gly Val Thr Pro Ala Ile Ile Pro Glu Leu His Ser Leu Val
            20                  25                  30

Asp Asp Arg Ile Thr Asn Glu Glu Ile Glu Leu Leu His Lys Lys Val
        35                  40                  45

Ser Thr Leu Ile Gly Leu Ser Ile Pro Val Leu Asn Ile Pro Arg Asp
    50                  55                  60

Ile Leu Lys Ala Phe Glu Pro Ser Gln Ile Gly Thr Ile Val Gly Thr
65                  70                  75                  80

Val Met Asp Ala Cys Ile Pro Gln Leu Asp Ser Ile Ile Glu Asp Ser
                85                  90                  95

Lys Val Ile Ala Asp Ile Gly Leu Gln Lys His Glu Gly Ile Leu Gly
            100                 105                 110

Glu Arg Glu Gly Tyr Pro Asp Tyr Lys Thr Asn Asp Gly Tyr Arg Leu
        115                 120                 125

Glu Leu Lys Leu Leu Tyr Val Asp Pro Asp Asp Val Glu Met Lys Lys
    130                 135                 140

Pro Pro Thr Pro Arg Glu Ala Ser Ala Arg Leu Thr Gln Lys Val Thr
145                 150                 155                 160

Tyr Lys Asn Val Asp Thr Ser Lys Asp Leu Leu Met Val Val Ala Tyr
                165                 170                 175

Gln Phe Arg Glu Thr His Asp Gln Ile Tyr Ser Pro Thr Ile Ile Asp
            180                 185                 190

Val Gly Ile Phe Pro Val Ile Asp Cys Ile Leu Ala Arg Asp Val Arg
        195                 200                 205

Leu Ser Leu Ser Pro Gly Arg Trp Phe Gly Asn Phe Glu Thr Pro Ala
```

```
    210                 215                 220

Ile Leu Ser Asn Ala Gly Lys Ile Lys Asn Ser Asn Gly Asp Pro Leu
225                 230                 235                 240

Asn Lys Ser Val Tyr Gly Arg Lys Glu Ser Glu Gly Leu Asp Phe Asn
                245                 250                 255

Glu Asp Thr Asn Val Gly Lys Leu Ala Arg Lys Pro Leu Lys Thr Leu
            260                 265                 270

Gln Glu Phe Leu Lys Lys Asn Asn Thr Lys Tyr Ala Ser Arg Gly Val
        275                 280                 285

Tyr Pro Ser Ala Trp Thr Ile Arg
    290                 295


<210> SEQ ID NO 123
<211> LENGTH: 2859
<212> TYPE: DNA
<213> ORGANISM: Providencia stuartii 164

<400> SEQUENCE: 123

atgagccgaa gcaacgccat aaaaattgcc aataagatta gtgcacgact gtcactacgc     60

gatccccaag atgaatcatt gcgtatctta tgcaacgtac ttgaacaatt cagtctcagt    120

aaagatcccg atcttaatcg ctggattgaa ttgctaagcc aacagtaccc tacagtgaaa    180

gggtttgaac gagcctttcc ttcattatgc ttcgcactgg ctactggtgt gggtaaaaca    240

cgcttaatgg gtgcaatgat tacttggcta tatttaaccg gacgcagccg tcatttcttc    300

atactatctc caaatttaac catctatgaa aaacttaaga tggatttttt acccggttca    360

ccaaagtatg ttttccaagg tattcctgaa cttgcacaaa cacctccggt tctaatcact    420

ggtgatgact atcaggaagg gcggggtgtt cgtctagatt atgcaattgc cgaaagcaaa    480

acgggtgatc tttttgacaa tgaaaccgct ccacacatta atatcttcaa tatttccaaa    540

ataaacgcac tggaaaatgc caaaggtgct gctaaatcta aggtcgctaa aattcgaaga    600

atacaggaat acatcggaga atcttatttt agctacctag cgaatctacc tgatttagtt    660

attttgatgg atgaagctca ccgttattat gccagcgcag gcgcacaggc acttaacgat    720

ctgaatccag tattgggtat tgaattaact gccacgccga aactgtgggg agcaaacccg    780

cgcgatttta aaaatattat ttatcactat cctctctcac gggcattaaa agatggatat    840

gtaaaaatcc cggcggttgc cacacgtaaa gagttccgcg ccgcaaatta ctctgaagaa    900

caactagaaa aaataaagtt ggaagacggt atccatcatc atgaatatgt gaaaacagag    960

ctaaccagct tcgctaacaa taccggtaac aaattaatta aaccttttat gctagttgtt   1020

gcacaggata ccgaccatgc agacagccta aaagtacgta ttgaacacga cgatttcttc   1080

aacggtgcct acaaaggcaa agtaatcacc gttcattcga accaaacggg tgaagaatca   1140

gaagagacta tgcagcgact tttggccgtt gagtatgata aagatacaga aatagtcatt   1200

catgtcaata agttaaaaga gggttgggat gttaccaacc tgtatactat tgttccatta   1260

cgtgcttctg cttctgaaat cctgactgag caaaccatag ggcgagggct acgcctaccg   1320

tacggtaaaa gaacaggcgt cgaagctgtt gatcgtctga caatcattgc ccatgatcgt   1380

tttcaagata ttatcgaccg tgccaataat gatgactcga ttattaaaaa agtcctttat   1440

atagggttag atgatgatga aaatggtatt ccagaagtaa aacctcagca aattgtcgta   1500

ccatcaatgg cagaatttct actgggaaat caagttattg ataataattt gcaggtgtgt   1560

gaacctcagg caatatatca aacgaattct atatcaaaac cggtgctcac cacgaacaca   1620

gaacgtaaag ttgcagaact cacgttcaaa gtagtctcag aagaagctaa acggttaacc   1680
```

agtagccacc aactcagcac cccagaggtg aaagcaagcg taactcggcg agtacaacaa 1740
gccttacgtg aatgggaaat ttcccaatct caaatttcat ccacttcgga acagagcgat 1800
ctgacagaaa taattgaaaa gcaagttgaa cagtcgaatt ccctatcaat ggaagatacg 1860
gaagttcagg agttagtcgg aacgattacc gaaaaactga tggaatatac tatcgatatt 1920
cctcgaatcg tggttttgcc agaacgcgaa gtcaattacg gatttaatga ttttaacctt 1980
tcccagttag atcgtattgc gctaaaacca ggtagcaaag aactcttact cacgcatctg 2040
gagaataacg aacaacgtac aatcagttgg caggaaggcg gagaagagga agaacgactt 2100
gaaaattacc tcattcgcta tctgctcgac cacgatgaaa ttgattacga tgaacatgcc 2160
gacatgctct ataaactggc cggacaaatg gtggggcatt tatgtagtta tcagtcccaa 2220
gaagatgctg aatccgttct gaaaaatgca ggtcggcagt tggcagaatt tatatgggtg 2280
caaatcaaac aaaatatgtg gacaacgcca acgggctata ctggacgtat aatacagggt 2340
tttgatgtaa tacatccagc cacattcaat tttgctggta atgaaagacc gagagatttc 2400
cgtgttgtga ttccagcagg agaaaaaaat aaagttcgcc agatgatttt cactggtttt 2460
actaagtgct gttatcctta tcagaaattt gactctgtag atggggagct ccgtctcgca 2520
caaatacttg agaatgatcc ttcagtgatt cgctggatga aacctcggcc aggtcaattc 2580
cgcattgagt atgctaatgg taaaaattat gaacctgatt ttgttgtcga aacggataat 2640
ggctattgtt taatcgaacc caaaaaagcg acagaaatcg acacgcctga agttaaagcc 2700
aaagcacaag cggctatccg gtggtgtgag tttgcaaatc aaaatgcaga taaacttaaa 2760
gggaaaactt ggcaatatgc tcttattcct cataatgaga ttgaattaag tcgttcaatc 2820
tcaggattac taactgattt taagatgtca tttcaatag 2859

<210> SEQ ID NO 124
<211> LENGTH: 952
<212> TYPE: PRT
<213> ORGANISM: Providencia stuartii 164

<400> SEQUENCE: 124

Met Ser Arg Ser Asn Ala Ile Lys Ile Ala Asn Lys Ile Ser Ala Arg
1 5 10 15

Leu Ser Leu Arg Asp Pro Gln Asp Glu Ser Leu Arg Ile Leu Cys Asn
20 25 30

Val Leu Glu Gln Phe Ser Leu Ser Lys Asp Pro Asp Leu Asn Arg Trp
35 40 45

Ile Glu Leu Leu Ser Gln Gln Tyr Pro Thr Val Lys Gly Phe Glu Arg
50 55 60

Ala Phe Pro Ser Leu Cys Phe Ala Leu Ala Thr Gly Val Gly Lys Thr
65 70 75 80

Arg Leu Met Gly Ala Met Ile Thr Trp Leu Tyr Leu Thr Gly Arg Ser
85 90 95

Arg His Phe Phe Ile Leu Ser Pro Asn Leu Thr Ile Tyr Glu Lys Leu
100 105 110

Lys Met Asp Phe Leu Pro Gly Ser Pro Lys Tyr Val Phe Gln Gly Ile
115 120 125

Pro Glu Leu Ala Gln Thr Pro Pro Val Leu Ile Thr Gly Asp Asp Tyr
130 135 140

Gln Glu Gly Arg Gly Val Arg Leu Asp Tyr Ala Ile Ala Glu Ser Lys
145 150 155 160

Thr Gly Asp Leu Phe Asp Asn Glu Thr Ala Pro His Ile Asn Ile Phe

```
                165                 170                 175

Asn Ile Ser Lys Ile Asn Ala Leu Glu Asn Ala Lys Gly Ala Ala Lys
            180                 185                 190

Ser Lys Val Ala Lys Ile Arg Arg Ile Gln Glu Tyr Ile Gly Glu Ser
        195                 200                 205

Tyr Phe Ser Tyr Leu Ala Asn Leu Pro Asp Leu Val Ile Leu Met Asp
    210                 215                 220

Glu Ala His Arg Tyr Tyr Ala Ser Ala Gly Ala Gln Ala Leu Asn Asp
225                 230                 235                 240

Leu Asn Pro Val Leu Gly Ile Glu Leu Thr Ala Thr Pro Lys Thr Val
                245                 250                 255

Gly Ala Asn Pro Arg Asp Phe Lys Asn Ile Ile Tyr His Tyr Pro Leu
            260                 265                 270

Ser Arg Ala Leu Lys Asp Gly Tyr Val Lys Ile Pro Ala Val Ala Thr
        275                 280                 285

Arg Lys Glu Phe Arg Ala Ala Asn Tyr Ser Glu Glu Gln Leu Glu Lys
    290                 295                 300

Ile Lys Leu Glu Asp Gly Ile His His His Glu Tyr Val Lys Thr Glu
305                 310                 315                 320

Leu Thr Ser Phe Ala Asn Asn Thr Gly Asn Lys Leu Ile Lys Pro Phe
                325                 330                 335

Met Leu Val Val Ala Gln Asp Thr Asp His Ala Asp Ser Leu Lys Val
            340                 345                 350

Arg Ile Glu His Asp Asp Phe Phe Asn Gly Ala Tyr Lys Gly Lys Val
        355                 360                 365

Ile Thr Val His Ser Asn Gln Thr Gly Glu Glu Ser Glu Glu Thr Met
    370                 375                 380

Gln Arg Leu Leu Ala Val Glu Tyr Asp Lys Asp Thr Glu Ile Val Ile
385                 390                 395                 400

His Val Asn Lys Leu Lys Glu Gly Trp Asp Val Thr Asn Leu Tyr Thr
                405                 410                 415

Ile Val Pro Leu Arg Ala Ser Ala Ser Glu Ile Leu Thr Glu Gln Thr
            420                 425                 430

Ile Gly Arg Gly Leu Arg Leu Pro Tyr Gly Lys Arg Thr Gly Val Glu
        435                 440                 445

Ala Val Asp Arg Leu Thr Ile Ile Ala His Asp Arg Phe Gln Asp Ile
    450                 455                 460

Ile Asp Arg Ala Asn Asn Asp Asp Ser Ile Ile Lys Lys Val Leu Tyr
465                 470                 475                 480

Ile Gly Leu Asp Asp Asp Glu Asn Gly Ile Pro Glu Val Lys Pro Gln
                485                 490                 495

Gln Ile Val Val Pro Ser Met Ala Glu Phe Leu Leu Gly Asn Gln Val
            500                 505                 510

Ile Asp Asn Asn Leu Gln Val Cys Glu Pro Gln Ala Ile Tyr Gln Thr
        515                 520                 525

Asn Ser Ile Ser Lys Pro Val Leu Thr Thr Asn Thr Glu Arg Lys Val
    530                 535                 540

Ala Glu Leu Thr Phe Lys Val Val Ser Glu Glu Ala Lys Arg Leu Thr
545                 550                 555                 560

Ser Ser His Gln Leu Ser Thr Pro Glu Val Lys Ala Ser Val Thr Arg
                565                 570                 575

Arg Val Gln Gln Ala Leu Arg Glu Trp Glu Ile Ser Gln Ser Gln Ile
            580                 585                 590
```

```
Ser Ser Thr Ser Glu Gln Ser Asp Leu Thr Glu Ile Ile Glu Lys Gln
        595                 600                 605

Val Glu Gln Ser Asn Ser Leu Ser Met Glu Asp Thr Glu Val Gln Glu
    610                 615                 620

Leu Val Gly Thr Ile Thr Glu Lys Leu Met Glu Tyr Thr Ile Asp Ile
625                 630                 635                 640

Pro Arg Ile Val Val Leu Pro Glu Arg Glu Val Asn Tyr Gly Phe Asn
                645                 650                 655

Asp Phe Asn Leu Ser Gln Leu Asp Arg Ile Ala Leu Lys Pro Gly Ser
            660                 665                 670

Lys Glu Leu Leu Leu Thr His Leu Glu Asn Asn Glu Gln Arg Thr Ile
        675                 680                 685

Ser Trp Gln Glu Gly Gly Glu Glu Glu Glu Arg Leu Glu Asn Tyr Leu
    690                 695                 700

Ile Arg Tyr Leu Leu Asp His Asp Glu Ile Asp Tyr Asp Glu His Ala
705                 710                 715                 720

Asp Met Leu Tyr Lys Leu Ala Gly Gln Met Val Gly His Leu Cys Ser
                725                 730                 735

Tyr Gln Ser Gln Glu Asp Ala Glu Ser Val Leu Lys Asn Ala Gly Arg
            740                 745                 750

Gln Leu Ala Glu Phe Ile Trp Val Gln Ile Lys Gln Asn Met Trp Thr
        755                 760                 765

Thr Pro Thr Gly Tyr Thr Gly Arg Ile Ile Gln Gly Phe Asp Val Ile
    770                 775                 780

His Pro Ala Thr Phe Asn Phe Ala Gly Asn Glu Arg Pro Arg Asp Phe
785                 790                 795                 800

Arg Val Val Ile Pro Ala Gly Glu Lys Asn Lys Val Arg Gln Met Ile
                805                 810                 815

Phe Thr Gly Phe Thr Lys Cys Cys Tyr Pro Tyr Gln Lys Phe Asp Ser
            820                 825                 830

Val Asp Gly Glu Leu Arg Leu Ala Gln Ile Leu Glu Asn Asp Pro Ser
        835                 840                 845

Val Ile Arg Trp Met Lys Pro Arg Pro Gly Gln Phe Arg Ile Glu Tyr
    850                 855                 860

Ala Asn Gly Lys Asn Tyr Glu Pro Asp Phe Val Val Glu Thr Asp Asn
865                 870                 875                 880

Gly Tyr Cys Leu Ile Glu Pro Lys Lys Ala Thr Glu Ile Asp Thr Pro
                885                 890                 895

Glu Val Lys Ala Lys Ala Gln Ala Ala Ile Arg Trp Cys Glu Phe Ala
            900                 905                 910

Asn Gln Asn Ala Asp Lys Leu Lys Gly Lys Thr Trp Gln Tyr Ala Leu
        915                 920                 925

Ile Pro His Asn Glu Ile Glu Leu Ser Arg Ser Ile Ser Gly Leu Leu
    930                 935                 940

Thr Asp Phe Lys Met Ser Phe Gln
945                 950
```

<210> SEQ ID NO 125
<211> LENGTH: 1008
<212> TYPE: DNA
<213> ORGANISM: Pseudomonas stutzeri 1660

<400> SEQUENCE: 125

```
atgccttact cctttgatca ttcggaagtt tgccataact gtcctttcgg aagttgcttt      60

gaggacagaa gggataatcc ggtaaggaat cgagatacaa aatttcggtt tcgccaaact     120
```

```
gccgcaatga gctgtacatt cgcagacttc atccctggga cggatagtga ccccatcccc    180

caaagaagct tcgaagagta tctaaaaaag ttcacctcga atgccatgct ggcaggtgaa    240

actctgtttg gtggtgagtt caacgttaag ggtgcggcca tcgccaaagt cgaaggtgat    300

gtctttgaac tccttgaggc tgcggcgctg tggaatgcta cagcggcttg gaacaggctt    360

atggactccg gttcgtgggg cgcatctgta ttcacttgtc ctcaatcggc tgtgcctacg    420

ccgacccgta aaattgccgt agtaaccctt ccaagagggt atgatgcaac aaagctattt    480

cgggacgaaa ttcgcagcag catccgtgct cacgaggagg ctcttcatct aagagggttg    540

tctcttgggt tgtcaagtcc tgacattgtt ggtgttcggc ttccttgccc gcttccggaa    600

gagcttggtt gcttcatgga gcctatcgaa aaccttggtg aagaaaacag ggtaaagctt    660

gaagaggctt acaagctgct tgaaggcaag attgaggcaa caggtttcct ctttgctatt    720

gccgtaaaga gaaccattcg gagtgatagg ctttaccagc cgcttttcga agccaatgtg    780

ttgaagtatc tgattgaggt ggtgctcaag gggcgctgcgt tcaggttcta cgctcacttc    840

aattcatttg aaggtgcgga tgtggaaggt cactacaagg cggcatcgct aatctcgcta    900

gccaggggtg gcactcctac aaaagcgatt gacgttctcc accttgcgga gtctcccctt    960

gcatcggcac aggctgtgct taatgacttt cccctgttcc atctttaa                1008


<210> SEQ ID NO 126
<211> LENGTH: 335
<212> TYPE: PRT
<213> ORGANISM: Pseudomonas stutzeri 1660

<400> SEQUENCE: 126

Met Pro Tyr Ser Phe Asp His Ser Glu Val Cys His Asn Cys Pro Phe
1               5                   10                  15

Gly Ser Cys Phe Glu Asp Arg Arg Asp Asn Pro Val Arg Asn Arg Asp
            20                  25                  30

Thr Lys Phe Arg Phe Arg Gln Thr Ala Ala Met Ser Cys Thr Phe Ala
        35                  40                  45

Asp Phe Ile Pro Gly Thr Asp Ser Asp Pro Ile Pro Gln Arg Ser Phe
    50                  55                  60

Glu Glu Tyr Leu Lys Lys Phe Thr Ser Asn Ala Met Leu Ala Gly Glu
65                  70                  75                  80

Thr Leu Phe Gly Gly Glu Phe Asn Val Lys Gly Ala Ala Ile Ala Lys
                85                  90                  95

Val Glu Gly Asp Val Phe Glu Leu Leu Glu Ala Ala Ala Leu Trp Asn
            100                 105                 110

Ala Thr Ala Ala Trp Asn Arg Leu Met Asp Ser Gly Ser Trp Gly Ala
        115                 120                 125

Ser Val Phe Thr Cys Pro Gln Ser Ala Val Pro Thr Pro Thr Arg Lys
    130                 135                 140

Ile Ala Val Val Thr Leu Pro Arg Gly Tyr Asp Ala Thr Lys Leu Phe
145                 150                 155                 160

Arg Asp Glu Ile Arg Ser Ser Ile Arg Ala His Glu Glu Ala Leu His
                165                 170                 175

Leu Arg Gly Leu Ser Leu Gly Leu Ser Ser Pro Asp Ile Val Gly Val
            180                 185                 190

Arg Leu Pro Cys Pro Leu Pro Glu Glu Leu Gly Cys Phe Met Glu Pro
        195                 200                 205

Ile Glu Asn Leu Gly Glu Glu Asn Arg Val Lys Leu Glu Glu Ala Tyr
    210                 215                 220
```

Lys Leu Leu Glu Gly Lys Ile Glu Ala Thr Gly Phe Leu Phe Ala Ile
225 230 235 240

Ala Val Lys Arg Thr Ile Arg Ser Asp Arg Leu Tyr Gln Pro Leu Phe
245 250 255

Glu Ala Asn Val Leu Lys Tyr Leu Ile Glu Val Val Leu Lys Gly Ala
260 265 270

Ala Phe Arg Phe Tyr Ala His Phe Asn Ser Phe Glu Gly Ala Asp Val
275 280 285

Glu Gly His Tyr Lys Ala Ala Ser Leu Ile Ser Leu Ala Arg Gly Gly
290 295 300

Thr Pro Thr Lys Ala Ile Asp Val Leu His Leu Ala Glu Ser Pro Leu
305 310 315 320

Ala Ser Ala Gln Ala Val Leu Asn Asp Phe Pro Leu Phe His Leu
325 330 335

<210> SEQ ID NO 127
<211> LENGTH: 603
<212> TYPE: DNA
<213> ORGANISM: Streptomyces achromogenes

<400> SEQUENCE: 127
atggcgccgg tggtgagccc cgacgatggc acgcagtacc acaaggactt cactctcagc 60
atcacgaagg cgctcggtga ccagctggca gcggctctgg acgggctaga cagggccccc 120
ctgacggacc ggagcatcgc ggccctcaag gaaaagcccg gcgtctacca gctctacttg 180
aacggcagct tcgtctacgt cggcaaggct gataggtcgt tgcccgcgcg gctccgcaac 240
cataagcgca agatctcggg gcgtcggagg atttcgctcg acgagatggc cttctcctgt 300
ctctacgtgg ccgaagactt ctcggcactc gcccccgaac agctcctgat cagccaccac 360
aagggcatgg gagacattcc ctggaacaac aacgggttcg gcaataagga ccccgggcgc 420
cagcgggaca gcaccgtact aaagcggaat cactttgacg tgctattccc catcgacctc 480
gaccggtcga gggcctacga gccggggaaa cgacactgca ggagctcctg gaagcggtta 540
aggtcggttt gccctacaac ttccgctatg ggaagcatga cggcttcaag agtcgatatg 600
tga 603

<210> SEQ ID NO 128
<211> LENGTH: 200
<212> TYPE: PRT
<213> ORGANISM: Streptomyces achromogenes

<400> SEQUENCE: 128

Met Ala Pro Val Val Ser Pro Asp Asp Gly Thr Gln Tyr His Lys Asp
1 5 10 15

Phe Thr Leu Ser Ile Thr Lys Ala Leu Gly Asp Gln Leu Ala Ala Ala
20 25 30

Leu Asp Gly Leu Asp Arg Ala Pro Leu Thr Asp Arg Ser Ile Ala Ala
35 40 45

Leu Lys Glu Lys Pro Gly Val Tyr Gln Leu Tyr Leu Asn Gly Ser Phe
50 55 60

Val Tyr Val Gly Lys Ala Asp Arg Ser Leu Pro Ala Arg Leu Arg Asn
65 70 75 80

His Lys Arg Lys Ile Ser Gly Arg Arg Arg Ile Ser Leu Asp Glu Met
85 90 95

Ala Phe Ser Cys Leu Tyr Val Ala Glu Asp Phe Ser Ala Leu Ala Pro
100 105 110

```
Glu Gln Leu Leu Ile Ser His His Lys Gly Met Gly Asp Ile Pro Trp
        115                 120                 125

Asn Asn Asn Gly Phe Gly Asn Lys Asp Pro Gly Arg Gln Arg Asp Ser
    130                 135                 140

Thr Val Leu Lys Arg Asn His Phe Asp Val Leu Phe Pro Ile Asp Leu
145                 150                 155                 160

Asp Arg Ser Arg Ala Tyr Glu Pro Gly Lys Arg His Cys Arg Ser Ser
                165                 170                 175

Trp Lys Arg Leu Arg Ser Val Cys Pro Thr Thr Ser Ala Met Gly Ser
            180                 185                 190

Met Thr Ala Ser Arg Val Asp Met
        195                 200


<210> SEQ ID NO 129
<211> LENGTH: 564
<212> TYPE: DNA
<213> ORGANISM: Serratia fonticola

<400> SEQUENCE: 129

atgaataata cattggatga ggcctttgct ttctatgcca gccatatcta tgacgaagaa      60

aaaattaatc tgttgaggtc acataacctc aaagttgcgg ggcatgttcc ctctgtctta     120

tgggagctgt ttggttcaat tcttacagga cgtcgtggta atggcattac tggggcagac     180

cttcaaggct gggaggttaa gtcgtccaca ttgaggagct ctttcgagta tcagtatcac     240

ttgaatacag gcgaagctaa gcttttggaa gattgcgaag ttaatcatct cttttgctcc     300

tattcaactg attatcgtga tcttatcgtc aaagcgattc cgggtgagga acttaaagag     360

accttttttg aagcttggtt gccagaatat agagcgaatt atgaccgtac tgtaggtagc     420

acttctaggc gccaacgttt taggaaggca ataccatatg gttttgttca agtacatggt     480

cgtacaatcc ttgaagttaa agctggtgaa atgtacagta gaaatgatag tcttttagaa     540

gagttcaata gattggtagg ctag                                            564


<210> SEQ ID NO 130
<211> LENGTH: 187
<212> TYPE: PRT
<213> ORGANISM: Serratia fonticola

<400> SEQUENCE: 130

Met Asn Asn Thr Leu Asp Glu Ala Phe Ala Phe Tyr Ala Ser His Ile
1               5                   10                  15

Tyr Asp Glu Glu Lys Ile Asn Leu Leu Arg Ser His Asn Leu Lys Val
            20                  25                  30

Ala Gly His Val Pro Ser Val Leu Trp Glu Leu Phe Gly Ser Ile Leu
        35                  40                  45

Thr Gly Arg Arg Gly Asn Gly Ile Thr Gly Ala Asp Leu Gln Gly Trp
    50                  55                  60

Glu Val Lys Ser Ser Thr Leu Arg Ser Ser Phe Glu Tyr Gln Tyr His
65                  70                  75                  80

Leu Asn Thr Gly Glu Ala Lys Leu Leu Glu Asp Cys Glu Val Asn His
                85                  90                  95

Leu Phe Cys Ser Tyr Ser Thr Asp Tyr Arg Asp Leu Ile Val Lys Ala
            100                 105                 110

Ile Pro Gly Glu Glu Leu Lys Glu Thr Phe Phe Glu Ala Trp Leu Pro
        115                 120                 125

Glu Tyr Arg Ala Asn Tyr Asp Arg Thr Val Gly Ser Thr Ser Arg Arg
```

-continued

```
    130                 135                 140

Gln Arg Phe Arg Lys Ala Ile Pro Tyr Gly Phe Val Gln Val His Gly
145                 150                 155                 160

Arg Thr Ile Leu Glu Val Lys Ala Gly Glu Met Tyr Ser Arg Asn Asp
                165                 170                 175

Ser Leu Leu Glu Glu Phe Asn Arg Leu Val Gly
            180                 185


<210> SEQ ID NO 131
<211> LENGTH: 567
<212> TYPE: DNA
<213> ORGANISM: Sphaerotilus natans

<400> SEQUENCE: 131

atgtcaatcg atcccaacaa gctaaacagc gccctttacg cgattcttgg aggctacaga      60

ggaaaattct ccaataaggt ctataacggc gaaaacgatg agttcgacat tttaatggaa     120

attttcggaa tttccccatt attgaaacgc gagagccgcc agtactgggg ccgagagctt     180

ggcatgtgct ggccacgact tgttgtggaa atttgcaaac agacgcgaaa tgacttcgga     240

tctgctttac aaattgatgg cggcgagcct tgtgatttga tagtaggcgg tttggcgatc     300

gaaaccaagt atagaatagg gtccggcgat gcaggcacct tgaaaaagtt ccaagcttac     360

ggctctctgc ttagttcaat ggggtatgag ccagtactct tgatagttcg tgaagacaac     420

cttggtgcag caatcacagc gtgccacgca ggcggctgga ccgttataac agggcaacgc     480

accttcgact accttcgcga ccttacagga attaacatta aggaactact cctgcagcgt     540

gccggaaaat ttcctgttgt ccggtga                                         567


<210> SEQ ID NO 132
<211> LENGTH: 188
<212> TYPE: PRT
<213> ORGANISM: Sphaerotilus natans

<400> SEQUENCE: 132

Met Ser Ile Asp Pro Asn Lys Leu Asn Ser Ala Leu Tyr Ala Ile Leu
1               5                   10                  15

Gly Gly Tyr Arg Gly Lys Phe Ser Asn Lys Val Tyr Asn Gly Glu Asn
            20                  25                  30

Asp Glu Phe Asp Ile Leu Met Glu Ile Phe Gly Ile Ser Pro Leu Leu
        35                  40                  45

Lys Arg Glu Ser Arg Gln Tyr Trp Gly Arg Glu Leu Gly Met Cys Trp
    50                  55                  60

Pro Arg Leu Val Val Glu Ile Cys Lys Gln Thr Arg Asn Asp Phe Gly
65                  70                  75                  80

Ser Ala Leu Gln Ile Asp Gly Gly Glu Pro Cys Asp Leu Ile Val Gly
                85                  90                  95

Gly Leu Ala Ile Glu Thr Lys Tyr Arg Ile Gly Ser Gly Asp Ala Gly
            100                 105                 110

Thr Leu Lys Lys Phe Gln Ala Tyr Gly Ser Leu Leu Ser Ser Met Gly
        115                 120                 125

Tyr Glu Pro Val Leu Leu Ile Val Arg Glu Asp Asn Leu Gly Ala Ala
    130                 135                 140

Ile Thr Ala Cys His Ala Gly Gly Trp Thr Val Ile Thr Gly Gln Arg
145                 150                 155                 160

Thr Phe Asp Tyr Leu Arg Asp Leu Thr Gly Ile Asn Ile Lys Glu Leu
                165                 170                 175
```

```
Leu Leu Gln Arg Ala Gly Lys Phe Pro Val Val Arg
            180                 185


<210> SEQ ID NO 133
<211> LENGTH: 846
<212> TYPE: DNA
<213> ORGANISM: Thermococcus litoralis

<400> SEQUENCE: 133

atggaaacta gcgtttgcca tactttgaag agccctgtta ttaagaagtt ctgtgagtct      60

ataactgaat tggccagaac ctctagggga tacttcgagc ctattcagga cgattttctg     120

aaagcatact atcaaatcgt tgaaaaagct cgtattaacg gcagacttcc agagggagaa     180

taccgacaga aaggaaacgc atttagagat tttatcagcg aattgattta cataagatct     240

gggggaatct accgcctaac agatagaaga attcctggct attctgagag aactcatgac     300

gttgatctcg cttatgtgag ggacgctact gttttggtgg ctggcgaagt caaaatgaca     360

ggtagcccaa ggcataagaa gggaacaacg gttcagaagg aaagaaagac gcagagcgat     420

ctagataaaa gattaaaaga agtcaagttc accgcagtgg atttaaaact tcgctacact     480

cccgaagagg ccataataaa tgccttaaac tccaagaata ctttttctga agtttctaat     540

aacagttggt ggatgcgatg gattcatacc tccattcccg gcttttactc gttctgggca     600

tccaggcttg cctcgggccg tcttgacaag aaaacaggaa ggagagtaga ctttgataat     660

cccgatcttc ttctcgaaaa attcaggaat ctactaaaat acaacaacgc agtaggtctt     720

ttcatgttcc gggaggagaa tggcagatac gttcccgttg aaactgagag aatcaaaagg     780

gaaagaattt caatagacga cgcggtgaag gatcttataa agttcctaga tactcacttg     840

gattag                                                                846


<210> SEQ ID NO 134
<211> LENGTH: 281
<212> TYPE: PRT
<213> ORGANISM: Thermococcus litoralis

<400> SEQUENCE: 134

Met Glu Thr Ser Val Cys His Thr Leu Lys Ser Pro Val Ile Lys Lys
1               5                   10                  15

Phe Cys Glu Ser Ile Thr Glu Leu Ala Arg Thr Ser Arg Gly Tyr Phe
            20                  25                  30

Glu Pro Ile Gln Asp Asp Phe Leu Lys Ala Tyr Tyr Gln Ile Val Glu
        35                  40                  45

Lys Ala Arg Ile Asn Gly Arg Leu Pro Glu Gly Glu Tyr Arg Gln Lys
    50                  55                  60

Gly Asn Ala Phe Arg Asp Phe Ile Ser Glu Leu Ile Tyr Ile Arg Ser
65                  70                  75                  80

Gly Gly Ile Tyr Arg Leu Thr Asp Arg Arg Ile Pro Gly Tyr Ser Glu
                85                  90                  95

Arg Thr His Asp Val Asp Leu Ala Tyr Val Arg Asp Ala Thr Val Leu
            100                 105                 110

Val Ala Gly Glu Val Lys Met Thr Gly Ser Pro Arg His Lys Lys Gly
        115                 120                 125

Thr Thr Val Gln Lys Glu Arg Lys Thr Gln Ser Asp Leu Asp Lys Arg
    130                 135                 140

Leu Lys Glu Val Lys Phe Thr Ala Val Asp Leu Lys Leu Arg Tyr Thr
145                 150                 155                 160

Pro Glu Glu Ala Ile Ile Asn Ala Leu Asn Ser Lys Asn Thr Phe Ser
```

```
                165                 170                 175

Glu Val Ser Asn Asn Ser Trp Trp Met Arg Trp Ile His Thr Ser Ile
            180                 185                 190

Pro Gly Phe Tyr Ser Phe Trp Ala Ser Arg Leu Ala Ser Gly Arg Leu
        195                 200                 205

Asp Lys Lys Thr Gly Arg Arg Val Asp Phe Asp Asn Pro Asp Leu Leu
    210                 215                 220

Leu Glu Lys Phe Arg Asn Leu Leu Lys Tyr Asn Asn Ala Val Gly Leu
225                 230                 235                 240

Phe Met Phe Arg Glu Glu Asn Gly Arg Tyr Val Pro Val Glu Thr Glu
                245                 250                 255

Arg Ile Lys Arg Glu Arg Ile Ser Ile Asp Asp Ala Val Lys Asp Leu
            260                 265                 270

Ile Lys Phe Leu Asp Thr His Leu Asp
        275                 280


<210> SEQ ID NO 135
<211> LENGTH: 1137
<212> TYPE: DNA
<213> ORGANISM: Thermus species 93170

<400> SEQUENCE: 135

atgaaaagat tagcaggctt aataagctta gcagacttaa tacaaggtga tactgagttt      60

aagataagct gggaaaaccg agggaaaaag gcgctcactc ttctggccga gaaggcaggc     120

atcagatgcg acgagcagct agatgatctt ctgtcgcaag ccctggatct tgcaaggagc     180

acgcttacct ccggcaaaaa tcctgatgct gacatcgctc acttctggga ggaggtcgaa     240

aaaaacgcca ccctcttaac gaaaaacgac tacctccgag cggctgtagt agctctttcg     300

tttgcccacc gctttgcccg aacagactac ggatcgtcaa ggcaacgcgg cttcgggcaa     360

ctctggggag atgcgattca aggcttcctt ggtgaaattg ccttccagaa gtttatgagg     420

tcagccacgt ctgggaggac catccctatt ttagacgcca gcgaagaaga tcttggagtc     480

gccctaagcg ctgacatagt tgaagtcatc acagagggga aatcaataaa gccctcaaaa     540

agaatcagca tcaagactac gaagctccat gggcgctggt tagatgtacc ctacgctcaa     600

aataagcaca gcgacattta cgttctggtt aaagtcggga ctgacgccga tgcgcttttc     660

aactttctgg caagcgtagg ggcgcttgag aaagtcttaa ccgcctatca agagggcggt     720

cttgctgaag gcgagcttcc ttttctcaac gaaggcgaag cgctcaaaag agctaaggaa     780

gaggtagaaa aaatgaagga aaaaaacatg cttttttttag cctttatagc tggctggaag     840

gagaaggatc ggctcagcca aaccttcgaa gctcacgagc acaacgccca aagagcccgc     900

acaaaaatca ctgtctacag cggagttggt acaatttcat ctggtagcgt gcgaacaaag     960

caaatcacct ttcgcggtcc cctccctaaa aacaatctgc tggttgagtt ttatccaata    1020

ggaaaattct ccaaaagcca gcatgcactg tgcagcacag atctgcttgt gaaggatctc    1080

aataagatag cagaacttct ctctgctcct gaagaggggg atgaatgcgc acagtaa      1137


<210> SEQ ID NO 136
<211> LENGTH: 378
<212> TYPE: PRT
<213> ORGANISM: Thermus species 93170

<400> SEQUENCE: 136

Met Lys Arg Leu Ala Gly Leu Ile Ser Leu Ala Asp Leu Ile Gln Gly
1               5                   10                  15
```

```
Asp Thr Glu Phe Lys Ile Ser Trp Glu Asn Arg Gly Lys Lys Ala Leu
            20                  25                  30

Thr Leu Leu Ala Glu Lys Ala Gly Ile Arg Cys Asp Glu Gln Leu Asp
        35                  40                  45

Asp Leu Leu Ser Gln Ala Leu Asp Leu Ala Arg Ser Thr Leu Thr Ser
    50                  55                  60

Gly Lys Asn Pro Asp Ala Asp Ile Ala His Phe Trp Glu Glu Val Glu
65                  70                  75                  80

Lys Asn Ala Thr Leu Leu Thr Lys Asn Asp Tyr Leu Arg Ala Ala Val
                85                  90                  95

Val Ala Leu Ser Phe Ala His Arg Phe Ala Arg Thr Asp Tyr Gly Ser
            100                 105                 110

Ser Arg Gln Arg Gly Phe Gly Gln Leu Trp Gly Asp Ala Ile Gln Gly
        115                 120                 125

Phe Leu Gly Glu Ile Ala Phe Gln Lys Phe Met Arg Ser Ala Thr Ser
    130                 135                 140

Gly Arg Thr Ile Pro Ile Leu Asp Ala Ser Glu Glu Asp Leu Gly Val
145                 150                 155                 160

Ala Leu Ser Ala Asp Ile Val Glu Val Ile Thr Glu Gly Lys Ser Ile
                165                 170                 175

Lys Pro Ser Lys Arg Ile Ser Ile Lys Thr Thr Lys Leu His Gly Arg
            180                 185                 190

Trp Leu Asp Val Pro Tyr Ala Gln Asn Lys His Ser Asp Ile Tyr Val
        195                 200                 205

Leu Val Lys Val Gly Thr Asp Ala Asp Ala Leu Phe Asn Phe Leu Ala
    210                 215                 220

Ser Val Gly Ala Leu Glu Lys Val Leu Thr Ala Tyr Gln Glu Gly Gly
225                 230                 235                 240

Leu Ala Glu Gly Glu Leu Pro Phe Leu Asn Glu Gly Glu Ala Leu Lys
                245                 250                 255

Arg Ala Lys Glu Glu Val Glu Lys Met Lys Glu Lys Asn Met Leu Phe
            260                 265                 270

Leu Ala Phe Ile Ala Gly Trp Lys Glu Lys Asp Arg Leu Ser Gln Thr
        275                 280                 285

Phe Glu Ala His Glu His Asn Ala Gln Arg Ala Arg Thr Lys Ile Thr
    290                 295                 300

Val Tyr Ser Gly Val Gly Thr Ile Ser Ser Gly Ser Val Arg Thr Lys
305                 310                 315                 320

Gln Ile Thr Phe Arg Gly Pro Leu Pro Lys Asn Asn Leu Leu Val Glu
                325                 330                 335

Phe Tyr Pro Ile Gly Lys Phe Ser Lys Ser Gln His Ala Leu Cys Ser
            340                 345                 350

Thr Asp Leu Leu Val Lys Asp Leu Asn Lys Ile Ala Glu Leu Leu Ser
        355                 360                 365

Ala Pro Glu Glu Gly Asp Glu Cys Ala Gln
    370                 375
```

<210> SEQ ID NO 137
<211> LENGTH: 855
<212> TYPE: DNA
<213> ORGANISM: Thermus species

<400> SEQUENCE: 137

```
atgaacgaaa tgtacgagat tgccaaagga gtggcctcat ttgaaggtgc tcctacctta      60

ccaggacgta cgacaggtga ggctagaggg ggccgagagt ttgaagctgt tgttgcggaa     120
```

```
ggtcttctga aatatggccg attgctggtc accgccgttc cctcattaag attacgcccg    180

gttgctgcag aaggaacttc aagacaaaac catctggctg acgctcttgc agtcgtaaac    240

gaagaaaata aaagagtctt ggtgttcaga ttacctgcat tcaggcacaa tcctctcttt    300

gctgagatta cttcaggcgc gctacagaac gatttcgttc gagttccgga ctcatttttg    360

aaaagggagt tcgttgtgga ggagtggtat acccccaagt taggggaact agcagaaaga    420

ggatggattc ctgaagagga tgaaccttat cctttttccg ggactaacta tccagaactg    480

tataggcgta agcgcaccca gttcgacggt gtgattatct tcttggaaag tggcacgcta    540

agggaaaaag ccctgctaga aataaaatct ctgaagtctt ctgagggggc cagggtcgat    600

ggtaacgccc acgaacggtt tgcgtaccag aatctagact atctcgagat aggggcccta    660

tatcctcgca caacgctctt gctacttaca aacgatgcca ttctcaagta cagaaacaaa    720

taccacacgg gaatcggtgt acatgcatta cggctaagct atgcgttttg ctggtacaag    780

tttgagatgg ttagctccgt tcgacagtac cttcgcctct tttctttgtg gaaggaatgg    840

ctggagggca aatga                                                     855
```

<210> SEQ ID NO 138
<211> LENGTH: 284
<212> TYPE: PRT
<213> ORGANISM: Thermus species

<400> SEQUENCE: 138

```
Met Asn Glu Met Tyr Glu Ile Ala Lys Gly Val Ala Ser Phe Glu Gly
1               5                   10                  15

Ala Pro Thr Leu Pro Gly Arg Thr Thr Gly Glu Ala Arg Gly Gly Arg
            20                  25                  30

Glu Phe Glu Ala Val Val Ala Glu Gly Leu Leu Lys Tyr Gly Arg Leu
        35                  40                  45

Leu Val Thr Ala Val Pro Ser Leu Arg Leu Arg Pro Val Ala Ala Glu
    50                  55                  60

Gly Thr Ser Arg Gln Asn His Leu Ala Asp Ala Leu Ala Val Val Asn
65                  70                  75                  80

Glu Glu Asn Lys Arg Val Leu Val Phe Arg Leu Pro Ala Phe Arg His
                85                  90                  95

Asn Pro Leu Phe Ala Glu Ile Thr Ser Gly Ala Leu Gln Asn Asp Phe
            100                 105                 110

Val Arg Val Pro Asp Ser Phe Leu Lys Arg Glu Phe Val Val Glu Glu
        115                 120                 125

Trp Tyr Thr Pro Lys Leu Gly Glu Leu Ala Glu Arg Gly Trp Ile Pro
    130                 135                 140

Glu Glu Asp Glu Pro Tyr Pro Phe Ser Gly Thr Asn Tyr Pro Glu Leu
145                 150                 155                 160

Tyr Arg Arg Lys Arg Thr Gln Phe Asp Gly Val Ile Ile Phe Leu Glu
                165                 170                 175

Ser Gly Thr Leu Arg Glu Lys Ala Leu Leu Glu Ile Lys Ser Leu Lys
            180                 185                 190

Ser Ser Glu Gly Ala Arg Val Asp Gly Asn Ala His Glu Arg Phe Ala
        195                 200                 205

Tyr Gln Asn Leu Asp Tyr Leu Glu Ile Gly Ala Leu Tyr Pro Arg Thr
    210                 215                 220

Thr Leu Leu Leu Leu Thr Asn Asp Ala Ile Leu Lys Tyr Arg Asn Lys
225                 230                 235                 240
```

-continued

```
Tyr His Thr Gly Ile Gly Val His Ala Leu Arg Leu Ser Tyr Ala Phe
                245                 250                 255

Cys Trp Tyr Lys Phe Glu Met Val Ser Ser Val Arg Gln Tyr Leu Arg
            260                 265                 270

Leu Phe Ser Leu Trp Lys Glu Trp Leu Glu Gly Lys
        275                 280


<210> SEQ ID NO 139
<211> LENGTH: 960
<212> TYPE: DNA
<213> ORGANISM: Thermus thermophilus strain 111

<400> SEQUENCE: 139

atggcgaata ctcttgagga ccatattact caagtattgg agagctttaa gggcgaagaa      60

ataaacagag ttatagcgat ttataagccg ccggatctcg agttagcaat tttttactca     120

aaaatcatat ccaagttgtc cccgataatc ggtaacgtgc ttgaaagatc cgttgcaaag     180

gaattggggg ttcgattgaa ggccccatat aagaggcaag atccggaatt tccagatgtt     240

gttgtggaat tgggaaaaga taaaaggata ggctttgaaa taaaagcgtg gtatgctctt     300

tcaacagaag cggctgcccg gttcagaaca agccaaaagg agctctcaag cggggcttac     360

gaggaggttt atctagtcgt aatagcttgg acaatgagca agctgtttta tggaaaacct     420

aaaataatca atcttttctt tgaaaaagcc attgagattg cccggacacg tgaccaaaag     480

taccacaatc ctccatggaa tatagtttta gagcctgtag acacatcagc gagaacaata     540

aacctacaac agaaagtagt catcggtaaa aaactacaag aagaaaatct tccagaaggt     600

gtacaagccg aagaagagct taaaaagctt gctcaggaca aaaaaataaa agactataag     660

gtctattcaa cgcaagaaga ttatgttgat ttcatacgaa atctggaaag agttttgcct     720

tatcgcgaag actccaattt tggcaagata gatcgcattc ctcatgaaag gctttcatct     780

ttcctcaaaa acaccaagaa attaaagcta ttagggctca ctttgaagga ctggatcaag     840

gtcatggagt acatatcaaa tcaggaggaa aaatctgctc aaaaatctaa aaaaaagaag     900

gagttagagg atctagtgga aaaagcacta aaaaagctcg gttaccctaa cacatactga     960


<210> SEQ ID NO 140
<211> LENGTH: 319
<212> TYPE: PRT
<213> ORGANISM: Thermus thermophilus strain 111

<400> SEQUENCE: 140

Met Ala Asn Thr Leu Glu Asp His Ile Thr Gln Val Leu Glu Ser Phe
1               5                   10                  15

Lys Gly Glu Glu Ile Asn Arg Val Ile Ala Ile Tyr Lys Pro Pro Asp
            20                  25                  30

Leu Glu Leu Ala Ile Phe Tyr Ser Lys Ile Ile Ser Lys Leu Ser Pro
        35                  40                  45

Ile Ile Gly Asn Val Leu Glu Arg Ser Val Ala Lys Glu Leu Gly Val
    50                  55                  60

Arg Leu Lys Ala Pro Tyr Lys Arg Gln Asp Pro Glu Phe Pro Asp Val
65                  70                  75                  80

Val Val Glu Leu Gly Lys Asp Lys Arg Ile Gly Phe Glu Ile Lys Ala
                85                  90                  95

Trp Tyr Ala Leu Ser Thr Glu Ala Ala Ala Arg Phe Arg Thr Ser Gln
            100                 105                 110

Lys Glu Leu Ser Ser Gly Ala Tyr Glu Glu Val Tyr Leu Val Val Ile
        115                 120                 125
```

```
Ala Trp Thr Met Ser Lys Leu Phe Tyr Gly Lys Pro Lys Ile Ile Asn
    130                 135                 140

Leu Phe Phe Glu Lys Ala Ile Glu Ile Ala Arg Thr Arg Asp Gln Lys
145                 150                 155                 160

Tyr His Asn Pro Pro Trp Asn Ile Val Leu Glu Pro Val Asp Thr Ser
                165                 170                 175

Ala Arg Thr Ile Asn Leu Gln Gln Lys Val Val Ile Gly Lys Lys Leu
            180                 185                 190

Gln Glu Glu Asn Leu Pro Glu Gly Val Gln Ala Glu Glu Glu Leu Lys
        195                 200                 205

Lys Leu Ala Gln Asp Lys Lys Ile Lys Asp Tyr Lys Val Tyr Ser Thr
    210                 215                 220

Gln Glu Asp Tyr Val Asp Phe Ile Arg Asn Leu Glu Arg Val Leu Pro
225                 230                 235                 240

Tyr Arg Glu Asp Ser Asn Phe Gly Lys Ile Asp Arg Ile Pro His Glu
                245                 250                 255

Arg Leu Ser Ser Phe Leu Lys Asn Thr Lys Lys Leu Lys Leu Leu Gly
            260                 265                 270

Leu Thr Leu Lys Asp Trp Ile Lys Val Met Glu Tyr Ile Ser Asn Gln
        275                 280                 285

Glu Glu Lys Ser Ala Gln Lys Ser Lys Lys Lys Lys Glu Leu Glu Asp
    290                 295                 300

Leu Val Glu Lys Ala Leu Lys Lys Leu Gly Tyr Pro Asn Thr Tyr
305                 310                 315
```

<210> SEQ ID NO 141
<211> LENGTH: 792
<212> TYPE: DNA
<213> ORGANISM: Xanthomonas campestris

<400> SEQUENCE: 141

```
atgccagtaa cacctccaca agacttgatc gattttatcg atgatattct ctcggatttg      60

cttacaaaca atccgcttgc cacttcctca gaggcgtatg tgcaaaacca catcgaattt     120

gagcttgtga ggaggaatca caatcctaag tattatttga ggatcggcat caactaccat     180

ggggagaaag tccagcatat catggtcgac ccgctcacag ggaagctaat tggctggaac     240

cctgcgggag atgcgctcgg caccggtgca aacgcgaaaa tgctactcgc gaattacaca     300

atatttgatc gtgcgcctgg cgaacacatg atgaccgact gcaaagttgg cggcggcccc     360

ctcgcggcgg gtcagtacgt ccgcgccgag ttcaaggtga ggggatggct tggcaaaaca     420

aagaatctgg atggcaagca atttcagaaa gatttggacc tcatgggcgc cgataaagcg     480

gacctgcttg tttggtgcct gtcagaaacc gctcattgca agttccgcgg cgaaggacct     540

gcacatcaag cgggtcgacg aacaggatgc caggatttcg cacccattct cctgcccact     600

aatcaaatcg ggatcgctcc tgtaacccgg caggtcccat atcgccggat cgagaccgca     660

aatttgccag ccgcgcaagc tttgtggatc aacacgcaaa attgggtcgt tcgcagtcgg     720

aaggtgacgg ctgcgccggg ctcactgatg cccggcgcag agcactacgt cacgatgtgc     780

tggcgcgtgt ag                                                         792
```

<210> SEQ ID NO 142
<211> LENGTH: 263
<212> TYPE: PRT
<213> ORGANISM: Xanthomonas campestris

<400> SEQUENCE: 142

Met Pro Val Thr Pro Pro Gln Asp Leu Ile Asp Phe Ile Asp Asp Ile
1 5 10 15

Leu Ser Asp Leu Leu Thr Asn Asn Pro Leu Ala Thr Ser Ser Glu Ala
20 25 30

Tyr Val Gln Asn His Ile Glu Phe Glu Leu Val Arg Arg Asn His Asn
35 40 45

Pro Lys Tyr Tyr Leu Arg Ile Gly Ile Asn Tyr His Gly Glu Lys Val
50 55 60

Gln His Ile Met Val Asp Pro Leu Thr Gly Lys Leu Ile Gly Trp Asn
65 70 75 80

Pro Ala Gly Asp Ala Leu Gly Thr Gly Ala Asn Ala Lys Met Leu Leu
85 90 95

Ala Asn Tyr Thr Ile Phe Asp Arg Ala Pro Gly Glu His Met Met Thr
100 105 110

Asp Cys Lys Val Gly Gly Gly Pro Leu Ala Ala Gly Gln Tyr Val Arg
115 120 125

Ala Glu Phe Lys Val Arg Gly Trp Leu Gly Lys Thr Lys Asn Leu Asp
130 135 140

Gly Lys Gln Phe Gln Lys Asp Leu Asp Leu Met Gly Ala Asp Lys Ala
145 150 155 160

Asp Leu Leu Val Trp Cys Leu Ser Glu Thr Ala His Cys Lys Phe Arg
165 170 175

Gly Glu Gly Pro Ala His Gln Ala Gly Arg Arg Thr Gly Cys Gln Asp
180 185 190

Phe Ala Pro Ile Leu Leu Pro Thr Asn Gln Ile Gly Ile Ala Pro Val
195 200 205

Thr Arg Gln Val Pro Tyr Arg Arg Ile Glu Thr Ala Asn Leu Pro Ala
210 215 220

Ala Gln Ala Leu Trp Ile Asn Thr Gln Asn Trp Val Val Arg Ser Arg
225 230 235 240

Lys Val Thr Ala Ala Pro Gly Ser Leu Met Pro Gly Ala Glu His Tyr
245 250 255

Val Thr Met Cys Trp Arg Val
260

<210> SEQ ID NO 143
<211> LENGTH: 624
<212> TYPE: DNA
<213> ORGANISM: Xanthomonas holcicola

<400> SEQUENCE: 143
ttgaaagtcg caaaaatcta ctcacatctg aacggcctgg aatttttaaa agttcaccat 60
gaaaaggtga ttttggagct ggatcgggtc attacccgta tagacgctga ggcttgccgc 120
accaaagaaa caaaagaggc aagaaaggca gggcggttcg ctgatggtct tctgtatagc 180
ccggtagcac tgaatgaagc ttttaacgat gctctgtcgc agcttcactg gtatgaagat 240
cgctattcct acttcgtgac cgatgacgct aggctcatta gagcgacatt agggttggac 300
agagcggagc aaaagcgaat aattgaggat gcaggtcata aggcgattgc aacctacaat 360
cagacggatt ttgtgaaaga cagggtggcc atagaagtgc agtttggaaa gtattcgttt 420
gtagcttacg atctttttgt caaacacatg gcattttatg ttggtgacaa aattgacgtc 480
ggcatagaaa ttctgccaat gaaatctttg caggagaata tgtcttcggg aattgcttac 540
tacgaaagtg agctttccaa tcttgtaagg caaggccgag gtgtgcccgc tgttcctctg 600
gtgctgatgg gcatagagcc ttaa 624

<210> SEQ ID NO 144
<211> LENGTH: 207
<212> TYPE: PRT
<213> ORGANISM: Xanthomonas holcicola

<400> SEQUENCE: 144

Leu Lys Val Ala Lys Ile Tyr Ser His Leu Asn Gly Leu Glu Phe Leu
1               5                   10                  15

Lys Val His His Glu Lys Val Ile Leu Glu Leu Asp Arg Val Ile Thr
            20                  25                  30

Arg Ile Asp Ala Glu Ala Cys Arg Thr Lys Glu Thr Lys Glu Ala Arg
        35                  40                  45

Lys Ala Gly Arg Phe Ala Asp Gly Leu Leu Tyr Ser Pro Val Ala Leu
    50                  55                  60

Asn Glu Ala Phe Asn Asp Ala Leu Ser Gln Leu His Trp Tyr Glu Asp
65                  70                  75                  80

Arg Tyr Ser Tyr Phe Val Thr Asp Asp Ala Arg Leu Ile Arg Ala Thr
                85                  90                  95

Leu Gly Leu Asp Arg Ala Glu Gln Lys Arg Ile Ile Glu Asp Ala Gly
            100                 105                 110

His Lys Ala Ile Ala Thr Tyr Asn Gln Thr Asp Phe Val Lys Asp Arg
        115                 120                 125

Val Ala Ile Glu Val Gln Phe Gly Lys Tyr Ser Phe Val Ala Tyr Asp
    130                 135                 140

Leu Phe Val Lys His Met Ala Phe Tyr Val Gly Asp Lys Ile Asp Val
145                 150                 155                 160

Gly Ile Glu Ile Leu Pro Met Lys Ser Leu Gln Glu Asn Met Ser Ser
                165                 170                 175

Gly Ile Ala Tyr Tyr Glu Ser Glu Leu Ser Asn Leu Val Arg Gln Gly
            180                 185                 190

Arg Gly Val Pro Ala Val Pro Leu Val Leu Met Gly Ile Glu Pro
        195                 200                 205

<210> SEQ ID NO 145
<211> LENGTH: 855
<212> TYPE: DNA
<213> ORGANISM: Bacillus brevis

<400> SEQUENCE: 145
tttaaccaat ttaatccgtt agtatataca cacggtggaa aacttgaacg gaagtctaag 60
aaggataaaa cagcaagtaa ggtgttcgaa gaatttggtg tgatggaggc ttataattgt 120
tggaaggaag cttccctatg tattcaacaa agagacaagg atagcgttct taaacttgta 180
gcagctctca atacgtataa agacgcagta gaaccaattt ttgactcaag actgaatagt 240
gcccaagaag ttctccaacc gtcgatttta gaagaatttt ttgaatatct gtttagcagg 300
attgactcta ttgttggagt gaatattcca attcgacatc cagcgaaggg ttatttaagt 360
ctcagcttta atccacataa tatagaaacg ctcatccaat cgccggagta cactgtaagg 420
gcgaaggatc atgattttat tattggtggg tcagcgaaat taaccattca aggacatggc 480
ggggaaggag aaacaaccaa cattgtggtt cctgctgtag cgattgaatg caagcggtac 540
cttgaacgaa acatgctaga tgaatgtgct ggtactgctg agcgcttaaa aagagcaaca 600
ccatattgtt tatacttcgt agttgcggag tacttaaaac tagatgatgg agcaccggaa 660
ttaaccgaga ttgatgagat ttacatactt cggcaccagc ggaactcaga gcggaataag 720

```
ccaggattta agcctaaccc catagatggt gaactgattt gggatttgta ccaagaagtt    780

atgaatcatc ttgggaagat ttggtgggat ccaaactcag ctttacaacg cggtaaagtg    840

tttaatcgac cataa                                                     855
```

<210> SEQ ID NO 146
<211> LENGTH: 285
<212> TYPE: PRT
<213> ORGANISM: Bacillus brevis

<400> SEQUENCE: 146

```
Met Phe Asn Gln Phe Asn Pro Leu Val Tyr Thr His Gly Gly Lys Leu
1               5                   10                  15

Glu Arg Lys Ser Lys Lys Asp Lys Thr Ala Ser Lys Val Phe Glu Glu
            20                  25                  30

Phe Gly Val Met Glu Ala Tyr Asn Cys Trp Lys Glu Ala Ser Leu Cys
        35                  40                  45

Ile Gln Gln Arg Asp Lys Asp Ser Val Leu Lys Leu Val Ala Ala Leu
    50                  55                  60

Asn Thr Tyr Lys Asp Ala Val Glu Pro Ile Phe Asp Ser Arg Leu Asn
65                  70                  75                  80

Ser Ala Gln Glu Val Leu Gln Pro Ser Ile Leu Glu Glu Phe Phe Glu
                85                  90                  95

Tyr Leu Phe Ser Arg Ile Asp Ser Ile Val Gly Val Asn Ile Pro Ile
            100                 105                 110

Arg His Pro Ala Lys Gly Tyr Leu Ser Leu Ser Phe Asn Pro His Asn
        115                 120                 125

Ile Glu Thr Leu Ile Gln Ser Pro Glu Tyr Thr Val Arg Ala Lys Asp
    130                 135                 140

His Asp Phe Ile Ile Gly Gly Ser Ala Lys Leu Thr Ile Gln Gly His
145                 150                 155                 160

Gly Gly Glu Gly Glu Thr Thr Asn Ile Val Val Pro Ala Val Ala Ile
                165                 170                 175

Glu Cys Lys Arg Tyr Leu Glu Arg Asn Met Leu Asp Glu Cys Ala Gly
            180                 185                 190

Thr Ala Glu Arg Leu Lys Arg Ala Thr Pro Tyr Cys Leu Tyr Phe Val
        195                 200                 205

Val Ala Glu Tyr Leu Lys Leu Asp Asp Gly Ala Pro Glu Leu Thr Glu
    210                 215                 220

Ile Asp Glu Ile Tyr Ile Leu Arg His Gln Arg Asn Ser Glu Arg Asn
225                 230                 235                 240

Lys Pro Gly Phe Lys Pro Asn Pro Ile Asp Gly Glu Leu Ile Trp Asp
                245                 250                 255

Leu Tyr Gln Glu Val Met Asn His Leu Gly Lys Ile Trp Trp Asp Pro
            260                 265                 270

Asn Ser Ala Leu Gln Arg Gly Lys Val Phe Asn Arg Pro
        275                 280                 285
```

<210> SEQ ID NO 147
<211> LENGTH: 591
<212> TYPE: DNA
<213> ORGANISM: Bacillus fragilis

<400> SEQUENCE: 147

```
atgaagaaat tcaagatttc aaatgatgag gttacggagt tgtcaaatgc tcctcaatat     60

caatttccaa agtatgtgac tcaggttatt aacttggtaa atagtaacgc tggcggtact    120
```

-continued

```
cgccctaagg tagttggtca gatgtcagaa ctggttaaag agtttgatgg taggaccatt    180

gacgagtgga ttgagtggta cacggagaga taccctgatg caattaatga tgctactgaa    240

aagatctggg ccatgtatga gaccatgaag ggtgctttca atgctatcac caaagagatg    300

gtcgagaatt gggtgaaaga tcttgtctat ggtaaaacct tctgtggttt gaaatttcag    360

acagctatta tttcagcgat agccaatcag ttagacaagt cttggagaga ggctgatcct    420

gaagaagaag ctcaaggtat tgatggcttt attggtgaca agccacttca gattaagtct    480

gctacatata aattagaagc acgcctttct gaaaccatca atgcaccaat agtgtactac    540

gacaagaaga aggatggcat aagtattgag tataacccaa ctgactttta a             591
```

<210> SEQ ID NO 148
<211> LENGTH: 196
<212> TYPE: PRT
<213> ORGANISM: Bacillus fragilis

<400> SEQUENCE: 148

```
Met Lys Lys Phe Lys Ile Ser Asn Asp Glu Val Thr Glu Leu Ser Asn
1               5                   10                  15

Ala Pro Gln Tyr Gln Phe Pro Lys Tyr Val Thr Gln Val Ile Asn Leu
            20                  25                  30

Val Asn Ser Asn Ala Gly Gly Thr Arg Pro Lys Val Val Gly Gln Met
        35                  40                  45

Ser Glu Leu Val Lys Glu Phe Asp Gly Arg Thr Ile Asp Glu Trp Ile
    50                  55                  60

Glu Trp Tyr Thr Glu Arg Tyr Pro Asp Ala Ile Asn Asp Ala Thr Glu
65                  70                  75                  80

Lys Ile Trp Ala Met Tyr Glu Thr Met Lys Gly Ala Phe Asn Ala Ile
                85                  90                  95

Thr Lys Glu Met Val Glu Asn Trp Val Lys Asp Leu Val Tyr Gly Lys
            100                 105                 110

Thr Phe Cys Gly Leu Lys Phe Gln Thr Ala Ile Ile Ser Ala Ile Ala
        115                 120                 125

Asn Gln Leu Asp Lys Ser Trp Arg Glu Ala Asp Pro Glu Glu Glu Ala
    130                 135                 140

Gln Gly Ile Asp Gly Phe Ile Gly Asp Lys Pro Leu Gln Ile Lys Ser
145                 150                 155                 160

Ala Thr Tyr Lys Leu Glu Ala Arg Leu Ser Glu Thr Ile Asn Ala Pro
                165                 170                 175

Ile Val Tyr Tyr Asp Lys Lys Lys Asp Gly Ile Ser Ile Glu Tyr Asn
            180                 185                 190

Pro Thr Asp Phe
        195
```

<210> SEQ ID NO 149
<211> LENGTH: 1620
<212> TYPE: DNA
<213> ORGANISM: Acinetobacter calcoaceticus 65

<400> SEQUENCE: 149

```
atgaaattaa atgctgagaa tttaagtatt caggaacaat tagcagaatt tgatcaatgg     60

ctcacagcta gactagataa aatcaaagat tcagaaaaat tcaattcaga aattaactcc    120

ctctgtaatt gtattaccgt attatctcct cttttagaaa acttcagtga tccttccacc    180

tgtacaattc atagcttagt gaatgcggtt atagaagcca gcaatagaat agtctctggt    240
```

```
agtagttttg gaggtgatga agctgctctc aacaactttt atgagtcttt ttttaacttg    300

ctattcctaa ccagtggggc aacagataac aacctaaaga atcattttct aattaaactt    360

aatgaagacg atattacacc tctcatacct aaacgtggtt caataaagaa acagatcaca    420

ttcaaacttt atgaaattcc tacaactact aaatctgact ttatcgctcg taccttagca    480

agttgtttta caggaactaa atatcccctc ctagtaaaga cagaaccatt tttcgatctt    540

gaaacatact ttaaaatttt tttagaagaa tacattaagc ttattcttga tgatgaagaa    600

gatttattac aactctgggc tatctgccac tcatttgttg aattatccac taaccctcat    660

ggttccaatt tgggtaaata tttattaaat tcttgtacga tttttaaagt tagaggtagt    720

gtatcagcat caggtggtca cgttactgaa tctatactta gggaaaagtt atcaaacatc    780

gggttaagag ctgatattga ttacaataat aatgatgtca aaattggtga tgatgaaatt    840

attgaagacg ggaaaagaaa aaagaaaact cgtgcgtatg actttataat tccttataaa    900

atagataact gggaaccaaa acctaagcta tttatccaat cacaatttta cgctggggat    960

tctggcagtg tatctcataa agtcgtagat caaactcaaa gttcaagagt atttacacta   1020

accaaatatc cgaatgctaa atttgttgaa tatttagatg gtgctggtta ctacgcttct   1080

ttaagaggtg atttacagca catgctatct ttcagcaata cagaatcttt ttttcaagta   1140

aaaagtattc ttttacgttt aagacgtgaa ttccaaaaga tcgatttttt aacagctatt   1200

gaaattcagc atgctgtact aatcagcaaa tctcggactc ataaagatct ccaaaatctt   1260

cttataaaag ataactattc tatccaagaa atagaaagag ctattcaaac caatttagaa   1320

ctaggtctta ttactaaaaa tgaatcagat gaaattgtaa tacctacaga acatatttgt   1380

atcgcccgga gacttttaat tttagatatt gctgcaaact attcatgctc tattactcag   1440

gcagaaaagt ctagccaaaa atatttatta gtaccgggca atggggccaa taaaggaatt   1500

aaggagtcta agctagctga gttagctttt gacttatgta aagatattaa tataacaccg   1560

actgaattta ttgaagacat cgaatggctc ttagatgagg gagtaattaa acgattttag   1620
```

<210> SEQ ID NO 150
<211> LENGTH: 539
<212> TYPE: PRT
<213> ORGANISM: Acinetobacter calcoaceticus 65

<400> SEQUENCE: 150

```
Met Lys Leu Asn Ala Glu Asn Leu Ser Ile Gln Glu Gln Leu Ala Glu
1               5                   10                  15

Phe Asp Gln Trp Leu Thr Ala Arg Leu Asp Lys Ile Lys Asp Ser Glu
            20                  25                  30

Lys Phe Asn Ser Glu Ile Asn Ser Leu Cys Asn Cys Ile Thr Val Leu
        35                  40                  45

Ser Pro Leu Leu Glu Asn Phe Ser Asp Pro Ser Thr Cys Thr Ile His
    50                  55                  60

Ser Leu Val Asn Ala Val Ile Glu Ala Ser Asn Arg Ile Val Ser Gly
65                  70                  75                  80

Ser Ser Phe Gly Gly Asp Glu Ala Ala Leu Asn Asn Phe Tyr Glu Ser
                85                  90                  95

Phe Phe Asn Leu Leu Phe Leu Thr Ser Gly Ala Thr Asp Asn Asn Leu
            100                 105                 110

Lys Asn His Phe Leu Ile Lys Leu Asn Glu Asp Asp Ile Thr Pro Leu
        115                 120                 125

Ile Pro Lys Arg Gly Ser Ile Lys Lys Gln Ile Thr Phe Lys Leu Tyr
    130                 135                 140
```

```
Glu Ile Pro Thr Thr Thr Lys Ser Asp Phe Ile Ala Arg Thr Leu Ala
145                 150                 155                 160

Ser Cys Phe Thr Gly Thr Lys Tyr Pro Leu Leu Val Lys Thr Glu Pro
                165                 170                 175

Phe Phe Asp Leu Glu Thr Tyr Phe Lys Ile Phe Leu Glu Glu Tyr Ile
            180                 185                 190

Lys Leu Ile Leu Asp Asp Glu Glu Asp Leu Leu Gln Leu Trp Ala Ile
        195                 200                 205

Cys His Ser Phe Val Glu Leu Ser Thr Asn Pro His Gly Ser Asn Leu
    210                 215                 220

Gly Lys Tyr Leu Leu Asn Ser Cys Thr Ile Phe Lys Val Arg Gly Ser
225                 230                 235                 240

Val Ser Ala Ser Gly Gly His Val Thr Glu Ser Ile Leu Arg Glu Lys
                245                 250                 255

Leu Ser Asn Ile Gly Leu Arg Ala Asp Ile Asp Tyr Asn Asn Asn Asp
            260                 265                 270

Val Lys Ile Gly Asp Asp Glu Ile Ile Glu Asp Gly Lys Arg Lys Lys
        275                 280                 285

Lys Thr Arg Ala Tyr Asp Phe Ile Ile Pro Tyr Lys Ile Asp Asn Trp
    290                 295                 300

Glu Pro Lys Pro Lys Leu Phe Ile Gln Ser Gln Phe Tyr Ala Gly Asp
305                 310                 315                 320

Ser Gly Ser Val Ser His Lys Val Val Asp Gln Thr Gln Ser Ser Arg
                325                 330                 335

Val Phe Thr Leu Thr Lys Tyr Pro Asn Ala Lys Phe Val Glu Tyr Leu
            340                 345                 350

Asp Gly Ala Gly Tyr Tyr Ala Ser Leu Arg Gly Asp Leu Gln His Met
        355                 360                 365

Leu Ser Phe Ser Asn Thr Glu Ser Phe Phe Gln Val Lys Ser Ile Leu
    370                 375                 380

Leu Arg Leu Arg Arg Glu Phe Gln Lys Ile Asp Phe Leu Thr Ala Ile
385                 390                 395                 400

Glu Ile Gln His Ala Val Leu Ile Ser Lys Ser Arg Thr His Lys Asp
                405                 410                 415

Leu Gln Asn Leu Leu Ile Lys Asp Asn Tyr Ser Ile Gln Glu Ile Glu
            420                 425                 430

Arg Ala Ile Gln Thr Asn Leu Glu Leu Gly Leu Ile Thr Lys Asn Glu
        435                 440                 445

Ser Asp Glu Ile Val Ile Pro Thr Glu His Ile Cys Ile Ala Arg Arg
    450                 455                 460

Leu Leu Ile Leu Asp Ile Ala Ala Asn Tyr Ser Cys Ser Ile Thr Gln
465                 470                 475                 480

Ala Glu Lys Ser Ser Gln Lys Tyr Leu Leu Val Pro Gly Asn Gly Ala
                485                 490                 495

Asn Lys Gly Ile Lys Glu Ser Lys Leu Ala Glu Leu Ala Phe Asp Leu
            500                 505                 510

Cys Lys Asp Ile Asn Ile Thr Pro Thr Glu Phe Ile Glu Asp Ile Glu
        515                 520                 525

Trp Leu Leu Asp Glu Gly Val Ile Lys Arg Phe
    530                 535
```

<210> SEQ ID NO 151
<211> LENGTH: 783
<212> TYPE: DNA

<213> ORGANISM: Bacillus stearothermophilus G668

<400> SEQUENCE: 151
atgtacaatt atttattaaa cgaaaatgca gatataattt atgatggaaa ggttatactc 60
acaaaagaac aagttgttga agcaattatt ataacaaata caaacttaaa gaaacttaat 120
gacattacga aagagtctgg tgtcgaagtg tttgaagcat taggaatgag aaacctaagt 180
ggttttattg gtgagttttt cgtaagcagt ctcgaacaag tatcaaataa gaacttagtt 240
aaaaatccac atcaagatgg atatccagat ttgttgctcg tagattctcc taaagctgcc 300
tcatacttta attcaatagt cgaaatagtt gatggaaaat tatatccaaa agaaaaaagt 360
ctgtttagcc catttaaata tggtggatta gaggtaaaag ccacttgtgg ttctacacct 420
tcagcaaaag ttatgcctaa gccattgatt ggcgagcaga gaattcacat cttaactgga 480
ttagattgga aggcccatca tagaggtact aacaatctaa taggaatata ttgggatttt 540
ttagatgagt taccaaccat ttgcgctgta ttttatagaa acgacctaac cgaagatgat 600
tggggaaaaa ttgttcgccc taaagaaggt gggggaagaa ccacaagtgt atccattatg 660
aactcaaagg gtgtcaaaaa aatgtgcaag aactggattg ctattattga taacgaagat 720
tatataaacg cattttctaa taaaaaatgg ataggatata atgtaaaaaa ctcatcaaat 780
tag 783

<210> SEQ ID NO 152
<211> LENGTH: 260
<212> TYPE: PRT
<213> ORGANISM: Bacillus stearothermophilus G668

<400> SEQUENCE: 152

Met Tyr Asn Tyr Leu Leu Asn Glu Asn Ala Asp Ile Ile Tyr Asp Gly
1               5                   10                  15

Lys Val Ile Leu Thr Lys Glu Gln Val Val Glu Ala Ile Ile Ile Thr
            20                  25                  30

Asn Thr Asn Leu Lys Lys Leu Asn Asp Ile Thr Lys Glu Ser Gly Val
        35                  40                  45

Glu Val Phe Glu Ala Leu Gly Met Arg Asn Leu Ser Gly Phe Ile Gly
    50                  55                  60

Glu Phe Phe Val Ser Ser Leu Glu Gln Val Ser Asn Lys Asn Leu Val
65                  70                  75                  80

Lys Asn Pro His Gln Asp Gly Tyr Pro Asp Leu Leu Leu Val Asp Ser
                85                  90                  95

Pro Lys Ala Ala Ser Tyr Phe Asn Ser Ile Val Glu Ile Val Asp Gly
            100                 105                 110

Lys Leu Tyr Pro Lys Glu Lys Ser Leu Phe Ser Pro Phe Lys Tyr Gly
        115                 120                 125

Gly Leu Glu Val Lys Ala Thr Cys Gly Ser Thr Pro Ser Ala Lys Val
    130                 135                 140

Met Pro Lys Pro Leu Ile Gly Glu Gln Arg Ile His Ile Leu Thr Gly
145                 150                 155                 160

Leu Asp Trp Lys Ala His His Arg Gly Thr Asn Asn Leu Ile Gly Ile
                165                 170                 175

Tyr Trp Asp Phe Leu Asp Glu Leu Pro Thr Ile Cys Ala Val Phe Tyr
            180                 185                 190

Arg Asn Asp Leu Thr Glu Asp Asp Trp Gly Lys Ile Val Arg Pro Lys
        195                 200                 205

Glu Gly Gly Gly Arg Thr Thr Ser Val Ser Ile Met Asn Ser Lys Gly

-continued

```
    210                 215                 220

Val Lys Lys Met Cys Lys Asn Trp Ile Ala Ile Ile Asp Asn Glu Asp
225                 230                 235                 240

Tyr Ile Asn Ala Phe Ser Asn Lys Lys Trp Ile Gly Tyr Asn Val Lys
                245                 250                 255

Asn Ser Ser Asn
            260


<210> SEQ ID NO 153
<211> LENGTH: 2640
<212> TYPE: DNA
<213> ORGANISM: Bacillus stearothermophilus F

<400> SEQUENCE: 153

atgttgagta ccataacaag gttgcctgta tatgatgatg atgaagtagg agttttccat     60

cctatttgcg agtctgcatt aaatcaggct ctgtctaatc ttggcttgga taaagagttt    120

aaagttttac atcatgaagc cgttggtagt cttgaagcag attttgcatt aatacgggag    180

tcaacaagaa aatatgtttt attcattgag gtgaagagga aaccagccgc tgtaagtagt    240

acaagatata gaatacaagc acagtcatat gttcaagaag caaaaaacagc agtagaaaaa    300

ccttattatg ctattactaa tttagaagta ctggatattt ttaagtatga tagtagcagg    360

ccttcagtta ctcagcaaat aattgaacca agtccagttc gtataggtac attttccgac    420

aatcccgtag aatttttttaa taacttagtt aaaacttttg aggatattat cactattgtt    480

gtaaatgaca gtggtacata caaagaacta actggaagtt ttattccatt actagaaaat    540

aataaaacta atcaacaacg ttggcatcaa agtttattag ttgccggata tgaatatatt    600

agaggtgtaa tgcaagcaag taaaagaaat atgacatgga aagcagcctt gaattacaaa    660

aatagaccta ataaattagt tgagaatatt cgatcagtaa attttagttc attagttgtt    720

ccaccgttac ctgctagtaa agatagtgaa atttggaata catcgatgtt agaggacttg    780

gtagagttag gaaaaaaaac aatgagtggt gatggactgg ctgaattagt tcattcaatt    840

gctgtttccg ggagggagca cgagggttta gtacctacag acttagagtt ggctaatatt    900

ttggctattt tatcaaaata tgttctcggt agagagttaa atgaaaatga gattatatgc    960

gatccagcag cgggaagtgg aaatttgtta gcagccatca gggcaggatt tgatacaata   1020

aatccaaaac aattatgggc aaatgataaa gagcagttat ttcttgaact actttctatt   1080

agattaggtt tgatgtttcc actaatagtc tcacctacaa actcaccttt agttacagga   1140

aaagatattt gtgaccttaa taagaacgat tttacgaatg ttagtgtagt tcttatgaat   1200

cctccatatg tttcaggggt aaaggaccct ataactaaga aaaaagttgc caaacgtata   1260

tttgatatta gtggaacaat gtccaagact aatattggac aagtaggaat agaagcacca   1320

ttcttagaac taattacaaa cttggtgaaa gataatacaa ttataggtgt ggttttccca   1380

aaacagtatt taaccgcgag aggtagagag gcagaagcat taagaaatta tttattaaat   1440

gatttcggtt taaaccttat ttttatatat ccgagagaag gaatattcaa agatgtaaca   1500

aaagatactg tagtactaat agggagaaag aataatcctt ctagcaaagt gaaagttata   1560

aaaagcgaaa ttccacttgc agaaataaat cttacaaaat ttaaacaagg cttgaataat   1620

ttaaaaacaa atagttcaat acattctctt gcatatggag ttgatgtaag ggaacttaat   1680

gcaaatgaat tgcatcagaa agttaaagat ggatggagaa gtcttacaaa tgttggtcaa   1740

aaaatagata attggattaa tagtactctt attccaatta gtgagaaatt atctggagtt   1800

cataatttaa aaaaaggaag aattggaaat gcaggtgcct cggacttatt atttataaac   1860
```

tcaaatcata aattatggga attggttaag catattattc caaaagattg gttatatcca 1920
gcccttcgac ttgtaaaaga tattaataac gtatttgtta attcatctac tacggatgtt 1980
cgttttcttg ccccatgtga aaaagcgttt caaacaggta caaaagaata tagtatttta 2040
gaagaaatat tagatatata cgaagaagta aaagcagaat ccttagtaaa aacaaaacaa 2100
ccaaagaaaa taaagactaa ggaagaattg cgaaagatat taaatagaga aagaaagaaa 2160
ataactagtc cttatactat tttaattcct cgtaatatta gaagatatgc tagggtattt 2220
attacaactg aaagtgcata catatcaaca aatgtaattg aggtaactgg tggaacaaag 2280
gatcaaaagt ggatcacgtt ttcatggttg ttaagtatat tttcgcaact tcaattagaa 2340
gtaatgtcaa aagagcaaga aggtgcaaga aagacagaag taggtagtat taaggattta 2400
cttttaccta agttcgaaaa cattgataac aaaatagtcg aaaaactaat aaatgagact 2460
gaaactagaa taggattttt ggatttatgt aatccatcaa ctactacaat tgataagtta 2520
tgggctgaag ttttatcttc ttcgaaacca gaagagatac tgaatcaagc attgtttta 2580 ttagaagaaa aagtgaatga gagatatcct gagtatttag tatcagatga tgatgaataa 2640

<210> SEQ ID NO 154
<211> LENGTH: 26
<212> TYPE: DNA
<213> ORGANISM: unknown
<220> FEATURE:
<223> OTHER INFORMATION: Methylophilus methylotrophus - recognition sequence for 5' to 3' direction
<220> FEATURE:
<221> NAME/KEY: misc_feature
<222> LOCATION: (7)..(26)
<223> OTHER INFORMATION: n is a, c, g, or t

<400> SEQUENCE: 154
tccracnnnn nnnnnnnnnn nnnnnn 26

<210> SEQ ID NO 155
<211> LENGTH: 26
<212> TYPE: DNA
<213> ORGANISM: unknown
<220> FEATURE:
<223> OTHER INFORMATION: Corynebacterium striatum M82B - recognition sequence - 5' to 3' direction
<220> FEATURE:
<221> NAME/KEY: misc_feature
<222> LOCATION: (7)..(26)
<223> OTHER INFORMATION: n is a, c, g, or t

<400> SEQUENCE: 155
aaggagnnnn nnnnnnnnnn nnnnnn 26

<210> SEQ ID NO 156
<211> LENGTH: 879
<212> TYPE: PRT
<213> ORGANISM: Bacillus stearothermophilus F

<400> SEQUENCE: 156

Met Leu Ser Thr Ile Thr Arg Leu Pro Val Tyr Asp Asp Asp Glu Val
1 5 10 15

Gly Val Phe His Pro Ile Cys Glu Ser Ala Leu Asn Gln Ala Leu Ser
20 25 30

Asn Leu Gly Leu Asp Lys Glu Phe Lys Val Leu His His Glu Ala Val
35 40 45

Gly Ser Leu Glu Ala Asp Phe Ala Leu Ile Arg Glu Ser Thr Arg Lys
50 55 60

```
Tyr Val Leu Phe Ile Glu Val Lys Arg Lys Pro Ala Ala Val Ser Ser
65                  70                  75                  80

Thr Arg Tyr Arg Ile Gln Ala Gln Ser Tyr Val Gln Glu Ala Lys Thr
                85                  90                  95

Ala Val Glu Lys Pro Tyr Tyr Ala Ile Thr Asn Leu Glu Val Leu Asp
            100                 105                 110

Ile Phe Lys Tyr Asp Ser Ser Arg Pro Ser Val Thr Gln Gln Ile Ile
        115                 120                 125

Glu Pro Ser Pro Val Arg Ile Gly Thr Phe Ser Asp Asn Pro Val Glu
    130                 135                 140

Phe Phe Asn Asn Leu Val Lys Thr Phe Glu Asp Ile Ile Thr Ile Val
145                 150                 155                 160

Val Asn Asp Ser Gly Thr Tyr Lys Glu Leu Thr Gly Ser Phe Ile Pro
                165                 170                 175

Leu Leu Glu Asn Asn Lys Thr Asn Gln Gln Arg Trp His Gln Ser Leu
            180                 185                 190

Leu Val Ala Gly Tyr Glu Tyr Ile Arg Gly Val Met Gln Ala Ser Lys
        195                 200                 205

Arg Asn Met Thr Trp Lys Ala Ala Leu Asn Tyr Lys Asn Arg Pro Asn
    210                 215                 220

Lys Leu Val Glu Asn Ile Arg Ser Val Asn Phe Ser Ser Leu Val Val
225                 230                 235                 240

Pro Pro Leu Pro Ala Ser Lys Asp Ser Glu Ile Trp Asn Thr Ser Met
                245                 250                 255

Leu Glu Asp Leu Val Glu Leu Gly Lys Lys Thr Met Ser Gly Asp Gly
            260                 265                 270

Leu Ala Glu Leu Val His Ser Ile Ala Val Ser Gly Arg Glu His Glu
        275                 280                 285

Gly Leu Val Pro Thr Asp Leu Glu Leu Ala Asn Ile Leu Ala Ile Leu
    290                 295                 300

Ser Lys Tyr Val Leu Gly Arg Glu Leu Asn Glu Asn Glu Ile Ile Cys
305                 310                 315                 320

Asp Pro Ala Ala Gly Ser Gly Asn Leu Leu Ala Ala Ile Arg Ala Gly
                325                 330                 335

Phe Asp Thr Ile Asn Pro Lys Gln Leu Trp Ala Asn Asp Lys Glu Gln
            340                 345                 350

Leu Phe Leu Glu Leu Leu Ser Ile Arg Leu Gly Leu Met Phe Pro Leu
        355                 360                 365

Ile Val Ser Pro Thr Asn Ser Pro Leu Val Thr Gly Lys Asp Ile Cys
    370                 375                 380

Asp Leu Asn Lys Asn Asp Phe Thr Asn Val Ser Val Val Leu Met Asn
385                 390                 395                 400

Pro Pro Tyr Val Ser Gly Val Lys Asp Pro Ile Thr Lys Lys Lys Val
                405                 410                 415

Ala Lys Arg Ile Phe Asp Ile Ser Gly Thr Met Ser Lys Thr Asn Ile
            420                 425                 430

Gly Gln Val Gly Ile Glu Ala Pro Phe Leu Glu Leu Ile Thr Asn Leu
        435                 440                 445

Val Lys Asp Asn Thr Ile Ile Gly Val Val Phe Pro Lys Gln Tyr Leu
    450                 455                 460

Thr Ala Arg Gly Arg Glu Ala Glu Ala Leu Arg Asn Tyr Leu Leu Asn
465                 470                 475                 480

Asp Phe Gly Leu Asn Leu Ile Phe Ile Tyr Pro Arg Glu Gly Ile Phe
```

-continued

```
                485                 490                 495

Lys Asp Val Thr Lys Asp Thr Val Val Leu Ile Gly Arg Lys Asn Asn
            500                 505                 510

Pro Ser Ser Lys Val Lys Val Ile Lys Ser Glu Ile Pro Leu Ala Glu
        515                 520                 525

Ile Asn Leu Thr Lys Phe Lys Gln Gly Leu Asn Asn Leu Lys Thr Asn
    530                 535                 540

Ser Ser Ile His Ser Leu Ala Tyr Gly Val Asp Val Arg Glu Leu Asn
545                 550                 555                 560

Ala Asn Glu Leu His Gln Lys Val Lys Asp Gly Trp Arg Ser Leu Thr
                565                 570                 575

Asn Val Gly Gln Lys Ile Asp Asn Trp Ile Asn Ser Thr Leu Ile Pro
            580                 585                 590

Ile Ser Glu Lys Leu Ser Gly Val His Asn Leu Lys Lys Gly Arg Ile
        595                 600                 605

Gly Asn Ala Gly Ala Ser Asp Leu Leu Phe Ile Asn Ser Asn His Lys
    610                 615                 620

Leu Trp Glu Leu Val Lys His Ile Ile Pro Lys Asp Trp Leu Tyr Pro
625                 630                 635                 640

Ala Leu Arg Leu Val Lys Asp Ile Asn Asn Val Phe Val Asn Ser Ser
                645                 650                 655

Thr Thr Asp Val Arg Phe Leu Ala Pro Cys Glu Lys Ala Phe Gln Thr
            660                 665                 670

Gly Thr Lys Glu Tyr Ser Ile Leu Glu Glu Ile Leu Asp Ile Tyr Glu
        675                 680                 685

Glu Val Lys Ala Glu Ser Leu Val Lys Thr Lys Gln Pro Lys Lys Ile
    690                 695                 700

Lys Thr Lys Glu Glu Leu Arg Lys Ile Leu Asn Arg Glu Arg Lys Lys
705                 710                 715                 720

Ile Thr Ser Pro Tyr Thr Ile Leu Ile Pro Arg Asn Ile Arg Arg Tyr
                725                 730                 735

Ala Arg Val Phe Ile Thr Thr Glu Ser Ala Tyr Ile Ser Thr Asn Val
            740                 745                 750

Ile Glu Val Thr Gly Gly Thr Lys Asp Gln Lys Trp Ile Thr Phe Ser
        755                 760                 765

Trp Leu Leu Ser Ile Phe Ser Gln Leu Gln Leu Glu Val Met Ser Lys
    770                 775                 780

Glu Gln Glu Gly Ala Arg Lys Thr Glu Val Gly Ser Ile Lys Asp Leu
785                 790                 795                 800

Leu Leu Pro Lys Phe Glu Asn Ile Asp Asn Lys Ile Val Glu Lys Leu
                805                 810                 815

Ile Asn Glu Thr Glu Thr Arg Ile Gly Phe Leu Asp Leu Cys Asn Pro
            820                 825                 830

Ser Thr Thr Thr Ile Asp Lys Leu Trp Ala Glu Val Leu Ser Ser Ser
        835                 840                 845

Lys Pro Glu Glu Ile Leu Asn Gln Ala Leu Phe Leu Leu Glu Glu Lys
    850                 855                 860

Val Asn Glu Arg Tyr Pro Glu Tyr Leu Val Ser Asp Asp Asp Glu
865                 870                 875
```

<210> SEQ ID NO 157
<211> LENGTH: 903
<212> TYPE: DNA
<213> ORGANISM: Bacillus species

<400> SEQUENCE: 157

```
atgattgaaa cggtgttaga gaaagttaca aataaaaaca attttgttac attacaaaat     60
tatacggatt ttgctttata ttttttagag tatattcaga agaataaaca agctacaatt    120
gtttcacaaa atgaacatgt atataacttt tatcaatata atagtgaagc gaattatcaa    180
gtaactcgcc ctttcaattc aaaaatttta tattctcacc aagatttttt ggataaccta    240
ggggaattca ataaaatatt gaaggatttg aaaagcgacc gtaatcatgc aaaaattttg    300
gatagaagta ttattaatag aacaatttat acggtacaac aaacaatagg ttttgcattg    360
gacggtcttg acgcaaatag gacaaatgta gctcgaaaac tgaatggaga ctatttcgag    420
cagttaattt tattactgct gcgagaaatc ggtgctcccg cgaataacgg ggttgtaaaa    480
gtccctgtaa atatggaaga caaacaacta ttcaatatga gttatcaaca cgatcttata    540
cttaaagaca aaaaaggcga ggtaaaattg attggttctg ttaaaacaac ttcaaaggat    600
agaattggaa agatttttgt cgataagttt ctatattcga aattaacgga aacaacagta    660
ccccacattg caattttctt acatgatgtt caaagaaaga ggaataaaga tccgcaaaaa    720
ttcgggataa atggcacctt tttagcagga cattttaaag gttacacggt taaattaaat    780
ccccttgatg gagtgtatta tttcgaccca cgcccacaaa tgcaaactga tgttctattg    840
agtgaacata tacaaacgtt cgaccatttg ctttgcgatg atatttggag ttatgttgat    900
tga                                                                  903
```

<210> SEQ ID NO 158
<211> LENGTH: 300
<212> TYPE: PRT
<213> ORGANISM: Bacillus species

<400> SEQUENCE: 158

```
Met Ile Glu Thr Val Leu Glu Lys Val Thr Asn Lys Asn Asn Phe Val
1               5                   10                  15

Thr Leu Gln Asn Tyr Thr Asp Phe Ala Leu Tyr Phe Leu Glu Tyr Ile
            20                  25                  30

Gln Lys Asn Lys Gln Ala Thr Ile Val Ser Gln Asn Glu His Val Tyr
        35                  40                  45

Asn Phe Tyr Gln Tyr Asn Ser Glu Ala Asn Tyr Gln Val Thr Arg Pro
    50                  55                  60

Phe Asn Ser Lys Ile Leu Tyr Ser His Gln Asp Phe Leu Asp Asn Leu
65                  70                  75                  80

Gly Glu Phe Asn Lys Ile Leu Lys Asp Leu Lys Ser Asp Arg Asn His
                85                  90                  95

Ala Lys Ile Leu Asp Arg Ser Ile Ile Asn Arg Thr Ile Tyr Thr Val
            100                 105                 110

Gln Gln Thr Ile Gly Phe Ala Leu Asp Gly Leu Asp Ala Asn Arg Thr
        115                 120                 125

Asn Val Ala Arg Lys Leu Asn Gly Asp Tyr Phe Glu Gln Leu Ile Leu
    130                 135                 140

Leu Leu Leu Arg Glu Ile Gly Ala Pro Ala Asn Asn Gly Val Val Lys
145                 150                 155                 160

Val Pro Val Asn Met Glu Asp Lys Gln Leu Phe Asn Met Ser Tyr Gln
                165                 170                 175

His Asp Leu Ile Leu Lys Asp Lys Lys Gly Glu Val Lys Leu Ile Gly
            180                 185                 190

Ser Val Lys Thr Thr Ser Lys Asp Arg Ile Gly Lys Ile Phe Val Asp
        195                 200                 205
```

```
Lys Phe Leu Tyr Ser Lys Leu Thr Glu Thr Thr Val Pro His Ile Ala
    210                 215                 220

Ile Phe Leu His Asp Val Gln Arg Lys Arg Asn Lys Asp Pro Gln Lys
225                 230                 235                 240

Phe Gly Ile Asn Gly Thr Phe Leu Ala Gly His Phe Lys Gly Tyr Thr
                245                 250                 255

Val Lys Leu Asn Pro Leu Asp Gly Val Tyr Tyr Phe Asp Pro Arg Pro
            260                 265                 270

Gln Met Gln Thr Asp Val Leu Leu Ser Glu His Ile Gln Thr Phe Asp
        275                 280                 285

His Leu Leu Cys Asp Asp Ile Trp Ser Tyr Val Asp
    290                 295                 300


<210> SEQ ID NO 159
<211> LENGTH: 1398
<212> TYPE: DNA
<213> ORGANISM: Bacillus thermosphaericus

<400> SEQUENCE: 159

atgaaacgaa ttttatactt gctaactgaa gaaagaccta aaataaatat tatacaccaa      60

attattaatc ttgaatataa agcaacatta cactttggtg cgaaaatagt accagttatg     120

aatgaggaaa ataagtttac atttatttat cacgtaaaag ggattgaagt tgagggattt     180

gatgcagtct taataaaaat tgtttcaggt catagttcat tcgttgatta ccttgttttt     240

gatagcaacg atctaaaacc tgaaaaaaat actattactc tatttgattt agatcaatat     300

gaactagatt taagttatta ttttggaaaa ggatggattg tacgaatccc aagtccttcc     360

gacttgccaa aatatgtggt tgaggaaaca aaaacagacg atcatgaatc gagaaatact     420

aatgcttatc aacgttcttc aaaatttgtt ttttgtgagc tctattatgg taaagaagta     480

aaaaaataca tgttatatga tatttctgat gggagaactt tatctgggac tgacactcat     540

aattttggta tgcgtatgtt agttacgaat aatgttaact tagtaggtgt tccaaatatg     600

tacttaccat ttacagatat aaaggagttt atcaatgaaa aaaatagaat agctgataat     660

ggaccaagtc ataatgtgcc tattcgactt aaattagata aggaaaagaa tgttatttat     720

atttcagcca aacttgataa aggtaatggg aaaaataaaa ataaaatttc aaatgatcca     780

aatattggag cggtagctat tatttctgca acattacgta atttaaattg gaaaggtgat     840

attgaaatta taaatcataa ccttttacct tcaagtatct catcacgtag caatggaaat     900

aagctattat atataatgaa aaaattagga gttcgtttta ataacattaa tgtaaattgg     960

aataatatta aaaataatat taattatttt ttctataata taacttctga gaaaatagtt    1020

tcaatatact atcaccttta tgttgaggat aaattaagta atgcaagagt aatctttgat    1080

aatcatgctg gctgtggtaa aagttatttt agaacactta ataataaaat tattccagtt    1140

ggtaaagaaa ttcccttacc agacttagta atttttgatt cagatcaaaa tattgtaaaa    1200

gttattgagg ctgaaaaagc agaaaatgtt tataatggtg ttgaacagct tagtacattt    1260

gacaaattta tagagtctta tattaataaa tattacccag gagccgcagt agaatgttct    1320

gtaattactt gggggaaatc aagcaatcca tatgtaagtt tttatttaga taaagatgga    1380

agcgctgttt ttctgtaa                                                  1398


<210> SEQ ID NO 160
<211> LENGTH: 465
<212> TYPE: PRT
<213> ORGANISM: Bacillus thermosphaericus
```

<400> SEQUENCE: 160

Met Lys Arg Ile Leu Tyr Leu Leu Thr Glu Glu Arg Pro Lys Ile Asn
1 5 10 15

Ile Ile His Gln Ile Ile Asn Leu Glu Tyr Lys Ala Thr Leu His Phe
20 25 30

Gly Ala Lys Ile Val Pro Val Met Asn Glu Glu Asn Lys Phe Thr Phe
35 40 45

Ile Tyr His Val Lys Gly Ile Glu Val Glu Gly Phe Asp Ala Val Leu
50 55 60

Ile Lys Ile Val Ser Gly His Ser Ser Phe Val Asp Tyr Leu Val Phe
65 70 75 80

Asp Ser Asn Asp Leu Lys Pro Glu Lys Asn Thr Ile Thr Leu Phe Asp
85 90 95

Leu Asp Gln Tyr Glu Leu Asp Leu Ser Tyr Tyr Phe Gly Lys Gly Trp
100 105 110

Ile Val Arg Ile Pro Ser Pro Ser Asp Leu Pro Lys Tyr Val Val Glu
115 120 125

Glu Thr Lys Thr Asp Asp His Glu Ser Arg Asn Thr Asn Ala Tyr Gln
130 135 140

Arg Ser Ser Lys Phe Val Phe Cys Glu Leu Tyr Tyr Gly Lys Glu Val
145 150 155 160

Lys Lys Tyr Met Leu Tyr Asp Ile Ser Asp Gly Arg Thr Leu Ser Gly
165 170 175

Thr Asp Thr His Asn Phe Gly Met Arg Met Leu Val Thr Asn Asn Val
180 185 190

Asn Leu Val Gly Val Pro Asn Met Tyr Leu Pro Phe Thr Asp Ile Lys
195 200 205

Glu Phe Ile Asn Glu Lys Asn Arg Ile Ala Asp Asn Gly Pro Ser His
210 215 220

Asn Val Pro Ile Arg Leu Lys Leu Asp Lys Glu Lys Asn Val Ile Tyr
225 230 235 240

Ile Ser Ala Lys Leu Asp Lys Gly Asn Gly Lys Asn Lys Asn Lys Ile
245 250 255

Ser Asn Asp Pro Asn Ile Gly Ala Val Ala Ile Ile Ser Ala Thr Leu
260 265 270

Arg Asn Leu Asn Trp Lys Gly Asp Ile Glu Ile Ile Asn His Asn Leu
275 280 285

Leu Pro Ser Ser Ile Ser Ser Arg Ser Asn Gly Asn Lys Leu Leu Tyr
290 295 300

Ile Met Lys Lys Leu Gly Val Arg Phe Asn Asn Ile Asn Val Asn Trp
305 310 315 320

Asn Asn Ile Lys Asn Asn Ile Asn Tyr Phe Phe Tyr Asn Ile Thr Ser
325 330 335

Glu Lys Ile Val Ser Ile Tyr Tyr His Leu Tyr Val Glu Asp Lys Leu
340 345 350

Ser Asn Ala Arg Val Ile Phe Asp Asn His Ala Gly Cys Gly Lys Ser
355 360 365

Tyr Phe Arg Thr Leu Asn Asn Lys Ile Ile Pro Val Gly Lys Glu Ile
370 375 380

Pro Leu Pro Asp Leu Val Ile Phe Asp Ser Asp Gln Asn Ile Val Lys
385 390 395 400

Val Ile Glu Ala Glu Lys Ala Glu Asn Val Tyr Asn Gly Val Glu Gln
405 410 415

```
Leu Ser Thr Phe Asp Lys Phe Ile Glu Ser Tyr Ile Asn Lys Tyr Tyr
            420                 425                 430

Pro Gly Ala Ala Val Glu Cys Ser Val Ile Thr Trp Gly Lys Ser Ser
        435                 440                 445

Asn Pro Tyr Val Ser Phe Tyr Leu Asp Lys Asp Gly Ser Ala Val Phe
    450                 455                 460

Leu
465
```

<210> SEQ ID NO 161
<211> LENGTH: 495
<212> TYPE: DNA
<213> ORGANISM: Bacillus thermoglucosidasius

<400> SEQUENCE: 161

```
atgaaaataa cagagggaat cgtccatgtt gcaatgcggc actttctaaa atcaaatggc      60

tggaaattaa ttgctgggca ataccctggt ggaagcgatg acgaattgac tgcacttaat     120

attgttgatc ctgtggtagc tcgtgataat agtcctgatc ctcgccgtca tagtttaggt     180

aaaattgttc ctgacctaat agcttataaa aacgatgatt tactcgttat tgaagcaaag     240

ccgaaatatt cgcaggatga tagggataaa ttactttact tgctttcaga aagaaaacat     300

gacttttacg cggctttaga aaaattcgct actgaaagga atcacccaga actactgccg     360

gtatctaagc tgaatattat acctgggtta gcgttttccg cttcagaaaa caaattcaaa     420

aaggatcccg gattcgttta cataagagta tctgggatct ttgaagcatt tatggagggc     480

tatgattggg ggtga                                                      495
```

<210> SEQ ID NO 162
<211> LENGTH: 164
<212> TYPE: PRT
<213> ORGANISM: Bacillus thermoglucosidasius

<400> SEQUENCE: 162

```
Met Lys Ile Thr Glu Gly Ile Val His Val Ala Met Arg His Phe Leu
1               5                   10                  15

Lys Ser Asn Gly Trp Lys Leu Ile Ala Gly Gln Tyr Pro Gly Gly Ser
            20                  25                  30

Asp Asp Glu Leu Thr Ala Leu Asn Ile Val Asp Pro Val Val Ala Arg
        35                  40                  45

Asp Asn Ser Pro Asp Pro Arg Arg His Ser Leu Gly Lys Ile Val Pro
    50                  55                  60

Asp Leu Ile Ala Tyr Lys Asn Asp Asp Leu Leu Val Ile Glu Ala Lys
65                  70                  75                  80

Pro Lys Tyr Ser Gln Asp Asp Arg Asp Lys Leu Leu Tyr Leu Leu Ser
                85                  90                  95

Glu Arg Lys His Asp Phe Tyr Ala Ala Leu Glu Lys Phe Ala Thr Glu
            100                 105                 110

Arg Asn His Pro Glu Leu Leu Pro Val Ser Lys Leu Asn Ile Ile Pro
        115                 120                 125

Gly Leu Ala Phe Ser Ala Ser Glu Asn Lys Phe Lys Lys Asp Pro Gly
    130                 135                 140

Phe Val Tyr Ile Arg Val Ser Gly Ile Phe Glu Ala Phe Met Glu Gly
145                 150                 155                 160

Tyr Asp Trp Gly
```

<210> SEQ ID NO 163
<211> LENGTH: 987
<212> TYPE: DNA
<213> ORGANISM: Bacillus thermoglucosidasius

<400> SEQUENCE: 163

```
atgcagatcg aacaattaat gaaaagtctc acaatctatt ttgacgacat acaagagggt     60
ttatggttta aaaacttgca tcctctatta gaatccgcgt ctcttgaggc gattactgga    120
tccctaaaaa gaaatccaaa cttagctgat gttttaaaat atgatagacc cgatatcatt    180
cttaccttga atcaaacacc catattagta atagagcgaa caattgaggt tccaagtggg    240
cataatgtcg gacaaagata tgggagatta gccgcagcat cggaagcagg agttccttta    300
gtctactttg gtccttacgc tgccagaaaa catggtgggg ctactgaagg accacgatac    360
atgaacttgc gtttatttta tgccctggat gtaatgcaaa aggtaaacgg ttctgctatt    420
accactataa attggcctgt agatcagaat ttcgaaatac tccaagatcc atctaaagat    480
aagagaatga aggagtattt agaaatgttc ttcgataatc ttttgaaata cggaatagcc    540
ggtataaatt tagcgattag aaattcctct tttcaagctg agcaattagc tgaaagagaa    600
aaatttgtgg aaactatgat aactaaccct gaacaatacg atgtcccgcc cgattcggtc    660
caaattctta atgctgaaag gttcttcaat gaattaggta tatcagaaaa taagagaata    720
atctgtgatg aggttgtttt atatcaagta ggaatgacat acgtcagatc agacccatat    780
actggaatgg ccctttttata taagtatctt tatatacttg ggagcgaacg aaatagatgt    840
cttattttaa agttccctaa tattacaact gatatgtgga aaaaggtggc ttttggaagt    900
agagagcgga aagacgtaag aatctaccga agtgtctcag atggaatatt gtttgcagat    960
ggttatttat caaaagaaga gttgtaa                                        987
```

<210> SEQ ID NO 164
<211> LENGTH: 328
<212> TYPE: PRT
<213> ORGANISM: Bacillus thermoglucosidasius

<400> SEQUENCE: 164

```
Met Gln Ile Glu Gln Leu Met Lys Ser Leu Thr Ile Tyr Phe Asp Asp
1               5                   10                  15

Ile Gln Glu Gly Leu Trp Phe Lys Asn Leu His Pro Leu Leu Glu Ser
            20                  25                  30

Ala Ser Leu Glu Ala Ile Thr Gly Ser Leu Lys Arg Asn Pro Asn Leu
        35                  40                  45

Ala Asp Val Leu Lys Tyr Asp Arg Pro Asp Ile Ile Leu Thr Leu Asn
    50                  55                  60

Gln Thr Pro Ile Leu Val Ile Glu Arg Thr Ile Glu Val Pro Ser Gly
65                  70                  75                  80

His Asn Val Gly Gln Arg Tyr Gly Arg Leu Ala Ala Ala Ser Glu Ala
                85                  90                  95

Gly Val Pro Leu Val Tyr Phe Gly Pro Tyr Ala Ala Arg Lys His Gly
            100                 105                 110

Gly Ala Thr Glu Gly Pro Arg Tyr Met Asn Leu Arg Leu Phe Tyr Ala
        115                 120                 125

Leu Asp Val Met Gln Lys Val Asn Gly Ser Ala Ile Thr Thr Ile Asn
    130                 135                 140

Trp Pro Val Asp Gln Asn Phe Glu Ile Leu Gln Asp Pro Ser Lys Asp
145                 150                 155                 160

Lys Arg Met Lys Glu Tyr Leu Glu Met Phe Phe Asp Asn Leu Leu Lys
```

-continued

```
                165                 170                 175

Tyr Gly Ile Ala Gly Ile Asn Leu Ala Ile Arg Asn Ser Ser Phe Gln
            180                 185                 190

Ala Glu Gln Leu Ala Glu Arg Glu Lys Phe Val Glu Thr Met Ile Thr
        195                 200                 205

Asn Pro Glu Gln Tyr Asp Val Pro Pro Asp Ser Val Gln Ile Leu Asn
    210                 215                 220

Ala Glu Arg Phe Phe Asn Glu Leu Gly Ile Ser Glu Asn Lys Arg Ile
225                 230                 235                 240

Ile Cys Asp Glu Val Val Leu Tyr Gln Val Gly Met Thr Tyr Val Arg
                245                 250                 255

Ser Asp Pro Tyr Thr Gly Met Ala Leu Leu Tyr Lys Tyr Leu Tyr Ile
            260                 265                 270

Leu Gly Ser Glu Arg Asn Arg Cys Leu Ile Leu Lys Phe Pro Asn Ile
        275                 280                 285

Thr Thr Asp Met Trp Lys Lys Val Ala Phe Gly Ser Arg Glu Arg Lys
    290                 295                 300

Asp Val Arg Ile Tyr Arg Ser Val Ser Asp Gly Ile Leu Phe Ala Asp
305                 310                 315                 320

Gly Tyr Leu Ser Lys Glu Glu Leu
                325
```

<210> SEQ ID NO 165
<211> LENGTH: 594
<212> TYPE: DNA
<213> ORGANISM: Escherichia coli

<400> SEQUENCE: 165

```
atgaatattg gtttataccc aaatgatagt agagattggg gagaagacga ttggcatcaa      60

tttttgcaag aattagttaa taataattta gtgtcatatg agcagatcac ttctctcgtt     120

ttggggcatt taaacccatc tcaagttggt acatcaatag cctctaaaaa aacatttcag     180

gcgcattatc ctcctcgtca atgttgggct gctgttcgtt cttggcattt tgagcagtcg     240

gggcgatgca tcgactgtgg aactcgcctt gaattacagg cagatcatgt gcttccgcga     300

gaattactag gtgatgaagc tgatcggctt gataatatgg ctttgagatg tcgaaggtgc     360

aacgttataa gaaggccaag tcatagaaac ggtggaatag ctcatcttac taccgaatca     420

gcactaatgt ggttgctctt tactcgtcag cctacaaatt atcaaacata tcgagatttg     480

tgtcgtgcat atggaatgac tatggcaagt atccgtttcg aagaagcatg ggctatggca     540

agatggctgg aaagagaagg tttgtattat atagacgaaa cttctatttt ttga           594
```

<210> SEQ ID NO 166
<211> LENGTH: 197
<212> TYPE: PRT
<213> ORGANISM: Escherichia coli

<400> SEQUENCE: 166

```
Met Asn Ile Gly Leu Tyr Pro Asn Asp Ser Arg Asp Trp Gly Glu Asp
1               5                   10                  15

Asp Trp His Gln Phe Leu Gln Glu Leu Val Asn Asn Asn Leu Val Ser
            20                  25                  30

Tyr Glu Gln Ile Thr Ser Leu Val Leu Gly His Leu Asn Pro Ser Gln
        35                  40                  45

Val Gly Thr Ser Ile Ala Ser Lys Lys Thr Phe Gln Ala His Tyr Pro
    50                  55                  60
```

-continued

Pro Arg Gln Cys Trp Ala Ala Val Arg Ser Trp His Phe Glu Gln Ser
65 70 75 80

Gly Arg Cys Ile Asp Cys Gly Thr Arg Leu Glu Leu Gln Ala Asp His
85 90 95

Val Leu Pro Arg Glu Leu Leu Gly Asp Glu Ala Asp Arg Leu Asp Asn
100 105 110

Met Ala Leu Arg Cys Arg Arg Cys Asn Val Ile Arg Arg Pro Ser His
115 120 125

Arg Asn Gly Gly Ile Ala His Leu Thr Thr Glu Ser Ala Leu Met Trp
130 135 140

Leu Leu Phe Thr Arg Gln Pro Thr Asn Tyr Gln Thr Tyr Arg Asp Leu
145 150 155 160

Cys Arg Ala Tyr Gly Met Thr Met Ala Ser Ile Arg Phe Glu Glu Ala
165 170 175

Trp Ala Met Ala Arg Trp Leu Glu Arg Glu Gly Leu Tyr Tyr Ile Asp
180 185 190

Glu Thr Ser Ile Phe
195

<210> SEQ ID NO 167
<211> LENGTH: 510
<212> TYPE: DNA
<213> ORGANISM: Fusobacterium nucleatum 4H

<400> SEQUENCE: 167
atgagtgata taaaaaaaat aacagatgtt gagtataaaa tggtaatttc gctttatcct 60
atttggaaag aactaaatag ttctataaaa agcatatatt ctcgtggtgt taattttcat 120
gaagtttttt ctgaatttat tgtatgctat ataaataatt actatcatag tcttgggagt 180
ggttcagaag atgcttatac aagtgatatg aaaaaaaagg ttcaagtaaa agctagttct 240
aattttaata gtgatttaac tagttttggt ccaactagtg aatttgatat tctagaattt 300
gctcgtttaa atcaagaaga aaataaatta tatctatata aaattccaat agataattta 360
tataatataa atgtaaattc taacgaaaca tttaaagaac aacaacaaag tggaagaaga 420
ccaagatttt ctattataga aaaatatata aaagaatata atctaaagca ctatgcagtt 480
gttgatatga taactggtct ttatttttaa 510

<210> SEQ ID NO 168
<211> LENGTH: 169
<212> TYPE: PRT
<213> ORGANISM: Fusobacterium nucleatum 4H

<400> SEQUENCE: 168

Met Ser Asp Ile Lys Lys Ile Thr Asp Val Glu Tyr Lys Met Val Ile
1 5 10 15

Ser Leu Tyr Pro Ile Trp Lys Glu Leu Asn Ser Ser Ile Lys Ser Ile
20 25 30

Tyr Ser Arg Gly Val Asn Phe His Glu Val Phe Ser Glu Phe Ile Val
35 40 45

Cys Tyr Ile Asn Asn Tyr Tyr His Ser Leu Gly Ser Gly Ser Glu Asp
50 55 60

Ala Tyr Thr Ser Asp Met Lys Lys Lys Val Gln Val Lys Ala Ser Ser
65 70 75 80

Asn Phe Asn Ser Asp Leu Thr Ser Phe Gly Pro Thr Ser Glu Phe Asp
85 90 95

Ile Leu Glu Phe Ala Arg Leu Asn Gln Glu Glu Asn Lys Leu Tyr Leu

```
            100                 105                 110

Tyr Lys Ile Pro Ile Asp Asn Leu Tyr Asn Ile Asn Val Asn Ser Asn
        115                 120                 125

Glu Thr Phe Lys Glu Gln Gln Gln Ser Gly Arg Arg Pro Arg Phe Ser
    130                 135                 140

Ile Ile Glu Lys Tyr Ile Lys Glu Tyr Asn Leu Lys His Tyr Ala Val
145                 150                 155                 160

Val Asp Met Ile Thr Gly Leu Tyr Phe
                165
```

<210> SEQ ID NO 169
<211> LENGTH: 858
<212> TYPE: DNA
<213> ORGANISM: Kluyvera ascorbata

<400> SEQUENCE: 169

```
atgagcgtta ttccgtgtaa aaaggacctt cagctaaaaa aattgattga atcctatgca      60

gaagccttga aagttgaggc ccataagcta ggagagcatg gattaactga agctgaattt     120

tatgatagcg gcctctttcg gggggctatc gagcgaattc gaggacagtt ctccgcgacc     180

atgcgggaga aaagaaattt cgttaagcat gttttaaatt acatgcagga taacgactac     240

attgctgatt gggagtcggc tggtgaatcg aatcgccatg attatatggt aactctcaat     300

tctgggcgca aagctgctat tgagctgaaa gggtgccttg atggcaataa cactaacatc     360

tttgatcgcc cccctcaggc agaagaattt gttatctgga gtgtatgcac aaatcctggt     420

gctgaccctc agcataatgt ttggtctggg cttcacacca gactaagtgc tgaaatcatt     480

tcacgggagc aaaggattga tggaatggtc atttgggact gggcttgtgg aacagtcgga     540

aggccatgcc ccaaaatagc aactgaacct gagcgggctg taacatttgg gccgttcaaa     600

ttgccgccac catgtttgta tcttttacct tcgacgattc caagcccaag aaacaacccg     660

tctccaagag ctcagcagat tgaagacgtg cagctaatca aagcgtttca cgattgtttt     720

gggtgccggt ctgaagaagt taatttcgtt aactttgatg ttggttatca tggtaaagat     780

accgtccgta aaacgactat cattcgaaac ggcatggtgg agcgtgaatc ggaaatgacg     840

gcaataaggc ggtcttaa                                                    858
```

<210> SEQ ID NO 170
<211> LENGTH: 285
<212> TYPE: PRT
<213> ORGANISM: Kluyvera ascorbata

<400> SEQUENCE: 170

```
Met Ser Val Ile Pro Cys Lys Lys Asp Leu Gln Leu Lys Lys Leu Ile
1               5                   10                  15

Glu Ser Tyr Ala Glu Ala Leu Lys Val Glu Ala His Lys Leu Gly Glu
            20                  25                  30

His Gly Leu Thr Glu Ala Glu Phe Tyr Asp Ser Gly Leu Phe Arg Gly
        35                  40                  45

Ala Ile Glu Arg Ile Arg Gly Gln Phe Ser Ala Thr Met Arg Glu Lys
    50                  55                  60

Arg Asn Phe Val Lys His Val Leu Asn Tyr Met Gln Asp Asn Asp Tyr
65                  70                  75                  80

Ile Ala Asp Trp Glu Ser Ala Gly Glu Ser Asn Arg His Asp Tyr Met
                85                  90                  95

Val Thr Leu Asn Ser Gly Arg Lys Ala Ala Ile Glu Leu Lys Gly Cys
            100                 105                 110
```

```
Leu Asp Gly Asn Asn Thr Asn Ile Phe Asp Arg Pro Pro Gln Ala Glu
        115                 120                 125

Glu Phe Val Ile Trp Ser Val Cys Thr Asn Pro Gly Ala Asp Pro Gln
    130                 135                 140

His Asn Val Trp Ser Gly Leu His Thr Arg Leu Ser Ala Glu Ile Ile
145                 150                 155                 160

Ser Arg Glu Gln Arg Ile Asp Gly Met Val Ile Trp Asp Trp Ala Cys
                165                 170                 175

Gly Thr Val Gly Arg Pro Cys Pro Lys Ile Ala Thr Glu Pro Glu Arg
            180                 185                 190

Ala Val Thr Phe Gly Pro Phe Lys Leu Pro Pro Pro Cys Leu Tyr Leu
        195                 200                 205

Leu Pro Ser Thr Ile Pro Ser Pro Arg Asn Asn Pro Ser Pro Arg Ala
    210                 215                 220

Gln Gln Ile Glu Asp Val Gln Leu Ile Lys Ala Phe His Asp Cys Phe
225                 230                 235                 240

Gly Cys Arg Ser Glu Glu Val Asn Phe Val Asn Phe Asp Val Gly Tyr
                245                 250                 255

His Gly Lys Asp Thr Val Arg Lys Thr Thr Ile Ile Arg Asn Gly Met
            260                 265                 270

Val Glu Arg Glu Ser Glu Met Thr Ala Ile Arg Arg Ser
        275                 280                 285
```

<210> SEQ ID NO 171
<211> LENGTH: 1023
<212> TYPE: DNA
<213> ORGANISM: Methylococcus capsulatus str. Bath

<400> SEQUENCE: 171

```
atgacaaaag aagaatttga aagctatttg gacgacatcg cctctaagct cagggacgaa     60

gccagaaaga cgccatttgc cgcagccaag cagttcgagc aacgtgttcg ggaaatcacc    120

aaggaaacga tccaagctcc cgggatcgag atcgatttca acccacaccc tcaagcattc    180

cccgacatag aaatcggtca gttcggaatt gaggtgaaat tcacgacaaa cgacgaatgg    240

aggagcgtcg ccaacagcgt gctggaaacc aaccgtatcg aatccgtgca gcacgtgtac    300

atcatgttcg gaaagatggg tggcaatccg gacgtgagat ggggtgaata cgagaaatgc    360

gtcatgcatg tcagaacatc ccacgtccct cgcttcgagg tgcagatcga tgccactcga    420

tccttattcg agatcatggg catttcttac gatcaattcc gggtgctcga aatgcacgag    480

aagatgcagt acatccggaa atacgcaaga agcaggctga agaacggaga acgcttatgg    540

tggctggaag attcgcccgg cgaagcccat accttgccta tgcaagctcg actattcact    600

gagctagagc agtccgagaa gattcgactt cgcgccgaag caatcctact ttgtcctcaa    660

atcgttcaat ctggcagagc ccggcataag tacgatgacg tcgcgttatt catgctgacc    720

tatcacggcg tgatctgcca tcagaccaga gatatgttct ctgccggtag cgttggaaac    780

ccggagaatg acgataacgg cggactctac atcgcgcgca tgctcaagct gatggaagcc    840

gagttggaga aggcagcggc gcgcatggat gccgcgctgt ttgaggaata ttggggcgtg    900

gctgtcccac ctgaggaaag aatagcggaa tggctgcgtc gcgcagacaa gttcgcgtcg    960

ggaatttgga agccatctga agagttgttc gatggtagat acgctcagcc aagaggagcg   1020

tag                                                                 1023
```

<210> SEQ ID NO 172

<211> LENGTH: 340
<212> TYPE: PRT
<213> ORGANISM: Methylococcus capsulatus str. Bath

<400> SEQUENCE: 172

Met Thr Lys Glu Glu Phe Glu Ser Tyr Leu Asp Asp Ile Ala Ser Lys
1 5 10 15

Leu Arg Asp Glu Ala Arg Lys Thr Pro Phe Ala Ala Ala Lys Gln Phe
20 25 30

Glu Gln Arg Val Arg Glu Ile Thr Lys Glu Thr Ile Gln Ala Pro Gly
35 40 45

Ile Glu Ile Asp Phe Asn Pro His Pro Gln Ala Phe Pro Asp Ile Glu
50 55 60

Ile Gly Gln Phe Gly Ile Glu Val Lys Phe Thr Thr Asn Asp Glu Trp
65 70 75 80

Arg Ser Val Ala Asn Ser Val Leu Glu Thr Asn Arg Ile Glu Ser Val
85 90 95

Gln His Val Tyr Ile Met Phe Gly Lys Met Gly Gly Asn Pro Asp Val
100 105 110

Arg Trp Gly Glu Tyr Glu Lys Cys Val Met His Val Arg Thr Ser His
115 120 125

Val Pro Arg Phe Glu Val Gln Ile Asp Ala Thr Arg Ser Leu Phe Glu
130 135 140

Ile Met Gly Ile Ser Tyr Asp Gln Phe Arg Val Leu Glu Met His Glu
145 150 155 160

Lys Met Gln Tyr Ile Arg Lys Tyr Ala Arg Ser Arg Leu Lys Asn Gly
165 170 175

Glu Arg Leu Trp Trp Leu Glu Asp Ser Pro Gly Glu Ala His Thr Leu
180 185 190

Pro Met Gln Ala Arg Leu Phe Thr Glu Leu Glu Gln Ser Glu Lys Ile
195 200 205

Arg Leu Arg Ala Glu Ala Ile Leu Leu Cys Pro Gln Ile Val Gln Ser
210 215 220

Gly Arg Ala Arg His Lys Tyr Asp Asp Val Ala Leu Phe Met Leu Thr
225 230 235 240

Tyr His Gly Val Ile Cys His Gln Thr Arg Asp Met Phe Ser Ala Gly
245 250 255

Ser Val Gly Asn Pro Glu Asn Asp Asp Asn Gly Gly Leu Tyr Ile Ala
260 265 270

Arg Met Leu Lys Leu Met Glu Ala Glu Leu Glu Lys Ala Ala Ala Arg
275 280 285

Met Asp Ala Ala Leu Phe Glu Glu Tyr Trp Gly Val Ala Val Pro Pro
290 295 300

Glu Glu Arg Ile Ala Glu Trp Leu Arg Arg Ala Asp Lys Phe Ala Ser
305 310 315 320

Gly Ile Trp Lys Pro Ser Glu Glu Leu Phe Asp Gly Arg Tyr Ala Gln
325 330 335

Pro Arg Gly Ala
340

<210> SEQ ID NO 173
<211> LENGTH: 1542
<212> TYPE: DNA
<213> ORGANISM: Neisseria cinerea

<400> SEQUENCE: 173

```
atgaaaataa ataaatttaa tttagaaaaa attttaaata aatttatatg cggtgattct     60

ttgcaaaaaa tgaaaaaatt acctagtaaa tcaatcgatt taatttttac ttcccctcct    120

tataatttaa aaaattcaac tggtaatgga atgaaagatg gtagaggcgg aaaatggtca    180

aatgccagat taattgaagg gtatgacaac catgatgatt gtatgccaca tgatgagtat    240

gtgaaatggc aacgtaaatg tttaaaagaa atgcttcgtc tgataaaaga tgatggtgct    300

atttttata atcataaatg gagagtacaa aatggtctat tacaagatag agcagacatt    360

gtaaaaggct ttcctgttcg ccaaattatt atttggaaaa gaaagggagg aattaatttt    420

aatcctggat attttttgcc aacttatgaa gtaatttatt taatttgcaa gaaacctttt    480

aaattggcaa aaggtgcaaa ttcatttgga gatatttggg aattcacgca agatatgaat    540

aatgaacatc ctgcaccatt tcctttagaa ttagctaagc gagttgtaca aagtacaaat    600

gctcaaatag tgcttgatcc atttatggga agtggaacaa ctgctattgc agcagcacta    660

ttagacagaa agtttattgg cattgaactt tcatctgaat atgtcaagat atctaaaaaa    720

agatataaca atatttttgg taatttattt ggagtagata tgaaaacttt tacaaaagaa    780

tctttaattc aagagctaaa ggaaattaaa aataaaggtc cggttcttaa taacagagga    840

agtaacaatg gggcttccgg gaatgtttta gaagatttgc tgggaattga agaaaataat    900

ctccctttag caaatgctgc agaatgggaa ataaaaacca aaaaaagatc atccaattca    960

ctggtaacac tatttcatgt tgaaccctct ccaaccgcat gtaaatttgt cccaaatata   1020

ttattaccta aatacggatg gaaacataaa gaggctggaa aaaaatatcc tgacactgaa   1080

aaaagtttta gacaaactat taagtgtggt ttattttctg atagaggatt ttctataaaa   1140

cttaatgata gcgaagaaaa aattgaagta aattttagat atgatctaat agatcaaaag   1200

cataatgaat ggaagcagga tatttctacc tttcagacat tggatacaat accatactgg   1260

ggatttaatg atatatatca taaacttggt gcaaaattgc ataactgttt ttttgcgata   1320

gtagatgttt gtaaaagagg agatgatgaa tattttacct atagtgaaat ttatatgctc   1380

cgtaatttat cgaaagataa atttatatct gcaatccgag atggaaagat atatatagat   1440

tttgatgcta gaacaggaca taatcatgga acaaaattta ggataaaaga aaaagatatt   1500

tttgacctct atgaagaatg catcgaaata tcaaacttat ag                      1542
```

<210> SEQ ID NO 174
<211> LENGTH: 513
<212> TYPE: PRT
<213> ORGANISM: Neisseria cinerea

<400> SEQUENCE: 174

```
Met Lys Ile Asn Lys Phe Asn Leu Glu Lys Ile Leu Asn Lys Phe Ile
1               5                   10                  15

Cys Gly Asp Ser Leu Gln Lys Met Lys Lys Leu Pro Ser Lys Ser Ile
            20                  25                  30

Asp Leu Ile Phe Thr Ser Pro Pro Tyr Asn Leu Lys Asn Ser Thr Gly
        35                  40                  45

Asn Gly Met Lys Asp Gly Arg Gly Gly Lys Trp Ser Asn Ala Arg Leu
    50                  55                  60

Ile Glu Gly Tyr Asp Asn His Asp Asp Cys Met Pro His Asp Glu Tyr
65                  70                  75                  80

Val Lys Trp Gln Arg Lys Cys Leu Lys Glu Met Leu Arg Leu Ile Lys
                85                  90                  95

Asp Asp Gly Ala Ile Phe Tyr Asn His Lys Trp Arg Val Gln Asn Gly
            100                 105                 110
```

```
Leu Leu Gln Asp Arg Ala Asp Ile Val Lys Gly Phe Pro Val Arg Gln
        115                 120                 125

Ile Ile Ile Trp Lys Arg Lys Gly Gly Ile Asn Phe Asn Pro Gly Tyr
    130                 135                 140

Phe Leu Pro Thr Tyr Glu Val Ile Tyr Leu Ile Cys Lys Lys Pro Phe
145                 150                 155                 160

Lys Leu Ala Lys Gly Ala Asn Ser Phe Gly Asp Ile Trp Glu Phe Thr
                165                 170                 175

Gln Asp Met Asn Asn Glu His Pro Ala Pro Phe Pro Leu Glu Leu Ala
            180                 185                 190

Lys Arg Val Val Gln Ser Thr Asn Ala Gln Ile Val Leu Asp Pro Phe
        195                 200                 205

Met Gly Ser Gly Thr Thr Ala Ile Ala Ala Ala Leu Leu Asp Arg Lys
    210                 215                 220

Phe Ile Gly Ile Glu Leu Ser Ser Glu Tyr Val Lys Ile Ser Lys Lys
225                 230                 235                 240

Arg Tyr Asn Asn Ile Phe Gly Asn Leu Phe Gly Val Asp Met Lys Thr
                245                 250                 255

Phe Thr Lys Glu Ser Leu Ile Gln Glu Leu Lys Glu Ile Lys Asn Lys
            260                 265                 270

Gly Pro Val Leu Asn Asn Arg Gly Ser Asn Asn Gly Ala Ser Gly Asn
        275                 280                 285

Val Leu Glu Asp Leu Leu Gly Ile Glu Glu Asn Asn Leu Pro Leu Ala
    290                 295                 300

Asn Ala Ala Glu Trp Glu Ile Lys Thr Lys Lys Arg Ser Ser Asn Ser
305                 310                 315                 320

Leu Val Thr Leu Phe His Val Glu Pro Ser Pro Thr Ala Cys Lys Phe
                325                 330                 335

Val Pro Asn Ile Leu Leu Pro Lys Tyr Gly Trp Lys His Lys Glu Ala
            340                 345                 350

Gly Lys Lys Tyr Pro Asp Thr Glu Lys Ser Phe Arg Gln Thr Ile Lys
        355                 360                 365

Cys Gly Leu Phe Ser Asp Arg Gly Phe Ser Ile Lys Leu Asn Asp Ser
    370                 375                 380

Glu Glu Lys Ile Glu Val Asn Phe Arg Tyr Asp Leu Ile Asp Gln Lys
385                 390                 395                 400

His Asn Glu Trp Lys Gln Asp Ile Ser Thr Phe Gln Thr Leu Asp Thr
                405                 410                 415

Ile Pro Tyr Trp Gly Phe Asn Asp Ile Tyr His Lys Leu Gly Ala Lys
            420                 425                 430

Leu His Asn Cys Phe Phe Ala Ile Val Asp Val Cys Lys Arg Gly Asp
        435                 440                 445

Asp Glu Tyr Phe Thr Tyr Ser Glu Ile Tyr Met Leu Arg Asn Leu Ser
    450                 455                 460

Lys Asp Lys Phe Ile Ser Ala Ile Arg Asp Gly Lys Ile Tyr Ile Asp
465                 470                 475                 480

Phe Asp Ala Arg Thr Gly His Asn His Gly Thr Lys Phe Arg Ile Lys
                485                 490                 495

Glu Lys Asp Ile Phe Asp Leu Tyr Glu Glu Cys Ile Glu Ile Ser Asn
            500                 505                 510

Leu
```

<210> SEQ ID NO 175

<211> LENGTH: 660
<212> TYPE: DNA
<213> ORGANISM: Nocardia rubra

<400> SEQUENCE: 175
atgggatttc ttgaagactg ggacctcagc tacgacgaga tcaacgagct tctcactgac 60
aaccccagcc ttcgatcgtt cgtgatgggg tacgcagcgg agatcaagtg tcgcaacatg 120
ttcttcgttg atcatccaca tatcaccaac atttacaagc ccgatgatca cgatcgcact 180
gaaaagggcg actggatcat caactacaag ggacaccgga tcggggtcga ggtcaagagt 240
ctccagacga actcactgcg gcttcgccga gatggcagtg tccgaccaaa ctaccagtgc 300
gacgcttcgg atgcccgcac cgtgatcttc gctgacggta gcgaagttca tacgaccgct 360
ctgttggtcg gagaatttga cgtagttgca gtcaatatcc atgcgttcga aaataagtgg 420
gattttgcgt tcgctaagaa cgaggatctc atcacgatgg agggtgcgac caggggcgca 480
gcgaaagact acaccgaact ccagaaacgc aatctcatca agactctcca accgatgcct 540
atggacgtgc cagccccgta cactcgagat cccttcaaac tcttcgacga gatcatcgaa 600
gagcgcatga agggtgagca gcctcagctc aaggcgaaga tcatcgaaga cgaagagtga 660

<210> SEQ ID NO 176
<211> LENGTH: 219
<212> TYPE: PRT
<213> ORGANISM: Nocardia rubra

<400> SEQUENCE: 176

Met Gly Phe Leu Glu Asp Trp Asp Leu Ser Tyr Asp Glu Ile Asn Glu
1               5                   10                  15

Leu Leu Thr Asp Asn Pro Ser Leu Arg Ser Phe Val Met Gly Tyr Ala
            20                  25                  30

Ala Glu Ile Lys Cys Arg Asn Met Phe Phe Val Asp His Pro His Ile
        35                  40                  45

Thr Asn Ile Tyr Lys Pro Asp Asp His Asp Arg Thr Glu Lys Gly Asp
    50                  55                  60

Trp Ile Ile Asn Tyr Lys Gly His Arg Ile Gly Val Glu Val Lys Ser
65                  70                  75                  80

Leu Gln Thr Asn Ser Leu Arg Leu Arg Arg Asp Gly Ser Val Arg Pro
                85                  90                  95

Asn Tyr Gln Cys Asp Ala Ser Asp Ala Arg Thr Val Ile Phe Ala Asp
            100                 105                 110

Gly Ser Glu Val His Thr Thr Ala Leu Leu Val Gly Glu Phe Asp Val
        115                 120                 125

Val Ala Val Asn Ile His Ala Phe Glu Asn Lys Trp Asp Phe Ala Phe
    130                 135                 140

Ala Lys Asn Glu Asp Leu Ile Thr Met Glu Gly Ala Thr Arg Gly Ala
145                 150                 155                 160

Ala Lys Asp Tyr Thr Glu Leu Gln Lys Arg Asn Leu Ile Lys Thr Leu
                165                 170                 175

Gln Pro Met Pro Met Asp Val Pro Ala Pro Tyr Thr Arg Asp Pro Phe
            180                 185                 190

Lys Leu Phe Asp Glu Ile Ile Glu Glu Arg Met Lys Gly Glu Gln Pro
        195                 200                 205

Gln Leu Lys Ala Lys Ile Ile Glu Asp Glu Glu
    210                 215

<210> SEQ ID NO 177

<211> LENGTH: 675
<212> TYPE: DNA
<213> ORGANISM: Shigella boydii 13

<400> SEQUENCE: 177
atgagagaac cctcgattct agaaagatgg gaaataagcg aagaaaaatt aactgacttg 60
gttgataaaa acccctctct tagaggaatg attttaggtt atgttgctga ggataaattt 120
cacgagctat tccttgaaga tgaaagagta aaggaggttt ctaaagacga cgatcatgac 180
agaaagaaaa aaggagatag aacctttatt tacaaaggta aaaaatttac agttgaagtt 240
aaaagcttgc aaaccgcaat gtgcaagaaa aatgaagacg gaacttattc aggaaaagcc 300
caagtagacg gcagtgatcg aagaatagta aaattcccag acaattcaga attaaatacg 360
acgttactct tgaaaggaga gtttgatcta ttagccgtta attgctttgc ttttggtgaa 420
ggatggaaat ttgcttttgc aaaaaattct gaccttccca cctcaacatt caaaaaatac 480
acagaagaac aaaggaaaca acttattgcc tcactgattc ctgtaacttg gccaccaaag 540
ccaccattca gtgatgaccc attccacctt ctggacgaga tgattgcagc gccagaagag 600
gaaccggtga tagaagaaag tagtgaatta aaagaagtaa aagaagatat agatgtagtt 660
aaagtgaaat cataa 675

<210> SEQ ID NO 178
<211> LENGTH: 224
<212> TYPE: PRT
<213> ORGANISM: Shigella boydii 13

<400> SEQUENCE: 178

Met Arg Glu Pro Ser Ile Leu Glu Arg Trp Glu Ile Ser Glu Glu Lys
1               5                   10                  15

Leu Thr Asp Leu Val Asp Lys Asn Pro Ser Leu Arg Gly Met Ile Leu
            20                  25                  30

Gly Tyr Val Ala Glu Asp Lys Phe His Glu Leu Phe Leu Glu Asp Glu
        35                  40                  45

Arg Val Lys Glu Val Ser Lys Asp Asp Asp His Asp Arg Lys Lys Lys
    50                  55                  60

Gly Asp Arg Thr Phe Ile Tyr Lys Gly Lys Lys Phe Thr Val Glu Val
65                  70                  75                  80

Lys Ser Leu Gln Thr Ala Met Cys Lys Lys Asn Glu Asp Gly Thr Tyr
                85                  90                  95

Ser Gly Lys Ala Gln Val Asp Gly Ser Asp Arg Arg Ile Val Lys Phe
            100                 105                 110

Pro Asp Asn Ser Glu Leu Asn Thr Thr Leu Leu Leu Lys Gly Glu Phe
        115                 120                 125

Asp Leu Leu Ala Val Asn Cys Phe Ala Phe Gly Glu Gly Trp Lys Phe
    130                 135                 140

Ala Phe Ala Lys Asn Ser Asp Leu Pro Thr Ser Thr Phe Lys Lys Tyr
145                 150                 155                 160

Thr Glu Glu Gln Arg Lys Gln Leu Ile Ala Ser Leu Ile Pro Val Thr
                165                 170                 175

Trp Pro Pro Lys Pro Pro Phe Ser Asp Asp Pro Phe His Leu Leu Asp
            180                 185                 190

Glu Met Ile Ala Ala Pro Glu Glu Glu Pro Val Ile Glu Glu Ser Ser
        195                 200                 205

Glu Leu Lys Glu Val Lys Glu Asp Ile Asp Val Val Lys Val Lys Ser
    210                 215                 220

<210> SEQ ID NO 179
<211> LENGTH: 825
<212> TYPE: DNA
<213> ORGANISM: Streptococcus faecium

<400> SEQUENCE: 179
atgaattact ctatcaatga acaattatta agatttaaat ttttaattga agattcaata 60
aaagaaggtg gtacaatagg aaaaacttct atgattagat cttcaaaaat gattaacctc 120
attcatgatg ctacaaagca agaattgata tgtaacggtg ttaaccccga taatatccgt 180
ccaccgcttg gacattcaaa acctgaatta aaaattgctg gcatacttaa acagaaagac 240
caagatgttt gtgttattcc aaccggcata taccccaccc caacccctat tacttgggga 300
cctctggctt ttaataaaaa aatcgatcct tacggttttg aatttagtga aaaaacttta 360
atcatcaatg ttcgtagcca aatgagtagc ttagccaaaa atgcagacac tttgtttgaa 420
agaacctttg cagaagcaca aaatttgcac ttaagatatc ctaatgccgt tttaggagag 480
gtatatctaa ttccagttaa tgaatatgat gatgctcttg tatctaaaca tcaagtaggt 540
tttaaaactc gtcagactga tttagaaaaa tacattagct tctttactga aatcaataat 600
cgttctattg gtgaacctcc acattcttat gagcggtgtg cattattgat cgttgatttt 660
aatcaacctc aacctcttct attttcgaat agtgatgaat taaaagctgc tggttacatc 720
tcttctgatt ttgatattga atatgcaaat attaattttc aaaattttgc ctcagatatt 780
ttaagcatct atgatcagcg ttttgacatc aattatctaa tataa 825

<210> SEQ ID NO 180
<211> LENGTH: 274
<212> TYPE: PRT
<213> ORGANISM: Streptococcus faecium

<400> SEQUENCE: 180

Met Asn Tyr Ser Ile Asn Glu Gln Leu Leu Arg Phe Lys Phe Leu Ile
1 5 10 15

Glu Asp Ser Ile Lys Glu Gly Gly Thr Ile Gly Lys Thr Ser Met Ile
20 25 30

Arg Ser Ser Lys Met Ile Asn Leu Ile His Asp Ala Thr Lys Gln Glu
35 40 45

Leu Ile Cys Asn Gly Val Asn Pro Asp Asn Ile Arg Pro Pro Leu Gly
50 55 60

His Ser Lys Pro Glu Leu Lys Ile Ala Gly Ile Leu Lys Gln Lys Asp
65 70 75 80

Gln Asp Val Cys Val Ile Pro Thr Gly Ile Tyr Pro Thr Pro Thr Pro
85 90 95

Ile Thr Trp Gly Pro Leu Ala Phe Asn Lys Lys Ile Asp Pro Tyr Gly
100 105 110

Phe Glu Phe Ser Glu Lys Thr Leu Ile Ile Asn Val Arg Ser Gln Met
115 120 125

Ser Ser Leu Ala Lys Asn Ala Asp Thr Leu Phe Glu Arg Thr Phe Ala
130 135 140

Glu Ala Gln Asn Leu His Leu Arg Tyr Pro Asn Ala Val Leu Gly Glu
145 150 155 160

Val Tyr Leu Ile Pro Val Asn Glu Tyr Asp Asp Ala Leu Val Ser Lys
165 170 175

His Gln Val Gly Phe Lys Thr Arg Gln Thr Asp Leu Glu Lys Tyr Ile
180 185 190

```
Ser Phe Phe Thr Glu Ile Asn Asn Arg Ser Ile Gly Glu Pro Pro His
        195                 200                 205

Ser Tyr Glu Arg Cys Ala Leu Leu Ile Val Asp Phe Asn Gln Pro Gln
    210                 215                 220

Pro Leu Leu Phe Ser Asn Ser Asp Glu Leu Lys Ala Ala Gly Tyr Ile
225                 230                 235                 240

Ser Ser Asp Phe Asp Ile Glu Tyr Ala Asn Ile Asn Phe Gln Asn Phe
                245                 250                 255

Ala Ser Asp Ile Leu Ser Ile Tyr Asp Gln Arg Phe Asp Ile Asn Tyr
            260                 265                 270

Leu Ile


<210> SEQ ID NO 181
<211> LENGTH: 768
<212> TYPE: DNA
<213> ORGANISM: Streptomyces tubercidicus

<400> SEQUENCE: 181

gtgtcagtga gtgcggtcga acaggtattt ttggaatgcg agcgcgctcg ggcagacggt      60

gacttgattc agcgggtctc cgccagtgat aaggagtacc actttcagaa ttgggtgcag     120

gcccgcatag aggcatgcag gctttcgtac gatgatcctg gccggaacac ctatccggac     180

ttccggctca tccatcaccc ggaagggtat gaggtcaagg gcctggagtt tcccggccgc     240

gaggcggact acgactcaaa ctcccaggtg cccaccggta accacggcgg ccgtgaggtc     300

ttctacgtgt tcggtcgcta cccgaaggca gagcgcggcg tcgatgagta tccagttgta     360

gatctggtgg tgtgccacgg cagcttcctc aatgccgata gtgagtacgt tcataagaac     420

aagtcgttcc gtggctttgg ctcgtacgga gacatcctgg tccgcgaccg caaaatgtac     480

gtcgtgccaa cgccgttcgc actagcttcc ggaaccgcag ggctcgcgac cctgatcgtg     540

cctactgaat tcgagccaca gtcggatact ctcgttcagg tgggtgaact tgatcggacc     600

gaggttgacg aggtcatcgt gtcgtacgag ttcaaccttc agacaaatga gatggtgacg     660

cataaggcgc cgaatctcaa tgcaggtaag gtccacagtt tccgagcata tcgctcgcgc     720

ggtgcgggcg attctaagcc ggtttccctc gcagggggtc ggctgtga                  768


<210> SEQ ID NO 182
<211> LENGTH: 255
<212> TYPE: PRT
<213> ORGANISM: Streptomyces tubercidicus

<400> SEQUENCE: 182

Met Ser Val Ser Ala Val Glu Gln Val Phe Leu Glu Cys Glu Arg Ala
1               5                   10                  15

Arg Ala Asp Gly Asp Leu Ile Gln Arg Val Ser Ala Ser Asp Lys Glu
            20                  25                  30

Tyr His Phe Gln Asn Trp Val Gln Ala Arg Ile Glu Ala Cys Arg Leu
        35                  40                  45

Ser Tyr Asp Asp Pro Gly Arg Asn Thr Tyr Pro Asp Phe Arg Leu Ile
    50                  55                  60

His His Pro Glu Gly Tyr Glu Val Lys Gly Leu Glu Phe Pro Gly Arg
65                  70                  75                  80

Glu Ala Asp Tyr Asp Ser Asn Ser Gln Val Pro Thr Gly Asn His Gly
                85                  90                  95

Gly Arg Glu Val Phe Tyr Val Phe Gly Arg Tyr Pro Lys Ala Glu Arg
            100                 105                 110
```

```
Gly Val Asp Glu Tyr Pro Val Val Asp Leu Val Val Cys His Gly Ser
        115                 120                 125

Phe Leu Asn Ala Asp Ser Glu Tyr Val His Lys Asn Lys Ser Phe Arg
    130                 135                 140

Gly Phe Gly Ser Tyr Gly Asp Ile Leu Val Arg Asp Arg Lys Met Tyr
145                 150                 155                 160

Val Val Pro Thr Pro Phe Ala Leu Ala Ser Gly Thr Ala Gly Leu Ala
                165                 170                 175

Thr Leu Ile Val Pro Thr Glu Phe Glu Pro Gln Ser Asp Thr Leu Val
            180                 185                 190

Gln Val Gly Glu Leu Asp Arg Thr Glu Val Asp Glu Val Ile Val Ser
        195                 200                 205

Tyr Glu Phe Asn Leu Gln Thr Asn Glu Met Val Thr His Lys Ala Pro
    210                 215                 220

Asn Leu Asn Ala Gly Lys Val His Ser Phe Arg Ala Tyr Arg Ser Arg
225                 230                 235                 240

Gly Ala Gly Asp Ser Lys Pro Val Ser Leu Ala Gly Gly Arg Leu
                245                 250                 255
```

<210> SEQ ID NO 183
<211> LENGTH: 1161
<212> TYPE: DNA
<213> ORGANISM: Salmonella typhi 27

<400> SEQUENCE: 183

```
ttgtttttaa ctgtcatttt tcctaactat cgatctgtta ccatacaacc tgctatctta     60

gcatctcatt tttactatgt ccatggtgag gatatgaatt tcaaggataa aaattgtttc    120

cctaacgaac tcatagcgtt ggcgaaaatt tcaaaaaatg atgttttaga taagttcgga    180

acggatgttt ttaaaaaggt tgtttatgat gttttaacag gtaaaaatgt tcgcgaattc    240

actgaaatac taactcgtac tagattgtta gaaagcaatc tctctttttt tgactttttt    300

gtggataaaa tgaaagaggg gataacgcca aagcagcttt atctctatgc aaaaaatgca    360

ttatcgaaca agtcttatgt taagtataat caacctgttc tcgagtggat ggttatgatg    420

acaaataaac agacccaaaa tgttttaaga gatgagcatg gggatggttt tgataggctt    480

gctttaagga cgcaagaaga aatacttaaa ataaaaaacg ggtatgaaga taaaattgga    540

gagatatcta ttggtgggca aaaggtgtct ttagaagatt tttgctatat tattttatct    600

cttggttcgc aaactttaac tattagggga tctgagaaat ctcttcatgg taaatatttt    660

gaaaagctaa tactcggttc tttatttaca ataatgggtt ttgaatataa agaaaaaatt    720

gaagaagggt taaatgctaa atgttttact ctttcaacaa gagctgatga cagggagtct    780

gatgctactc ttatttttaa tgggaaggcg attagggttg atattggttt tattggtagg    840

ggtaacacag aaataagttt ggataaagta tctagattta gacgaatgga tgatattggc    900

ggagtgatgc ataatataag cacaatggtt attgttgacg ttattggtga tagaagtaga    960

atagttaata tggctgaaga gattgatggt aaagttgttg cgatgagtga cccgtattgg   1020

gttgcaaagg tctcttccta tattagttcg aaactgaatg tagatgatct tttagaggat   1080

aaacctcaac ttaaatacat acagtctttt atatctgatg cattagagaa tgtagatctg   1140

gaaaaataca ttaaattata a                                             1161
```

<210> SEQ ID NO 184
<211> LENGTH: 386
<212> TYPE: PRT
<213> ORGANISM: Salmonella typhi 27

-continued

<400> SEQUENCE: 184

```
Met Phe Leu Thr Val Ile Phe Pro Asn Tyr Arg Ser Val Thr Ile Gln
1               5                   10                  15

Pro Ala Ile Leu Ala Ser His Phe Tyr Tyr Val His Gly Glu Asp Met
            20                  25                  30

Asn Phe Lys Asp Lys Asn Cys Phe Pro Asn Glu Leu Ile Ala Leu Ala
        35                  40                  45

Lys Ile Ser Lys Asn Asp Val Leu Asp Lys Phe Gly Thr Asp Val Phe
    50                  55                  60

Lys Lys Val Val Tyr Asp Val Leu Thr Gly Lys Asn Val Arg Glu Phe
65                  70                  75                  80

Thr Glu Ile Leu Thr Arg Thr Arg Leu Leu Glu Ser Asn Leu Ser Phe
                85                  90                  95

Phe Asp Phe Phe Val Asp Lys Met Lys Glu Gly Ile Thr Pro Lys Gln
            100                 105                 110

Leu Tyr Leu Tyr Ala Lys Asn Ala Leu Ser Asn Lys Ser Tyr Val Lys
        115                 120                 125

Tyr Asn Gln Pro Val Leu Glu Trp Met Val Met Met Thr Asn Lys Gln
    130                 135                 140

Thr Gln Asn Val Leu Arg Asp Glu His Gly Asp Gly Phe Asp Arg Leu
145                 150                 155                 160

Ala Leu Arg Thr Gln Glu Glu Ile Leu Lys Ile Lys Asn Gly Tyr Glu
                165                 170                 175

Asp Lys Ile Gly Glu Ile Ser Ile Gly Gly Gln Lys Val Ser Leu Glu
            180                 185                 190

Asp Phe Cys Tyr Ile Ile Leu Ser Leu Gly Ser Gln Thr Leu Thr Ile
        195                 200                 205

Arg Gly Ser Glu Lys Ser Leu His Gly Lys Tyr Phe Glu Lys Leu Ile
    210                 215                 220

Leu Gly Ser Leu Phe Thr Ile Met Gly Phe Glu Tyr Lys Glu Lys Ile
225                 230                 235                 240

Glu Glu Gly Leu Asn Ala Lys Cys Phe Thr Leu Ser Thr Arg Ala Asp
                245                 250                 255

Asp Arg Glu Ser Asp Ala Thr Leu Ile Phe Asn Gly Lys Ala Ile Arg
            260                 265                 270

Val Asp Ile Gly Phe Ile Gly Arg Gly Asn Thr Glu Ile Ser Leu Asp
        275                 280                 285

Lys Val Ser Arg Phe Arg Arg Met Asp Asp Ile Gly Gly Val Met His
    290                 295                 300

Asn Ile Ser Thr Met Val Ile Val Asp Val Ile Gly Asp Arg Ser Arg
305                 310                 315                 320

Ile Val Asn Met Ala Glu Glu Ile Asp Gly Lys Val Val Ala Met Ser
                325                 330                 335

Asp Pro Tyr Trp Val Ala Lys Val Ser Ser Tyr Ile Ser Ser Lys Leu
            340                 345                 350

Asn Val Asp Asp Leu Leu Glu Asp Lys Pro Gln Leu Lys Tyr Ile Gln
        355                 360                 365

Ser Phe Ile Ser Asp Ala Leu Glu Asn Val Asp Leu Glu Lys Tyr Ile
    370                 375                 380

Lys Leu
385
```

<210> SEQ ID NO 185

<211> LENGTH: 858
<212> TYPE: DNA
<213> ORGANISM: Bacillus species

<400> SEQUENCE: 185
atgacaaaag ttaaagaatt gtttggattg aatacaagtg ttaaagggac tgattgggga 60
aaagttgtta cagaacagca ttgccccttt ttgaataaaa agtgtataaa aaatagaaag 120
agtcaggcag aaatagcaat tggcacatgt actatgagtt atggcaaagt aagtaaagat 180
ataattatct gtccacatag attactagaa aacagaaaaa tattcataga ttgtattcat 240
ttactaacaa tgcatgagcc tggtaatgag ttacatgttg tatcagaagt gtctattcca 300
ggaggtaatg tagattactt tttagtctca gcaaaagatg gtaaagtaaa agattttgtt 360
gggattgagc tacagactat ggataccaca ggtactgtat ggcctgaaag agaaaggttt 420
ctaaaagatg ctggatatag tggatatgat aaagaggcaa tagactctga taagtccttt 480
ggaatgaatt ggaagcatac agcaaaaact attcttgtac agttacatca taaggtcaaa 540
acctttgagc atgttaataa aaaattggtc ttagtgatac aagaaccttt aatagattat 600
atgaaaaaag aatttagttt ttctcatgta ggaaatgcta agttaggtga cccactacat 660
tttcacccat attccttaga tactagagaa gataatcaat tacatttaaa tttaaaaact 720
agacttagta cagactcaga tggaatggca atgtgtttag gattacaagc tgaggcaaaa 780
gttgaattaa cagaaattat tgctaaatta gaagaaaaaa tgaaaaatgc tacagtcagt 840
acattattaa ctttgtaa 858

<210> SEQ ID NO 186
<211> LENGTH: 285
<212> TYPE: PRT
<213> ORGANISM: Bacillus species

<400> SEQUENCE: 186

Met Thr Lys Val Lys Glu Leu Phe Gly Leu Asn Thr Ser Val Lys Gly
1 5 10 15

Thr Asp Trp Gly Lys Val Val Thr Glu Gln His Cys Pro Phe Leu Asn
20 25 30

Lys Lys Cys Ile Lys Asn Arg Lys Ser Gln Ala Glu Ile Ala Ile Gly
35 40 45

Thr Cys Thr Met Ser Tyr Gly Lys Val Ser Lys Asp Ile Ile Ile Cys
50 55 60

Pro His Arg Leu Leu Glu Asn Arg Lys Ile Phe Ile Asp Cys Ile His
65 70 75 80

Leu Leu Thr Met His Glu Pro Gly Asn Glu Leu His Val Val Ser Glu
85 90 95

Val Ser Ile Pro Gly Gly Asn Val Asp Tyr Phe Leu Val Ser Ala Lys
100 105 110

Asp Gly Lys Val Lys Asp Phe Val Gly Ile Glu Leu Gln Thr Met Asp
115 120 125

Thr Thr Gly Thr Val Trp Pro Glu Arg Glu Arg Phe Leu Lys Asp Ala
130 135 140

Gly Tyr Ser Gly Tyr Asp Lys Glu Ala Ile Asp Ser Asp Lys Ser Phe
145 150 155 160

Gly Met Asn Trp Lys His Thr Ala Lys Thr Ile Leu Val Gln Leu His
165 170 175

His Lys Val Lys Thr Phe Glu His Val Asn Lys Lys Leu Val Leu Val
180 185 190

```
Ile Gln Glu Pro Leu Ile Asp Tyr Met Lys Lys Glu Phe Ser Phe Ser
        195                 200                 205

His Val Gly Asn Ala Lys Leu Gly Asp Pro Leu His Phe His Pro Tyr
    210                 215                 220

Ser Leu Asp Thr Arg Glu Asp Asn Gln Leu His Leu Asn Leu Lys Thr
225                 230                 235                 240

Arg Leu Ser Thr Asp Ser Asp Gly Met Ala Met Cys Leu Gly Leu Gln
                245                 250                 255

Ala Glu Ala Lys Val Glu Leu Thr Glu Ile Ile Ala Lys Leu Glu Glu
            260                 265                 270

Lys Met Lys Asn Ala Thr Val Ser Thr Leu Leu Thr Leu
        275                 280                 285


<210> SEQ ID NO 187
<211> LENGTH: 1292
<212> TYPE: DNA
<213> ORGANISM: Bacillus sphaericus

<400> SEQUENCE: 187

atgagacgat tagcaaaaaa ttcacggaac gacagttatt taagtaatag ggattaccag      60

gaaatcgtga gggaaaatac cactacaata tcgtttccct taaaagaaaa acatactctg     120

actttaacga aaaaaatagg gctaaatcag actgctggat tcggaggatg gtttttccct     180

gattcaccat gtttattaac agtaactgta ctatcctctt tcggtacaaa ggtaacttct     240

aaaacccttta gcctttctaa agattggaat cgtgttgggc ttgcttggat taacgagcat    300

tcgagtgaca ccatagcatt gtcctagagt ttagtgatgt ggaaatagtt catacatggg     360

gacttacatg tgatgttttt aatgtccatg aattaattat tgatgctata gaagatcaaa     420

ataaactaat agacgtgcta aatcaagaac atttatctcc tgaaacatat tatttaaacc     480

atgactctga tactgattta attgagaatt tggaatctac agaagagata aagatagtta     540

accaaagcca aaagcaaatc tctttaaaaa aatgctgtta ttgtcaacgt tatatgcctg     600

tgaacatatt agttcgttca aattcatcat ttcataaaca caagagtaag aaaactggtt     660

ttcaaaatga atgtcgggct tgtaagaagt ggagaataaa taattcattc aatccagtca     720

gaacaaaaga ccaactacat gaatcagcag ttattacacg tgaaaaaaaa atattactta     780

aagaacctga aatattacag aaaatcaaaa atagaaataa cggtgagggc ttaaaaagta     840

ttatatggaa aaaatttgat aaaaaatgct ttaattgtga aaaagaatta accattgaag     900

aggtacgcct agaccataca agaccacttg cttatctgtg gcctatcgat gaacacgcaa     960

cttgtttatg tgaaaaatgc aacaatacaa aacatgatat gtttcctatc gatttttatc    1020

aaggggacga agacaaatta agacgtttag ctagaattac ggggttagat tatgaatctc    1080

tagttaagag ggacgtaaat gaagttgaac ttgcaagaat aatcaataac attgaagact    1140

ttgcaactaa tgtagaggca cgtacttttc gctcaataag aaataaagta aaagaagtac    1200

gtcccgatac tgacctattt gaaattctta aatctaaaaa tattaattta tataatgaac    1260

ttcaatatga acttcttacc cgtaaggatt aa                                  1292


<210> SEQ ID NO 188
<211> LENGTH: 430
<212> TYPE: PRT
<213> ORGANISM: Bacillus sphaericus

<400> SEQUENCE: 188

Met Arg Arg Leu Ala Lys Asn Ser Arg Asn Asp Ser Tyr Leu Ser Asn
1               5                   10                  15
```

```
Arg Asp Tyr Gln Glu Ile Val Arg Glu Asn Thr Thr Thr Ile Ser Phe
            20                  25                  30

Pro Leu Lys Glu Lys His Thr Leu Thr Leu Thr Lys Lys Ile Gly Leu
        35                  40                  45

Asn Gln Thr Ala Gly Phe Gly Gly Trp Phe Phe Pro Asp Ser Pro Cys
    50                  55                  60

Leu Leu Thr Val Thr Val Leu Ser Ser Phe Gly Thr Lys Val Thr Ser
65                  70                  75                  80

Lys Thr Phe Ser Leu Ser Lys Asp Trp Asn Arg Val Gly Leu Ala Trp
                85                  90                  95

Ile Asn Glu His Ser Ser Asp Thr Met Ser Ile Val Leu Glu Phe Ser
            100                 105                 110

Asp Val Glu Ile Val His Thr Trp Gly Leu Thr Cys Asp Val Phe Asn
        115                 120                 125

Val His Glu Leu Ile Ile Asp Ala Ile Glu Asp Gln Asn Lys Leu Ile
    130                 135                 140

Asp Val Leu Asn Gln Glu His Leu Ser Pro Glu Thr Tyr Tyr Leu Asn
145                 150                 155                 160

His Asp Ser Asp Thr Asp Leu Ile Glu Asn Leu Glu Ser Thr Glu Glu
                165                 170                 175

Ile Lys Ile Val Asn Gln Ser Gln Lys Gln Ile Ser Leu Lys Lys Cys
            180                 185                 190

Cys Tyr Cys Gln Arg Tyr Met Pro Val Asn Ile Leu Val Arg Ser Asn
        195                 200                 205

Ser Ser Phe His Lys His Lys Ser Lys Lys Thr Gly Phe Gln Asn Glu
    210                 215                 220

Cys Arg Ala Cys Lys Lys Trp Arg Ile Asn Asn Ser Phe Asn Pro Val
225                 230                 235                 240

Arg Thr Lys Asp Gln Leu His Glu Ser Ala Val Ile Thr Arg Glu Lys
                245                 250                 255

Lys Ile Leu Leu Lys Glu Pro Glu Ile Leu Gln Lys Ile Lys Asn Arg
            260                 265                 270

Asn Asn Gly Glu Gly Leu Lys Ser Ile Ile Trp Lys Lys Phe Asp Lys
        275                 280                 285

Lys Cys Phe Asn Cys Glu Lys Glu Leu Thr Ile Glu Glu Val Arg Leu
    290                 295                 300

Asp His Thr Arg Pro Leu Ala Tyr Leu Trp Pro Ile Asp Glu His Ala
305                 310                 315                 320

Thr Cys Leu Cys Glu Lys Cys Asn Asn Thr Lys His Asp Met Phe Pro
                325                 330                 335

Ile Asp Phe Tyr Gln Gly Asp Glu Asp Lys Leu Arg Arg Leu Ala Arg
            340                 345                 350

Ile Thr Gly Leu Asp Tyr Glu Ser Leu Val Lys Arg Asp Val Asn Glu
        355                 360                 365

Val Glu Leu Ala Arg Ile Ile Asn Asn Ile Glu Asp Phe Ala Thr Asn
    370                 375                 380

Val Glu Ala Arg Thr Phe Arg Ser Ile Arg Asn Lys Val Lys Glu Val
385                 390                 395                 400

Arg Pro Asp Thr Asp Leu Phe Glu Ile Leu Lys Ser Lys Asn Ile Asn
                405                 410                 415

Leu Tyr Asn Glu Leu Gln Tyr Glu Leu Leu Thr Arg Lys Asp
            420                 425                 430
```

<210> SEQ ID NO 189
<211> LENGTH: 278
<212> TYPE: PRT
<213> ORGANISM: unknown
<220> FEATURE:
<223> OTHER INFORMATION: Bacillus caldolyticus

<400> SEQUENCE: 189

Met Gln Pro Asn Pro Lys Phe Ile Asn Lys Ser Ser Ala Phe Trp Ala
1 5 10 15

Tyr Ala Lys Leu Leu Ser Glu Gln Leu Gly Tyr Ser Lys Asp Gly Val
20 25 30

Val Ile Ser Tyr Ser Glu Ala Gln Ala Arg Ala Lys Leu Lys Lys Leu
35 40 45

Gly Ile Asn Val Lys Glu Gly Ile Phe Lys Asp Val Leu Arg Tyr Leu
50 55 60

Lys Tyr Arg Ala Glu Leu Leu Asn Lys His Lys Asp Tyr Leu Met Asp
65 70 75 80

Val Glu Glu Ala Arg Lys Tyr Phe Gln Val Ala Leu Lys Gln His Gln
85 90 95

Gln Asn Asn Tyr Thr Cys Lys Leu Pro Leu Asn Lys Gln Lys Asn Glu
100 105 110

Lys Lys Asp Tyr Ala Tyr Phe Thr Cys Ile Ile Asn Ile Ile Ala Glu
115 120 125

Thr Glu Leu Arg Tyr Phe Ala Asn Asn Asn Gly Leu Val Tyr Gly Lys
130 135 140

Asp Ile Tyr Phe Asp Asp Asn Pro Met Asn Leu Ser Tyr Ile Leu Asn
145 150 155 160

Phe Asn Arg Glu Leu Glu Gly Ile Met Ser Arg Arg Phe Asp Gly Ala
165 170 175

Phe Pro Ser Thr Val Asn Pro Ile Leu Ile Trp Glu Ile Lys Glu Tyr
180 185 190

Tyr Tyr Thr Thr Thr Phe Gly Ser Arg Ile Ala Asp Gly Val Tyr Glu
195 200 205

Thr Gln Leu Asp Gly Tyr Glu Ile Lys Thr Ile Arg Glu Glu Thr Asn
210 215 220

Lys Asn Ile Gln His Ile Tyr Phe Ile Asp Asp Tyr Asn Thr Trp Trp
225 230 235 240

Asn Met Gly Lys Ser Tyr Leu Cys Arg Ile Ile Asp Met Leu His Met
245 250 255

Gly Leu Val Asp Glu Val Ile Met Gly Lys Glu Val Phe Glu Arg Trp
260 265 270

Pro Gln Ile Leu Arg Ala
275

<210> SEQ ID NO 190
<211> LENGTH: 293
<212> TYPE: PRT
<213> ORGANISM: unknown
<220> FEATURE:
<223> OTHER INFORMATION: Corynebacterium glutamicum

<400> SEQUENCE: 190

Met Lys Ala Glu Pro Lys Trp Ile Asn Arg Pro Pro Gln Phe Trp His
1 5 10 15

Tyr Val Arg Val Ile Ser Gln His Leu Gly Tyr Ala Arg Lys Gly Glu
20 25 30

Ile Tyr Arg His Glu Pro Glu Ala Ile Glu Arg Ala Leu Arg Glu Leu

```
        35                  40                  45

Glu Leu Ser Val Asp Ala Leu Arg Leu Thr Pro Ile Pro Gly Leu Ser
    50                  55                  60

Val Gly Glu Leu Ala Glu Tyr Phe Asp Phe Arg Ala Asp Leu Ile His
65                  70                  75                  80

Gly Thr Ile Ala Ala Asn Leu Gln Asn Ala Ser Glu Ala Lys Lys Thr
                85                  90                  95

Phe Glu Gln Val Val Glu Lys Phe Thr Thr Gly Met Thr Pro Gln Phe
            100                 105                 110

Lys Gly Gly Lys Glu Asn Ser Arg Leu Tyr Arg Val Asn Gly Gly Val
        115                 120                 125

Pro Val Val Val Pro Tyr Asn Lys Gln Lys Gly Asp Lys Arg Asp Ile
    130                 135                 140

Asp Phe Leu Thr Gly Thr Thr Asn Ile Leu Leu Ser Tyr Tyr Leu Gly
145                 150                 155                 160

Gly Glu Ser Phe Asp Gln Asp Pro Arg Gln Leu Pro Val Val Thr Glu
                165                 170                 175

Asp Gly Val Val Ser Gly Ser Met Ser Arg Arg Met Asp Gly Ala Tyr
            180                 185                 190

Pro Asp Ser Val Asn Pro Ser Ala Ile Trp Glu Phe Lys Cys Tyr Tyr
        195                 200                 205

Tyr Thr Thr Thr Phe Gly Ser Lys Ile Ser Asp Ala Val Tyr Ile Thr
    210                 215                 220

Asp Leu Asp Gly Tyr Glu Arg Gly Glu Ile Leu Lys Ala Ser His Lys
225                 230                 235                 240

Arg Val Glu Asn Asn Val Phe Leu Asp Ala Tyr Ser Val Phe Met Glu
                245                 250                 255

Gln Gly Leu Ser Phe Leu Val Arg Leu Val Asp Met Leu Gln Arg Gly
            260                 265                 270

Ala Val Asp Asn Leu Val Phe Gly Lys Glu Val Leu Thr Ala Val Pro
        275                 280                 285

Glu Ile Val Lys Gly
    290


<210> SEQ ID NO 191
<211> LENGTH: 137
<212> TYPE: PRT
<213> ORGANISM: unknown
<220> FEATURE:
<223> OTHER INFORMATION: Bacillus caldolyticus

<400> SEQUENCE: 191

Lys Asp Ile Tyr Phe Asp Asp Asn Pro Met Asn Leu Ser Tyr Ile Leu
1               5                   10                  15

Asn Phe Asn Arg Glu Leu Glu Gly Ile Met Ser Arg Arg Phe Asp Gly
            20                  25                  30

Ala Phe Pro Ser Thr Val Asn Pro Ile Leu Ile Trp Glu Ile Lys Glu
        35                  40                  45

Tyr Tyr Tyr Thr Thr Thr Phe Gly Ser Arg Ile Ala Asp Gly Val Tyr
    50                  55                  60

Glu Thr Gln Leu Asp Gly Tyr Glu Ile Lys Thr Ile Arg Glu Glu Thr
65                  70                  75                  80

Asn Lys Asn Ile Gln His Ile Tyr Phe Ile Asp Asp Tyr Asn Thr Trp
                85                  90                  95

Trp Asn Met Gly Lys Ser Tyr Leu Cys Arg Ile Ile Asp Met Leu His
            100                 105                 110
```

Met Gly Leu Val Asp Glu Val Ile Met Gly Lys Glu Val Phe Glu Arg
115 120 125

Trp Pro Gln Ile Leu Arg Ala Val Leu
130 135

<210> SEQ ID NO 192
<211> LENGTH: 194
<212> TYPE: PRT
<213> ORGANISM: unknown
<220> FEATURE:
<223> OTHER INFORMATION: Magnetococcus sp. MC-1

<400> SEQUENCE: 192

Lys Gly Ile Gln Phe Asp Pro Asp Pro Gln Asn Arg Cys Val Trp Ile
1 5 10 15

Asn Asp Asn Arg Leu His Val Thr Ser Arg Asn Leu Asp Gly Ala Ile
20 25 30

Pro Gly Leu Thr Asn Pro Glu Ile Ile Trp Glu Ile Lys Glu Tyr Trp
35 40 45

Gly Lys Thr Lys Gly Gly Ser Lys Met Ser Asp Gly Val Tyr Glu Thr
50 55 60

Gln Leu Asp Gly Tyr Glu Ile Lys Thr Ile Arg Glu Glu Thr Asn Lys
65 70 75 80

Asn Ile Gln His Ile Tyr Phe Ile Asp Asp Tyr Asn Thr Trp Trp Asn
85 90 95

Met Gly Lys Ser Tyr Leu Cys Arg Ile Ile Asp Met Leu His Met Gly
100 105 110

Leu Val Asp Glu Val Ile Asp Ala Val Tyr Glu Cys Gln Leu Val Gly
115 120 125

Arg Glu Leu Arg Glu Tyr Glu Glu Lys Cys Asn Lys Lys Ile Met His
130 135 140

Phe Val Phe Leu Asp Gly Lys Asp Gln Trp Ser His Arg Lys Ser Asp
145 150 155 160

Leu Lys Arg Phe Ile Asp Leu Trp Cys Gln Gly Leu Ile Asp Thr Leu
165 170 175

Phe Val Gly Lys Gln Val Glu Ser Leu Trp Glu Lys Thr Leu Glu Lys
180 185 190

Leu Leu

<210> SEQ ID NO 193
<211> LENGTH: 297
<212> TYPE: PRT
<213> ORGANISM: unknown
<220> FEATURE:
<223> OTHER INFORMATION: Enterobacter agglomerans

<400> SEQUENCE: 193

Lys Lys Arg Arg Asp Leu Val Glu Val Phe Gly Tyr Asn Pro Met Asp
1 5 10 15

Leu Ser Pro Glu Val Arg Ala Leu Trp Asn Leu Gly Ala Cys Pro Phe
20 25 30

Leu Asn Lys Glu Cys Ile Lys Ile Asn His Asp Gln Thr Ile Ile Tyr
35 40 45

Gly Thr Cys Ser Val Thr Ser Pro Tyr Gly Asp Val Ile Ile Cys Pro
50 55 60

Asn Arg Leu Tyr Ala Asn Asp Tyr Glu Thr Leu His Lys Val Ser Arg
65 70 75 80

Asp Ala Phe Gly Asp Asp Val Pro Phe Leu Thr Tyr Ser Asn Phe Ile
85 90 95

Lys Tyr Arg Ala Thr Tyr Lys Asp Cys Ile Val Ala Leu Gly Lys Asn
100 105 110

Ser Gly Lys Glu Val Gln Val Gly Arg Ala Leu Ser Met Asp Trp Val
115 120 125

Leu Val Arg Ile Thr Asp Gly Glu Leu Lys Glu Tyr Val Gly Val Glu
130 135 140

Ile Gln Ser Ile Asp Ile Thr Gly Asn Tyr Arg Asp Ala Trp His Ala
145 150 155 160

Tyr Lys Asn Leu Lys Pro Ile Asp Ile Ile Asp Asn Leu Pro Thr Ser
165 170 175

Gln His Gly Leu Asn Trp Ala Asn Val His Lys Arg Leu Ile Pro Gln
180 185 190

Ile Ile Arg Lys Gly Val Val Tyr Ser Arg Ser Asn Tyr Val Lys Lys
195 200 205

Gly Leu Tyr Phe Ile Leu Pro Glu Ile Val Tyr Asn Lys Phe Glu Asp
210 215 220

Val Ile Gly Ala Asp Ile Pro Leu Leu Lys Thr Gln Thr Asn Lys Ser
225 230 235 240

Ile Thr Val His Thr Tyr Ser Leu Gly Glu Pro Ala Ala Asn Gly Glu
245 250 255

Gln Arg Lys Leu Ile Ser Glu Arg Glu Ile Ile Phe Asp Leu Asp Glu
260 265 270

Phe Ser Lys Arg Phe Thr Thr Gly Pro Asn Leu Pro Lys Gly Asp Asp
275 280 285

Leu Asp Ala Val Ile Lys Lys Ala Leu
290 295

<210> SEQ ID NO 194
<211> LENGTH: 276
<212> TYPE: PRT
<213> ORGANISM: unknown
<220> FEATURE:
<223> OTHER INFORMATION: Chloroflexus aurantiacus J-10-fl

<400> SEQUENCE: 194

Gln Thr Gln Gln Pro Leu Ala Glu Val Phe Gly Tyr Gln Ile Thr Asp
1 5 10 15

Gln Ser Glu Ala Ala Ala Arg Cys Arg Ser Ala Arg Leu Cys Pro Phe
20 25 30

Gln Gly Gln Asp Arg Lys Cys Thr Lys Asp Lys Ala Asn Asn Pro Leu
35 40 45

Gly Val Cys Ala Ile Tyr His Asn Asn Glu Pro Val Ile Thr Cys Pro
50 55 60

Ile Arg Phe Arg Gln Asn Trp Leu Ile Ala Gln Asp Ala Ala Leu Phe
65 70 75 80

Phe Phe Gly Glu Gly Thr Arg Trp Ser Ile Leu Thr Glu Ile Arg Leu
85 90 95

Pro Asp Ala Phe Gly Lys Ser Ala Gly Asn Ile Asp Val Val Leu Val
100 105 110

Ser Tyr Asp Asp Glu Gly Arg Ile Thr Asp Phe Gly Ala Ile Glu Ile
115 120 125

Gln Ala Val Tyr Ile Ser Gly Asn Val Arg Ser Phe Phe Glu His Tyr
130 135 140

Met Arg Asp Pro Gln Gly Tyr Ile Val Gly Asp Trp Ile Gly Glu Thr

```
145                 150                 155                 160

Pro Val Pro Arg Pro Asp Tyr Leu Ser Ser Ser Arg Lys Arg Leu Val
                165                 170                 175

Pro Gln Leu Met Tyr Lys Gly Ala Ile Leu Arg Ala Trp Asn Lys Lys
            180                 185                 190

Met Ala Val Val Val Asp Glu Gln Phe Phe Gln Thr Leu Pro Gln Leu
        195                 200                 205

Ala Ser Ile Pro Pro Gln Asp Ala Asn Met Ala Trp Phe Ile Tyr Arg
    210                 215                 220

Leu Met Pro Gly Arg Gln Ala His Glu Gly Thr Glu Arg Tyr Tyr Leu
225                 230                 235                 240

Glu Lys Val Thr Glu Val Phe Thr Asp Phe Glu Gln Val Ile Arg Val
                245                 250                 255

Met Thr Thr Ser Ser Pro Gly Arg Ser Glu Asp Phe Ile Lys Phe Leu
            260                 265                 270

Gln Ala Lys Leu
        275


<210> SEQ ID NO 195
<211> LENGTH: 294
<212> TYPE: PRT
<213> ORGANISM: unknown
<220> FEATURE:
<223> OTHER INFORMATION: Enterobacter agglomerans

<400> SEQUENCE: 195

Leu Val Glu Val Phe Gly Tyr Asn Pro Met Asp Leu Ser Pro Glu Val
1               5                   10                  15

Arg Ala Leu Trp Asn Leu Gly Ala Cys Pro Phe Leu Asn Lys Glu Cys
            20                  25                  30

Ile Lys Ile Asn His Asp Gln Thr Ile Ile Tyr Gly Thr Cys Ser Val
        35                  40                  45

Thr Ser Pro Tyr Gly Asp Val Ile Ile Cys Pro Asn Arg Leu Tyr Ala
    50                  55                  60

Asn Asp Tyr Glu Thr Leu His Lys Val Ser Arg Asp Ala Phe Gly Asp
65                  70                  75                  80

Asp Val Pro Phe Leu Thr Tyr Ser Asn Phe Ile Lys Tyr Arg Ala Thr
                85                  90                  95

Tyr Lys Asp Cys Ile Val Ala Leu Gly Lys Asn Ser Gly Lys Glu Val
            100                 105                 110

Gln Val Gly Arg Ala Leu Ser Met Asp Trp Val Leu Val Arg Ile Thr
        115                 120                 125

Asp Gly Glu Leu Lys Glu Tyr Val Gly Val Glu Ile Gln Ser Ile Asp
    130                 135                 140

Ile Thr Gly Asn Tyr Arg Asp Ala Trp His Ala Tyr Lys Asn Leu Lys
145                 150                 155                 160

Pro Ile Asp Ile Ile Asp Asn Leu Pro Thr Ser Gln His Gly Leu Asn
                165                 170                 175

Trp Ala Asn Val His Lys Arg Leu Ile Pro Gln Ile Ile Arg Lys Gly
            180                 185                 190

Val Val Tyr Ser Arg Ser Asn Tyr Val Lys Lys Gly Leu Tyr Phe Ile
        195                 200                 205

Leu Pro Glu Ile Val Tyr Asn Lys Phe Glu Asp Val Ile Gly Ala Asp
    210                 215                 220

Ile Pro Leu Leu Lys Thr Gln Thr Asn Lys Ser Ile Thr Val His Thr
225                 230                 235                 240
```

```
Tyr Ser Leu Gly Glu Pro Ala Ala Asn Gly Glu Gln Arg Lys Leu Ile
                245                 250                 255

Ser Glu Arg Glu Ile Ile Phe Asp Leu Asp Glu Phe Ser Lys Arg Phe
            260                 265                 270

Thr Thr Gly Pro Asn Leu Pro Lys Gly Asp Asp Leu Asp Ala Val Ile
        275                 280                 285

Lys Lys Ala Leu Gly Met
    290
```

<210> SEQ ID NO 196
<211> LENGTH: 297
<212> TYPE: PRT
<213> ORGANISM: unknown
<220> FEATURE:
<223> OTHER INFORMATION: Rhodobacterales bacterium HTCC2654

<400> SEQUENCE: 196

```
Ile Phe Glu Phe Phe Gly Tyr Arg Ala Asp Asp Arg Ser Asp Ile Ala
1               5                   10                  15

Lys His Ala Ala Asp Thr Glu Val Cys Pro Ile Ser Gly Glu Thr Cys
            20                  25                  30

Gln Lys Ser Phe Asn Asp Gly Val Val Ser Gly Val Cys Ala Ile Lys
        35                  40                  45

Pro Ile Thr Ser Glu Pro Val Ile Cys Cys Pro Ile Arg Leu Tyr Ala
    50                  55                  60

Asp Asp Tyr Arg Ile Leu Ser Asp Ile Ala Asp Arg Val Phe Gly Pro
65                  70                  75                  80

Asn Leu Lys Leu Val Ala Gly Arg Asp Ala Val Asn Tyr Ser Ile Asp
                85                  90                  95

Asn Arg Glu Ala Cys Val Ala Val Phe Gly Lys Gly Trp Gly Gly Glu
            100                 105                 110

Leu Arg Leu Pro Gln Lys Ser Lys Lys Gly Gly Tyr Phe Val Asp Trp
        115                 120                 125

Val Leu Ala Lys Ile Ser Glu Glu Gly Asp Leu Val Glu Phe Val Ala
    130                 135                 140

Val Glu Val Gln Thr Ile Asp Thr Thr Gly Thr Tyr Arg Pro Gly Tyr
145                 150                 155                 160

Asp Ala Leu Lys Gln Asp Gly Leu Val Glu Lys Thr Thr Ala Gly Leu
                165                 170                 175

Asn Trp Glu Asn Val Ala Lys Arg Ile Leu Pro Gln Leu Ile Tyr Lys
            180                 185                 190

Gly Gln Ile Leu Gln Arg Glu Glu Leu Cys Lys Asn Gly Leu Phe Phe
        195                 200                 205

Val Cys Pro Glu Pro Val Phe Arg Arg Ile Met Glu Arg Leu Gly Gly
    210                 215                 220

Gln Glu Gly Leu Val Arg Tyr Ala Leu Gln Pro Ala Ser Ile Thr Phe
225                 230                 235                 240

Ala Val Tyr Asp Tyr Asp Phe Ser Ser Glu Pro Ser Asp Glu Thr Leu
                245                 250                 255

Val Pro Leu Lys Asn Thr Leu Asn His Ser Thr Thr Val Tyr Lys Val
            260                 265                 270

Gln Glu Ala Phe Asn Asn Val Thr Leu Pro Ile Glu Asn Val Tyr Arg
        275                 280                 285

Asp Ala Ile Arg Arg Ala Leu Gly Ile
    290                 295
```

<210> SEQ ID NO 197
<211> LENGTH: 297
<212> TYPE: PRT
<213> ORGANISM: unknown
<220> FEATURE:
<223> OTHER INFORMATION: Enterobacter agglomerans

<400> SEQUENCE: 197

Lys Lys Arg Arg Asp Leu Val Glu Val Phe Gly Tyr Asn Pro Met Asp
1               5                   10                  15

Leu Ser Pro Glu Val Arg Ala Leu Trp Asn Leu Gly Ala Cys Pro Phe
            20                  25                  30

Leu Asn Lys Glu Cys Ile Lys Ile Asn His Asp Gln Thr Ile Ile Tyr
        35                  40                  45

Gly Thr Cys Ser Val Thr Ser Pro Tyr Gly Asp Val Ile Ile Cys Pro
    50                  55                  60

Asn Arg Leu Tyr Ala Asn Asp Tyr Glu Thr Leu His Lys Val Ser Arg
65                  70                  75                  80

Asp Ala Phe Gly Asp Asp Val Pro Phe Leu Thr Tyr Ser Asn Phe Ile
                85                  90                  95

Lys Tyr Arg Ala Thr Tyr Lys Asp Cys Ile Val Ala Leu Gly Lys Asn
            100                 105                 110

Ser Gly Lys Glu Val Gln Val Gly Arg Ala Leu Ser Met Asp Trp Val
        115                 120                 125

Leu Val Arg Ile Thr Asp Gly Glu Leu Lys Glu Tyr Val Gly Val Glu
    130                 135                 140

Ile Gln Ser Ile Asp Ile Thr Gly Asn Tyr Arg Asp Ala Trp His Ala
145                 150                 155                 160

Tyr Lys Asn Leu Lys Pro Ile Asp Ile Ile Asp Asn Leu Pro Thr Ser
                165                 170                 175

Gln His Gly Leu Asn Trp Ala Asn Val His Lys Arg Leu Ile Pro Gln
            180                 185                 190

Ile Ile Arg Lys Gly Val Val Tyr Ser Arg Ser Asn Tyr Val Lys Lys
        195                 200                 205

Gly Leu Tyr Phe Ile Leu Pro Glu Ile Val Tyr Asn Lys Phe Glu Asp
    210                 215                 220

Val Ile Gly Ala Asp Ile Pro Leu Leu Lys Thr Gln Thr Asn Lys Ser
225                 230                 235                 240

Ile Thr Val His Thr Tyr Ser Leu Gly Glu Pro Ala Ala Asn Gly Glu
                245                 250                 255

Gln Arg Lys Leu Ile Ser Glu Arg Glu Ile Ile Phe Asp Leu Asp Glu
            260                 265                 270

Phe Ser Lys Arg Phe Thr Thr Gly Pro Asn Leu Pro Lys Gly Asp Asp
        275                 280                 285

Leu Asp Ala Val Ile Lys Lys Ala Leu
    290                 295

<210> SEQ ID NO 198
<211> LENGTH: 333
<212> TYPE: PRT
<213> ORGANISM: unknown
<220> FEATURE:
<223> OTHER INFORMATION: Chlorobium phaeobacteroides BS1

<400> SEQUENCE: 198

Lys Asn Ala Gln Pro Leu Ala Glu Val Phe Gly His Pro Val Thr Asp
1               5                   10                  15

```
Ala Ser Ser Arg Ala Asp Arg Tyr Arg Ser Gln Arg Leu Cys Pro Phe
            20                  25                  30

Asn Asn Lys Val Pro Asn Cys Thr Lys Asp Lys Ala Lys Ser Pro Leu
        35                  40                  45

Gly Val Cys Ser Ile Gln His Asp Gly Ser Pro Val Ile Thr Cys Pro
    50                  55                  60

Ile Arg Phe Arg Glu Asp Trp Leu Ile Thr Asp Asp Ala Ala Ser Phe
65                  70                  75                  80

Phe Phe Pro Glu Gly Thr Lys Trp Ser Ser Leu Thr Glu Ile Arg Leu
                85                  90                  95

Asn Asp Gly Asn Gly Lys Ser Ala Gly Asn Ile Asp Ile Val Leu Val
            100                 105                 110

Ala Tyr Asp Asp Asn Gly Lys Val Lys Asp Phe Gly Ala Leu Glu Ile
        115                 120                 125

Gln Ala Val Tyr Ile Ser Gly Asn Val Arg Asp Pro Phe Glu Tyr Phe
    130                 135                 140

Met Glu Glu Pro Lys Gly Arg Ala Phe Met Asp Trp Ser Asn Gln Pro
145                 150                 155                 160

Asn Tyr Pro Arg Pro Asp Tyr Leu Ser Ser Ser Arg Lys Arg Leu Val
                165                 170                 175

Pro Gln Leu Phe Phe Lys Gly Gly Ile Leu His Ser Trp Lys Lys Lys
            180                 185                 190

Ser Ala Val Ala Leu Asn Lys Ser Phe Phe Asp Thr Leu Pro Pro Leu
        195                 200                 205

Ile Gly Ala Asp Ile Pro Leu Leu Lys Thr Gln Thr Asn Lys Ser Ile
    210                 215                 220

Thr Val His Thr Tyr Ser Leu Gly Glu Pro Ala Ala Asn Gly Glu Gln
225                 230                 235                 240

Arg Lys Leu Ile Ser Glu Arg Glu Ile Ile Phe Asp Leu Asp Glu Phe
                245                 250                 255

Ser Lys Arg Phe Thr Thr Gly Pro Asn Leu Pro Thr Thr Val Ser Arg
            260                 265                 270

Lys Lys Ala Asp Ile Ala Trp Leu Ile Tyr Asp Ile Glu Leu Cys Gly
        275                 280                 285

Ser Gly Ala Glu Lys Arg Tyr Arg Leu Lys Lys Val Asp Glu Val Phe
    290                 295                 300

Thr Glu Phe Glu Pro Ala Leu Leu Ser Ile Thr Thr Pro Val Pro Gly
305                 310                 315                 320

Arg Ile Asp Asp Phe Met Asn Met Leu Gln Val Lys Ile
                325                 330
```

<210> SEQ ID NO 199
<211> LENGTH: 285
<212> TYPE: PRT
<213> ORGANISM: unknown
<220> FEATURE:
<223> OTHER INFORMATION: Enterobacter agglomerans

<400> SEQUENCE: 199

```
Asp Leu Val Glu Val Phe Gly Tyr Asn Pro Met Asp Leu Ser Pro Glu
1               5                   10                  15

Val Arg Ala Leu Trp Asn Leu Gly Ala Cys Pro Phe Leu Asn Lys Glu
            20                  25                  30

Cys Ile Lys Ile Asn His Asp Gln Thr Ile Ile Tyr Gly Thr Cys Ser
        35                  40                  45

Val Thr Ser Pro Tyr Gly Asp Val Ile Ile Cys Pro Asn Arg Leu Tyr
```

```
    50                  55                  60

Ala Asn Asp Tyr Glu Thr Leu His Lys Val Ser Arg Asp Ala Phe Gly
65                  70                  75                  80

Asp Asp Val Pro Phe Leu Thr Tyr Ser Asn Phe Ile Lys Tyr Arg Ala
                85                  90                  95

Thr Tyr Lys Asp Cys Ile Val Ala Leu Gly Lys Asn Ser Gly Lys Glu
            100                 105                 110

Val Gln Val Gly Arg Ala Leu Ser Met Asp Trp Val Leu Val Arg Ile
        115                 120                 125

Thr Asp Gly Glu Leu Lys Glu Tyr Val Gly Val Glu Ile Gln Ser Ile
    130                 135                 140

Asp Ile Thr Gly Asn Tyr Arg Asp Ala Trp His Ala Tyr Lys Asn Leu
145                 150                 155                 160

Lys Pro Ile Asp Ile Ile Asp Asn Leu Pro Thr Ser Gln His Gly Leu
                165                 170                 175

Asn Trp Ala Asn Val His Lys Arg Leu Ile Pro Gln Ile Ile Arg Lys
            180                 185                 190

Gly Val Val Tyr Ser Arg Ser Asn Tyr Val Lys Lys Gly Leu Tyr Phe
        195                 200                 205

Ile Leu Pro Glu Ile Val Tyr Asn Lys Phe Glu Asp Val Ile Gly Ala
    210                 215                 220

Asp Ile Pro Leu Leu Lys Thr Gln Thr Asn Lys Ser Ile Thr Val His
225                 230                 235                 240

Thr Tyr Ser Leu Gly Glu Pro Ala Ala Asn Gly Glu Gln Arg Lys Leu
                245                 250                 255

Ile Ser Glu Arg Glu Ile Ile Phe Asp Leu Asp Glu Phe Ser Lys Arg
            260                 265                 270

Phe Thr Thr Gly Pro Asn Leu Pro Lys Gly Asp Asp Leu
        275                 280                 285


<210> SEQ ID NO 200
<211> LENGTH: 263
<212> TYPE: PRT
<213> ORGANISM: unknown
<220> FEATURE:
<223> OTHER INFORMATION: Chlorobium chlorochromatii CaD3

<400> SEQUENCE: 200

Pro Leu Gly Glu Val Phe Gly Phe Ala Ala Thr Asp Gln Ser Pro Lys
1               5                   10                  15

Ala Gln Arg Tyr Arg Ser His Arg His Cys Pro Phe Asn Asn Lys Ser
            20                  25                  30

Pro Asn Cys Thr Asn Ser His Thr Glu Asn Pro Leu Gly Val Cys Ser
        35                  40                  45

Ile Leu His Asn Asn Lys Ala Ile Ile Thr Cys Pro Ile Arg Phe Arg
    50                  55                  60

Glu Asp Trp Leu Ile Thr Asp Asp Ala Ala Ser Phe Phe Phe Glu Pro
65                  70                  75                  80

Gly Val Arg Trp Ser Ser Leu Thr Asp Val Arg Leu Ala Asp Ala Asn
                85                  90                  95

Gly Thr Ser Ala Gly Asn Met Asp Val Met Leu Val Ala Tyr Asp Lys
            100                 105                 110

Glu Gly Lys Ile Ile Asp Phe Gly Ala Ile Gln Ile Gln Thr Ala His
        115                 120                 125

Ile Asp Gly Asn Val Arg Glu Pro Phe Glu Cys Tyr Met Lys Asp Pro
    130                 135                 140
```

```
Lys Thr Asn Ala Met Met Asp Trp Thr Arg Gln Pro Asn Tyr Pro Glu
145                 150                 155                 160

Pro Asp Phe Leu Ser Ala Met Arg Thr Ser Val Val Pro Glu Leu Leu
                165                 170                 175

Tyr Lys Gly Gly Ile Leu His Ser Trp Asn Lys Lys Met Ala Ile Ala
            180                 185                 190

Ile Asn Lys Ser Met Phe Glu Thr Leu Pro Pro Leu Thr Arg Val Lys
        195                 200                 205

Lys Asp Glu Ala Asp Ile Ala Trp Leu Leu Tyr Glu Leu Glu Ala Val
    210                 215                 220

Asn Asp Gly Glu Lys Glu Ala Tyr Gln Leu Lys Lys Ser Glu Val Val
225                 230                 235                 240

Tyr Thr Ala Phe Gln Pro Thr Leu Leu Ala Leu Thr Ala Ile Ala Pro
                245                 250                 255

Gly Asn Val Asn Asp Phe Met
            260


<210> SEQ ID NO 201
<211> LENGTH: 280
<212> TYPE: PRT
<213> ORGANISM: unknown
<220> FEATURE:
<223> OTHER INFORMATION: Enterobacter agglomerans

<400> SEQUENCE: 201

Leu Ser Pro Glu Val Arg Ala Leu Trp Asn Leu Gly Ala Cys Pro Phe
1               5                   10                  15

Leu Asn Lys Glu Cys Ile Lys Ile Asn His Asp Gln Thr Ile Ile Tyr
            20                  25                  30

Gly Thr Cys Ser Val Thr Ser Pro Tyr Gly Asp Val Ile Ile Cys Pro
        35                  40                  45

Asn Arg Leu Tyr Ala Asn Asp Tyr Glu Thr Leu His Lys Val Ser Arg
    50                  55                  60

Asp Ala Phe Gly Asp Asp Val Pro Phe Leu Thr Tyr Ser Asn Phe Ile
65                  70                  75                  80

Lys Tyr Arg Ala Thr Tyr Lys Asp Cys Ile Val Ala Leu Gly Lys Asn
                85                  90                  95

Ser Gly Lys Glu Val Gln Val Gly Arg Ala Leu Ser Met Asp Trp Val
            100                 105                 110

Leu Val Arg Ile Thr Asp Gly Glu Leu Lys Glu Tyr Val Gly Val Glu
        115                 120                 125

Ile Gln Ser Ile Asp Ile Thr Gly Asn Tyr Arg Asp Ala Trp His Ala
    130                 135                 140

Tyr Lys Asn Leu Lys Pro Ile Asp Ile Ile Asp Asn Leu Pro Thr Ser
145                 150                 155                 160

Gln His Gly Leu Asn Trp Ala Asn Val His Lys Arg Leu Ile Pro Gln
                165                 170                 175

Ile Ile Arg Lys Gly Val Val Tyr Ser Arg Ser Asn Tyr Val Lys Lys
            180                 185                 190

Gly Leu Tyr Phe Ile Leu Pro Glu Ile Val Tyr Asn Lys Phe Glu Asp
        195                 200                 205

Val Ile Gly Ala Asp Ile Pro Leu Leu Lys Thr Gln Thr Asn Lys Ser
    210                 215                 220

Ile Thr Val His Thr Tyr Ser Leu Gly Glu Pro Ala Ala Asn Gly Glu
225                 230                 235                 240
```

Gln Arg Lys Leu Ile Ser Glu Arg Glu Ile Ile Phe Asp Leu Asp Glu
245 250 255

Phe Ser Lys Arg Phe Thr Thr Gly Pro Asn Leu Pro Lys Gly Asp Asp
260 265 270

Leu Asp Ala Val Ile Lys Lys Ala
275 280

<210> SEQ ID NO 202
<211> LENGTH: 271
<212> TYPE: PRT
<213> ORGANISM: Jannaschia sp. CCS1

<400> SEQUENCE: 202

Arg Ser Lys Leu Ala Gln Gln Gln Ala Glu Glu Leu Pro Cys Pro Phe
1 5 10 15

Arg Thr Asp Ser Pro His Pro Thr Cys Thr Lys Pro Gly Gly Val Cys
20 25 30

Ser Ile Arg Ile Tyr Arg Glu Glu Ala Gly Val Ile Ala Pro Ile Asp
35 40 45

Gly Glu Arg Gly Arg Leu Arg Ala Leu Cys Pro Trp Arg Phe His Gln
50 55 60

Asp Gly Thr Ala Phe Asp Lys Ile Gly Glu Ser Leu Leu Ala Asp Pro
65 70 75 80

Ser Pro Leu Arg Ala Gly Glu Val Gly Phe Leu Glu Ser Thr Gly Asn
85 90 95

Leu Asp Ser Ala Ala Gly Glu Asp Val Gly Arg Ile Asp Met Ile Leu
100 105 110

Val Lys Ser Asn Ser Val Asp Gly Ala Pro Met Asp Trp Val Ala Val
115 120 125

Glu Val Gln Ala Val Tyr Phe Ser Gly Lys Lys Met Ser Ile Glu Phe
130 135 140

Asp His Leu Lys Leu Thr Gln Gly Arg Leu Ser Met Ala Gln Glu Lys
145 150 155 160

Arg Arg Pro Asp Tyr Arg Ser Ser Gly Val Lys Arg Leu Met Pro Gln
165 170 175

Leu Leu Thr Lys Val Pro Thr Leu Arg Arg Trp Gly Lys Lys Met Ala
180 185 190

Val Val Val Asp Ala Pro Phe Phe Tyr Ser Met Gly Lys Met Glu Arg
195 200 205

Val Pro His Leu Ser Asn Ala Asp Ile Val Trp Phe Leu Val Asp Phe
210 215 220

Lys Gln Ala Ala Pro Gly Ala Pro Phe Gln Leu Glu Val Val Glu Glu
225 230 235 240

Phe Tyr Thr Thr Leu Glu Ser Ala Thr Leu Gly Leu Thr Gly Gly Val
245 250 255

Pro Val Ser Gln Gly Ala Phe Glu Ala Arg Ile Thr Ala Lys Ala
260 265 270

<210> SEQ ID NO 203
<211> LENGTH: 292
<212> TYPE: PRT
<213> ORGANISM: unknown
<220> FEATURE:
<223> OTHER INFORMATION: Enterobacter agglomerans

<400> SEQUENCE: 203

Leu Val Glu Val Phe Gly Tyr Asn Pro Met Asp Leu Ser Pro Glu Val
1 5 10 15

Arg Ala Leu Trp Asn Leu Gly Ala Cys Pro Phe Leu Asn Lys Glu Cys
20 25 30

Ile Lys Ile Asn His Asp Gln Thr Ile Ile Tyr Gly Thr Cys Ser Val
35 40 45

Thr Ser Pro Tyr Gly Asp Val Ile Ile Cys Pro Asn Arg Leu Tyr Ala
50 55 60

Asn Asp Tyr Glu Thr Leu His Lys Val Ser Arg Asp Ala Phe Gly Asp
65 70 75 80

Asp Val Pro Phe Leu Thr Tyr Ser Asn Phe Ile Lys Tyr Arg Ala Thr
85 90 95

Tyr Lys Asp Cys Ile Val Ala Leu Gly Lys Asn Ser Gly Lys Glu Val
100 105 110

Gln Val Gly Arg Ala Leu Ser Met Asp Trp Val Leu Val Arg Ile Thr
115 120 125

Asp Gly Glu Leu Lys Glu Tyr Val Gly Val Glu Ile Gln Ser Ile Asp
130 135 140

Ile Thr Gly Asn Tyr Arg Asp Ala Trp His Ala Tyr Lys Asn Leu Lys
145 150 155 160

Pro Ile Asp Ile Ile Asp Asn Leu Pro Thr Ser Gln His Gly Leu Asn
165 170 175

Trp Ala Asn Val His Lys Arg Leu Ile Pro Gln Ile Ile Arg Lys Gly
180 185 190

Val Val Tyr Ser Arg Ser Asn Tyr Val Lys Lys Gly Leu Tyr Phe Ile
195 200 205

Leu Pro Glu Ile Val Tyr Asn Lys Phe Glu Asp Val Ile Gly Ala Asp
210 215 220

Ile Pro Leu Leu Lys Thr Gln Thr Asn Lys Ser Ile Thr Val His Thr
225 230 235 240

Tyr Ser Leu Gly Glu Pro Ala Ala Asn Gly Glu Gln Arg Lys Leu Ile
245 250 255

Ser Glu Arg Glu Ile Ile Phe Asp Leu Asp Glu Phe Ser Lys Arg Phe
260 265 270

Thr Thr Gly Pro Asn Leu Pro Lys Gly Asp Asp Leu Asp Ala Val Ile
275 280 285

Lys Lys Ala Leu
290

<210> SEQ ID NO 204
<211> LENGTH: 346
<212> TYPE: PRT
<213> ORGANISM: unknown
<220> FEATURE:
<223> OTHER INFORMATION: Nocardia otitidiscaviarum

<400> SEQUENCE: 204

Ile Ala Glu Phe Phe Gly His Arg Val Tyr Pro Glu Val Val Ser Thr
1 5 10 15

Glu Ala Ala Arg Asn Asp Gln Ala Thr Gly Thr Cys Pro Phe Leu Thr
20 25 30

Ala Ala Lys Leu Val Glu Thr Ser Cys Val Lys Ala Glu Thr Ser Arg
35 40 45

Gly Val Cys Val Val Asn Thr Ala Val Asp Asn Glu Arg Tyr Asp Trp
50 55 60

Leu Val Cys Pro Asn Arg Ala Leu Asp Pro Leu Phe Met Ser Ala Ala
65 70 75 80

```
Ser Arg Lys Leu Phe Gly Tyr Gly Pro Thr Glu Pro Leu Gln Phe Ile
                85                  90                  95

Ala Ala Pro Thr Leu Ala Asp Gln Ala Val Arg Asp Gly Ile Arg Glu
            100                 105                 110

Trp Leu Asp Arg Gly Val His Val Val Ala Tyr Phe Gln Glu Lys Leu
        115                 120                 125

Gly Gly Glu Leu Ser Ile Ser Lys Thr Asp Ser Ser Pro Glu Phe Ser
    130                 135                 140

Phe Asp Trp Thr Leu Ala Glu Val Glu Ser Ile Tyr Pro Val Pro Lys
145                 150                 155                 160

Ile Lys Arg Tyr Gly Val Leu Glu Ile Gln Thr Met Asp Phe His Gly
                165                 170                 175

Ser Tyr Lys His Ala Val Gly Ala Ile Asp Ile Ala Leu Val Glu Gly
            180                 185                 190

Ile Asp Phe His Gly Trp Leu Pro Thr Pro Ala Gly Arg Ala Ala Leu
        195                 200                 205

Ser Lys Lys Met Glu Gly Pro Asn Leu Ser Asn Val Phe Lys Arg Thr
    210                 215                 220

Phe Tyr Gln Met Ala Tyr Lys Phe Ala Leu Ser Gly His Gln Arg Cys
225                 230                 235                 240

Ala Gly Thr Gly Phe Ala Ile Pro Gln Ser Val Trp Lys Ser Trp Leu
                245                 250                 255

Arg His Leu Ala Asn Pro Thr Leu Ile Asp Asn Gly Asp Gly Thr Phe
            260                 265                 270

Ser Leu Gly Asp Thr Arg Asn Asp Ser Glu Asn Ala Trp Ile Phe Val
        275                 280                 285

Phe Glu Leu Asp Pro Asp Thr Asp Ala Ser Pro Arg Pro Leu Ala Pro
    290                 295                 300

His Leu Glu Ile Arg Val Asn Val Asp Thr Leu Ile Asp Leu Ala Leu
305                 310                 315                 320

Arg Glu Ser Pro Arg Ala Ala Leu Gly Pro Ser Gly Pro Val Ala Thr
                325                 330                 335

Phe Thr Asp Lys Val Glu Ala Arg Met Leu
            340                 345


<210> SEQ ID NO 205
<211> LENGTH: 282
<212> TYPE: PRT
<213> ORGANISM: unknown
<220> FEATURE:
<223> OTHER INFORMATION: Enterobacter agglomerans

<400> SEQUENCE: 205

Leu Ser Pro Glu Val Arg Ala Leu Trp Asn Leu Gly Ala Cys Pro Phe
1               5                   10                  15

Leu Asn Lys Glu Cys Ile Lys Ile Asn His Asp Gln Thr Ile Ile Tyr
            20                  25                  30

Gly Thr Cys Ser Val Thr Ser Pro Tyr Gly Asp Val Ile Ile Cys Pro
        35                  40                  45

Asn Arg Leu Tyr Ala Asn Asp Tyr Glu Thr Leu His Lys Val Ser Arg
    50                  55                  60

Asp Ala Phe Gly Asp Asp Val Pro Phe Leu Thr Tyr Ser Asn Phe Ile
65                  70                  75                  80

Lys Tyr Arg Ala Thr Tyr Lys Asp Cys Ile Val Ala Leu Gly Lys Asn
                85                  90                  95

Ser Gly Lys Glu Val Gln Val Gly Arg Ala Leu Ser Met Asp Trp Val
```

```
            100                 105                 110

Leu Val Arg Ile Thr Asp Gly Glu Leu Lys Glu Tyr Val Gly Val Glu
        115                 120                 125

Ile Gln Ser Ile Asp Ile Thr Gly Asn Tyr Arg Asp Ala Trp His Ala
    130                 135                 140

Tyr Lys Asn Leu Lys Pro Ile Asp Ile Ile Asp Asn Leu Pro Thr Ser
145                 150                 155                 160

Gln His Gly Leu Asn Trp Ala Asn Val His Lys Arg Leu Ile Pro Gln
                165                 170                 175

Ile Ile Arg Lys Gly Val Val Tyr Ser Arg Ser Asn Tyr Val Lys Lys
            180                 185                 190

Gly Leu Tyr Phe Ile Leu Pro Glu Ile Val Tyr Asn Lys Phe Glu Asp
        195                 200                 205

Val Ile Gly Ala Asp Ile Pro Leu Leu Lys Thr Gln Thr Asn Lys Ser
    210                 215                 220

Ile Thr Val His Thr Tyr Ser Leu Gly Glu Pro Ala Ala Asn Gly Glu
225                 230                 235                 240

Gln Arg Lys Leu Ile Ser Glu Arg Glu Ile Ile Phe Asp Leu Asp Glu
                245                 250                 255

Phe Ser Lys Arg Phe Thr Thr Gly Pro Asn Leu Pro Lys Gly Asp Asp
            260                 265                 270

Leu Asp Ala Val Ile Lys Lys Ala Leu Gly
        275                 280


<210> SEQ ID NO 206
<211> LENGTH: 273
<212> TYPE: PRT
<213> ORGANISM: unknown
<220> FEATURE:
<223> OTHER INFORMATION: Silicibacter pomeroyi DSS-3

<400> SEQUENCE: 206

Arg Asp Lys Leu Thr Arg Gln Gln Ala Glu Glu Ile Pro Cys Pro Phe
1               5                   10                  15

Arg Pro Asp Thr Pro Asn Ala Thr Cys Thr Lys Pro Gly Gly Val Cys
            20                  25                  30

Ser Ile Arg Val Tyr Arg Gly Glu Lys Asn Arg Val Glu Pro Ile Thr
        35                  40                  45

Gly Glu Arg Gly Arg Leu Arg Ala Leu Cys Pro Trp Arg Phe His Gln
    50                  55                  60

Asp Gly Lys Ala Phe Ser Glu Val Gly Lys Arg Leu Leu Asn Asp Pro
65                  70                  75                  80

Asp Pro Ile Lys Ala Gly Glu Val Gly Phe Leu Glu Ser Ser Gly Asn
                85                  90                  95

Leu Asp Ser Asp Pro Gly Glu Asp Val Gly Arg Ile Asp Met Ile Leu
            100                 105                 110

Val Lys Ser Asn Gly Val Glu Gly Ala Pro Met Asp Trp Val Ala Val
        115                 120                 125

Glu Val Gln Ala Val Tyr Phe Ser Gly Lys Lys Met Ser Ile Glu Phe
    130                 135                 140

Asp His Leu Ile Lys Thr Gln Gly Lys Ile Ser Met Ala Arg Glu Lys
145                 150                 155                 160

Arg Arg Pro Asp Tyr Arg Ser Ser Gly Val Lys Arg Leu Met Pro Gln
                165                 170                 175

Leu Gln Thr Lys Val Pro Thr Leu Arg Arg Trp Gly Lys Lys Met Ala
            180                 185                 190
```

```
Val Val Val Asp Ala Pro Phe Phe Tyr Ser Met Gly Glu Met Ala Arg
        195                 200                 205

Glu Arg Asp Val Ser Asn Ala Asp Ile Ile Trp Phe Leu Ala Asp Phe
    210                 215                 220

Lys Glu Asp Leu Asn Gly Gly Gly Phe Lys Leu Glu Ile Val Glu Glu
225                 230                 235                 240

Phe Tyr Thr Thr Leu Glu Ser Ala Thr Leu Gly Leu Thr Gly Gly Thr
                245                 250                 255

Pro Val Ser Gln Gly Asp Phe Glu Ala Arg Ile Arg Ala Lys Thr Asp
            260                 265                 270

Gly


<210> SEQ ID NO 207
<211> LENGTH: 259
<212> TYPE: PRT
<213> ORGANISM: unknown
<220> FEATURE:
<223> OTHER INFORMATION: Enterobacter agglomerans

<400> SEQUENCE: 207

Leu Val Glu Val Phe Gly Tyr Asn Pro Met Asp Leu Ser Pro Glu Val
1               5                   10                  15

Arg Ala Leu Trp Asn Leu Gly Ala Cys Pro Phe Leu Asn Lys Glu Cys
            20                  25                  30

Ile Lys Ile Asn His Asp Gln Thr Ile Ile Tyr Gly Thr Cys Ser Val
        35                  40                  45

Thr Ser Pro Tyr Gly Asp Val Ile Ile Cys Pro Asn Arg Leu Tyr Ala
    50                  55                  60

Asn Asp Tyr Glu Thr Leu His Lys Val Ser Arg Asp Ala Phe Gly Asp
65                  70                  75                  80

Asp Val Pro Phe Leu Thr Tyr Ser Asn Phe Ile Lys Tyr Arg Ala Thr
                85                  90                  95

Tyr Lys Asp Cys Ile Val Ala Leu Gly Lys Asn Ser Gly Lys Glu Val
            100                 105                 110

Gln Val Gly Arg Ala Leu Ser Met Asp Trp Val Leu Val Arg Ile Thr
        115                 120                 125

Asp Gly Glu Leu Lys Glu Tyr Val Gly Val Glu Ile Gln Ser Ile Asp
    130                 135                 140

Ile Thr Gly Asn Tyr Arg Asp Ala Trp His Ala Tyr Lys Asn Leu Lys
145                 150                 155                 160

Pro Ile Asp Ile Ile Asp Asn Leu Pro Thr Ser Gln His Gly Leu Asn
                165                 170                 175

Trp Ala Asn Val His Lys Arg Leu Ile Pro Gln Ile Ile Arg Lys Gly
            180                 185                 190

Val Val Tyr Ser Arg Ser Asn Tyr Val Lys Lys Gly Leu Tyr Phe Ile
        195                 200                 205

Leu Pro Glu Ile Val Tyr Asn Lys Phe Glu Asp Val Ile Gly Ala Asp
    210                 215                 220

Ile Pro Leu Leu Lys Thr Gln Thr Asn Lys Ser Ile Thr Val His Thr
225                 230                 235                 240

Tyr Ser Leu Gly Glu Pro Ala Ala Asn Gly Glu Gln Arg Lys Leu Ile
                245                 250                 255

Ser Glu Arg


<210> SEQ ID NO 208
```

<211> LENGTH: 238
<212> TYPE: PRT
<213> ORGANISM: unknown
<220> FEATURE:
<223> OTHER INFORMATION: Xylella fastidiosa Ann-1

<400> SEQUENCE: 208

Val Val Glu Leu Phe Gly Lys Ala Ala Asp Ala Pro Gly Ile Asp Trp
1 5 10 15

Gln Asn Glu Ile Ala Asp Gln Gln Cys Pro Phe Leu Gly Lys Arg Cys
20 25 30

Tyr Lys Val Arg Lys Ser Asn Pro Glu Ile Ser Ile Gly Ser Cys Thr
35 40 45

Val Leu Tyr Gly Arg Glu Pro Glu Pro Ile Ile Ile Cys Pro Thr Arg
50 55 60

Leu Ile Gln Arg Gly Gln Ile Phe Thr Asp Cys Leu His Leu Leu Thr
65 70 75 80

Ser His Glu Pro Gly Asn Glu Leu His Leu Val Ser Glu Val Thr Val
85 90 95

Pro Gly Gly Ser Ile Asp Tyr Val Leu Val Ser Ala Lys Glu Gly Lys
100 105 110

Val Arg Asp Phe Val Gly Ile Glu Leu Gln Thr Leu Asp Thr Thr Gly
115 120 125

Thr Val Trp Pro Glu Arg Gln Arg Leu Leu Lys Glu Leu Gly Val Ala
130 135 140

Arg Gly Asp Asn Gly Glu Glu Ser Asp Lys Ser Phe Gly Met Asn Trp
145 150 155 160

Lys Met Thr Ala Lys Thr Ile Leu Val Gln Met His His Lys Val Gln
165 170 175

Thr Phe Glu His Val Asn Arg Lys Leu Val Leu Val Val Gln Asp Lys
180 185 190

Phe Leu Ala Tyr Met Thr Lys Glu Phe Lys Phe Asp His Met Lys Asn
195 200 205

Pro Ala Ala Val Gly Asp Ser Met His Leu His Ser Tyr Arg Met Ala
210 215 220

Arg Ala Asp Asp Gly Asn Phe Arg Leu Ser Met Ala Ser Arg
225 230 235

<210> SEQ ID NO 209
<211> LENGTH: 259
<212> TYPE: PRT
<213> ORGANISM: unknown
<220> FEATURE:
<223> OTHER INFORMATION: Enterobacter agglomerans

<400> SEQUENCE: 209

Leu Val Glu Val Phe Gly Tyr Asn Pro Met Asp Leu Ser Pro Glu Val
1 5 10 15

Arg Ala Leu Trp Asn Leu Gly Ala Cys Pro Phe Leu Asn Lys Glu Cys
20 25 30

Ile Lys Ile Asn His Asp Gln Thr Ile Ile Tyr Gly Thr Cys Ser Val
35 40 45

Thr Ser Pro Tyr Gly Asp Val Ile Ile Cys Pro Asn Arg Leu Tyr Ala
50 55 60

Asn Asp Tyr Glu Thr Leu His Lys Val Ser Arg Asp Ala Phe Gly Asp
65 70 75 80

Asp Val Pro Phe Leu Thr Tyr Ser Asn Phe Ile Lys Tyr Arg Ala Thr
85 90 95

```
Tyr Lys Asp Cys Ile Val Ala Leu Gly Lys Asn Ser Gly Lys Glu Val
            100                 105                 110

Gln Val Gly Arg Ala Leu Ser Met Asp Trp Val Leu Val Arg Ile Thr
        115                 120                 125

Asp Gly Glu Leu Lys Glu Tyr Val Gly Val Glu Ile Gln Ser Ile Asp
    130                 135                 140

Ile Thr Gly Asn Tyr Arg Asp Ala Trp His Ala Tyr Lys Asn Leu Lys
145                 150                 155                 160

Pro Ile Asp Ile Ile Asp Asn Leu Pro Thr Ser Gln His Gly Leu Asn
                165                 170                 175

Trp Ala Asn Val His Lys Arg Leu Ile Pro Gln Ile Ile Arg Lys Gly
            180                 185                 190

Val Val Tyr Ser Arg Ser Asn Tyr Val Lys Lys Gly Leu Tyr Phe Ile
        195                 200                 205

Leu Pro Glu Ile Val Tyr Asn Lys Phe Glu Asp Val Ile Gly Ala Asp
    210                 215                 220

Ile Pro Leu Leu Lys Thr Gln Thr Asn Lys Ser Ile Thr Val His Thr
225                 230                 235                 240

Tyr Ser Leu Gly Glu Pro Ala Ala Asn Gly Glu Gln Arg Lys Leu Ile
                245                 250                 255

Ser Glu Arg


<210> SEQ ID NO 210
<211> LENGTH: 238
<212> TYPE: PRT
<213> ORGANISM: unknown
<220> FEATURE:
<223> OTHER INFORMATION: Xylella fastidiosa 9a5c

<400> SEQUENCE: 210

Val Val Glu Leu Phe Gly Lys Ala Ala Asp Ala Pro Gly Ile Asp Trp
1               5                   10                  15

Gln Asn Glu Ile Ala Asp Gln Gln Cys Pro Phe Leu Gly Lys Arg Cys
            20                  25                  30

Tyr Asn Val Arg Lys Ser Asn Pro Glu Ile Ser Ile Gly Ser Cys Thr
        35                  40                  45

Val Leu Tyr Gly Arg Glu Pro Glu Pro Ile Ile Ile Cys Pro Thr Arg
    50                  55                  60

Leu Ile Gln Arg Gly Gln Ile Phe Thr Asp Cys Leu His Leu Leu Thr
65                  70                  75                  80

Ser His Glu Pro Gly Asn Glu Leu His Leu Val Ser Glu Val Thr Val
                85                  90                  95

Pro Gly Gly Ser Ile Asp Tyr Val Leu Val Ser Ala Lys Glu Gly Lys
            100                 105                 110

Val Arg Asp Phe Val Gly Ile Glu Leu Gln Thr Leu Asp Thr Thr Gly
        115                 120                 125

Thr Val Trp Pro Glu Arg Gln Arg Leu Leu Lys Glu Leu Gly Val Ala
    130                 135                 140

Arg Gly Asp Asn Gly Glu Glu Ser Asp Lys Ser Phe Gly Met Asn Trp
145                 150                 155                 160

Lys Met Thr Ala Lys Thr Ile Leu Val Gln Met His His Lys Val Gln
                165                 170                 175

Thr Phe Glu His Val Asn Arg Lys Leu Val Leu Val Val Gln Asp Lys
            180                 185                 190

Phe Leu Ala Tyr Met Thr Lys Glu Phe Lys Phe Asp His Met Lys Asn
```

```
        195                 200                 205

Pro Ala Ala Val Gly Asp Ser Met His Leu His Ser Tyr Arg Met Ala
    210                 215                 220

Arg Ala Asp Asp Gly Asn Phe Arg Leu Ser Met Ala Ser Arg
225                 230                 235


<210> SEQ ID NO 211
<211> LENGTH: 290
<212> TYPE: PRT
<213> ORGANISM: unknown
<220> FEATURE:
<223> OTHER INFORMATION: Enterobacter agglomerans

<400> SEQUENCE: 211

Leu Val Glu Val Phe Gly Tyr Asn Pro Met Asp Leu Ser Pro Glu Val
1               5                   10                  15

Arg Ala Leu Trp Asn Leu Gly Ala Cys Pro Phe Leu Asn Lys Glu Cys
            20                  25                  30

Ile Lys Ile Asn His Asp Gln Thr Ile Ile Tyr Gly Thr Cys Ser Val
        35                  40                  45

Thr Ser Pro Tyr Gly Asp Val Ile Ile Cys Pro Asn Arg Leu Tyr Ala
    50                  55                  60

Asn Asp Tyr Glu Thr Leu His Lys Val Ser Arg Asp Ala Phe Gly Asp
65                  70                  75                  80

Asp Val Pro Phe Leu Thr Tyr Ser Asn Phe Ile Lys Tyr Arg Ala Thr
                85                  90                  95

Tyr Lys Asp Cys Ile Val Ala Leu Gly Lys Asn Ser Gly Lys Glu Val
            100                 105                 110

Gln Val Gly Arg Ala Leu Ser Met Asp Trp Val Leu Val Arg Ile Thr
        115                 120                 125

Asp Gly Glu Leu Lys Glu Tyr Val Gly Val Glu Ile Gln Ser Ile Asp
    130                 135                 140

Ile Thr Gly Asn Tyr Arg Asp Ala Trp His Ala Tyr Lys Asn Leu Lys
145                 150                 155                 160

Pro Ile Asp Ile Ile Asp Asn Leu Pro Thr Ser Gln His Gly Leu Asn
                165                 170                 175

Trp Ala Asn Val His Lys Arg Leu Ile Pro Gln Ile Ile Arg Lys Gly
            180                 185                 190

Val Val Tyr Ser Arg Ser Asn Tyr Val Lys Lys Gly Leu Tyr Phe Ile
        195                 200                 205

Leu Pro Glu Ile Val Tyr Asn Lys Phe Glu Asp Val Ile Gly Ala Asp
    210                 215                 220

Ile Pro Leu Leu Lys Thr Gln Thr Asn Lys Ser Ile Thr Val His Thr
225                 230                 235                 240

Tyr Ser Leu Gly Glu Pro Ala Ala Asn Gly Glu Gln Arg Lys Leu Ile
                245                 250                 255

Ser Glu Arg Glu Ile Ile Phe Asp Leu Asp Glu Phe Ser Lys Arg Phe
            260                 265                 270

Thr Thr Gly Pro Asn Leu Pro Lys Gly Asp Asp Leu Asp Ala Val Ile
        275                 280                 285

Lys Lys
    290


<210> SEQ ID NO 212
<211> LENGTH: 299
<212> TYPE: PRT
<213> ORGANISM: unknown
```

<220> FEATURE:
<223> OTHER INFORMATION: Burkholderia cepacia

<400> SEQUENCE: 212

```
Ile Gly Glu Trp Phe Gly Phe Asn Leu Thr Gln Leu Ser Gly Glu Glu
1               5                   10                  15

Arg Arg Gln Leu Ala Ala Glu Val Leu Lys Pro Lys Lys Glu Arg Thr
            20                  25                  30

Pro Gln Pro Cys Pro Phe Gln Ala Arg Lys Thr Gly Ala Val Cys Ser
        35                  40                  45

Lys Asp Gly Gly Val Cys Ser Leu Arg Leu Tyr Ser Tyr Asn Thr His
    50                  55                  60

Pro Asp Asn Gly Arg Ala Val Gly Val Pro Val Glu Gly Lys Gln Gly
65                  70                  75                  80

Asp Leu Arg Ala Thr Cys Pro Tyr Arg Phe His Asp Glu Leu Asp Val
                85                  90                  95

Phe Lys Trp Val Gly Glu Thr Ile Leu Gly Asp Pro Asp Pro Leu Leu
            100                 105                 110

Val Gly Glu Val Gly Phe Leu Glu Ala Gly Ala Ser Thr Asp Ser Glu
        115                 120                 125

Gly Gly Asp Asp Val Gly Arg Ile Asp Met Val Leu Val Ser Ser Lys
    130                 135                 140

Thr Pro Lys Glu Ala Pro Met Asn Trp Ala Ala Leu Glu Ile Gln Ala
145                 150                 155                 160

Val Tyr Phe Ser Gly Asn Ala Met Lys Gly Glu Phe Glu Ala Phe Asn
                165                 170                 175

Asp Asp Ala Val Asp Trp Val Ile Phe Pro Ala Gly Arg Arg Arg Pro
            180                 185                 190

Asp Tyr Arg Ser Ser Gly Pro Lys Arg Leu Met Pro Gln Leu Gln Ile
        195                 200                 205

Lys Val Pro Thr Leu Arg Arg Trp Gly Lys Lys Met Ala Val Val Val
    210                 215                 220

Asp Arg Ala Phe Phe Asp Ser Ile Gly Glu Met Asp Asn Val Ala Asp
225                 230                 235                 240

Ile Ser Asn Ala Asp Ile Ala Trp Phe Ile Val Arg Phe Glu Glu Val
                245                 250                 255

Glu Gly Gln Lys Arg Thr Arg Ile Val Arg Asp Glu Val Arg Tyr Thr
            260                 265                 270

Thr Leu Glu Arg Ser Val Glu Gly Leu Thr Gly Gly Lys Pro Val Pro
        275                 280                 285

Leu Pro Val Phe Glu Thr Arg Ile Thr Asp Lys
    290                 295
```

<210> SEQ ID NO 213
<211> LENGTH: 190
<212> TYPE: PRT
<213> ORGANISM: unknown
<220> FEATURE:
<223> OTHER INFORMATION: Enterobacter agglomerans

<400> SEQUENCE: 213

```
Leu Val Glu Val Phe Gly Tyr Asn Pro Met Asp Leu Ser Pro Glu Val
1               5                   10                  15

Arg Ala Leu Trp Asn Leu Gly Ala Cys Pro Phe Leu Asn Lys Glu Cys
            20                  25                  30

Ile Lys Ile Asn His Asp Gln Thr Ile Ile Tyr Gly Thr Cys Ser Val
        35                  40                  45
```

```
Thr Ser Pro Tyr Gly Val Gln Val Gly Arg Ala Leu Ser Met Asp Trp
    50                  55                  60

Val Leu Val Arg Ile Thr Asp Gly Glu Leu Lys Glu Tyr Val Gly Val
65                  70                  75                  80

Glu Ile Gln Ser Ile Asp Ile Thr Gly Asn Tyr Arg Asp Ala Trp His
                85                  90                  95

Ala Tyr Lys Asn Leu Lys Pro Ile Asp Ile Ile Asp Asn Leu Pro Thr
            100                 105                 110

Ser Gln His Gly Leu Asn Trp Ala Asn Val His Lys Arg Leu Ile Pro
        115                 120                 125

Gln Ile Ile Arg Lys Gly Val Val Tyr Ser Arg Ser Asn Tyr Val Lys
    130                 135                 140

Lys Gly Leu Tyr Phe Ile Leu Pro Glu Ile Val Tyr Asn Lys Phe Glu
145                 150                 155                 160

Asp Val Ile Gly Ala Asp Ile Pro Leu Leu Lys Thr Gln Thr Asn Lys
                165                 170                 175

Ser Ile Thr Val His Thr Tyr Ser Leu Gly Glu Pro Ala Ala
            180                 185                 190


<210> SEQ ID NO 214
<211> LENGTH: 229
<212> TYPE: PRT
<213> ORGANISM: unknown
<220> FEATURE:
<223> OTHER INFORMATION: Arthrospira platensis

<400> SEQUENCE: 214

Ile Ile Glu Ile Phe Gly Tyr Ser Ile Asn Gln Pro Glu His Ile Asp
1               5                   10                  15

Trp Thr Ser Leu Ile Arg Glu Gln His Cys Pro Tyr Leu Gln Arg Arg
            20                  25                  30

Cys Ile Lys Val Arg Lys Ser Gln Pro Asp Ile Ser Ile Gly Thr Cys
        35                  40                  45

Ser Val Ile Tyr Gly Lys Asn Ala Ile Pro Val Ile Ile Cys Pro His
    50                  55                  60

Arg Leu Leu Glu Arg Lys Gln Ile Phe Ile Asp Cys Leu His Leu Leu
65                  70                  75                  80

Thr Asn His Glu Pro Gly Asn Glu Leu His Leu Val Ser Glu Ile Ser
                85                  90                  95

Ile Pro Gly Gly Asn Val Asp Tyr Phe Leu Val Ser Ala Leu Asn Asn
            100                 105                 110

Lys Val Lys Asp Phe Val Gly Ile Glu Leu Gln Thr Leu Asp Thr Thr
        115                 120                 125

Gly Thr Val Trp Pro Glu Arg Gln Arg Leu Leu Glu Glu Leu Gly Val
    130                 135                 140

Pro Thr Glu Asp Asn Gln Ser Gln Ser Gln Lys Thr Phe Gly Met Asn
145                 150                 155                 160

Trp Lys Met Thr Ala Lys Thr Ile Leu Ile Gln Leu His His Lys Ile
                165                 170                 175

Glu Thr Phe Glu His Ile Asn Lys Lys Leu Val Leu Val Ile Gln Asp
            180                 185                 190

Cys Phe Leu Asp Tyr Ile Gln Arg Glu Phe Ser Phe Ser His Ile Ser
        195                 200                 205

His Gln Ala Gln Leu Gly Asp Ser Met His Ile His Ala Tyr Gln Met
    210                 215                 220
```

Thr Glu Gln Pro Asp
225

<210> SEQ ID NO 215
<211> LENGTH: 248
<212> TYPE: PRT
<213> ORGANISM: unknown
<220> FEATURE:
<223> OTHER INFORMATION: Enterobacter agglomerans

<400> SEQUENCE: 215

```
Leu Val Glu Val Phe Gly Tyr Asn Pro Met Asp Leu Ser Pro Glu Val
1               5                   10                  15

Arg Ala Leu Trp Asn Leu Gly Ala Cys Pro Phe Leu Asn Lys Glu Cys
            20                  25                  30

Ile Lys Ile Asn His Asp Gln Thr Ile Ile Tyr Gly Thr Cys Ser Val
        35                  40                  45

Thr Ser Pro Tyr Gly Asp Val Ile Ile Cys Pro Asn Arg Leu Tyr Ala
    50                  55                  60

Asn Asp Tyr Glu Thr Leu His Lys Val Ser Arg Asp Ala Phe Gly Asp
65                  70                  75                  80

Asp Val Pro Phe Leu Thr Tyr Ser Asn Phe Ile Lys Tyr Arg Ala Thr
                85                  90                  95

Tyr Lys Asp Cys Ile Val Ala Leu Gly Lys Asn Ser Gly Lys Glu Val
            100                 105                 110

Gln Val Gly Arg Ala Leu Ser Met Asp Trp Val Leu Val Arg Ile Thr
        115                 120                 125

Asp Gly Glu Leu Lys Glu Tyr Val Gly Val Glu Ile Gln Ser Ile Asp
    130                 135                 140

Ile Thr Gly Asn Tyr Arg Asp Ala Trp His Ala Tyr Lys Asn Leu Lys
145                 150                 155                 160

Pro Ile Asp Ile Ile Asp Asn Leu Pro Thr Ser Gln His Gly Leu Asn
                165                 170                 175

Trp Ala Asn Val His Lys Arg Leu Ile Pro Gln Ile Ile Arg Lys Gly
            180                 185                 190

Val Val Tyr Ser Arg Ser Asn Tyr Val Lys Lys Gly Leu Tyr Phe Ile
        195                 200                 205

Leu Pro Glu Ile Val Tyr Asn Lys Phe Glu Asp Val Ile Gly Ala Asp
    210                 215                 220

Ile Pro Leu Leu Lys Thr Gln Thr Asn Lys Ser Ile Thr Val His Thr
225                 230                 235                 240

Tyr Ser Leu Gly Glu Pro Ala Ala
                245
```

<210> SEQ ID NO 216
<211> LENGTH: 226
<212> TYPE: PRT
<213> ORGANISM: unknown
<220> FEATURE:
<223> OTHER INFORMATION: Nostoc punctiforme PCC 73102

<400> SEQUENCE: 216

```
Val Val Glu Leu Tyr Gly Asn Pro Thr Asn Gln Ser Leu Ile Trp Ser
1               5                   10                  15

Asp Ile Ala Ser Ser Gln Asn Cys Pro Phe Leu Ser Arg Lys Cys Leu
            20                  25                  30

Lys Asn Arg Lys Ser Glu Pro Asp Leu Thr Ile Gly Ser Cys Thr Val
        35                  40                  45
```

```
Ser Tyr Gly Arg Glu Ala Arg Asn Ile Ile Ile Cys Pro Phe Arg Leu
    50                  55                  60

Leu Glu Arg Ser Gln Ile Phe Thr Asp Cys Ile His Leu Leu Thr Leu
65                  70                  75                  80

His Glu Pro Gly Asn Glu Leu Arg Ile Val Pro Glu Ile Ala Val Pro
                85                  90                  95

Gly Gly Ser Ile Asp Tyr Cys Leu Ala Ser Val Arg Ser Gly Lys Val
            100                 105                 110

Ile Asp Phe Ile Ser Ile Glu Leu Gln Thr Leu Asp Thr Thr Gly Thr
        115                 120                 125

Val Trp Pro Glu Arg Gln Arg Phe Leu Gln Arg His Gly Val Ser Val
    130                 135                 140

Arg Asp Val Asp Val Ala Ser Gly Lys Gly Phe Gly Met Asn Trp Lys
145                 150                 155                 160

Met Thr Ala Lys Thr Ile Leu Met Gln Leu His His Lys Ile His Thr
                165                 170                 175

Phe Glu His Leu Ser Lys His Leu Val Leu Val Val Gln Asp Cys Leu
            180                 185                 190

Ile Asp Tyr Met Gln Arg Glu Phe Ser Phe Glu His Ile Gln Asp Ala
        195                 200                 205

Arg Leu Gly Asn Pro Met His Phe His Ser Tyr Glu Leu Leu Thr Glu
    210                 215                 220

Ala Ser
225
```

<210> SEQ ID NO 217
<211> LENGTH: 216
<212> TYPE: PRT
<213> ORGANISM: unknown
<220> FEATURE:
<223> OTHER INFORMATION: Enterobacter agglomerans

<400> SEQUENCE: 217

```
Ala Phe Gly Asp Asp Val Pro Phe Leu Thr Tyr Ser Asn Phe Ile Lys
1               5                   10                  15

Tyr Arg Ala Thr Tyr Lys Asp Cys Ile Val Ala Leu Gly Lys Asn Ser
            20                  25                  30

Gly Lys Glu Val Gln Val Gly Arg Ala Leu Ser Met Asp Trp Val Leu
        35                  40                  45

Val Arg Ile Thr Asp Gly Glu Leu Lys Glu Tyr Val Gly Val Glu Ile
    50                  55                  60

Gln Ser Ile Asp Ile Thr Gly Asn Tyr Arg Asp Ala Trp His Ala Tyr
65                  70                  75                  80

Lys Asn Leu Lys Pro Ile Asp Ile Ile Asp Asn Leu Pro Thr Ser Gln
                85                  90                  95

His Gly Leu Asn Trp Ala Asn Val His Lys Arg Leu Ile Pro Gln Ile
            100                 105                 110

Ile Arg Lys Gly Val Val Tyr Ser Arg Ser Asn Tyr Val Lys Lys Gly
        115                 120                 125

Leu Tyr Phe Ile Leu Pro Glu Ile Val Tyr Asn Lys Phe Glu Asp Val
    130                 135                 140

Ile Gly Ala Asp Ile Pro Leu Leu Lys Thr Gln Thr Asn Lys Ser Ile
145                 150                 155                 160

Thr Val His Thr Tyr Ser Leu Gly Glu Pro Ala Ala Asn Gly Glu Gln
                165                 170                 175

Arg Lys Leu Ile Ser Glu Arg Glu Ile Ile Phe Asp Leu Asp Glu Phe
```

```
            180                 185                 190

Ser Lys Arg Phe Thr Thr Gly Pro Asn Leu Pro Lys Gly Asp Asp Leu
        195                 200                 205

Asp Ala Val Ile Lys Lys Ala Leu
    210                 215


<210> SEQ ID NO 218
<211> LENGTH: 201
<212> TYPE: PRT
<213> ORGANISM: unknown
<220> FEATURE:
<223> OTHER INFORMATION: Syntrophomonas wolfei str. Goettingen

<400> SEQUENCE: 218

Met Val Thr Ile Asp Ala Ala Ser Phe Phe Phe Ser Pro Gly Thr Lys
1               5                   10                  15

Trp Thr Thr Leu Thr Glu Val Arg Leu Asn Asp Ile Asn Gly His Thr
            20                  25                  30

Ala Gly Asn Ile Asp Ile Val Leu Val Ala Tyr Asp Asp Tyr Gly Lys
        35                  40                  45

Ile Thr Asp Phe Gly Ala Leu Glu Ile Gln Ser Val Tyr Ile Ser Gly
    50                  55                  60

Asn Ile Arg Arg Pro Phe Glu Ala Tyr Ile Gln Glu Pro Glu Leu Met
65                  70                  75                  80

Tyr Asn Met Asp Trp Leu Ser Lys Pro Asn Tyr Pro Arg Pro Asp Tyr
                85                  90                  95

Leu Ser Ser Ser Arg Lys Arg Leu Val Pro Gln Leu Ile Tyr Lys Gly
            100                 105                 110

Lys Ile Leu Asn Val Trp Ser Lys Lys Ile Ala Val Ala Leu His Ser
        115                 120                 125

Gly Phe Phe Ser Thr Leu Pro Gln Leu Pro Arg Val Ser Ala Asp Lys
    130                 135                 140

Ala Glu Ile Ala Trp Leu Ile Tyr Asp Ile Glu Leu Lys Gln Glu Thr
145                 150                 155                 160

Asn Arg Tyr Asn Leu Val His Thr Asp Thr Ile Tyr Thr Leu Phe Gln
                165                 170                 175

Asn Ser Leu Asp Arg Ile Val Thr Pro Glu Ser Gly Leu Ile Asp Asp
            180                 185                 190

Phe Ile Glu Val Leu Gln Gly Lys Leu
        195                 200


<210> SEQ ID NO 219
<211> LENGTH: 204
<212> TYPE: PRT
<213> ORGANISM: unknown
<220> FEATURE:
<223> OTHER INFORMATION: Enterobacter agglomerans

<400> SEQUENCE: 219

Ala Phe Gly Asp Asp Val Pro Phe Leu Thr Tyr Ser Asn Phe Ile Lys
1               5                   10                  15

Tyr Arg Ala Thr Tyr Lys Asp Cys Ile Val Ala Leu Gly Lys Asn Ser
            20                  25                  30

Gly Lys Glu Val Gln Val Gly Arg Ala Leu Ser Met Asp Trp Val Leu
        35                  40                  45

Val Arg Ile Thr Asp Gly Glu Leu Lys Glu Tyr Val Gly Val Glu Ile
    50                  55                  60

Gln Ser Ile Asp Ile Thr Gly Asn Tyr Arg Asp Ala Trp His Ala Tyr
```

65 70 75 80

Lys Asn Leu Lys Pro Ile Asp Ile Ile Asp Asn Leu Pro Thr Ser Gln
85 90 95

His Gly Leu Asn Trp Ala Asn Val His Lys Arg Leu Ile Pro Gln Ile
100 105 110

Ile Arg Lys Gly Val Val Tyr Ser Arg Ser Asn Tyr Val Lys Lys Gly
115 120 125

Leu Tyr Phe Ile Leu Pro Glu Ile Val Tyr Asn Lys Phe Glu Asp Val
130 135 140

Ile Gly Ala Asp Ile Pro Leu Leu Lys Thr Gln Thr Asn Lys Ser Ile
145 150 155 160

Thr Val His Thr Tyr Ser Leu Gly Glu Pro Ala Ala Asn Gly Glu Gln
165 170 175

Arg Lys Leu Ile Ser Glu Arg Glu Ile Ile Phe Asp Leu Asp Glu Phe
180 185 190

Ser Lys Arg Phe Thr Thr Gly Pro Asn Leu Pro Lys
195 200

<210> SEQ ID NO 220
<211> LENGTH: 192
<212> TYPE: PRT
<213> ORGANISM: unknown
<220> FEATURE:
<223> OTHER INFORMATION: Chlorobium phaeobacteroides DSM 266

<400> SEQUENCE: 220

Met Ile Thr Asp Asp Ala Ala Ser Phe Phe Phe Asp Glu Ser Thr Thr
1 5 10 15

Trp Ser Ser Leu Thr Glu Val Arg Leu Asn Asp Ala Tyr Gly Lys Ser
20 25 30

Ala Gly Asn Thr Asp Val Val Leu Val Ala Tyr Asp Lys Thr Gly Lys
35 40 45

Val Ile Asp Phe Gly Ala Leu Glu Ile Gln Ala Val Tyr Ile Ser Gly
50 55 60

Asn Val Arg Glu Pro Phe Glu Gln Phe Met Lys Glu Pro Glu Thr His
65 70 75 80

Glu Asn Met Asn Trp Thr Thr Gln Pro Asn Tyr Pro Arg Pro Asp Tyr
85 90 95

Leu Ser Ser Ser Arg Lys Arg Leu Ala Pro Gln Leu Leu Phe Lys Gly
100 105 110

Gly Ile Leu Asn Ile Arg Lys Lys Lys Thr Ala Val Ala Ile Asn Lys
115 120 125

Ser Phe Phe Asp Thr Leu Pro Ser Phe Lys Gln Val Glu Lys Ser Lys
130 135 140

Ala Thr Ile Ala Trp Ile Val Tyr Asp Leu Glu Leu Ser Asp Glu Asp
145 150 155 160

Gly Leu Glu Arg Tyr His Leu Lys Lys Ile Asp Glu Val Tyr Thr Glu
165 170 175

Phe Glu Pro Ala Leu Val Ala Ile Thr Thr Ala Thr Pro Gly Lys Arg
180 185 190